United States Patent
Blake et al.

(10) Patent No.: US 9,670,208 B2
(45) Date of Patent: Jun. 6, 2017

(54) SERINE/THREONINE KINASE INHIBITORS

(71) Applicants: Array BioPharma Inc., Boulder, CO (US); Genentech, Inc., South San Francisco, CA (US)

(72) Inventors: James F. Blake, Boulder, CO (US); Adam Cook, Boulder, CO (US); John Gaudino, Boulder, CO (US); Indrani W. Gunawardana, Boulder, CO (US); Erik James Hicken, Boulder, CO (US); Kevin W. Hunt, Boulder, CO (US); Michael Lyon, Boulder, CO (US); Andrew T. Metcalf, Boulder, CO (US); Peter J. Mohr, Boulder, CO (US); David A. Moreno, Boulder, CO (US); Brad Newhouse, Boulder, CO (US); Li Ren, Boulder, CO (US); Jacob Schwarz, South San Francisco, CA (US); Huifen Chen, South San Francisco, CA (US); Lewis Gazzard, South San Francisco, CA (US); Jane Schmidt, South San Francisco, CA (US); Steve Do, South San Francisco, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/197,445

(22) Filed: Jun. 29, 2016

(65) Prior Publication Data
US 2016/0304519 A1    Oct. 20, 2016

Related U.S. Application Data

(63) Continuation of application No. PCT/US2014/072555, filed on Dec. 29, 2014.

(60) Provisional application No. 61/922,042, filed on Dec. 30, 2013.

(51) Int. Cl.
| C07D 471/04 | (2006.01) |
| A61K 45/06 | (2006.01) |
| A61K 31/5377 | (2006.01) |
| A61K 31/506 | (2006.01) |
| A61K 31/444 | (2006.01) |
| C07D 487/04 | (2006.01) |
| C07D 519/00 | (2006.01) |
| A61K 31/55 | (2006.01) |

(52) U.S. Cl.
CPC .......... *C07D 471/04* (2013.01); *A61K 31/444* (2013.01); *A61K 31/506* (2013.01); *A61K 31/5377* (2013.01); *A61K 31/55* (2013.01); *A61K 45/06* (2013.01); *C07D 487/04* (2013.01); *C07D 519/00* (2013.01)

(58) Field of Classification Search
CPC .. A61K 31/506; A61K 31/5377; A61K 31/55; A61K 45/06; C07D 471/04; C07D 487/04; C07D 519/00
See application file for complete search history.

(56) References Cited

U.S. PATENT DOCUMENTS

| 8,697,715 B2 | 4/2014 | Blake et al. |
| 9,133,187 B2 | 9/2015 | Blake et al. |
| 9,187,462 B2 | 11/2015 | Blake et al. |
| 9,259,470 B2 | 2/2016 | Blake et al. |
| 9,388,171 B2 | 7/2016 | Blake et al. |
| 2015/0182537 A1 | 7/2015 | Kolesnikov et al. |
| 2016/0122316 A1 | 5/2016 | Blake et al. |
| 2016/0303126 A1 | 10/2016 | Blake et al. |

FOREIGN PATENT DOCUMENTS

| WO | 03044021 A1 | 5/2003 | |
| WO | WO 03044021 A2 * | 5/2003 | ........... C07D 401/04 |
| WO | 2012118850 A1 | 9/2012 | |
| WO | 2013020062 A1 | 2/2013 | |
| WO | 2013130976 A1 | 9/2013 | |

OTHER PUBLICATIONS

Hohno, et al., "Pharmacological inhibitors of the ERK signaling pathway: application as anticancer drugs", Prog in Cell Cycle Res 5, 219 (2003).
Ma, et al., "The ERK/MAPK pathway, as a target for the treatment of neuropathic pain", Expert Opin. Ther. Targets, 9 (4), 699-713 (2005).
Patent Cooperation Treaty, "International Searching Authority, Search Report and Written Opinion for PCT/US2014/072555, 8 pages, Feb. 10, 2015."
Sommer, et al., "Resolvins and inflammatory pain", F1000 Medicine Reports, 3, 19, 6 pages (2011).

* cited by examiner

*Primary Examiner* — Yong Chu
(74) *Attorney, Agent, or Firm* — Viksnins Harris & Padys PLLP

(57) ABSTRACT

Compounds of Formula I or a stereoisomer, tautomer or pharmaceutically acceptable salt thereof are provided, which are useful for the treatment of diseases. Methods of using compounds of Formula I or a stereoisomer, tautomer or pharmaceutically acceptable salt thereof, for in vitro, in situ, and in vivo diagnosis, prevention or treatment of such diseases, or associated pathological conditions are disclosed.

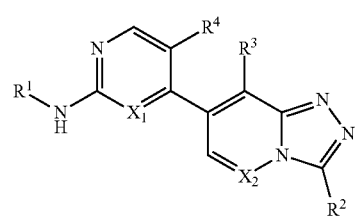

19 Claims, No Drawings

SERINE/THREONINE KINASE INHIBITORS

PRIORITY OF INVENTION

This application is a continuation of International Patent Application No. PCT/US2014/072555, filed Dec. 29, 2014, which claims priority to U.S. Provisional Application No. 61/922,042 that was filed on Dec. 30, 2013 both of which are incorporated herein by reference in their entirety.

BACKGROUND OF THE INVENTION

Field of the Invention

The present invention relates to compounds that inhibit serine/threonine kinases and are useful for treating hyperproliferative and neoplastic diseases by inhibiting signal transduction pathways, which are commonly overactive or overexpressed in cancerous tissue. The present compounds are selective inhibitors of ERK (extracellular-signal regulated kinase). The present invention further relates to methods for treating cancer or hyperproliferative diseases with compounds of the present invention.

Description of the State of the Art

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase ("RTK's"), such as ErbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events, including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers, including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anti-cancer therapies in a broad spectrum of human tumors (M. Hohno and J. Pouyssegur, Prog. in Cell Cycle Res. 2003 5:219).

The ERK pathway has also been cited as a promising therapeutic target for the treatment of pain and inflammation (Ma, Weiya and Remi Quirion. "The ERK/MAPK pathway, as a target for the treatment of neuropathic pain." *Expert Opin. Ther. Targets.* 9(4) (2005): pp. 699-713, and Sommer, Claudia and Frank Birklein. "Resolvins and inflammatory pain." *F1000 Medicine Reports.* 3:19 (2011)).

International Patent Application Publications WO 2012/118850, WO 2013/020062 and WO 2013/130976 disclose ERK inhibitors.

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer, as well as a treatment for pain and inflammation, such as arthritis, low back pain, inflammatory bowel disease, and rheumatism. Such a contribution is provided herein.

SUMMARY OF THE INVENTION

There is a continuing need for new and novel therapeutic agents that can be used for cancer and hyperproliferative conditions. The Raf/MEK/ERK pathway is an important signaling pathway, which is frequently overexpressed and/or overactive in many cancerous tissues. Design and development of new pharmaceutical compounds is essential.

More specifically, one aspect provides compounds of Formula I:

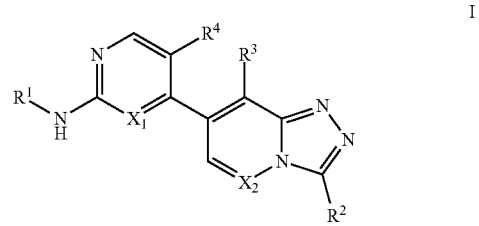

or a stereoisomer, tautomer or pharmaceutically acceptable salt thereof, wherein $X_1$, $X_2$, $R^1$, $R^2$, $R^3$ and $R^4$ are as defined herein.

Another aspect provides compounds of Formulas II, III, IV, V, VI, VII, VIII, IX or X, or a stereoisomer, tautomer or pharmaceutically acceptable salt thereof.

Another aspect provides a method for treating a hyperproliferative disorder by administering a therapeutically effective quantity of a compound according to Formula I, II, III, IV, V, VI, VII, VIII, IX or X, or a stereoisomer, tautomer or pharmaceutically acceptable salt thereof, to a patient in need thereof. The compound can be administered alone or co-administered with at least one other anti-hyperproliferative or chemotherapeutic compound.

Another aspect provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another aspect provides methods of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative disorders, such as cancer.

Another aspect provides methods of treating or preventing cancer, comprising administering to a mammal in need of such treatment an effective amount of a compound of Formula I, II, III, IV, V, VI, VII, VIII, IX or X, or a stereoisomer, tautomer or pharmaceutically acceptable salt thereof, alone or in combination with one or more additional compounds having anti-cancer properties.

Another aspect provides a method of treating a hyperproliferative disease in a mammal comprising administering a therapeutically effective amount of a compound of Formula I, II, III, IV, V, VI, VII, VIII, IX or X, or a stereoisomer, tautomer or pharmaceutically acceptable salt thereof, to the mammal.

Another aspect provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease.

Another aspect provides a compound of Formula I, II, III, IV, V, VI, VII, VIII, IX or X, or a stereoisomer, tautomer or pharmaceutically acceptable salt thereof, for use in the treatment of hyperproliferative diseases.

Another aspect provides a pharmaceutical composition comprising a compound of Formula I, II, III, IV, V, VI, VII, VIII, IX or X, or a stereoisomer, tautomer or pharmaceutically acceptable salt thereof, and a pharmaceutically acceptable carrier, diluent or excipient.

Another aspect provides intermediates for preparing compounds of Formula I, II, III, IV, V, VI, VII, VIII, IX or X. Certain compounds of the Formulas may be used as intermediates for other compounds of the Formulas.

Another aspect includes processes for preparing, methods of separation, and methods of purification of the compounds described herein.

DETAILED DESCRIPTION OF THE INVENTION

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein" refers to the broadest definition for each group as provided in the Detailed Description of the Invention or the broadest claim. In all other embodiments provided below, substituents that can be present in each embodiment, and which are not explicitly defined, retain the broadest definition provided in the Detailed Description of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Certain compounds of Formula I, II, III, IV, V, VI, VII, VIII, IX or X may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—CH2-→—C(—OH)=CH—), amide/imidic acid (—C(=O)—NH—→—C(—OH)=N—) and amidine (—C(=NR)—NH—→—C(—

NHR)=N—) tautomers. The latter two are particularly common in heteroaryl and heterocyclic rings, and the present invention encompasses all tautomeric forms of the compounds.

It will be appreciated by the skilled artisan that some of the compounds of Formula I, II, III, IV, V, VI, VII, VIII, IX or X may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of Formula I, II, III, IV, V, VI, VII, VIII, IX or X and, where appropriate, the individual tautomeric forms thereof.

The compounds of Formula I, II, III, IV, V, VI, VII, VIII, IX or X may contain a basic center and suitable acid addition salts are formed from acids that form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts, see Berge, Stephen M., et al. "Pharmaceutical salts." *J. Pharm. Sci.* Vol. 66, No. 1 (1977): 1-19, and Paulekuhn, G. Steffen, et al. "Trends in Active Pharmaceutical Ingredient Salt Selection based on Analysis of the Orange Book Database." *J. Med. Chem. Vol.* 50, No. 26 (2007): 6665-6672.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Hardman, Joel Griffith, et al. *Goodman & Gilman's The Pharmacological Basis of Therapeutics.* New York: McGraw-Hill Professional, 2001. The starting materials and reagents used in preparing these compounds generally are either available from commercial suppliers, such as Sigma-Aldrich (St. Louis, Mo.), or are prepared by methods known to those skilled in the art following procedures set forth in references. Materials, reagents and the like to which reference are made in the following description and examples are obtainable from commercial sources, unless otherwise noted. General synthetic procedures have been described in treatises, such as Louis F. Fieser and Mary Fieser, *Reagents for Organic Synthesis.* v. 1-23, New York: Wiley 1967-2006 ed. (also available via the Wiley Inter-Science® website); LaRock, Richard C., *Comprehensive Organic Transformations: A Guide to Functional Group Preparations.* New York: Wiley-VCH, 1999; B. Trost and I. Fleming, eds. *Comprehensive Organic Synthesis.* v. 1-9, Oxford: Pergamon 1991; A. R. Katritzky and C. W. Rees, eds. *Comprehensive Heterocyclic Chemistry.* Oxford: Pergamon 1984; A. R. Katritzky and C. W. Rees, eds. *Comprehensive Heterocyclic Chemistry II.* Oxford: Pergamon 1996; and Paquette, Leo A., ed. *Organic Reactions.* v. 1-40, New York: Wiley & Sons 1991; and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with at least one substituent selected from the other specifically-named group. Thus, for example, "phenylalkyl" refers to an alkyl group having at least one phenyl substituent, and thus includes benzyl and phenylethyl. An "alkylaminoalkyl" is an alkyl group having at least one alkylamino substituent. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "$C_1$-$C_4$ acyloxy-$C_1$-$C_2$ alkyl" as used herein denotes a group of formula —$(CH_2)_{1-2}OC(O)(CH_2)_{0-3}H$. The term "$C_1$-$C_4$ acyloxy" as used herein denotes the radical —OC(O)R, wherein R contains 1 to 4 carbon atoms (e.g., $C_1$ is formyl).

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations used throughout the application may include, for example, benzyl ("Bn"), phenyl ("Ph") and acetate ("Ac").

The terms "alkenyl" and "alkynyl" also include linear or branched-chain radicals of carbon atoms.

The term "haloalkyl" as used herein denotes an unbranched or branched chain alkyl group as defined above, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl, 2,2,2-trifluoroethyl, 2-chloro-3-fluoropropyl and 1,1,2,2,2-pentafluoroethyl (perfluoroethyl).

The term "heteroalkyl" as used herein means an alkyl radical as defined herein, wherein one or two hydrogen atoms have been replaced with a substituent independently selected from the group consisting of —$OR^\alpha$ and —$NR^\beta R^\gamma$, with the understanding that the point of attachment of the heteroalkyl radical is through a carbon atom. $R^\alpha$ is hydrogen or alkyl and $R^\beta$ and $R^\gamma$ are independently of each other hydrogen, acyl, alkyl, or $R^\beta$ and $R^\gamma$ together with the nitrogen to which they are attached form a cyclic amine. Hydroxyalkyl, alkoxyalkyl, aminoalkyl, alkylaminoalkyl and dialkylaminoalkyl moieties are subgenera encompassed by the term "heteroalkyl". Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-methylaminopropyl, and the like.

The term "heteroaryl" includes five to six membered monocyclic and nine to ten membered bicyclic aromatic rings containing one, two, three or four heteroatoms selected from the group consisting of oxygen, nitrogen and sulfur, with the proviso that the ring does not contain two adjacent O or S atoms. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

Heteroaryl groups may include, for example, pyrrolyl, thiophenyl (thienyl), furanyl (furyl), imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridinyl (pyridyl), pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, benzofuranyl, benzothiophenyl, indolyl, benzimidazolyl, indazolyl, benzotriazolyl, pyrrolopyridinyl, imidazopyridinyl, pyrazolopyridine, isoindolyl, indazolyl, purinyl, indolininyl, pyrrolopyridazinyl, imidazopyrimidinyl, quinolinyl, isoquinolinyl, cinnolinyl, quinazolinyl, quinoxalinyl, phthalazinyl, napthyridinyl, pyridopyrimidinyl, pyridopyrazinyl, pyrimidopyrimidinyl and pyraziniopyrazinyl.

The terms "heterocycle", "heterocyclic" and "heterocyclyl" include three to seven membered monocyclic saturated or partially unsaturated rings containing one, two or three heteroatoms selected from the group consisting of oxygen, nitrogen, sulfur, S(=O) and S(=O)$_2$, with the proviso that the ring does not contain two adjacent O or S atoms. In certain instances, these terms may be specifically further limited, such as, "five to six membered heterocyclyl" only including five and six membered rings. Bicyclic heterocyclic groups include five to fourteen membered bicyclic saturated or partially unsaturated rings containing one, two or three heteroatoms selected from the group consisting of oxygen, nitrogen, sulfur, S(=O) and S(=O)$_2$. In certain instances, these terms may be specifically further limited, such as, "seven to ten membered heterocyclyl" only including seven to ten membered bicyclic rings. In certain embodiments, bicyclic heterocyclic groups are nine to ten membered saturated or partially unsaturated rings containing one, two or three heteroatoms selected from the group consisting of oxygen, nitrogen, sulfur, S(=O) and S(=O)$_2$, with the proviso that the ring does not contain two adjacent O or S atoms.

Heterocyclic groups may include, for example, oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahyrdothiopyranyl, piperidinyl, dioxanyl, oxathianyl, morpholinyl (morpholino), dithianyl, piperazinyl, azathianyl, oxepanyl, thiepanyl, azepanyl, dioxepanyl, oxathiepanyl, oxaazepanyl, dithiepanyl, thieazepanyl, diazepanyl, dihydrofuranyl, dihydropyranyl, pyranyl and tetrahydropyridinyl. Further examples of the 5- and 6-membered ring systems discussed above can be found in U.S. Pat. No. 4,278,793.

The terms "hydroxyalkyl" and "alkoxyalkyl" as used herein denotes alkyl radical as herein defined, wherein one to three hydrogen atoms on different carbon atoms is/are replaced by hydroxyl or alkoxy groups respectively. A $C_1$-$C_3$ alkoxy-$C_1$-$C_6$ alkyl moiety refers to a $C_1$-$C_6$ alkyl substituent in which one to three hydrogen atoms are replaced by a $C_1$-$C_3$ alkoxy and the point of attachment of the alkoxy is the oxygen atom.

A bond drawn into ring system (as opposed to connected at a distinct vertex) indicates that the bond may be attached to any of the suitable ring atoms.

Methods of this invention encompass methods of treating, preventing and/or managing various types of cancer and diseases and disorders associated with, or characterized by, undesired angiogenesis. As used herein, unless otherwise specified, the term "treating" or "treat" refers to the administration of a compound of the invention or other additional active agent after the onset of symptoms of the particular disease or disorder. The terms "treat" or "treatment" also refer to therapeutic or palliative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder. As used herein, unless otherwise specified, the term "preventing" refers to the administration prior to the onset of symptoms, particularly to patients at risk of cancer, and other diseases and disorders associated with, or characterized by, undesired angiogenesis. The term "prevention" includes the inhibition of a symptom of the particular disease or disorder. Patients with familial history of cancer and diseases and disorders associated with, or characterized by, undesired angiogenesis are preferred candidates for preventive regimens. As used herein and unless otherwise indicated, the term "managing" encompasses preventing the recurrence of the particular disease or disorder in a patient who had suffered from it, and/or lengthening the time a patient who had suffered from the disease or disorder remains in remission.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholinodoxorubicin, cyanomorpholino-doxorubicin, 2-pyrrolinodoxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound described herein.

The compounds described herein also include other salts of such compounds that are not necessarily pharmaceutically acceptable salts, and which may be useful as intermediates for preparing and/or purifying compounds described herein and/or for separating enantiomers of compounds described herein.

The term "mammal" means a warm-blooded animal that has or is at risk of developing a disease described herein and includes, but is not limited to, guinea pigs, dogs, cats, rats, mice, hamsters, and primates, including humans.

ERK Compounds

Provided herein are compounds, and pharmaceutical formulations thereof, that are potentially useful in the treatment of diseases, conditions and/or disorders modulated by ERK.

One embodiment provides compounds of Formula I:

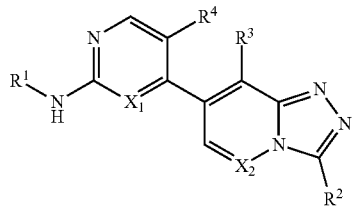

I or a stereoisomer, tautomer or pharmaceutically acceptable salt thereof, wherein:

$X_1$ is selected from CH and N;
$X_2$ is selected from CH and N;
$R^1$ is selected from $C_1$-$C_{12}$ alkyl, $C_2$-$C_{12}$ alkenyl, $C_2$-$C_{12}$ alkynyl, $C_3$-$C_7$ cycloalkyl, phenyl, a 3 to 7 membered saturated or partially unsaturated heterocyclyl, a 5 to 6 membered heteroaryl, $C_5$-$C_{14}$ bicyclic cycloalkyl, naphthyl, a 5 to 14 membered bicyclic saturated or partially unsaturated heterocycle, and a 9 to 10 membered bicyclic heteroaryl, wherein the alkyl, alkenyl, alkynyl, cycloalkyls, phenyl, heterocyclyls, heteroaryls and naphthyl are optionally substituted with one or more groups independently selected from halogen, $OR^a$, $NR^bR^c$, oxo, oxide, CN, $C_3$-$C_6$ cycloalkyl, cyclopropylmethyl, a 3 to 7 membered heterocycle, $C_1$-$C_6$ haloalkyl, $C_1$-$C_3$ hydroxyalkyl, $C_1$-$C_4$ acyloxy-$C_1$-$C_2$ alkyl, phenyl and $C_1$-$C_6$ alkyl optionally substituted with one or more groups independently selected from oxo and $OR^d$;

$R^2$ is selected from hydrogen, $C_1$-$C_{12}$ alkyl, $C_2$-$C_{12}$ alkenyl, $C_2$-$C_{12}$ alkynyl, $OR^g$, $C_3$-$C_7$ cycloalkyl, phenyl, a 4 to 7 membered saturated or partially unsaturated heterocyclyl, a 5 to 6 membered heteroaryl, $C_5$-$C_{14}$ bicyclic cycloalkyl, naphthyl, a 5 to 14 membered bicyclic saturated or partially unsaturated heterocyclyl, and a 9 to 10 membered bicyclic heterocyclyl, wherein the alkyl, alkenyl, alkynyl, cycloalkyls, phenyl, heterocyclyls, heteroaryls and naphthyl may be optionally substituted with one to eight groups selected from (a) halogen; (b) CN; (c) oxo; (d) $OR^j$; (e) $SR^k$; (f) $S(O)R^k$; (g) $S(O)_2R^k$; (h) $NR^mR^n$; (i) $C_1$-$C_6$ alkyl optionally substituted with one to six groups selected from halogen; OH; CN; oxo; cyclopropyl; $C_1$-$C_3$ alkoxy optionally substituted with halogen or OH; and phenyl optionally substituted with one to three groups selected from halogen, OH, CN, methyl and methoxy; (j) $C_1$-$C_6$ alkoxy optionally substituted by halogen or OH (k) $C_3$-$C_6$ cycloalkyl optionally substituted with one to three $R^p$ groups; (l) phenyl optionally substituted by one to four $R^q$ groups; (m) a 4 to 7 membered saturated or partially unsaturated heterocyclyl containing one to three heteroatoms selected from N, O and S, wherein the heterocyclyl may be optionally substituted with one to three groups selected from halogen, oxo and $C_1$-$C_3$ alkyl optionally substituted with halogen; (n) a 5 to 6 membered heteroaryl containing one to four heteroatoms selected from N, O and S, wherein the heteroaryl may be optionally substituted by one to three $R^s$ groups; (o) $C_7$-$C_{10}$ bicyclic cycloalkyl optionally substituted with one to three groups selected from halogen and $C_1$-$C_3$ alkyl optionally substituted with halogen; (p) a 9 to 10 membered bicyclic heterocyclyl containing one to three heteroatoms selected from N, O and S, wherein the bicyclic heterocyclyl may be optionally substituted with one to three groups selected from halogen and $C_1$-$C_3$ alkyl optionally substituted with halogen; (q) a 9 to 10 membered bicyclic heteroaryl containing one to four heteroatoms selected from N, O and S, wherein the bicyclic heteroaryl is substituted with one to three groups selected from halogen and $C_1$-$C_3$ alkyl optionally substituted with halogen; and (r) adamantanyl $R^3$ is selected from hydrogen and halogen;
$R^4$ is selected from hydrogen and halogen;
each $R^a$, $R^b$, $R^c$ and $R^d$ are independently selected from hydrogen and $C_1$-$C_6$ alkyl;
each $R^j$ is independently selected from hydrogen, $C_1$-$C_4$ alkyl, cyclopropyl and phenyl, wherein the alkyl and phenyl may be optionally substituted with one to three groups selected from halogen, OH, CN methyl and methoxy;
each $R^k$ is independently selected from $C_1$-$C_4$ alkyl, $C_5$ cycloalkyl, phenyl and benzyl, wherein the phenyl may be optionally substituted with halogen;
each $R^m$ and $R^n$ are independently selected from hydrogen, $C_1$-$C_2$ alkyl and phenyl, wherein the alkyl may be substituted with oxo or phenyl substituted with halogen, and wherein the phenyl may be substituted with halogen;
each $R^p$ is independently selected from halogen, $OR^t$, cyclopropyl and $C_1$-$C_3$ alkyl optionally substituted with halogen;
each $R^q$ is independently selected from halogen, CN, $OR^u$, $SR^u$, $C_3$-$C_6$ cycloalkyl optionally substituted with halogen, $C_1$-$C_3$ alkoxy and $C_1$-$C_3$ alkyl optionally substituted with halogen;
each $R^s$ is independently selected from halogen, CN, $OR^w$, $C_1$-$C_3$ alkyl, $C_3$-$C_6$ cycloalkyl, phenyl and benzyl, wherein the alkyl, cycloalkyl, phenyl and benzyl may be optionally substituted with one to three groups selected from halogen and methyl;
each $R^t$ is independently selected from hydrogen and $C_1$-$C_4$ alkyl optionally substituted with halogen;
each $R^u$ is independently selected from hydrogen and $C_1$-$C_4$ alkyl optionally substituted with halogen; and
each $R^w$ is independently selected from hydrogen and $C_1$-$C_3$ alkyl optionally substituted with halogen.

One embodiment provides compounds of Formula I or a stereoisomer, tautomer or pharmaceutically acceptable salt thereof, wherein:

$X_1$ is selected from CH and N;
$X_2$ is selected from CH and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and OR$^d$; (d) a 3 to 7 membered saturated or partially unsaturated heterocyclyl optionally substituted with one or more groups independently selected from halogen, OR$^a$, oxo, CN, C$_3$-C$_6$ cycloalkyl and C$_1$-C$_3$ alkyl optionally substituted with one or more groups independently selected from halogen and OR$^d$; (e) a 5 to 6 membered heteroaryl optionally substituted with one or more groups independently selected from halogen, OR$^e$, oxide, CN, C$_3$-C$_6$ cycloalkyl and C$_1$-C$_3$ alkyl optionally substituted with one or more groups independently selected from halogen, oxo and OR$^d$; and (f) a 7 to 10 membered bicyclic heterocycle optionally substituted with one or more groups independently selected from halogen, OR$^a$, oxo, CN, C$_3$-C$_6$ cycloalkyl and C$_1$-C$_3$ alkyl optionally substituted with one or more groups independently selected from halogen and OR$^d$;

R$^2$ is selected from (a) hydrogen; (b) C$_1$-C$_{12}$ alkyl optionally substituted by one to eight R$^f$ groups; (c) C$_2$-C$_{12}$ alkenyl optionally substituted by one to eight R$^f$ groups; (d) OR$^g$; (e) C$_3$-C$_7$ cycloalkyl optionally substituted with one to six groups selected from halogen; OH; C$_1$-C$_3$ alkyl optionally substituted with halogen, OH or phenyl optionally substituted with halogen; C(=O)O(C$_1$-C$_3$ alkyl), wherein the alkyl may be optionally substituted with halogen or OH; and phenyl optionally substituted with halogen; (f) phenyl optionally substituted with one to four groups selected from halogen, C$_1$-C$_3$ alkyl optionally substituted with halogen, OH or methoxy, and phenoxy optionally substituted with halogen, OH or methoxy; (g) 4 to 7 membered saturated or partially unsaturated heterocyclyl containing one to three heteroatoms selected from N, O and S, wherein the heterocyclyl may be optionally substituted with one to four R$^h$ groups; (h) a 5 to 6 membered heteroaryl containing one to four heteroatoms selected from N, O and S, wherein the heteroaryl may be optionally substituted with one to four R$^i$ groups; and (i) a 9 to 10 membered bicyclic heterocyclyl containing one to three heteroatoms selected from N, O and S, wherein the heterocyclyl may be optionally substituted with one to four R$^h$ groups;

R$^3$ is selected from hydrogen and halogen;

R$^4$ is selected from hydrogen and halogen;

each R$^a$, R$^b$, R$^c$, R$^d$ and R$^e$ are independently selected from hydrogen and C$_1$-C$_6$ alkyl;

each R$^f$ is independently selected from (a) halogen; (b) CN; (c) oxo; (d) OR$^j$; (e) SR$^k$; (f) S(O)R$^k$; (g) S(O)$_2$R$^k$; (h) NR$^m$R$^n$; (i) C$_3$-C$_6$ cycloalkyl optionally substituted with one to three R$^p$ groups; (j) phenyl optionally substituted by one to four R$^q$ groups; (k) a 4 to 7 membered saturated or partially unsaturated heterocyclyl containing one to three heteroatoms selected from N, O and S, wherein the heterocyclyl may be optionally substituted with one to three groups selected from halogen, oxo and C$_1$-C$_3$ alkyl optionally substituted with halogen; (l) a 5 to 6 membered heteroaryl containing one to four heteroatoms selected from N, O and S, wherein the heteroaryl may be optionally substituted by one to three R$^s$ groups; (m) C$_7$-C$_{10}$ bicyclic cycloalkyl optionally substituted with one to three groups selected from halogen and C$_1$-C$_3$ alkyl optionally substituted with halogen; (n) a 9 to 10 membered bicyclic heterocyclyl containing one to three heteroatoms selected from N, O and S, wherein the bicyclic heterocyclyl may be optionally substituted with one to three groups selected from halogen and C$_1$-C$_3$ alkyl optionally substituted with halogen; (o) a 9 to 10 membered bicyclic heteroaryl containing one to four heteroatoms selected from N, O and S, wherein the bicyclic heteroaryl is substituted with one to three groups selected from halogen and C$_1$-C$_3$ alkyl optionally substituted with halogen; and (p) adamantanyl;

R$^g$ is independently selected from hydrogen, C$_1$-C$_4$ alkyl, C$_3$-C$_6$ cycloalkyl and phenyl, wherein the alkyl, cycloalkyl and phenyl may be optionally substituted with halogen;

each R$^h$ is selected from halogen; OH; C$_1$-C$_3$ alkyl optionally substituted with one to three groups selected from halogen, OH, CN, methoxy, oxo, cyclopropyl and phenyl optionally substituted by one to three groups selected from halogen, CN, methyl and methoxy; C$_1$-C$_3$ alkoxy optionally substituted by halogen or OH; oxo; phenyl optionally substituted with one to three groups selected from halogen, OH, CN, methyl and methoxy; phenoxy wherein the phenoxy optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy;

each R$^i$ is selected from halogen; OH; C$_1$-C$_4$ alkyl optionally substituted with one to three groups selected from halogen, OH, CN, methoxy, oxo, cyclopropyl and phenyl optionally substituted by one to three groups selected from halogen, CN, methyl and methoxy; C$_1$-C$_3$ alkoxy optionally substituted by halogen or OH; phenyl optionally substituted with one to three groups selected from halogen, OH, CN, methyl and methoxy; benzyl optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy;

each R$^j$ is independently selected from hydrogen, C$_1$-C$_4$ alkyl, cyclopropyl and phenyl, wherein the alkyl and phenyl may be optionally substituted with halogen;

each R$^k$ is independently selected from C$_1$-C$_4$ alkyl, C$_5$ cycloalkyl, phenyl and benzyl, wherein the phenyl may be optionally substituted with halogen;

each R$^m$ and R$^n$ are independently selected from hydrogen, C$_1$-C$_2$ alkyl and phenyl, wherein the alkyl may be substituted with oxo or phenyl substituted with halogen, and wherein the phenyl may be substituted with halogen;

each R$^p$ is independently selected from halogen, OR$^t$, cyclopropyl and C$_1$-C$_3$ alkyl optionally substituted with halogen;

each R$^q$ is independently selected from halogen, CN, OR$^u$, SR$^u$, C$_3$-C$_6$ cycloalkyl optionally substituted with halogen, and C$_1$-C$_3$ alkyl optionally substituted with halogen;

each R$^s$ is independently selected from halogen, CN, OR$^w$, C$_1$-C$_3$ alkyl, C$_3$-C$_6$ cycloalkyl, phenyl and benzyl, wherein the alkyl, cycloalkyl, phenyl and benzyl may be optionally substituted with one to three groups selected from halogen and methyl;

each R$^t$ is independently selected from hydrogen and C$_1$-C$_4$ alkyl optionally substituted with halogen;

each R$^u$ is independently selected from hydrogen and C$_1$-C$_4$ alkyl optionally substituted with halogen; and each R$^w$ is independently selected from hydrogen and C$_1$-C$_3$ alkyl optionally substituted with halogen.

In certain embodiments, of Formula I:

R$^1$ is selected from (a) C$_1$-C$_6$ alkyl optionally substituted with OH; (b) 5 to 6 membered heterocyclyl; and (c) 5 to 6 membered heteroaryl substituted with C$_1$-C$_3$ alkyl;

R$^2$ is selected from (a) hydrogen; (b) C$_1$-C$_6$ alkyl optionally substituted by one to seven R$^f$ groups; (c) C$_4$-C$_5$ alkenyl substituted with phenyl; (d) OR$^g$; (e) C$_3$-C$_6$ cycloalkyl optionally substituted with one to four groups selected from C$_1$-C$_3$ alkyl optionally substituted with halogen, OH or phenyl; C(=O)O(C$_1$-C$_3$ alkyl); and phenyl substituted with halogen; (f) phenyl optionally substituted with halogen or phenoxy substituted with halogen or methoxy; (g) a 5 to 6 membered saturated or partially unsaturated heterocyclyl containing one or two heteroatoms selected from N and O, wherein the heterocyclyl may be optionally substituted with one to three R$^h$ groups; (h) a 5 membered heteroaryl containing two heteroatoms selected from N and O, wherein the heteroaryl is substituted with one to three R$^i$ groups; and (i) a 10 membered bicyclic heterocyclyl containing one O heteroatom;

each R$^f$ is independently selected from (a) halogen; (b) CN; (c) oxo; (d) OR$^j$; (e) SR$^k$; (f) S(O)R$^k$; (g) S(O)$_2$R$^k$; (h) NR$^m$R$^n$; (i) C$_3$-C$_6$ cycloalkyl optionally substituted with one or two RP groups; (j) phenyl optionally substituted by one to three R$^q$ groups; (k) a 4 to 7 membered saturated or partially unsaturated heterocyclyl containing one or two heteroatoms selected from N and O, wherein the heterocyclyl may be optionally substituted with one or two groups selected from oxo and C$_1$-C$_3$ alkyl; (l) a 5 to 6 membered heteroaryl containing one to four heteroatoms selected from N and S, wherein the heteroaryl may be optionally substituted by one or two R$^s$ groups; (m) C$_7$ bicyclic cycloalkyl; (n) a 9 to 10 membered bicyclic heterocyclyl containing two O heteroatoms; (o) a 9 membered bicyclic heteroaryl containing one or two N heteroatoms, and wherein the heteroaryl is substituted with halogen or methyl; and (p) adamantanyl R$^g$ is phenyl substituted with methoxy;

each R$^h$ is selected from C$_1$-C$_3$ alkyl optionally substituted with one to three groups selected from halogen, oxo, cyclopropyl and phenyl optionally substituted by two groups selected from halogen, CN and methoxy; oxo; phenyl optionally substituted with halogen; phenoxy optionally substituted with halogen; and a 6 membered heteroaryl containing one N heteroatom, wherein the heteroaryl is substituted by two groups selected from halogen and methoxy;

each R$^i$ is selected from C$_1$-C$_4$ alkyl, phenyl, benzyl, and a 6 membered heteroaryl containing one N heteroatom, wherein the alkyl, phenyl and benzyl may be optionally substituted with halogen;

each R$^j$ is independently selected from hydrogen, C$_1$-C$_4$ alkyl, cyclopropyl and phenyl, wherein the alkyl and phenyl may be optionally substituted with halogen;

each R$^k$ is independently selected from C$_1$-C$_4$ alkyl, C$_5$ cycloalkyl, phenyl and benzyl, wherein the phenyl may be optionally substituted with halogen;

each R$^m$ and R$^n$ are independently selected from hydrogen, C$_1$-C$_2$ alkyl and phenyl, wherein the alkyl may be substituted with oxo or phenyl substituted with halogen, and wherein the phenyl may be substituted with halogen;

each R$^p$ is independently selected from halogen, OR$^t$, cyclopropyl and C$_1$-C$_3$ alkyl optionally substituted with halogen;

each R$^q$ is independently selected from halogen, methyl, CN, CF$_3$, methoxy, ethoxy, difluoromethoxy, trifluoromethoxy, methylthio and C$_3$-C$_4$ cycloalkyl;

each R$^s$ is independently selected from halogen, OH, CN, methoxy, ethoxy, cyclopropyl, benzyl, C$_1$-C$_3$ alkyl optionally substituted with halogen, and phenyl optionally substituted with one or two groups selected from halogen and methyl; and each R$^t$ is independently C$_1$-C$_4$ alkyl optionally substituted with halogen.

In certain embodiments, X$_1$ is CH (such compounds have the structure of Formula II). In certain embodiments, X$_1$ is N (such compounds have the structure of Formula III).

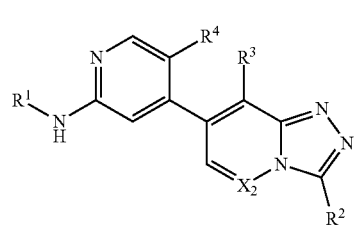

II

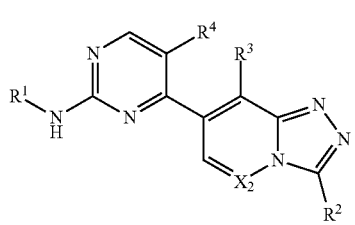

III

In certain embodiments, X$_2$ is CH (such compounds have the structure of Formula IV). In certain embodiments, X$_2$ is N (such compounds have the structure of Formula V).

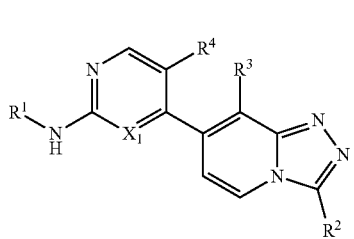

IV

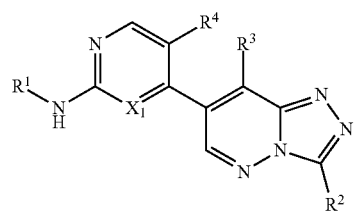

V

In certain embodiments, X$_1$ is CH and X$_2$ is CH (such compounds have the structure of Formula VI). In certain embodiments, X$_1$ is CH and X$_2$ is N (such compounds have the structure of Formula VII). In certain embodiments, X$_1$ is N and X$_2$ is CH (such compounds have the structure of Formula VIII). In certain embodiments, X$_1$ is N and X$_2$ is N (such compounds have the structure of Formula IX).

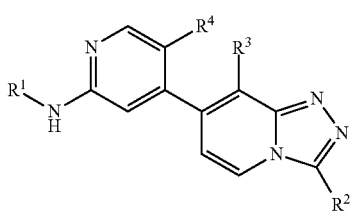

VI

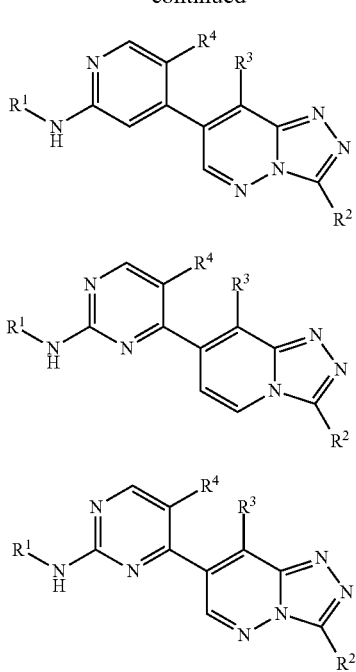

In certain embodiments, $X_1$ is CH and $X_2$ is CH; $X_1$ is CH and $X_2$ is N; or $X_1$ is N and $X_2$ is CH.

International Patent Application Publications WO 2012/118850 (—NH—$R^b$ of Formula I) and WO 2013/020062 (—NH—$R^2$ of Formula I) disclose amines that may be used in the instant application at the $R^1$ position of Formula I, II, III, IV, V, VI, VII, VIII, IX or X.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$; (d) a 3 to 7 membered saturated or partially unsaturated heterocyclyl optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$; and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; wherein each $R^a$, $R^b$, $R^c$, $R^d$ and $R^e$ are independently selected from hydrogen and $C_1$-$C_6$ alkyl.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, wherein the heteroaryl contains one, two, three or four heteroatoms selected from the group consisting of O, N and S, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$; wherein each $R^a$, $R^b$, $R^c$, $R^d$ and $R^e$ are independently selected from hydrogen and $C_1$-$C_6$ alkyl.

In certain embodiments, $R^1$ is selected from (a) $C_1$-$C_6$ alkyl optionally substituted with one to six groups independently selected from halogen, $OR^a$, $NR^bR^c$, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one to four groups independently selected from halogen and $OR^a$, (c) phenyl optionally substituted with one to four groups independently selected from halogen and $C_1$-$C_3$ alkyl, (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl, methoxy, oxo and halogen, wherein the heteroaryl contains one, two, three or four heteroatoms selected from the group consisting of 0, N and S, and (f) a 7 to 10 membered bicyclic heterocycle optionally substituted with one or two groups selected from $C_1$-$C_3$ alkyl and oxo, wherein the heterocycle contains one, two or three heteroatoms selected from the group consisting of O, N, S, S(=O) and S(=O)$_2$; wherein each $R^a$, $R^b$, $R^c$, $R^d$ and $R^e$ are independently selected from hydrogen and $C_1$-$C_6$ alkyl.

In certain embodiments, $R^1$ is selected from optionally substituted $C_1$-$C_{10}$ alkyl; optionally substituted aryl or aryl-$C_1$-$C_6$ alkyl; optionally substituted heteroaryl or heteroaryl-$C_1$-$C_6$ alkyl, wherein said heteroaryl is selected from the group consisting of isoxazole, pyridinyl, pyridone, pyrimidinyl, pyrazinyl, pyrazole, thiazolyl, triazolyl, N—$C_1$-$C_6$ alkyl-pyrazolyl, N-benzylpyrazolyl, N—$C_1$-$C_6$ alkyl triazolyl and 2-oxo-tetrahydroquinolin-6-yl; heterocyclyl or heterocyclyl-$C_1$-$C_6$ alkyl, wherein said heterocyclyl is selected from the group consisting of tetrahydropyranyl, tetrahydrofuranyl, piperidinyl, pyrrolidinyl, morpholinyl, N—$C_1$-$C_6$ alkyl-piperidinyl and N—$C_1$-$C_6$ alkyl-2-oxo-pyrrolidinyl; and $C_3$-$C_7$ cycloalkyl or $C_3$-$C_7$ cycloalkyl-$C_1$-$C_6$ alkyl; wherein the alkyl, aryl, heteroaryl, heterocyclyl and cycloalkyl are optionally substituted with OH, oxo (except not on aromatic rings), halogen, CN, $C_1$-$C_4$ alkyl, $C_1$-$C_4$ hydroxyalkyl, $C_1$-$C_6$ alkoxy, benzyl, phenyl, $C_3$-$C_7$ cycloalkyl, 3 to 6 membered heterocyclyl or 5 to 6 membered heteroaryl, wherein the phenyl, cycloalkyl, heterocyclyl and heteroaryl are optionally substituted with halogen or $C_1$-$C_4$ alkyl.

In certain embodiments, $R^1$ is in the (S) configuration. In certain embodiments, $R^1$ is in the (R) configuration.

In certain embodiments, $R^1$ is selected from methyl, ethyl, isopropyl, tert-butyl, isobutyl, 2-hydroxyethyl, 1-hydroxymethylpropyl, 2-hydroxy-1-methyl-ethyl (or 1-hydroxypropan-2-yl), 2-methoxy-1-methyl-ethyl, 2-hydroxypropyl, 2-hydroxy-1-hydroxymethyl-ethyl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, 1-hydroxy-2,2-dimethylpropan-3-yl, 2-hydroxy-2-methylpropan-1-yl, 1,2-dihydroxypropan-3-yl, oxetan-3-ylmethyl, 2-methyl-1-morpholinopropan-2-yl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 1-methyl-1H-1,2,4-triazol-5-yl, 5-chloropyrazin-2-yl, 1,3-dimethyl-1H-pyrazol-4-yl, oxetan-3-yl, 1,3,5-trimethyl-1H-pyrazol-4-yl, 3-cyclopropyl-1-methyl-1H-pyrazol-5-yl, 1-methyl-1H-tetrazol-5-yl, 2-methyl-2H-tetrazol-5-yl, 5-methyl-1,3,4-thiadizol-2-yl, 3-methyloxetan-3-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopropyl, cyclobutyl, cyclopentyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl. In another embodiment, $R^1$ is selected from (S)-2-hydroxy-1-methyl-ethyl, (S)-1-hydroxymethyl-propyl, (1S,3S)-3-hydroxycyclopentyl and tetrahydropyran-4-yl. In another embodiment, $R^1$ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl. In certain embodiments, $R^1$ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

In certain embodiments, $R^1$ is selected from methyl, ethyl, isopropyl, tert-butyl, isobutyl, 2-hydroxyethyl, 1-hydroxymethylpropyl, 2-hydroxy-1-methyl-ethyl (or 1-hydroxypropan-2-yl), 2-methoxy-1-methyl-ethyl, 2-hydroxypropyl, 2-hydroxy-1-hydroxymethyl-ethyl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 1-methyl-1H-1,2,4-triazol-5-yl, 5-chloropyrazin-2-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopentyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl. In another embodiment, $R^1$ is selected from (S)-2-hydroxy-1-methyl-ethyl, (S)-1-hydroxymethyl-propyl, (1S,3S)-3-hydroxycyclopentyl and tetrahydropyran-4-yl. In another embodiment, $R^1$ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl. In certain embodiments, $R^1$ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl, oxetanyl, piperidinyl, N—$C_1$-$C_6$ alkyl-piperidinyl and N—$C_1$-$C_6$ alkyl-2-oxo-pyrrolidinyl, and wherein said heterocycle or heterocyclyl-$C_1$-$C_6$ alkyl is optionally substituted by 1 to 3 groups independently selected from $C_1$-$C_6$ alkyl, $C_1$-$C_6$ haloalkyl, $C_1$-$C_4$ acyloxy-$C_1$-$C_2$ alkyl, halogen, hydroxyl, phenyl, $C_1$-$C_3$ hydroxyalkyl and oxo; (d) $C_3$-$C_7$ cycloalkyl or $C_3$-$C_7$ cycloalkyl-$C_1$-$C_6$ alkyl, wherein said cycloalkyl is optionally substituted by hydroxyl or halo; and (e) $C_1$-$C_6$ heteroalkyl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl, oxetanyl, piperidinyl, N—$C_1$-$C_6$ alkyl-piperidinyl and N—$C_1$-$C_6$ alkyl-2-oxo-pyrrolidinyl, and wherein said heterocycle or heterocyclyl-$C_1$-$C_6$ alkyl is optionally substituted by 1 to 3 groups independently selected from $C_1$-$C_6$ alkyl, $C_1$-$C_4$ acyloxy-$C_1$-$C_2$ alkyl, halogen, and $C_1$-$C_3$ hydroxyalkyl; (d) $C_3$-$C_7$ cycloalkyl or $C_3$-$C_7$ cycloalkyl-$C_1$-$C_6$ alkyl, wherein said cycloalkyl is optionally substituted by hydroxyl or halo; and (e) $C_1$-$C_6$ heteroalkyl.

In certain embodiments, each $R^a$ is independently selected from hydrogen and $C_1$-$C_6$ alkyl. In certain embodiments, each $R^a$ is independently selected from hydrogen and $C_1$-$C_3$ alkyl. In certain embodiments, each $R^a$ is independently selected from hydrogen and methyl.

In certain embodiments, each $R^b$ and $R^c$ are independently selected from hydrogen and $C_1$-$C_6$ alkyl. In certain embodiments, each $R^b$ and $R^c$ are independently selected from hydrogen and $C_1$-$C_3$ alkyl. In certain embodiments, each $R^b$ and $R^c$ are independently selected from hydrogen and methyl.

In certain embodiments, each $R^d$ is independently selected from hydrogen and $C_1$-$C_6$ alkyl. In certain embodiments, each $R^d$ is independently selected from hydrogen and $C_1$-$C_3$ alkyl. In certain embodiments, each $R^d$ is selected from hydrogen and methyl.

In certain embodiments, each $R^e$ is independently selected from hydrogen and $C_1$-$C_6$ alkyl. In certain embodiments, each $R^e$ is independently selected from hydrogen and $C_1$-$C_3$ alkyl. In certain embodiments, each $R^e$ is independently selected from methyl and ethyl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 1-hydroxy-2,2-dimethylpropan-3-yl, 2-hydroxy-2-methylpropan-1-yl, 1,2-dihydroxypropan-3-yl, 2-methyl-1-morpholinopropan-2-yl, cyclopropylmethyl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 3-methyloxetan-3-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methyl-1,2,3-triazol-4-yl, 1-methyl-1,2,4-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 3-cyclopropyl-1-methyl-1H-pyrazol-5-yl, 2-methyl-2H-tetrazol-5-yl, 5-methyl-1,3,4-thiadizol-2-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methyl-1,2,3-triazol-4-yl, 1-methyl-1,2,4-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl and oxetanyl and wherein said heterocycle is optionally substituted by C₁-C₆ alkyl, halogen, C₁-C₃ hydroxyalkyl or C₁-C₄ acyloxy-C₁-C₂ alkyl; (d) C₃-C₇ cycloalkyl or C₃-C₇ cycloalkyl-C₁-C₆ alkyl, wherein said cycloalkyl is optionally substituted by hydroxyl; and (e) C₁-C₆ heteroalkyl.

In certain embodiments, $R^1$ is selected from the group consisting of (a) tetrahydropyranyl; (b) tetrahydrofuranyl; (c) oxetanyl; (d) 2-hydroxy-1-methyl-ethan-1-yl; (e) 2,2,2-trifluoro-1-methyl-ethan-1-yl; (f) 1-cyclopropyl-ethan-1-yl; (g) 2-methoxyethyl; (h) 3-fluoropropyl; (i) cyclopropylmethyl; (j) oxetanylmethyl; (k) 4-hydroxycyclohexyl; and (l) pyrazolyl;

wherein said (a) tetrahydropyranyl, (b) tetrahydrofuranyl and (c) oxetanyl are optionally substituted with one to three groups independently selected from C₁-C₆ alkyl, C₁-C₆ haloalkyl, C₁-C₄ acyloxy-C₁-C₂ alkyl, C₁-C₃ hydroxyalkyl and halogen; and wherein said (l) pyrazolyl moiety is optionally substituted with one to three groups independently selected from C₁-C₆ alkyl, C₁-C₆ haloalkyl and halogen.

In certain embodiments, $R^1$ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydro-2H-pyran-4-yl, 3-fluorotetrahydropyran-4-yl, 2-(hydroxymethyl) tetrahydropyran-4-yl, (4-tetrahydro-2H-pyran-2-yl)methyl acetate, tetrahydrofuran-3-yl, 3-methyloxetan-3-yl, oxetanyl-3-ylmethyl, 2-methoxyethyl, 1-methyl-1H-pyrazol-5-yl, 1-methyl-1H-pyrazol-4-yl, 2-methylpyrazol-3-yl, 2,5-dimethylpyrazol-3-yl, 1,3-dimethylpyrazol-4-yl, 2-methyl-2H-1,2,3-triazol-4-yl and 1-methyl-1H-1,2,4-triazol-5-yl.

In certain embodiments, $R^1$ is selected from (a) C₁-C₆ alkyl optionally substituted with OH; (b) 5 to 6 membered heterocyclyl; and (c) 5 to 6 membered heteroaryl substituted with C₁-C₃ alkyl. In certain embodiments, $R^1$ is selected from C₁-C₆ alkyl optionally substituted with OH, 5 to 6 membered heterocyclyl containing one O heteroatom, and 5 to 6 membered heteroaryl containing two or three N heteroatoms, wherein the heteroaryl is substituted with C₁-C₃ alkyl. In certain embodiments, $R^1$ is selected from C₁-C₆ alkyl optionally substituted with OH, 5 to 6 membered heterocyclyl selected from tetrahydropyranyl, and 5 to 6 membered heteroaryl selected from pyrazolyl and triazolyl, wherein the heteroaryl is substituted with C₁-C₃ alkyl. In certain embodiments, $R^1$ is selected from isopropyl, 1-hydroxypropan-2-yl, 1-methyl-1H-pyrazol-5-yl, 1-methyl-1H-pyrazol-4-yl, tetrahydro-2H-pyran-4-yl, 2-methyl-2H-1,2,3-triazol-4-yl and 1-methyl-1H-1,2,4-triazol-5-yl. In certain embodiments, $R^1$ is selected from 1-methyl-1H-pyrazol-5-yl, 1-methyl-1H-pyrazol-4-yl and tetrahydro-2H-pyran-4-yl.

In certain embodiments, $R^2$ is selected from (a) hydrogen; (b) C₁-C₁₂ alkyl optionally substituted by one to eight $R^f$ groups; (c) C₂-C₁₂ alkenyl optionally substituted by one to eight $R^f$ groups; (d) $OR^g$; (e) C₃-C₇ cycloalkyl optionally substituted with one to six groups selected from halogen; OH; C₁-C₃ alkyl optionally substituted with halogen, OH or phenyl optionally substituted with halogen; C(=O)O(C₁-C₃ alkyl), wherein the alkyl may be optionally substituted with halogen or OH; and phenyl optionally substituted with halogen; (f) phenyl optionally substituted with one to four groups selected from halogen, C₁-C₃ alkyl optionally substituted with halogen, OH or methoxy, and phenoxy optionally substituted with halogen, OH or methoxy; (g) 4 to 7 membered saturated or partially unsaturated heterocyclyl containing one to three heteroatoms selected from N, O and S, wherein the heterocyclyl may be optionally substituted with one to four $R^h$ groups; (h) a 5 to 6 membered heteroaryl containing one to four heteroatoms selected from N, O and S, wherein the heteroaryl may be optionally substituted with one to four $R^i$ groups; and (i) a 9 to 10 membered bicyclic heterocyclyl containing one to three heteroatoms selected from N, O and S, wherein the heterocyclyl may be optionally substituted with one to four $R^h$ groups.

In certain embodiments, $R^2$ is selected from (a) hydrogen; (b) C₁-C₆ alkyl optionally substituted by one to seven $R^f$ groups; (c) C₄-C₅ alkenyl substituted with phenyl; (d) $OR^g$; (e) C₃-C₆ cycloalkyl optionally substituted with one to four groups selected from C₁-C₃ alkyl optionally substituted with halogen, OH or phenyl; C(=O)O(C₁-C₃ alkyl); and phenyl substituted with halogen; (f) phenyl optionally substituted with halogen or phenoxy substituted with halogen or methoxy; (g) a 5 to 6 membered saturated or partially unsaturated heterocyclyl containing one or two heteroatoms selected from N and O, wherein the heterocyclyl may be optionally substituted with one to three $R^h$ groups; (h) a 5 membered heteroaryl containing two heteroatoms selected from N and O, wherein the heteroaryl is substituted with one to three R' groups; and (i) a 10 membered bicyclic heterocyclyl containing one O heteroatom.

In certain embodiments, $R^2$ is selected from hydrogen, methyl, ethyl, 2-methylbutyl, 2,3-dimethylbutyl, 2,2-dimethylbutyl, 2-ethylbutyl, 3-methylpentyl, 2-methylpentyl, isopentyl, neopentyl, isobutyl, 3,3-dimethylbutyl, butyl, propyl, trifluoromethyl, 4-methylpentyl, 3-methylbutan-2-yl, 2-fluorobutyl, 4,4,4-trifluoro-2-methylbutyl, 3,3,3-trifluoro-2-methylpropyl, 2,2,2-trifluoroethyl, 3,3,3-trifluoropropyl, 2-fluoro-2-methylpropyl, 3,3,3-trifluoro-2-(trifluoromethyl) propyl, 1,1-difluoroprop yl, 3-fluoro-3-methylbutyl, 2,2-difluoropropyl, 2-(trifluoromethyl)butyl, 3-fluoro-2-(fluoromethyl)propyl, 2-cyano-2-methylpropyl, 1-oxoethyl, 1-hydroxy-3-methylbutyl, 2-methoxy-3-methylbutyl, 2-ethoxybutyl, phenoxymethyl, (4-fluorophenoxy)methyl, 3-methoxy-2-methylpropyl, 3,3,3-trifluoro-2-methoxypropyl, 2-ethoxy-3,3,3-trifluoropropyl, 2-ethoxyethyl, 1-(tert-butoxy)ethyl, 1-hydroxybutyl, tert-butoxymethyl, 3,3,3-trifluoro-2-hydroxy-2-(trifluoromethyl)propyl, isopropoxymethyl, 2-methoxyethyl, isobutoxymethyl, 1-hydroxy-2-methylpropyl, methoxymethyl, 2-hydroxy-2-methylpropyl, 2-hydroxyethyl, 1-hydroxy-2-methylbutyl, 1-methoxy-2-methylpropyl, 2-methoxybutyl, 2-hydroxy-3-methylbutyl, 2-hydroxybutyl, 2-methoxypropyl, 3-hydroxy-2-methylpropyl, 2-methoxy-2-methylpropyl, 3,3,4,4,4-pentafluoro-2-(hydroxy)butyl, 3,3,3-trifluoro-2-(hydroxy) propyl, 2-(2-fluoroethoxy)propyl, 2-(cyclopropylmethoxy) propyl, 5,5,5-trifluoro-2-hydroxypentyl, 5,5,5-trifluoro-2-methoxypentyl, (benzylthio)methyl, 2-(methylthio)butyl, 2-(methylthio)ethyl, 2-(methylthio)propyl, (phenylthio)methyl, 2-(phenylthio)ethyl, ((4-fluorophenyl)thio)methyl, ((2-fluorophenyl)thio)methyl, (isopropylthio)methyl, (tert-butylthio)methyl, (isobutylthio)methyl, (cyclopentylthio)methyl, (phenylsulfinyl)methyl, (phenylsulfonyl)methyl, 2-(phenylsulfonyl)ethyl, (dimethylamino)methyl, 2-((4-fluorophenyl)amino)-2-oxoethyl, (diethylamino)methyl, 2-(2,4-difluoro-N-methylbenzamido)ethyl, (methylamino) oxomethyl, 2-acetamido-3,3,3-trifluoropropyl, cyclohexyl (hydroxyl)methyl, (1-methoxycyclobutyl)methyl, (1-methoxycyclopropyl)methyl, (1-(2-fluoroethoxy)cyclopropyl)methyl, [1,1'-bi(cyclopropan)]-1-ylmethyl, (1-ethyl cyclobutyl)methyl, (1-(trifluoromethyl)cyclopropyl)methyl, (1-isopropylcyclopropyl)methyl, (1-ethylcyclopropyl) methyl, (1-methylcyclopropyl)methyl, (2,2-difluorocyclopropyl)methyl, cyclopentylmethyl, cyclohexylmethyl, (1-(trifluoromethyl)cyclobutylmethyl, cyclopropylethyl, (4-methylcyclohexyl)methyl, cyclopropylmethyl, cyclobutylmethyl, (3,3-difluorocyclobutyl)methyl, 2-cyclopropyl-2- methylpropyl, 2-cyclopropylpropyl, (4,4-difluorocyclohexyl)methyl, (1-isobutoxycyclopropyl)methyl, (1-isopropoxycyclopropyl)methyl, 2-cyclopropyl-2-methoxyethyl, 2-cyclopentylethyl, 2-cyclohexylethyl, 3-cyclopropyl-2-hydroxypropyl, 2-cyclopropyl-2-hydroxyethyl, (1-ethoxycyclobutyl)methyl, 2-cyclopropyl-3,3,3-trifluoropropyl, 3-cyclopropyl-2-methoxypropyl, 4-cyclopropyl-2-methoxybutyl, 2-cyclopropyl-2-fluoroethyl, 2-cyclopentyl-3,3,3-trifluoropropyl, 3-cyclopropyl-2-fluoropropyl, 2-cyclopropyl-2-hydroxypropyl, 3-cyclopentyl-2-methoxypropyl, benzyl, 2-fluorobenzyl, 2-chlorobenzyl, 2-methoxybenzyl, 2-(trifluoromethyl)benzyl, 2-methylbenzyl, 3-bromobenzyl, 3-chlorobenzyl, 3-fluorobenzyl, 3-cyclopropylbenzyl, 3-cyclobutylbenzyl, 3-(trifluoromethyl)benzyl, 3-methoxybenzyl, 3-(difluoromethoxy)benzyl, 3-(trifluoromethoxy)benzyl, 3-cyanobenzyl, 4-chlorobenzyl, 4-fluorobenzyl, 4-(trifluoromethyl)benzyl, 4-methoxybenzyl, 4-(difluoromethoxy)benzyl, 4-(methylthio)benzyl, 4-methylbenzyl, 4-(trifluoromethoxy)benzyl, 4-ethoxybenzyl, 2,3-difluorobenzyl, 2,3-dichlorobenzyl, 2-fluoro-4-methoxybenzyl, 2-chloro-4-fluorobenzyl, 2,4-dichlorobenzyl, 2,4-difluorobenzyl, 2-fluoro-4-(trifluoromethyl)benzyl, 2,5-difluorobenzyl, 2-chloro-6-fluorobenzyl, 2,6-difluorobenzyl, 3-fluoro-4-methoxybenzyl, 3-fluoro-4-(trifluoromethoxy)benzyl, 3,4-difluorobenzyl, 3-chloro-4-fluorobenzyl, 3-chloro-4-methoxybenzyl, 3-chloro-5-fluorobenzyl, 3-fluoro-5-(trifluoromethyl)benzyl, 3,5-difluorobenzyl, 3,5-difluorobenzyl, 4-chloro-2-fluorobenzyl, 4-(difluoromethoxy)-2-fluorobenzyl, 4-chloro-3-fluorobenzyl, 4-fluoro-3-methoxybenzyl, 2,3-difluoro-4-methoxybenzyl, 2,3,4-trifluorobenzyl, 2,4,5-trifluorobenzyl, 3,5-difluoro-4-methoxybenzyl, 4-ethoxy-2,3-difluorobenzyl, (3-chlorophenyl)(hydroxy)methyl, (4-chlorophenyl)(methoxy)methyl, 3-hydroxy-1-(4-methoxyphenyl)-2-methylpropyl, 3-hydroxy-1-(4-methoxyphenyl)propyl, phenethyl, 3-chlorophenethyl, 4-chlorophenethyl, 1-(4-chlorophenyl)ethyl, 2-(4-fluorophenyl)-1-hydroxy-2-methylpropyl, 1-hydroxy-2-phenylethyl, 2-(4-fluorophenyl)-1-hydroxyethyl, 1-methoxy-2-phenylethyl, 1-(3-fluoro-4-methoxyphenyl)-3-hydroxypropan-2-yl, 1-(4-chlorophenyl)-2-methylpropyl, 1-phenylethyl, 2-(4-chlorophenyl)propan-2-yl, methoxy(phenyl)methyl, (4-chlorophenyl)difluoromethyl, 1-methoxy-1-phenylethyl, difluoro(3-fluoro-4-methoxyphenyl)methyl, 3-fluoro-4-methoxyphenethyl, 2-amino-1-phenethyl, 1-(4-chloro-3-fluorophenyl)-2-(hydroxy)ethyl, 1-(3-fluoro-4-methoxyphenyl)-2-(hydroxy)ethyl, (dimethylamino)(4-fluorophenyl)methyl, 2-chlorophenethyl, 2-(4-fluorophenyl)-2-methylpropyl, 2-(4-methoxyphenyl)-2-methylpropyl, 2-acetamido-2-phenylethyl, 2-acetamido-2-(3-chloro-4-fluorophenyl)ethyl, 2-methoxy-2-(4-methoxyphenyl)ethyl, 3,3,3-trifluoro-2-(4-methoxyphenyl)propyl, 3,3,3-trifluoro-2-(4-fluorophenyl)propyl, 2-(4-chlorophenyl)-2-methoxyethyl, 2-(4-chlorophenyl)-2-hydroxyethyl, 3,3,3-trifluoro-2-(4-methoxyphenyl)propyl, 2-hydroxy-2-(4-methoxyphenyl)ethyl, 2-(4-methoxyphenyl)-2-oxoethyl, phenyl(piperidin-1-yl)methyl, (tetrahydropyran-2-yl)methyl, (tetrahydrofuran-2-yl)methyl, piperdin-1-ylmethyl, (tetrahydropyran-4-yl)methyl, (tetrahydrofuran-3yl)methyl, morpholinomethyl, (5,5-dimethyltetrahydrofuran-2-yl)methyl, (6,6-dimethyltetrahydropyran-2-yl)methyl, (tetrahydropyran-3-yl)methyl, (3-ethyloxetan-3-yl)methyl, (4-methoxyphenyl)(morpholino)methyl, (1-methyl-6-oxo-1,6-dihydropyridin-3-yl)methyl, pyrrolidin-1-ylmethyl, (1-methyl-6-oxo-1,6-dihydropyridin-3-yl)methyl, azepan-1-ylmethyl, (2-methylpiperidin-1-yl)methyl, pyrrolidine-1-carbonyl, (4,4-dimethyltetrahydrofuran-2-yl)methyl, (2-oxopyrrolidin-1-yl)methyl, (1-methyl-2-oxo-1,2-dihydropyridin-4-yl)methyl, thiophen-2-ylmethyl, pyridin-3-ylmethyl, pyrimidin-2-ylmethyl, pyrimidin-5-ylmethyl, pyridin-4-ylmethyl, thiazol-2-ylmethyl, pyrazin-2-ylmethyl, pyridin-2-ylmethyl, (1-methylpyrazol-3-yl)methyl, (1-methylpyrazol-4-yl)methyl, (1-methylimidazol-2-yl)methyl, (1-benzylimidazol-2-yl)methyl, (1-(2-fluoro-4-methylphenyl)-1,2,3-triazol-5-yl)methyl, (1-methylpyrazol-4-yl)(phenyl)methyl, (1-cyclopropyl-3,5-dimethylpyrazol-4-yl)methyl, (1,3-dimethylpyrazol-5-yl)methyl, (2-methoxypyridin-3-yl)methyl, (2-chloropyridin-3-yl)methyl, (2-hydroxypyridin-3-yl)methyl, (2-methylpyridin-3-yl)methyl, (3-chloropyridin-2-yl)methyl, (3-cyclopropylpyrazol-1-yl)methyl, (4-cyclopropylpyridin-2-yl)methyl, (4-methylpyridin-2-yl)methyl, (4-methylthiazol-2-yl)methyl, (4-isopropyl-5-methylthiazol-2-yl)methyl, (4-(trifluoromethyl)pyridin-2-yl)methyl, (4-isopropylpyridin-2-yl)methyl, (4-cyclopropyl-6-methylpyridin-2-yl)methyl, (4-cyclopropyl-3-fluoropyridin-2-yl)methyl, (4-bromopyridin-2-yl)methyl, (4-methoxypyridin-2-yl)methyl, (4-(trifluoromethyl)pyrazol-1-yl)methyl, (4-ethoxypyridin-2-yl)methyl, (5-bromopyridin-3-yl)methyl, (5-chloropyridin-3-yl)methyl, (5-fluoropyridin-3-yl)methyl, (5-cyclopropylpyridin-3-yl)methyl, (5-methylpyridin-3-yl)methyl, (5-chloropyridin-2-yl)methyl, (5-methylthiazol-2-yl)methyl, (5-cyclopropyl-2-hydroxypyridin-3-yl)methyl, (5-cyclopropyl-2-methoxypyridin-3-yl)methyl, (5-chlorothiophen-2-yl)methyl, (5-cyclopropylthiophen-2-yl)methyl, (5-cyanothiophen-2-yl)methyl, (6-chloropyridin-2-yl)methyl, (6-methoxypyridin-2-yl)methyl, (6-isopropylpyridin-2-yl)methyl, (6-cyclopropylpyridin-2-yl)methyl, (6-methylpyridin-2-yl)methyl, (6-methoxypyridin-3-yl)methyl, (6-(trifluoromethyl)pyridin-2-yl)methyl, (6-phenylpyridin-2-yl)methyl, (6-chloropyridin-3-yl)methyl, (6-hydroxypyridin-2-yl)methyl, (6-cyanopyridin-2-yl)methyl, (6-ethoxypyridin-3-yl)methyl, (6-hydroxypyridin-3-yl)methyl, (6-chloro-4-methoxypyridin-2-yl)methyl, 2-(pyridin-2-yl)ethyl, 2-(pyridin-3-yl)ethyl, 2-(pyridin-4-yl)ethyl, 2-(4-(p-tolyl)-1,2,3-triazol-1-yl)ethyl, 2-(5-(p-tolyl)-1,2,3-triazol-1-yl)ethyl, 2-(3-methyl-1-phenyl-1,2,4-triazol-5-yl)ethyl, 2-(1-(p-tolyl)tetrazol-5-yl)ethyl, 2-amino-2-(3-chloro-4-fluorophenyl)ethyl, 2-(3-cyclopropylpyrazol-1-yl)ethyl, 2-(4-(trifluoromethyl)pyrazol-1-yl)ethyl, 2-(5-chlorothiophen-2-yl)-2-methoxyethyl, bicyclo[2.2.1]heptan-2-ylmethyl, (2,3-dihydrobenzo[b][1,4]dioxin-6-yl)methyl, benzo[d][1,3]dioxol-5-ylmethyl, (5-fluoroindol-3-yl)methyl, (6-fluoroindol-3-yl)methyl, (6-methylimidazo[1,2-a]pyridin-3-yl)methyl, adamantan-1-ylmethyl, 3-methyl-1-phenylbut-1-en-1-yl, but-1-en-1-yl, 4-methoxyphenoxy, 2-(2-fluoropropan-2-yl)cyclopropyl, cyclohexyl, 2,2-dimethylcyclopropyl, 2-(ethoxycarbonyl)cyclopropyl, 2-(2-hydroxypropan-2-yl)cyclopropyl, 2-(trifluoromethyl)cyclobutyl, 2-methylcyclopropyl, 1-(4-chlorophenyl)cyclopropyl, 1-(4-chlorophenyl)cyclobutyl, 1-(4-chlorophenyl)cyclopentyl, 2,2,3,3-tetramethylcyclopropyl, 2-phenylcyclopropyl, 2-benzylcyclopropyl, phenyl, 2-chlorophenyl, 2-fluorophenyl, 2-(4-methoxyphenoxy)phenyl, 3-chlorophenyl, 3-fluorophenyl, 4-chlorophenyl, 2-chloro-4-fluorophenyl, 2-(4-fluorophenoxy)phenyl, 4-(2-fluoro-6-methoxybenzyl)morpholin-2-yl, 1-(2-fluoro-6-methoxybenzyl)piperidin-3-yl, 5-(2,6-difluorophenoxy)-1-methylpiperidin-3-yl, (5-chloro-2-fluorobenzyl)piperidin-3-yl, piperdin-3-yl, ((5-fluoro-2-methoxypyridin-3-yl)methyl)piperidin-3-yl, 1-(5-cyano-2-fluorobenzyl)piperidin-3-yl, 1-methyl-5-oxo-3-phenylpyrrolidin-2-yl, 4-(cyclopropylmethyl)morpholin-2-yl, 4-(2-fluoro-6-methoxybenzoyl)morpholin-2-yl, 4-(2,6-difluorobenzoyl)morpholin-2-yl, 4-(3,3,3-trifluoropropyl)morpholin-2-yl, 4-(3-fluorophenyl)pyrrolidin-3-yl, 4-phenylpyrrolidin-3-yl, 1-benzyl-4-(3-fluorophenyl)pyrrolidin-3-yl, 4-(4-chloro-3-fluorophenyl)pyrrolidin-3-yl, morpholin-2-yl, 1-phenyl-1H-pyrazol-5-yl, 1-methyl-3-(pyridin-3-yl)-1H-pyrazol-4-yl, 3-phenyl-1H-pyrazol-4-yl, 3-isopropyl-1-methyl-1H-pyrazol-4-yl, 3-methyl-5-phenylisoxazol-4-yl, 3-isobutyl-1-methyl-1H-pyrazol-4-yl, 5-isobutyl-1-methyl-1H-pyrazol-4-yl, 5-isopropyl-1-methyl-1H-pyrazol-4-yl, 1-(3-fluorophenyl)-1H-pyrazol-5-yl, 1-(3-fluorophenyl)-5-methyl-1H-pyrazol-3-yl, 1-(3-fluorophenyl)-3-methyl-1H-pyrazol-5-yl, 1-(3-fluorophenyl)-3-(trifluoromethyl)-1H-pyrazol-5-yl, 1-(3-chlorophenyl)-3-(trifluoromethyl)-1H-pyrazol-5-yl, 1-(4-fluorophenyl)-3-methyl-1H-pyrazol-5-yl, 1-(4-fluorophenyl)-5-methyl-1H-pyrazol-3-yl, 1-(4-fluorophenyl)-1H-pyrazol-5-yl, 1-(4-fluorophenyl)-1H-pyrazol-3-yl, 3-(3-chlorophenyl)-1,5-dimethyl-1H-pyrazol-4-yl, 3-(3-fluorophenyl)-1,5-dimethyl-1H-pyrazol-4-yl, 3-(3-fluorobenzyl)-1-methyl-1H-pyrazol-4-yl, 3-(3-fluorophenyl)-1-methyl-1H-pyrazol-4-yl, 3-(4-fluorophenyl)-1-methyl-1H-pyrazol-4-yl, 3-(4-chlorophenyl)-1-methyl-1H-pyrazol-4-yl, 3-(4-fluorobenzyl)-1-methyl-1H-pyrazol-4-yl, 3-(3,4-difluorophenyl)-1-methyl-1H-pyrazol-4-yl, 4-(3-chlorophenyl)-1-methyl-1H-pyrazol-5-yl, 4-(3-chlorophenyl)-1-methyl-1H-pyrazol-3-yl, 4-(3-chlorophenyl)-1,3-dimethyl-1H-pyrazol-5-yl, 4-(4-chlorophenyl)-1-methyl-1H-pyrazol-5-yl, 4-(4-chlorophenyl)-1-methyl-1H-pyrazol-3-yl, 4-(4-chlorophenyl)-1,3-dimethyl-1H-pyrazol-5-yl, 5-(3-fluorophenyl)-1-methyl-1H-pyrazol-4-yl, 5-(3-fluorobenzyl)-1-methyl-1H-pyrazol-4-yl, 5-(3-chlorophenyl)-1,3-dimethyl-1H-pyrazol-4-yl, 5-(4-fluorobenzyl)-1-methyl-1H-pyrazol-4-yl, 5-(4-fluorophenyl)-1-methyl-1H-pyrazol-4-yl, 5-(4-chlorophenyl)-1-methyl-1H-pyrazol-4-yl, 5-(4-chloro-3-fluorophenyl)-1,3-dimethyl-1H-pyrazol-4-yl, 5-(4-chlorophenyl)-1,3-dimethyl-1H-pyrazol-4-yl, 5-(3,4-difluorophenyl)-1-methyl-1H-pyrazol-4-yl, 5-(3,4-difluorophenyl)-1,3-dimethyl-1H-pyrazol-4-yl, 1,5-dimethyl-3-phenyl-1H-pyrazol-4-yl and isochroman-1-yl.

In certain embodiments, $R^2$ is hydrogen.

In certain embodiments, $R^2$ is $C_1$-$C_{12}$ alkyl optionally substituted by one to eight $R^f$ groups. In certain embodiments, $R^2$ is $C_1$-$C_{12}$ alkyl optionally substituted by one to seven $R^f$ groups. In certain embodiments, $R^2$ is $C_1$-$C_{12}$ alkyl. In certain embodiments, $R^2$ is $C_1$-$C_{10}$ alkyl optionally substituted by one to eight $R^f$ groups. In certain embodiments, $R^2$ is $C_1$-$C_{10}$ alkyl optionally substituted by one to seven $R^f$ groups. In certain embodiments, $R^2$ is $C_1$-$C_{10}$ alkyl. In certain embodiments, $R^2$ is $C_1$-$C_8$ alkyl optionally substituted by one to eight $R^f$ groups. In certain embodiments, $R^2$ is $C_1$-$C_8$ alkyl optionally substituted by one to seven $R^f$ groups. In certain embodiments, $R^2$ is $C_1$-$C_8$ alkyl. In certain embodiments, $R^2$ is $C_1$-$C_6$ alkyl optionally substituted by one to eight $R^f$ groups. In certain embodiments, $R^2$ is $C_1$-$C_6$ alkyl optionally substituted by one to seven $R^f$ groups. In certain embodiments, $R^2$ is $C_1$-$C_6$ alkyl.

In certain embodiments, each $R^f$ is independently selected from (a) halogen; (b) CN; (c) oxo; (d) $OR^j$; (e) $SR^k$; (f) $S(O)R^k$; (g) $S(O)_2R^k$; (h) $NR^mR^n$; (i) $C_3$-$C_6$ cycloalkyl optionally substituted with one to three $R^p$ groups; (j) phenyl optionally substituted by one to four $R^q$ groups; (k) a 4 to 7 membered saturated or partially unsaturated heterocyclyl containing one to three heteroatoms selected from N, O and S, wherein the heterocyclyl may be optionally substituted with one to three groups selected from halogen, oxo and $C_1$-$C_3$ alkyl optionally substituted with halogen; (l) a 5 to 6 membered heteroaryl containing one to four heteroatoms selected from N, O and S, wherein the heteroaryl may be optionally substituted by one to three $R^s$ groups; (m) $C_7$-$C_{10}$ bicyclic cycloalkyl optionally substituted with one to three groups selected from halogen and $C_1$-$C_3$ alkyl optionally substituted with halogen; (n) a 9 to 10 membered bicyclic heterocyclyl containing one to three heteroatoms selected from N, O and S, wherein the bicyclic heterocyclyl may be optionally substituted with one to three groups selected from halogen and $C_1$-$C_3$ alkyl optionally substituted with halogen; (o) a 9 to 10 membered bicyclic heteroaryl containing one to four heteroatoms selected from N, O and S, wherein the bicyclic heteroaryl is substituted with one to three groups selected from halogen and $C_1$-$C_3$ alkyl optionally substituted with halogen; and (p) adamantanyl.

In certain embodiments, each $R^f$ is independently selected from (a) halogen; (b) CN; (c) oxo; (d) $OR^j$; (e) $SR^k$; (f) $S(O)R^k$; (g) $S(O)_2R^k$; (h) $NR^mR^n$; (i) $C_3$-$C_6$ cycloalkyl optionally substituted with one or two $R^p$ groups; (j) phenyl optionally substituted by one to three $R^q$ groups; (k) a 4 to 7 membered saturated or partially unsaturated heterocyclyl containing one or two heteroatoms selected from N and O, wherein the heterocyclyl may be optionally substituted with one or two groups selected from oxo and $C_1$-$C_3$ alkyl; (l) a 5 to 6 membered heteroaryl containing one to four heteroatoms selected from N and S, wherein the heteroaryl may be optionally substituted by one or two $R^s$ groups; (m) $C_7$ bicyclic cycloalkyl; (n) a 9 to 10 membered bicyclic heterocyclyl containing two O heteroatoms; (o) a 9 membered bicyclic heteroaryl containing one or two N heteroatoms, and wherein the heteroaryl is substituted with halogen or methyl; and (p) adamantanyl.

In certain embodiments, each $R^j$ is independently selected from hydrogen, $C_1$-$C_4$ alkyl, cyclopropyl and phenyl, wherein the alkyl and phenyl may be optionally substituted with halogen.

In certain embodiments, each $R^k$ is independently selected from $C_1$-$C_4$ alkyl, $C_5$ cycloalkyl, phenyl and benzyl, wherein the phenyl may be optionally substituted with halogen.

In certain embodiments, each $R^m$ and $R^n$ are independently selected from hydrogen, $C_1$-$C_2$ alkyl and phenyl, wherein the alkyl may be substituted with oxo or phenyl substituted with halogen, and wherein the phenyl may be substituted with halogen.

In certain embodiments, each $R^p$ is independently selected from halogen, $OR^t$, cyclopropyl and $C_1$-$C_3$ alkyl optionally substituted with halogen.

In certain embodiments, each $R^t$ is independently selected from hydrogen and $C_1$-$C_4$ alkyl optionally substituted with halogen. In certain embodiments, each $R^t$ is independently $C_1$-$C_4$ alkyl optionally substituted with halogen.

In certain embodiments, each $R^q$ is independently selected from halogen, CN, $OR^u$, $SR^u$, $C_3$-$C_6$ cycloalkyl optionally substituted with halogen, and $C_1$-$C_3$ alkyl optionally substituted with halogen. In certain embodiments, each $R^q$ is independently selected from halogen, CN, $OR^u$, $SR^u$, $C_3$-$C_6$ cycloalkyl, and $C_1$-$C_3$ alkyl optionally substituted with halogen. In certain embodiments, each $R^q$ is independently selected from halogen, CN, $OR^u$, $SR^u$, $C_3$-$C_4$ cycloalkyl optionally substituted with halogen, and $C_1$-$C_3$ alkyl optionally substituted with halogen. In certain embodiments, each $R^q$ is independently selected from halogen, CN, $OR^u$, $SR^u$, $C_3$-$C_4$ cycloalkyl, and $C_1$-$C_3$ alkyl optionally substituted with halogen. In certain embodiments, each $R^q$ is independently selected from halogen, methyl, CN, CF$_3$, methoxy, ethoxy, difluoromethoxy, trifluoromethoxy, methylthio and C$_3$-C$_4$ cycloalkyl.

In certain embodiments, each R$^u$ is independently selected from hydrogen and C$_1$-C$_4$ alkyl optionally substituted with halogen. In certain embodiments, each R$^u$ is independently selected from hydrogen and C$_1$-C$_3$ alkyl optionally substituted with halogen. In certain embodiments, each R$^u$ is independently selected from hydrogen and C$_1$-C$_2$ alkyl optionally substituted with halogen. In certain embodiments, each R$^u$ is independently C$_1$-C$_2$ alkyl optionally substituted with halogen.

In certain embodiments, each R$^s$ is independently selected from halogen, CN, OR$^w$, C$_1$-C$_3$ alkyl, C$_3$-C$_6$ cycloalkyl, phenyl and benzyl, wherein the alkyl, cycloalkyl, phenyl and benzyl may be optionally substituted with one to three groups selected from halogen and methyl. In certain embodiments, each R$^s$ is independently selected from halogen, CN, OR$^w$, C$_1$-C$_3$ alkyl, C$_3$-C$_6$ cycloalkyl, benzyl and phenyl optionally substituted with one to three groups selected from halogen and methyl. In certain embodiments, each R$^s$ is independently selected from halogen, CN, OR$^w$, C$_1$-C$_3$ alkyl, cyclopropyl, benzyl and phenyl optionally substituted with one or two groups selected from halogen and methyl. In certain embodiments, each R$^s$ is independently selected from halogen, OH, CN, methoxy, ethoxy, cyclopropyl, benzyl, C$_1$-C$_3$ alkyl optionally substituted with halogen, and phenyl optionally substituted with one or two groups selected from halogen and methyl.

In certain embodiments, each R$^w$ is independently selected from hydrogen and C$_1$-C$_3$ alkyl optionally substituted with halogen. In certain embodiments, each R$^w$ is independently selected from hydrogen and C$_1$-C$_3$ alkyl.

In certain embodiments, R$^2$ is selected from methyl, ethyl, 2-methylbutyl, 2,3-dimethylbutyl, 2,2-dimethylbutyl, 2-ethylbutyl, 3-methylpentyl, 2-methylpentyl, isopentyl, neopentyl, isobutyl, 3,3-dimethylbutyl, butyl, propyl, trifluoromethyl, 4-methylpentyl, 3-methylbutan-2-yl, 2-fluorobutyl, 4,4,4-trifluoro-2-methylbutyl, 3,3,3-trifluoro-2-methylpropyl, 2,2,2-trifluoroethyl, 3,3,3-trifluoropropyl, 2-fluoro-2-methylpropyl, 3,3,3-trifluoro-2-(trifluoromethyl)propyl, 1,1-difluoropropyl, 3-fluoro-3-methylbutyl, 2,2-difluoropropyl, 2-(trifluoromethyl)butyl, 3-fluoro-2-(fluoromethyl)propyl, 2-cyano-2-methylpropyl, 1-oxoethyl, 1-hydroxy-3-methylbutyl, 2-methoxy-3-methylbutyl, 2-ethoxybutyl, phenoxymethyl, (4-fluorophenoxy)methyl, 3-methoxy-2-methylpropyl, 3,3,3-trifluoro-2-methoxypropyl, 2-ethoxy-3,3,3-trifluoropropyl, 2-ethoxyethyl, 1-(tert-butoxy)ethyl, 1-hydroxybutyl, tert-butoxymethyl, 3,3,3-trifluoro-2-hydroxy-2-(trifluoromethyl)propyl, isopropoxymethyl, 2-methoxyethyl, isobutoxymethyl, 1-hydroxy-2-methylpropyl, methoxymethyl, 2-hydroxy-2-methylpropyl, 2-hydroxyethyl, 1-hydroxy-2-methylbutyl, 1-methoxy-2-methylpropyl, 2-methoxybutyl, 2-hydroxy-3-methylbutyl, 2-hydroxybutyl, 2-methoxypropyl, 3-hydroxy-2-methylpropyl, 2-methoxy-2-methylpropyl, 3,3,4,4,4-pentafluoro-2-(hydroxy)butyl, 3,3,3-trifluoro-2-(hydroxy)propyl, 2-(2-fluoroethoxy)propyl, 2-(cyclopropylmethoxy)propyl, 5,5,5-trifluoro-2-hydroxypentyl, 5,5,5-trifluoro-2-methoxypentyl, (benzylthio)methyl, 2-(methylthio)butyl, 2-(methylthio) ethyl, 2-(methylthio)propyl, (phenylthio)methyl, 2-(phenylthio)ethyl, ((4-fluorophenyl)thio)methyl, ((2-fluorophenyl)thio)methyl, (isopropylthio)methyl, (tert-butylthio)methyl, (isobutylthio)methyl, (cyclopentylthio)methyl, (phenylsulfinyl)methyl, (phenylsulfonyl)methyl, 2-(phenylsulfonyl) ethyl, (dimethylamino)methyl, 2-((4-fluorophenyl)amino)-2-oxoethyl, (diethylamino)methyl, 2-(2,4-difluoro-N-methylbenzamido)ethyl, (methylamino)oxomethyl, 2-acetamido-3,3,3-trifluoropropyl, cyclohexyl(hydroxyl)methyl, (1-methoxycyclobutyl)methyl, (1-methoxycyclopropyl)methyl, (1-(2-fluoroethoxy)cyclopropyl)methyl, [1,1'-bi (cyclopropan)]-1-ylmethyl, (1-ethylcyclobutyl)methyl, (1-(trifluoromethyl)cyclopropyl)methyl, (1-isopropylcyclopropyl)methyl, (1-ethylcyclopropyl) methyl, (1-methylcyclopropyl)methyl, (2,2-difluorocyclopropyl)methyl, cyclopentylmethyl, cyclohexylmethyl, (1-(trifluoromethyl)cyclobutyl)methyl, cyclopropylethyl, (4-methylcyclohexyl)methyl, cyclopropylmethyl, cyclobutylmethyl, (3,3-difluorocyclobutyl)methyl, 2-cyclopropyl-2-methylpropyl, 2-cyclopropylpropyl, (4,4-difluorocyclohexyl)methyl, (1-isobutoxycyclopropyl)methyl, (1-isopropoxycyclopropyl)methyl, 2-cyclopropyl-2-methoxyethyl, 2-cyclopentylethyl, 2-cyclohexylethyl, 3-cyclopropyl-2-hydroxypropyl, 2-cyclopropyl-2-hydroxyethyl, (1-ethoxycyclobutyl)methyl, 2-cyclopropyl-3,3,3-trifluoropropyl, 3-cyclopropyl-2-methoxypropyl, 4-cyclopropyl-2-methoxybutyl, 2-cyclopropyl-2-fluoroethyl, 2-cyclopentyl-3,3,3-trifluoropropyl, 3-cyclopropyl-2-fluoropropyl, 2-cyclopropyl-2-hydroxypropyl, 3-cyclopentyl-2-methoxypropyl, benzyl, 2-fluorobenzyl, 2-chlorobenzyl, 2-methoxybenzyl, 2-(trifluoromethyl)benzyl, 2-methylbenzyl, 3-bromobenzyl, 3-chlorobenzyl, 3-fluorobenzyl, 3-cyclopropylbenzyl, 3-cyclobutylbenzyl, 3-(trifluoromethyl)benzyl, 3-methoxybenzyl, 3-(difluoromethoxy)benzyl, 3-(trifluoromethoxy)benzyl, 3-cyanobenzyl, 4-chlorobenzyl, 4-fluorobenzyl, 4-(trifluoromethyl)benzyl, 4-methoxybenzyl, 4-(difluoromethoxy)benzyl, 4-(methylthio)benzyl, 4-methylbenzyl, 4-(trifluoromethoxy)benzyl, 4-ethoxybenzyl, 2,3-difluorobenzyl, 2,3-dichlorobenzyl, 2-fluoro-4-methoxybenzyl, 2-chloro-4-fluorobenzyl, 2,4-dichlorobenzyl, 2,4-difluorobenzyl, 2-fluoro-4-(trifluoromethyl)benzyl, 2,5-difluorobenzyl, 2-chloro-6-fluorobenzyl, 2,6-difluorobenzyl, 3-fluoro-4-methoxybenzyl, 3-fluoro-4-(trifluoromethoxy)benzyl, 3,4-difluorobenzyl, 3-chloro-4-fluorobenzyl, 3-chloro-4-methoxybenzyl, 3-chloro-5-fluorobenzyl, 3-fluoro-5-(trifluoromethyl)benzyl, 3,5-difluorobenzyl, 3,5-difluorobenzyl, 4-chloro-2-fluorobenzyl, 4-(difluoromethoxy)-2-fluorobenzyl, 4-chloro-3-fluorobenzyl, 4-fluoro-3-methoxybenzyl, 2,3-difluoro-4-methoxybenzyl, 2,3,4-trifluorobenzyl, 2,4,5-trifluorobenzyl, 3,5-difluoro-4-methoxybenzyl, 4-ethoxy-2,3-difluorobenzyl, (3-chlorophenyl)(hydroxy)methyl, (4-chlorophenyl)(methoxy)methyl, 3-hydroxy-1-(4-methoxyphenyl)-2-methylpropyl, 3-hydroxy-1-(4-methoxyphenyl)propyl, phenethyl, 3-chlorophenethyl, 4-chlorophenethyl, 1-(4-chlorophenyl)ethyl, 2-(4-fluorophenyl)-1-hydroxy-2-methylpropyl, 1-hydroxy-2-phenylethyl, 2-(4-fluorophenyl)-1-hydroxyethyl, 1-methoxy-2-phenyl ethyl, 1-(3-fluoro-4-methoxyphenyl)-3-hydroxypropan-2-yl, 1-(4-chlorophenyl)-2-methylpropyl, 1-phenylethyl, 2-(4-chlorophenyl)propan-2-yl, methoxy(phenyl)methyl, (4-chlorophenyl)difluoromethyl, 1-methoxy-1-phenylethyl, difluoro (3-fluoro-4-methoxyphenyl)methyl, 3-fluoro-4-methoxyphenethyl, 2-amino-1-phenethyl, 1-(4-chloro-3-fluorophenyl)-2-(hydroxy)ethyl, 1-(3-fluoro-4-methoxyphenyl)-2-(hydroxy)ethyl, (dimethylamino)(4-fluorophenyl)methyl, 2-chlorophenethyl, 2-(4-fluorophenyl)-2-methylpropyl, 2-(4-methoxyphenyl)-2-methylpropyl, 2-acetamido-2-phenylethyl, 2-acetamido-2-(3-chloro-4-fluorophenyl)ethyl, 2-methoxy-2-(4-methoxyphenyl)ethyl, 3,3,3-trifluoro-2-(4-methoxyphenyl)propyl, 3,3,3-trifluoro-2-(4-fluorophenyl) propyl, 2-(4-chlorophenyl)-2-methoxyethyl, 2-(4-chlorophenyl)-2-hydroxyethyl, 3,3,3-trifluoro-2-(4-methoxyphenyl)propyl, 2-hydroxy-2-(4-methoxyphenyl)

ethyl, 2-(4-methoxyphenyl)-2-oxoethyl, phenyl(piperidin-1-yl)methyl, (tetrahydropyran-2-yl)methyl, (tetrahydrofuran-2-yl)methyl, piperdin-1-ylmethyl, (tetrahydropyran-4-yl)methyl, (tetrahydrofuran-3yl)methyl, morpholinomethyl, (5,5-dimethyltetrahydrofuran-2-yl)methyl, (6,6-dimethyltetrahydropyran-2-yl)methyl, (tetrahydropyran-3-yl)methyl, (3-ethyloxetan-3-yl)methyl, (4-methoxyphenyl)(morpholino)methyl, (1-methyl-6-oxo-1,6-dihydropyridin-3-yl)methyl, pyrrolidin-1-ylmethyl, (1-methyl-6-oxo-1,6-dihydropyridin-3-yl)methyl, azepan-1-ylmethyl, (2-methylpiperidin-1-yl)methyl, pyrrolidine-1-carbonyl, (4,4-dimethyltetrahydrofuran-2-yl)methyl, (2-oxopyrrolidin-1-yl)methyl, (1-methyl-2-oxo-1,2-dihydropyridin-4-yl)methyl, thiophen-2-ylmethyl, pyridin-3-ylmethyl, pyrimidin-2-ylmethyl, pyrimidin-5-ylmethyl, pyridin-4-ylmethyl, thiazol-2-ylmethyl, pyrazin-2-ylmethyl, pyridin-2-ylmethyl, (1-methylpyrazol-3-yl)methyl, (1-methylpyrazol-4-yl)methyl, (1-methylimidazol-2-yl)methyl, (1-benzylimidazol-2-yl)methyl, (1-(2-fluoro-4-methylphenyl)-1,2,3-triazol-5-yl)methyl, (1-methylpyrazol-4-yl)(phenyl)methyl, (1-cyclopropyl-3,5-dimethylpyrazol-4-yl)methyl, (1,3-dimethylpyrazol-5-yl)methyl, (2-methoxypyridin-3-yl)methyl, (2-chloropyridin-3-yl)methyl, (2-hydroxypyridin-3-yl)methyl, (2-methylpyridin-3-yl)methyl, (3-chloropyridin-2-yl)methyl, (3-cyclopropylpyrazol-1-yl)methyl, (4-cyclopropylpyridin-2-yl)methyl, (4-methylpyridin-2-yl)methyl, (4-methylthiazol-2-yl)methyl, (4-isopropyl-5-methylthiazol-2-yl)methyl, (4-(trifluoromethyl)pyridin-2-yl)methyl, (4-isopropylpyridin-2-yl)methyl, (4-cyclopropyl-6-methylpyridin-2-yl)methyl, (4-cyclopropyl-3-fluoropyridin-2-yl)methyl, (4-bromopyridin-2-yl)methyl, (4-methoxypyridin-2-yl)methyl, (4-(trifluoromethyl)pyrazol-1-yl)methyl, (4-ethoxypyridin-2-yl)methyl, (5-bromopyridin-3-yl)methyl, (5-chloropyridin-3-yl)methyl, (5-fluoropyridin-3-yl)methyl, (5-cyclopropylpyridin-3-yl)methyl, (5-methylpyridin-3-yl)methyl, (5-chloropyridin-2-yl)methyl, (5-methylthiazol-2-yl)methyl, (5-cyclopropyl-2-hydroxypyridin-3-yl)methyl, (5-cyclopropyl-2-methoxypyridin-3-yl)methyl, (5-chlorothiophen-2-yl)methyl, (5-cyclopropylthiophen-2-yl)methyl, (5-cyanothiophen-2-yl)methyl, (6-chloropyridin-2-yl)methyl, (6-methoxypyridin-2-yl)methyl, (6-isopropylpyridin-2-yl)methyl, (6-cyclopropylpyridin-2-yl)methyl, (6-methylpyridin-2-yl)methyl, (6-methoxypyridin-3-yl)methyl, (6-(trifluoromethyl)pyridin-2-yl)methyl, (6-phenylpyridin-2-yl)methyl, (6-chloropyridin-3-yl)methyl, (6-hydroxypyridin-2-yl)methyl, (6-cyanopyridin-2-yl)methyl, (6-ethoxypyridin-3-yl)methyl, (6-hydroxypyridin-3-yl)methyl, (6-chloro-4-methoxypyridin-2-yl)methyl, 2-(pyridin-2-yl)ethyl, 2-(pyridin-3-yl)ethyl, 2-(pyridin-4-yl)ethyl, 2-(4-(p-tolyl)-1,2,3-triazol-1-yl)ethyl, 2-(5-(p-tolyl)-1,2,3-triazol-1-yl)ethyl, 2-(3-methyl-1-phenyl-1,2,4-triazol-5-yl)ethyl, 2-(1-(p-tolyl)tetrazol-5-yl)ethyl, 2-amino-2-(3-chloro-4-fluorophenyl)ethyl, 2-(3-cyclopropylpyrazol-1-yl)ethyl, 2-(4-(trifluoromethyl)pyrazol-1-yl)ethyl, 2-(5-chlorothiophen-2-yl)-2-methoxyethyl, bicyclo[2.2.1]heptan-2-ylmethyl, (2,3-dihydrobenzo[b][1,4]dioxin-6-yl)methyl, benzo[d][1,3]dioxol-5-ylmethyl, (5-fluoroindol-3-yl)methyl, (6-fluoroindol-3-yl)methyl, (6-methylimidaz[1,2-a]pyridin-3-yl)methyl and adamantan-1-ylmethyl.

In certain embodiments, $R^2$ is a $C_2$-$C_{12}$ alkenyl optionally substituted by one to eight $R^f$ groups. In certain embodiments, $R^2$ is a $C_2$-$C_{12}$ alkenyl optionally substituted by one to three $R^f$ groups. In certain embodiments, $R^2$ is a $C_2$-$C_{10}$ alkenyl optionally substituted by one to eight $R^f$ groups. In certain embodiments, $R^2$ is a $C_2$-$C_{10}$ alkenyl optionally substituted by one to three $R^f$ groups. In certain embodiments, $R^2$ is a $C_2$-$C_8$ alkenyl optionally substituted by one to eight $R^f$ groups. In certain embodiments, $R^2$ is a $C_2$-$C_8$ alkenyl optionally substituted by one to three $R^f$ groups. In certain embodiments, $R^2$ is a $C_2$-$C_6$ alkenyl optionally substituted by one to eight $R^f$ groups. In certain embodiments, $R^2$ is a $C_2$-$C_6$ alkenyl optionally substituted by one to three $R^f$ groups. In certain embodiments, $R^2$ is a $C_2$-$C_6$ alkenyl optionally substituted by one to three groups selected from halogen; CN; $SR^h$; $S(O)R^h$; $S(O)_2R^h$; $NR^iR^j$; $C_3$-$C_6$ cycloalkyl optionally substituted with one to three $R^k$ groups; phenyl optionally substituted by one to four $R^m$ groups; a 4 to 7 membered saturated or partially unsaturated heterocyclyl containing one to three heteroatoms selected from N, O and S, wherein the heterocyclyl may be optionally substituted with one to three groups selected from halogen, oxo and $C_1$-$C_3$ alkyl optionally substituted with halogen; and a 5 to 6 membered heteroaryl containing one to four heteroatoms selected from N, O and S, wherein the heteroaryl may be optionally substituted by one to three $R^n$ groups. In certain embodiments, $R^2$ is a $C_2$-$C_6$ alkenyl optionally substituted by one to three groups selected from halogen; CN; $SR^h$; $S(O)R^h$; $S(O)_2R^h$; $NR^iR^j$; $C_3$-$C_6$ cycloalkyl; phenyl; a 4 to 7 membered saturated or partially unsaturated heterocyclyl containing one to three heteroatoms selected from N, O and S; and a 5 to 6 membered heteroaryl containing one to four heteroatoms selected from N, O and S. In certain embodiments, $R^2$ is a $C_2$-$C_6$ alkenyl optionally substituted by one to three groups selected from halogen; CN; $NR^iR^j$; $C_3$-$C_6$ cycloalkyl; phenyl; a 4 to 7 membered saturated or partially unsaturated heterocyclyl containing one to three heteroatoms selected from N, O and S; and a 5 to 6 membered heteroaryl containing one to four heteroatoms selected from N, O and S. In certain embodiments, $R^2$ is a $C_2$-$C_6$ alkenyl optionally substituted by phenyl. In certain embodiments, $R^2$ is a $C_4$-$C_5$ alkenyl optionally substituted with phenyl. In certain embodiments, $R^2$ is selected from 3-methyl-1-phenylbut-1-en-1-yl and but-1-en-1-yl. In certain embodiments, $R^2$ is selected from (Z)-3-methyl-1-phenylbut-1-en-1-yl and (E)-but-1-en-1-yl.

In certain embodiments, $R^2$ is $OR^g$. In certain embodiments, $R^g$ is independently selected from hydrogen, $C_1$-$C_4$ alkyl, $C_3$-$C_6$ cycloalkyl and phenyl, wherein the alkyl, cycloalkyl and phenyl may be optionally substituted with halogen. In certain embodiments, $R^g$ is independently selected from hydrogen, $C_1$-$C_4$ alkyl, cyclopropyl and phenyl, wherein the alkyl and phenyl may be optionally substituted with halogen. In certain embodiments, $R^g$ is phenyl optionally substituted with methoxy. In certain embodiments, $R^g$ is phenyl substituted with methoxy. In certain embodiments, $R^2$ is 4-methoxyphenoxy.

In certain embodiments, $R^2$ is a $C_3$-$C_7$ cycloalkyl optionally substituted with one to six groups selected from halogen; OH; $C_1$-$C_3$ alkyl optionally substituted with halogen, OH or phenyl optionally substituted with halogen; C(=O)O($C_1$-$C_3$ alkyl), wherein the alkyl may be optionally substituted with halogen or OH; and phenyl optionally substituted with halogen. In certain embodiments, $R^2$ is a $C_3$-$C_7$ cycloalkyl optionally substituted with one to four groups selected from halogen; OH; $C_1$-$C_3$ alkyl optionally substituted with halogen, OH or phenyl optionally substituted with halogen; C(=O)O($C_1$-$C_3$ alkyl), wherein the alkyl may be optionally substituted with halogen or OH; and phenyl optionally substituted with halogen. In certain embodiments, $R^2$ is a $C_3$-$C_7$ cycloalkyl optionally substituted with one to six groups selected from $C_1$-$C_3$ alkyl optionally substituted with halogen, OH or phenyl optionally substituted with halogen; C(=O)O($C_1$-$C_3$ alkyl), wherein the alkyl may be optionally substituted with halogen or OH; and phenyl optionally substituted with halogen. In certain embodiments, $R^2$ is a $C_3$-$C_7$ cycloalkyl optionally substituted with one to six groups selected from $C_1$-$C_3$ alkyl optionally substituted with halogen, OH or phenyl optionally substituted with halogen; C(=O)O($C_1$-$C_3$ alkyl); and phenyl optionally substituted with halogen. In certain embodiments, $R^2$ is a $C_3$-$C_6$ cycloalkyl optionally substituted with one to six groups selected from halogen; OH; $C_1$-$C_3$ alkyl optionally substituted with halogen, OH or phenyl optionally substituted with halogen; C(=O)O($C_1$-$C_3$ alkyl), wherein the alkyl may be optionally substituted with halogen or OH; and phenyl optionally substituted with halogen. In certain embodiments, $R^2$ is a $C_3$-$C_6$ cycloalkyl optionally substituted with one to six groups selected from $C_1$-$C_3$ alkyl optionally substituted with halogen, OH or phenyl optionally substituted with halogen; C(=O)O($C_1$-$C_3$ alkyl), wherein the alkyl may be optionally substituted with halogen or OH; and phenyl optionally substituted with halogen. In certain embodiments, $R^2$ is a $C_3$-$C_6$ cycloalkyl optionally substituted with one to six groups selected from $C_1$-$C_3$ alkyl optionally substituted with halogen, OH or phenyl optionally substituted with halogen; C(=O)O($C_1$-$C_3$ alkyl); and phenyl optionally substituted with halogen. In certain embodiments, $R^2$ is a $C_3$-$C_6$ cycloalkyl optionally substituted with one to four groups selected from $C_1$-$C_3$ alkyl optionally substituted with halogen, OH or phenyl optionally substituted with halogen; C(=O)O($C_1$-$C_3$ alkyl); and phenyl optionally substituted with halogen. In certain embodiments, $R^2$ is a $C_3$-$C_6$ cycloalkyl optionally substituted with one to four groups selected from $C_1$-$C_3$ alkyl optionally substituted with halogen, OH or phenyl; C(=O)O($C_1$-$C_3$ alkyl); and phenyl substituted with halogen. In certain embodiments, $R^2$ is selected from 2-(2-fluoropropan-2-yl)cyclopropyl, cyclohexyl, 2,2-dimethylcyclopropyl, 2-(ethoxycarbonyl)cyclopropyl, 2-(2-hydroxypropan-2-yl)cyclopropyl, 2-(trifluoromethyl)cyclobutyl, 2-methylcyclopropyl, 1-(4-chlorophenyl)cyclopropyl, 1-(4-chlorophenyl)cyclobutyl, 1-(4-chlorophenyl)cyclopentyl, 2,2,3,3-tetramethylcyclopropyl, 2-phenylcyclopropyl and 2-benzylcyclopropyl.

In certain embodiments, $R^2$ is phenyl optionally substituted with one to four groups selected from halogen, $C_1$-$C_3$ alkyl optionally substituted with halogen, OH or methoxy, and phenoxy optionally substituted with halogen, OH or methoxy. In certain embodiments, $R^2$ is phenyl optionally substituted with halogen or phenoxy substituted with halogen or methoxy. In certain embodiments, $R^2$ is selected from phenyl, 2-chlorophenyl, 2-fluorophenyl, 2-(4-methoxyphenoxy)phenyl, 3-chlorophenyl, 3-fluorophenyl, 4-chlorophenyl, 2-chloro-4-fluorophenyl and 2-(4-fluorophenoxy)phenyl.

In certain embodiments, $R^2$ is a 4 to 7 membered saturated or partially unsaturated heterocyclyl containing one to three heteroatoms selected from N, O and S, wherein the heterocyclyl may be optionally substituted with one to four $R^h$ groups. In certain embodiments, $R^2$ is a 4 to 7 membered saturated or partially unsaturated heterocyclyl containing one or two heteroatoms selected from N and O, wherein the heterocyclyl may be optionally substituted with one to four $R^h$ groups. In certain embodiments, $R^2$ is a 4 to 7 membered saturated or partially unsaturated heterocyclyl containing one or two heteroatoms selected from N and O, wherein the heterocyclyl may be optionally substituted with one to three $R^h$ groups. In certain embodiments, $R^2$ is a 5 to 6 membered saturated or partially unsaturated heterocyclyl containing one or two heteroatoms selected from N and O, wherein the heterocyclyl may be optionally substituted with one to four $R^h$ groups. In certain embodiments, $R^2$ is a 5 to 6 membered saturated or partially unsaturated heterocyclyl containing one or two heteroatoms selected from N and O, wherein the heterocyclyl may be optionally substituted with one to three $R^h$ groups.

In certain embodiments, each $R^h$ is selected from halogen; OH; $C_1$-$C_3$ alkyl optionally substituted with one to three groups selected from halogen, OH, CN, methoxy, oxo, cyclopropyl and phenyl optionally substituted by one to three groups selected from halogen, CN, methyl and methoxy; $C_1$-$C_3$ alkoxy optionally substituted by halogen or OH; oxo; phenyl optionally substituted with one to three groups selected from halogen, OH, CN, methyl and methoxy; phenoxy wherein the phenoxy optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy. In certain embodiments, each $R^h$ is selected from $C_1$-$C_3$ alkyl optionally substituted with one to three groups selected from halogen, oxo, cyclopropyl and phenyl optionally substituted by two groups selected from halogen, CN and methoxy; oxo; phenyl optionally substituted with halogen; phenoxy optionally substituted with halogen; and a 6 membered heteroaryl containing one N heteroatom, wherein the heteroaryl is may be optionally substituted by two groups selected from halogen and methoxy. In certain embodiments, each $R^h$ is selected from $C_1$-$C_3$ alkyl optionally substituted with one to three groups selected from halogen, oxo, cyclopropyl and phenyl optionally substituted by two groups selected from halogen, CN and methoxy; oxo; phenyl optionally substituted with halogen; phenoxy optionally substituted with halogen; and a 6 membered heteroaryl containing one N heteroatom, wherein the heteroaryl is substituted by two groups selected from halogen and methoxy.

In certain embodiments, $R^2$ is selected from 4-(2-fluoro-6-methoxybenzyl)morpholin-2-yl, 1-(2-fluoro-6-methoxybenzyl)piperidin-3-yl, 5-(2,6-difluorophenoxy)-1-methylpiperidin-3-yl, (5-chloro-2-fluorobenzyl)piperidin-3-yl, piperdin-3-yl, ((5-fluoro-2-methoxypyridin-3-yl)methyl)piperidin-3-yl, 1-(5-cyano-2-fluorobenzyl)piperidin-3-yl, 1-methyl-5-oxo-3-phenylpyrrolidin-2-yl, 4-(cyclopropylmethyl)morpholin-2-yl, 4-(2-fluoro-6-methoxybenzoyl)morpholin-2-yl, 4-(2,6-difluorobenzoyl)morpholin-2-yl, 4-(3,3,3-trifluoropropyl)morpholin-2-yl, 4-(3-fluorophenyl)pyrrolidin-3-yl, 4-phenylpyrrolidin-3-yl, 1-benzyl-4-(3-fluorophenyl)pyrrolidin-3-yl, 4-(4-chloro-3-fluorophenyl)pyrrolidin-3-yl and morpholin-2-yl.

In certain embodiments, $R^2$ is a 5 to 6 membered heteroaryl containing one to four heteroatoms selected from N, O and S, wherein the heteroaryl may be optionally substituted with one to four $R^i$ groups. In certain embodiments, $R^2$ is a 5 to 6 membered heteroaryl containing one or two heteroatoms selected from N, O and S, wherein the heteroaryl may be optionally substituted with one to four $R^i$ groups. In certain embodiments, $R^2$ is a 5 to 6 membered heteroaryl containing one or two heteroatoms selected from N, O and S, wherein the heteroaryl may be optionally substituted with one to three $R^i$ groups. In certain embodiments, $R^2$ is a 5 membered heteroaryl containing two heteroatoms selected from N and O, wherein the heteroaryl may be optionally substituted with one to three $R^i$ groups. In certain embodiments, $R^2$ is a 5 membered heteroaryl containing two heteroatoms selected from N and O, wherein the heteroaryl is substituted with one to three $R^i$ groups.

In certain embodiments, each $R^i$ is selected from halogen; OH; $C_1$-$C_4$ alkyl optionally substituted with one to three groups selected from halogen, OH, CN, methoxy, oxo, cyclopropyl and phenyl optionally substituted by one to three groups selected from halogen, CN, methyl and methoxy; $C_1$-$C_3$ alkoxy optionally substituted by halogen or OH; phenyl optionally substituted with one to three groups selected from halogen, OH, CN, methyl and methoxy; benzyl optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy. In certain embodiments, each R' is selected from halogen; $C_1$-$C_4$ alkyl; phenyl; benzyl; and a 5 to 6 membered heteroaryl containing one to four heteroatoms selected from N, O and S; wherein the alkyl, phenyl, benzyl and heteroaryl may be optionally substituted with halogen. In certain embodiments, each $R^1$ is selected from halogen; $C_1$-$C_4$ alkyl; phenyl; benzyl; and a 5 to 6 membered heteroaryl containing one to four heteroatoms selected from N, O and S; wherein the alkyl, phenyl and benzyl may be optionally substituted with halogen. In certain embodiments, each R' is selected from halogen; $C_1$-$C_4$ alkyl; phenyl; benzyl; and a 5 to 6 membered heteroaryl containing one N heteroatom; wherein the alkyl, phenyl, benzyl and heteroaryl may be optionally substituted with halogen. In certain embodiments, each $R^i$ is selected from $C_1$-$C_4$ alkyl, phenyl, benzyl, and a 6 membered heteroaryl containing one N heteroatom, wherein the alkyl, phenyl and benzyl may be optionally substituted with halogen.

In certain embodiments, $R^2$ is selected from 1-phenyl-1H-pyrazol-5-yl, 1-methyl-3-(pyridin-3-yl)-1H-pyrazol-4-yl, 3-phenyl-1H-pyrazol-4-yl, 3-isopropyl-1-methyl-1H-pyrazol-4-yl, 3-methyl-5-phenylisoxazol-4-yl, 3-isobutyl-1-methyl-1H-pyrazol-4-yl, 5-isobutyl-1-methyl-1H-pyrazol-4-yl, 5-isopropyl-1-methyl-1H-pyrazol-4-yl, 1-(3-fluorophenyl)-1H-pyrazol-5-yl, 1-(3-fluorophenyl)-5-methyl-1H-pyrazol-3-yl, 1-(3-fluorophenyl)-3-methyl-1H-pyrazol-5-yl, 1-(3-fluorophenyl)-3-(trifluoromethyl)-1H-pyrazol-5-yl, 1-(3-chlorophenyl)-3-(trifluoromethyl)-1H-pyrazol-5-yl, 1-(4-fluorophenyl)-3-methyl-1H-pyrazol-5-yl, 1-(4-fluorophenyl)-5-methyl-1H-pyrazol-3-yl, 1-(4-fluorophenyl)-1H-pyrazol-5-yl, 1-(4-fluorophenyl)-1H-pyrazol-3-yl, 3-(3-chlorophenyl)-1,5-dimethyl-1H-pyrazol-4-yl, 3-(3-fluorophenyl)-1,5-dimethyl-1H-pyrazol-4-yl, 3-(3-fluorobenzyl)-1-methyl-1H-pyrazol-4-yl, 3-(3-fluorophenyl)-1-methyl-1H-pyrazol-4-yl, 3-(4-fluorophenyl)-1-methyl-1H-pyrazol-4-yl, 3-(4-chlorophenyl)-1-methyl-1H-pyrazol-4-yl, 3-(4-fluorobenzyl)-1-methyl-1H-pyrazol-4-yl, 3-(3,4-difluorophenyl)-1-methyl-1H-pyrazol-4-yl, 4-(3-chlorophenyl)-1-methyl-1H-pyrazol-5-yl, 4-(3-chlorophenyl)-1-methyl-1H-pyrazol-3-yl, 4-(3-chlorophenyl)-1,3-dimethyl-1H-pyrazol-5-yl, 4-(4-chlorophenyl)-1-methyl-1H-pyrazol-5-yl, 4-(4-chlorophenyl)-1-methyl-1H-pyrazol-3-yl, 4-(4-chlorophenyl)-1,3-dimethyl-1H-pyrazol-5-yl, 5-(3-fluorophenyl)-1-methyl-1H-pyrazol-4-yl, 5-(3-fluorobenzyl)-1-methyl-1H-pyrazol-4-yl, 5-(3-chlorophenyl)-1,3-dimethyl-1H-pyrazol-4-yl, 5-(4-fluorobenzyl)-1-methyl-1H-pyrazol-4-yl, 5-(4-fluorophenyl)-1-methyl-1H-pyrazol-4-yl, 5-(4-chlorophenyl)-1-methyl-1H-pyrazol-4-yl, 5-(4-chloro-3-fluorophenyl)-1,3-dimethyl-1H-pyrazol-4-yl, 5-(4-chlorophenyl)-1,3-dimethyl-1H-pyrazol-4-yl, 5-(3,4-difluorophenyl)-1-methyl-1H-pyrazol-4-yl, 5-(3,4-difluorophenyl)-1,3-dimethyl-1H-pyrazol-4-yl and 1,5-dimethyl-3-phenyl-1H-pyrazol-4-yl.

In certain embodiments, $R^2$ is a 9 to 10 membered bicyclic heterocyclyl containing one to three heteroatoms selected from N, O and S, wherein the heterocyclyl may be optionally substituted with one to four $R^h$ groups. In certain embodiments, $R^2$ is a 9 to 10 membered bicyclic heterocyclyl containing one to three heteroatoms selected from N, O and S, wherein the heterocyclyl may be optionally substituted with one to three $R^h$ groups. In certain embodiments, $R^2$ is a 9 to 10 membered bicyclic heterocyclyl containing one to three heteroatoms selected from N, O and S, wherein the heterocyclyl may be optionally substituted with one to three groups selected from halogen, methyl and methoxy.

In certain embodiments, $R^2$ is a 9 to 10 membered bicyclic heterocyclyl containing one O heteroatom, wherein the heterocyclyl may be optionally substituted with one to four $R^h$ groups. In certain embodiments, $R^2$ is a 9 to 10 membered bicyclic heterocyclyl containing one O heteroatom, wherein the heterocyclyl may be optionally substituted with one to three $R^h$ groups. In certain embodiments, $R^2$ is a 9 to 10 membered bicyclic heterocyclyl containing one O heteroatom, wherein the heterocyclyl may be optionally substituted with one to three groups selected from halogen, methyl and methoxy. In certain embodiments, $R^2$ is a 10 membered bicyclic heterocyclyl containing one O heteroatom, wherein the heterocyclyl may be optionally substituted with one to three $R^h$ groups. In certain embodiments, $R^2$ is a 10 membered bicyclic heterocyclyl containing one O heteroatom, wherein the heterocyclyl may be optionally substituted with one to three groups selected from halogen, methyl and methoxy. In certain embodiments, $R^2$ is a 10 membered bicyclic heterocyclyl containing one O heteroatom. In certain embodiments, $R^2$ is isochroman-1-yl.

In certain embodiments, $R^2$ is —$CH_2R^f$ (such compounds have the structure of Formula X).

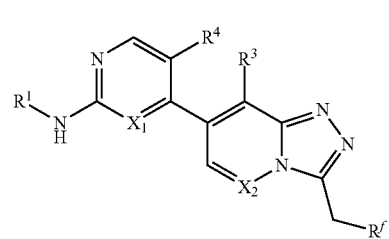

In certain embodiments, $R^3$ is selected from hydrogen and halogen. In certain embodiments, $R^3$ is hydrogen. In certain embodiments, $R^3$ is halogen. In certain embodiments, $R^3$ is selected from hydrogen, fluorine and chlorine. In certain embodiments, $R^3$ is selected from hydrogen and fluorine. In certain embodiments, $R^3$ is fluorine.

In certain embodiments, $R^4$ is selected from hydrogen and halogen. In certain embodiments, $R^4$ is hydrogen. In certain embodiments, $R^4$ is halogen. In certain embodiments, $R^4$ is selected from hydrogen, fluorine and chlorine. In certain embodiments, $R^4$ is selected from hydrogen and fluorine. In certain embodiments, $R^4$ is fluorine.

In certain embodiments, $R^3$ and $R^4$ are selected from hydrogen and halogen. In certain embodiments, $R^3$ and $R^4$ are selected from hydrogen, fluorine and chlorine. In certain embodiments, $R^3$ and $R^4$ are selected from hydrogen and fluorine. In certain embodiments, $R^3$ and $R^4$ are hydrogen. In certain embodiments, $R^3$ is hydrogen; and $R^4$ is selected from hydrogen and halogen. In certain embodiments, $R^3$ is hydrogen; and $R^4$ is selected from hydrogen, fluorine and chlorine. In certain embodiments, $R^3$ is hydrogen; and $R^4$ is selected from hydrogen and fluorine. In certain embodiments, $R^3$ is selected from hydrogen and halogen; and $R^4$ is hydrogen. In certain embodiments, $R^3$ is selected from hydrogen, fluorine and chlorine; and $R^4$ is hydrogen. In certain embodiments, $R^3$ is selected from hydrogen and fluorine; and $R^4$ is hydrogen. In certain embodiments, $R^3$ is hydrogen and $R^4$ is selected from hydrogen and halogen, or $R^3$ is selected from hydrogen and halogen and $R^4$ is hydrogen. In certain embodiments, $R^3$ is hydrogen and $R^4$ is selected from hydrogen, fluorine and chlorine, or $R^3$ is selected from hydrogen, fluorine and chlorine and $R^4$ is hydrogen. In certain embodiments, $R^3$ is hydrogen and $R^4$ is selected from hydrogen and fluorine, or $R^3$ is selected from hydrogen and fluorine and $R^4$ is hydrogen.

In certain embodiments, a compound of Examples 1 to 570 is provided.

In certain embodiments, a compound of Formula I, II, III, IV, V, VI, VII, VIII, IX or X is provided.

It will be appreciated that certain compounds described herein may contain asymmetric or chiral centers, and therefore exist in different stereoisomeric forms. It is intended that all stereoisomeric forms of the compounds described herein, including but not limited to, diastereomers, enantiomers and atropisomers, as well as mixtures thereof such as racemic mixtures, form part of the present compounds.

In the structures shown herein, where the stereochemistry of any particular chiral atom is not specified, then all stereoisomers are contemplated and included as the compounds described herein. Where stereochemistry is specified by a solid wedge or dashed line representing a particular configuration, then that stereoisomer is so specified and defined.

It will also be appreciated that certain compounds of Formula I, II, III, IV, V, VI, VII, VIII, IX or X may be used as intermediates for further compounds of Formula I, II, III, IV, V, VI, VII, VIII, IX or X.

It will be further appreciated that the compounds described herein may exist in unsolvated as well as solvated forms with pharmaceutically acceptable solvents such as water, ethanol, and the like, and it is intended that the compounds embrace both solvated and unsolvated forms.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1-4 show general methods for preparing the compounds described herein, as well as key intermediates. For a more detailed description of the individual reaction steps, see the Examples section below. Those skilled in the art will appreciate that other synthetic routes may be used to synthesize the compounds.

Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

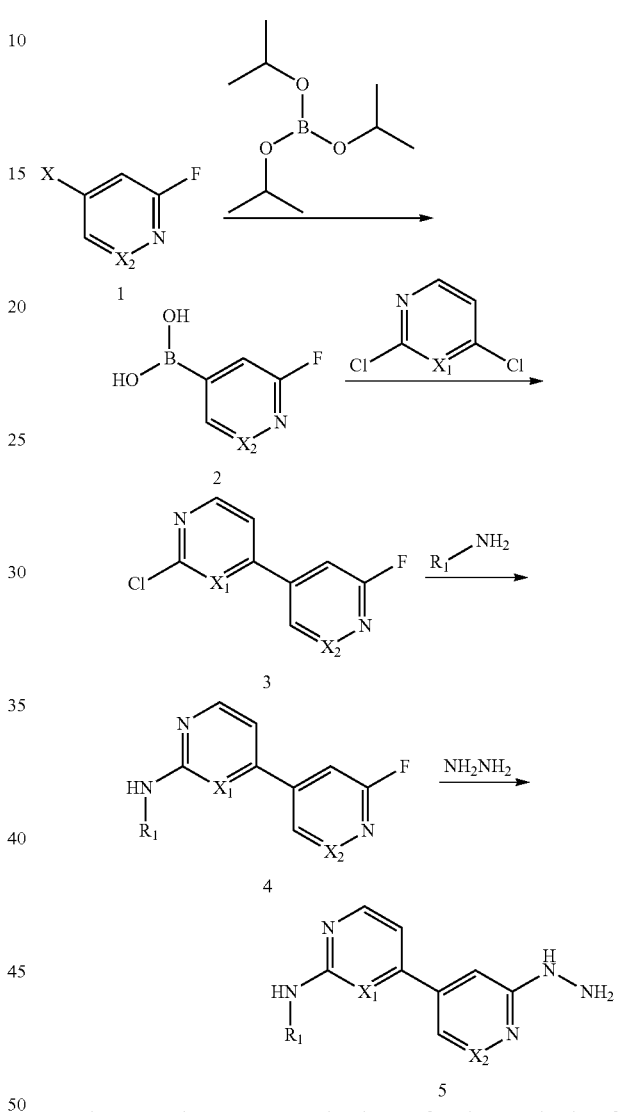

Scheme 1 shows a general scheme for the synthesis of compound 5, wherein $X_1$, $X_2$ and $R^1$ are as defined herein. The synthesis can be started either from compound 1, wherein X is Cl or Br, 4-halo substituted 2-fluoro pyridine analog or from the commercially available (2-fluoropyridin-4-yl)boronic acid. (2-Fluoropyridin-4-yl)boronic acid can be prepared according to the methods described in the literature (WO 03/000689; Bouillon, Alexandre, et al. "Synthesis of novel halopyridinylboronic acids and esters. Part 3: 2, or 3-Halopyridin-4-yl-boronic acids and esters." *Tetrahedron*. 58(22) (2002): pp. 4369-4373). Compound 2 may be subjected to a Pd mediated coupling reaction, such as Suzuki reaction, with a 2,6-dichloropyrimidine analog to provide compound 3. The reaction of compound 3 with an appropriate amine under Buchwald reaction condition can provide the intermediate 4. $S_NAr$ reaction of compound 4 with hydrazine or hydrazine monohydrate will furnish the advanced intermediate 5.

Scheme 2

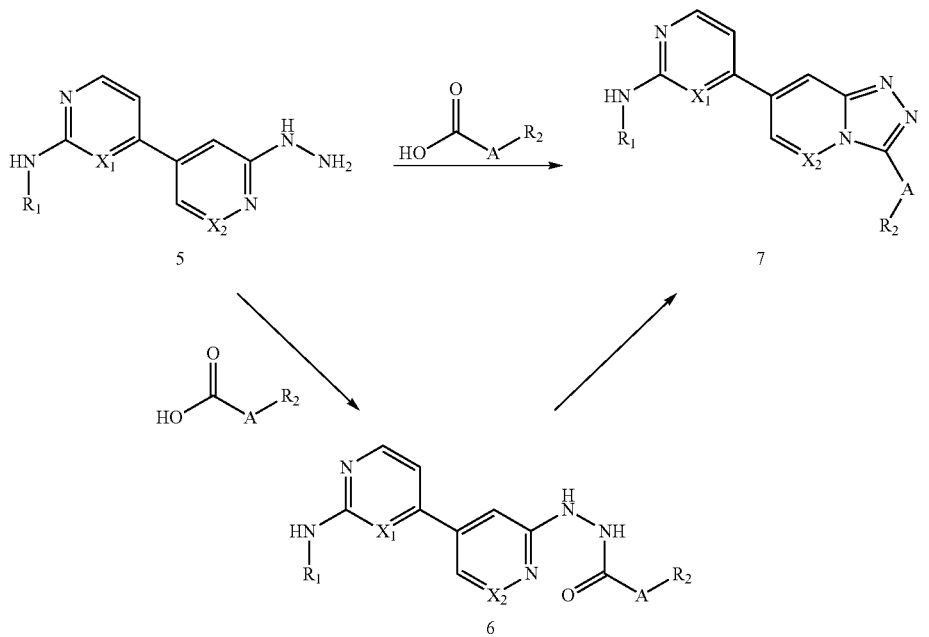

Scheme 2 shows a general scheme for the synthesis of compound 7, wherein $X_1$, $X_2$, $R^1$ and $R^2$ are as defined herein. The hydrazine intermediate 5 may be reacted with a suitable acid (alkyl, substituted alkyl, aryl, heteroaryl, etc.) in the presence of trichloroacetonitrile, $Ph_3P$ and an organic base, such as $Et_3N$ or Hunig's base, as shown in Scheme 2, to provide the triazolopyridine analog 7. Alternatively, compound 7 may be prepared from a two-step sequence. The first step is to carry out a standard coupling reaction of compound 5 with a suitable acid in the presence of a coupling agent, such as 1-ethyl-3-(3-dimethylaminopropyl)carbodiimide ("EDC"), 1,1'-carbonyldiimidazole ("CDI"), etc., and a base, such as $Et_3N$, Hunig's, N-methyl morpholine, to provide the amide intermediate 6. Intermediate 6 may then be cyclized in the presence of an acid, such as acetic acid, with heating to furnish the triazolopyridine analogue 7. The heating can be either microwave assistant or under reflux conditions, for example.

Scheme 3

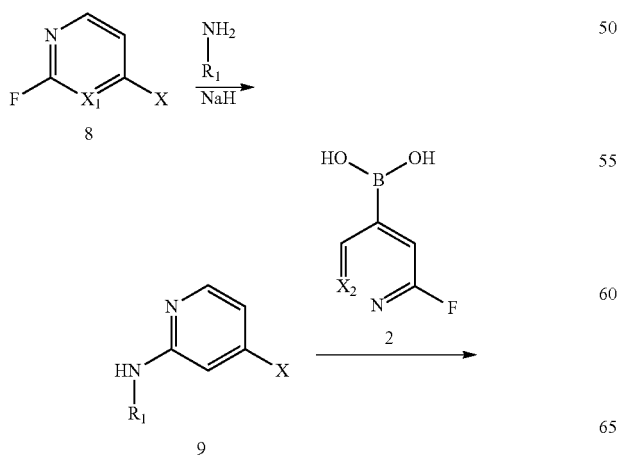

-continued

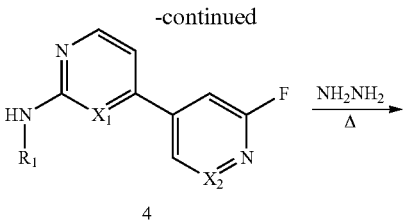

Scheme 3 shows a general scheme for the synthesis of compound 5, wherein $X_1$, $X_2$, and $R^1$ are as defined herein. In this method a 4-halo-2-fluoropyridine analogue 8, where X is Br or Cl, may be subjected to $S_NAr$ reaction with an appropriate amine in the presence of a base (NaH, $K_2CO_3$, $Cs_2CO_3$, etc.) to prepare compound 9. Compound 9 may then be subjected to a Pd mediated coupling reaction (such as Suzuki) with a 2-fluoropyridyl boronate or boronic acid 2 to provide compound 4. Compound 4 may be treated with hydrazine to provide compound 5 as described in Scheme 1. A subsequent coupling reaction of compound 5 with an acid, and the cyclization of the amide intermediate 6 can be achieved as described for the synthesis of compound 7 in Scheme 2.

Scheme 4

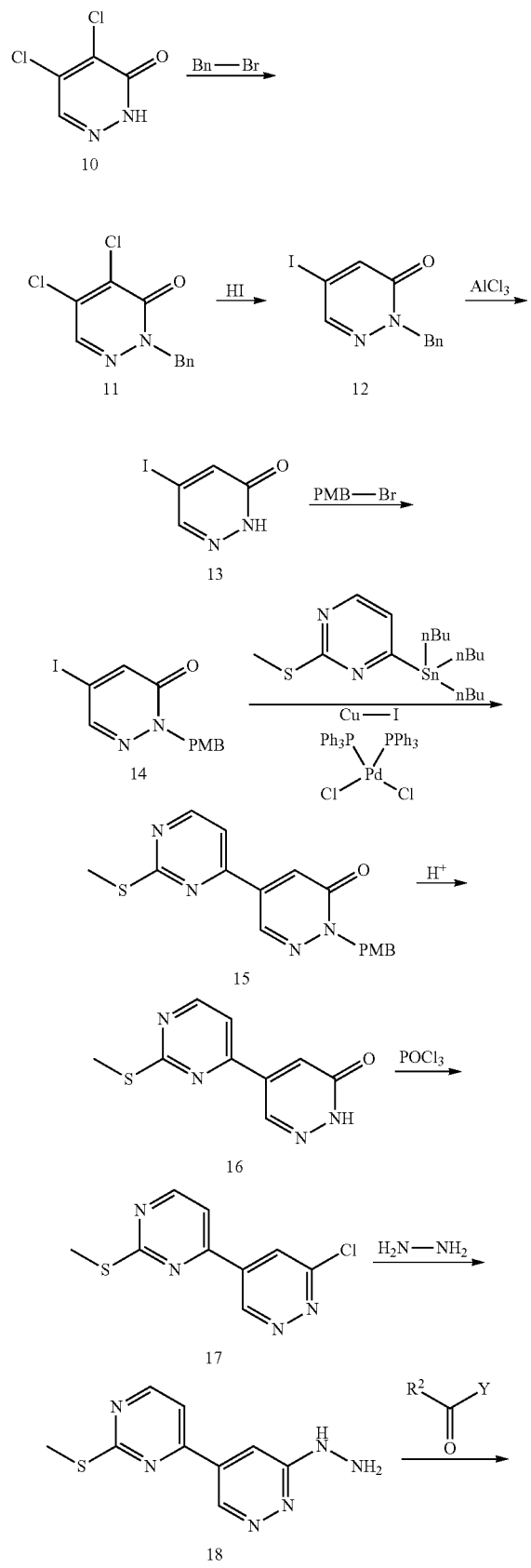

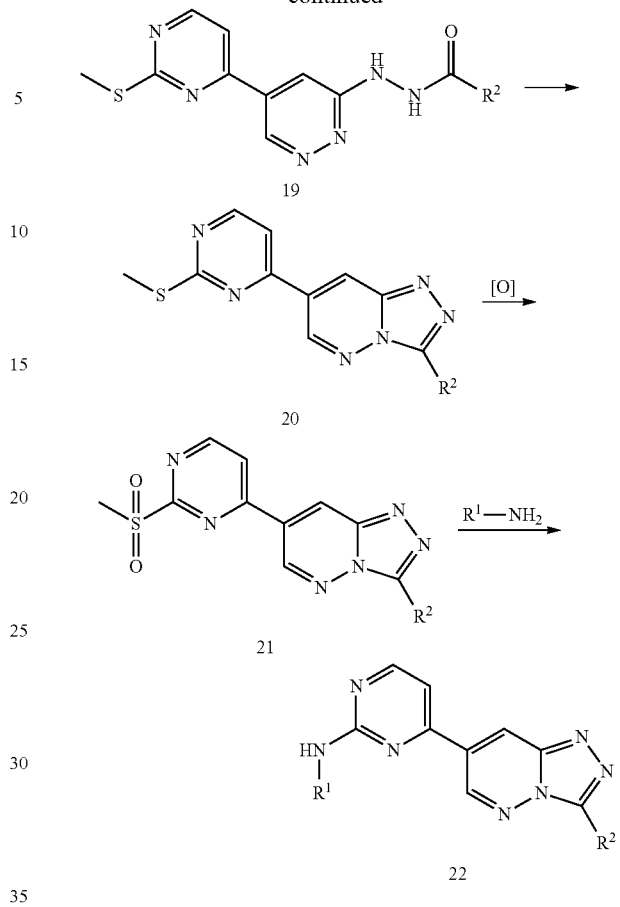

Scheme 4 outlines the general synthetic method for the preparation of [1,2,4]triazolo[4,3-b]pyridazine analogues 22, wherein $R^1$ and $R^2$ are as defined herein. Compound 13 may be either purchased from a vendor or it can be prepared according to the methods described in the literature (Step 1: US 2006/0287323; Step 2: Coelho, Alberto, et al. "Pyridazine derivatives. Part 39: Reactivity of 5-iodopyridazine-3(2H)-ones in palladium-catalysed reactions." *Tetrahedron.* 60(52) (2004): pp. 12177-12190). Compound 13 or the N-protected analogue 14 (which may be prepared by the reaction of compound 13 with p-methoxybenzyl ether-Br in the presence of a base, such as $K_2CO_3$, $Cs_2CO_3$, etc.) may be subjected to a Pd mediated coupling reaction with a pyrimidine stannate derivative to prepare compound 15. Compound 15 may be treated with a strong acid, such as $H_2SO_4$, trifluoroacetic acid ("TFA") or combination of TFA: concentrated $H_2SO_4$) to achieve the deprotection of the p-methoxybenzyl ether ("PMB") group and to obtain pyridazinone 16. Treatment of pyridazinone 16 with $POCl_3$, followed by the $S_NAr$ reaction of the resulting 2-chloropyridazine 17 will provide the corresponding hydrazine intermediate 18. This hydrazine intermediate 18 may be subjected to a coupling reaction with an appropriate acid chloride in the presence of a base, such as $Et_3N$, Hunig's, etc.) to make the amide analogue 19. Alternatively, the hydrazine intermediate 18 may be subjected to a coupling reaction with an appropriate acid in the presence of a coupling reagent, such as EDC, to prepare compound 19. The ring closure of compound 19 may be achieved by heating it in a suitable solvent with or without an acid, such as acetic acid. Oxidation of the SMe group in compound 20 with an oxidating agent such as meta-chloroperoxybenzoic acid ("m-CPBA"), followed by the $S_NAR$ reaction of the resulting sulfone 21 may give rise to the fully elaborated [1,2,4]triazolo[4,3-b]pyridazine analogue 22.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral high-performance liquid chromatography ("HPLC") column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr.* 113(3) (1975): pp. 283-302). Racemic mixtures of chiral compounds described herein may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem.* Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., Ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

Determination of the activity of ERK activity of a compound of Formula I, II, III, IV, V, VI, VII, VIII, IX or X is possible by a number of direct and indirect detection methods. Certain exemplary compounds described herein were assayed for their ERK inhibition assay (Biological Example 1). The range of ERK binding activities was less than 10 nM (nanomolar) to less than about 1 μM (micromolar). A cell-based function assay (Biological Example 2) was used to determine the effect of ERK inhibitors on down-stream signaling by assaying phosphorylation of P90RSK.

Administration and Pharmaceutical Formulations

The compounds described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a compound of Formula I, II, III, IV, V, VI, VII, VIII, IX or X or a stereoisomer or pharmaceutically acceptable salt thereof. A further embodiment provides a pharmaceutical composition comprising a compound of Formula I, II, III, IV, V, VI, VII, VIII, IX or X or a stereoisomer or pharmaceutically acceptable salt thereof, together with a pharmaceutically acceptable carrier or excipient.

Methods of Treatment with Compounds of the Invention

Also provided are methods of treating or preventing disease or condition by administering one or more compounds described herein, or a stereoisomer or pharmaceutically acceptable salt thereof. In one embodiment, a method of treating a hyperproliferative disease in a mammal comprising administering a therapeutically effective amount of the compound of Formula I, II, III, IV, V, VI, VII, VIII, IX or X, or a stereoisomer, tautomer or pharmaceutically acceptable salt thereof, to the mammal is provided.

Another embodiment provides a method of treating or preventing cancer in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing pain in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing an inflammatory disorder in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another embodiment provides a method of inhibiting ERK protein kinase activity in a patient in need thereof comprising the step of administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising co-administering to said patient a compound according to Formula I, II, III, IV, V, VI, VII, VIII, IX or X, or a stereoisomer, tautomer or pharmaceutically acceptable salt thereof, with at least one other chemotherapeutic agent used to treat or ameliorate the hyperproliferative disorder.

Another embodiment provides a method of treating or ameliorating the severity of pain in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of an inflammatory disorder in a patient in need thereof comprising administering to said patient a compound according to Formula I, II, III, IV, V, VI, VII, VIII, IX or X, or a stereoisomer, tautomer or pharmaceutically acceptable salt thereof.

In another embodiment, a method of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative diseases, such as cancer, and pain or inflammatory diseases.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease. Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of cancer.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of pain.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of an inflammatory disease.

Another embodiment provides the use of a compound of Formula I, II, III, IV, V, VI, VII, VIII, IX or X, or a stereoisomer, tautomer or pharmaceutically acceptable salt thereof, for use in the treatment of hyperproliferative diseases. Another embodiment provides the use of a compound of Formula I, II, III, IV, V, VI, VII, VIII, IX or X, or a stereoisomer, tautomer or pharmaceutically acceptable salt thereof, for use in the treatment of cancer.

Another embodiment provides the use of a compound of Formula I, II, III, IV, V, VI, VII, VIII, IX or X, or a stereoisomer, tautomer or pharmaceutically acceptable salt thereof, for use in the treatment of pain.

Another embodiment provides the use of a compound of Formula I, II, III, IV, V, VI, VII, VIII, IX or X, or a stereoisomer, tautomer or pharmaceutically acceptable salt thereof, for use in the treatment of inflammatory diseases.

In certain embodiments, the hyperproliferative disease is cancer. In certain embodiments, the cancer may be selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In certain embodiments, the cancer disorder is melanoma. In certain embodiments, the cancer is pancreatic cancer. In certain embodiments, the cancer is thyroid cancer. In certain embodiments, the cancer is colorectal cancer. In certain embodiments, the cancer is lung cancer. In certain embodiments, the cancer is breast cancer. In certain embodiments, the cancer is ovarian cancer. In certain embodiments, the cancer is acute myelogenous leukemia. In certain embodiments, the cancer is chronic myelomonocytic leukemia. In certain embodiments, the cancer is chronic myelogenous leukemia. In certain embodiments, the cancer is multiple myeloma. In certain embodiments, the cancer is myeloid leukemia.

In certain embodiments, the inflammatory disorder may be selected from arthritis, low back pain, inflammatory bowel disease, and rheumatism.

Combination Therapy

The compounds described herein and stereoisomers, tautomers and pharmaceutically acceptable salts thereof may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Biological Example 1

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in dimethylsulfoxide ("DMSO") in 3-fold serial dilutions at 100× final concentrations. In addition to compound, the assay contained 50 mM HEPES [pH 7.3], 10 mM $MgCl_2$, 1 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and $IC_{50}$ values were determined using a four-parameter fit. Table 1 contains representative data for Examples disclosed herein. The reported $IC_{50}$ in Table 1 may be from a single assay or the mean of multiple assays. Examples 1-570 were tested in the above assay and were found to have an $IC_{50}$ of less than 1 μM. Examples 1-130, 133-135, 137-210, 212-386, 388-418, 420-511, 513-562 and 564-570 (562 out of 570 examples) were tested in the above assay and were found to have an $IC_{50}$ of less than 100 nM. Many of the Examples (507 out of 570) were tested in the above assay and were found to have an $IC_{50}$ of less than 10 nM.

Biological Example 2

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

HepG2 cells were obtained from ATCC (Manassas, Va.) and grown in DMEM supplemented with 10% fetal bovine serum. Cells were plated in 96-well plates at 35,000 cells/well and allowed to attach overnight at 37° C./5% $CO_2$. Diluted compounds were then added at a final concentration of 0.5% DMSO. After 1.5 hours compound incubation, cells were stimulated with the addition of phorbol 12-myristate 13-acetate ("PMA") at a final concentration of 100 ng/mL; the PMA stimulation was a 30-minute incubation at 37° C./5% $CO_2$. After the 30-minute PMA stimulation, cells were washed with phosphate buffered saline ("PBS") and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK (Ser380) signal was normalized to GAPDH signal. Table 1 contains representative data for Examples disclosed herein. The reported $IC_{50}$ in Table 1 may be from a single assay or the mean of multiple assays.

Table 1 contains Examples tested in the above assays:

TABLE 1

| Example # | Biological Example 1 $IC_{50}$ (nM) | Biological Example 2 $IC_{50}$ (nM) |
|---|---|---|
| Example 35 | 0.8 | 17 |
| Example 40 | 3.3 | 6.5 |
| Example 49 | 0.8 | 6.6 |
| Example 51 | 2.6 | 8.9 |
| Example 57 | 0.5 | 4.6 |
| Example 67 | 2.8 | 7.5 |
| Example 84 | 3.2 | 15.7 |
| Example 108 | 3.4 | 38.2 |
| Example 111 | 2.9 | 27.9 |
| Example 112 | 17 | 861.8 |
| Example 113 | 3.4 | 38 |
| Example 115 | 2.8 | 8.3 |
| Example 116 | 3.3 | 19.3 |
| Example 121 | 0.9 | 34.7 |
| Example 123 | 2.8 | 25.6 |
| Example 131 | 223.7 | 2377.1 |
| Example 132 | 197.4 | >5000 |
| Example 136 | 171.3 | |
| Example 140 | 7.5 | 485.6 |
| Example 150 | 2.8 | 39.2 |
| Example 163 | 2.4 | 20.7 |
| Example 169 | 2.7 | 30 |
| Example 192 | 6 | 37.5 |
| Example 195 | 24.9 | 39.7 |
| Example 211 | 171.6 | |
| Example 258 | 5.7 | 177.7 |
| Example 272 | 0.9 | 95.4 |
| Example 275 | 1.5 | 20 |
| Example 276 | 0.9 | 51.7 |
| Example 278 | 0.8 | 67.6 |
| Example 279 | 0.6 | 51.9 |
| Example 295 | 0.4 | 116.8 |
| Example 306 | 1.8 | 63.7 |
| Example 307 | 3.5 | 32.2 |
| Example 317 | 0.9 | 35.8 |
| Example 377 | 5.4 | 82.9 |
| Example 379 | 2.4 | 24.7 |
| Example 387 | 116.8 | |
| Example 396 | 3.3 | 35.4 |
| Example 398 | 3 | 15.5 |
| Example 402 | 0.6 | 27.4 |
| Example 403 | 0.9 | 18.6 |
| Example 411 | 11 | 606.7 |
| Example 419 | 134.8 | |
| Example 467 | 1.8 | 3351 |
| Example 493 | 0.8 | 116.7 |
| Example 512 | 171.7 | >5000 |
| Example 563 | 660.7 | >5000 |

Example A

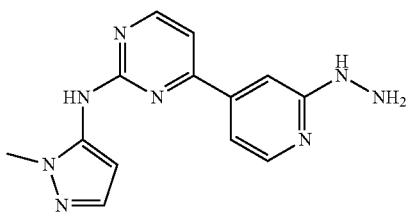 [SMILES: Cn1nccc1Nc1nccc(-c2ccnc(NN)c2)n1]

4-(2-hydrazinylpyridin-4-yl)-N-(1-methyl-1H-pyrazol-5-yl)pyrimidin-2-amine

Step 1: To a solution of anhydrous toluene and tetrahydrofuran ("THF") (4:1, 250 mL) were added 4-bromo-2- fluoropyridine 1 (30.0 g, 0.17 mol) and triisopropyl borate (38.4 g, 0.20 mol). The mixture was cooled to −78° C. under a nitrogen atmosphere. Then, n-butyllithium (80 mL, 0.20 mol) (2.5 M in hexanes) was added dropwise over 30 minutes, followed by stirring at the same temperature for an additional 30 minutes. The mixture was finally warmed up to −20° C. over 1 hour. Thin layer chromatography ("TLC") (petroleum ether ("PE"):ethyl acetate ("EtOAc")=1:1) indicated that the starting material was consumed. The reaction mixture was acidified to a pH of 2 with 3N HCl (50 mL) and then stirred at room temperature for 15 minutes. The mixture was partitioned between EtOAc (150 mL) and water (150 mL). The organic layer was isolated, washed with water, brine, dried over anhydrous $MgSO_4$, then filtered and evaporated to provide (2-fluoropyridin-4-yl)boronic acid (22.0 g, 91%) as a solid.

Step 2: To a solution of dioxane and water (5:1, 300 mL) was added (2-fluoropyridin-4-yl)boronic acid (20.0 g, 141.94 mmol), 2,4-dichloropyrimidine (22.2 g, 149.03 mmol), cesium carbonate (69.3 g, 212.90 mmol) and Pd(dppf)$Cl_2$ (5.2 g, 7.1 mmol). The reaction mixture was heated at 90° C. with stirring under a nitrogen atmosphere for 4 hours. TLC (PE:EtOAc=5:1) indicated that the starting material was consumed. The mixture was cooled to room temperature, and then the filtrate was partitioned between EtOAc (200 mL) and water (100 mL). After separation, the organic layer was washed with water, brine, dried over anhydrous $MgSO_4$, filtered, concentrated and purified by column chromatography on silica gel (PE:EtOAc=20:1 to about 5:1) to provide 2-chloro-4-(2-fluoropyridin-4-yl)pyrimidine (15.0 g, 50%) as a solid.

Step 3: To a solution of dioxane (150 mL) was added 2-chloro-4-(2-fluoropyridin-4-yl)pyrimidine (15.0 g, 72.1 mmol), 1-methyl-1H-pyrazol-5-amine (7.6 g, 79.3 mmol), cesium carbonate (35.3 g, 108.0 mmol), $Pd_2(dba)_3$ (6.6 g, 7.2 mmol) and xantphos (8.3 g, 14.4 mmol). The mixture was heated at 80° C. under a nitrogen atmosphere for 2 hours. TLC (PE:EtOAc=5:1) indicated that the starting material was consumed. The mixture was cooled to room temperature and filtered through a bed of Celite®. The filtrate was then partitioned between EtOAc (200 mL) and water (100 mL). After separation, the organic layer was washed with water, brine, dried over anhydrous $MgSO_4$, filtered, concentrated and then purified by column chromatography on silica gel (PE:EtOAc=10:1 to about 1:1) to provide 4-(2-fluoropyridin-4-yl)-N-(1-methyl-1H-pyrazol-5-yl)pyrimidin-2-amine (14.5 g, 74%) as a solid.

Step 4: To isopropanol (50 mL) was added 4-(2-fluoropyridin-4-yl)-N-(1-methyl-1H-pyrazol-5-yl)pyrimidin-2-amine (14.5 g, 53.7 mmol) and hydrazine hydrate (9.47 g, 161.1 mmol, 85%). The mixture was heated at 100° C. with stirring for 6 hours. LC/MS indicated that the starting material was consumed. The mixture was cooled to room temperature, then concentrated to give a solid residue that was triturated with cold water (50 mL) and dichloromethane (50 mL). The residual material was then dried to provide 4-(2-hydrazinylpyridin-4-yl)-N-(1-methyl-1H-pyrazol-5-yl)pyrimidin-2-amine (11.7 g, 77%) as solid. $^1$H NMR ((CD$_3$)$_2$SO, 400 MHz) δ 9.56 (s, 1H), 8.57 (d, J=5.2 Hz, 1H), 8.13 (d, J=5.2 Hz, 1H), 7.67 (s, 1H), 7.39 (s, 1H), 7.37 (m 1H), 7.13 (d, J=5.2 Hz, 1H), 6.29 (s, 1H), 4.22 (s, 2H), 3.70 (s, 3H).

Example B

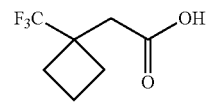

2-(1-(trifluoromethyl)cyclobutyl)acetic acid

Step 1: Lithium aluminum hydride (5.46 mL, 5.46 mmol) was slowly added to methyl 1-(trifluoromethyl)cyclobutanecarboxylate (0.829 g, 4.55 mmol) in THF (5 mL, 4.55 mmol) at 0° C. This was then stirred for 2 hours at room temperature. The mixture was quenched at 0° C. with water (1 mL), then 2N NaOH (1 mL), and then water (1 mL) again. The mixture was stirred for 5 minutes at room temperature and then filtered. The filtrate was concentrated down to give (1-(trifluoromethyl)cyclobutyl)methanol (0.70 g, 4.54 mmol, 99.8% yield).

Step 2: A mixture of (1-(trifluoromethyl)cyclobutyl)methanol (0.70 g, 4.54 mmol), methanesulfonic anhydride (0.949 g, 5.45 mmol) and triethylamine ("TEA") (d. 0.726) (0.950 mL, 6.81 mmol) in dichloromethane ("DCM") (9.08 mL, 4.54 mmol) was stirred at room temperature for 4 hours. The mixture was worked up with saturated $Na_2CO_3$ and DCM to give (1-(trifluoromethyl)cyclobutyl)methyl methanesulfonate (0.851 g, 3.66 mmol, 80.7% yield).

Step 3: A mixture of (1-(trifluoromethyl)cyclobutyl)methyl methanesulfonate (0.851 g, 3.66 mmol) and cyanosodium (0.269 g, 5.50 mmol) in DMSO (d=1.101) (7.33 mL, 3.66 mmol) was stirred at 70° C. overnight. The mixture was worked up with ether and water. The organics were extracted twice with ether and dried with brine and then $Mg_2SO_2$. This was concentrated down to give 2-(1-(trifluoromethyl)cyclobutyl)acetonitrile (0.315 g, 1.93 mmol, 52.7% yield).

Step 4: A mixture of 2-(1-(trifluoromethyl)cyclobutyl)acetonitrile (0.315 g, 1.93 mmol) in NaOH (3 mL, 18.0 mmol) and EtOH (6 mL, 1.93 mmol) was heated to reflux overnight. The mixture was worked up with 2 N HCl and DCM. The organics were extracted twice with DCM, washed with brine and dried with $Na_2SO_4$. This was then concentrated down to give 2-(1-(trifluoromethyl)cyclobutyl) acetic acid (0.169 g, 0.928 mmol, 48.1% yield). $^1$H NMR (400 MHz, CDCl$_3$) 2.50 (s, 2H), 1.99 (m, 6H).

Example C

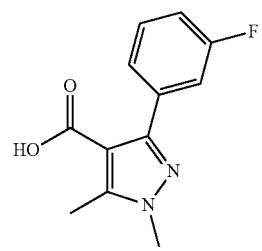 [SMILES: Cc1c(C(=O)O)c(-c2cccc(F)c2)nn1C]

3-(3-fluorophenyl)-1,5-dimethyl-1H-pyrazole-4-carboxylic acid

Step 1: (Z)-Ethyl 3-(methylamino)but-2-enoate (0.500 g, 3.49 mmol) and 3-fluorobenzonitrile (4.23 g, 34.9 mmol)

were placed in dimethylacetamide ("DMA") (2 mL) and heated at 120° C. overnight, cooled to room temperature, filtered through Celite®, worked up with water and EtOAc and then purified by column chromatography using 500:10 DCM:MeOH to give ethyl 3-(3-fluorophenyl)-1,5-dimethyl-1H-pyrazole-4-carboxylate (0.66 g, 72.06% yield).

Step 2: Ethyl 3-(3-fluorophenyl)-1,5-dimethyl-1H-pyrazole-4-carboxylate (0.50 g, 1.9 mmol) was placed in 3:1 THF:water. LiOH (5.7 mL, 5.7 mmol) was then added, and the mixture was stirred for 24 hours at room temperature. The mixture was adjusted to pH 3 with 1M HCl, and extracted with EtOAc to give 3-(3-fluorophenyl)-1,5-dimethyl-1H-pyrazole-4-carboxylic acid (0.4 g, 90% yield).

Example D

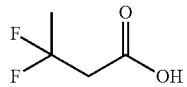

3,3-difluorobutanoic acid

A glass sealable pressure tube was charged with ethyl 3,3-difluorobutanoate (100 mg, 0.657 mmol) and a mixture of concentrated HCl:glacial acetic acid (2 mL, 1:1). The tube was capped with a Teflon cap and heated to 80° C. for 18 hours. The mixture was allowed to cool to room temperature and then to 0° C. The reaction mixture was transferred to a separatory funnel, diluted with 5% MeOH:DCM (25 mL) and washed with water (2×10 mL). The organic layer was separated, dried (MgSO$_4$), filtered and concentrated in vacuo to provide 3,3-difluorobutanoic acid (40 mg, 49.0% yield) as an oil. $^1$H NMR (400 MHz, CDCl$_3$) δ 2.988 (t, J=14.055 Hz, 2H), 1.80 (t, J=18.74 Hz, 3H).

Example E

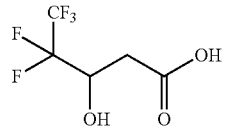

4,4,5,5,5-pentafluoro-3-hydroxypentanoic acid

Step 1: Ethyl 4,4,5,5,5-pentafluoro-3-hydroxypentanoate was prepared as described in Jagodzinska, Monika, et al. "Studies on a three-step preparation of β-fluoroalkyl acrylates from fluoroacetic esters." Tetrahedron. Vol. 63, No. 9 (2007): pp. 2042-2046. To a solution of ethyl 4,4,5,5,5-pentafluoro-3-oxopentanoate (2.00 g, 8.54 mmol) in toluene (61.0 mL, 8.54 mmol) at 0° C. under N$_2$ was added NaBH$_4$ (0.339 g, 8.97 mmol) in small portions. The mixture was then allowed to warm to ambient temperature and stirred for 3.5 hours. The mixture was re-cooled to 0° C. and quenched with 1 N HCl. The phases were separated, and the aqueous layer was extracted with EtOAc. The combined organic layers were dried (MgSO$_4$), filtered and concentrated in vacuo to provide ethyl 4,4,5,5,5-pentafluoro-3-hydroxypentanoate (1.79 g, 88.7% yield) as an oil. $^1$H NMR (400 MHz, CDCl$_3$) δ 4.602 (m, 1H), 4.23 (q, J=7.027 Hz, 2H), 3.55 (d, J=5.856 Hz, 1H), 2.75-2.73 (m, 1H), 1.301 (t, J=7.418 Hz, 3H).

Step 2: A sealable glass pressure tube was charged with a solution of crude ethyl 4,4,5,5,5-pentafluoro-3-hydroxypentanoate (400 mg, 1.69 mmol) in a mixture of acetic acid and concentrated HCl (1:1, 4 mL). The tube was capped with a Teflon screw cap, and the mixture was heated at 80° C. overnight. The mixture was cooled to 0° C., diluted with EtOAc (50 mL) and washed with water (4×). The organic layer was separated, dried (MgSO$_4$), filtered and concentrated in vacuo to provide the crude as an oil. This was dissolved in 1 N NaOH (30 mL) and washed with EtOAc (3×10 mL). The basic aqueous layer was separated, made acidic with 1 N HCl and extracted into EtOAc (3×10 mL). The acidic organics were combined, dried (MgSO$_4$), filtered and concentrated in vacuo to provide 4,4,5,5,5-pentafluoro-3-hydroxypentanoic acid (240 mg, 68% yield) as a solid. $^1$H MR (400 MHz, CDCl$_3$) δ 4.627-4.540 (m, 1H), 2.875-2.79 (m, 2H).

Example F

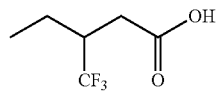

3-(trifluoromethyl)pentanoic acid

Step 1: A solution of ethyl 2-(triphenylphosphoranylidene)acetate (15 g, 44 mmol) in dichloromethane (26 mL, 40 mmol) was cooled to 0° C. and treated with 1,1,1-trifluorobutan-2-one (5 g, 40 mmol). The mixture was stirred at 0° C. for 15 minutes. The reaction mixture was concentrated in vacuo (water bath below 10° C. and vacuum at 170 Torr). With concentration Ph$_3$PO started to precipitate out. The solids were filtered off washing with Et$_2$O. The filtrate collected was treated with Et$_2$O (20 mL), and the solids formed were decanted off. The liquid isolated was subjected to fractional distillation (oil bath at 45-50° C. vacuum at 300 Torr) to provide a mixture of E and Z isomers of ethyl 3-(trifluoromethyl)pent-2-enoate. NMR (400 MHz, CDCl$_3$) δ 6.269 (s, 1H), 4.23 (q, J=7.027 Hz, 2H), 2.72-2.663 (m, 2H), 1.317 (t, J=7.027, 3H), 1.208 (t, J=7.027 Hz, 3H).

Step 2: To a suspension of 10% palladium on activated carbon (wet) (1.1 g, 1.0 mmol) in EtOH (20 mL) under N$_2$ was added a solution of E and Z isomers of ethyl 3-(trifluoromethyl)pent-2-enoate in MeOH (10 mL). The mixture was purged under N$_2$ (3 cycles) and back filled with H$_2$. The mixture was then stirred under H$_2$ balloon for 8 hours. The mixture was filtered through a Celite® pad, and the Celite® cake was washed well with additional EtOH. The filtrate collected was treated with lithium hydroxide hydrate (1.1 g, 25 mmol) in water (5 mL). The mixture was stirred at ambient temperature for 4 hours. The mixture was diluted with water (100 mL) and adjusted to pH 12 with 1 N NaOH. The mixture was washed with EtOAc (2×60 mL), and the basic aqueous layer was made acidic with 2 N HCl then partitioned with DCM (3×50 mL). The combined organic layer was dried (MgSO$_4$), filtered and concentrated in vacuo to provide 3-(trifluoromethyl)pentanoic acid as an oil. $^1$H NMR (400 MHz, CDCl$_3$) δ 2.69-2.629 (m, 2H), 2.481-2.412

(m, 1H), 1.813-1.709 (m, 1H), 1.582-1.473 (m, 1H), 1.281-1.231 (m, 1H), 1.019 (t, J=8.589 Hz, 3H).

Example G

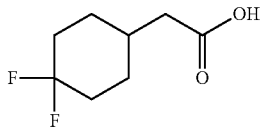

2-(4,4-difluorocyclohexyl)acetic acid

Step 1: Methyl 2-(4,4-difluorocyclohexyl)acetate was prepared according to a method described in U.S. Pat. Appl. Publ. 2008/0019978. A solution of methyl 2-(4-oxocyclohexyl)acetate (500 mg, 2.94 mmol) in dichloromethane (14688 μL, 2.94 mmol) at ambient temperature was treated with diethylamino sulfurtrifluoride ("DAST") (1164 μL, 8.81 mmol). The resulting mixture was stirred at ambient temperature for one overnight. The mixture was diluted with DCM (20 mL) and poured into ice water (10 mL). The organic layer was separated, washed with saturated NaHCO$_3$, dried (MgSO$_4$), filtered and concentrated in vacuo. The residue obtained was purified by flash chromatography on silica (Ready Sep 40 g) eluting with 10% EtOAc:hexane to provide methyl 2-(4,4-difluorocyclohexyl) acetate (520 mg, 92% yield) as an oil. $^1$H NMR (400 MHz, CDCl$_3$) δ 3.682 (s, 3H), 2.262 (d, J=7.027 Hz, 2H), 2.113-2.05 (m, 2H), 1.93-1.65 (m, 4H), 1.385-1.313 (m, 2H), 1.125 (t, J=7.027 Hz, 1H).

Step 2: 2-(4,4-Difluorocyclohexyl)acetic acid was prepared from methyl 2-(4,4-difluorocyclohexypacetate (520 mg, 2.71 mmol) according to the method described for the preparation of the same compound in U.S. Pat. Appl. Publ. 2008/0019978. LCMS (APCI) m/z 177 (M–1).

Example H

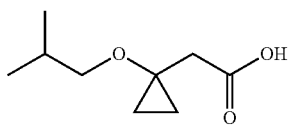

2-(1-isobutoxycyclopropyl)acetic acid

The following reaction was carried out according to the method described in Stewart, Ian C., et al. "Phosphine-Catalyzed Hydration and Hydroalkoxylation of Activated Olefins: Use of a Strong Nucleophile to Generate a Strong Base." *J. Am. Chem. Soc.* Vol. 125, No. 29 (2003): pp. 8696-97. To a solution of ethyl 2-cyclopropylideneacetate (200 mg, 1.59 mmol) in 2-methylpropan-1-ol (5 mL) was added trimethylphosphine (82.0 μL, 0.793 mmol). The reaction vessel was sealed and heated to 45° C. for 4 days. The reaction mixture was concentrated in vacuo, and the residue was dissolved in MeOH:THF (1:1, 5 mL) and treated with 2 M sodium hydroxide (1585 μL, 3.17 mmol). The mixture was stirred at room temperature for one overnight. The mixture was concentrated in vacuo, and the residue obtained was dissolved in water (20 mL) and 1 N NaOH (5 mL) The basic aqueous layer was washed with EtOAc (3×). The aqueous layer was made acidic (pH 2, with 2 N HCl) and extracted into 5% MeOH:DCM (3×). The organics were combined, dried (MgSO$_4$), filtered and concentrated in vacuo to provide 2-(1-isobutoxycyclopropyl)acetic acid (103 mg, 37.7% yield) as an oil. $^1$H NMR (400 MHz, CDCl$_3$) δ 3.275 (d, J=6.637 Hz, 2H), 2.612 (s, 2H), 1.812-1.715 (m, 1H), 0.925-0.893 (m, 2H), 0.869 (d, 0.1=6.637 Hz, 6H), 0.649-0.618 (m, 2H).

Example I

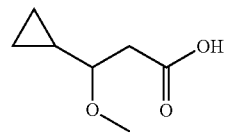

3-cyclopropyl-3-methoxypropanoic acid

Step 1: To a suspension of sodium hydride 60% in mineral oil (3.14 g, 78.5 mmol) in dry tetrahydrofuran (143 mL, 71.3 mmol) at 0° C. was added dropwise (over 20 minutes) ethyl 2-(diethoxyphosphoryl)acetate (15.7 mL, 78.5 mmol) maintaining internal temperature below 10° C. Vigorous gas evolution was observed during the addition. The resulting mixture was stirred at 0° C. for 30 minutes and treated dropwise with cyclopropanecarbaldehyde (5.0 g, 71.3 mmol). The mixture was stirred at room temperature for 1 overnight. Then saturated NH$_4$Cl (50 mL) was added to the mixture, and the layers were separated. The aqueous layer was extracted with EtOAc (2×30 mL). The combined organic layers were washed with brine (1×30 mL), dried (MgSO$_4$), filtered and concentrated in vacuo (water bath 34° C., pressure 80 Torr) and crude isolated was purified by silica gel flash chromatography (Ready Sep 80 g) eluting with 1-15% EtOAc:hexanes (10 CV) on Biotage SP1 unit to provide (E)-ethyl 3-cyclopropylacrylate (8.81 g, 62.8 mmol, 88.1% yield) as an oil. $^1$H NMR (400 MHz, CDCl$_3$) δ 6.421 (dd, J1=15.616 Hz, J2=10.151 Hz, 1H), 5.88 (d, J=15.226 Hz, 1H), 4.167 (q, J=7.027 Hz, 2H), 1.277 (t, J=7.808 Hz, 3H), 0.958-0.927 (m, 2H), 0.90-0.868 (m, 1H), 0.65-0.615 (m, 2H).

Step 2: A sealable glass pressure tube was charged with a solution of (E)-ethyl 3-cyclopropylacrylate (1.0 g, 7.13 mmol) in methanol (7.13 mL, 7.13 mmol) and trimethylphosphine (0.369 mL, 3.57 mmol). The reaction vessel was capped with a Teflon screw cap, and the reaction mixture was heated to 45° C. for 2 days. The reaction mixture was concentrated in vacuo, and the residue obtained was purified by silica gel flash chromatography (Ready Sep 80 g) eluting with 0-10% EtOAc:hexanes (10 CV) on Biotage SP1 unit to provide methyl 3-cyclopropyl-3-methoxypropanoate (260 mg, 1.64 mmol, 23.0% yield). $^1$H NMR (400 MHz, CDCl$_3$) δ 3.692 (s, 3H), 3.416 (s, 3H), 3.014-2.96 (m, 1H), 2.68-2.538 (m, 2H), 0.90-0.83 (m, 1H), 0.69-0.629 (m, 1H), 0.498-0.420 (m, 2H), 0.131-0.063 (m, 1H).

Step 3: A solution of methyl 3-cyclopropyl-3-methoxypropanoate (254 mg, 1.61 mmol) in methanol (1606 μL, 1.61 mmol) and tetrahydrofuran (6422 μL, 1.61 mmol) was treated with a solution of lithium hydroxide hydrate (135 mg, 3.21 mmol) in water (0.5 mL). The mixture was stirred at room temperature for 1 hour. The mixture was diluted with water (10 mL) and adjusted to pH 14 with 1 N NaOH. The basic aqueous layer was washed with EtOAc to remove organic impurities. Then the aqueous layer was made acidic (pH 1-2) with 1 N HCl and extracted with DCM (3×10 mL). The combined DCM layers were dried (MgSO$_4$), filtered and concentrated in vacuo to provide 3-cyclopropyl-3-methoxypropanoic acid (200 mg, 1.39 mmol, 86.4% yield) as an oil. $^1$H NMR (400 MHz, CDCl$_3$) δ 3.454 (s, 3H), 3.008-2.955 (m, 1H), 2.71-2.64 (m, 2H), 0.926-0.838 (m, 1H), 0.736-0.662 (m, 1H), 0.534-0.442 (m, 2H), 0.156-0.088 (m, 1H).

Example J

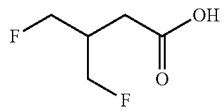

4-fluoro-3-(fluoromethyl)butanoic acid

Step 1: A solution of benzyl 2-(triphenylphosphoranylidene)acetate (19.2 g, 46.8 mmol) in dichloromethane (28.4 mL, 42.5 mmol) was cooled to 0° C. and treated with 1,3-difluoropropan-2-one (4 g, 42.5 mmol). The mixture was stirred at 0° C. and allowed to warm to ambient temperature slowly overnight. The reaction mixture was directly subjected to fractional distillation to remove DCM (oil bath 30° C., pressure at 300-170 Torr). The pot containing the product and Ph$_3$PO was cooled to 0° C., and the solid formed was filtered off. The filtrate containing the product and a small amount of Ph$_3$PO was purified by flash chromatography on silica gel (Ready Sep 80 g) eluting with a gradient of 1-15% EtOAc:hexanes (10CV) on Biotage SP1 unit to provide benzyl 4-fluoro-3-(fluoromethyl)but-2-enoate (9.25 g, 96.2% yield) as an oil. $^1$H NMR (400 MHz, CDCl$_3$) δ 7.36 (m, 5H), 6.076 (s, 1H), 5.64 (d, J=47.63 Hz, 2H), 5.17 (s, 2H), 5.14 (d, J=46.46 Hz, 2H).

Step 2: To a suspension of Wilkinson's catalyst (4 mg, 0.00432 mmol) in EtOH (50 mL) under N$_2$ was added a solution of benzyl 4-fluoro-3-(fluoromethyl)but-2-enoate (200 mg, 0.884 mmol) in EtOH (10 mL). The mixture was purged under N$_2$ (3 cycles) and back filled with H$_2$ (3 cycles). Then the reaction mixture was stirred at ambient temperature under an H$_2$ balloon. After 4 hours, the mixture was charged with additional catalyst (10 mg, 0.012 equivalents, 0.011 mmol) and stirred under H$_2$ overnight. The mixture was once again treated with additional catalyst (12 mg, 0.013 mmol, 0.0147 equivalents), purged with N$_2$ and backfilled with H$_2$ (3 cycles, new balloon). The mixture was allowed to stir at room temperature under H$_2$ for additional 24 hours. The mixture was then concentrated in vacuo, and the residue obtained was purified by flash chromatography on silica gel (Ready Sep 24 g) eluting with 0-10% EtOAc:hexanes (25CV) on Biotage SP1 unit to provide benzyl 4-fluoro-3-(fluoromethyl)butanoate (190 mg, 94.2% yield) as an oil. $^1$H NMR (400 MHz, CDCl$_3$) δ 7.373-7.328 (m, 5H), 5.142 (s, 2H), 4.52 (dd, J1=46.85 Hz, J2=5.075 Hz, 4H), 2.657-2.51 (m, 1H), 2.51-2.494 (m, 2H).

Step 3: To a suspension of 10% palladium on activated charcoal (wet) (12 mg, 0.012 mmol) in ethanol (4644 µL, 0.23 mmol) under N$_2$ was added a solution of benzyl 4-fluoro-3-(fluoromethyl)butanoate (53 mg, 0.23 mmol) in EtOH (2 mL). The reaction vessel was purged under N$_2$ (2 cycles) and back filled with H$_2$ (3 cycles). The mixture was then stirred under H$_2$ balloon for 1 hour. The mixture was purged and backfilled with N$_2$, filtered through a Celite® pad, and the filtrate collected was concentrated in vacuo to provide 4-fluoro-3-(fluoromethyl)butanoic acid (35 mg, 109% yield) as an oil. $^1$H NMR (400 MHz, CDCl$_3$) δ 9.894 (br s, 1H), 4.525 (dd, J1=46.849 Hz, J2=5.075 Hz, 4H), 2.648-2/535 (m, 1H), 2.505-2.49 (m, 2H).

Example K

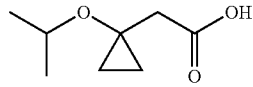

2-(1-isopropoxycyclopropyl)acetic acid

A mixture of ethyl 2-cyclopropylideneacetate (200 mg, 1.59 mmol), isopropyl alcohol ("IPA") (5 mL) and trimethylphosphine (82.0 µL, 0.793 mmol) were processed as described for the synthesis of Example H to provide 2-(1-isopropoxycyclopropyl)acetic acid (111 mg, 44.3% yield) as an oil. $^1$H NMR (400 MHz, CDCl$_3$) δ 3.961-3.899 (m, 1H), 2.601 (s, 2H), 1.178 (d, J=6.247 Hz, 6H), 0.96-0.924 (m, 2H), 0.64-0.61 (m, 2H).

Example L

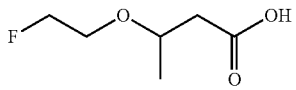

3-(2-fluoroethoxy)butanoic acid

A mixture of ethyl but-2-enoate (500 mg, 4.38 mmol), MeOH (5 mL) and trimethylphosphine (227 µL, 2.19 mmol) were processed as described for the synthesis of Example H to provide 3-(2-fluoroethoxy)butanoic acid (210 mg, 32% yield) as an oil. $^1$H NMR (400 MHz, CDCl$_3$) δ 4.002-4.581 (m, 1H), 4.483-4.461 (m, 1H), 3.98-3.625 (m, 3H), 2.676-2.575 (m, 1H), 2.509-2.457 (m, 1H), 1.274 (d, J=6.247 Hz, 3H).

Example M

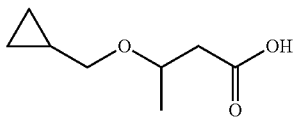

3-(cyclopropylmethoxy)butanoic acid 3-(Cyclopropylmethoxy)butanoic acid (519 mg, 75% yield) was prepared from ethyl but-2-enoate (500 mg, 4.38 mmol), cyclopropylmethanol (2 mL) and trimethylphosphine (227 μL, 2.19 mmol) followed by the treatment of NaOH as described for the synthesis of Example H. $^1$H NMR (400 MHz, CDCl$_3$) δ 3.942-3.860 (m, 1H), 3.44-3.37 (m, 1H), 3.29-3.24 (m, 1H), 2.644-2.587 (m, 1H), 2.503-2.452 (M, 1H0, 1.244 (d, J=6.247 hz, 3H), 1.126-1.002 (m, 1H), 0.563-0.530 (m, 2H), 0.222-0.197 (m, 2H).

Example N

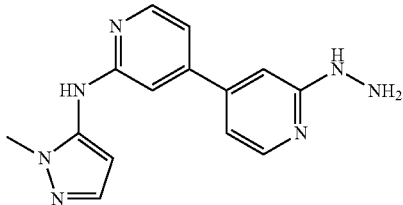 [SMILES: Cn1nccc1Nc1cc(-c2ccnc(NN)c2)ccn1]

2'-hydrazinyl-N-(1-methyl-1H-pyrazol-5-yl)-[4,4'-bipyridin]-2-amine

Step 1: 5-Amino-1-methyl-1H-pyrazole (6.25 g, 64.4 mmol) was dissolved in THF (120 ml) and treated with sodium hydride (3.51 g, 87.8 mmol). The reaction was heated to 35° C. for 30 minutes and then treated with a dimethylformamide ("DMF") solution (24 mL) of 4-bromo-2-fluoropyridine (10.3 g, 58.5 mmol). The reaction was heated to 50° C. and stirred for 1 hour. The reaction was allowed to cool and treated with water, and the organics were concentrated. The residue was diluted with ethyl acetate and washed with water and brine. The organics were dried over Na$_2$SO$_4$, filtered and concentrated. The material was purified on silica gel eluting with 30-100% ethyl acetate/hexanes followed by 25% methanol:DCM to afford 4-bromo-N-(1-methyl-1H-pyrazol-5-yl)pyridin-2-amine (6.55 g, 25.9 mmol, 44.2% yield).

Step 2: 4-Bromo-N-(1-methyl-1H-pyrazol-5-yl)pyridin-2-amine (6.91 g, 27.3 mmol) was dissolved in 4:1 acetonitrile ("ACN"):water (55 mL) and treated with 2-fluoropyridyl-4-boronic acid (4.04 g, 28.7 mmol) and potassium carbonate (11.3 g, 81.9 mmol). The reaction mixture was degassed with argon and treated with 1,1'-bis(diphenylphosphino)ferrocene palladium (II) chloride complex with dichloromethane (2.25 g, 2.73 mmol). The reaction was purged with argon for an additional 5 minutes, sealed, and heated to 90° C. The reaction was allowed to heat at this temperature for 16 hours. The reaction was cooled to ambient temperature, filtered and concentrated. The reaction was diluted with ethyl acetate and washed with water and brine. The organics were dried over sodium sulfate, filtered and concentrated. The material was purified on silica gel eluting with 30-100% acetone:hexanes to afford 2'-fluoro-N-(1-methyl-1H-pyrazol-5-yl)[4,4'-bipyridin]-2-amine (3.1 g, 11.51 mmol, 42.2% yield).

Step 3: 2'-Fluoro-N-(1-methyl-1H-pyrazol-5-yl)[4,4'-bipyridin]-2-amine (3.1 g, 11.5 mmol) was dissolved in ethanol (23 mL) and treated with hydrazine (3.61 mL, 115 mmol). The reaction was heated to 80° C. and stirred for 16 hours. The reaction was allowed to cool to ambient temperature and then concentrated. The residue was diluted with water, sonicated and filtered to afford 2'-hydrazinyl-N-(1-methyl-1H-pyrazol-5-yl)-[4,4'-bipyridin]-2-amine (2.44 g, 8.67 mmol, 75.3% yield).

Example O

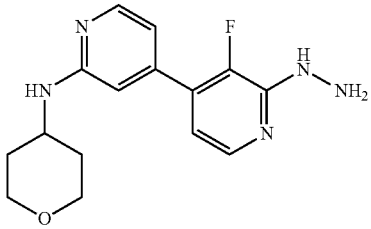 [SMILES: NNc1nccc(-c2ccnc(NC3CCOCC3)c2)c1F]

3'-fluoro-2'-hydrazinyl-N-(tetrahydro-2H-pyran-4-yl)-[4,4'-bipyridin]-2-amine

Step 1: To a solution of 4-bromo-2-fluoropyridine (5.0 g, 28.4 mmol) in DMSO (56.8 mL, 28.4 mmol) was sequentially added tetrahydro-2H-pyran-4-amine (3.30 g, 32.7 mmol) and cesium carbonate (18.5 g, 56.8 mmol). The mixture was then stirred at 80° C. for 4 hours and cooled to ambient temperature. The mixture was then poured into water and extracted into EtOAc (200 mL). The combined organics were washed with half saturated brine (50 mL), dried (MgSO$_4$), filtered and concentrated in vacuo. The crude isolated was purified by flash chromatography (Ready Sep 120 g) eluting with a gradient of 1-10% MeOH:DCM (10 CV) to provide 4-bromo-N-(tetrahydro-2H-pyran-4-yl)pyridin-2-amine (2.80 g, 38.3% yield). LCMS (APCI+) m/z 257, 259 (M+1) with one bromine isotope.

Step 2: A mixture of 4-bromo-N-(tetrahydro-2H-pyran-4-yl)pyridin-2-amine (294 mg, 1.14 mmol), (2,3-difluoropyridin-4-yl)boronic acid (200 mg, 1.26 mmol), PdCl$_2$(dppf) *dcm (47 mg, 0.057 mmol) and Na$_2$CO$_3$ 20% aqueous (1.15 mL, 2.29 mmol) in dioxane (5.7 mL, 1.14 mmol) was heated to 90° C. with stirring for 18 hours and allowed to cool to room temperature. The mixture was diluted with EtOAc (50 mL) and washed with brine (20 mL). The organic layer was dried (MgSO$_4$), filtered and concentrated in vacuo. The crude isolated was purified by flash chromatography on silica gel (Ready Sep 40 g) eluting with a gradient of 0-6% MeOH:DCM (20 CV) and then crystallized from MeOH to provide 2',3'-difluoro-N-(tetrahydro-2H-pyran-4-yl)-[4,4'-bipyridin]-2-amine (210 mg, 63.0% yield) as a solid. LCMS (APCI+) m/z 292.1 (M+1).

Step 3: To a solution of 2',3'-difluoro-N-(tetrahydro-2H-pyran-4-yl)-[4,4'-bipyridin]-2-amine (50 mg, 0.17 mmol) in 2-butanol (1.7 mL, 0.17 mmol) was added hydrazine (17 mg, 0.51 mmol). The mixture was stirred at 50° C. After 30 minutes, additional hydrazine (17 mg, 0.51 mmol) was added, and the mixture was stirred at 60° C. After 1 hour, the mixture was cooled to ambient temperature and partitioned between 5% MeOH:DCM and half saturated NaHCO$_3$. The organic layers were combined, dried (MgSO$_4$), filtered and concentrated in vacuo to provide crude 3'-fluoro-2'-hydrazinyl-N-(tetrahydro-2H-pyran-4-yl)-[4,4'-bipyridin]-2-amine (46 mg, 0.15 mmol, 88% yield) as a solid. LCMS (APCI+) m/z 304.1 (M+1).

Example P

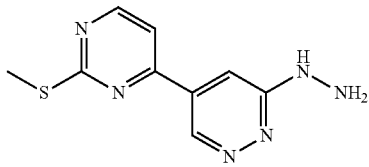 [SMILES: CSc1nccc(-c2cnnc(NN)c2)n1]

3-hydrazinyl-5-(2-(methylthio)pyrimidin-4-yl)pyridazine

Step 1: 2-Benzyl-4,5-dichloropyridazin-3(2H)-one (41 g, 63.9% yield) was prepared from 4,5-dichloropyridazin-3(2H)-one (41.5 g, 252 mmol) and (bromomethyl)benzene (43.0 g, 252 mmol) as described for the synthesis of the same compound in US 2006/0287323. $^1$H NMR (400 MHz, CDCl$_3$) δ 7.776 (s, 1H), 7.454-7.431 (m, 2H), 7.35-7.305 (m, 3H), 5.32 (s, 2H).

Step 2: 2-Benzyl-5-iodopyridazin-3(2H)-one was prepared according to the method described in Coelho, supra. A solution of 2-benzyl-4,5-dichloropyridazin-3(2H)-one (30 g, 118 mmol) in 57% hydrogen iodide (155 mL, 1176 mmol) was heated at reflux for 24 hours and allowed to cool to room temperature. The mixture was diluted with DCM (6×100 mL) and poured into ice water (200 mL), and solid Na$_2$S$_2$O$_3$ was added with stirring. The layers were separated, and the aqueous phase was extracted with DCM until there was no product left in the aqueous phase. The combined organics were washed with saturated NaHCO$_3$ (2×), brine, dried (MgSO$_4$) and concentrated in vacuo. The solid residue obtained was triturated with CH$_3$CN to provide 2-benzyl-5-iodopyridazin-3(2H)-one (28.3 g, 77.1% yield) as a solid. LCMS (APCI+) m/z 213 (M+1).

Step 3: A mixture of 2-benzyl-5-iodopyridazin-3(2H)-one (28 g, 90 mmol) and AlCl$_3$ (60 g, 449 mmol) in dry toluene (748 mL, 90 mmol) were processed according to the method described in Coelho, supra, to provide 5-iodopyridazin-3(2H)-one (12 g, 60% yield) as a solid. LCMS (APCI+) m/z 222.9 (M+1).

Step 4: To a solution of 5-iodopyridazin-3(2H)-one (5 g, 23 mmol) in N,N-dimethylformamide (45 mL, 23 mmol) was sequentially added 1-(bromomethyl)-4-methoxybenzene (4.5 g, 23 mmol) and K$_2$CO$_3$ (3.4 g, 25 mmol). The mixture was stirred at ambient temperature under N$_2$ atmosphere. After 48 hours, additional 1-(bromomethyl)-4-methoxybenzene (450 mg, 0.1 equivalent) was added, and the mixture was stirred at ambient temperature for 4 more hours. The mixture was poured into ice water (100 mL) and extracted with EtOAc (3×75 mL). The combined organic layers were washed with 2% HCl followed by brine. The organic layer was dried (MgSO$_4$), filtered and concentrated in vacuo. The residue obtained was triturated with EtOAc:hexane to provide the first batch of the product. Mother liquor was concentrated and triturated with CH$_3$CN to provide the second batch of the product. The combined batches gave 5-iodo-2-(4-methoxybenzyl)pyridazin-3(2H)-one (6.2 g, 80% yield) as a solid.

Step 5: A resealable glass pressure tube was charged with a suspension of 5-iodo-2-(4-methoxybenzyl)pyridazin-3(2H)-one (2.78 g, 8.13 mmol), 4-(dibutyl(propyl)stannyl)-2-(methylthio)pyrimidine (3.26 g, 8.13 mmol), Cu(I)I (0.155 g, 0.813 mmol) and PdCl$_2$(PPh$_3$)$_2$ (0.570 g, 0.813 mmol) in 1-methylpyrrolidin-2-one ("NMP") (16.3 mL, 8.13 mmol). The mixture was sparged with N$_2$ for 5 minutes, and the tube was sealed and stirred at 120° C. under N$_2$ for 18 hours. The mixture was cooled to ambient temperature, diluted with hot THF (100 mL), and filtered. The filtrate was concentrated in vacuo, and the resulting residue containing NMP was allowed to stand at room temperature for 5 hours. The solid formed was filtered, washed with CH$_3$CN (5 mL) to provide the first batch of the desired product (1.3 g). Mother liquor was concentrated, and the resulting residue was dissolved in 5% MeOH:DCM (150 mL) and washed with 0.1% HCl (50 mL) followed by saturated NaHCO$_3$ (30 mL) and brine (30 mL). The organics were dried (MgSO$_4$), filtered and concentrated in vacuo. The residue obtained was crystallized from EtOAc to provide the second batch of the desired product. A third batch was also obtained by crystallizing the second mother liquor with CH$_3$CN. The combined batches gave 2-(4-methoxybenzyl)-5-(2-(methylthio)pyrimidin-4-yl)pyridazin-3(2H)-one (2.4 g, 86.8% yield) as a solid. LCMS (APCI+) m/z 341.0 (M+1).

Step 6: To a mixture of 2-(4-methoxybenzyl)-5-(2-(methylthio)pyrimidin-4-yl)pyridazin-3(2H)-one (1.78 g, 5.234 mmol) in anisole (10 mL) was carefully added TFA (30 mL) and concentrated H$_2$SO$_4$ (5 mL). The resulting mixture was heated at 120° C. for 3 hours. The mixture was cooled to room temperature and concentrated in vacuo. The residue obtained was dissolved in ice water and very carefully poured into a solution of ice cold saturated NaHCO$_3$ solution. The pH of the mixture was adjusted to 7.5 with additional saturated NaHCO$_3$ and diluted with additional water (total volume was about 500 mL). The resulting suspension was stirred at ambient temperature for overnight. The solid formed was filtered, washed with additional water (20 mL) then with CH$_3$CN (5 mL) and dried to provide 5-(2-(methylthio)pyrimidin-4-yl)pyridazin-3(2H)-one (1.1 g, 95.5% yield) as a solid. LCMS (APCI+) m/z 221.1 (M+1).

Step 7: A mixture of 5-(2-(methylthio)pyrimidin-4-yl)pyridazin-3(21)-one (205 mg, 0.931 mmol) and POCl$_3$ (5 mL) was stirred at 50° C. for 1 hour and concentrated in vacuo. The residue obtained was dissolved in 5% MeOH:DCM and washed with saturated NaHCO$_3$ (2×) followed by brine. The organics were dried (MgSO$_4$), filtered and concentrated under reduced pressure. The crude isolated was purified by flash chromatography on silica gel (Ready Sep 40 g) eluting with 10-45% EtOAc:hexanes to provide 3-chloro-5-(2-(methylthio)pyrimidin-4-yl)pyridazine (138 mg, 62.1% yield) as a solid. LCMS (APCI+) m/z 239.0 (M+1).

Step 8: A mixture of 3-chloro-5-(2-(methylthio)pyrimidin-4-yl)pyridazine (136 mg, 0.570 mmol) and hydrazine monohydrate (143 mg, 2.85 mmol) in 2-butanol (3798 μL, 0.570 mmol) was heated at 78° C. for 1.5 hours. The solid formed with cooling was dissolved in DCM (100 mL) and washed with saturated aqueous NaHCO$_3$ (2×20 mL) and brine. The organic layer was dried (MgSO$_4$), filtered and concentrated in vacuo to provide the crude 3-hydrazinyl-5-(2-(methylthio)pyrimidin-4-yl)pyridazine (94 mg, 70.4% yield) as a solid. LCMS (APCI+) m/z 235.1 (M+1).

Example 1

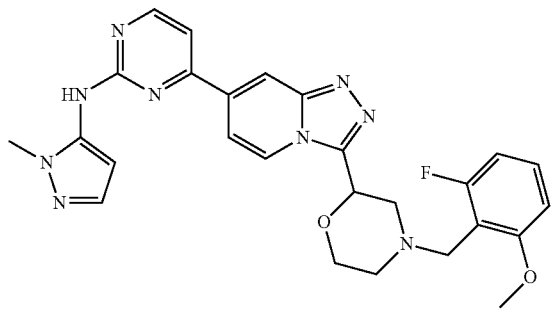 [SMILES: COc1cccc(F)c1CN1CCOC(c2nnc3cc(-c4ccnc(Nc5ccnn5C)n4)ccn23)C1]

4-(3-(4-(2-fluoro-6-methoxybenzyl)morpholin-2-yl)-[1,2,4]triazolo[4,3-a]pyridin-7-yl)-N-(1-methyl-1H-pyrazol-5-yl)pyrimidin-2-amine Step 1: 4-(2-Hydrazinylpyridin-4-yl)-N-(1-methyl-1H-pyrazol-5-yl)pyrimidin-2-amine (0.40 g, 1.42 mmol) and tert-butyl 2-formylmorpholine-4-carboxylate (0.305 g, 1.42 mmol) were placed in EtOH (5 mL) and stirred at room temperature overnight. This was concentrate to dryness and suspended in DCM. Iodobenzene diacetate (0.593 g, 1.84 mmol) was added, and the mixture was stirred at room temperature for 3 hours. This was poured into water, and the organics were extracted with DCM. The combined organic fractions were dried with $MgSO_4$, filtered, and concentrated to give the crude product, which was purified by column chromatography (500:15-500:25 DCM:MeOH) to give tert-butyl 2-(7-(2-((1-methyl-1H-pyrazol-5-yl)amino)pyrimidin-4-yl)-[1,2,4]triazolo[4,3-a]pyridin-3-yl)morpholine-4-carboxylate (0.200 g, 29.6% yield).

Step 2: tert-Butyl 2-(7-(2-((1-methyl-1H-pyrazol-5-yl)amino)pyrimidin-4-yl)-[1,2,4]triazolo[4,3-a]pyridin-3-yl)morpholine-4-carboxylate (0.200 g, 0.41883 mmol) was placed in DCM. HCl (0.698 mL, 4.188 mmol) in IPA (6 M) was added, and this was stirred for 3 hours at room temperature. The reaction was then concentrated to dryness to give N-(1-methyl-1H-pyrazol-5-yl)-4-(3-(morpholin-2-yl)-[1,2,4]triazolo[4,3-a]pyridin-7-yl)pyrimidin-2-amine hydrochloride (0.166 g, 95.766% yield).

Step 3: N-(1-Methyl-1H-pyrazol-5-yl)-4-(3-(morpholin-2-yl)-[1,2,4]triazolo[4,3-a]pyridin-7-yl)pyrimidin-2-amine hydrochloride (0.075 g, 0.181 mmol), 2-fluoro-6-methoxybenzaldehyde (0.0335 g, 0.217 mmol), $NaBH(OAc)_3$ (0.0576 g, 0.272 mmol), N,N-diisopropylethylamine ("DIEA") (d 0.742) (0.0947 mL, 0.544 mmol) was placed in THF (5 mL) and stirred at room temperature for 24 hours. The mixture was poured into water and extracted with DCM. The combined organic fractions were dried with $MgSO_4$, filtered, and concentrated to give the crude product, which was purified by column chromatography (500:25 DCM:MeOH) to give 4-(3-(4-(2-fluoro-6-methoxybenzyl)morpholin-2-yl)-[1,2,4]triazolo[4,3-a]pyridin-7-yl)-N-(1-methyl-1H-pyrazol-5-yl)pyrimidin-2-amine (0.002 g, 2.1%). $^1$H NMR (400 MHz, $CDCl_3$) 8.55 (d, 1H), 8.46 (d, 1H), 8.37 (s, 1H), 7.50 (m, 2H), 7.25 (m, 1H), 6.99 (s, 1H), 6.70 (s, 2H), 6.35 (s, 1H), 5.23 (d, 1H), 3.90 (m, 10H), 3.41 (d, 1H), 2.85 (m, 2H), 2.50 (m, 1H), 1.25 (m, 1H). LCMS (APCI+) m/z=516.2.

Example 2

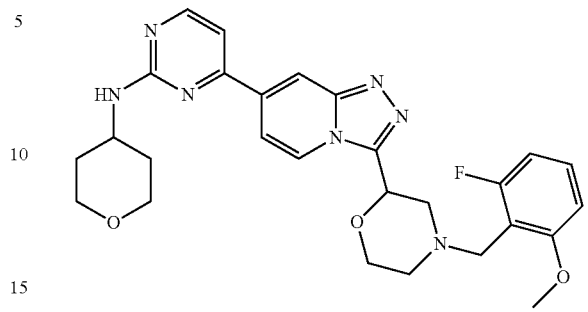

4-(3-(4-(2-fluoro-6-methoxybenzyl)morpholin-2-yl)-[1,2,4]triazolo[4,3-a]pyridin-7-yl)-N-(tetrahydro-2H-pyran-4-yl)pyrimidin-2-amine 4-(3-(4-(2-Fluoro-6-methoxybenzyl)morpholin-2-yl)-[1,2,4]triazolo[4,3-a]pyridin-7-yl)-N-(tetrahydro-2H-pyran-4-yl)pyrimidin-2-amine (0.022 g, 24% yield) was made according to the procedure of Example 1, substituting 4-(2-hydrazinylpyridin-4-yl)-N-(tetrahydro-2H-pyran-4-yl)pyrimidin-2-amine for 4-(2-hydrazinylpyridin-4-yl)-N-(1-methyl-1H-pyrazol-5-yl)pyrimidin-2-amine. $^1$H NMR (400 MHz, $CDCl_3$) 8.43 (m, 3H), 7.49 (d, 1H), 7.23 (m, 1H), 7.02 (d, 1H), 6.71 (m, 1H), 5.17 (d, 1H), 4.16 (s, 1H), 4.03 (d, 1H), 3.86 (s, 3H), 3.81 (s, 1H), 3.59 (t, 2H), 3.42 (d, 1H), 2.86 (m, 2H), 2.51 (m, 1H), 2.09 (d, 2H), 1.59 (m, 4H). LCMS (APCI+) m/z=520.2.

Example 3

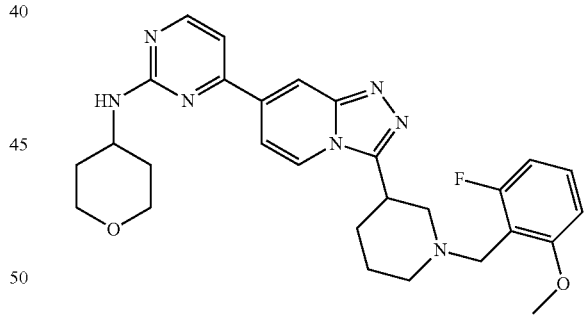

4-(3-(1-(2-fluoro-6-methoxybenzyl)piperidin-3-yl)-[1,2,4]triazolo[4,3-a]pyridin-7-yl)-N-(tetrahydro-2H-pyran-4-yl)pyrimidin-2-amine 4-(3-(1-(2-Fluoro-6-methoxybenzyl)piperidin-3-yl)-[1,2,4]triazolo[4,3-a]pyridin-7-yl)-N-(tetrahydro-2H-pyran-4-yl)pyrimidin-2-amine (0.022 g, 24% yield) was made according the procedures of Examples 1 and 2, substituting tert-butyl 3-formylpiperidine-1-carboxylate for tert-butyl 2-formylmorpholine-4-carboxylate. $^1$H NMR (400 MHz, $CDCl_3$) 8.41 (d, 2H), 8.06 (d, 1H), 7.52 (d, 1H), 7.22 (m, 1H), 7.02 (d, 2H), 6.69 (t, 2H), 5.18 (d, 1H), 4.17 (s, 1H), 4.03 (d, 1H), 3.82 (s, 3H), 3.60 (t, 2H), 3.45 (s, 1H), 3.28 (d, 1H), 3.09 (d, 1H), 2.64 (m, 1H), 2.29 (s, 1H), 2.10 (d, 3H), 1.86 (s, 3H), 1.61 (m, 3H). LCMS (APCI+) m/z=518.2.

Example 4

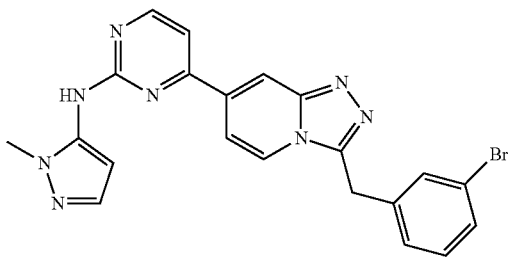 [SMILES: Cn1nccc1Nc1nccc(-c2ccn3c(Cc4cccc(Br)c4)nnc3c2)n1]

4-(3-(3-bromobenzyl)-[1,2,4]triazolo[4,3-a]pyridin-7-yl)-N-(1-methyl-1H-pyrazol-5-yl)pyrimidin-2-amine A mixture of 4-(2-hydrazinylpyridin-4-yl)-N-(1-methyl-1H-pyrazol-5-yl)pyrimidin-2-amine (0.080 g, 0.283 mmol), 2-(3-bromophenyl)acetic acid (0.0609 g, 0.283 mmol), 2,2,2-trichloroacetonitrile (0.114 mL, 1.134 mmol), PPh$_3$ (0.223 g, 0.850 mmol) and Hunig's base (0.0937 mL, 0.567 mmol) in DCM (0.945 mL, 0.283 mmol) was heated to 150° C. for 4 minutes in the microwave. The mixture was purified on a column and then further purified on preparative HPLC to give 4-(3-(3-bromobenzyl)-[1,2,4]triazolo[4,3-a]pyridin-7-yl)-N-(1-methyl-1H-pyrazol-5-yl)pyrimidin-2-amine (0.011 g, 0.0238 mmol, 8.41% yield). $^1$H NMR (400 MHz, CDCl$_3$) 8.55 (d, 1H), 8.40 (s, 1H), 7.77 (d, 1H), 7.50 (d, 1H), 7.47 (dd, 1H), 7.42 (m, 2H), 7.27 (d, 1H), 7.20 (d, 2H), 6.94 (s, 1H), 6.33 (d, 1H), 4.56 (s, 2H), 3.81 (s, 3H). LCMS (APCI+) m/z=461.1, 463.1 (one bromine).

Example 5

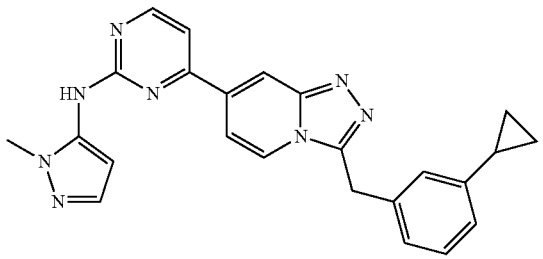 [SMILES: Cn1nccc1Nc1nccc(-c2ccn3c(Cc4cccc(C5CC5)c4)nnc3c2)n1]

4-(3-(3-cyclopropylbenzyl)-[1,2,4]triazolo[4,3-a]pyridin-7-yl)-N-(1-methyl-1H-pyrazol-5-yl)pyrimidin-2-amine A mixture of 4-(3-(3-bromobenzyl)-[1,2,4]triazolo[4,3-a]pyridin-7-yl)-N-(1-methyl-1H-pyrazol-5-yl)pyrimidin-2-amine (0.050 g, 0.11 mmol), cyclopropylzinc(II) bromide (0.65 mL, 0.33 mmol), Pd(OAc)$_2$ (0.0024 g, 0.011 mmol) and S-Phos (0.0089 g, 0.022 mmol) in THF was stirred at 90° C. overnight. The mixture was purified on a column using DCM:MeOH:NH$_4$OH (90:10:1) and then further purified on preparative HPLC to give 4-(3-(3-cyclopropylbenzyl)-[1,2,4]triazolo[4,3-a]pyridin-7-yl)-N-(1-methyl-1H-pyrazol-5-yl)pyrimidin-2-amine (0.0071 g, 0.014 mmol, 13% yield). $^1$H NMR (400 MHz, CDCl$_3$) 8.89 (s, 1H), 8.56 (d, 1H), 7.97 (d, 1H), 7.68 (d, 1H), 7.62 (d, 1H), 7.50 (d, 1H), 7.26 (d, 1H), 7.23 (d, 1H), 7.01 (d, 2H), 6.96 (d, 1H), 6.49 (d, 1H), 4.58 (s, 2H), 3.90 (s, 3H), 1.84 (m, 1H), 0.97 (m, 2H), 0.66 (m, 2H). LCMS (APCI+) m/z=423.2.

Example 6

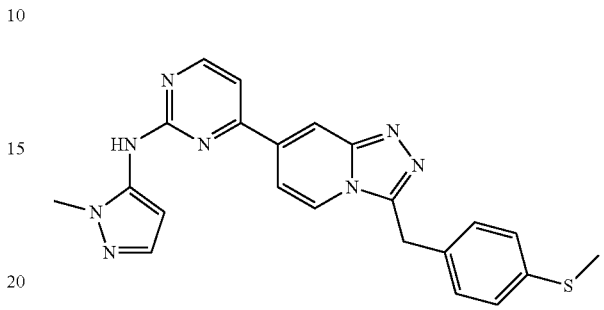

N-(1-methyl-1H-pyrazol-5-yl)-4-(3-(4-(methylthio)benzyl)-[1,2,4]triazolo[4,3-a]pyridin-7-yl)pyrimidin-2-amine Step 1: A mixture of 4-(2-hydrazinylpyridin-4-yl)-N-(1-methyl-1H-pyrazol-5-yl)pyrimidin-2-amine (0.050 g, 0.177 mmol), 1H-benzo[d][1,2,3]triazol-1-ol (0.0239 g, 0.177 mmol), 2-(4-(methylthio)phenyl)acetic acid (0.0339 g, 0.186 mmol), N1-((ethylimino)methylene)-N3,N3-dimethylpropane-1,3-diamine hydrochloride (0.034 g, 0.177 mmol) and Hunig's base (0.0617 mL, 0.354 mmol) in DMF (1 mL, 0.177 mmol) was stirred overnight at room temperature. The mixture of N'-(4-(2-((1-methyl-1H-pyrazol-5-yl)amino)pyrimidin-4-yl)pyridin-2-yl)-2-(4-(methylthio)phenyl)acetohydrazide was concentrated down and taken into the next step crude.

Step 2: A mixture of N'-(4-(2-((1-methyl-1H-pyrazol-5-yl)amino)pyrimidin-4-yl)pyridin-2-yl)-2-(4-(methylthio)phenyl)acetohydrazide (0.08 g, 0.179 mmol) in acetic acid (1 mL) was heated to 180° C. for 10 minutes in the microwave. The mixture was concentrated down and purified on a column using DCM:MeOH:NH$_4$OH (90:10:1). The product was further purified on preparative HPLC to give N-(1-methyl-1H-pyrazol-5-yl)-4-(3-(4-(methylthio)benzyl)-[1,2,4]triazolo[4,3-a]pyridin-7-yl)pyrimidin-2-amine (0.0301 g, 0.0573 mmol, 32.0% yield). $^1$H NMR (400 MHz, CDCl$_3$) 8.83 (s, 1H), 8.56 (d, 1H), 7.96 (d, 1H), 7.67 (d, 1H), 7.61 (d, 1H), 7.47 (d, 1H), 7.20 (m, 4H), 6.43 (d, 1H), 4.57 (s, 2H), 3.90 (s, 3H), 2.46 (s, 3H). LCMS (APCI+) m/z=429.2.

Example 7

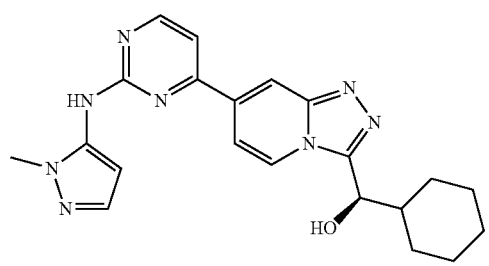 [SMILES: Cn1nccc1Nc1nccc(-c2ccn3c([C@H](O)C4CCCCC4)nnc3c2)n1]

(R)-cyclohexyl(7-(2-((1-methyl-1H-pyrazol-5-yl)amino)pyrimidin-4-yl)-[1,2,4]triazolo[4,3-a]pyridin-3-yl)methanol (R)-Cyclohexyl(7-(2-((1-methyl-1H-pyrazol-5-yl)amino)pyrimidin-4-yl)-[1,2,4]triazolo[4,3-a]pyridin-3-yl)methanol (0.0322 g, 0.0642 mmol, 36.7% yield) was made according to the procedure of Example 6, substituting (R)-2-cyclohexyl-2-hydroxyacetic acid for 2-(4-(methylthio)phenyl)acetic acid. $^1$H NMR (400 MHz, CDCl$_3$) 8.85 (d, 2H), 8.61 (d, 1H), 7.78 (dd, 1H), 7.65 (d, 1H), 7.52 (d, 1H), 6.59 (d, 1H), 5.16 (d, 1H), 3.95 (s, 3H), 2.05 (m, 2H), 1.84 (m, 1H), 1.70 (m, 2H), 1.43 (m, 1H), 1.20 (m, 4H), 1.10 (m, 1H). LCMS (APCI+) m/z=405.2.

Example 8

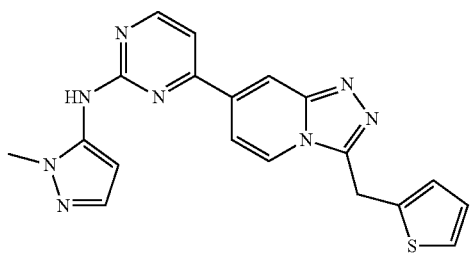 [SMILES: Cn1nccc1Nc1nccc(-c2ccn3c(Cc4cccs4)nnc3c2)n1]

N-(1-methyl-1H-pyrazol-5-yl)-4-(3-(thiophen-2-ylmethyl)-[1,2,4]triazolo[4,3-a]pyridin-7-yl)pyrimidin-2-amine N-(1-Methyl-1H-pyrazol-5-yl)-4-(3-(thiophen-2-ylmethyl)-[1,2,4]triazolo[4,3-a]pyridin-7-yl)pyrimidin-2-amine (0.035 g, 0.090 mmol, 46% yield) was made according to the procedure of Example 6, substituting 2-(thiophen-2-yl)acetic acid for 2-(4-(methylthio)phenyl)acetic acid. $^1$H NMR (400 MHz, CDCl$_3$) 8.80 (s, 1H), 8.58 (d, 2H), 8.07 (d, 1H), 7.66 (d, 1H), 7.59 (m, 1H), 7.44 (d, 1H), 7.26 (dd, 1H), 6.97 (m, 2H), 6.50 (d, 1H), 4.82 (s, 2H), 3.89 (s, 3H). LCMS (APCI+) m/z=389.1.

Example 9

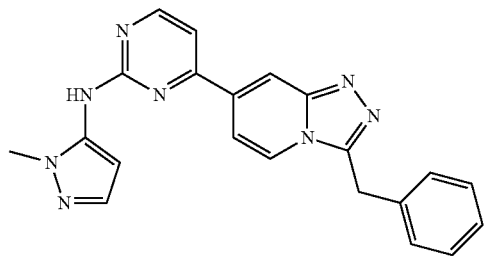 [SMILES: Cn1nccc1Nc1nccc(-c2ccn3c(Cc4ccccc4)nnc3c2)n1]

4-(3-benzyl-[1,2,4]triazolo[4,3-a]pyridin-7-yl)-N-(1-methyl-1H-pyrazol-5-yl)pyrimidin-2-amine A mixture of 4-(2-hydrazinylpyridin-4-yl)-N-(1-methyl-1H-pyrazol-5-yl)pyrimidin-2-amine (0.050 g, 0.1771 mmol) and 2-phenylacetaldehyde (0.0238 mL, 0.213 mmol) in ethanol (0.886 mL, 0.177 mmol) was stirred overnight at room temperature. This was concentrated down and taken up in DCM. Iodobenzene diacetate (0.0690 mL, 0.2302 mmol) was then added, and this was stirred at room temperature for 3 hours. TLC showed that the reaction was complete. The mixture was worked up with DCM and water. The organics were extracted with DCM, washed with brine and dried with Na$_2$SO$_4$. This was then concentrated down and purified on a column using DCM:MeOH:NH$_4$OH (90:10:1) and then purified on preparative HPLC to give 4-(3-benzyl-[1,2,4]triazolo[4,3-a]pyridin-7-yl)-N-(1-methyl-1H-pyrazol-5-yl)pyrimidin-2-amine (0.007 g, 0.0183 mmol, 10.33% yield). $^1$H NMR (400 MHz, CDCl$_3$) 8.54 (d, 1H), 8.39 (s, 1H), 7.76 (d, 1H), 7.50 (d, 1H), 7.41 (d, 1H), 7.33 (m, 2H), 7.29 (m, 1H), 7.25, (m, 2H), 6.89 (s, 1H), 6.33 (d, 1H), 4.60 (s, 2H), 3.80 (s, 3H). LCMS (APCI+) m/z=383.2.

Example 10

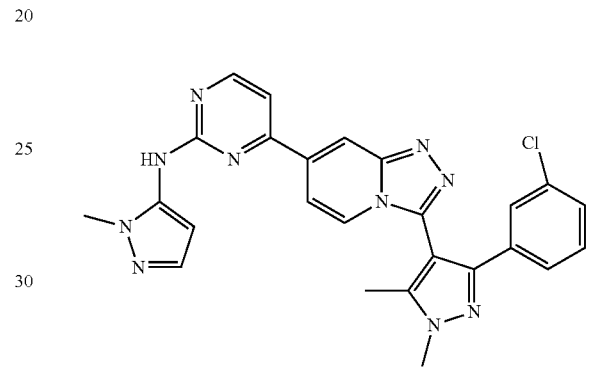

4-(3-(3-(3-chlorophenyl)-1,5-dimethyl-1H-pyrazol-4-yl)-[1,2,4]triazolo[4,3-a]pyridin-7-yl)-N-(1-methyl-1H-pyrazol-5-yl)pyrimidin-2-amine 4-(3-(3-(3-Chlorophenyl)-1,5-dimethyl-1H-pyrazol-4-yl)-[1,2,4]triazolo[4,3-a]pyridin-7-yl)-N-(1-methyl-1H-pyrazol-5-yl)pyrimidin-2-amine (0.0082 g, 0.0138 mmol, 9.74% yield) was made according to the procedure of Example 4, substituting 3-(3-chlorophenyl)-1,5-dimethyl-1H-pyrazole-4-carboxylic acid for 2-(3-bromophenyl)acetic acid. $^1$H NMR (400 MHz, CDCl$_3$) 8.93 (s, 1H), 8.56 (d, 1H), 7.63 (m, 1H), 7.51 (m, 6H), 7.11 (t, 1H), 6.98 (d, 1H), 6.52 (m, 1H), 4.00 (s, 3H), 3.91 (s, 3H), 2.42 (s, 3H). LCMS (APCI+) m/z=497.1.

Example 11

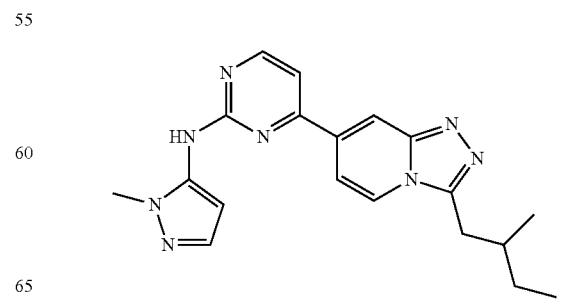

N-(1-methyl-1H-pyrazol-5-yl)-4-(3-(2-methylbutyl)-[1,2,4]triazolo[4,3-a]pyridin-7-yl)pyrimidin-2-amine N-(1-Methyl-1H-pyrazol-5-yl)-4-(3-(2-methylbutyl)-[1,2,4]triazolo[4,3-a]pyridin-7-yl)pyrimidin-2-amine (0.0189 g, 0.0521 mmol, 36.8% yield) was made according to the procedure of Example 4, substituting 3-methylpentanoic acid for 2-(3-bromophenyl)acetic acid. ¹H NMR (400 MHz, CDCl₃) 8.55 (d, 1H), 8.39 (s, 1H), 7.97 (d, 1H), 7.53 (m, 2H), 7.29 (d, 1H), 7.08 (s, 1H), 6.36 (m, 1H), 3.83 (s, 3H), 3.12 (m, 1H), 2.96 (m, 1H), 2.09 (m, 1H), 1.51 (m, 1H), 1.35 (m, 1H), 0.99 (m, 6H). LCMS (APCI+) m/z=363.2.

Example 12

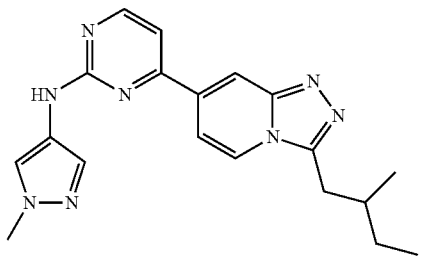 [SMILES: CCC(C)Cc1nnc2cc(-c3ccnc(Nc4cnn(C)c4)n3)ccn12]

N-(1-methyl-1H-pyrazol-4-yl)-4-(3-(2-methylbutyl)-[1,2,4]triazolo[4,3-a]pyridin-7-yl)pyrimidin-2-amine A mixture of 4-(2-hydrazinylpyridin-4-yl)-N-(1-methyl-1H-pyrazol-4-yl)pyrimidin-2-amine (0.040 g, 0.142 mmol), 3-methylpentanoic acid (0.0182 mL, 0.142 mmol), 2,2,2-trichloroacetonitrile (0.0568 mL, 0.567 mmol), PPh₃ (0.111 g, 0.425 mmol) and Hunig's base (0.0468 mL, 0.283 mmol) in DCM (0.945 mL, 0.142 mmol) was heated to 150° C. for 5 minutes in the microwave. This was worked up with DCM and water. The organics were extracted twice with DCM, washed with brine and dried with Na₂SO₄. This was then purified on a column using DCM:MeOH:NH₄OH (90:10:1). The product was further purified on preparative HPLC to give N-(1-methyl-1H-pyrazol-4-yl)-4-(3-(2-methylbutyl)-[1,2,4]triazolo[4,3-a]pyridin-7-yl)pyrimidin-2-amine (0.0286 g, 0.0622 mmol, 43.9% yield). ¹H NMR (400 MHz, CDCl₃) 8.84 (s, 1H), 8.34 (s, 1H), 8.16 (d, 1H), 7.83 (m, 3H), 7.33 (d, 1H), 3.96 (s, 3H), 3.18 (m, 1H), 3.01 (m, 1H), 2.10 (m, 1H), 1.52 (m, 1H), 1.38 (m, 1H), 1.01 (m, 6H). LCMS (APCI+) m/z=363.2.

Example 13

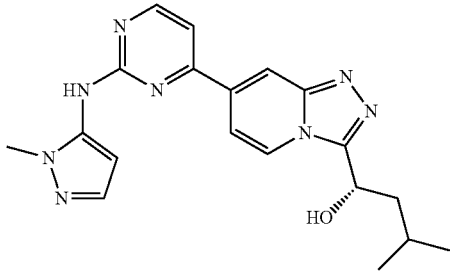 [SMILES: CC(C)C[C@H](O)c1nnc2cc(-c3ccnc(Nc4ccnn4C)n3)ccn12]

(S)-3-methyl-1-(7-(2-((1-methyl-1H-pyrazol-5-yl)amino)pyrimidin-4-yl)-[1,2,4]triazolo[4,3-a]pyridin-3-yl)butan-1-ol (S)-3-Methyl-1-(7-(2-((1-methyl-1H-pyrazol-4-yl)amino)pyrimidin-4-yl)-[1,2,4]triazolo[4,3-a]pyridin-3-yl)butan-1-ol (0.0396 g, 0.0833 mmol, 44.6% yield) was made according to the procedure of Example 6, substituting (S)-2-hydroxy-4-methylpentanoic acid for 2-(4-(methylthio)phenyl)acetic acid. ¹H NMR (400 MHz, CDCl₃) 8.89 (s, 1H), 8.85 (d, 1H), 8.62 (d, 1H), 7.84 (dd, 1H), 7.69 (d, 1H), 7.58 (d, 1H), 6.61 (d, 1H), 5.46 (m, 1H), 3.97 (s, 3H), 2.09 (m, 1H), 1.92 (m, 2H), 1.03 (m, 6H). LCMS (APCI+) m/z=379.2.

Example 14

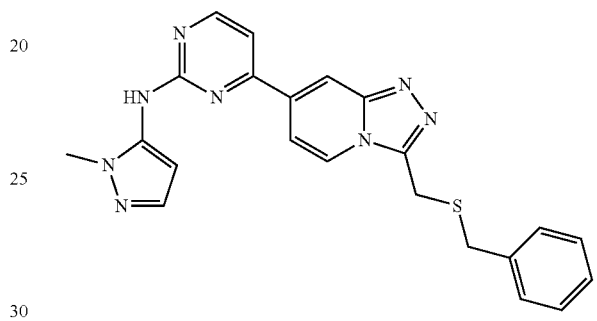

4-(3-((benzylthio)methyl)-[1,2,4]triazolo[4,3-a]pyridin-7-yl)-N-(1-methyl-1H-pyrazol-5-yl)pyrimidin-2-amine 4-(3-((Benzylthio)methyl)-[1,2,4]triazolo[4,3-a]pyridin-7-yl)-N-(1-methyl-1H-pyrazol-5-yl)pyrimidin-2-amine (0.0428 g, 0.0814 mmol, 40.4% yield) was made according to the procedure of Example 6, substituting 2-(4-(methylthio)phenyl)acetic acid for (2-(benzylthio)acetic acid. ¹H NMR (400 MHz, CDCl₃) 8.79 (s, 1H), 8.59 (d, 1H), 8.23 (d, 1H), 7.74 (d, 1H), 7.65 (d, 1H), 7.51 (d, 1H), 7.20 (m, 5H), 6.56 (d, 1H), 4.19 (s, 2H), 3.94 (s, 3H), 3.63 (s, 2H). LCMS (APCI+) m/z=429.2.

Example 15

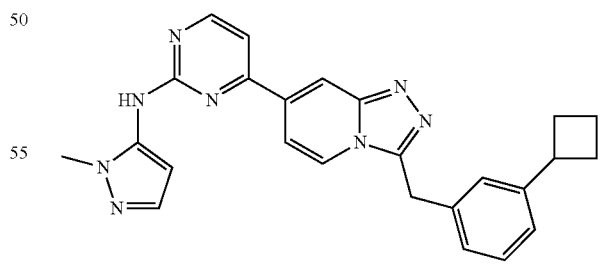

4-(3-(3-cyclobutylbenzyl)-[1,2,4]triazolo[4,3-a]pyridin-7-yl)-N-(1-methyl-1H-pyrazol-5-yl)pyrimidin-2-amine 4-(3-(3-Cyclobutylbenzyl)-[1,2,4]triazolo[4,3-a]pyridin-7-yl)-N-(1-methyl-1H-pyrazol-5-yl)pyrimidin-2-amine was made according to the procedure of Example 5, substituting cyclobutylzinc(II) bromide for cyclopropylzinc(II) bromide. LCMS (APCI+) m/z=437.2.

Example 16

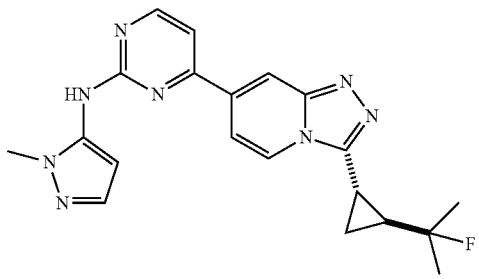

4-(3-((1S*,2S*)-2-(2-fluoropropan-2-yl)cyclopropyl)-[1,2,4]triazolo[4,3-a]pyridin-7-yl)-N-(1-methyl-1H-pyrazol-5-yl)pyrimidin-2-amine Step 1: Methylmagnesium bromide (0.249 mL, 0.748 mmol) was added to (1S,2S)-ethyl 2-(7-(2-((1-methyl-1H-pyrazol-5-yl)amino)pyrimidin-4-yl)-[1,2,4]triazolo[4,3-a]pyridin-3-yl)cyclopropanecarboxylate (0.072 g, 0.178 mmol) in ether (1.78 mL, 0.178 mmol) at 0° C. The mixture was then stirred at room temp for 30 minutes. This was then quenched with NH₄Cl at 0° C. The mixture was worked up with EtOAc and water. The organics were extracted with EtOAc twice, washed with brine and dried with Na₂SO₄. This was then purified on a column using DCM:MeOH:NH₄ (90:10:1) and further purified on preparative HPLC to give 2-((1S*,2S*)-2-(7-(2-((1-methyl-1H-pyrazol-5-yl)amino)pyrimidin-4-yl)-[1,2,4]triazolo[4,3-a]pyridin-3-yl)cyclopropyl)propan-2-ol (0.0267 g, 0.0548 mmol, 30.8% yield). LCMS (APCI+) m/z=391.2.

Step 2: DAST (0.00690 mL, 0.0564 mmol) was added to 2-((1S*,2S*)-2-(7-(2-((1-methyl-1H-pyrazol-5-yl)amino)pyrimidin-4-yl)-[1,2,4]triazolo[4,3-a]pyridin-3-yl)cyclopropyl)propan-2-ol (0.020 g, 0.051 mmol) in DCM (0.17 mL, 0.051 mmol) at −78° C. This was stirred for 1 hour. This was then quenched with saturated NaHCO₃ and worked up with DCM and water. The organics were extracted with DCM, washed with brine and dried with Na₂SO₄. This was then purified on a column using DCM:MeOH:NH₄ (90:10:1) and further purified on a preparative HPLC to give 4-(3-((1S*,2S*)-2-(2-fluoropropan-2-yl)cyclopropyl)-[1,2,4]triazolo[4,3-a]pyridin-7-yl)-N-(1-methyl-1H-pyrazol-5-yl)pyrimidin-2-amine (0.0106 g, 0.0217 mmol, 42.3% yield). LCMS (APCI+) m/z=393.2.

Example 17

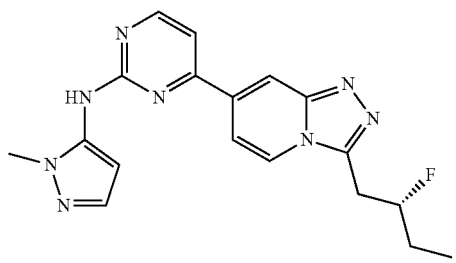

(R)-4-(3-(2-fluorobutyl)-[1,2,4]triazolo[4,3-a]pyridin-7-yl)-N-(1-methyl-1H-pyrazol-5-yl)pyrimidin-2-amine Step 1: 4-(2-Hydrazinylpyridin-4-yl)-N-(1-methyl-1H-pyrazol-5-yl)pyrimidin-2-amine (80 mg, 0.28 mmol) was dissolved in DMF (4 mL) and treated with (S)-3-hydroxypentanoic acid (40.1 mg, 0.34 mmol), 1-(3-dimethylaminopropyl)-3-ethylcarbodiimidehydrochloride (59.76 mg, 0.3117 mmol), 1-hydroxybenzotriazole (42.12 mg, 0.3117 mmol), and N,N-diisopropylethylamine (74.0402 μL, 0.425074 mmol). The mixture was stirred at room temperature for 1 hour and LC/MS showed complete conversion to the desired product. The mixture was diluted with water, and the aqueous layer was extracted with 20% IPA:DCM, then dried, filtered and concentrated. The crude product was taken forward to the next step.

Step 2: A solution of (S)-3-hydroxy-N'-(4-(2-((1-methyl-1H-pyrazol-5-yl)amino)pyrimidin-4-yl)pyridin-2-yl)pentanehydrazide (108 mg, 0.282 mmol) in acetic acid (3 mL) was place in a microwave reactor at 180° C. for 30 minutes. The mixture was concentrated, and the residue was purified via reverse phase HPLC to give (S)-1-(7-(2-((1-methyl-1H-pyrazol-5-yl)amino)pyrimidin-4-yl)-[1,2,4]triazolo[4,3-a]pyridin-3-yl)butan-2-ol (18 mg, 17%).

Step 3: To a cold (−78° C.) solution of deoxyfluor (11 mg, 0.045 mmol) in DCM (5 mL) was added (S)-1-(7-(2-((1-methyl-1H-pyrazol-5-yl)amino)pyrimidin-4-yl)-[1,2,4]triazolo[4,3-a]pyridin-3-yl)butan-2-ol (0.015 g, 0.041 mmol) as a solution in DCM (2 mL). LC/MS after 1 hour showed no reaction. To this was added another 1.0 equivalent of deoxyfluor, and the mixture was stirred at room temperature for another hour. To this was added another 3.0 equivalents of deoxyfluor, and the mixture and this was stirred at room temperature for another hour. The mixture was diluted with DCM quenched with saturated NaHCO₃. The aqueous layer was extracted with DCM, and the organics were dried, filtered and concentrated. The crude product was purified via reverse phase HPLC to give (R)-4-(3-(2-fluorobutyl)-[1,2,4]triazolo[4,3-a]pyridin-7-yl)-N-(1-methyl-1H-pyrazol-5-yl)pyrimidin-2-amine (7.5 mg, 45%). ¹H NMR (400 MHz, CDCl₃) 8.56 (d, 1H), 8.39 (s, 1H), 8.15 (d, 1H), 7.53 (m, 2H), 7.29 (d, 1H), 7.03 (s, 1H), 6.36 (s, 1H), 4.93 (d, 1H), 3.83 (s, 3H), 3.51 (m, 2H), 1.79 (m, 2H), 1.08 (t, 3H). LCMS (APCI+) m/z=367.2.

Example 18

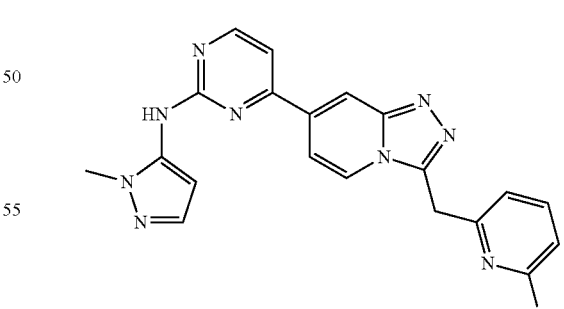

4-(3-((6-chloropyridin-2-yl)methyl)-[1,2,4]triazolo[4,3-a]pyridin-7-yl)-N-(1-methyl-1H-pyrazol-5-yl)pyrimidin-2-amine Step 1: 4-(2-Hydrazinylpyridin-4-yl)-N-(1-methyl-1H-pyrazol-5-yl)pyrimidin-2-amine (76.8 mg, 0.272 mmol) was dissolved in DMF (4 mL) and treated with 2-(6-chloropyridin-2-yl)acetic acid (49.0 mg, 0.286 mmol), 1-(3-dimethylaminopropyl)-3-ethylcarbodiimidehydrochloride (57.4 mg, 0.299 mmol), 1-hydroxybenzotriazole (40.4 mg, 0.299 mmol), and N,N-diisopropylethylamine (0.0948 mL, 0.544 mmol). The mixture was stirred at room temperature overnight. The mixture was diluted with ethyl acetate and washed with water (3×) and brine (1×). The organics were dried over $Na_2SO_4$, filtered and concentrated. The crude product was purified via column chromatography, eluting with ethyl acetate and ethyl acetate:MeOH (20:1) to give 2-(6-chloropyridin-2-yl)-N'-(4-(2-((1-methyl-1H-pyrazol-5-yl)amino)pyrimidin-4-yl)pyridin-2-yl)acetohydrazide (80 mg, 67%).

Step 2: In a microwave vessel, 2-(6-chloropyridin-2-yl)-N'-(4-(2-((1-methyl-1H-pyrazol-5-yl)amino)pyrimidin-4-yl)pyridin-2-yl)acetohydrazide (80 mg, 0.1835 mmol) was dissolved in ACN (6 mL) and treated with phosphorous oxychloride (85.54 μL, 0.9177 mmol). The mixture was heated to 100° C. overnight. The mixture was cooled and concentrated. The residue was taken up in MeOH and purified via reverse phase HPLC to give 4-(3-((6-chloropyridin-2-yl)methyl)-[1,2,4]triazolo[4,3-a]pyridin-7-yl)-N-(1-methyl-1H-pyrazol-5-yl)pyrimidin-2-amine (7.1 mg, 9.2%). $^1$H NMR (400 MHz, $CDCl_3$) 8.56 (d, 1H), 8.40 (m, 2H), 7.61 (t, 1H), 7.54 (m, 2H), 7.27 (m, 2H), 6.87 (s, 1H), 4.71 (s, 2H), 3.82 (s, 3H). LCMS (APCI+) m/z=418.1.

Example 19

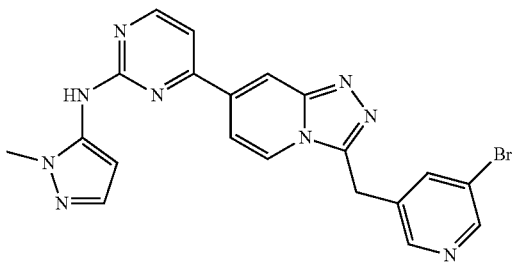 [SMILES: Cn1nccc1Nc1nccc(-c2ccn3c(Cc4cncc(Br)c4)nnc3c2)n1]

4-(3-((5-bromopyridin-3-yl)methyl)-[1,2,4]triazolo[4,3-a]pyridin-7-yl)-N-(1-methyl-1H-pyrazol-5-yl)pyrimidin-2-amine Step 1: 4-(2-Hydrazinylpyridin-4-yl)-N-(1-methyl-1H-pyrazol-5-yl)pyrimidin-2-amine (200 mg, 0.708 mmol) was dissolved in DMF (4 mL) and treated with 2-(5-bromopyridin-3-yl)acetic acid (160.7 mg, 0.744 mmol), 1-(3-dimethylaminopropyl)-3-ethylcarbodiimidehydrochloride (149.4 mg, 0.7793 mmol), 1-hydroxybenzotriazole (105.3 mg, 0.7793 mmol), and N,N-diisopropylethylamine (185.1 μL, 1.063 mmol). The mixture was stirred at room temperature overnight. The mixture was diluted with water, and the aqueous layer was extracted with 20% IPA:DCM, dried, filtered and concentrated. The product, 2-(5-bromopyridin-3-yl)-N'-(4-(2-((1-methyl-1H-pyrazol-5-yl)amino)pyrimidin-4-yl)pyridin-2-yl)acetohydrazide, was take forward as a crude product.

Step 2: A solution of 2-(5-bromopyridin-3-yl)-N'-(4-(2-((1-methyl-1H-pyrazol-5-yl)amino)pyrimidin-4-yl)pyridin-2-yl)acetohydrazide (340 mg, 0.708 mmol) in acetic acid was placed in a microwave reactor at 180° C. for 30 minutes. The mixture was concentrated, and the residue was purified column chromatography, eluting with ethyl acetate:MeOH (9:1) to give 4-(3-((5-bromopyridin-3-yl)methyl)-[1,2,4]triazolo[4,3-a]pyridin-7-yl)-N-(1-methyl-1H-pyrazol-5-yl)pyrimidin-2-amine (0.327 g, 61%). $^1$H NMR (400 MHz, MeOD) 9.60 (s, 1H), 8.67 (d, 1H), 8.62 (m, 3H), 8.58 (s, 1H), 8.03 (t, 1H), 7.68 (m, 2H), 7.40 (d, 1H), 6.31 (d, 1H), 4.63 (s, 2H), 3.71 (s, 3H). LCMS (APCI+) m/z=462.1, 464.1 (bromine isotope).

Example 20

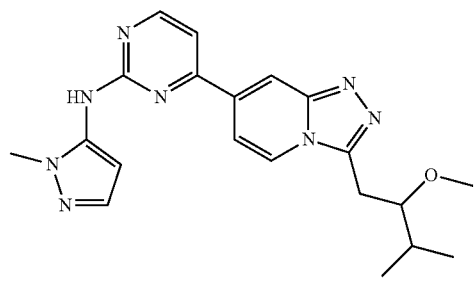

4-(3-(2-methoxy-3-methylbutyl)-[1,2,4]triazolo[4,3-a]pyridin-7-yl)-N-(1-methyl-1H-pyrazol-5-yl)pyrimidin-2-amine Step 1: To a solution of (E)-methyl 4-methylpent-2-enoate (3.71 g, 28.9 mmol) in MeOH (10 mL) was added by trimethylphosphine (0.599 mL, 5.79 mmol). The reaction vessel was sealed, and the mixture was heated to 45° C. for 7 days. The mixture was concentrated, and the residue was taken up in MeOH (5 mL) and stirred with 4N sodium hydroxide (14.5 mL, 57.9 mmol) at room temperature overnight. The next morning, the mixture was concentrated to remove MeOH, and the residue was washed with ethyl acetate (2×). The aqueous layer was acidified to pH of about 2 and then extracted with ethyl acetate (2×). The combined organics were dried, filtered and concentrated to give 3-methoxy-4-methylpentanoic acid (1.4 g, 33%).

Step 2: 4-(2-Hydrazinylpyridin-4-yl)-N-(1-methyl-1H-pyrazol-5-yl)pyrimidin-2-amine (160 mg, 0.567 mmol) was dissolved in DMF (4 mL) and treated with 3-methoxy-4-methylpentanoic acid (124 mg, 0.85 mmol), 1-(3-dimethylaminopropyl)-3-ethylcarbodiimidehydrochloride (119.5 mg, 0.623 mmol), 1-hydroxybenzotriazole (84.24 mg, 0.6234 mmol), and N,N-diisopropylethylamine (148.1 μL, 0.8501 mmol). The mixture was stirred at room temperature for 1 hour. The mixture was diluted with water, and the aqueous layer was extracted with ethyl acetate (2×), dried, filtered and concentrated to give 3-methoxy-4-methyl-N'-(4-(2-((1-methyl-1H-pyrazol-5-yl)amino)pyrimidin-4-yl)pyridin-2-yl)pentanehydrazide. This was taken forward as crude.

Step 3: A solution of 3-methoxy-4-methyl-N'-(4-(2-((1-methyl-1H-pyrazol-5-yl)amino)pyrimidin-4-yl)pyridin-2-yl)pentanehydrazide (232 mg, 0.565 mmol) in acetic acid (3 mL) was placed in a microwave reactor at 150° C. for 15 minutes. The mixture was concentrated and purified via reverse phase HPLC to give 4-(3-(2-methoxy-3-methylbutyl)-[1,2,4]triazolo[4,3-a]pyridin-7-yl)-N-(1-methyl-1H-pyrazol-5-yl)pyrimidin-2-amine (137 mg, 61%). $^1$H NMR (400 MHz, $CDCl_3$) 8.56 (dd, 1H), 8.36 (s, 1H), 8.25 (d, 1H), 7.93 (d, 1H), 7.51 (m, 2H), 7.30 (dd, 1H), 6.86 (s, 1H), 6.37

(s, 1H), 3.83 (s, 3H), 3.48 (m, 1H), 3.12 (s, 3H), 2.02 (m, 1H), 1.85 (s, 1H), 1.79 (s, 1H), 1.60 (s, 6H). LCMS (APCI+) m/z=393.2.

Example 21

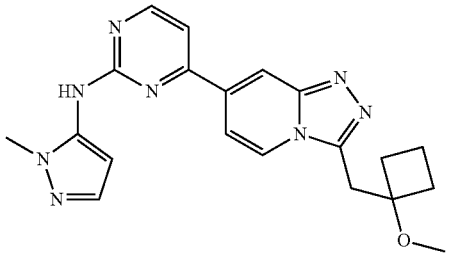

4-(3-((1-methoxycyclobutyl)methyl)-[1,2,4]triazolo[4,3-a]pyridin-7-yl)-N-(1-methyl-1H-pyrazol-5-yl)pyrimidin-2-amine 4-(3-((1-Methoxycyclobutyl)methyl)-[1,2,4]triazolo[4,3-a]pyridin-7-yl)-N-(1-methyl-1H-pyrazol-5-yl)pyrimidin-2-amine (0.047 g, 42%) was made according to the procedure of Example 20, substituting cyclobutylidene-acetic acid ethyl ester for (E)-methyl 4-methylpent-2-enoate. LCMS (APCI+) m/z=391.1.

Example 22

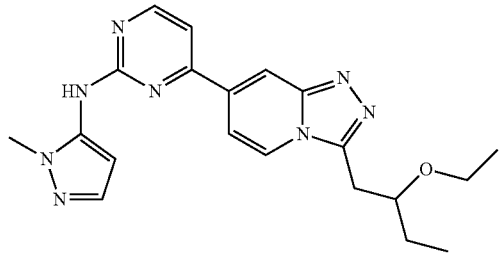 [SMILES: CCOC(CC)Cc1nnc2cc(-c3ccnc(Nc4ccnn4C)n3)ccn12]

4-(3-(2-ethoxybutyl)-[1,2,4]triazolo[4,3-a]pyridin-7-yl)-N-(1-methyl-1H-pyrazol-5-yl)pyrimidin-2-amine 4-(3-(2-Ethoxybutyl)-[1,2,4]triazolo[4,3-a]pyridin-7-yl)-N-(1-methyl-1H-pyrazol-5-yl)pyrimidin-2-amine (0.058 g, 26%) was made according to the procedure of Example 20, substituting (E)-methyl pent-2-enoate for (E)-methyl 4-methylpent-2-enoate and substituting ethanol for methanol in Step 1. LCMS (APCI+) m/z=393.2.

Example 23

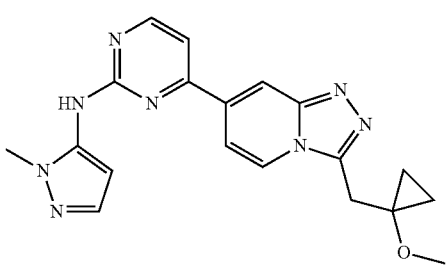

4-(3-((1-methoxycyclopropyl)methyl)-[1,2,4]triazolo[4,3-a]pyridin-7-yl)-N-(1-methyl-1H-pyrazol-5-yl)pyrimidin-2-amine 4-(3-((1-Methoxycyclopropyl)methyl)-[1,2,4]triazolo[4,3-a]pyridin-7-yl)-N-(1-methyl-1H-pyrazol-5-yl)pyrimidin-2-amine (0.060 g, 56%) was made according to the procedure of Example 20, substituting ethyl 2-cyclopropylideneacetate for (E)-methyl 4-methylpent-2-enoate and substituting ethanol for methanol in Step 1. LCMS (APCI+) m/z=377.2.

Example 24

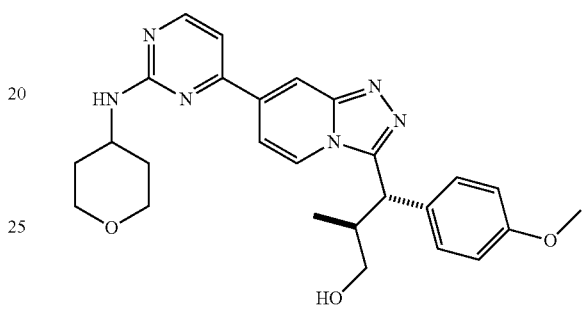

(2S*,3S*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol Step 1: A suspension of 2-(4-methoxyphenyl)acetic acid (3.33 g, 20.0 mmol), 1-chloropropan-2-one (1.68 mL, 20.0 mmol), $K_2CO_3$ (9.97 g, 72.1 mmol) in ACN (40 mL) was refluxed for 12 hours. The mixture was cooled to room temperature, and the insolubles were removed by filtration. The filtrate was concentrated to give 3-(4-methoxyphenyl)-4-methylfuran-2(5H)-one (3.5 g, 85.5%).

Step 2: To a solution of 3-(4-methoxyphenyl)-4-methylfuran-2(5H)-one (0.99 g, 4.8 mmol) in MeOH:ethyl acetate (1:1, 20 mL) was added Pd/C (0.52 g, 0.48 mmol). The mixture was purged with $N_2$ for 10 minutes and then placed under a $H_2$ balloon at room temperature for 12 hours. The Pd was removed by filtration, and the filtrate was concentrated to give (3S*,4S*)-3-(4-methoxyphenyl)-4-methyldihydrofuran-2(3H)-one (0.95 g, 95%).

Step 3: To a cold (−78° C.) solution of (3S*,4S*)-3-(4-methoxyphenyl)-4-methyldihydrofuran-2(3H)-one (0.56 g, 2.72 mmol) in THF (6 mL) was added 1.5 M DIBAL-H (2.44 mL, 3.67 mmol) in toluene dropwise, and the reaction mixture was stirred for 30 minutes, at which time the bath temperature had reached −30° C. TLC showed complete conversion to a more polar spot. The reaction mixture was carefully quenched with water and then diluted with ethyl acetate and 0.5 N sodium potassium tartrate. The reaction mixture was stirred for 1 hour, and the layers were separated. The organics were dried, filtered and concentrated. The crude product was purified via column chromatography, eluting with hexanes:ethyl acetate (5:1) to give (2S*,3S*,4S*)-3-(4-methoxyphenyl)-4-methyltetrahydrofuran-2-ol (0.46 g, 81.3%).

Step 4: To a solution of (2S*,3S*,4S*)-3-(4-methoxyphenyl)-4-methyltetrahydrofuran-2-ol (0.27 g, 1.3 mmol) in DMF (4 mL) was added tert-butyldimethylsilyl chloride ("TBDMS-Cl") (0.250 g, 1.66 mmol), imidazole (0.124 g, 1.82 mmol) and 1,8-diazabicycloundec-7-ene ("DBU") (0.0194 mL, 0.130 mmol). The reaction mixture was stirred at room temperature for 3 hours. LC/MS showed complete conversion to two less polar peaks. TLC showed two spots. The reaction mixture was diluted with ethyl acetate, and the organics were washed with brine (2×), dried, filtered and concentrated. The crude product was purified via column chromatography, eluting with hexanes:ethyl acetate (100:1) to give (2S*,3S*)-4-(tert-butyldimethylsilyloxy)-2-(4-methoxyphenyl)-3-methylbutanal (0.131 g, 31%).

Step 5: 4-(2-Hydrazinylpyridin-4-yl)-N-(tetrahydro-2H-pyran-4-yl)pyrimidin-2-amine (0.116 g, 0.406 mmol) was dissolved in EtOH (6 mL) and treated with (2S*,3S*)-4-(tert-butyldimethylsilyloxy)-2-(4-methoxyphenyl)-3-methylbutanal (0.131 g, 0.406 mmol). The reaction mixture was stirred at room temperature overnight. The reaction mixture was concentrated, and the residue was dissolved in DCM (6 mL) and treated with iodobenzene diacetate (0.170 g, 0.528 mmol). LC/MS after 3 hours showed formation of the desired product with TBS still on (M+1 589). The reaction mixture was concentrated, and the residue was taken up in THF and treated with 4 N HCl (2 mL) for 30 minutes. LC/MS showed complete conversion to the desired product. The reaction mixture was concentrated, and the residue was basified and extracted with ethyl acetate. The organics were dried, filtered and concentrated. The crude product was purified via column chromatography, eluting with ethyl acetate, ethyl acetate:MeOH (20:1) to give (2S*,3S*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol (0.058 g, 30%). LCMS (APCI+) m/z=475.2.

Example 25

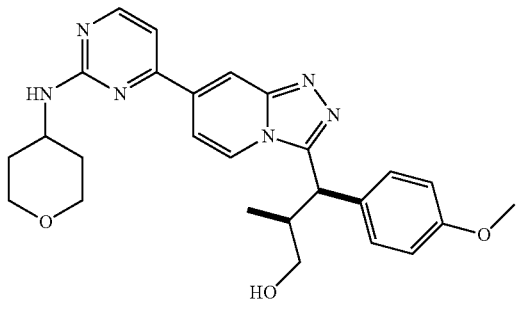 [SMILES: COc1ccc([C@H](c2nnc3cc(-c4ccnc(NC5CCOCC5)n4)ccn23)[C@H](C)CO)cc1]

(2S*,3R*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol Step 1: A solution of (3S,4S)-3-(4-methoxyphenyl)-4-methyldihydrofuran-2(3H)-one (0.40 g, 1.94 mmol) in MeOH (5 mL) was treated with DBU (0.0289 mL, 0.194 mmol) at room temperature for 12 hours. Crude NMR showed a 9:1 ratio of trans/cis mixture. The mixture was concentrated, and the crude product was purified via column chromatography, eluting with hexanes:ethyl acetate (7:1) to give (3R*,4S*)-3-(4-methoxyphenyl)-4-methyldihydrofuran-2(3H)-one (0.284 g, 71%).

Step 2: To a cold (−78° C.) solution of (3R*,4S*)-3-(4-methoxyphenyl)-4-methyldihydrofuran-2(3H)-one (0.284 g, 1.377 mmol) in THF (6 mL) was added 1.5 M DIBAL-H (1.239 mL, 1.859 mmol) in toluene dropwise, and the mixture was stirred for 30 minutes, at which time the bath temperature has reached −30° C. TLC showed formation of a more polar spot along with some starting material. The reaction mixture was cooled to −60° C., and to this was added additional 1.5 M DIBAL (0.2 mL). The mixture was stirred for 30 minutes, and it was carefully quenched with water and diluted with EtOAc and 0.5 N sodium potassium tartrate. The mixture was stirred for 1 hour, and the layers were separated. The organics were dried, filtered and concentrated. The crude product was purified using column chromatography, eluting with hexanes:ethyl acetate (5:1) to give (3R*,4S*)-3-(4-methoxyphenyl)-4-methyltetrahydrofuran-2-ol (0.263 g, 91%).

Step 3: To a solution of (3R*,4S*)-3-(4-methoxyphenyl)-4-methyltetrahydrofuran-2-ol (0.263 g, 1.263 mmol) in DMF (4 mL) was added TBDMS-Cl (0.2436 g, 1.616 mmol) and imidazole (0.1204 g, 1.768 mmol). The mixture was stirred at ambient temperature for 2 hours. The mixture was diluted with EtOAc, and the organics were washed with brine (2×), dried, filtered and concentrated. The crude product was purified via column chromatography, eluting with hexanes:ethyl acetate (100:1) to give (2R*,3S*)-4-((tert-butyldimethylsilyl)oxy)-2-(4-methoxyphenyl)-3-methylbutanal (0.35 g, 85.9%).

Step 4: 4-(2-Hydrazinylpyridin-4-yl)-N-(tetrahydro-2H-pyran-4-yl)pyrimidin-2-amine (0.032 g, 0.11 mmol) was dissolved in EtOH (6 mL) and treated with (2R,3S)-4-((tert-butyldimethylsilyl)oxy)-2-(4-methoxyphenyl)-3-methylbutanal (0.036 g, 0.11 mmol). The mixture was stirred at ambient temperature for 12 hours. The mixture was concentrated, and the residue was dissolved in DCM (6 mL) and treated with iodobenzene diacetate (0.047 g, 0.15 mmol). The reaction was stirred at ambient temperature for 12 hours. The mixture was concentrated and purified via column chromatography, eluting with hexanes:ethyl acetate (1:2), hexanes:ethyl acetate (1:4), ethyl acetate to give 4-(3-((1R*,2S*)-3-((tert-butyldimethylsilyl)oxy)-1-(4-methoxyphenyl)-2-methylpropyl)-[1,2,4]triazolo[4,3-a]pyridin-7-yl)-N-(tetrahydro-2H-pyran-4-yl)pyrimidin-2-amine (0.052 g, 79%).

Step 5: A solution of 4-(3-((1R*,2S*)-3-((tert-butyldimethylsilyl)oxy)-1-(4-methoxyphenyl)-2-methylpropyl)-[1,2,4]triazolo[4,3-a]pyridin-7-yl)-N-(tetrahydro-2H-pyran-4-yl)pyrimidin-2-amine (0.052 g, 0.088 mmol) in THF (5 mL) was treated with 1.0 M TBAF at ambient temperature for 30 minutes. The mixture was concentrated, and the residue was taken up in EtOAc and washed with brine twice. The organics were dried, filtered and concentrated. The crude product was purified via column chromatography, eluting with ethyl acetate:MeOH (20:1), ethyl acetate:MeOH (1:1) to give (2S*,3R*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol (0.030 g, 71.5%). LCMS (APCI+) m/z=475.2.

Example 26

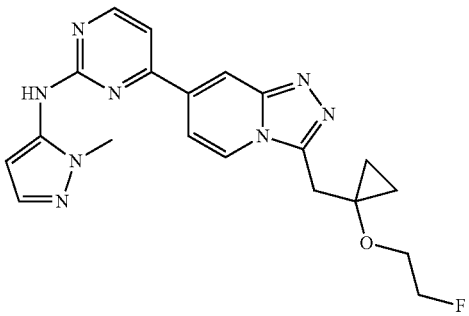 [SMILES: Cn1nccc1Nc1nccc(-c2ccn3c(CC4(OCCF)CC4)nnc3c2)n1]

4-(3-((1-(2-fluoroethoxy)cyclopropyl)methyl)-[1,2,4]triazolo[4,3-a]pyridin-7-yl)-N-(1-methyl-1H-pyrazol-5-yl)pyrimidin-2-amine 4-(3-((1-(2-Fluoroethoxy)cyclopropyl)methyl)-[1,2,4]triazolo[4,3-a]pyridin-7-yl)-N-(1-methyl-1H-pyrazol-5-yl)pyrimidin-2-amine (0.066 g, 57%) was made according to the procedure of Example 23, substituting 2-fluoroethanol for methanol. LCMS (APCI+) m/z=409.2.

Example 27

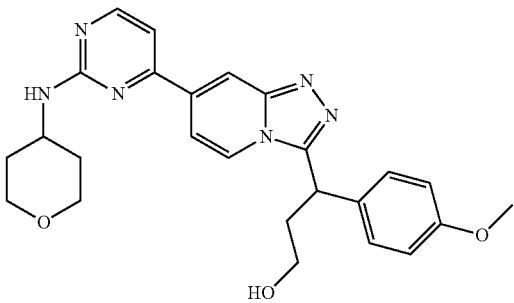 [SMILES: COc1ccc(C(CCO)c2nnc3cc(-c4ccnc(NC5CCOCC5)n4)ccn23)cc1]

3-(4-methoxyphenyl)-3-(7-(2-((tetrahydro-2H-pyran-4-yl)amino)pyrimidin-4-yl)-[1,2,4]triazolo[4,3-a]pyridin-3-yl)propan-1-ol Step 1: To a −78° C. solution of diisopropylamine (5.84 mL, 41.7 mmol) in THF (12 mL) was added a solution of 2.5 M butyllithium (16.7 mL, 41.7 mmol) in hexanes via a syringe. The mixture was stirred at −78° C. for 10 minutes, warmed to 0° C. for 5 minutes and cooled to −78° C. for 10 minutes. A solution of 2-(4-methoxyphenyl)acetic acid (3.30 g, 19.9 mmol) in THF (12 mL) was added to the lithium diisopropylamide ("LDA") solution at −78° C. using a cannula. The reaction mixture was stirred at −78° C. for 20 minutes, warmed to ambient temperature and stirred for 45 minutes. A solution of 1,3,2-dioxathiolane 2,2-dioxide (2.46 g, 19.9 mmol) in THF (12 mL) was added via a syringe. Dimethyl ether ("DME") (10 mL) was added, and the reaction mixture was refluxed for 16 hours. Cool to ambient temperature and concentrated. The residue was partitioned between EtOAc and water. The aqueous layer was extracted with EtOAc (3×). The combined organics were washed with saturated NaHCO₃, dried, filtered and concentrated to give 3-(4-methoxyphenyl)dihydrofuran-2(3H)-one (2.22 g, 58.2%).

Step 2: To a cold (−78° C.) solution of 3-(4-methoxyphenyl)dihydrofuran-2(3H)-one (0.22 g, 1.14 mmol) in THF (6 mL) was added 1.5 M DIBAL-H (1.03 mL, 1.55 mmol) in toluene drop wise, and the mixture was stirred for 30 minutes at which time the bath temperature had reached −30° C. The mixture was carefully quenched with water and diluted with EtOAc and 0.5 N sodium potassium tartrate. The mixture was stirred for 1 hour, and the layers were separated. The organics were dried, filtered and concentrated. The crude product was purified via column chromatography, eluting with hexanes:ethyl acetate (5:1) to give 3-(4-methoxyphenyl)tetrahydrofuran-2-ol (0.14 g, 63%).

Step 3: To a solution of 3-(4-methoxyphenyl)tetrahydrofuran-2-ol (0.140 g, 0.721 mmol) in DMF (4 mL) was added TBDMS-Cl (0.139 g, 0.923 mmol), imidazole (0.0687 g, 1.01 mmol) and DBU (0.0108 mL, 0.0721 mmol). The mixture was stirred at ambient temperature overnight. LC/MS showed complete conversion to a less polar peak. The mixture was diluted with EtOAc, and the organics were washed with brine (2×), dried, filtered and concentrated. The crude product was purified via column chromatography, eluting with hexanes:EtOAc (50:1) to give 4-(tert-butyldimethylsilyloxy)-2-(4-methoxyphenyl)butanal.

Step 4: 4-(2-Hydrazinylpyridin-4-yl)-N-(tetrahydro-2H-pyran-4-yl)pyrimidin-2-amine (0.0687 g, 0.240 mmol) was dissolved in EtOH (6 mL) and treated with 4-(tert-butyldimethylsilyloxy)-2-(4-methoxyphenyl)butanal (0.074 g, 0.240 mmol). The reaction mixture was stirred at ambient for 1 hour. The mixture was concentrated, and the residue was dissolved in DCM (6 mL) and treated with Iodobenzene diacetate (0.100 g, 0.312 mmol). The reaction mixture was stirred at ambient temperature for 24 hours. The mixture was concentrated and purified by reverse phase HPLC. The TBS group had fallen off in the HPLC purification (solvent contains 0.1% TFA). The material was further purified on preparative TLC plate eluting with ethyl acetate:MeOH (20:1) to give 3-(4-methoxyphenyl)-3-(7-(2-((tetrahydro-2H-pyran-4-yl)amino)pyrimidin-4-yl)-[1,2,4]triazolo[4,3-a]pyridin-3-yl)propan-1-ol (0.0058 g, 5.25%). LCMS (APCI+) m/z=461.2.

Example 28

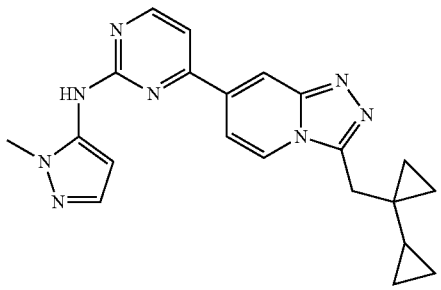 [SMILES: Cn1nccc1Nc1nccc(-c2ccn3c(CC4(C5CC5)CC4)nnc3c2)n1]

4-(3-([1,1'-bi(cyclopropan)]-1-ylmethyl)-[1,2,4]triazolo[4,3-a]pyridin-7-yl)-N-(1-methyl-1H-pyrazol-5-yl)pyrimidin-2-amine 4-(3-([1,1'-Bi(cyclopropan)]-1-ylmethyl)-[1,2,4]triazolo[4,3-a]pyridin-7-yl)-N-(1-methyl-1H-pyrazol-5-yl)pyrimidin-2-amine (36.2 mg, 34.4%) was made according to the procedure of Example 6, substituting 2-([1,1'-bi(cyclopropan)]-1-yl)acetic acid for 2-(4-(methylthio)phenyl)acetic acid. $^1$H NMR (400 MHz, CDCl$_3$) 9.59 (s, 1H), 8.69 (d, 1H), 8.61 (d, 1H), 8.55 (s, 1H), 7.69 (d, 1H), 7.63 (d, 1H), 7.40 (d, 1H), 6.31 (d, 1H), 3.71 (s, 3H), 3.28 (s, 2H), 1.14 (m, 1H), 0.45 (t, 2H), 0.21 (t, 2H), 0.12 (m, 2H), −0.24 (m, 2H). LCMS (APCI+) m/z=387.2.

Example 29

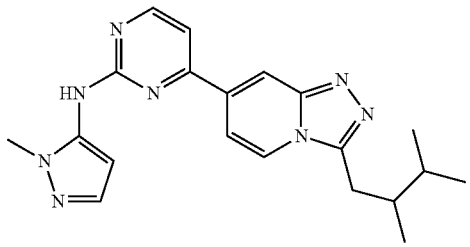 [SMILES: CC(C)C(C)Cc1nnc2cc(-c3ccnc(Nc4ccnn4C)n3)ccn12]

4-(3-(2,3-dimethylbutyl)-[1,2,4]triazolo[4,3-a]pyridin-7-yl)-N-(1-methyl-1H-pyrazol-5-yl)pyrimidin-2-amine 4-(3-(2,3-Dimethylbutyl)-[1,2,4]triazolo[4,3-a]pyridin-7-yl)-N-(1-methyl-1H-pyrazol-5-yl)pyrimidin-2-amine (0.044 g, 34.5%) was made according to the procedure of Example 6, substituting 3,4-dimethylpentanoic acid for 2-(4-(methylthio)phenyl)acetic acid. $^1$H NMR (400 MHz, CDCl$_3$) 9.60 (s, 1H), 8.60 (m, 2H), 8.54 (s, 1H), 7.69 (d, 1H), 7.62 (d, 1H), 7.40 (s, 1H), 6.31 (s, 1H), 3.71 (s, 3H), 3.15 (dd, 1H), 2.95 (dd, 1H), 2.01 (m, 1H), 1.68 (m, 1H), 0.92 (dd, 6H), 0.83 (d, 3H). LCMS (APCI+) m/z=377.2.

Example 30

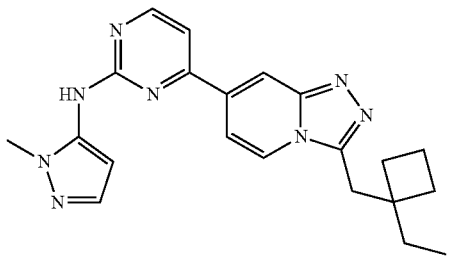 [SMILES: CCC1(Cc2nnc3cc(-c4ccnc(Nc5ccnn5C)n4)ccn23)CCC1]

4-(3-((1-ethylcyclobutyl)methyl)-[1,2,4]triazolo[4,3-a]pyridin-7-yl)-N-(1-methyl-1H-pyrazol-5-yl)pyrimidin-2-amine Step 1: Ethyl 2-cyclobutylideneacetate (408.9 mg, 2.917 mmol) was dissolved in THF (14.6 mL, 0.2 M). The solution was degassed with N$_2$, and treated with copper (I) iodide (611.1 mg, 3.209 mmol). This was cooled to 0° C. and treated with chlorotrimethylsilane (405.8 µL, 3.209 mmol). The mixture was stirred at 0° C. for 10 minutes and then treated with ethylmagnesium bromide (2917 µL, 2.917 mmol). This was stirred at 0° C. for 1 hour. The mixture was quenched with water, and the organics were extracted with Et$_2$O twice, washed with brine and dried with Na$_2$SO$_4$. This was then concentrated down to give ethyl 2-(1-ethylcyclobutyl)acetate (0.2675 g, 53.8%).

Step 2: Ethyl 2-(1-ethylcyclobutyl)acetate (267.5 mg, 1.571 mmol) was dissolved in 4:1 THF:MeOH (7.9 mL, 0.2 M) and treated with potassium hydroxide (2 M in water) (2357 µL, 4.714 mmol). This was stirred for 16 hours at ambient temperature. The mixture was worked up with DCM and 4.0 N HCl. The organics were extracted twice with DCM, washed with brine and dried with Na$_2$SO$_4$. This was concentrated down to give 2-(1-ethylcyclobutyl)acetic acid.

Step 3: 4-(2-Hydrazinylpyridin-4-yl)-N-(1-methyl-1H-pyrazol-5-yl)pyrimidin-2-amine (63.6 mg, 0.225 mmol) was dissolved in DMF (1.2 mL, 0.2 M) and treated with 2-(1-ethylcyclobutyl)acetic acid (35.24 mg, 0.2478 mmol), 1-(3-dimethylaminopropyl)-3-ethylcarbodiimidehydrochloride (47.51 mg, 0.2478 mmol), 1-hydroxybenzotriazole (33.49 mg, 0.2478 mmol), and N,N-diisopropylethylamine (78.48 µL, 0.4506 mmol). The mixture was stirred at ambient temperature for 16 hours. The mixture was concentrated down and taken forward to the next step as crude.

Step 4: 2-(1-Ethylcyclobutyl)-N'-(4-(2-((1-methyl-1H-pyrazol-5-yl)amino)pyrimidin-4-yl)pyridin-2-yl)acetohydrazide (91.0 mg, 0.224 mmol) was dissolved in AcOH (2.3 mL, 0.1 M) and heated to 180° C. for 10 minutes in the microwave. The mixture was concentrated down and purified on reverse phase prep HPLC to give 4-(3-((1-ethylcyclobutyl)methyl)-[1,2,4]triazolo[4,3-a]pyridin-7-yl)-N-(1-methyl-1H-pyrazol-5-yl)pyrimidin-2-amine (32.6 mg, 37.5%). $^1$H NMR (400 MHz, CDCl$_3$) 9.59 (s, 1H), 8.68 (d, 1H), 8.61 (d, 1H), 8.55 (s, 1H), 7.69 (d, 1H), 7.63 (d, 1H), 7.40 (d, 1H), 6.31 (s, 1H), 3.72 (s, 3H), 3.24 (s, 2H), 1.94 (m, 2H), 1.78 (m, 4H), 1.56 (m, 2H), 0.88 (t, 3H). LCMS (APCI+) m/z=389.2.

Example 31

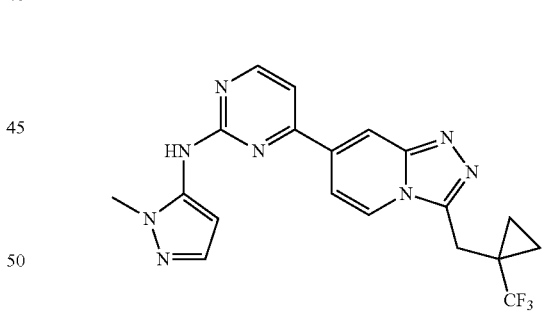

N-(1-methyl-1H-pyrazol-5-yl)-4-(3-((1-(trifluoromethyl)cyclopropyl)methyl)-[1,2,4]triazolo[4,3-a]pyridin-7-yl)pyrimidin-2-amine N-(1-Methyl-1H-pyrazol-5-yl)-4-(3-((1-(trifluoromethyl)cyclopropyl)methyl)-[1,2,4]triazolo[4,3-a]pyridin-7-yl)pyrimidin-2-amine (0.0502 g, 34.2%) was made according to the procedure of Example 6, substituting 2-(1-(trifluoromethyl)cyclopropyl)acetic acid for 2-(4-(methylthio)phenyl)acetic acid. $^1$H NMR (400 MHz, CDCl$_3$) 9.60 (s, 1H), 8.62 (m, 2H), 8.56 (s, 1H), 7.68 (m, 2H), 7.40 (d, 1H), 6.32 (d, 1H), 3.72 (s, 3H), 3.61 (s, 2H), 1.05 (m, 4H). LCMS (APCI+) m/z=415.1.

Example 32

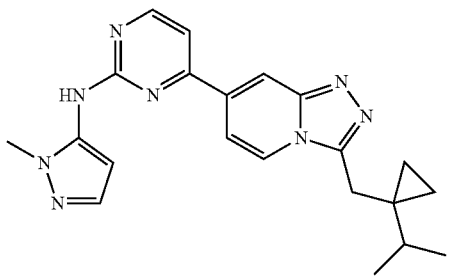 [SMILES: CC(C)C1(Cc2nnc3cc(-c4ccnc(Nc5ccnn5C)n4)ccn23)CC1]

4-(3-((1-isopropylcyclopropyl)methyl)-[1,2,4]triazolo[4,3-a]pyridin-7-yl)-N-(1-methyl-1H-pyrazol-5-yl)pyrimidin-2-amine 4-(3-((1-Isopropylcyclopropyl)methyl)-[1,2,4]triazolo[4,3-a]pyridin-7-yl)-N-(1-methyl-1H-pyrazol-5-yl)pyrimidin-2-amine (0.025.6 g, 24.1%) was made according to the procedure of Example 6, substituting 2-(1-isopropylcyclopropyl)acetic acid for 2-(4-(methylthio)phenyl)acetic acid. $^1$H NMR (400 MHz, CDCl$_3$) 9.54 (s, 1H), 8.62 (d, 1H), 8.52 (d, 2H), 7.66 (m, 2H), 7.40 (d, 1H), 6.31 (s, 1H), 3.72 (s, 3H), 3.26 (s, 2H), 1.32 (m, 1H), 0.89 (d, 6H), 0.35 (m, 2H), 0.26 (m, 2H). LCMS (APCI+) m/z=389.2.

Example 33

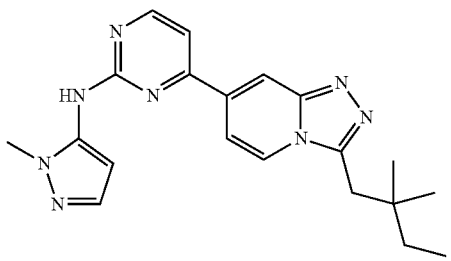 [SMILES: CCC(C)(C)Cc1nnc2cc(-c3ccnc(Nc4ccnn4C)n3)ccn12]

4-(3-(2,2-dimethylbutyl)-[1,2,4]triazolo[4,3-a]pyridin-7-yl)-N-(1-methyl-1H-pyrazol-5-yl)pyrimidin-2-amine 4-(3-(2,2-Dimethylbutyl)-[1,2,4]triazolo[4,3-a]pyridin-7-yl)-N-(1-methyl-1H-pyrazol-5-yl)pyrimidin-2-amine (0.0456 g, 33.8%) was made according to the procedure of Example 6, substituting 3,3-dimethylpentanoic acid for 2-(4-(methylthio)phenyl)acetic acid. $^1$H NMR (400 MHz, CDCl$_3$) 9.59 (s, 1H), 8.71 (d, 1H), 8.61 (d, 1H), 8.54 (s, 1H), 7.69 (d, 1H), 7.61 (d, 1H), 7.40 (s, 1H), 6.31 (s, 1H), 3.72 (s, 3H), 3.05 (s, 2H), 1.37 (m, 2H), 0.92 (s, 6H), 0.89 (t, 3H). LCMS (APCI+) m/z=377.2.

Example 34

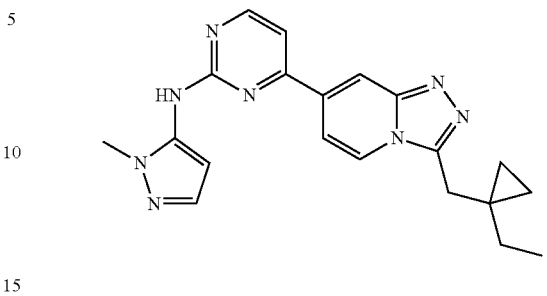

4-3-((1-ethylcyclopropyl)methyl)-[1,2,4]triazolo[4,3-a]pyridin-7-yl)-N-(1-methyl-1H-pyrazol-5-yl)pyrimidin-2-amine 4-(3-((1-Ethylcyclopropyl)methyl)-[1,2,4]triazolo[4,3-a]pyridin-7-yl)-N-(1-methyl-1H-pyrazol-5-yl)pyrimidin-2-amine (0.0456 g, 33.8%) was made according to the procedure of Example 6, substituting 2-(1-ethylcyclopropyl)acetic acid for 2-(4-(methylthio)phenyl)acetic acid. $^1$H NMR (400 MHz, CDCl$_3$) 9.59 (s, 1H), 8.61 (m, 2H), 8.54 (s, 1H), 7.68 (d, 1H), 7.63 (d, 1H), 7.40 (s, 1H), 6.31 (s, 1H), 3.72 (s, 3H), 3.19 (s, 2H), 1.28 (m, 2H), 0.91 (t, 3H), 0.47 (m, 2H), 0.36 (m, 2H). LCMS (APCI+) m/z=375.2.

Example 35

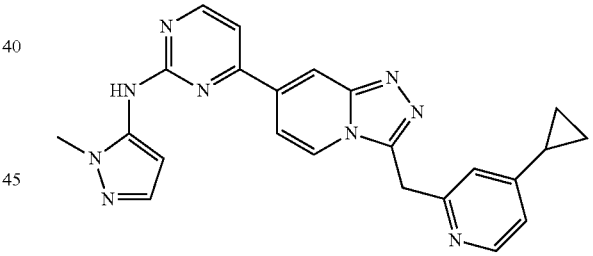

4-(3-((4-cyclopropylpyridin-2-yl)methyl)-[1,2,4]triazolo[4,3-a]pyridin-7-yl)-N-(1-methyl-1H-pyrazol-5-yl)pyrimidin-2-amine 4-(3-((4-Cyclopropylpyridin-2-yl)methyl)-[1,2,4]triazolo[4,3-a]pyridin-7-yl)-N-(1-methyl-1H-pyrazol-5-yl)pyrimidin-2-amine (0.0043, 15.5%) was made according to the procedure of Example 6, substituting 2-(4-cyclopropylpyridin-2-yl)acetic acid for 2-(4-(methylthio)phenyl)acetic acid. $^1$H NMR (400 MHz, CDCl$_3$) 8.53 (d, 1H), 8.44 (d, 1H), 8.36 (s, 1H), 8.33 (d, 1H), 7.51 (d, 1H), 7.47 (dd, 1H), 7.08 (s, 1H), 7.04 (s, 1H), 6.82 (d, 1H), 6.35 (d, 1H), 4.68 (s, 2H), 3.82 (s, 3H), 1.79 (m, 1H), 1.05 (m, 2H), 0.74 (m, 2H). LCMS (APCI+) m/z=424.2.

Example 36

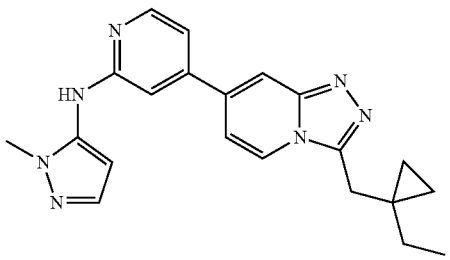 [SMILES: CCC1(Cc2nnc3cc(-c4ccnc(Nc5ccnn5C)c4)ccn23)CC1]

4-(3-((1-ethylcyclopropyl)methyl)-[1,2,4]triazolo[4,3-a]pyridin-7-yl)-N-(1-methyl-1H-pyrazol-5-yl)pyridin-2-amine Step 1: 2'-Hydrazinyl-N-(1-methyl-1H-pyrazol-5-yl)-[4,4'-bipyridin]-2-amine (89.7 mg, 0.319 mmol) was dissolved in DMF (1.6 mL, 0.2 M) and treated with 2-(1-ethylcyclopropyl)acetic acid (44.95 mg, 0.3507 mmol), 1-(3-dimethylaminopropyl)-3-ethylcarbodiimidehydrochloride (67.24 mg, 0.3507 mmol), 1-hydroxybenzotriazole (47.39 mg, 0.3507 mmol), and N,N-diisopropylethylamine (111.08 µL, 0.6377 mmol). The mixture was stirred at ambient temperature for 16 hours. The mixture was concentrated down and taken to the next step as crude.

Step 2: 2-(1-Ethylcyclopropyl)-N'-(2'-((1-methyl-1H-pyrazol-5-yl)amino)-[4,4'-bipyridin]-2-yl)acetohydrazide (124.0 mg, 0.3168 mmol) was dissolved in AcOH (1.6 mL, 0.1 M) and heated to 180° C. for 10 minutes in the microwave. The mixture was concentrated down and purified on reverse phase prep HPLC to give 4-(3-((1-ethylcyclopropyl)methyl)-[1,2,4]triazolo[4,3-a]pyridin-7-yl)-N-(1-methyl-1H-pyrazol-5-yl)pyridin-2-amine (0.0393 g, 33.2%). $^1$H NMR (400 MHz, CDCl$_3$) 8.92 (s, 1H), 8.58 (d, 1H), 8.23 (d, 1H), 8.10 (s, 1H), 7.35 (s, 1H), 7.26 (m, 2H), 7.13 (s, 1H), 6.30 (s, 1H), 3.70 (s, 3H), 3.19 (s, 2H), 1.28 (m, 2H), 0.92 (t, 3H). LCMS (APCI+) m/z=374.2.

Example 37

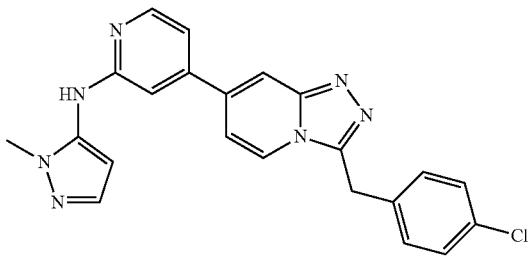 [SMILES: Cn1nccc1Nc1cc(-c2ccn3c(Cc4ccc(Cl)cc4)nnc3c2)ccn1]

4-(3-(4-chlorobenzyl)-[1,2,4]triazolo[4,3-a]pyridin-7-yl)-N-(1-methyl-1H-pyrazol-5-yl)pyridin-2-amine 4-(3-(4-Chlorobenzyl)-[1,2,4]triazolo[4,3-a]pyridin-7-yl)-N-(1-methyl-1H-pyrazol-5-yl)pyridin-2-amine (0.0267 g, 14.5%) was made according to the procedure of Example 36, substituting 2-(4-chlorophenyl)acetic acid for 2-(1-ethylcyclopropyl)acetic acid. $^1$H NMR (400 MHz, CDCl$_3$) 8.91 (s, 1H), 8.49 (d, 1H), 8.23 (d, 1H), 8.12 (s, 1H), 7.37 (m, 5H), 7.25 (dd, 2H), 7.11 (s, 1H), 6.28 (d, 1H), 4.60 (s, 2H), 3.69 (s, LCMS (APCI+) m/z=416.1.

Example 38

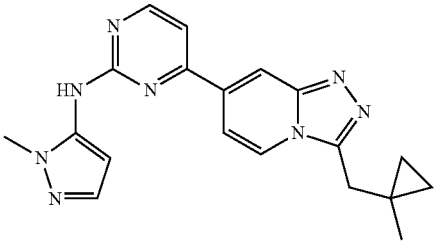 [SMILES: Cn1nccc1Nc1nccc(-c2ccn3c(CC4(C)CC4)nnc3c2)n1]

N-(1-methyl-1H-pyrazol-5-yl)-4-(3-((1-methylcyclopropyl)methyl)-[1,2,4]triazolo[4,3-a]pyridin-7-yl)pyrimidin-2-amine N-(1-Methyl-1H-pyrazol-5-yl)-4-(3-((1-methylcyclopropyl)methyl)-[1,2,4]triazolo[4,3-a]pyridin-7-yl)pyrimidin-2-amine (0.0028 g, 5.25%) was made according to the procedure of Example 6, substituting 2-(1-methylcyclopropyl)acetic acid for 2-(4-(methylthio)phenyl)acetic acid. $^1$H NMR (400 MHz, CDCl$_3$) 8.56 (d, 1H), 8.40 (s, 1H), 8.07 (d, 1H), 7.56 (d, 1H), 7.52 (d, 1H), 7.30 (d, 1H), 7.03 (s, 1H), 6.36 (d, 1H), 3.83 (s, 3H), 3.17 (s, 2H), 1.12 (s, 3H), 0.87 (m, 1H), 0.52 (t, 2H), 0.49 (t, 2H). LCMS (APCI+) m/z=361.2.

Example 39

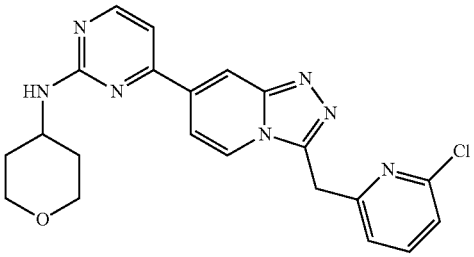 [SMILES: Clc1cccc(Cc2nnc3cc(-c4ccnc(NC5CCOCC5)n4)ccn23)n1]

4-(3-((6-chloropyridin-2-yl)methyl)-[1,2,4]triazolo[4,3-a]pyridin-7-yl)-N-(tetrahydro-2H-pyran-4-yl)pyrimidin-2-amine 4-(2-Hydrazinylpyridin-4-yl)-N-(tetrahydro-2H-pyran-4-yl)pyrimidin-2-amine (102.2 mg, 0.3569 mmol) was dissolved in DCM (3.6 mL, 0.1 M) and treated with (6-chloropyridin-2-yl)acetic acid (61.24 mg, 0.3569 mmol), triphenylphosphine (280.85 mg, 1.0708 mmol), N,N-diisopropylethylamine (124.34 µL, 0.71386 mmol) and trichloroacetonitrile (143.2 µL, 1.428 mmol). This was then heated to 150° C. for 5 minutes in the microwave. The mixture was concentrated down and purified on reverse phase prep HPLC to give 4-(3-((6-chloropyridin-2-yl)methyl)-[1,2,4]triazolo[4,3-a]pyridin-7-yl)-N-(tetrahydro-2H-pyran-4-yl)pyrimidin-2-amine (0.0218 g, 14.4%). $^1$H NMR (400 MHz, CDCl$_3$) 8.56 (m, 2H), 8.44 (d, 1H), 7.86 (t, 1H), 7.69 (d, 1H), 7.44 (dd, 2H), 7.37 (d, 2H), 4.78 (s, 2H), 4.06 (s, 1H), 3.90 (d, 2H), 3.44 (m, 2H), 1.89 (d, 2H), 1.56 (m, 2H). LCMS (APCI+) m/z=422.1.

Example 40

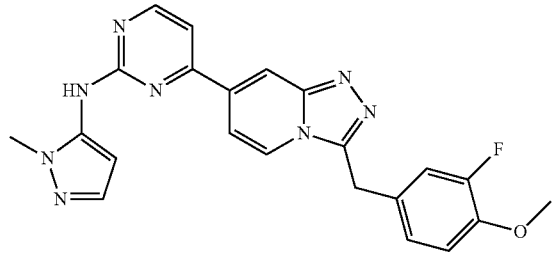

4-(3-(3-fluoro-4-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(3-fluoro-4-methoxyphenyl)acetic acid. $^1$H NMR (400 MHz, (CD$_3$)$_2$SO) δ 9.60 (s, 1H), 8.61 (d, 1H), 8.55 (m, 2H), 7.67 (d, 1H), 7.62 (d, 1H), 7.39 (d, 1H), 7.23 (dd, 1H), 7.09 (m, 2H), 6.31 (d, 1H), 4.52 (s, 2H), 3.79 (s, 3H), 3.71 (s, 3H); m/z (APCI–pos) M+1=431.2.

Example 41

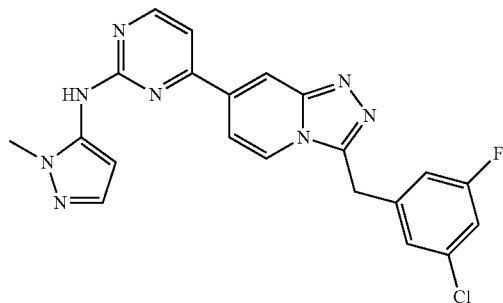 [SMILES: Cn1nccc1Nc1nccc(-c2ccn3c(Cc4cc(F)cc(Cl)c4)nnc3c2)n1]

4-(3-(3-chloro-5-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(3-chloro-5-fluorophenyl)acetic acid. $^1$H NMR (400 MHz, (CD$_3$)$_2$SO) δ 9.60 (s, 1H), 8.61 (m, 2H), 8.55 (s, 1H), 7.67 (m, 2H), 7.39 (d, 1H), 7.34 (m, 2H), 7.23 (d, 1H), 6.31 (d, 1H), 4.63 (s, 2H), 3.71 (s, 3H); m/z (APCI–pos) M+1=435.1.

Example 42

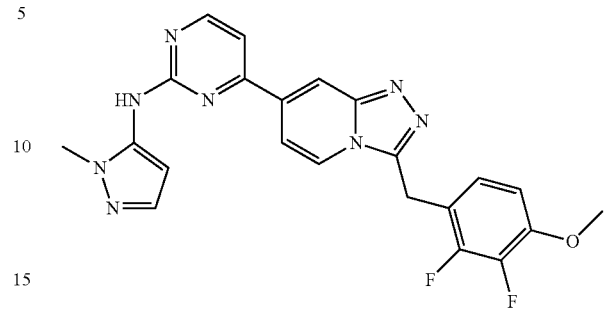

4-(3-(2,3-difluoro-4-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(2,3-difluoro-4-methoxyphenyl)acetic acid. $^1$H NMR (400 MHz, (CD$_3$)$_2$SO) δ 9.60 (s, 1H), 8.61 (d, 1H), 8.57 (m, 2H), 7.67 (m, 2H), 7.39 (d, 1H), 6.95-7.10 (m, 2H), 6.31 (d, 1H), 4.57 (s, 2H), 3.86 (s, 3H), 3.71 (s, 3H); m/z (APCI–pos) M+1=449.2.

Example 43

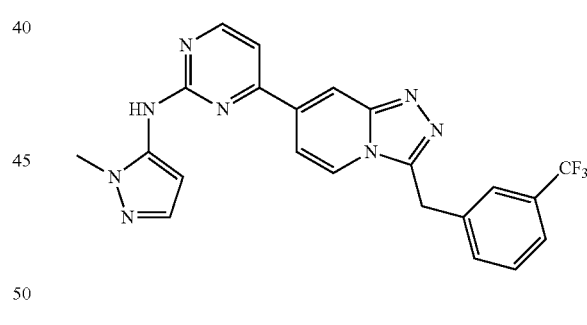

N-(1-methyl-1H-pyrazol-5-yl)-4-(3-(3-(trifluoromethyl)benzyl)-[1,2,4]triazolo[4,3-a]pyridin-7-yl)pyrimidin-2-amine Prepared according to Example 6, using 2-(3-(trifluoromethyl)phenyl)acetic acid. $^1$H NMR (400 MHz, (CD$_3$)$_2$SO) δ 9.60 (s, 1H), 8.63 (m, 2H), 8.57 (s, 1H), 7.80 (s, 1H), 7.55-7.70 (m, 5H), 7.40 (s, 1H), 6.31 (s, 1H), 4.70 (s, 2H), 3.71 (s, 3H); m/z (APCI–pos) M+1=451.2.

Example 44

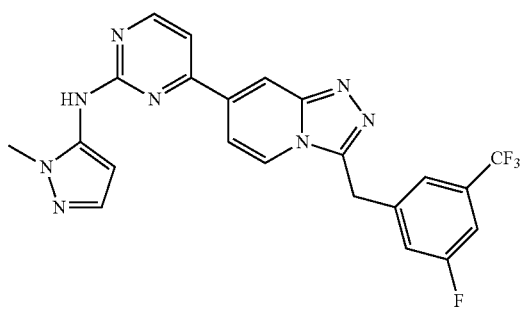 [SMILES: Cn1nccc1Nc1nccc(-c2ccn3c(Cc4cc(F)cc(C(F)(F)F)c4)nnc3c2)n1]

4-(3-(3-fluoro-5-(trifluoromethyl)benzyl)-[1,2,4]triazolo[4,3-a]pyridin-7-yl)-N-(1-methyl-1H-pyrazol-5-yl)pyrimidin-2-amine Prepared according to Example 6, using 2-(3-fluoro-5-(trifluoromethyl)phenyl)acetic acid. $^1$H NMR (400 MHz, (CD$_3$)$_2$SO) δ 9.60 (s, 1H), 8.68 (d, 1H), 8.61 (d, 1H), 8.58 (s, 1H), 7.66 (m, 3H), 7.60 (t, 1H), 7.40 (s, 1H), 6.31 (s, 1H), 4.71 (s, 2H), 3.71 (s, 3H); m/z (APCI–pos) M+1=469.1.

Example 45

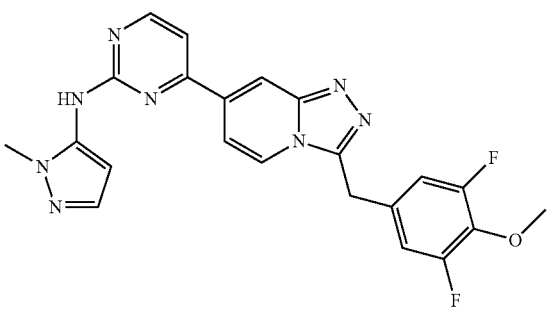

4-(3-(3,5-difluoro-4-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(3,5-difluoro-4-methoxyphenyl)acetic acid. $^1$H NMR (400 MHz, (CD$_3$)$_2$SO) δ 9.60 (s, 1H), 8.61 (m, 3H), 7.68 (d, 1H), 7.65 (d, 1H), 7.39 (d, 1H), 7.14 (d, 2H), 6.31 (d, 1H), 4.55 (s, 2H), 3.89 (s, 3H), 3.71 (s, 3H); m/z (APCI–pos) M+1=449.2.

Example 46

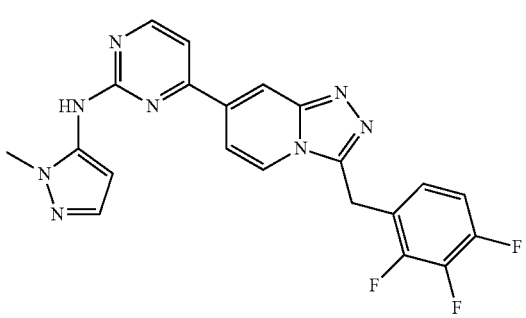 [SMILES: Cn1nccc1Nc1nccc(-c2ccn3c(Cc4ccc(F)c(F)c4F)nnc3c2)n1]

N-(1-methyl-1H-pyrazol-5-yl)-4-(3-(2,3,4-trifluorobenzyl)-[1,2,4]triazolo[4,3-a]pyridin-7-yl)pyrimidin-2-amine Prepared according to Example 6, using 2-(2,3,4-trifluorophenyl)acetic acid. $^1$H NMR (400 MHz, (CD$_3$)$_2$SO) δ 9.60 (s, 1H), 8.61 (m, 3H), 7.68 (m, 2H), 7.40 (d, 1H), 7.18-7.34 (m, 2H), 6.31 (s, 1H), 4.64 (s, 2H), 3.71 (s, 3H); m/z (APCI–pos) M+1=437.1.

Example 47

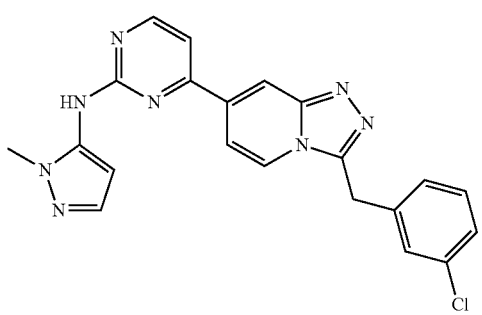

4-(3-(3-chlorobenzyl)-[1,2,4]triazolo[4,3-a]pyridin-7-yl)-N-(1-methyl-1H-pyrazol-5-yl)pyrimidin-2-amine Prepared according to Example 4, using 2-(3-chlorophenyl)acetic acid. $^1$H NMR (400 MHz, CD$_3$OD) δ 8.62 (d, 1H), 8.58 (s, 1H), 8.50 (d, 1H), 7.86 (d, 1H), 7.57 (d, 1H), 7.51 (d, 1H), 7.42 (s, 1H), 7.25-7.35 (m, 3H), 6.41 (d, 1H), 4.66 (s, 2H), 3.79 (s, 3H); m/z (APCI–pos) M+1=417.1.

Example 48

4-(3-(2-fluoro-4-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(2-fluoro-4-methoxyphenyl)acetic acid. $^1$H NMR (400 MHz, (CD$_3$)$_2$SO) δ 9.60 (s, 1H), 8.61 (d, 1H), 8.56 (s, 1H), 8.53 (d, 1H), 7.65 (m, 2H), 7.39 (d, 1H), 7.23 (t, 1H), 6.89 (dd, 1H), 6.75 (dd, 1H), 6.31 (d, 1H), 4.51 (s, 2H), 3.75 (s, 3H), 3.71 (s, 3H); m/z (APCI–pos) M+1=431.2.

Example 49

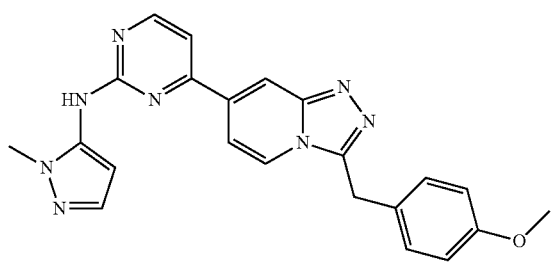

4-(3-(4-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(4-methoxyphenyl)acetic acid. $^1$H NMR (400 MHz, (CD$_3$)$_2$SO) δ 9.60 (s, 1H), 8.61 (d, 1H), 8.55 (s, 1H), 8.48 (d, 1H), 7.65 (d, 1H), 7.59 (d, 1H), 7.39 (d, 1H), 7.24 (d, 2H), 6.89 (d, 2H), 6.30 (d, 1H), 4.51 (s, 2H), 3.71 (s, 6H); m/z (APCI–pos) M+1=413.2.

Example 50

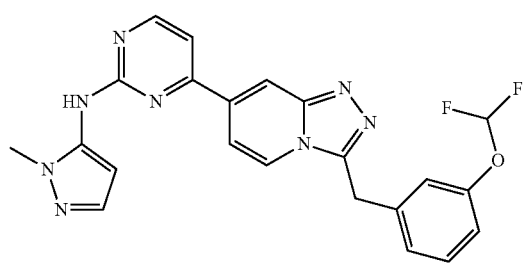 [SMILES: Cn1nccc1Nc1nccc(-c2ccn3c(Cc4cccc(OC(F)F)c4)nnc3c2)n1]

4-(3-(3-(difluoromethoxy)benzyl)-[1,2,4]triazolo[4,3-a]pyridin-7-yl)-N-(1-methyl-1H-pyrazol-5-yl)pyrimidin-2-amine Prepared according to Example 6, using 2-(3-(difluoromethoxy)phenyl)acetic acid. $^1$H NMR (400 MHz, (CD$_3$)$_2$SO) δ 9.60 (s, 1H), 8.61 (d, 1H), 8.57 (m, 2H), 7.66 (d, 1H), 7.62 (d, 1H), 7.00-7.40 (m, 5H), 6.30 (d, 1H), 4.61 (s, 2H), 3.71 (s, 3H); m/z (APCI–pos) M+1=449.2.

Example 51

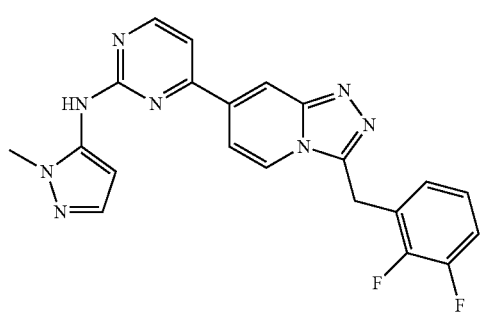 [SMILES: Cn1nccc1Nc1nccc(-c2ccn3c(Cc4cccc(F)c4F)nnc3c2)n1]

4-(3-(2,3-difluorobenzyl)-[1,2,4]triazolo[4,3-a]pyridin-7-yl)-N-(1-methyl-1H-pyrazol-5-yl)pyrimidin-2-amine Prepared according to Example 4, using 2-(2,3-difluorophenyl)acetic acid. $^1$H NMR (400 MHz, CD$_3$OD) δ 8.62 (d, 1H), 8.56 (m, 2H), 7.91 (d, 1H), 7.59 (d, 1H), 7.51 (d, 1H), 7.11-7.34 (m, 4H), 6.42 (d, 1H), 4.71 (s, 2H), 3.79 (s, 3H); m/z (APCI–pos) M+1=419.1.

Example 52

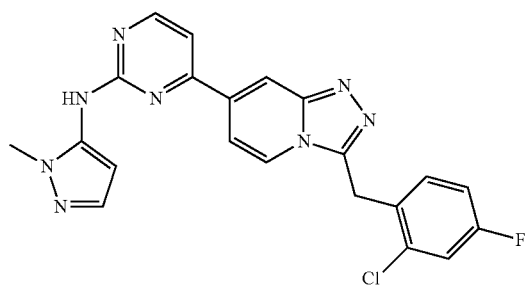 [SMILES: Cn1nccc1Nc1nccc(-c2ccn3c(Cc4ccc(F)cc4Cl)nnc3c2)n1]

4-(3-(2-chloro-4-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(2-chloro-4-fluorophenyl)acetic acid. $^1$H NMR (400 MHz, (CD$_3$)$_2$SO) δ 9.60 (s, 1H), 8.61 (m, 2H), 8.55 (s, 1H), 7.67 (m, 2H), 7.39 (d, 1H), 7.34 (m, 2H), 7.23 (d, 1H), 6.31 (d, 1H), 4.63 (s, 2H), 3.71 (s, 3H); m/z (APCI–pos) M+1=435.1.

Example 53

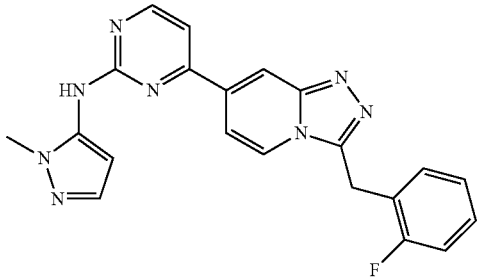 [SMILES: Cn1nccc1Nc1nccc(-c2ccn3c(Cc4ccccc4F)nnc3c2)n1]

4-(3-(2-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(2-fluorophenyl)acetic acid. $^1$H NMR (400 MHz, (CD$_3$)$_2$SO) δ 9.60 (s, 1H), 8.62 (d, 1H), 8.57 (m, 2H), 7.67 (m, 2H), 7.39 (d, 1H), 7.34 (m, 2H), 7.23 (m, 2H), 6.31 (d, 1H), 4.61 (s, 2H), 3.71 (s, 3H); m/z (APCI–pos) M+1=401.2.

Example 54

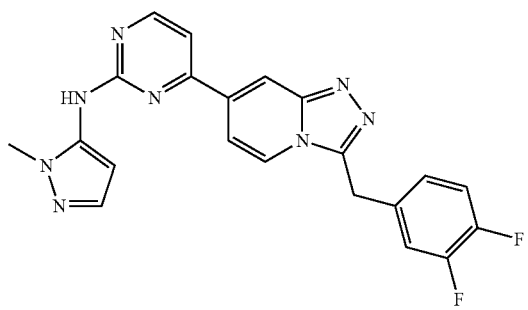 [SMILES: Cn1nccc1Nc1nccc(-c2ccn3c(Cc4ccc(F)c(F)c4)nnc3c2)n1]

4-(3-(3,4-difluorobenzyl)-[1,2,4]triazolo[4,3-a]pyridin-7-yl)-N-(1-methyl-1H-pyrazol-5-yl)pyrimidin-2-amine Prepared according to Example 6, using 2-(3,4-difluorophenyl)acetic acid. $^1$H NMR (400 MHz, (CD$_3$)$_2$SO) δ 9.60 (s, 1H), 8.60 (m, 3H), 7.68 (d, 1H), 7.62 (d, 1H), 7.32-7.35 (m, 3H), 7.15 (m, 1H), 7.23 (m, 2H), 6.31 (d, 1H), 4.61 (s, 2H), 3.71 (s, 3H); m/z (APCI-pos) M+1=419.1.

Example 55

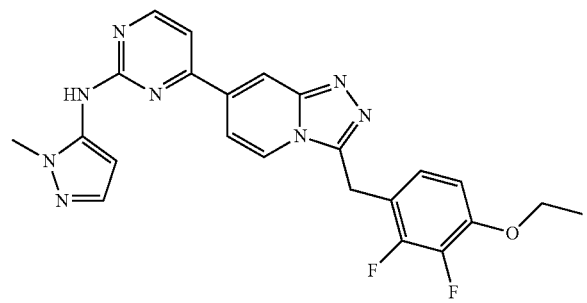 [SMILES: CCOc1ccc(Cc2nnc3cc(-c4ccnc(Nc5ccnn5C)n4)ccn23)c(F)c1F]

4-(3-(4-ethoxy-2,3-difluorobenzyl)-[1,2,4]triazolo[4,3-a]pyridin-7-yl)-N-(1-methyl-1H-pyrazol-5-yl)pyrimidin-2-amine Prepared according to Example 6, using 2-(4-ethoxy-2,3-difluorophenyl)acetic acid. $^1$H NMR (400 MHz, (CD$_3$)$_2$SO) δ 9.60 (s, 1H), 8.62 (d, 1H), 8.55 (m, 2H), 7.66 (m, 2H), 7.40 (d, 1H), 6.94-7.08 (m, 2H), 6.31 (d, 1H), 4.57 (s, 2H), 4.12 (q, 2H), 3.71 (s, 3H), 1.35 (t, 3H); m/z (APCI-pos) M+1=463.2.

Example 56

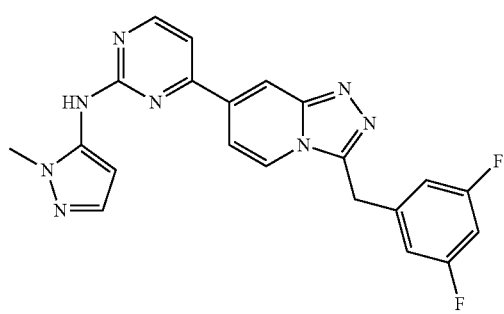 [SMILES: Cn1nccc1Nc1nccc(-c2ccn3c(Cc4cc(F)cc(F)c4)nnc3c2)n1]

4-(3-(3,5-difluorobenzyl)-[1,2,4]triazolo[4,3-a]pyridin-7-yl)-N-(1-methyl-1H-pyrazol-5-yl)pyrimidin-2-amine Prepared according to Example 6, using 2-(3,5-difluorophenyl)acetic acid. $^1$H NMR (400 MHz, (CD$_3$)$_2$SO) δ 9.60 (s, 1H), 8.61 (m, 2H), 8.57 (s, 1H), 7.66 (d, 1H), 7.64 (d, 1H), 7.39 (d, 1H), 7.05-7.22 (m, 3H), 6.31 (d, 1H), 4.62 (s, 2H), 3.71 (s, 3H); m/z (APCI-pos) M+1=419.1.

Example 57

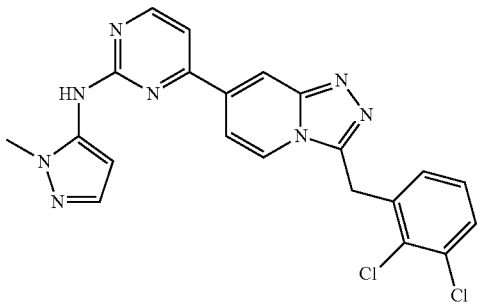 [SMILES: Cn1nccc1Nc1nccc(-c2ccn3c(Cc4cccc(Cl)c4Cl)nnc3c2)n1]

4-(3-(2,3-dichlorobenzyl)-[1,2,4]triazolo[4,3-a]pyridin-7-yl)-N-(1-methyl-1H-pyrazol-5-yl)pyrimidin-2-amine Prepared according to Example 6, using 2-(2,3-dichlorophenyl)acetic acid. $^1$H NMR (400 MHz, (CD$_3$)$_2$SO) δ 9.60 (s, 1H), 8.61 (m, 3H), 7.68 (m, 2H), 7.60 (d, 1H), 7.39 (d, 1H), 7.24-7.38 (m, 2H), 6.31 (d, 1H), 4.71 (s, 2H), 3.71 (s, 3H); m/z (APCI-pos) M+1=451.1.

Example 58

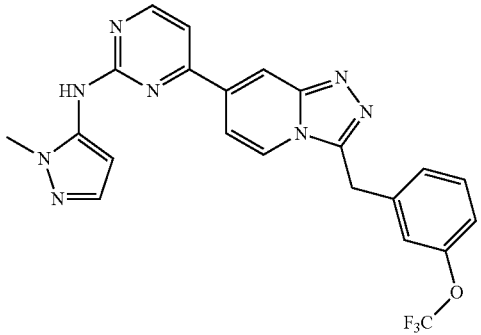 [SMILES: Cn1nccc1Nc1nccc(-c2ccn3c(Cc4cccc(OC(F)(F)F)c4)nnc3c2)n1]

N-(1-methyl-1H-pyrazol-5-yl)-4-(3-(3-(trifluoromethoxy)benzyl)-[1,2,4]triazolo[4,3-a]pyridin-7-yl)pyrimidin-2-amine Prepared according to Example 6, using 2-(3-(trifluoromethoxy)phenyl)acetic acid. $^1$H NMR (400 MHz, (CD$_3$)$_2$SO) δ 9.60 (s, 1H), 8.61 (m, 3H), 8.57 (s, 1H), 7.66 (d, 1H), 7.63 (d, 1H), 7.39-7.48 (m, 3H), 7.34 (d, 1H), 7.25 (d, 1H), 6.31 (d, 1H), 4.66 (s, 2H), 3.71 (s, 3H); m/z (APCI-pos) M+1=467.1.

Example 59

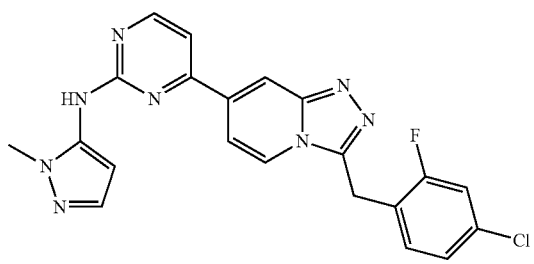 [SMILES: Cn1nccc1Nc1nccc(-c2ccn3c(Cc4ccc(Cl)cc4F)nnc3c2)n1]

4-(3-(4-chloro-2-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(4-chloro-2-fluorophenyl)acetic acid. $^1$H NMR (400 MHz, (CD$_3$)$_2$SO) δ 9.60 (s, 1H), 8.61 (m, 3H), 7.69 (m, 2H), 7.47 (dd, 1H), 7.39 (d, 1H), 7.34 (d, 1H), 7.27 (d, 1H), 6.31 (d, 1H), 4.59 (s, 2H), 3.71 (s, 3H); m/z (APCI–pos) M+1=435.1.

Example 60

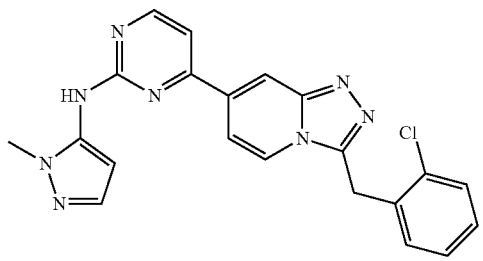 [SMILES: Cn1nccc1Nc1nccc(-c2ccn3c(Cc4ccccc4Cl)nnc3c2)n1]

4-(3-(2-chlorobenzyl)-[1,2,4]triazolo[4,3-a]pyridin-7-yl)-N-(1-methyl-1H-pyrazol-5-yl)pyrimidin-2-amine Prepared according to Example 4, using 2-(2-chlorophenyl)acetic acid. $^1$H NMR (400 MHz, CD$_3$OD) δ 8.61 (m, 3H), 7.92 (d, 1H), 7.59 (d, 1H), 7.52 (d, 1H), 7.48 (m, 1H), 7.32 (m, 3H), 6.41 (d, 1H), 4.75 (s, 2H), 3.80 (s, 3H); m/z (APCI–pos) M+1=417.1.

Example 61

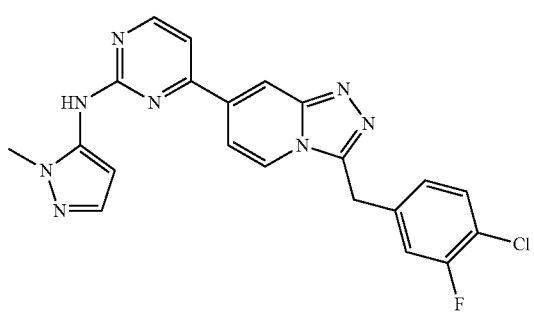 [SMILES: Cn1nccc1Nc1nccc(-c2ccn3c(Cc4ccc(Cl)c(F)c4)nnc3c2)n1]

4-(3-(4-chloro-3-fluorobenzyl)-[1,2,4]triazolo[4,3-a]pyridin-7-yl)-N-(1-methyl-1H-pyrazol-5-yl)pyrimidin-2-amine Prepared according to Example 4, using 2-(4-chloro-3-fluorophenyl)acetic acid. $^1$H NMR (400 MHz, CD$_3$OD) δ 8.54-8.62 (m, 3H), 7.98 (s, 1H), 7.93 (m, 1H), 7.63 (m, 1H), 7.49 (d, 1H), 7.41 (d, 1H), 7.31-7.37 (m, 3H), 4.75 (s, 2H), 3.91 (s, 3H); m/z (APCI–pos) M+1=435.1.

Example 62

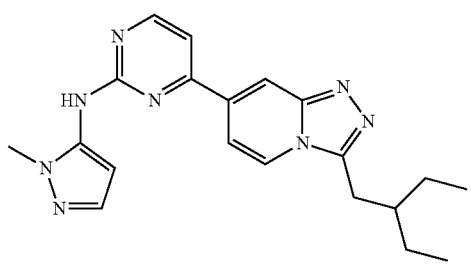 [SMILES: CCC(CC)Cc1nnc2cc(-c3ccnc(Nc4ccnn4C)n3)ccn12]

4-(3-(2-ethylbutyl)-[1,2,4]triazolo[4,3-a]pyridin-7-yl)-N-(1-methyl-1H-pyrazol-5-yl)pyrimidin-2-amine Prepared according to Example 6, using 3-ethylpentanoic acid. $^1$H NMR (400 MHz, (CD$_3$)$_2$SO) δ 9.60 (s, 1H), 8.62 (d, 1H), 8.56 (d, 1H), 8.54 (s, 1H), 7.67 (d, 1H), 7.61 (d, 1H), 7.39 (d, 1H), 6.31 (d, 1H), 3.71 (s, 3H), 3.06 (d, 2H), 1.88 (m, 1H), 1.35 (m, 4H), 0.87 (t, 6H); m/z (APCI–pos) M+1=377.2.

Example 63

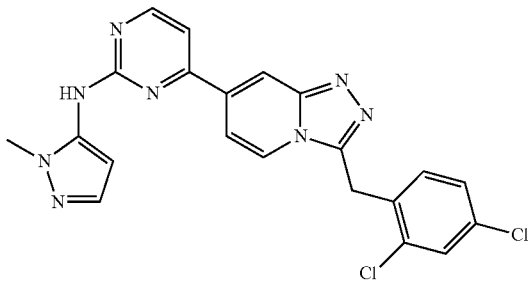 [SMILES: Cn1nccc1Nc1nccc(-c2ccn3c(Cc4ccc(Cl)cc4Cl)nnc3c2)n1]

4-(3-(2,4-dichlorobenzyl)-[1,2,4]triazolo[4,3-a]pyridin-7-yl)-N-(1-methyl-1H-pyrazol-5-yl)pyrimidin-2-amine Prepared according to Example 6, using 2-(2,4-dichlorophenyl)acetic acid. $^1$H NMR (400 MHz, (CD$_3$)$_2$SO) δ 9.60 (s, 1H), 8.60 (m, 3H), 7.69 (m, 3H), 7.40 (m, 3H), 6.31 (d, 1H), 4.64 (s, 2H), 3.71 (s, 3H); m/z (APCI–pos) M+1=454.1.

Example 64

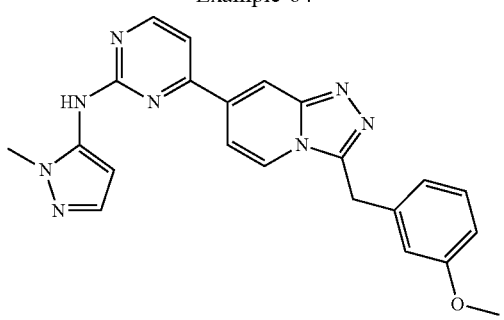

4-(3-(3-methoxybenzyl)-[1,2,4]triazolo[4,3-a]pyridin-7-yl)-N-(1-methyl-1H-pyrazol-5-yl)pyrimidin-2-amine Prepared according to Example 6, using 2-(3-methoxyphenyl)acetic acid. $^1$H NMR (400 MHz, (CD$_3$)$_2$SO) δ 9.60 (s, 1H), 8.61 (d, 1H), 8.55 (s, 1H), 8.52 (d, 1H), 7.65 (d, 1H), 7.61 (d, 1H), 7.39 (d, 1H), 7.22 (t, 1H), 6.92 (m, 1H), 6.78-6.87 (m, 2H), 6.30 (d, 1H), 4.56 (s, 2H), 3.72 (s, 3H), 3.71 (s, 3H); m/z (APCI–pos) M+1=413.2.

Example 65

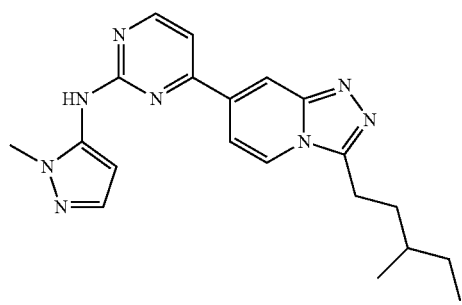 [SMILES: CCC(C)CCc1nnc2cc(-c3ccnc(Nc4ccnn4C)n3)ccn12]

N-(1-methyl-1H-pyrazol-5-yl)-4-(3-(3-methylpentyl)-[1,2,4]triazolo[4,3-a]pyridin-7-yl)pyrimidin-2-amine Prepared according to Example 6, using 4-methylhexanoic acid. $^1$H NMR (400 MHz, (CD$_3$)$_2$SO) δ 9.60 (s, 1H), 8.62 (d, 1H), 8.56 (d, 1H), 8.54 (s, 1H), 7.67 (d, 1H), 7.61 (d, 1H), 7.39 (d, 1H), 6.31 (d, 1H), 3.71 (s, 3H), 3.12 (m, 2H), 1.85 (m, 1H), 1.63 (m, 1H), 1.43 (m, 2H), 1.21 (m, 1H), 0.94 (d, 3H), 0.87 (t, 3H); m/z (APCI–pos) M+1=377.2.

Example 66

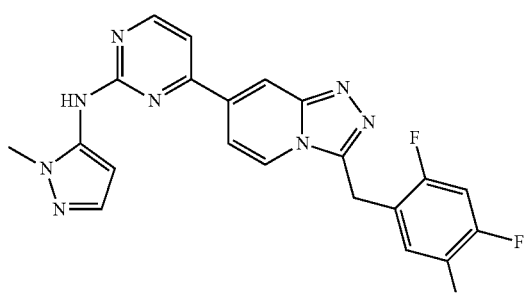

N-(1-methyl-1H-pyrazol-5-yl)-4-(3-(2,4,5-trifluorobenzyl)-[1,2,4]triazolo[4,3-a]pyridin-7-yl)pyrimidin-2-amine Prepared according to Example 6, using 2-(2,4,5-trifluorophenyl)acetic acid. $^1$H NMR (400 MHz, (CD$_3$)$_2$SO) δ 9.60 (s, 1H), 8.61 (m, 2H), 8.56 (s, 1H), 7.68 (m, 2H), 7.58 (m, 2H), 7.39 (d, 1H), 6.31 (d, 1H), 4.57 (s, 2H), 3.71 (s, 3H); m/z (APCI–pos) M+1=437.1.

Example 67

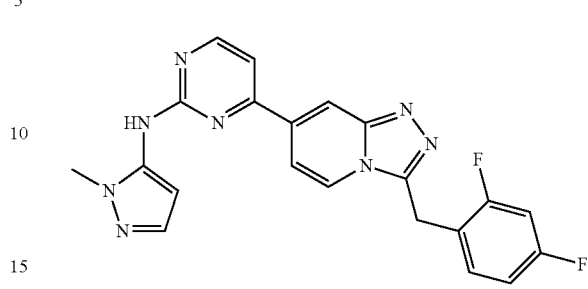

4-(3-(2,4-difluorobenzyl)-[1,2,4]triazolo[4,3-a]pyridin-7-yl)-N-(1-methyl-1H-pyrazol-5-yl)pyrimidin-2-amine Prepared according to Example 4, using 2-(2,4-difluorophenyl)acetic acid. $^1$H NMR (400 MHz, CD$_3$OD) δ 8.60 (m, 3H), 7.92 (d, 1H), 7.60 (d, 1H), 7.52 (d, 1H), 7.40 (m, 1H), 6.93-7.07 (m, 3H), 6.41 (d, 1H), 4.64 (s, 2H), 3.80 (s, 3H); m/z (APCI–pos) M+1=419.2.

Example 68

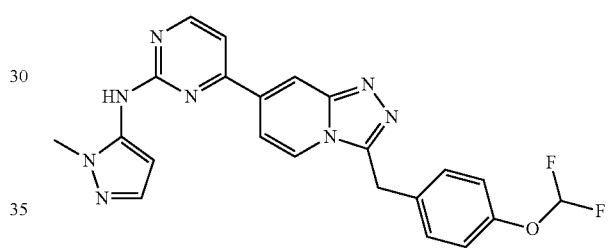

4-(3-(4-(difluoromethoxy)benzyl)-[1,2,4]triazolo[4,3-a]pyridin-7-yl)-N-(1-methyl-1H-pyrazol-5-yl)pyrimidin-2-amine Prepared according to Example 6, using 2-(4-(difluoromethoxy)phenyl)acetic acid. $^1$H NMR (400 MHz, (CD$_3$)$_2$SO) δ 9.60 (s, 1H), 8.61 (d, 1H), 8.56 (m, 2H), 7.66 (d, 1H), 7.62 (d, 1H), 7.36-7.42 (m, 3H), 7.18 (t, 1H), 7.12 (d, 1H), 6.30 (d, 1H), 4.59 (s, 2H), 3.71 (s, 3H); m/z (APCI–pos) M+1=449.1.

Example 69

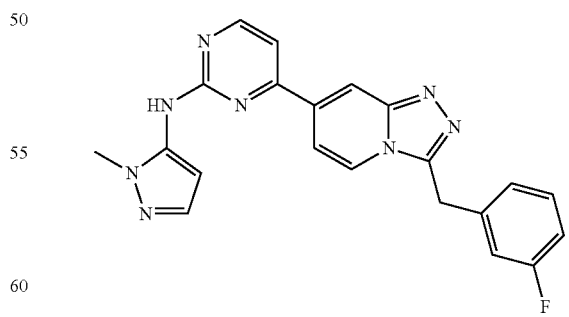

4-(3-(3-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(3-fluorophenyl)acetic acid. $^1$H NMR (400 MHz, CDCl$_3$) δ 8.54 (d, 1H), 8.41 (s, 1H), 7.76 (d, 1H), 7.51 (d, 1H), 7.46 (dd, 1H), 7.22-7.33 (m, 2H), 7.16 (s, 1H), 6.93-7.06 (m, 3H), 6.34 (d, 1H), 4.59 (s, 2H), 3.81 (s, 3H); m/z (APCI-pos) M+1=401.1.

Example 70

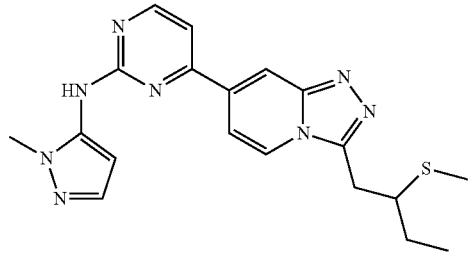

N-(1-methyl-1H-pyrazol-5-yl)-4-(3-(2-(methylthio) butyl)-[1,2,4]triazolo[4,3-a]pyridin-7-yl)pyrimidin-2-amine Prepared according to Example 6, using 3-(methylthio) pentanoic acid. $^1$H NMR (400 MHz, (CD$_3$)$_2$SO) δ 9.60 (s, 1H), 8.64 (d, 1H), 8.62 (d, 1H), 8.54 (s, 1H), 7.67 (d, 1H), 7.61 (d, 1H), 7.39 (d, 1H), 6.31 (d, 1H), 3.71 (s, 3H), 3.43 (d, 2H), 3.12 (m, 1H), 1.99 (s, 3H), 1.55-1.78 (m, 2H), 1.01 (t, 3H); m/z (APCI-pos) M+1=395.2.

Example 71

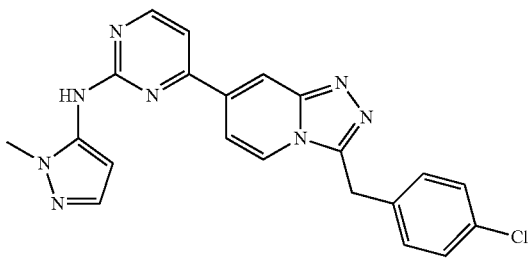 [SMILES: Cn1nccc1Nc1nccc(-c2ccn3c(Cc4ccc(Cl)cc4)nnc3c2)n1]

4-(3-(4-chlorobenzyl)-[1,2,4]triazolo[4,3-a]pyridin-7-yl)-N-(1-methyl-1H-pyrazol-5-yl)pyrimidin-2-amine Prepared according to Example 4, using 2-(4-chlorophenyl)acetic acid. $^1$H NMR (400 MHz, CD$_3$OD) δ 8.62 (d, 1H), 8.58 (s, 1H), 8.45 (d, 1H), 7.83 (d, 1H), 7.57 (d, 1H), 7.50 (d, 1H), 7.30-7.40 (m, 4H), 6.41 (d, 1H), 4.64 (s, 2H), 3.79 (s, 3H); m/z (APCI-pos) M+1=417.1.

Example 72

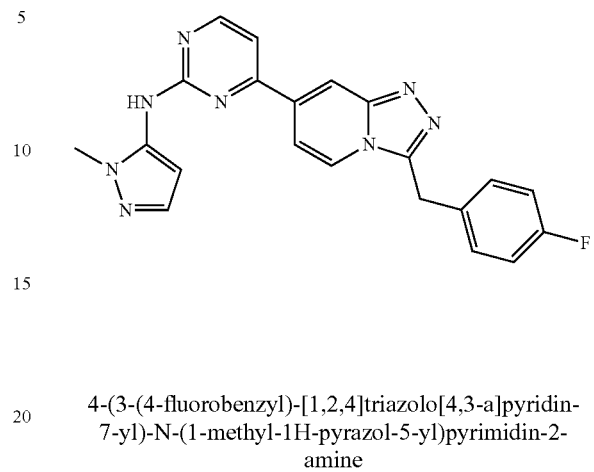

4-(3-(4-fluorobenzyl)-[1,2,4]triazolo[4,3-a]pyridin-7-yl)-N-(1-methyl-1H-pyrazol-5-yl)pyrimidin-2-amine Prepared according to Example 6, using 2-(4-fluorophenyl)acetic acid. $^1$H NMR (400 MHz, (CD$_3$)$_2$SO) δ 9.60 (s, 1H), 8.61 (d, 1H), 8.56 (m, 2H), 7.66 (d, 1H), 7.61 (d, 1H), 7.38 (m, 3H), 7.16 (m, 2H), 6.31 (d, 1H), 4.58 (s, 2H), 3.71 (s, 3H); m/z (APCI-pos) M+1=401.1.

Example 73

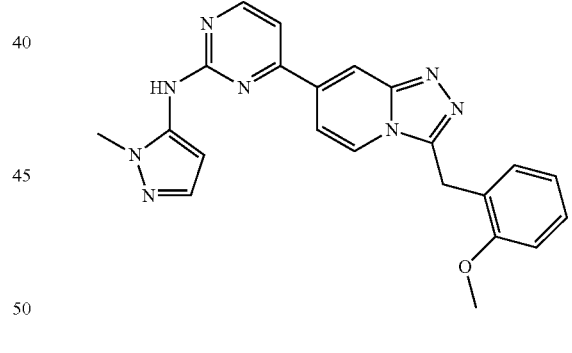

4-(3-(2-methoxybenzyl)-[1,2,4]triazolo[4,3-a]pyridin-7-yl)-N-(1-methyl-1H-pyrazol-5-yl)pyrimidin-2-amine Prepared according to Example 4, using 2-(2-methoxyphenyl)acetic acid. $^1$H NMR (400 MHz, CD$_3$OD) δ 8.65 (m, 2H), 8.60 (s, 1H), 7.95 (d, 1H), 7.60 (d, 1H), 7.52 (d, 1H), 7.29 (m, 2H), 7.01 (d, 1H), 6.92 (t, 1H), 6.43 (d, 1H), 4.61 (s, 2H), 3.80 (s, 3H), 3.79 (s, 3H); m/z (APCI-pos) M+1=413.2.

Example 74

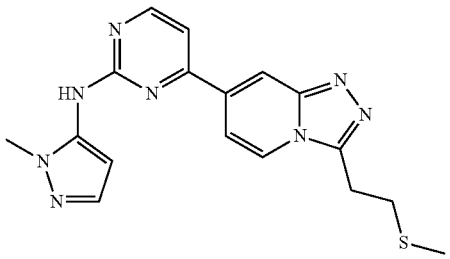

N-(1-methyl-1H-pyrazol-5-yl)-4-(3-(2-(methylthio) ethyl)-[1,2,4]triazolo[4,3-a]pyridin-7-yl)pyrimidin-2-amine Prepared according to Example 6, using 3-(methylthio)propanoic acid. $^1$H NMR (400 MHz, (CD$_3$)$_2$SO) δ 9.60 (s, 1H), 8.64 (d, 1H), 8.62 (d, 1H), 8.54 (s, 1H), 7.69 (d, 1H), 7.63 (d, 1H), 7.39 (d, 1H), 6.31 (d, 1H), 3.71 (s, 3H), 3.43 (t, 2H), 3.02 (t, 2H), 2.12 (s, 3H); m/z (APCI–pos) M+1=367.1.

Example 75

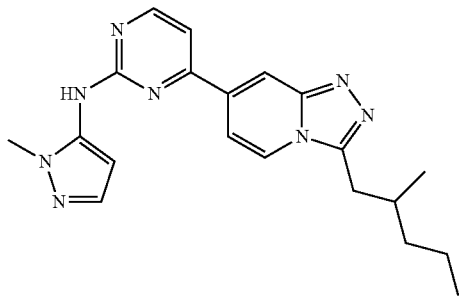

N-(1-methyl-1H-pyrazol-5-yl)-4-(3-(2-methylpentyl)-[1,2,4]triazolo[4,3-a]pyridin-7-yl)pyrimidin-2-amine Prepared according to Example 6, using 3-methylhexanoic acid. $^1$H NMR (400 MHz, (CD$_3$)$_2$SO) δ 9.60 (s, 1H), 8.61 (m, 2H), 8.54 (s, 1H), 7.68 (d, 1H), 7.61 (d, 1H), 7.39 (d, 1H), 6.31 (d, 1H), 3.71 (s, 3H), 3.11 (m, 1H), 2.97 (m, 1H), 2.07 (m, 1H), 1.18-1.43 (m, 4H), 0.91 (d, 3H), 0.85 (m, 3H); m/z (APCI–pos) M+1=377.2.

Example 76

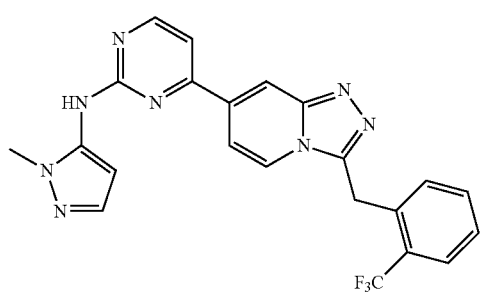 [SMILES: Cn1nccc1Nc1nccc(-c2ccn3c(Cc4ccccc4C(F)(F)F)nnc3c2)n1]

N-(1-methyl-1H-pyrazol-5-yl)-4-(3-(2-(trifluoromethyl)benzyl)-[1,2,4]triazolo[4,3-a]pyridin-7-yl)pyrimidin-2-amine Prepared according to Example 4, using 2-(2-(trifluoromethyl)phenyl)acetic acid. $^1$H NMR (400 MHz, CD$_3$OD) δ 8.64 (d, 1H), 8.61 (s, 1H), 8.50 (d, 1H), 7.91 (d, 1H), 7.81 (d, 1H), 7.51-7.66 (m, 5H), 7.31 (d, 1H), 6.43 (d, 1H), 4.83 (s, 2H), 3.80 (s, 3H); m/z (APCI–pos) M+1=451.2.

Example 77

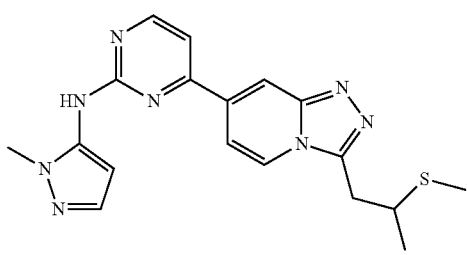

N-(1-methyl-1H-pyrazol-5-yl)-4-(3-(2-(methylthio)propyl)-[1,2,4]triazolo[4,3-a]pyridin-7-yl)pyrimidin-2-amine Prepared according to Example 6, using 3-(methylthio)butanoic acid. $^1$H NMR (400 MHz, (CD$_3$)$_2$SO) δ 9.60 (s, 1H), 8.65 (d, 1H), 8.61 (d, 1H), 8.54 (s, 1H), 7.69 (d, 1H), 7.63 (d, 1H), 7.39 (d, 1H), 6.31 (d, 1H), 3.71 (s, 3H), 3.28-3.49 (m, 3H), 2.06 (s, 3H), 1.33 (d, 3H); m/z (APCI–pos) M+1=381.1.

Example 78

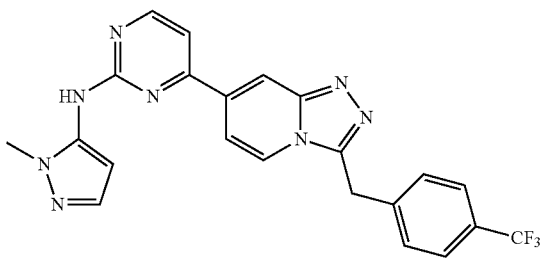 [SMILES: Cn1nccc1Nc1nccc(-c2ccn3c(Cc4ccc(C(F)(F)F)cc4)nnc3c2)n1]

N-(1-methyl-1H-pyrazol-5-yl)-4-(3-(4-(trifluoromethyl)benzyl)-[1,2,4]triazolo[4,3-a]pyridin-7-yl)pyrimidin-2-amine Prepared according to Example 6, using 2-(4-(trifluoromethyl)phenyl)acetic acid. $^1$H NMR (400 MHz, (CD$_3$)$_2$SO) δ 9.60 (s, 1H), 8.60 (m, 3H), 7.69 (m, 4H), 7.56 (d, 2H), 7.40 (m, 1H), 6.31 (d, 1H), 4.71 (s, 2H), 3.71 (s, 3H); m/z (APCI–pos) M+1=451.2.

Example 79

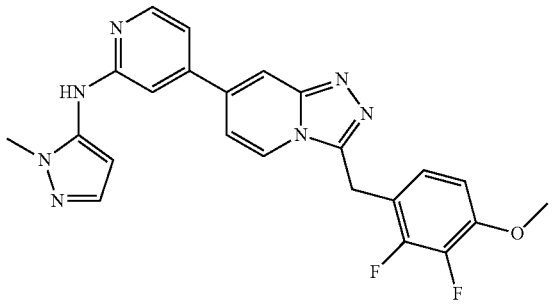

4-(3-(2,3-difluoro-4-methoxybenzyl)-[1,2,4]triazolo[4,3-a]pyridin-7-yl)-N-(1-methyl-1H-pyrazol-5-yl)pyridin-2-amine Step 1: 2'-Hydrazinyl-N-(1-methyl-1H-pyrazol-5-yl)-[4,4'-bipyridin]-2-amine (40 mg, 0.14 mmol), hydroxybenzotriazole ("HOBT") (21 mg, 0.16 mmol), 1-(3-dimethylaminopropyl)-3-ethylcarbodiimide hydrochloride (30 mg, 0.16 mmol) and 2-(2,3-difluoro-4-methoxyphenyl)acetic acid (29 mg, 0.14 mmol) were diluted with DMF (1 mL), followed by the addition of DIEA (d 0.742) (50 µL, 0.28 mmol). After stirring for 3 hours, the reaction was concentrated to afford 2-(2,3-difluoro-4-methoxyphenyl)-N'-(2'-((1-methyl-1H-pyrazol-5-yl)amino)-[4,4'-bipyridin]-2-yl)acetohydrazide (66 mg, 0.14 mmol, 100% yield). The material was taken on as crude.

Step 2: 2-(2,3-Difluoro-4-methoxyphenyl)-N'-(2'-((1-methyl-1H-pyrazol-5-yl)amino)-[4,4'-bipyridin]-2-yl)acetohydrazide (55 mg, 0.12 mmol) was diluted with neat glacial acetic acid (1 mL), sealed and heated to 150° C. in the microwave for 10 minutes. The reaction was allowed to cool and then concentrated. The material was purified on silica gel eluting with 10% methanol:DCM (1% NH$_4$OH) to afford 4-(3-(2,3-difluoro-4-methoxybenzyl)-[1,2,4]triazolo[4,3-a]pyridin-7-yl)-N-(1-methyl-1H-pyrazol-5-yl)pyridin-2-amine (33 mg, 0.074 mmol, 62% yield). $^1$H NMR (400 MHz, (CD$_3$)$_2$SO) δ 8.92 (s, 1H), 8.52 (d, 1H), 8.23 (d, 4H), 8.12 (s, 1H), 7.33 (s, 1H), 7.29 (d, 1H), 7.23 (d, 1H), 7.11 (s, 1H), 7.04 (t, 1H), 6.99 (t, 1H), 6.29 (d, 1H), 4.58 (s, 2H), 3.87 (s, 3H), 3.70 (s, 3H); m/z (APCI–pos) M+1=448.2.

Example 80

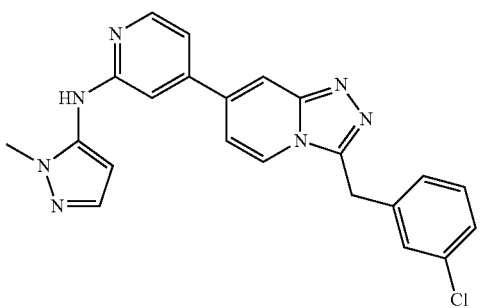 [SMILES: Cn1nccc1Nc1cc(-c2ccn3c(Cc4cccc(Cl)c4)nnc3c2)ccn1]

4-(3-(3-chlorobenzyl)-[1,2,4]triazolo[4,3-a]pyridin-7-yl)-N-(1-methyl-1H-pyrazol-5-yl)pyridin-2-amine Prepared according to Example 79, substituting 2-(3-chlorophenyl)acetic acid for 2-(2,3-difluoro-4-methoxyphenyl)acetic acid. $^1$H NMR (400 MHz, (CD$_3$)$_2$SO) δ 8.92 (s, 1H), 8.53 (d, 1H), 8.22 (d, 1H), 8.13 (s, 1H), 7.45 (s, 1H), 7.19-7.38 m (6H), 7.10 (s, 1H), 6.23 (d, 1H), 4.61 (s, 2H), 3.68 (s, 3H); m/z (APCI–pos) M+1=416.1.

Example 81

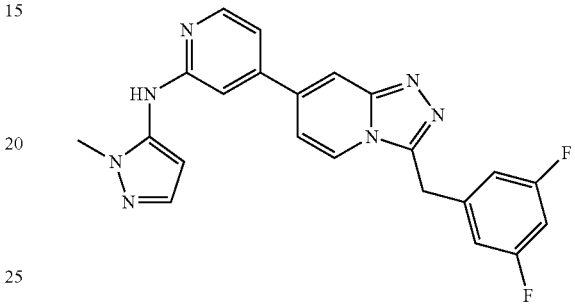

4-(3-(3,5-difluorobenzyl)-[1,2,4]triazolo[4,3-a]pyridin-7-yl)-N-(1-methyl-1H-pyrazol-5-yl)pyridin-2-amine Prepared according to Example 79, substituting 2-(3,5-difluorophenyl)acetic acid for 2-(2,3-difluoro-4-methoxyphenyl)acetic acid. $^1$H NMR (400 MHz, (CD$_3$)$_2$SO) δ 8.92 (s, 1H), 8.55 (d, 1H), 8.22 (d, 1H), 8.13 (s, 1H), 7.35 (d, 1H), 7.29 (dd, 1H), 7.22 (d, 1H), 7.05-7.20 (m, 4H), 6.29 (d, 1H), 4.61 (s, 2H), 3.68 (s, 3H); m/z (APCI–pos) M+1=418.1.

Example 82

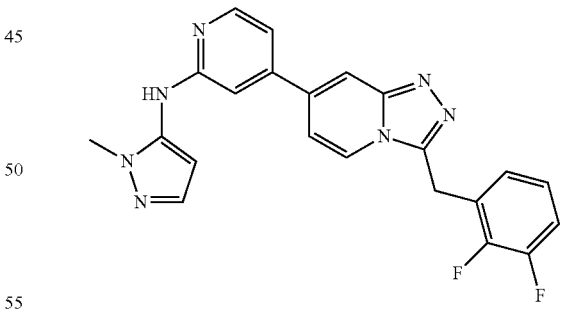

4-(3-(2,3-difluorobenzyl)-[1,2,4]triazolo[4,3-a]pyridin-7-yl)-N-(1-methyl-1H-pyrazol-5-yl)pyridin-2-amine Prepared according to Example 79, substituting 2-(2,3-difluorophenyl)acetic acid for 2-(2,3-difluoro-4-methoxyphenyl)acetic acid. $^1$H NMR (400 MHz, (CD$_3$)$_2$SO) δ 8.92 (s, 1H), 8.55 (d, 1H), 8.22 (d, 1H), 8.13 (s, 1H), 7.07-7.41 (m, 7H), 6.29 (d, 1H), 4.67 (s, 2H), 3.70 (s, 3H); m/z (APCI–pos) M+1=418.1.

Example 83

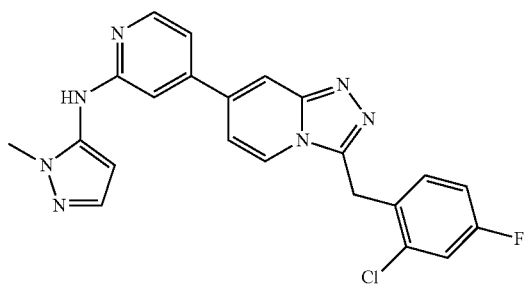

4-(3-(2-chloro-4-fluorobenzyl)-[1,2,4]triazolo[4,3-a]pyridin-7-yl)-N-(1-methyl-1H-pyrazol-5-yl)pyridin-2-amine Prepared according to Example 79, substituting 2-(2-chloro-4-fluorophenyl)acetic acid for 2-(2,3-difluoro-4-methoxyphenyl)acetic acid. $^1$H NMR (400 MHz, (CD$_3$)$_2$SO) δ 8.92 (s, 1H), 8.58 (d, 1H), 8.22 (d, 1H), 8.13 (s, 1H), 7.50 (dd, 1H), 7.20-7.41 (m, 5H), 7.11 (s, 1H), 6.29 (d, 1H), 4.62 (s, 2H), 3.68 (s, 3H); m/z (APCI–pos) M+1=434.1.

Example 84

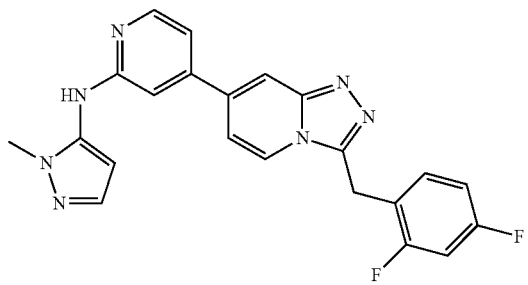

4-(3-(2,4-difluorobenzyl)-[1,2,4]triazolo[4,3-a]pyridin-7-yl)-N-(1-methyl-1H-pyrazol-5-yl)pyridin-2-amine Prepared according to Example 79, substituting 2-(2,4-difluorophenyl)acetic acid for 2-(2,3-difluoro-4-methoxyphenyl)acetic acid. $^1$H NMR (400 MHz, (CD$_3$)$_2$SO) δ 8.92 (s, 1H), 8.58 (d, 1H), 8.22 (d, 1H), 8.13 (s, 1H), 7.20-7.43 (m, 5H), 7.10 (s, 1H), 7.05 (m, 1H), 6.29 (d, 1H), 4.58 (s, 2H), 3.68 (s, 3H); m/z (APCI–pos) M+1=418.1.

Example 85

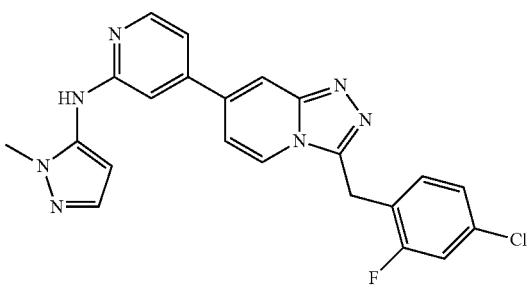 [SMILES: Cn1nccc1Nc1cc(-c2ccn3c(Cc4ccc(Cl)cc4F)nnc3c2)ccn1]

4-(3-(4-chloro-2-fluorobenzyl)-[1,2,4]triazolo[4,3-a]pyridin-7-yl)-N-(1-methyl-1H-pyrazol-5-yl)pyridin-2-amine Prepared according to Example 79, substituting 2-(4-chloro-2-fluorophenyl)acetic acid for 2-(2,3-difluoro-4-methoxyphenyl)acetic acid. $^1$H NMR (400 MHz, (CD$_3$)$_2$SO) δ 8.92 (s, 1H), 8.55 (d, 1H), 8.22 (d, 1H), 8.13 (s, 1H), 7.47 (dd, 1H), 7.20-7.43 (m, 5H), 7.10 (s, 1H), 6.29 (d, 1H), 4.59 (s, 2H), 3.68 (s, 3H); m/z (APCI–pos) M+1=434.1.

Example 86

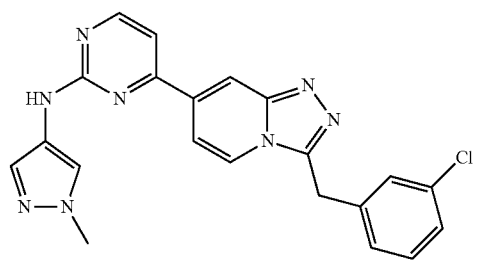 [SMILES: Cn1cc(Nc2nccc(-c3ccn4c(Cc5cccc(Cl)c5)nnc4c3)n2)cn1]

4-(3-(3-chlorobenzyl)-[1,2,4]triazolo[4,3-a]pyridin-7-yl)-N-(1-methyl-1H-pyrazol-4-yl)pyrimidin-2-amine Prepared according to Example 47, substituting 1-methyl-1H-pyrazol-4-amine for 1-methyl-1H-pyrazol-5-amine. $^1$H NMR (400 MHz, CDCl$_3$) δ 8.51 (d, 1H), 8.41 (s, 1H), 7.80 (s, 1H), 7.77 (d, 1H), 7.57 (s, 1H), 7.51 (d, 1H), 7.27 (m, 2H), 7.13 (m, 2H), 7.00 (m, 1H), 4.58 (s, 2H), 3.92 (s, 3H); m/z (APCI–pos) M+1=417.1.

Example 87

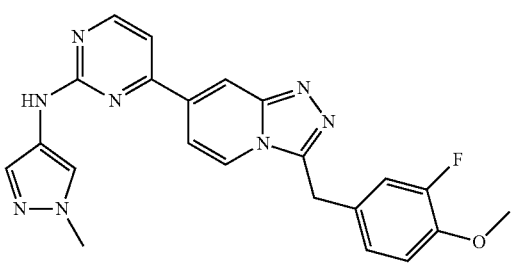 [SMILES: COc1ccc(Cc2nnc3cc(-c4ccnc(Nc5cnn(C)c5)n4)ccn23)cc1F]

4-(3-(3-fluoro-4-methoxybenzyl)-[1,2,4]triazolo[4,3-a]pyridin-7-yl)-N-(1-methyl-1H-pyrazol-4-yl)pyrimidin-2-amine Prepared according to Example 86, substituting 2-(3-fluoro-4-methoxyphenyl)acetic acid for 2-(3-chlorophenyl)acetic acid. $^1$H NMR (400 MHz, CD$_3$OD) δ 8.62 (s, 1H), 8.56 (d, 1H), 8.53 (d, 1H), 7.95 (m, 2H), 7.64 (s, 1H), 7.41 (d, 1H), 7.04-7.18 (m, 3H), 4.61 (s, 2H), 3.91 (s, 3H), 3.85 (s, 3H); m/z (APCI–pos) M+1=431.2.

Example 88

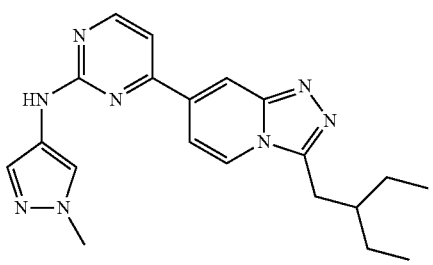 [SMILES: CCC(CC)Cc1nnc2cc(-c3ccnc(Nc4cnn(C)c4)n3)ccn12]

4-(3-(2-ethylbutyl)-[1,2,4]triazolo[4,3-a]pyridin-7-yl)-N-(1-methyl-1H-pyrazol-4-yl)pyrimidin-2-amine Prepared according to Example 86, substituting 3-ethylpentanoic acid for 2-(3-chlorophenyl)acetic acid. $^1$H NMR (400 MHz, (CD$_3$)$_2$SO) δ 9.62 (s, 1H), 8.54 (m, 3H), 7.92 (s, 1H), 7.70 (d, 1H), 7.60 (br s, 1H), 7.50 (d, 1H), 3.84 (s, 3H), 3.08 (d, 2H), 1.90 (m, 1H), 1.37 (m, 4H), 0.88 (t, 6H); m/z (APCI-pos) M+1=377.2.

Example 89

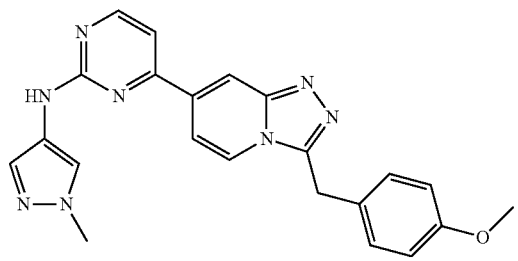 [SMILES: COc1ccc(Cc2nnc3cc(-c4ccnc(Nc5cnn(C)c5)n4)ccn23)cc1]

4-(3-(4-methoxybenzyl)-[1,2,4]triazolo[4,3-a]pyridin-7-yl)-N-(1-methyl-1H-pyrazol-4-yl)pyrimidin-2-amine Prepared according to Example 86, substituting 2-(4-methoxyphenyl)acetic acid for 2-(3-chlorophenyl)acetic acid. $^1$H NMR (400 MHz, (CD$_3$)$_2$SO) δ 9.61 (s, 1H), 8.55 (s, 2H), 8.48 (d, 1H), 7.90 (s, 1H), 7.66 (d, 1H), 7.57 (br s, 1H), 7.49 (d, 1H), 7.24 (d, 2H), 6.88 (d, 2H), 4.53 (s, 2H), 3.83 (s, 3H), 3.70 (s, 3H); m/z (APCI-pos) M+1=413.2.

Example 90

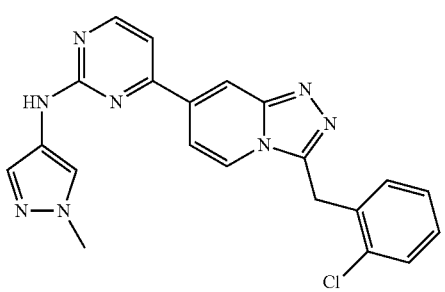 [SMILES: Cn1cc(Nc2nccc(-c3ccn4c(Cc5ccccc5Cl)nnc4c3)n2)cn1]

4-(3-(2-chlorobenzyl)-[1,2,4]triazolo[4,3-a]pyridin-7-yl)-N-(1-methyl-1H-pyrazol-4-yl)pyrimidin-2-amine Prepared according to Example 86, substituting 2-(2-chlorophenyl)acetic acid for 2-(3-chlorophenyl)acetic acid. $^1$H NMR (400 MHz, CD$_3$OD) δ 8.61 (s, 1H), 8.55 (m, 2H), 7.97 (s, 1H), 7.92 (m, 1H), 7.63 (s, 1H), 7.48 (d, 1H), 7.41 (d, 1H), 7.32 (m, 3H), 4.76 (s, 2H), 3.90 (s, 3H); m/z (APCI-pos) M+1=417.1.

Example 91

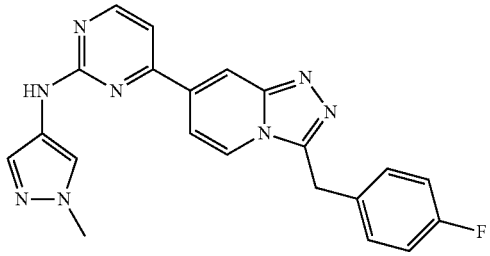 [SMILES: Cn1cc(Nc2nccc(-c3ccn4c(Cc5ccc(F)cc5)nnc4c3)n2)cn1]

4-(3-(4-fluorobenzyl)-[1,2,4]triazolo[4,3-a]pyridin-7-yl)-N-(1-methyl-1H-pyrazol-4-yl)pyrimidin-2-amine Prepared according to Example 86, substituting 2-(4-fluorophenyl)acetic acid for 2-(3-chlorophenyl)acetic acid. $^1$H NMR (400 MHz, d6-DMSO) δ 9.61 (s, 8.55 (m, 3H), 7.91 (s, 1H), 7.68 (d, 1H), 7.57 (br s, 1H), 7.49 (d, 1H), 7.38 (m, 2H), 7.15 (t, 21-), 4.60 (s, 2H), 3.83 (s, 3H); m/z (APCI-pos) M+1=401.1.

Example 92

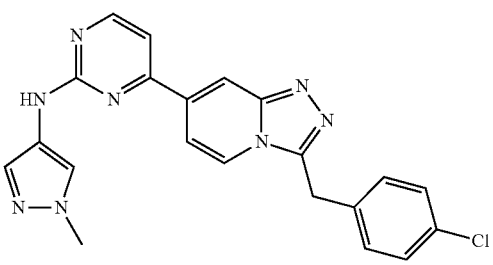 [SMILES: Cn1cc(Nc2nccc(-c3ccn4c(Cc5ccc(Cl)cc5)nnc4c3)n2)cn1]

4-(3-(4-chlorobenzyl)-[1,2,4]triazolo[4,3-a]pyridin-7-yl)-N-(1-methyl-1H-pyrazol-4-yl)pyrimidin-2-amine Prepared according to Example 86, substituting 2-(4-chlorophenyl)acetic acid for 2-(3-chlorophenyl)acetic acid. $^1$H NMR (400 MHz, CD$_3$OD) δ 8.61 (s, 1H), 8.55 (m, 2H), 7.97 (s, 1H), 7.91 (m, 1H), 7.63 (s, 1H), 7.49 (d, 1H), 7.41 (d, 1H), 7.32 (m, 3H), 4.76 (s, 2H), 3.90 (s, 3H); m/z (APCI-pos) M+1=417.1.

Example 93

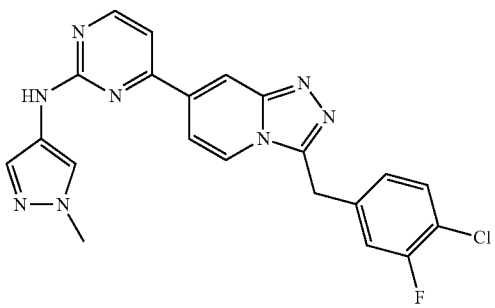 [SMILES: Cn1cc(Nc2nccc(-c3ccn4c(Cc5ccc(Cl)c(F)c5)nnc4c3)n2)cn1]

4-(3-(4-chloro-3-fluorobenzyl)-[1,2,4]triazolo[4,3-a]pyridin-7-yl)-N-(1-methyl-1H-pyrazol-4-yl)pyrimidin-2-amine Prepared according to Example 86, substituting 2-(4-chloro-3-fluorophenyl)acetic acid for 2-(3-chlorophenyl)acetic acid. $^1$H NMR (400 MHz, CD$_3$OD) δ 8.62 (s, 1H), 8.55 (m, 2H), 7.97 (s, 1H), 7.93 (d, 1H), 7.63 (s, 1H), 7.47 (t, 1H), 7.41 (d, 1H), 7.30 (dd, 1H), 7.17 (d, 2H), 4.68 (s, 2H), 3.90 (s, 3H); m/z (APCI–pos) M+1=435.

Example 94

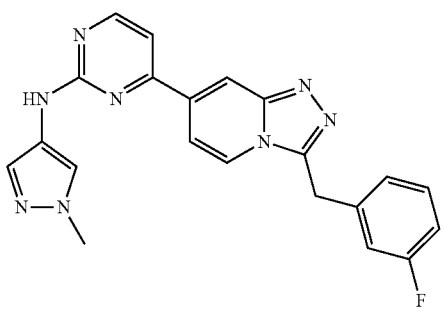 [SMILES: Cn1cc(Nc2nccc(-c3ccn4c(Cc5cccc(F)c5)nnc4c3)n2)cn1]

4-(3-(3-fluorobenzyl)-[1,2,4]triazolo[4,3-a]pyridin-7-yl)-N-(1-methyl-1H-pyrazol-4-yl)pyrimidin-2-amine Prepared according to Example 86, substituting 2-(3-fluorophenyl)acetic acid for 2-(3-chlorophenyl)acetic acid. $^1$H NMR (400 MHz, CDCl$_3$) δ 8.51 (d, 1H), 8.41 (s, 1H), 7.78 (m, 2H), 7.56 (s, 1H), 7.49 (d, 1H), 7.31 (m, 1H), 7.11 (d, 1H), 7.03 (d, 1H), 6.98 (m, 3H), 4.60 (s, 2H), 3.92 (s, 3H); m/z (APCI–pos) M+1=401.2.

Example 95

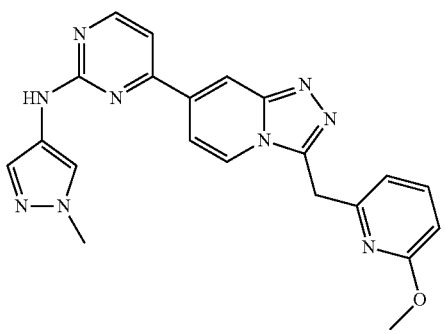 [SMILES: COc1cccc(Cc2nnc3cc(-c4ccnc(Nc5cnn(C)c5)n4)ccn23)n1]

4-(3-((6-methoxypyridin-2-yl)methyl)-[1,2,4]triazolo[4,3-a]pyridin-7-yl)-N-(1-methyl-1H-pyrazol-4-yl)pyrimidin-2-amine Prepared according to Example 86, substituting 2-(6-methoxypyridin-2-yl)acetic acid for 2-(3-chlorophenyl)acetic acid. $^1$H NMR (400 MHz, CDCl$_3$) δ 8.51 (m, 2H), 8.41 (s, 1H), 7.83 (s, 1H), 7.56 (m, 3H), 7.15 (d, 1H), 6.91 (d, 1H), 6.63 (d, 1H), 4.65 (s, 2H), 3.92 (s, 3H), 3.80 (s, 3H); m/z (APCI–pos) M+1=414.2.

Example 96

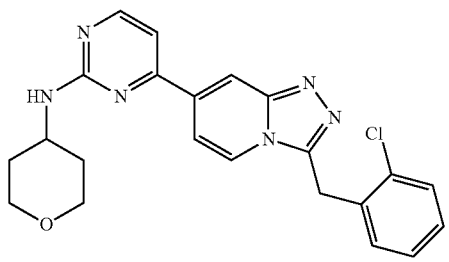 [SMILES: Clc1ccccc1Cc1nnc2cc(-c3ccnc(NC4CCOCC4)n3)ccn12]

4-(3-(2-chlorobenzyl)-[1,2,4]triazolo[4,3-a]pyridin-7-yl)-N-(tetrahydro-2H-pyran-4-yl)pyrimidin-2-amine Prepared according to Example 60, substituting tetrahydro-2H-pyran-4-amine for 1-methyl-1H-pyrazol-5-amine. $^1$H NMR (400 MHz, CD$_3$OD) δ 8.65 (s, 1H), 8.56 (d, 1H), 8.44 (d, 1H), 7.94 (dd, 1H), 7.50 (m, 1H), 7.41 (d, 1H), 7.31-7.37 (m, 3H), 4.76 (s, 2H), 4.02 (m, 2H), 3.59 (m, 2H), 2.04 (m, 2H), 1.68 (m, 2H); m/z (APCI–pos) M+1=421.1.

Example 97

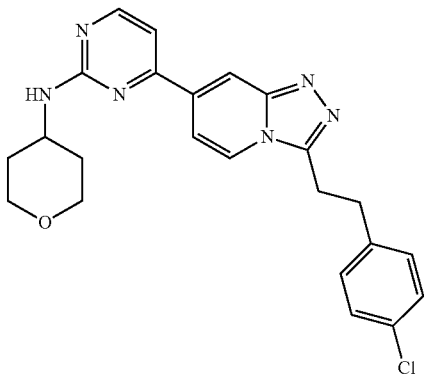 [SMILES: Clc1ccc(CCc2nnc3cc(-c4ccnc(NC5CCOCC5)n4)ccn23)cc1]

4-(3-(4-chlorophenethyl)-[1,2,4]triazolo[4,3-a]pyridin-7-yl)-N-(tetrahydro-2H-pyran-4-yl)pyrimidin-2-amine Prepared according to Example 96, substituting 3-(4-chlorophenyl)propanoic acid for 2-(2-chlorophenyl)acetic acid. $^1$H NMR (400 MHz, CD$_3$OD) δ 8.58 (s, 1H), 8.49 (d, 1H), 8.44 (d, 1H), 7.87 (d, 1H), 7.36 (d, 1H), 7.25 (m, 4H), 4.01 (m, 2H), 3.59 (m, 2H), 3.53 (t, 2H), 3.26 (t, 2H), 2.04 (m, 2H), 1.68 (m, 2H); m/z (APCI–pos) M+1=435.2.

Example 98

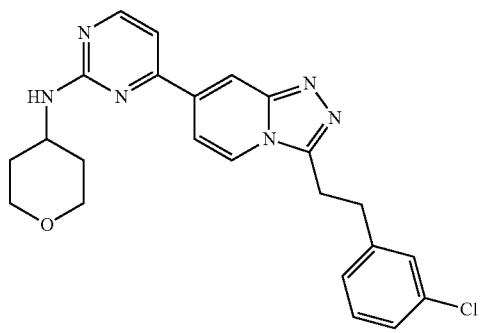 [SMILES: Clc1cccc(CCc2nnc3cc(-c4ccnc(NC5CCOCC5)n4)ccn23)c1]

4-(3-(3-chlorophenethyl)-[1,2,4]triazolo[4,3-a]pyridin-7-yl)-N-(tetrahydro-2H-pyran-4-yl)pyrimidin-2-amine Prepared according to Example 96, substituting 3-(3-chlorophenyl)propanoic acid for 2-(2-chlorophenyl)acetic acid. $^1$H NMR (400 MHz, CD$_3$OD) δ 8.58 (s, 1H), 8.52 (d, 1H), 8.44 (d, 1H), 7.89 (d, 1H), 7.36 (d, 1H), 7.32 (s, 1H), 7.16-7.28 (m, 3H), 4.01 (m, 2H), 3.59 (m, 2H), 3.55 (t, 2H), 3.26 (t, 2H), 2.04 (m, 2H), 1.68 (m, 2H); m/z (APCI–pos) M+1=435.1.

Example 99

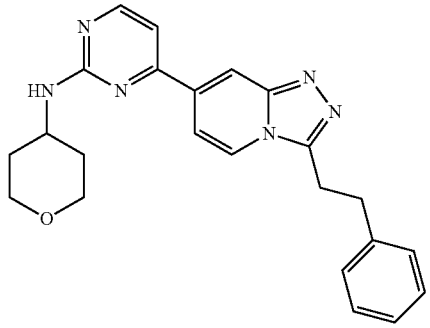 [SMILES: c1ccc(CCc2nnc3cc(-c4ccnc(NC5CCOCC5)n4)ccn23)cc1]

4-(3-phenethyl-[1,2,4]triazolo[4,3-a]pyridin-7-yl)-N-(tetrahydro-2H-pyran-4-yl)pyrimidin-2-amine Prepared according to Example 96, substituting 3-phenylpropanoic acid for 2-(2-chlorophenyl)acetic acid. $^1$H NMR (400 MHz, CD$_3$OD) δ 8.61 (s, 1H), 8.47 (d, 1H), 8.45 (d, 1H), 7.89 (d, 1H), 7.38 (d, 1H), 7.24 (m, 4H), 7.19 (m, 1H), 4.01 (m, 2H), 3.56 (m, 4H), 3.27 (t, 2H), 2.04 (m, 2H), 1.68 (m, 2H); m/z (APCI–pos) M+1=401.2.

Example 100

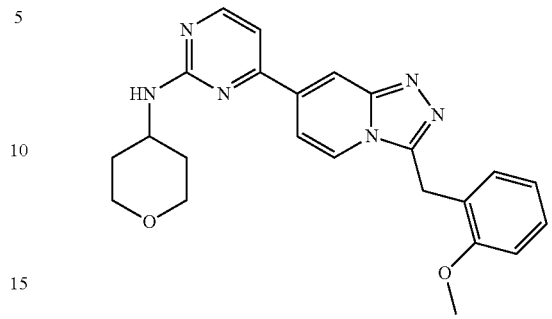

4-(3-(2-methoxybenzyl)-[1,2,4]triazolo[4,3-a]pyridin-7-yl)-N-(tetrahydro-2H-pyran-4-yl)pyrimidin-2-amine Prepared according to Example 96, substituting 2-(2-methoxyphenyl)acetic acid for 2-(2-chlorophenyl)acetic acid. $^1$H NMR (400 MHz, (CD$_3$)$_2$SO) δ 8.54 (m, 2H), 8.45 (d, 1H), 7.71 (d, 1H), 7.41 (m, 1H), 7.37 (d, 1H), 7.27 (t, 1H), 7.10 (d, 1H), 7.02 (d, 1H), 6.89 (t, 1H), 4.48 (s, 2H), 3.90 (m, 2H), 3.75 (s, 3H), 3.42 (m, 2H), 1.89 (m, 2H), 1.55 (m, 2H); m/z (APCI–pos) M+1=417.2.

Example 101

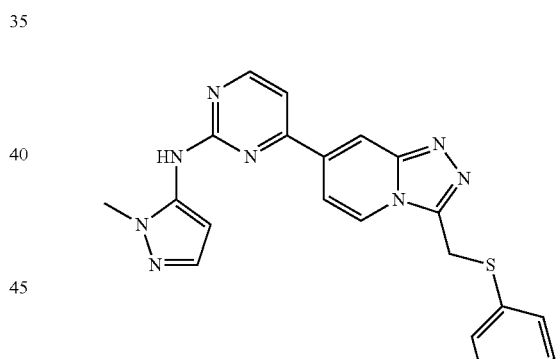

N-(1-methyl-1H-pyrazol-5-yl)-4-(3-((phenylthio)methyl)-[1,2,4]triazolo[4,3-a]pyridin-7-yl)pyrimidin-2-amine N-(1-Methyl-1H-pyrazol-5-yl)-4-(3-((phenylthio)methyl)-[1,2,4]triazolo[4,3-a]pyridin-7-yl)pyrimidin-2-amine (0.056 g, 74%) was made according to the procedure of Example 6, substituting 2-(phenylthio)acetic acid for 2-(4-(methylthio)phenyl)acetic acid. $^1$H NMR (400 MHz, CDCl$_3$) δ 8.57 (d, 1H), 8.38 (s, 1H), 8.21 (dd, 1H), 7.58 (dd, 1H), 7.52 (d, 1H), 7.31 (m, 3H), 7.23 (m, 2H), 7.06 (s, 1H), 6.37 (d, 1H), 4.65 (s, 2H), 3.84 (s, 3H). LCMS (APCI+) m/z=415.1.

Example 102

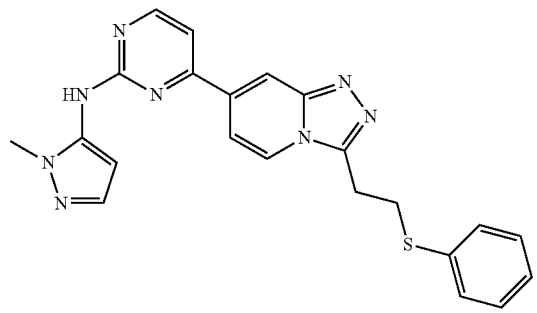 [SMILES: Cn1nccc1Nc1nccc(-c2ccn3c(CCSc4ccccc4)nnc3c2)n1]

N-(1-methyl-1H-pyrazol-5-yl)-4-(3-(2-(phenylthio) ethyl)-[1,2,4]triazolo[4,3-a]pyridin-7-yl)pyrimidin-2-amine N-(1-Methyl-1H-pyrazol-5-yl)-4-(3-(2-(phenylthio) ethyl)-[1,2,4]triazolo[4,3-a]pyridin-7-yl)pyrimidin-2-amine (0.070 g, 83%) was made according to the procedure of Example 6, substituting 3-(phenylthio)propanoic acid for 2-(4-(methylthio)phenyl)acetic acid. $^1$H NMR (400 MHz, CDCl$_3$) δ 8.56 (d, 1H), 8.35 (s, 1H), 7.87 (d, 1H), 7.52 (m, 2H), 7.34 (m, 2H), 7.29 (m, 2H), 7.20 (d, 1H), 7.00 (s, 1H), 6.36 (d, 1H), 3.83 (s, 3H), 3.53 (m, 2H), 3.42 (m, 2H). LCMS (APCI+) m/z=429.1.

Example 103

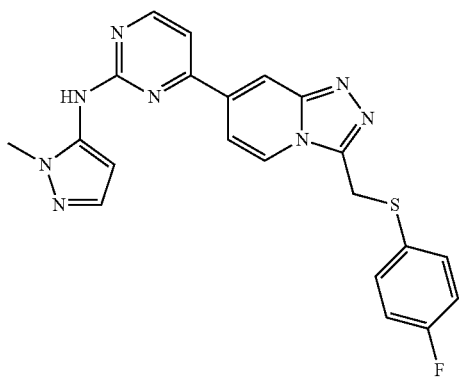 [SMILES: Cn1nccc1Nc1nccc(-c2ccn3c(CSc4ccc(F)cc4)nnc3c2)n1]

4-(3-(((4-fluorophenyl)thio)methyl-[1,2,4]triazolo[4,3-a]pyridin-7-yl)-N-(1-methyl-1H-pyrazol-5-yl)pyrimidin-2-amine 4-(3-(((4-Fluorophenyl)thio)methyl)-[1,2,4]triazolo[4,3-a]pyridin-7-yl)-N-(1-methyl-1H-pyrazol-5-yl)pyrimidin-2-amine (0.042 g, 56%) was made according to the procedure of Example 6, substituting 2-((4-fluorophenyl)thio)acetic acid for 2-(4-(methylthio)phenyl)acetic acid. $^1$H NMR (400 MHz, CDCl$_3$) 8.57 (d, 1H), 8.39 (s, 1H), 8.21 (d, 1H), 7.61 (d, 1H), 7.53 (s, 1H), 7.30 (m, 2H), 7.07 (m, 2H), 6.93 (t, 2H), 6.37 (s, 1H), 4.59 (s, 2H), 3.84 (s, 3H). LCMS (APCI+) m/z=433.1.

Example 104

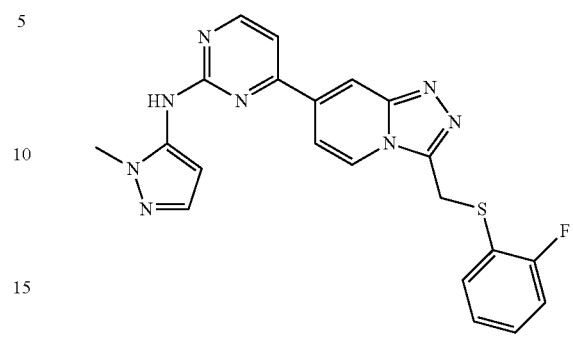

4-(3-(((2-fluorophenyl)thio)methyl)-[1,2,4]triazolo[4,3-a]pyridin-7-yl)-N-(1-methyl-1H-pyrazol-5-yl) pyrimidin-2-amine 4-(3-(((2-Fluorophenyl)thio)methyl)-[1,2,4]triazolo[4,3-a]pyridin-7-yl)-N-(1-methyl-1H-pyrazol-5-yl)pyrimidin-2-amine (0.030 g, 92%) was made according to the procedure of Example 6, substituting 2-((2-fluorophenyl)thio)acetic acid for 2-(4-(methylthio)phenyl)acetic acid. $^1$H NMR (400 MHz, CDCl$_3$) 8.55 (d, 1H), 8.39 (s, 1H), 8.30 (d, 1H), 7.61 (d, 1H), 7.52 (d, 1H), 7.37 (t, 1H), 7.30 (m, 2H), 7.03 (m, 2H), 6.38 (d, 1H), 4.64 (s, 2H), 3.84 (s, 3H). LCMS (APCI+) m/z=433.1.

Example 105

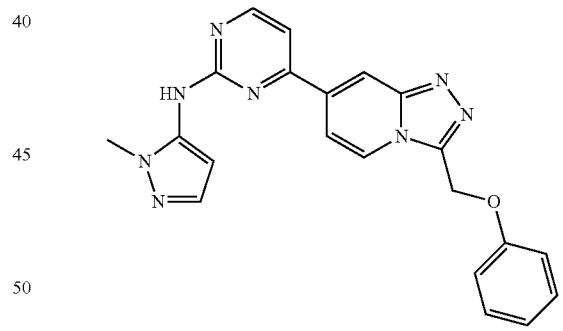

N-(1-methyl-1H-pyrazol-5-yl)-4-(3-(phenoxymethyl)-[1,2,4]triazolo[4,3-a]pyridin-7-yl)pyrimidin-2-amine N-(1-Methyl-1H-pyrazol-5-yl)-4-(3-(phenoxymethyl)-[1,2,4]triazolo[4,3-a]pyridin-7-yl)pyrimidin-2-amine (0.021 g, 50%) was made according to the procedure of Example 6, substituting 2-phenoxyacetic acid for 2-(4-(methylthio)phenyl)acetic acid. $^1$H NMR (400 MHz, CDCl$_3$) 8.56 (d, 1H), 8.42 (s, 1H), 8.35 (d, 1H), 7.60 (dd, 1H), 7.52 (d, 1H), 7.31 (m, 3H), 7.09 (m, 2H), 7.02 (t, 1H), 6.92 (s, 1H), 6.36 (s, 1H), 5.69 (s, 2H) 3.82 (s, 3H). LCMS (APCI+) m/z=399.2.

Example 106

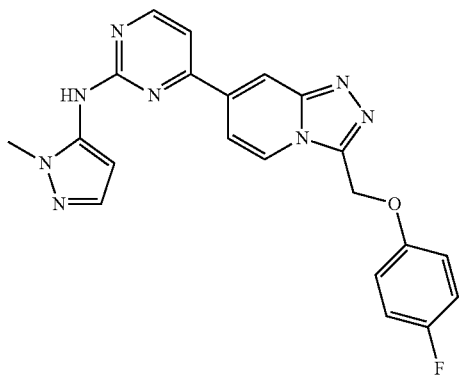 [SMILES: Cn1nccc1Nc1nccc(-c2ccn3c(COc4ccc(F)cc4)nnc3c2)n1]

4-(3-((4-fluorophenoxy)methyl)-[1,2,4]triazolo[4,3-a]pyridin-7-yl)-N-(1-methyl-1H-pyrazol-5-yl)pyrimidin-2-amine 4-(3-((4-Fluorophenoxy)methyl)-[1,2,4]triazolo[4,3-a]pyridin-7-yl)-N-(1-methyl-1H-pyrazol-5-yl)pyrimidin-2-amine (0.041 g, 56%) was made according to the procedure of Example 6, substituting 2-(4-fluorophenoxy)acetic acid for 2-(4-(methylthio)phenyl)acetic acid. $^1$H NMR (400 MHz, CDCl$_3$) 8.57 (d, 1H), 8.42 (s, 1H), 8.34 (d, 1H), 7.61 (dd, 1H), 7.52 (d, 1H), 7.30 (d, 1H), 7.01 (m, 4H), 6.91 (s, 1H), 6.35 (d, 1H), 5.65 (s, 2H), 3.82 (s, 3H). LCMS (APCI+) m/z=417.1.

Example 107

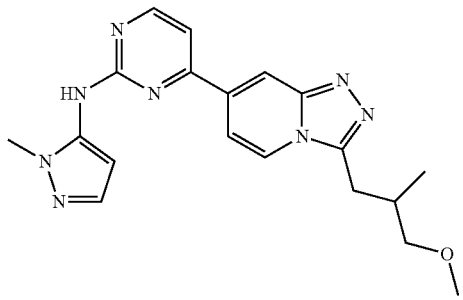

4-(3-(3-methoxy-2-methylpropyl)-[1,2,4]triazolo[4,3-a]pyridin-7-yl)-N-(1-methyl-1H-pyrazol-5-yl)pyrimidin-2-amine Step 1: A solution of benzyl 2-(triphenylphosphoranylidene)acetate (15.4 g, 37.5 mmol) in dichloromethane (22.7 mL, 34.1 mmol) was cooled to 0° C. and treated with 1-methoxypropan-2-one (3.0 g, 34.1 mmol). The mixture was stirred at 0° C. and allowed to warm to ambient temperature slowly overnight. The reaction mixture was concentrated in vacuo, and the solid formed was filtered off washing with Et$_2$O. The filtrate collected was concentrated in vacuo. The precipitate formed was once again filtered off washing with Et$_2$O. The second filtrate was concentrated in vacuo, and the crude was purified by flash chromatography on silica gel (Ready Sep 80 g) eluting with a gradient of 1-20% EtOAc:hexanes (12 CV) on Biotage SP1 unit to provide a mixture of (E) and (Z) isomers of benzyl 4-methoxy-3-methylbut-2-enoate (700 mg, 9.3% yield) as an oil. Major isomer; $^1$H NMR (400 MHz, CDCl$_3$) δ 7.31 (m, 5H), 5.99 (m, 1H), 5.16 (s, 2H), 3.90 (m, 2H), 3.35 (s, 3H), 2.11 (s, 3H).

Step 2: To a suspension of 10% palladium on activated charcoal (wet) (169 mg, 0.159 mmol) in ethanol (31780 µL, 3.18 mmol) under N$_2$ was added a solution of crude (E)-benzyl 4-methoxy-3-methylbut-2-enoate (700 mg, 3.18 mmol) in EtOH (2 mL). The reaction vessel was purged under N$_2$ (2 cycles) and back filled with H$_2$ (3 cycles). The mixture was then stirred under H$_2$ balloon for 1 hour. The mixture was purged and backfilled with N$_2$ and then filtered through a Celite® pad washing with additional EtOH. The filtrate collected was concentrated in vacuo, and the residue obtained was purified by silica gel flash chromatography (Ready Sep 40 g) eluting with 10-60% EtOAc:hexanes (20 CV) on Biotage SP1 unit to provide 4-methoxy-3-methylbutanoic acid (100 mg, 24% yield) as an oil. $^1$H NMR (400 MHz, CDCl$_3$) δ 3.40 (s, 3H), 3.32-3.20 (m, 2H), 2.50 (dd, 1H), 2.31-2.16 (m, 2H), 0.99 (d, 3H).

Step 3: A solution of 4-(2-hydrazinylpyridin-4-yl)-N-(1-methyl-1H-pyrazol-5-yl)pyrimidin-2-amine (80 mg, 0.283 mmol), 4-methoxy-3-methylbutanoic acid, HOBT (52.1 mg, 0.340 mmol), N-ethyl-N-isopropylpropan-2-amine (148 µL, 0.850 mmol) in N,N-dimethylformamide (1417 µL, 0.283 mmol) was treated with EDC (65.2 mg, 0.340 mmol). The resulting mixture was stirred at room temperature for 18 hours. The reaction mixture was diluted with DCM (30 mL) and washed with water (2×10 mL). The organic layer was separated, dried (MgSO$_4$), filtered and concentrated in vacuo to provide the crude 4-methoxy-3-methyl-N'-(4-(2-((1-methyl-1H-pyrazol-5-yl)amino)pyrimidin-4-yl)pyridin-2-yl)butanehydrazide, which was used for the next reaction without purification. LCMS (APCI+) m/z 397.2 (M+1), retention time=0.943 minutes.

Step 4: A solution of crude 4-methoxy-3-methyl-N'-(4-(2-((1-methyl-1H-pyrazol-5-yl)amino)pyrimidin-4-yl)pyridin-2-yl)butanehydrazide (112 mg, 0.283 mmol) in acetic acid (2 mL) was heated at 120° C. for 7 hours. The mixture was concentrated in vacuo, and the residue obtained was purified by silica gel flash chromatography (Ready Sep 24 g) eluting with a gradient of 1-12% MeOH:DCM (25 CV) on Biotage SP1 unit to provide 4-(3-(3-methoxy-2-methylpropyl)-[1,2,4]triazolo[4,3-a]pyridin-7-yl)-N-(1-methyl-1H-pyrazol-5-yl)pyrimidin-2-amine (42 mg, 39% yield) as a solid. LCMS (APCI+) m/z 379.2 (M+1), retention time 1.129 minutes.

Example 108

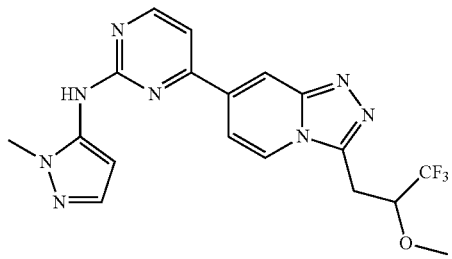

N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine Step 1: 4,4,4-Trifluoro-3-methoxybutanoic acid was made according to the procedure described in WO 2008/143332. To a solution of (E)-ethyl 4,4,4-trifluorobut-2-enoate (500 mg, 2.97 mmol) in MeOH (5 mL) was added portion wise sodium methoxide (241 mg, 4.46 mmol) at ambient temperature, and the mixture was stirred over the weekend. The mixture was filtered, and the filtrate was made acidic with 10% HCl and extracted into $Et_2O$ (2×30 mL). The organic layers were combined, dried ($MgSO_4$), filtered and concentrated in vacuo to provide 4,4,4-trifluoro-3-methoxybutanoic acid (480 mg, 2.79 mmol, 93.8% yield) was isolated as an oil. $^1$H NMR (400 MHz, $CDCl_3$) δ 4.103-4.023 (m, with fluorine coupling, 1H), 3.60 (s, 3H), 2.76 (d, J=5.075 Hz, 2H).

Step 2: 4,4,4-Trifluoro-3-methoxy-N'-(4-(2-((1-methyl-1H-pyrazol-5-yl)amino)pyrimidin-4-yl)pyridin-2-yl)butanehydrazide was made according to the method described for the synthesis of Example 107, Step 3, except substituting 4,4,4-trifluoro-3-methoxybutanoic acid for 4-methoxy-3-methylbutanoic acid. LCMS (APCI+) m/z 437.2 (M+1), retention time=1.096 minutes.

Step 3: The crude 4,4,4-trifluoro-3-methoxy-N'-(4-(2-((1-methyl-1H-pyrazol-5-yl)amino)pyrimidin-4-yl)pyridin-2-yl)butanehydrazide and glacial acetic acid were processed as described for the synthesis of Example 107, Step 4, to provide N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine 2,2,2-trifluoroacetate (16 mg, 25% yield) as a solid. $^1$H NMR (400 MHz, $CDCl_3$) δ 8.575 (d, J=5.466 Hz, 1H), 8.407 (m, 1H), 8.162 (dd, J1=7.418 Hz, J2=1.171 Hz, 1H), 7.566 (dd, J1=7.418 Hz, J2=1.562 Hz, 1H), 7.52 (d, J=1.568 Hz, 1H), 7.309 (d, J=5.075 Hz, 1H), 6.890 (br s, 1H), 6.368 (d, J=1.562 Hz, 1H), 54.262-4.180 (m, 1H), 3.833 (s, 3H), 3.57 (dd, J1=15.226 Hz, J2=2.733 Hz, 1H), 3.48 (s, 3H), 3.34 (dd, J1=15.226 hz, J2=10.151 Hz, 1H). LCMS (APCI+) m/z 419.1 (M+1), retention time=1.248 minutes.

Example 109

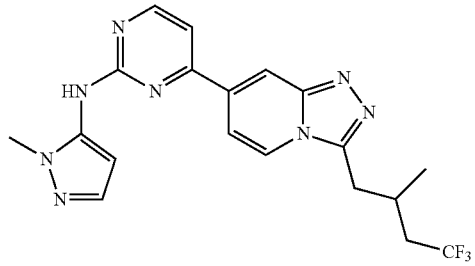 [SMILES: CC(Cc1nnc2cc(-c3ccnc(Nc4ccnn4C)n3)ccn12)CC(F)(F)F]

N-(1-methyl-1H-pyrazol-5-yl)-4-(3-(4,4,4-trifluoro-2-methylbutyl)-[1,2,4]triazolo[4,3-a]pyridin-7-yl)pyrimidin-2-amine Step 1: A solution of benzyl 2-(triphenylphosphoranylidene)acetate (17.9 g, 43.6 mmol) and 4,4,4-trifluorobutan-2-one (5 g, 39.7 mmol) were processed according to the method described in Example 107, Step 1, to provide a mixture of E and Z isomers of benzyl 5,5,5-trifluoro-3-methylpent-2-enoate (800 mg, 7.8% yield) as an oil. $^1$H NMR (400 MHz, $CDCl_3$) δ 7.376-7.358 (m, 5H), 5.90 (s, 1H), 5.163 (s, 2H), 2.894 (q, J=10.541 Hz, 2H), 2.279 (s, 3H).

Step 2: Benzyl 5,5,5-trifluoro-3-methylpent-2-enoate (300 mg, 1.16 mmol) was treated with 10% palladium on activated charcoal (61.8 mg, 0.0581 mmol) in ethanol (11617 µL, 1.16 mmol) according to the method described in Example 107, Step 2, to provide 5,5,5-trifluoro-3-methylpentanoic acid (150 mg, 0.882 mmol, 75.9% yield) as an oil. $^1$H NMR (400 MHz, $CDCl_3$) δ 10.032 (br s, 1H), 2.468-2.191 (m, 4H), 2.067-2.002 (m, 1H), 1.113 (d, J=5.856 Hz, 3H).

Step 3: 5,5,5-Trifluoro-3-methyl-N'-(4-(2-((1-methyl-1H-pyrazol-5-yl)amino)pyrimidin-4-yl)pyridin-2-yl)pentanehydrazide was prepared from 4-(2-hydrazinylpyridin-4-yl)-N-(1-methyl-1H-pyrazol-5-yl)pyrimidin-2-amine (80 mg, 0.283 mmol) according to the method described in Example 107, Step 3, except substituting 4-methoxy-3-methylbutanoic acid with 5,5,5-trifluoro-3-methylpentanoic acid. LCMS (APCI+) m/z 435.2 (M+1), retention time=1.160 minutes.

Step 4: A solution of crude 5,5,5-trifluoro-3-methyl-N'-(4-(2-((1-methyl-1H-pyrazol-5-yl)amino)pyrimidin-4-yl)pyridin-2-yl)pentanehydrazide (104 mg, 0.239 mmol) was treated with acetic acid as described in Example 107, Step 4, to provide N-(1-methyl-1H-pyrazol-5-yl)-4-(3-(4,4,4-trifluoro-2-methylbutyl)-[1,2,4]triazolo[4,3-a]pyridin-7-yl)pyrimidin-2-amine as a solid. $^1$H NMR (400 MHz, $CDCl_3$) δ 8.566 (d, J=5.075 Hz, 1H), 8.409 (s, 1H), 7.959 (d, J=7.418 Hz, 1H), 7.597 (dd, J1=7.027 Hz, J2=1.562 Hz, 1H), 7.524 (d, J=1.952 Hz, 1H), 7.30 (d, J=5.075 Hz, 1H), 6.93 (br s, 1H), 6.35 (d, J=1.952 Hz, 1H), 3.831 (s, 3H), 3.242 (dd, J1=15.226 Hz, J2=5.856 Hz, 1H), 3.087 (dd, J1=15.226 Hz, J2=7.808 Hz, 1H), 2.636-2.55 (m, 1H), 2.468-2.35 (m, 1H), 2.28-2.174 (m, 1H), 1.202 (d, J=6.637 Hz, 3H). LCMS (APCI+) m/z 417.2 (M+1), retention time 1.319 minutes.

Example 110

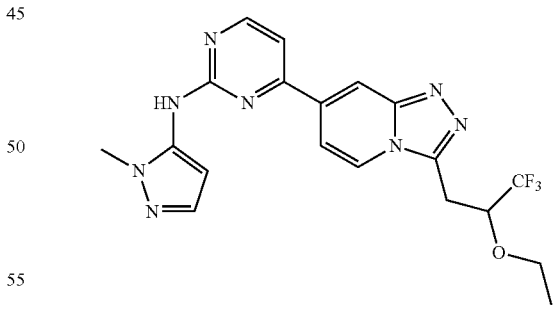

4-(3-(2-ethoxy-3,3,3-trifluoropropyl)-[1,2,4]triazolo[4,3-a]pyridin-7-yl)-N-(1-methyl-1H-pyrazol-5-yl)pyrimidin-2-amine Step 1: To a solution of ethyl 4,4,4-trifluoro-3-hydroxybutanoate (500 mg, 2.69 mmol) in a mixture of THF:MeOH (2:1, 20 mL) was added a solution of lithium hydroxide hydrate (338 mg, 8.06 mmol) in water (1 mL). The mixture was stirred at ambient temperature for 2 hours. The mixture was then concentrated, and the aqueous residue obtained was acidified with 6 N HCl. The resulting clear solution was extracted with EtOAc (3×50 mL). The organic layers were combined, dried (MgSO$_4$), filtered, concentrated in vacuo and dried under high vacuum to provide 4,4,4-trifluoro-3-hydroxybutanoic acid (330 mg, 77.7% yield) as a solid. $^1$H NMR (400 MHz, (CD$_3$)$_2$SO) δ 12.571 (br s, 1H), 6.498 (br s, 1H), 4.357-4.269 (m, 1H), 2.62 (dd, J1=16.041 Hz, J2=3.521 Hz, 1H), 2.392 (dd, J1=16.041 Hz, J2=9.781 Hz, 1H).

Step 2: To a solution of 4,4,4-trifluoro-3-hydroxybutanoic acid (220 mg, 1.39 mmol) in dichloromethane (14 mL) was added and iodoethane (668 µL, 8.35 mmol) and Ag$_2$O (1.94 g, 8.35 mmol). The mixture was stirred at reflux for 6 hours and at 35° C. for one overnight. The mixture was diluted with additional DCM (30 mL) and filtered through a pad of Celite®. The filtrate collected was concentrated in vacuo to provide the crude ethyl 3-ethoxy-4,4,4-trifluorobutanoate (296 mg, 99.3% yield) as an oil. $^1$H NMR (400 MHz, CDCl$_3$) δ 4.226-4.146 (m, 3H), 3.891-3.815 (m, 1H), 3.738-3.662 (m, 1H), 2.642 (d, J=7.027 Hz, 2H), 1.287 (t, J=7.027 Hz, 3H), 1.197 (t, J=7.027 Hz, 3H).

Step 3: To a solution of crude ethyl 3-ethoxy-4,4,4-trifluorobutanoate (295 mg, 1.38 mmol) in MeOH:THF (1:1, 5 mL) was added a solution of lithium hydroxide hydrate (144 mg, 3.44 mmol) in water (0.5 mL) The resulting mixture was stirred at ambient temperature for 1.5 hours. The mixture was then diluted with water (10 mL) and washed with EtOAc (2×10 mL). The aqueous layer was made acidic (pH 1) with 1 N HCl and extracted into DCM (3×10 mL). The combined DCM layers were dried (MgSO$_4$), filtered and concentrated in vacuo, and dried under high vacuum for 5 minutes to provide 3-ethoxy-4,4,4-trifluorobutanoic acid (220 mg, 85.8% yield) as an oil. $^{19}$F and $^1$H NMR (400 MHz, CDCl$_3$) δ 4.161-4.137 (m, 1H), 3.863-3.844 (m, 1H), 3.731-3.691 (m, 1H), 2.722-2.704 (m, 2H), 1.279-1.207 (m, 3).

Step 4: A solution of 4-(2-hydrazinylpyridin-4-yl)-N-(1-methyl-1H-pyrazol-5-yl)pyrimidin-2-amine (70 mg, 0.248 mmol), 3-ethoxy-4,4,4-trifluorobutanoic acid (46.2 mg, 0.248 mmol), HOBT (45.6 mg, 0.298 mmol), N-ethyl-N-isopropylpropan-2-amine (130 µL, 0.744 mmol) in N,N-dimethylformamide (1240 µL, 0.248 mmol) was treated with EDC (57.0 mg, 0.298 mmol). The resulting mixture was stirred at room temperature for 18 hours. The reaction mixture was diluted with DCM (30 mL) and washed with water (2×10 mL). The organic layer was separated, dried (MgSO$_4$), filtered and concentrated in vacuo to provide the crude 3-ethoxy-4,4,4-trifluoro-N'-(4-(2-((1-methyl-1H-pyrazol-5-yl)amino)pyrimidin-4-yl)pyridin-2-yl)butanehydrazide (95 mg, 85.1% yield). This was used for the next reaction without purification. LCMS (APCI+) m/z 451.2 (M+1), retention time=1.179 minutes.

Step 5: 3-Ethoxy-4,4,4-trifluoro-N'-(4-(2-((1-methyl-1H-pyrazol-5-yl)amino)pyrimidin-4-yl)pyridin-2-yl)butanehydrazide (95 mg, 0.21 mmol) in acetic acid (2 mL) was heated at 120° C. for 7 hours and concentrated in vacuo. The residue obtained was and purified by silica gel flash chromatography (Ready Sep 24 g) eluting with a gradient of 1-12% MeOH:DCM (25 CV) on Biotage SP1 unit to provide 4-(3-(2-ethoxy-3,3,3-trifluoropropyl)-[1,2,4]triazolo[4,3-a]pyridin-7-yl)-N-(1-methyl-1H-pyrazol-5-yl)pyrimidin-2-amine (28 mg, 31% yield) as a solid. $^1$H NMR (400 MHz, CDCl$_3$) δ 8.576 (d, J=5.466 Hz, 1H), 8.408 (s, 1H), 8.203 (d, J=7.418 Hz, 1H), 7.574 (dd, J1=7.418 Hz, J2=1.562 Hz, 1H), 7.52 (d, J=1.952 Hz, 1H), 7.311 (d, J=5.075 Hz, 1H), 6.915 (s, 1H), 6.368 (d, J=1.562 Hz, 1H), 4.286-4.211 (m, 1H), 3.833 (s, 3H), 3.803-3.726 (m, 1H), 3.629 (dd, J1=14.835 Hz, J2=2.733 Hz, 1H), 3.388-3.31 (m, 2H), 0.858 (t, J=7.02 Hz, 3H). LCMS (APCI+) m/z 433.2 (M+1); Retention time 1.311 minutes.

Example 111

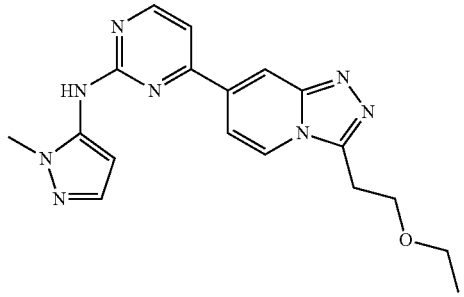 [SMILES: CCOCCc1nnc2cc(-c3ccnc(Nc4ccnn4C)n3)ccn12]

4-(3-(2-ethoxyethyl)-[1,2,4]triazolo[4,3-a]pyridin-7-yl)-N-(1-methyl-1H-pyrazol-5-yl)pyrimidin-2-amine Step 1: A solution of 4-(2-hydrazinylpyridin-4-yl)-N-(1-methyl-1H-pyrazol-5-yl)pyrimidin-2-amine (70 mg, 0.248 mmol), 3-ethoxypropanoic acid (32.2 mg, 0.273 mmol), HOBT (45.6 mg, 0.298 mmol), N-ethyl-N-isopropylpropan-2-amine (130 µL, 0.744 mmol), EDC (57.0 mg, 0.298 mmol) and N,N-dimethylformamide (1240 µL, 0.248 mmol) were processed according to the method described in Example 110, Step 4, to provide crude 3-ethoxy-N'-(4-(2-((1-methyl-1H-pyrazol-5-yl)amino)pyrimidin-4-yl)pyridin-2-yl)propanehydrazide (85 mg, 89.6% yield). This was used for the next reaction without purification. LCMS (APCI+) m/z 383.2 (M+1), retention time=0.903 minutes.

Step 2: Crude 3-ethoxy-N'-(4-(2-((1-methyl-1H-pyrazol-5-yl)amino)pyrimidin-4-yl)pyridin-2-yl)propanehydrazide (85 mg, 0.22 mmol) and acetic acid (3 mL) were processed according to the method described in Example 110, Step 5, to provide 4-(3-(2-ethoxyethyl)-[1,2,4]triazolo[4,3-a]pyridin-7-yl)-N-(1-methyl-1H-pyrazol-5-yl)pyrimidin-2-amine (24 mg, 30% yield) as a solid. $^1$H NMR (400 MHz, CDCl$_3$) δ 8.55 (d, J=5.075 Hz, 1H), 8.37 (t, J=1.171 Hz, 1H), 8.26 (dd, J1=7.418 Hz, J2=0.781 Hz, 1H), 7.521 (d, J=1.952 Hz, 1H), 7.501 (dd, J1=7.412 Hz, J2=1.562 Hz, 1H), 7.29 (d, J=5.075 Hz, 1H), 6.946 (s, 1H), 6.37 (d, J=1.952 Hz, 1H), 3.897 (t, J=5.856 Hz, 2H), 3.833 (s, 3H), 3.49-3.41 (m, 4H), 1.125 (t, J=7.027 Hz, 3H). LCMS (APCI+) m/z 365.2 (M+1); Retention time 1.081 minutes.

Example 112

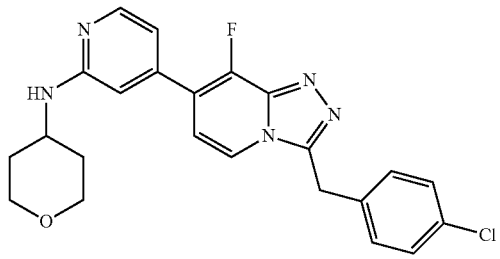 [SMILES: Fc1c(-c2ccnc(NC3CCOCC3)c2)ccn2c(Cc3ccc(Cl)cc3)nnc12]

4-(3-(4-chlorobenzyl)-8-fluoro-[1,2,4]triazolo[4,3-a]pyridin-7-yl)-N-(tetrahydro-2H-pyran-4-yl)pyridin-2-amine A mixture of 3'-fluoro-T-hydrazinyl-N-(tetrahydro-2H-pyran-4-yl)-[4,4'-bipyridin]-2-amine (46 mg, 0.15 mmol), 2-(4-chlorophenyl)acetic acid (26 mg, 0.152 mmol), 1H-benzo[d][1,2,3]triazol-1-ol hydrate (35 mg, 0.23 mmol), EDC (29 mg, 0.15 mmol) in DMF (1.5 mL) and 4-methylmorpholine (50 µL, 0.46 mmol) were processed according to the method described in Example 107, Step 3, to provide 2-(4-chlorophenyl)-N'-(3-fluoro-2'-((tetrahydro-2H-pyran-4-yl)amino)-[4,4'-bipyridin]-2-yl)acetohydrazide. Then it was directly treated with acetic as described in Example 110, Step 5, to provide 4-(3-(4-chlorobenzyl)-8-fluoro-[1,2,4]triazolo[4,3-a]pyridin-7-yl)-N-(tetrahydro-2H-pyran-4-yl)pyridin-2-amine (23 mg, 34.6% yield) as a solid. LCMS (APCI+) m/z 438.1 (M+1).

Example 113

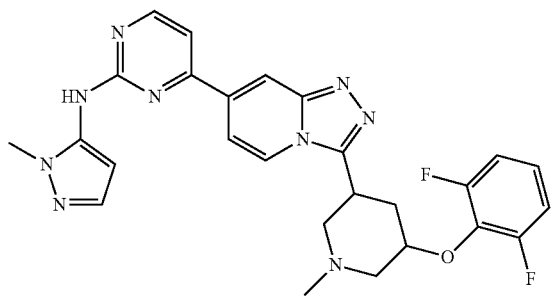 [SMILES: CN1CC(Oc2c(F)cccc2F)CC(c2nnc3cc(-c4ccnc(Nc5ccnn5C)n4)ccn23)C1]

4-(3-(5-(2,6-difluorophenoxy)-1-methylpiperidin-3-yl)-[1,2,4]triazolo[4,3-a]pyridin-7-yl)-N-(1-methyl-1H-pyrazol-5-yl)pyrimidin-2-amine Step 1: A solution of methyl 5-hydroxynicotinate (4.50 g, 29.4 mmol) in methanol (90 mL) in a 500 mL Parr bomb equipped with inlet valve and pressure gauge was reacted with Rh/Al (5%) (1.21 g, 0.588 mmol) (Degussa type G214 RA/D, Aldrich catalog #663468). The bomb was sealed and purged with hydrogen gas for 5 minutes. The pressure was then adjusted to 60 psi with hydrogen gas and stirred at 70° C. in an oil bath. After 24 hours, LC/MS shows a very early eluting peak with the correct mass for product plus a later eluting peak with starting material mass. The reaction was allowed to proceed for another 48 hours. LC/MS at that point showed complete loss of starting material, and the early eluting product peak as major. The reaction was filtered through GF/F filter paper with methanol, and the filtrate concentrated to provide methyl 5-hydroxypiperidine-3-carboxylate (4.6 grams, quantitative yield) as an oil. It is assumed that the cis product is favored.

Step 2: To a stirred solution of crude methyl 5-hydroxypiperidine-3-carboxylate (1.09 g, 6.85 mmol) in dioxane (20 mL) at room temperature under nitrogen was added TEA (1.91 mL, 13.7 mmol) neat by syringe, followed by Boc₂O (1.64 g, 7.53 mmol) neat as a solid. After 1 hour, LC/MS showed a new peak with a later elution time than starting material with the same mass. This likely indicates a Boc protected material. TLC in 9:1 dichloromethane:methanol shows complete loss of starting material (streak from the origin, ninhydrin:TFA:isopropanol visualization) and a new major higher rf spot. After the reaction had stirred for 2 hours, it was concentrated by rotovap and high vacuum. The crude product was loaded in dichloromethane onto a 100 gram SNAP silica gel cartridge prewet with dichloromethane. The material was eluted with a step gradient of dichloromethane (500 mL), 97.5:2.5 dichloromethane:methanol (500 mL) and finally 95:5 dichloromethane:methanol (500 mL). Product containing fractions were identified with ninhydrin:TFA:isopropanol visualization and were pooled and concentrated. A slightly lower rf spot was also isolated that was thought to be the trans diastereomer. TLC of the pooled cis product fractions show a high rf impurity thought to be (Boc)₂O related. The material was re-chromatographed on a 50 gram SNAP cartridge using 35:65 ethyl acetate:hexanes. Again product containing fractions were pooled and concentrated to provide 1-tert-butyl 3-methyl 5-hydroxypiperidine-1,3-dicarboxylate (680 mg, 38% yield) as an oil that eventually solidified.

Step 3: To a stirred solution of 1-tert-butyl 3-methyl 5-hydroxypiperidine-1,3-dicarboxylate (421 mg, 1.624 mmol) in THF (4.8 mL) at room temperature under nitrogen was added 2,6-difluorophenol (253.5 mg, 1.948 mmol) neat as a solid, followed by triphenylphosphine (511.0 mg, 1.948 mmol) neat as a solid and diisopropyl azodicarboxylate ("DIAD") (383.6 µL, 1.948 mmol) dropwise by syringe. After 1 hour, TLC in 1:1 ethyl acetate:hexanes shows complete loss of starting material, and two new higher rf spots that are both UV active and visible by staining with ninhydrin:TFA:isopropanol. After stirring overnight, the reaction mixture was concentrated to dryness by rotovap and high vacuum and then loaded onto a SNAP samplet with a minimum of dichloromethane. The samplet was dried under high vacuum for 5 minutes and then put into a 100 gram SNAP silica gel column that was prewet with 9:1 hexanes:ethyl acetate. The column was eluted with that solvent. Two bands eluted that were yellow when visualized with ninhydrin:TFA:isopropanol on TLC. Fractions containing the low rf material were pooled and concentrated to provide 1-tert-butyl 3-methyl 5-(2,6-difluorophenoxy)piperidine-1,3-dicarboxylate (145 mg, 24% yield) as an oil.

Step 4: To a stirred solution of 1-tert-butyl 3-methyl 5-(2,6-difluorophenoxy)piperidine-1,3-dicarboxylate (35 mg, 0.094 mmol) in dichloromethane (1 mL) at room temperature in a capped flask was added TFA (1 mL). After stirring for 1 hour, LC/MS showed a single peak with the correct mass for the desired product. The mixture was concentrated to dryness by rotovap and high vacuum. The residue was stirred in dichloromethane (10 mL) and 20% sodium carbonate solution (10 mL) for 5 minutes. The layers were separated, and the aqueous phase extracted with dichloromethane (2×10 mL). The combined organics were dried over MgSO₄, filtered and concentrated to provide methyl 5-(2,6-difluorophenoxy)piperidine-3-carboxylate (23 mg, 90% yield) as an oil.

Step 5: To a stirred solution of methyl 5-(2,6-difluorophenoxy)piperidine-3-carboxylate (23 mg, 0.0848 mmol) in formic acid (813 µL, 21.2 mmol) at room temperature in a capped reaction vial was added formaldehyde (31.6 µL, 0.424 mmol) (37% aqueous solution) by syringe. The solution was warmed to 80° C. After stirring overnight, LC/MS showed a single LC peak with the desired product mass. The reaction was cooled to room temperature and concentrated by rotovap and high vacuum. The residue was stirred with dichloromethane (10 mL) and 20% sodium carbonate solution (10 mL) for 5 minutes. Then, the layers were separated, and the aqueous phase extracted with dichloromethane (2×10 mL). The combined organics were dried over MgSO$_4$, filtered and concentrated to provide methyl 5-(2,6-difluorophenoxy)-1-methylpiperidine-3-carboxylate (24 mg, quantitative yield) as an oil.

Step 6: To a stirred solution of methyl 5-(2,6-difluorophenoxy)-1-methylpiperidine-3-carboxylate (24 mg, 0.0841 mmol) in 3:2 THF:H$_2$O (1 mL) at room temperature under nitrogen was added lithium hydroxide monohydrate (7 mg, 0.168 mmol) neat as a solid. After stirring overnight, LC/MS showed a clean early eluting LC peak with desired mass for the acid. The reaction mixture was concentrated to dryness by rotovap and high vacuum to provide lithium 5-(2,6-difluorophenoxy)-1-methylpiperidine-3-carboxylate (23 mg, quantitative yield) as a solid.

Step 7: To a stirred suspension of lithium 5-(2,6-difluorophenoxy)-1-methylpiperidine-3-carboxylate (23 mg, 0.085 mmol) in DMF (850 μL) at room temperature under nitrogen was added EDC (13 mg, 0.085 mmol) neat as a solid, followed by HOBT (11 mg, 0.085 mmol) also neat as a solid. After 5 minutes, 4-(2-hydrazinylpyridin-4-yl)-N-(1-methyl-1H-pyrazol-5-yl)pyrimidin-2-amine (24 mg, 0.085 mmol) was added neat as a solid. The mixture was stirred overnight. LC/MS showed a main LC peak with the desired product mass (negative ionization). The mixture was diluted with ethyl acetate (1 mL) and 20% sodium carbonate solution (2 mL) and stirred for 5 minutes. The mixture was then partitioned between ethyl acetate (15 mL) and water (15 mL) The organics were isolated and washed with water (3×15 mL) and brine (15 mL). The organics were isolated again, dried over MgSO$_4$, filtered and concentrated. The crude product was loaded onto a 10 gram SNAP silica gel column and eluted with 9:1 ethyl acetate:methanol. Product containing fractions were pooled and concentrated to provide 5-(2,6-difluorophenoxy)-1-methyl-N'-(4-(2-((1-methyl-1H-pyrazol-5-yl)amino)pyrimidin-4-yl)pyridin-2-yl)piperidine-3-carbohydrazide (26 mg, 57% yield) as an oil.

Step 8: 5-(2,6-Difluorophenoxy)-1-methyl-N'-(4-(2-((1-methyl-1H-pyrazol-5-yl)amino)pyrimidin-4-yl)pyridin-2-yl)piperidine-3-carbohydrazide (26 mg, 0.049 mmol) was dissolved in glacial acetic acid (2 mL) in a microwave vial equipped with a stir bar and was capped and heated in the microwave at 180° C. for 30 minutes. After cooling to room temperature, LC/MS showed two main LC peaks, each with the desired mass for product. The reaction was concentrated to dryness by rotovap and high vacuum. The residue was dissolved in dichloromethane (5 mL) and 20% sodium carbonate solution (5 mL) and stirred rapidly for 5 minutes. The layers were separated, and the aqueous phase was extracted with dichloromethane (2×5 mL). The combined organics were dried over MgSO$_4$, filtered and concentrated to an oil. The crude product was loaded onto a Biotage 12M reverse phase samplet with dichloromethane, and the samplet was dried under high vacuum. The samplet was then loaded onto a Biotage 12M C18 reverse phase column and eluted with a 10% to 80% acetonitrile:water gradient. Product containing fractions were pooled and concentrated to provide 4-(3-(5-(2,6-difluorophenoxy)-1-methylpiperidin-3-yl)-[1,2,4]triazolo[4,3-a]pyridin-7-yl)-N-(1-methyl-1H-pyrazol-5-yl)pyrimidin-2-amine (16 mg, 64% yield) as an oil. The material was assumed to be a mixture of diastereomers. $^1$H NMR (400 MHz, CDCl$_3$) δ 8.56 (d, 1H), 8.42 (d, 1H), 8.19 (d, 0.5H), 8.04 (d, 0.5H), 7.58 (m, 1H), 7.53 (m, 1H), 7.29 (d, 1H), 7.06-6.88 (m, 3H), 6.36 (d, 1H), 4.42 (m, 0.5H), 4.14 (m, 0.5H), 3.84 (s, 1.5H), 3.83 (s, 1.5H), 3.43 (m, 1H), 3.30 (m, 1H), 2.66-2.50 (m, 1H), 2.45 (s, 1.5H), 2.43 (s, 1.5H), 2.44-2.26 (m, 1H), 2.11 (m, 1H). LCMS (APCI+, 3 minute method) m/z 518.2 (M+H)+; Retention time 1.04 minutes.

Example 114

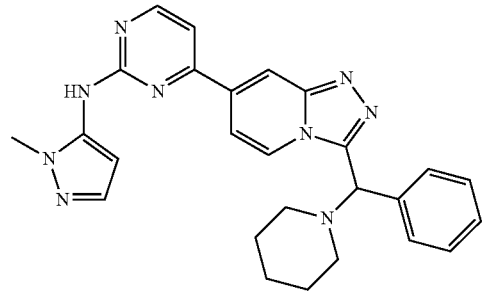 [SMILES: Cn1nccc1Nc1nccc(-c2ccn3c(C(c4ccccc4)N4CCCCC4)nnc3c2)n1]

N-(1-methyl-1H-pyrazol-5-yl)-4-(3-(phenyl(piperidin-1-yl)methyl)-[1,2,4]triazolo[4,3-a]pyridin-7-yl)pyrimidin-2-amine Step 1: To a stirred suspension of 2-phenyl-2-(piperidin-1-yl)acetic acid hydrochloride (50.7 mg, 0.198 mmol) in DMF (1 mL) at room temperature under nitrogen was added DIEA (104 μL, 0.595 mmol) neat by syringe followed by EDC (30.8 mg, 0.198 mmol) neat as a solid and HOBT (26.8 mg, 0.198 mmol) neat as a solid. After 10 minutes, 4-(2-hydrazinylpyridin-4-yl)-N-(1-methyl-1H-pyrazol-5-yl)pyrimidin-2-amine (56 mg, 0.198 mmol) was added neat as a solid. The mixture was stirred overnight. LC/MS showed two main LC peaks. The earlier eluting peak appears to be residual starting material, while the later main LC peak shows the desired product mass. The reaction was diluted with ethyl acetate (30 mL) and washed with water (4×30 mL) and brine (30 mL). The combined organics were dried over MgSO$_4$, filtered and concentrated. The crude product was loaded onto a samplet with 9:1 dichloromethane:methanol, and the samplet was dried under high vacuum. The samplet was placed in a 25 gram SNAP silica gel column prewet with dichloromethane and eluted with a step gradient of dichloromethane (200 mL), 2.5:97.5 methanol:dichloromethane (200 mL) and 5:95 methanol:dichloromethane (400 mL). Product eluted with 5:95 methanol:dichloromethane. Product containing fractions were pooled and concentrated to provide N'-(4-(2-((1-methyl-1H-pyrazol-5-yl)amino)pyrimidin-4-yl)pyridin-2-yl)-2-phenyl-2-(piperidin-1-yl)acetohydrazide (64 mg, 67% yield) as a solid.

Step 2: To a stirred suspension of N'-(4-(2-((1-methyl-1H-pyrazol-5-yl)amino)pyrimidin-4-yl)pyridin-2-yl)-2-phenyl-2-(piperidin-1-yl)acetohydrazide (20 mg, 0.041 mmol) in THF (410 μL) at room temperature under nitrogen was added triphenylphosphine (13 mg, 0.05 mmol) neat as a solid, followed by trimethylsilyl azide (6.6 μL, 0.05 mmol) neat by syringe. Diethyl azodicarboxylate ("DEAD") (20 μL, 0.05 mmol) was then added neat by syringe. After 3 hours, the reaction was still a suspension. LC/MS showed a mixture of what appears to be desired product and triphenylphosphine oxide as the main components. The reaction was concentrated to dryness by rotovap and was then dissolved in a minimum of 9:1 dichloromethane:methanol and loaded onto a 0.5 mm×20 cm×20 cm prep plate. After thorough drying, the prep plate was eluted twice with 9:1 dichloromethane:methanol. Two main bands were apparent by UV and were scraped from the plate. The silica gel scraped from the plate was stirred rapidly in 9:1 dichloromethane:methanol (50 mL) for 10 minutes and was then filtered. The filtrates were concentrated to a small volume. LC/MS showed that the high rf material was desired product while the low rf material was recovered starting material. The high rf material was concentrated to dryness to provide N-(1-methyl-1H-pyrazol-5-yl)-4-(3-(phenyl(piperidin-1-yl)methyl)-[1,2,4]triazolo[4,3-a]pyridin-7-yl)pyrimidin-2-amine (10 mg, 41% yield) as a solid. $^1$H NMR (400 MHz, CDCl$_3$) δ 8.88 (d, 1H), 8.54 (d, 1H), 8.33 (s, 1H), 7.58-7.48 (m, 4H), 7.33 (m, 2H), 7.25 (m, 1H), 7.02 (br s, 1H), 6.50 (br s, 1H), 6.36 (d, 1H), 5.27 (s, 1H), 3.83 (s, 3H), 2.60 (m, 2H), 2.26 (m, 2H), 1.64 (m, 4H), 1.50 (m, 2H). LCMS (APCI+, 3 minute method) m/z 466.2 (M+H)+; Retention time 1.33 minutes.

Example 115

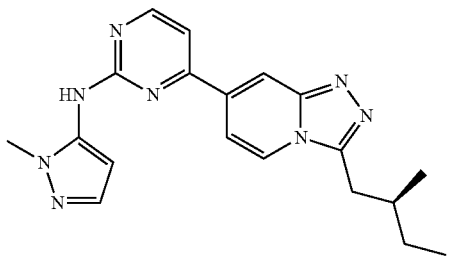 [SMILES: CC[C@H](C)Cc1nnc2cc(-c3ccnc(Nc4ccnn4C)n3)ccn12]

(S)—N-(1-methyl-1H-pyrazol-5-yl)-4-(3-(2-methylbutyl)-[1,2,4]triazolo[4,3-a]pyridin-7-yl)pyrimidin-2-amine Step 1: A mixture of 4-(2-hydrazinylpyridin-4-yl)-N-(1-methyl-1H-pyrazol-5-yl)pyrimidin-2-amine (1.02 g, 3.631 mmol), N1-((ethylimino)methylene)-N3,N3-dimethylpropane-1,3-diamine hydrochloride (0.765 g, 3.99 mmol), (S)-3-methylpentanoic acid (0.4762 mL, 3.812 mmol), HOBT (0.5397 g, 3.994 mmol) and Hunig's base (1.265 mL, 7.262 mmol) in DMF (12.1 mL, 3.63 mmol) was stirred overnight at room temperature. The mixture of (S)-3-methyl-N'-(4-(2-((1-methyl-1H-pyrazol-5-yl)amino)pyrimidin-4-yl)pyridin-2-yl)pentanehydrazide was concentrated down and taken into the next step crude.

Step 2: A mixture of (S)-3-methyl-N'-(4-(2-((1-methyl-1H-pyrazol-5-yl)amino)pyrimidin-4-yl)pyridin-2-yl)pentanehydrazide (1.38 g, 3.62 mmol) in acetic acid (25 mL) was heated to 130° C. for 12 hours. The mixture was concentrated down and purified on a column using DCM:MeOH:NH$_4$OH (90:10:1) to give (S)—N-(1-methyl-1H-pyrazol-5-yl)-4-(3-(2-methylbutyl)-[1,2,4]triazolo[4,3-a]pyridin-7-yl)pyrimidin-2-amine (0500 g, 1.38 mmol, 38.0% yield). $^1$H NMR (400 MHz, CDCl$_3$) 8.55 (d, 1H), 8.39 (s, 1H), 7.97 (d, 1H), 7.53 (m, 2H), 7.29 (d, 1H), 7.08 (s, 1H), 6.36 (m, 1H), 3.83 (s, 3H), 3.12 (m, 1H), 2.96 (m, 1H), 2.09 (m, 1H), 1.51 (m, 1H), 1.35 (m, 1H), 0.99 (m, 6H). LCMS (APCI+) m/z=363.2.

Example 116

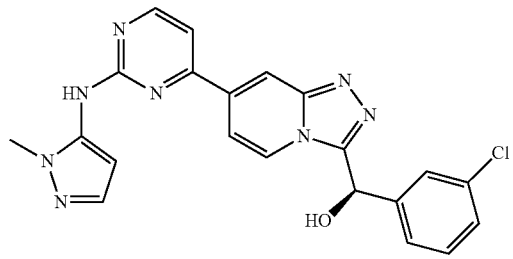 [SMILES: Cn1nccc1Nc1nccc(-c2ccn3c([C@H](O)c4cccc(Cl)c4)nnc3c2)n1]

(R)-(3-chlorophenyl)(7-(2-((1-methyl-1H-pyrazol-5-yl)amino)pyrimidin-4-yl)-[1,2,4]triazolo[4,3-a]pyridin-3-yl)methanol Step 1: To a stirred solution of (R)-2-(3-chlorophenyl)-2-hydroxyacetic acid (81.4 mg, 0.436 mmol) in DMF (1.2 mL) at room temperature under nitrogen was added DIEA (208 lit, 1.19 mmol) neat by syringe, followed by HOBT (59.0 mg, 0.436 mmol) and EDC (67.7 mg, 0.436 mmol) as solids. After 5 minutes, 4-(2-hydrazinylpyridin-4-yl)-N-(1-methyl-1H-pyrazol-5-yl)pyrimidin-2-amine (112 mg, 0.397 mmol) was added neat as a solid. The reaction was allowed to stir overnight. LC/MS showed a main LC peak with desired product mass. The reaction was diluted with ethyl acetate (30 mL) and washed with water (4×30 mL) and brine (30 mL). The combined organics were dried over MgSO$_4$, filtered and concentrated to provide (R)-2-(3-chlorophenyl)-2-hydroxy-N'-(4-(2-((1-methyl-1H-pyrazol-5-yl)amino)pyrimidin-4-yl)pyridin-2-yl)acetohydrazide (120 mg, 67% yield) as a solid.

Step 2: A stirred solution of (R)-2-(3-chlorophenyl)-2-hydroxy-N'-(4-(2-((1-methyl-1H-pyrazol-5-yl)amino)pyrimidin-4-yl)pyridin-2-yl)acetohydrazide (115 mg, 0.255 mmol) in glacial acetic acid (2.5 mL) was heated by microwave at 110° C. for 90 minutes. After cooling, LC/MS showed desired product as the major LC and MS peak. The material was concentrated by rotovap and high vacuum. The crude solid was triturated with ethyl acetate with sonication. Filtration and rinse with ethyl acetate gave a solid. Drying under high vacuum provided (R)-(3-chlorophenyl)(7-(2-((1-methyl-1H-pyrazol-5-yl)amino)pyrimidin-4-yl)-[1,2,4]triazolo[4,3-a]pyridin-3-yl)methanol (60 mg, 54% yield) as a powder. $^1$H NMR (400 MHz, CDCl$_3$) δ 8.54 (m, 1H), 8.41 (s, 1H), 8.32 (d, 1H), 7.56 (s, 1H), 7.48 (d, 1H), 7.47 (m, 1H), 7.31 (m, 4H), 6.49 (s, 1H), 6.38 (m, 1H), 3.80 (s, 3H). LCMS (APCI−, 3 minute method) m/z 431.1 (M−H)−; Retention time 1.05 minutes.

Example 117

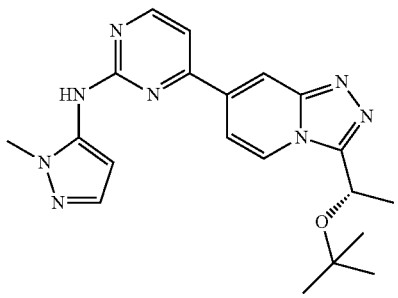 [SMILES: C[C@H](OC(C)(C)C)c1nnc2cc(-c3ccnc(Nc4ccnn4C)n3)ccn12]

(S)-4-(3-(1-(tert-butoxy)ethyl)-[1,2,4]triazolo[4,3-a]
pyridin-7-yl)-N-(1-methyl-1H-pyrazol-5-yl)pyrimi-
din-2-amine Step 1: To a stirred solution of (S)-methyl 2-hydroxypropanoate (1.1 g, 11 mmol) in dichloromethane (8 mL) at room temperature in a sealed tube was added concentrated sulfuric acid (80 μL). Isobutylene was then bubbled through the solution for about 10 minutes using a pipet. The reaction was sealed and stirred overnight. At that point, TLC in 4:1 hexanes:ethyl acetate showed some residual starting material but a major high rf spot (PMA visualization). The reaction was poured into saturated sodium bicarbonate solution (20 mL) with stirring. After 5 minutes, the layers were separated, and the aqueous phase extracted with dichloromethane (10 mL). The combined organics were dried over MgSO$_4$, filtered and concentrated by rotovap and then loaded onto a 50 gram SNAP silica gel cartridge prewet with 9:1 hexanes:ethyl acetate and eluted. Product containing fractions were pooled and concentrated to provide (S)-methyl 2-(tert-butoxy)propanoate (1.2 g, 71% yield) as an oil.

Step 2: To a stirred solution of (S)-methyl 2-(tert-butoxy)propanoate (240 mg, 1.50 mmol) in 3:2 THF:H$_2$O (7.3 mL) at room temperature under nitrogen was added lithium hydroxide monohydrate (126 mg, 3.00 mmol). The reaction was stirred overnight and then partitioned between ethyl acetate (15 mL) and 2 N HCl (15 mL). The organics were isolated and washed with water (15 mL) and brine (15 mL). The organics were isolated, dried over MgSO$_4$, filtered and concentrated to provide (S)-2-(tert-butoxy)propanoic acid (200 mg, 91% yield) as an oil.

Step 3: To a stirred solution of (S)-2-(tert-butoxy)propanoic acid (49 mg, 0.335 mmol) in dichloromethane (1 mL) at room temperature under nitrogen was added DIEA (117 μL, 0.670 mmol) neat by syringe, followed by HOBT (37.9 mg, 0.280 mmol) and EDC (43.5 mg, 0.280 mmol) as solids. After 5 minutes, 4-(2-hydrazinylpyridin-4-yl)-N-(1-methyl-1H-pyrazol-5-yl)pyrimidin-2-amine (52.8 mg, 0.187 mmol) was added neat as a solid. The reaction was allowed to stir overnight. LC/MS showed a main LC peak with desired product mass and a later eluting minor peak that appears to be a diacylated product. The reaction was diluted with dichloromethane (15 mL) and stirred with 20% sodium carbonate solution (15 mL). The layers were separated, and the aqueous phase was extracted with dichloromethane (15 mL). The combined organics were dried over MgSO$_4$, filtered and concentrated. The crude product was loaded onto a 10 gram SNAP silica gel column prewet with dichloromethane and eluted with a step gradient of dichloromethane (200 mL), 2.5:97.5 methanol:dichloromethane (200 mL) and 5:95 methanol:dichloromethane (400 mL) Product eluted with 5:95 methanol:dichloromethane. Product containing fractions were pooled and concentrated to provide (S)-2-(tert-butoxy)-N'-(4-(2-((1-methyl-1H-pyrazol-5-yl)amino)pyrimidin-4-yl)pyridin-2-yl)propanehydrazide (63 mg, 69% yield) as an oil.

Step D: A stirred solution of (S)-2-(tert-butoxy)-N'-(4-(2-((1-methyl-1H-pyrazol-5-yl)amino)pyrimidin-4-yl)pyridin-2-yl)propanehydrazide (63 mg, 0.15 mmol) in glacial acetic acid (2.5 mL) was heated by microwave at 150° C. for 30 minutes. After cooling, LC/MS shows desired product, plus a smaller earlier eluting LC peak which appears to be the result of t-butyl loss. The material was concentrated by rotovap and then stirred rapidly in a mixture of dichloromethane (30 mL) and saturated sodium bicarbonate (30 mL). The layers were separated, and the aqueous phase was extracted with dichloromethane (15 mL). The combined organics were dried over MgSO$_4$, filtered and concentrated. The crude product was loaded onto a 10 gram SNAP silica gel cartridge with dichloromethane and eluted with a step gradient of dichloromethane (200 mL), 2.5:97.5 methanol:dichloromethane, 5:95 methanol:dichloromethane. Product containing fractions were pooled and concentrated to provide (S)-4-(3-(1-(tert-butoxy)ethyl)-[1,2,4]triazolo[4,3-a]pyridin-7-yl)-N-(1-methyl-1H-pyrazol-5-yl)pyrimidin-2-amine (40 mg, 66% yield) as an oil. $^1$H NMR (400 MHz, CDCl$_3$) δ 8.66 (d, 1H), 8.54 (d, 1H), 8.41 (s, 1H), 8.38 (m, 1H), 7.53 (d, 1H), 7.50 (m, 1H), 7.42 (br s, 1H), 7.30 (d, 1H), 6.39 (d, 1H), 5.52 (q, 1H), 3.84 (s, 3H), 1.61 (d, 3H). LCMS (APCI+, 3 minute method) m/z 393.2 (M+H)+; Retention time 1.07 minutes.

Example 118

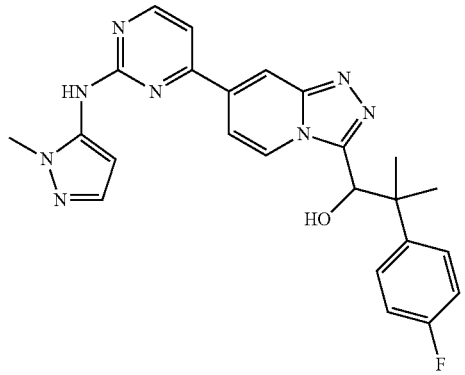 [SMILES: Cn1nccc1Nc1nccc(-c2ccn3c(C(O)C(C)(C)c4ccc(F)cc4)nnc3c2)n1]

2-(4-fluorophenyl)-2-methyl-1-(7-(2-((1-methyl-1H-
pyrazol-5-yl)amino)pyrimidin-4-yl)-[1,2,4]triazolo
[4,3-a]pyridin-3-yl)propan-1-ol Step 1: To a stirred solution of 4-fluorobenzaldehyde (5.36 mL, 50 mmol) in acetic anhydride (100 mL) at room temperature under nitrogen was added 2-acetamidoacetic acid (5.9 g, 50 mmol) neat as a solid, followed by sodium acetate (2.95 g, 50 mmol) neat as a solid. The mixture was heated to 140° C. for 5 hours and was then cooled to room temperature. The precipitate that formed was filtered off and rinsed with water and then dried under high vacuum to provide (Z)-4-(4-fluorobenzylidene)-2-methyloxazol-5 (4H)-one (3.4 grams, 33% yield) as a solid.

Step 2: A suspension of (Z)-4-(4-fluorobenzylidene)-2-methyloxazol-5(4H)-one (2.00 g, 9.75 mmol) in 3 N HCl (60 mL) was heated to reflux. The reaction was allowed to cool to room temperature and then was cooled in an ice bath with stirring. The solid was isolated by filtration and rinsing with water followed by drying under high vacuum to provide 3-(4-fluorophenyl)-2-oxopropanoic acid (1.56 g, 86% yield) as a solid.

Step 3: To a stirred solution of 3-(4-fluorophenyl)-2-oxopropanoic acid (90 mg, 0.49 mmol) in THF (500 µL) at 0° C. under nitrogen was added methyl iodide (93 µL, 1.5 mmol) neat by syringe, followed by NaOH (288 µL, 1.7 mmol) (6 N aqueous). The reaction was allowed to warm to room temperature and stir overnight. LC/MS showed a major peak with the desired product mass. The reaction was partitioned between ethyl acetate (30 mL) and 2 N HCl (30 mL) The organics were isolated, washed with brine (30 mL), re-isolated, dried over MgSO₄, filtered and concentrated to an oil that eventually solidified to provide 3-(4-fluorophenyl)-3-methyl-2-oxobutanoic acid (85 mg, 82% yield) as a solid.

Step 4: To a stirred solution of 3-(4-fluorophenyl)-3-methyl-2-oxobutanoic acid (85 mg, 0.40 mmol) in 1:1 MeOH:THF (4 mL) at 0° C. under nitrogen was added TMS-diazomethane (303 µL, 0.61 mmol) (2 M in hexanes) by syringe. After 15 minutes, the reaction was concentrated to dryness. The crude product was loaded onto a 10 gram SNAP column on the Isolera purification system and eluted with an ethyl acetate:hexanes gradient (0% ethyl acetate to 20% ethyl acetate). Product containing fractions were pooled and concentrated to provide methyl 3-(4-fluorophenyl)-3-methyl-2-oxobutanoate (55 mg, 61% yield) as an oil.

Step 5: To a stirred solution of methyl 3-(4-fluorophenyl)-3-methyl-2-oxobutanoate (55 mg, 0.25 mmol) in methanol (2.5 mL) at 0° C. under nitrogen was added NaBH₄ (5.6 mg, 0.25 mmol). The reaction was stirred for 10 minutes at 0° C. and then allowed to warm to room temperature. After 1 hour, the reaction was concentrated to dryness by rotovap and high vacuum. The residue was then stirred rapidly in ethyl acetate (15 mL) and saturated sodium bicarbonate solution (15 mL) for 5 minutes. The layers were separated, and the organics were washed with brine (15 mL), isolated, dried over MgSO₄, filtered and concentrated to provide methyl 3-(4-fluorophenyl)-2-hydroxy-3-methylbutanoate (32 mg, 58% yield) as an oil.

Step 6: To a stirred solution of methyl 3-(4-fluorophenyl)-2-hydroxy-3-methylbutanoate (32 mg, 0.14 mmol) in 3:2 THF:H₂O (1.4 mL) at room temperature under nitrogen was added lithium hydroxide monohydrate (12 mg, 0.28 mmol) neat as a solid. After stirring overnight, TLC in 3:7 ethyl acetate:hexanes showed complete loss of starting material and a new streak at the origin. The reaction was partitioned between ethyl acetate (15 mL) and 2 N HCl (15 mL). The organics were isolated, washed with brine (15 mL), isolated again, dried over MgSO₄, filtered and concentrated to an oil that eventually solidified to provide 3-(4-fluorophenyl)-2-hydroxy-3-methylbutanoic acid (25 mg, 83% yield) as a glass.

Step 7: To a stirred solution of 3-(4-fluorophenyl)-2-hydroxy-3-methylbutanoic acid (25 mg, 0.118 mmol) in DMF (55 µL) at room temperature under nitrogen was added DIEA (20.6 µL, 0.118 mmol) by syringe followed by HOBT (15.9 mg, 0.118 mmol) and EDC (18.3 mg, 0.118 mmol) neat as solids. After 5 minutes, 4-(2-hydrazinylpyridin-4-yl)-N-(1-methyl-1H-pyrazol-5-yl)pyrimidin-2-amine (30.2 mg, 0.107 mmol) was added neat as a solid. After stirring overnight, LC/MS showed a major LC peak with desired product mass. The reaction was diluted to 30 mL with ethyl acetate and washed with water (3×30 mL) and brine (30 mL). The organics were isolated, dried over MgSO₄, filtered and concentrated to provide 3-(4-fluorophenyl)-2-hydroxy-3-methyl-N'-(4-(2-((1-methyl-1H-pyrazol-5-yl)amino)pyrimidin-4-yl)pyridin-2-yl)butanehydrazide (51 mg, quantitative yield) as a solid.

Step 8: A stirred solution of 3-(4-fluorophenyl)-2-hydroxy-3-methyl-N'-(4-(2-((1-methyl-1H-pyrazol-5-yl)amino)pyrimidin-4-yl)pyridin-2-yl)butanehydrazide (51 mg, 0.11 mmol) in glacial acetic acid (2 mL) was heated by microwave at 120° C. for 30 minutes. After cooling, LC/MS showed desired product and starting material in an approximate 1:1 ratio. The reaction was reheated in the microwave to 120° C. for another 90 minutes. LC/MS showed complete consumption of starting material. The material was concentrated by rotovap and high vacuum. The crude material was loaded in dichloromethane onto a SNAP 10 gram silica gel cartridge prewet with dichloromethane. The column was eluted with a dichloromethane:methanol gradient (0% MeOH to 10% methanol) on an Isolera instrument. Two main peaks were separated with the later eluting peak appearing to be desired product. All product containing fractions were pooled and concentrated to provide 2-methyl-1-(7-(2-((1-methyl-1H-pyrazol-5-yl)amino)pyrimidin-4-yl)-[1,2,4]triazolo[4,3-a]pyridin-3-yl)-2-phenylpropan-1-ol (24 mg, 49% yield) as an oil. ¹H NMR (400 MHz, CDCl₃) δ 8.58 (d, 1H), 8.10 (s, 1H), 7.53 (d, 1H), 7.46 (d, 1H), 7.42 (br s, 1H), 7.20 (m, 2H), 7.13 (d, 1H), 7.02 (d, 1H), 6.87 (m, 2H), 6.32 (d, 1H), 5.33 (s, 1H), 3.80 (s, 3H), 1.60 (s, 3H), 1.47 (s, 3H). LCMS (APCI+, 3 minute method) m/z 459.2 (M+H)+; Retention time 1.15 minutes.

Example 119

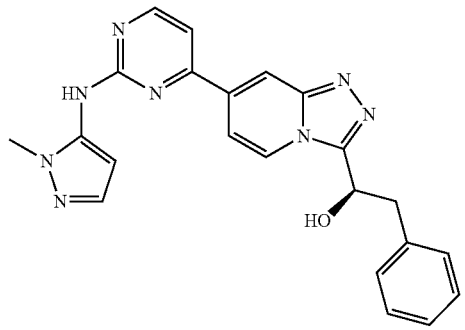 [SMILES: Cn1nccc1Nc1nccc(-c2ccn3c([C@H](O)Cc4ccccc4)nnc3c2)n1]

(R)-1-(7-(2-((1-methyl-1H-pyrazol-5-yl)amino)pyrimidin-4-yl)-[1,2,4]triazolo[4,3-a]pyridin-3-yl)-2-phenylethanol Step 1: To a stirred solution of (R)-2-hydroxy-3-phenylpropanoic acid (72.5 mg, 0.436 mmol) in DMF (1.2 mL) at room temperature under nitrogen was added DIEA (208 µL, 1.19 mmol) neat by syringe followed by HOBT (59.0 mg, 0.436 mmol) and EDC (67.7 mg, 0.436 mmol) as solids. After 5 minutes, 4-(2-hydrazinylpyridin-4-yl)-N-(1-methyl-1H-pyrazol-5-yl)pyrimidin-2-amine (112 mg, 0.397 mmol) was added neat as a solid. The reaction was allowed to stir overnight. LC/MS showed a main LC peak with desired product mass. The reaction was diluted with ethyl acetate (30 mL) and washed with water (4×30 mL) and brine (30 mL) The combined organics were dried over MgSO₄, filtered and concentrated. The crude product was triturated with ethyl acetate:sonication and filtered off Drying under high vacuum provided (R)-2-hydroxy-N'-(4-(2-((1-methyl-1H-pyrazol-5-yl)amino)pyrimidin-4-yl)pyridin-2-yl)-3-phenylpropanehydrazide (80 mg, 47% yield) as a solid.

Step 2: A stirred solution of (R)-2-hydroxy-N'-(4-(2-((1-methyl-1H-pyrazol-5-yl)amino)pyrimidin-4-yl)pyridin-2-yl)-3-phenylpropanehydrazide (80 mg, 0.19 mmol) in glacial acetic acid (2.5 mL) was heated by microwave at 150° C. for 30 minutes. After cooling, LC/MS showed desired product plus a smaller later eluting LC peak which appears to be 0-acetate. The material was concentrated by rotovap and then loaded onto a 10 gram SNAP silica gel cartridge with dichloromethane and eluted with a step gradient of dichloromethane (200 mL), 2.5:97.5 methanol:dichloromethane, 5:95 methanol:dichloromethane. Product containing fractions were pooled and concentrated to provide (R)-1-(7-(2-((1-methyl-1H-pyrazol-5-yl)amino)pyrimidin-4-yl)-[1,2,4]triazolo[4,3-a]pyridin-3-yl)-2-phenylethanol (62 mg, 73% yield) as an oil. ¹H NMR (400 MHz, CDCl₃) δ 8.48 (d, 1H), 8.30 (d, 1H), 8.21 (s, 1H), 7.63 (s, 1H), 7.44 (d, 1H), 7.32 (d, 1H), 7.26-7.17 (m, 6H), 6.33 (d, 1H), 5.54 (m, 1H), 5.30 (s, 1H), 3.79 (s, 3H), 3.45 (m, 2H). LCMS (APCI+, 3 minute method) m/z 413.2 (M+H)+; Retention time 0.973 minutes.

Example 120

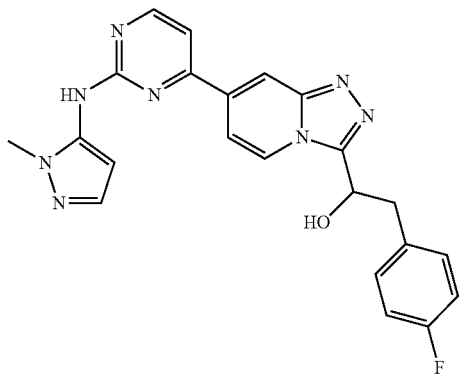 [SMILES: Cn1nccc1Nc1nccc(-c2ccn3c(C(O)Cc4ccc(F)cc4)nnc3c2)n1]

2-(4-fluorophenyl)-1-(7-(2-((1-methyl-1H-pyrazol-5-yl)amino)pyrimidin-4-yl)-[1,2,4]triazolo[4,3-a]pyridin-3-yl)ethanol Step 1: To a stirred suspension of 3-(4-fluorophenyl)-2-oxopropanoic acid (182 mg, 0.999 mmol; prepared according to Steps 1-2, Example 118) in water (3 mL) at room temperature was added NaOH (183 μL, 1.10 mmol) (6 M solution) by syringe. The resulting solution was cooled to 0° C., and NaBH₄ (34.5 mg, 1.50 mmol) was added as a solid. After 2 hours, the reaction was made acidic with 2 N HCl (pH<3). The mixture was partitioned between ethyl acetate (30 mL) and water (30 mL). The organics were washed with brine (30 mL), isolated, dried over MgSO₄, filtered and concentrated to provide crude 3-(4-fluorophenyl)-2-hydroxypropanoic acid (184 mg, quantitative yield) as an oil.

Step 2: To a stirred solution of 3-(4-fluorophenyl)-2-hydroxypropanoic acid (97.9 mg, 0.531 mmol) in DMF (1.5 mL) at room temperature under nitrogen was added DIEA (116 A, 0.664 mmol) by syringe, followed by HOBT (71.8 mg, 0.531 mmol) and EDC (82.5 mg, 0.531 mmol) neat as solids. After 5 minutes, 4-(2-hydrazinylpyridin-4-yl)-N-(1-methyl-1H-pyrazol-5-yl)pyrimidin-2-amine (125 mg, 0.443 mmol) was added neat as a solid. After one hour, LC/MS showed two major LC peaks with the major corresponding to starting material and the other corresponding to desired product mass. The reaction was allowed to proceed overnight and LC/MS showed some more progress. The reaction was diluted to 30 mL with ethyl acetate and washed with water (3×30 mL) and brine (30 mL). The organics were isolated, dried over MgSO₄, filtered and concentrated to an oil. The crude product was loaded in dichloromethane and a minimum of methanol to aid dissolution onto a 25 gram SNAP silica gel cartridge and eluted on an Isolera system with a dichloromethane:methanol gradient (0% methanol to 10% methanol). Product containing fractions were pooled and concentrated to provide 3-(4-fluorophenyl)-2-hydroxy-N'-(4-(2-((1-methyl-1H-pyrazol-5-yl)amino)pyrimidin-4-yl)pyridin-2-yl)propanehydrazide (28 mg, 14% yield) as a solid.

Step 3: A solution of 3-(4-fluorophenyl)-2-hydroxy-N'-(4-(2-((1-methyl-1H-pyrazol-5-yl)amino)pyrimidin-4-yl)pyridin-2-yl)propanehydrazide (28 mg, 0.062 mmol) in acetic acid (2.5 mL) was stirred in a microwave vial and heated to 120° C. for 90 minutes. After cooling to room temperature, the reaction was concentrated to dryness by rotovap and high vacuum. The residual solid was triturated with ethyl acetate and sonication. Filtration and rinsing gave a solid which, after drying under high vacuum provided 2-(4-fluorophenyl)-1-(7-(2-((1-methyl-1H-pyrazol-5-yl)amino)pyrimidin-4-yl)-[1,2,4]triazolo[4,3-a]pyridin-3-yl)ethanol (25 mg, 93% yield) as a solid. ¹H-NMR (400 MHz, CDCl₃) δ 8.55 (d, 1H), 8.37 (s, 1H), 8.35 (d, 1H), 7.50 (d, 1H), 7.46 (d, 1H), 7.44 (d, 1H), 7.31 (d, 1H), 7.17 (m, 2H), 6.95 (m, 2H), 6.39 (d, 1H), 5.46 (m, 1H), 3.81 (s, 3H), 3.39 (m, 2H), 3.38 (m, 1H), 1.47 (s, 3H). LCMS (APCI−, 3 minute method) m/z 429.2 (M−H)−; Retention time 1.00 minutes.

Example 121

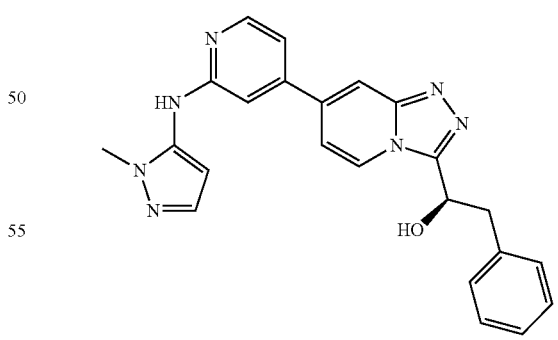

(R)-1-(7-(2-((1-methyl-1H-pyrazol-5-yl)amino)pyridin-4-yl)-[1,2,4]triazolo[4,3-a]pyridin-3-yl)-2-phenylethanol Step 1: Carried out according to the procedure of Example 119, Step 1, substituting 2'-hydrazinyl-N-(1-methyl-1H- pyrazol-5-yl)-[4,4'-bipyridin]-2-amine for 4-(2-hydrazinylpyridin-4-yl)-N-(1-methyl-1H-pyrazol-5-yl)pyrimidin-2-amine to provide (R)-2-hydroxy-N'-(2'-((1-methyl-1H-pyrazol-5-yl)amino)-[4,4'-bipyridin]-2-yl)-3-phenylpropanehydrazide (128 mg, quantitative yield) as a solid.

Step 2: Carried out according to the procedure of Example 119, Step 2, substituting (R)-2-hydroxy-N'-(2'-((1-methyl-1H-pyrazol-5-yl)amino)-[4,4'-bipyridin]-2-yl)-3-phenylpropanehydrazide for (R)-2-hydroxy-N'-(4-(2-((1-methyl-1H-pyrazol-5-yl)amino)pyrimidin-4-yl)pyridin-2-yl)-3-phenylpropanehydrazide to provide (R)-1-(7-(2-((1-methyl-1H-pyrazol-5-yl)amino)pyrimidin-4-yl)-[1,2,4]triazolo[4,3-a]pyridin-3-yl)-2-phenylethanol (52 mg, 42% yield) as a solid. $^1$H NMR (400 MHz, CDCl$_3$) δ 8.29 (d, 1H), 8.21 (d, 1H), 7.76 (s, 1H), 7.46 (d, 1H), 7.32 (br s, 1H), 7.24-7.15 (m, 6H), 6.93 (d, 1H), 6.86 (d, 1H), 6.82 (s, 1H), 6.20 (d, 1H), 5.51 (m, 1H), 3.75 (s, 3H), 3.41 (m, 2H). LCMS (APCI+, 3 minute method) m/z 412.1 (M+H)+; Retention time 1.00 minutes.

Example 122

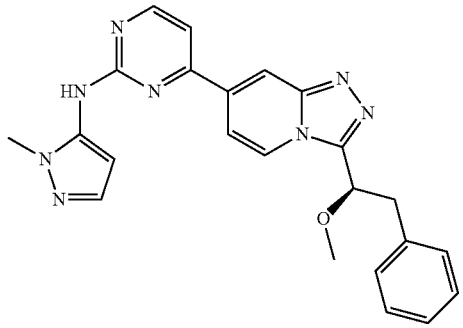 [SMILES: CO[C@H](Cc1ccccc1)c1nnc2cc(-c3ccnc(Nc4ccnn4C)n3)ccn12]

(R)-4-(3-(1-methoxy-2-phenylethyl)-[1,2,4]triazolo[4,3-a]pyridin-7-yl)-N-(1-methyl-1H-pyrazol-5-yl)pyrimidin-2-amine Step 1: To a stirred solution of (R)-2-hydroxy-3-phenylpropanoic acid (332 mg, 2.00 mmol) in THF (6 mL) at room temperature under nitrogen was added NaH (176 mg, 4.40 mmol) (60% oil dispersion) neat as a solid. After 40 minutes, methyl iodide (1249 μL, 20.0 mmol) was added neat by syringe. The reaction was allowed to stir overnight. TLC in 4:1 hexanes:ethyl acetate showed a clean high rf spot and no streaks from the origin. Water (1 mL) was added to quench the reaction and then hydrolyze the methyl ester. After stirring for 4 hours, the reaction was acidified to pH<3 with 2 N HCl. The reaction was partitioned between ethyl acetate (30 mL) and water (30 mL). The organics were isolated, washed with brine (30 mL), isolated again, dried over MgSO$_4$, filtered and concentrated to provide (R)-2-methoxy-3-phenylpropanoic acid (350 mg, 97% yield) as a solid.

Step 2: Carried out according to the procedure from Example 120, Step 2, substituting (R)-2-hydroxy-3-phenylpropanoic acid for 3-(4-fluorophenyl)-2-hydroxypropanoic acid to provide (R)-2-methoxy-N'-(4-(2-((1-methyl-1H-pyrazol-5-yl)amino)pyrimidin-4-yl)pyridin-2-yl)-3-phenylpropanehydrazide (235 mg, 99% yield) as a solid.

Step 3: Carried out according to the procedure from Example 120, Step 3, substituting (R)-2-methoxy-N'-(4-(2-((1-methyl-1H-pyrazol-5-yl)amino)pyrimidin-4-yl)pyridin-2-yl)-3-phenylpropanehydrazide for 3-(4-fluorophenyl)-2-hydroxy-N'-(4-(2-((1-methyl-1 II-pyrazol-5-yl)amino)pyrimidin-4-yl)pyridin-2-yl)propanehydrazide to provide (R)-4-(3-(1-methoxy-2-phenylethyl)-[1,2,4]triazolo[4,3-a]pyridin-7-yl)-N-(1-methyl-1H-pyrazol-5-yl)pyrimidin-2-amine (126 mg, 56% yield) as a solid. $^1$H NMR (400 MHz, CDCl$_3$) δ 8.55 (d, 1H), 8.38 (s, 1H), 8.11 (d, 1H), 7.52 (d, 1H), 7.36 (d, 1H), 7.27 (d, 1H), 7.26-7.17 (m, 3H), 7.12 (m, 2H), 6.36 (d, 1H), 5.30 (m, 1H), 3.83 (s, 3H), 3.35 (d, 2H), 3.29 (s, 3H). LCMS (APCI+, 3 minute method) m/z 427.2 (M+H)+; Retention time 1.11 minutes.

Example 123

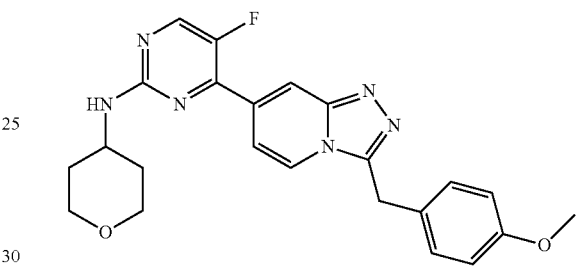

5-fluoro-4-(3-(4-methoxybenzyl)-[1,2,4]triazolo[4,3-a]pyridin-7-yl)-N-(tetrahydro-2H-pyran-4-yl)pyrimidin-2-amine Step 1: Hydrazine (5.46 mL, 174 mmol) was added to 4-bromo-2-fluoropyridine (3.06 g, 17.4 mmol) dropwise, and the resulting suspension was stirred at room temperature for 30 minutes. An exotherm was observed, and the initial thin suspension gradually thickened and became difficult to stir. The reaction mixture was stirred at room temperature overnight. The mixture was then diluted with water (20 mL), and the pH was adjusted to about 7 with 2 N NaOH. The solids were then collected by filtration and dried under vacuum to provide 4-bromo-2-hydrazinylpyridine (2.9 grams, 89% yield) as a solid.

Step 2: A mixture of 4-bromo-2-hydrazinylpyridine (1.1 g, 5.9 mmol) and 2-(4-methoxyphenyl)acetyl chloride (1.3 g, 7.0 mmol) in acetonitrile (6 mL) was refluxed under nitrogen overnight with stirring. The reaction was cooled to room temperature and concentrated by rotovap. The residual solid was washed with 10% sodium carbonate solution, triturated with ether and dried under high vacuum to provide N'-(4-bromopyridin-2-yl)-2-(4-methoxyphenyl)acetohydrazide (1.4 grams, 71% yield) as a solid.

Step 3: A suspension of N'-(4-bromopyridin-2-yl)-2-(4-methoxyphenyl)acetohydrazide (1.4 g, 4.16 mmol) and POCl$_3$ (1.14 mL, 12.5 mmol) in acetonitrile (8 mL) was refluxed under nitrogen with stirring. LC/MS after stirring overnight showed complete consumption of starting material and a 1:1 mixture of the desired material and an unknown byproduct with MS=274. The reaction mixture was cooled to room temperature and concentrated by rotovap. The residue was poured into a cold 10% sodium carbonate solution (30 mL) and extracted with ethyl acetate (30 mL). The organics were isolated, dried over MgSO$_4$, filtered and concentrated to provide 7-bromo-3-(4-methoxybenzyl)-[1,2,4]triazolo[4,3-a]pyridine and an unknown byproduct in a 1:1 mixture as a solid. The material was used as is in the next reaction.

Step 4: A suspension of 7-bromo-3-(4-methoxybenzyl)-[1,2,4]triazolo[4,3-a]pyridine (0.400 g, 1.26 mmol), 4,4,4',4',5,5,5',5'-octamethyl-2,2'-bi(1,3,2-dioxaborolane) (0.479 g, 1.89 mmol), KOAc (0.370 g, 3.77 mmol) and PdCl$_2$(dppf) dichloromethane adduct (0.103 g, 0.126 mmol) in dioxane (6 mL) was sparged with argon for 15 minutes and then heated to 90° C. under argon. After stirring overnight, the reaction was cooled to room temperature and concentrated. The residue was dissolved in ethyl acetate, and the insoluble material was removed by filtration. The filtrate was concentrated and purified via silica gel column chromatography, eluting with hexanes:ethyl acetate (1:4). Product containing fractions were pooled and concentrated to provide 3-(4-methoxybenzyl)-7-(4,4,5,5-tetramethyl-1,3,2-dioxaborolan-2-yl)-[1,2,4]triazolo[4,3-a]pyridine (66 mg, 14% yield) as a solid.

Step 5: A suspension of 2,4-dichloro-5-fluoropyrimidine (0.034 g, 0.20 mmol), 3-(4-methoxybenzyl)-7-(4,4,5,5-tetramethyl-1,3,2-dioxaborolan-2-yl)-[1,2,4]triazolo[4,3-a]pyridine (0.066 g, 0.18 mmol), sodium carbonate (0.18 mL, 0.37 mmol) and PdCl$_2$(dppf) dichloromethane adduct (0.015 g, 0.018 mmol) in dioxane (6 mL) was heated to 90° C. under argon for 2 hours. LC/MS showed complete conversion to the desired product. After cooling to room temperature, the reaction mixture was concentrated, and the residue was partitioned between ethyl acetate (30 mL) and water (30 mL). The aqueous layer was extracted with ethyl acetate (30 mL) The combined organics were dried over MgSO$_4$, filtered and concentrated. The crude product was purified via silica gel column chromatography, eluting with hexanes: ethyl acetate (1:3). Product containing fractions were pooled and concentrated to provide 7-(2-chloro-5-fluoropyrimidin-4-yl)-3-(4-methoxybenzyl)-[1,2,4]triazolo[4,3-a]pyridine (53 mg, 78% yield) as a solid.

Step 6: A solution of 7-(2-chloro-5-fluoropyrimidin-4-yl)-3-(4-methoxybenzyl)-[1,2,4]triazolo[4,3-a]pyridine (0.0206 g, 0.0557 mmol) and tetrahydro-2H-pyran-4-amine (0.0282 g, 0.279 mmol) in DMA (1.0 mL) was heated to 120° C. in a microwave reactor for 1 hour. LC/MS showed formation of the desired product. The reaction mixture was diluted with ethyl acetate (15 mL) and washed with water (2×15 mL). The organics were isolated, dried over MgSO$_4$, filtered and concentrated. The crude product was purified via silica gel column chromatography, eluting with hexanes:ethyl acetate (1:3), then ethyl acetate. Product containing fractions were pooled and concentrated to provide 5-fluoro-4-(3-(4-methoxybenzyl)-[1,2,4]triazolo[4,3-a]pyridin-7-yl)-N-(tetrahydro-2H-pyran-4-yl)pyrimidin-2-amine (12 mg, 50% yield) as a solid. $^1$H NMR (400 MHz, CDCl$_3$) δ 8.56 (s, 1H), 8.28 (m, 1H), 7.76 (d, 1H), 7.48 (d, 1H), 7.18 (d, 2H), 6.86 (d, 2H), 5.08 (d, 1H), 4.54 (s, 2H), 4.01 (m, 3H), 3.78 (s, 3H), 3.56 (m, 2H), 2.05 (d, 2H), 1.58 (m, 4H). LCMS (APCI+, 5 minute method) m/z 435.1 (M+H)+; Retention time 2.41 minutes.

Example 124

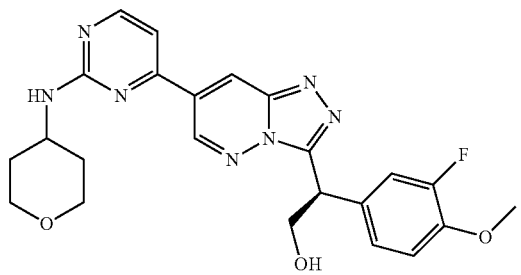 [SMILES: COc1ccc([C@@H](CO)c2nnc3cc(-c4ccnc(NC5CCOCC5)n4)cnn23)cc1F]

(R)-2-(3-fluoro-4-methoxyphenyl)-2-(7-(2-((tetrahydro-2H-pyran-4-yl)amino)pyrimidin-4-yl)-[1,2,4]triazolo[4,3-b]pyridazin-3-yl)ethanol Step 1: (R)-3-(2-(3-fluoro-4-methoxyphenyl)acetyl)-4-phenyloxazolidin-2-one was made according to the procedure described in Prashad, Mahavir, et al. "An Efficient and Large-Scale Enantioselective Synthesis of PNP405: A Purine Nucleoside Phosphorylase Inhibitor." *J. Org. Chem.* 67(19) (2002): pp. 6612-6617. A 500 mL 3-neck round bottom flask equipped with a temperature probe and stir bar was charged with 2-(3-fluoro-4-methoxyphenyl)acetic acid (10.3 g, 184.2 mmol), (R)-4-phenyloxazolidin-2-one (8.3 g, 50.9 mmol) and dry toluene (120 mL) The mixture was warmed to an internal temperature of 80° C. and treated dropwise with pivaloyl chloride (7.5 mL, 61 mmol) followed by TEA (21.3 mL, 153 mmol). Additional toluene (100 mL) was added to the mixture to facilitate stirring. This mixture was stirred at 80° C. for another 3 hours and was allowed to cool to room temperature, and ice was added followed by water (200 mL). The resulting mixture was extracted with EtOAc (2×), and the combined extracts were washed with 2 M aqueous HCl, followed by 2 M aqueous sodium carbonate. The organic layer was dried (Na$_2$SO$_4$), filtered and concentrated in vacuo. The residue obtained was purified by flash chromatography on silica gel (220 g Redi Sep) eluting with 35% EtOAc:hexanes to give (R)-3-(2-(3-fluoro-4-methoxyphenyl)acetyl)-4-phenyloxazolidin-2-one (7.4 g, 44% yield). $^1$H NMR (400 MHz, CDCl$_3$) δ 7.38-7.31 (m, 3H), 7.25-7.19 (m, 2H), 6.99-6.92 (m, 2H), 6.90-6.83 (m, 1H), 5.44-5.39 (m, 1H), 4.72-4.65 (m, 1H), 4.29-4.25 (m, 1H), 4.20 (s, 2H), 3.85 (s, 3H).

Step 2: (R)-3-((S)-2-(3-fluoro-4-methoxyphenyl)-3-hydroxypropanoyl)-4-phenyloxazolidin-2-one was made according to the procedure described in Takacs, James M., et al. "Preparation of Chiral Oxazolidin-2-ones and Vicinal Amino Alcohols." *J. Org. Chem.* 63(8) (1998): pp. 2742-2748. A round bottom flask equipped with a stir bar and nitrogen inlet was charged with (R)-3-(2-(3-fluoro-4-methoxyphenyl)acetyl)-4-phenyloxazolidin-2-one (3 g, 9.11 mmol) and dry DCM (4 mL). This solution was cooled to 0° C. and treated dropwise with TiCl$_4$ (1 M in toluene, 1.051 mL, 9.565 mmol). The mixture was stirred at 0° C. for 5 minutes and then treated dropwise with Hunig's base (1.745 mL, 10.02 mmol). The resulting mixture was stirred at 0° C. for 1 hour. A solution of trioxane (0.9437 g, 10.48 mmol) in DCM was then added, followed by another 1.05 equivalents of the TiCl$_4$. The mixture was stirred at 0° C. for 2 hours. This was then quenched with saturated NH$_4$Cl solution and extracted with DCM (2×). The combined organic extracts were dried (Na₂SO₄), filtered and concentrated in vacuo to provide crude (R)-3-((S)-2-(3-fluoro-4-methoxyphenyl)-3-hydroxypropanoyl)-4-phenyloxazolidin-2-one (3.3 g, 100% yield). ¹H NMR (400 MHz, CDCl₃) δ 7.44-7.30 (m, 5H), 7.14-7.08 (m, 2H), 6.95-6.89 (m, 1H), 5.42-5.37 (m, 1H), 5.21-5.17 (m, 2H), 4.63-4.56 (m, 1H), 4.25-4.19 (m, 1H), 4.08-4.00 m, 1H), 3.87 (s, 3H), 3.78-3.71 (m, 1H).

Step 3: To a solution of crude (R)-3-((S)-2-(3-fluoro-4-methoxyphenyl)-3-hydroxypropanoyl)-4-phenyloxazolidin-2-one (3.3 g, 9.2 mmol) in DMF (90 mL) was sequentially added imidazole (1.3 g, 18 mmol) and TBSCl (1.5 g, 10 mmol). The mixture was stirred at room temperature for 16 hours, then diluted with water and extracted with EtOAc (2×). The organic extracts were washed with brine (2×), dried (Na₂SO₄), filtered and concentrated in vacuo. The residue obtained was purified by silica gel flash chromatography (Redi Sep 220 g), eluting with 15-35% EtOAc:hexane to provide (R)-3-((S)-3-(tert-butyldimethylsilyloxy)-2-(3-fluoro-4-methoxyphenyl)propanoyl)-4-phenyl oxazolidin-2-one (2.4 g, 55% yield). ¹H NMR (400 MHz, CDCl₃) δ (7.42-7.31 (m, 5H), 7.18-7.10 (m, 2H), 6.94-6.88 (m, 1H), 5.43-5.39 (m, 1H), 5.29-5.24 (m, 1H), 4.63-4.56 (m, 1H), 4.25-4.20 (m, 1H), 4.19-4.11 (m, 1H), 3.87 (s, 3H), 3.67-3.62 (m, 1H), 0.76 (s, 911), 0.08 (s, 3H), −0.13 (s, 3H).

Step 4: To a solution of (R)-3-((S)-3-(tert-butyldimethylsilyloxy)-2-(3-fluoro-4-methoxyphenyl)propanoyl)-4-phenyloxazolidin-2-one (1.34 g, 2.829 mmol) in THF (35 mL) and water (10 mL) at 0° C. was added dropwise hydrogen peroxide (3.2 mL, 28.29 mmol) followed by LiOH.H₂O (1 M in water, 5.659 mmol). This mixture was allowed to stir at 0° C. for 10 minutes, and then warmed to room temperature. The mixture was cooled back to 0° C. and treated with 1 M aqueous sodium sulfite (25 mL). The mixture was stirred at 0° C. for 10 minutes, and then the pH was adjusted to about pH 2-3 with 1 M aqueous KHSO₄. This mixture was extracted with EtOAc (2×). The combined organic layers were dried (MgSO₄), filtered and concentrated in vacuo. The residue obtained was triturated with hexanes and MTBE. The solids were filtered off, and the filtrate collected was concentrated to provide (S)-3-(tert-butyldimethylsilyloxy)-2-(3-fluoro-4-methoxyphenyl)propanoic acid (655 mg, 70.5% yield). ¹H NMR (400 MHz, CDCl₃) δ 7.12-6.88 (m, 31-), 4.12-4.02 (m, 1H), 3.88 (s, 3H), 3.86-3.73 (m, 2H), 0.86 (s, 9H), 0.05-0.02 (m, 6H).

Step 5: To a solution of 3-hydrazinyl-5-(2-(methylthio)pyrimidin-4-yl)pyridazine (100 mg, 0.427 mmol) in DMF (2.1 mL, 0.427 mmol) was added (S)-3-((tert-butyldimethylsilyl)oxy)-2-(3-fluoro-4-methoxyphenyl)propanoic acid (154 mg, 0.470 mmol), 1H-benzo[d][1,2,3]triazol-1-ol hydrate (98 mg, 0.640 mmol), EDC (123 mg, 0.640 mmol) and 4-methylmorpholine (130 mg, 1.28 mmol). The mixture was stirred at room temperature overnight. The mixture was diluted with EtOAc (50 mL) and washed with brine (2×10 mL). The organic layer was dried (MgSO₄), filtered and concentrated in vacuo to give crude (S)-3-((tert-butyldimethylsilyl)oxy)-2-(3-fluoro-4-methoxyphenyl)-N'-(5-(2-(methylthio)pyrimidin-4-yl)pyridazin-3-yl)propanehydrazide, which was used for the next reaction directly. LCMS (APCI+) m/z 545 (M+1).

Step 6: A mixture of crude (8)-3-((tert-butyldimethylsilyl)oxy)-2-(3-fluoro-4-methoxyphenyl)-N'-(5-(2-(methylthio)pyrimidin-4-yl)pyridazin-3-yl)propanehydrazide (233 mg, 0.428 mmol) in a mixture of acetic acid and THF (3 mL, 1:1) was heated at 80° C. for 1.5 hours. The mixture was then cooled to room temperature, diluted with EtOAc (50 mL) and washed with saturated NaHCO₃ (2×10 mL) followed by brine (10 mL). The organic layer was separated, dried (MgSO₄), filtered and concentrated in vacuo. The crude isolated was purified by flash chromatography on silica gel (Redi Sep 12 g) eluting with a gradient of 0-10% MeOH:DCM (20 CV). From this purification two major peaks were isolated. Peak 1 was found to be (R)-3-(2-((tert-butyldimethyl silyl)oxy)-1-(3-fluoro-4-methoxyphenyl)ethyl)-7-(2-(methylthio)pyrimidin-4-yl)-[1,2,4]triazolo[4,3-b]pyridazine (183 mg, 0.285 mmol, 66.6% yield); LCMS (APCI+) m/z 527 (M+1). Peak 2 was the desired alcohol, (R)-2-(3-fluoro-4-methoxyphenyl)-2-(7-(2-(methylthio)pyrimidin-4-yl)-[1,2,4]triazolo[4,3-b]pyridazin-3-yl)ethanol (47 mg, 0.114 mmol, 26.6% yield); LCMS (APCI+) m/z 413 (M+1).

Step 7: To a solution of (R)-2-(3-fluoro-4-methoxyphenyl)-2-(7-(2-(methylthio)pyrimidin-4-yl)-[1,2,4]triazolo[4,3-b]pyridazin-3-yl)ethanol (47 mg, 0.11 mmol) in dichloromethane (1.15 mL, 0.11 mmol) was added 3-chlorobenzoperoxoic acid (77% pure, 51 mg, 0.23 mmol), and the mixture was stirred at room temperature for 2 hours. The mixture was diluted with EtOAc (50 mL) and washed with saturated NaHCO₃ (2×10 mL) followed by brine (10 mL) The organic layer was separated, dried (MgSO₄), filtered and concentrated in vacuo to provide crude (R)-2-(3-fluoro-4-methoxyphenyl)-2-(7-(2-(methylsulfonyl)pyrimidin-4-yl)-[1,2,4]triazolo[4,3-b]pyridazin-3-yl)ethanol (62 mg, 94% yield). LCMS (APCI+) m/z 445.1, retention time 1.095 minutes. The crude was used for the next reaction directly.

Step 8: A resealable glass tube was charged with a mixture of crude (R)-2-(3-fluoro-4-methoxyphenyl)-2-(7-(2-(methylsulfonyl)pyrimidin-4-yl)-[1,2,4]triazolo[4,3-b]pyridazin-3-yl)ethanol (30 mg, 0.068 mmol) and tetrahydro-2H-pyran-4-amine (34 mg, 0.34 mmol) in 2-butanol (675 µL, 0.068 mmol). The tube was sealed with a Teflon cap, and the mixture was heated at 80° C. with stirring. After 18 hours, the mixture was cooled to ambient temperature, transferred to a round bottom flask and concentrated in vacuo. The residue obtained was dissolved in DCM (50 mL) and washed with saturated NaHCO₃ (5×) followed by brine. The organic layer was dried (MgSO₄), filtered and concentrated in vacuo. The residue obtained was purified by C-18 reverse phase chromatography (Biotage C-18, 12M+) eluting with a gradient of 0-65% CH₃CN/water to provide (R)-2-(3-fluoro-4-methoxyphenyl)-2-(7-(2-((tetrahydro-2H-pyran-4-yl)amino)pyrimidin-4-yl)-[1,2,4]triazolo[4,3-b]pyridazin-3-yl)ethanol (3 mg, 9.5% yield) as a solid. ¹H NMR (400 MHz, CDCl₃) δ 8.998 (s, 1H), 8.639 (s, 1H), 8.45 (d, J=5.09 Hz, 1H), 7.11-7.05 (m, 2H), 7.003 (d, J=4.69 Hz, 1H), 6.90 (t, J=8.61 Hz, 1H), 5.26-5.22 (m, 1H), 4.86-4.82 (m, 1H), 4.53-4.48 (m, 1H), 4.31-4.09 (m, 1H), 4.17-4.09 (m, 1H), 4.05-4.01 (m, 2H), 3.85 (s, 3H), 3.61-3.55 (m, 2H), 3.14-3.05 (m, 1H), 2.1-2.05 (m, 2H), 1.64-1.55 (m, 2H); LCMS (APCI+) m/z 465 (M+1).

Example 125

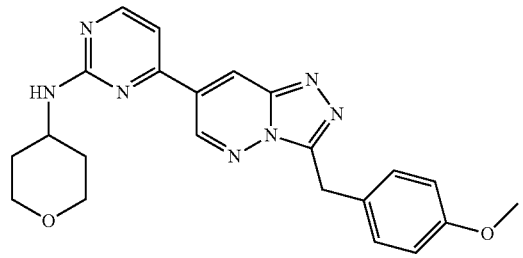 [SMILES: COc1ccc(Cc2nnc3cc(-c4ccnc(NC5CCOCC5)n4)cnn23)cc1]

4-(3-(4-methoxybenzyl)-[1,2,4]triazolo[4,3-b]pyridazin-7-yl)-N-(tetrahydro-2H-pyran-4-yl)pyrimidin-2-amine Step 1: To a suspension of 3-hydrazinyl-5-(2-(methylthio)pyrimidin-4-yl)pyridazine (98 mg, 0.418 mmol) in 1,4-dioxane (8366 µL, 0.418 mmol) and triethylamine (58.3 µL, 0.418 mmol) was added dropwise 2-(4-methoxyphenyl)acetyl chloride (84.9 mg, 0.460 mmol). The mixture was stirred at room temperature for 30 minutes and then heated at reflux for 2 hours. The mixture was cooled to room temperature, and the solvent was removed in vacuo. The residue obtained was partitioned between DCM (30 mL) and saturated aqueous NaHCO$_3$ (5 mL). The organic layer was dried (MgSO$_4$), filtered and concentrated in vacuo. The solid residue obtained was triturated with CH$_3$CN to provide 3-(4-methoxybenzyl)-7-(2-(methylthio)pyrimidin-4-yl)-[1,2,4]triazolo[4,3-b]pyridazine (90 mg, 59% yield) as a solid. LCMS (APCI+) m/z 365.1 (M+1).

Step 2: To a solution of 3-(4-methoxybenzyl)-7-(2-(methylthio)pyrimidin-4-yl)-[1,2,4]triazolo[4,3-b]pyridazine (88 mg, 0.24 mmol) in dichloromethane (4830 µL, 0.24 mmol) was added m-CPBA 77% (114 mg, 0.51 mmol), and the mixture was stirred at room temperature for 4 hours. The mixture was diluted with DCM (50 mL) and washed with saturated NaHCO$_3$ (2×10 mL) and followed by brine (10 mL). The organic layer was separated, dried (MgSO$_4$), filtered and concentrated in vacuo. The crude obtained was purified by flash chromatography on silica gel (Ready Sep, 12 g) eluting with 0-6% MeOH:DCM (25 CV) to provide 3-(4-methoxybenzyl)-7-(2-(methylsulfonyl)pyrimidin-4-yl)-[1,2,4]triazolo[4,3-b]pyridazine (85 mg, 89% yield) as a solid. LCMS (APCI+) m/z 397.1 (M+1).

Step 3: A suspension of 3-(4-methoxybenzyl)-7-(2-(methylsulfonyl)pyrimidin-4-yl)-[1,2,4]triazolo[4,3-b]pyridazine (40 mg, 0.10 mmol) and tetrahydro-2H-pyran-4-amine (30 mg, 0.29 mmol) in 2-methylpropan-1-ol (1 mL, 0.10 mmol) was heated at 115° C. for 5 hours and allowed to cool to room temperature. The mixture was diluted with DCM (20 mL) and washed with saturated NaHCO$_3$ (2×5 mL). The organic layer was separated, dried (MgSO$_4$) and concentrated in vacuo. The crude isolated was purified by flash chromatography (Ready Sep, 12 g) eluting with 0-12% MeOH:DCM (25 CV) to provide 4-(3-(4-methoxybenzyl)-[1,2,4]triazolo[4,3-b]pyridazin-7-yl)-N-(tetrahydro-2H-pyran-4-yl)pyrimidin-2-amine (30 mg, 71% yield) as a solid. LCMS (APCI+) m/z 418.2 (M+1), retention time 1.331 minutes.

Example 126

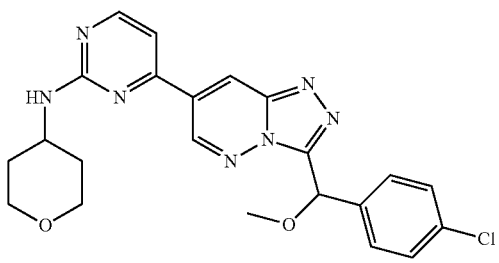 [SMILES: COC(c1ccc(Cl)cc1)c1nnc2cc(-c3ccnc(NC4CCOCC4)n3)cnn12]

4-(3-((4-chlorophenyl)(methoxy)methyl)-[1,2,4]triazolo[4,3-b]pyridazin-7-yl)-N-(tetrahydro-2H-pyran-4-yl)pyrimidin-2-amine Step 1: A solution of 2-(4-chlorophenyl)-2-hydroxyacetic acid (5.00 g, 26.8 mmol) in MeOH (20 mL) and concentrated H$_2$SO$_4$ (2 mL) was heated at reflux for 4 hours. The organic solvent was removed in vacuo, and the aqueous residue was dissolved in EtOAc (200 mL) Then it was washed with saturated aqueous NaHCO$_3$ (2×) and brine. The organics were dried (MgSO$_4$), filtered and concentrated in vacuo to provide mixture of methyl 2-(4-chlorophenyl)-2-hydroxyacetate (4.4 g, 82% yield) and a small amount of methyl 2-(4-chlorophenyl)-2-methoxyacetate (886 mg, 15.4% yield). Methyl 2-(4-chlorophenyl)-2-hydroxyacetate: $^1$H NMR (400 MHz, CDCl$_3$) δ 7.383-7.348 (m, 4H), 5.155 (m, 1H), 3.77 (s, 3H).

Step 2: To a suspension of sodium hydride (60% suspension in mineral oil, 1.10 g, 27.4 mmol) in THF (20 mL) at 0° C. under N$_2$ was added dropwise a solution of crude methyl 2-(4-chlorophenyl)-2-hydroxyacetate in tetrahydrofuran (49.8 mL, 24.9 mmol). Once the addition was complete, the mixture was treated with iodomethane (1.77 mL, 37.4 mmol). The resulting suspension was stirred at room temperature for 1 hour. The reaction was quenched with slow addition of water (30 mL). The organic solvent was removed in vacuo, and the residue was partitioned between EtOAc and brine. The organic layer was separated, dried (MgSO$_4$), filtered and concentrated in vacuo. The residue isolated was purified by flash chromatography on silica gel (Ready Sep 120 g) eluting with a gradient of 0-30% EtOAc:hexanes (12 CV) on Biotage SP1 unit to provide methyl 2-(4-chlorophenyl)-2-methoxyacetate (3.02 g, 63.4% yield) as an oil. $^1$H NMR (400 MHz, CDCl$_3$) δ 7.40-7.33 (m, 4H), 4.753 (s, 1H), 3.726 (s, 3), 3.407 (s, 3H).

Step 3: A solution of methyl 2-(4-chlorophenyl)-2-methoxyacetate (3.02 g, 14.1 mmol) in methanol (14.1 mL, 14.1 mmol) and THF (28 mL, 14.1 mmol) at room temperature was treated with LiOH.H$_2$O (1.48 g, 35.2 mmol) in water (7 mL, 14 mmol) and stirred for 1.5 hours. The organic solvents were removed in vacuo. The aqueous residue obtained was diluted with water (50 mL) and made acidic with 1 N HCl. The resulting suspension was partitioned with EtOAc. The organic layers were combined, dried (MgSO$_4$), filtered and concentrated in vacuo to provide 2-(4-chlorophenyl)-2-methoxyacetic acid (2.81 g, 99.6% yield) as an oil. $^1$H NMR (400 MHz, (CD$_3$)$_2$SO) δ 12.92 (br s, 1H), 7.456-7.393 (m, 4H), 4.80 (s, 3H), 3.31 (s, 3H).

Step 4: To a mixture of 3-hydrazinyl-5-(2-(methylthio)pyrimidin-4-yl)pyridazine (73 mg, 0.312 mmol), 2-(4-chlorophenyl)-2-methoxyacetic acid (93.8 mg, 0.467 mmol), 1H-benzo[d][1,2,3]triazol-1-ol hydrate (71.6 mg, 0.467 mmol), EDC (59.7 mg, 0.312 mmol) in DMF (3 mL, 0.312 mmol) was added 4-methylmorpholine (103 µL, 0.935 mmol). The mixture was stirred at room temperature over the weekend. The mixture was diluted with 5% MeOH:DCM (50 mL) and washed with water (2×10 mL). The organics were separated, dried (MgSO$_4$), filtered and concentrated in vacuo to provide crude 2-(4-chlorophenyl)-2-methoxy-N'-(5-(2-(methylthio)pyrimidin-4-yl)pyridazin-3-yl)acetohydrazide. LCMS (APCI1) m/z 415.1 (M−1).

Step 5: Crude 2-(4-chlorophenyl)-2-methoxy-N'-(5-(2-(methylthio)pyrimidin-4-yl)pyridazin-3-yl)acetohydrazide was dissolved in glacial acetic acid (5 mL) and heated at 80° C. for 30 minutes. The mixture was cooled to room temperature, diluted with DCM (100 mL) and washed with saturated NaHCO$_3$. The organic layer was separated, dried (MgSO₄), filtered and concentrated in vacuo. Crystallization of the crude from CH₃CN gave 3-((4-chlorophenyl)(methoxy)methyl)-7-(2-(methylthio)pyrimidin-4-yl)-[1,2,4]triazolo[4,3-b]pyridazine (56 mg, 45.1% yield) as a solid. LCMS (APCI+) m/z 399.1 (M+1).

Step 6: 3-((4-Chlorophenyl)(methoxy)methyl)-7-(2-(methylthio)pyrimidin-4-yl)-[1,2,4]triazolo[4,3-b]pyridazine (56 mg, 0.14 mmol) and m-CPBA 77% (66 mg, 0.29 mmol) were processed according to the method described in Example 125, Step 2, to provide 3-((4-chlorophenyl)(methoxy)methyl)-7-(2-(methylsulfonyl)pyrimidin-4-yl)-[1,2,4]triazolo[4,3-b]pyridazine (49 mg, 81% yield) as a solid. LCMS (APCI+) m/z 431.0 (M+1).

Step 7: 3-((4-Chlorophenyl)(methoxy)methyl)-7-(2-(methylsulfonyl)pyrimidin-4-yl)-[1,2,4]triazolo[4,3-b]pyridazine (20 mg, 0.046 mmol) and tetrahydro-2H-pyran-4-amine (14 mg, 0.13 mmol) in 2-BuOH (464 μL, 0.046 mmol) were processed as for the synthesis of 4-(3-(4-methoxybenzyl)-[1,2,4]triazolo[4,3-b]pyridazin-7-yl)-N-(tetrahydro-2H-pyran-4-yl)pyrimidin-2-amine to provide 4-(3-((4-chlorophenyl)(methoxy)methyl)-[1,2,4]triazolo[4,3-b]pyridazin-7-yl)-N-(tetrahydro-2H-pyran-4-yl)pyrimidin-2-amine (11 mg, 52% yield) as a solid. LCMS (APCI+) m/z 452.1 (M+1).

The following compounds in Table 2 were prepared according to the above procedures using appropriate starting materials and intermediates.

TABLE 2

| Ex. # | Structure | Name | MS (ACPI+) M + 1 (retention time) |
|---|---|---|---|
| 127 | 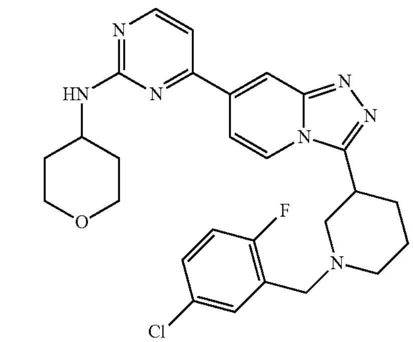 [SMILES: Fc1ccc(Cl)cc1CN1CCCC(c2nnc3cc(-c4ccnc(NC5CCOCC5)n4)ccn23)C1] | 4-(3-(1-(5-chloro-2-fluorobenzyl)piperidin-3-yl)-[1,2,4]triazolo[4,3-a]pyridin-7-yl)-N-(tetrahydro-2H-pyran-4-yl)pyrimidin-2-amine | 522.2 (1.31 min) |
| 128 | 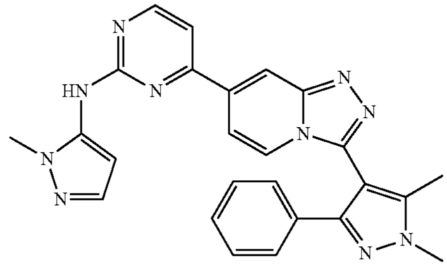 | 4-(3-(1,5-dimethyl-3-phenyl-1H-pyrazol-4-yl)-[1,2,4]triazolo[4,3-a]pyridin-7-yl)-N-(1-methyl-1H-pyrazol-5-yl)pyrimidin-2-amine | 463.2 (1.01 min) |
| 129 | 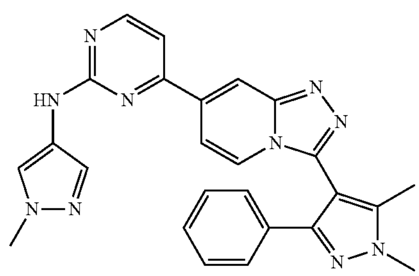 | 4-(3-(1,5-dimethyl-3-phenyl-1H-pyrazol-4-yl)-[1,2,4]triazolo[4,3-a]pyridin-7-yl)-N-(1-methyl-1H-pyrazol-4-yl)pyrimidin-2-amine | 463.2 (1.03 min) |
| 130 | 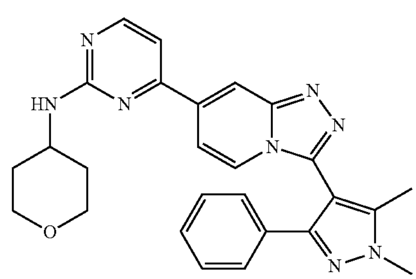 [SMILES: Cc1c(-c2nnc3cc(-c4ccnc(NC5CCOCC5)n4)ccn23)c(-c2ccccc2)nn1C] | 4-(3-(1,5-dimethyl-3-phenyl-1H-pyrazol-4-yl)-[1,2,4]triazolo[4,3-a]pyridin-7-yl)-N-(tetrahydro-2H-pyran-4-yl)pyrimidin-2-amine | 467.2 (1.08 min) |

TABLE 2-continued

| Ex. # | Structure | Name | MS (ACPI+) M + 1 (retention time) |
|---|---|---|---|
| 131 | 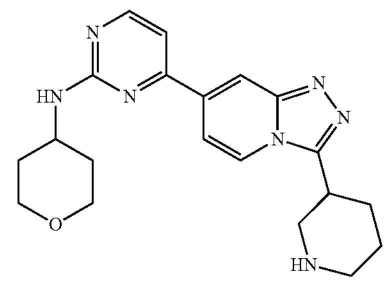 | 4-(3-(piperidin-3-yl)-[1,2,4]triazolo[4,3-a]pyridin-7-yl)-N-(tetrahydro-2H-pyran-4-yl)pyrimidin-2-amine | 380.2 (0.727 min) |
| 132 | 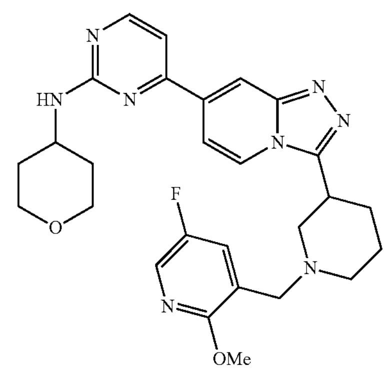 [SMILES: COc1ncc(F)cc1CN1CCCC(c2nnc3cc(-c4ccnc(NC5CCOCC5)n4)ccn23)C1] | 4-(3-(1-((5-fluoro-2-methoxypyridin-3-yl)methyl)piperidin-3-yl)-[1,2,4]triazolo[4,3-a]pyridin-7-yl)-N-(tetrahydro-2H-pyran-4-yl)pyrimidin-2-amine | 519.2 (1.14 min) |
| 133 | 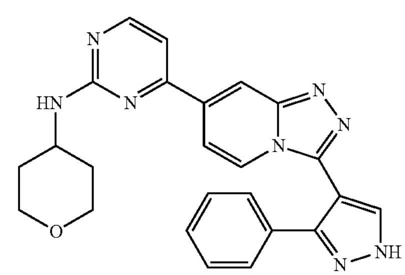 [SMILES: c1ccc(-c2n[nH]cc2-c2nnc3cc(-c4ccnc(NC5CCOCC5)n4)ccn23)cc1] | 4-(3-(3-phenyl-1H-pyrazol-4-yl)-[1,2,4]triazolo[4,3-a]pyridin-7-yl)-N-tetrahydro-2H-pyran-4-yl)pyrimidin-2-amine | 437.2 (M − 1) (0.98 min) |
| 134 | 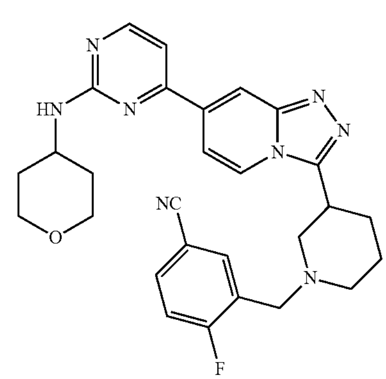 [SMILES: N#Cc1ccc(F)c(CN2CCCC(c3nnc4cc(-c5ccnc(NC6CCOCC6)n5)ccn34)C2)c1] | 4-fluoro-3-((3-(7-(2-((tetrahydro-2H-pyran-4-yl)amino)pyrimidin-4-yl)-[1,2,4]triazolo[4,3-a]pyridin-3-yl)piperidin-1-yl)methyl)benzonitrile | 513.2 (1.15 min) |

TABLE 2-continued

| Ex. # | Structure | Name | MS (ACPI+) M + 1 (retention time) |
|---|---|---|---|
| 135 | 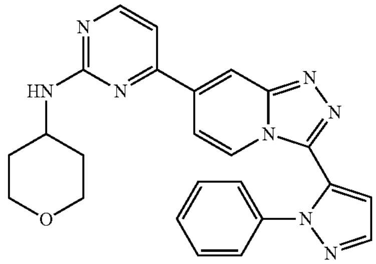 [SMILES: c1ccc(-n2nccc2-c2nnc3cc(-c4ccnc(NC5CCOCC5)n4)ccn23)cc1] | 4-(3-(1-phenyl-1H-pyrazol-5-yl)-[1,2,4]triazolo[4,3-a]pyridin-7-yl)-N-(tetrahydro-2H-pyran-4-yl)pyrimidin-2-amine | 439.2 (1.06 min) |
| 136 | 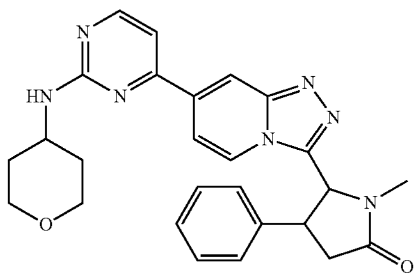 [SMILES: CN1C(=O)CC(c2ccccc2)C1c1nnc2cc(-c3ccnc(NC4CCOCC4)n3)ccn12] | 1-methyl-4-phenyl-5-(7-(2-((tetrahydro-2H-pyran-4-yl)amino)pyrimidin-4-yl)-[1,2,4]triazolo[4,3-a]pyridin-3-yl)pyrrolidin-2-one | 470.2 (0.94 min) |
| 137 | 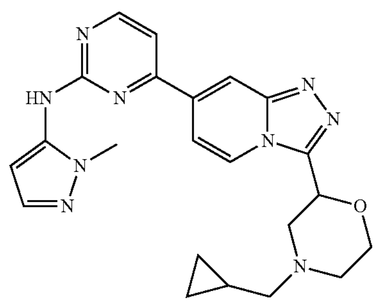 [SMILES: Cn1nccc1Nc1nccc(-c2ccn3c(C4CN(CC5CC5)CCO4)nnc3c2)n1] | 4-(3-(4-(cyclopropylmethyl)morpholin-2-yl)-[1,2,4]triazolo[4,3-a]pyridin-7-yl)-N-(1-methyl-1H-pyrazol-5-yl)pyrimidin-2-amine | 432.2 (0.90 min) |
| 138 | 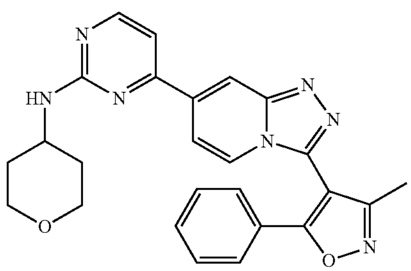 [SMILES: Cc1noc(-c2ccccc2)c1-c1nnc2cc(-c3ccnc(NC4CCOCC4)n3)ccn12] | 4-(3-(3-methyl-5-phenylisoxazol-4-yl)-[1,2,4]triazolo[4,3-a]pyridin-7-yl)-N-(tetrahydro-2H-pyran-4-yl)pyrimidin-2-amine | 454.1 (1.18 min) |
| 139 | 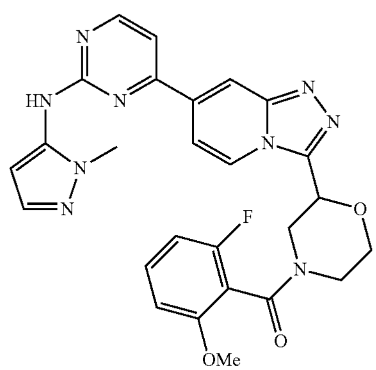 [SMILES: COc1cccc(F)c1C(=O)N1CCOC(c2nnc3cc(-c4ccnc(Nc5ccnn5C)n4)ccn23)C1] | (2-fluoro-6-methoxyphenyl)(2-(7-(2-((1-methyl-1H-pyrazol-5-yl)amino)pyrimidin-4-yl)-[1,2,4]triazolo[4,3-a]pyridin-3-yl)morpholino)methanone | 530.2 (1.00 min) |

TABLE 2-continued

| Ex. # | Structure | Name | MS (ACPI+) M + 1 (retention time) |
|---|---|---|---|
| 140 | 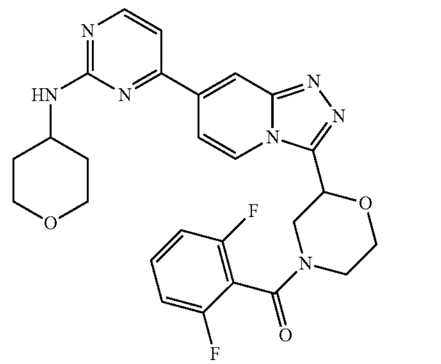 [SMILES: O=C(c1c(F)cccc1F)N1CCOC(c2nnc3cc(-c4ccnc(NC5CCOCC5)n4)ccn23)C1] | (2,6-difluorophenyl)(2-(7-(2-((tetrahydro-2H-pyran-4-yl)amino)pyrimidin-4-yl)-[1,2,4]triazolo[4,3-a]pyridin-3-yl)morpholino)methanone | 522.2 (1.07 min) |
| 141 | 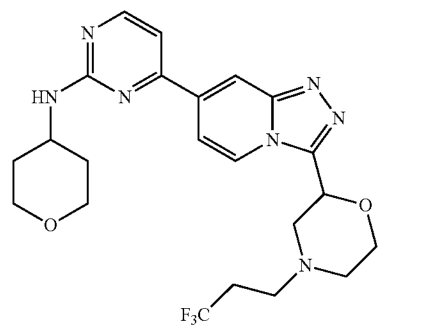 [SMILES: FC(F)(F)CCN1CCOC(c2nnc3cc(-c4ccnc(NC5CCOCC5)n4)ccn23)C1] | N-(tetrahydro-2H-pyran-4-yl)-4-(3-(4-(3,3,3-trifluoropropyl)morpholin-2-yl)-[1,2,4]triazolo[4,3-a]pyridin-7-yl)pyrimidin-2-amine | 478.1 (0.85 min) |
| 142 | 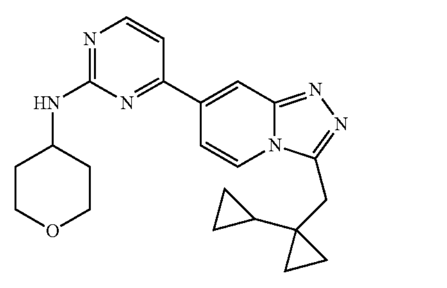 [SMILES: c1cc(-c2ccn3c(CC4(C5CC5)CC4)nnc3c2)nc(NC2CCOCC2)n1] | 4-(3-([1,1'-bi(cyclopropan)]-1-ylmethyl)-[1,2,4]triazolo[4,3-a]pyridin-7-yl)-N-(tetrahydro-2H-pyran-4-yl)pyrimidin-2-amine | 391.2 (1.36 min) |
| 143 | 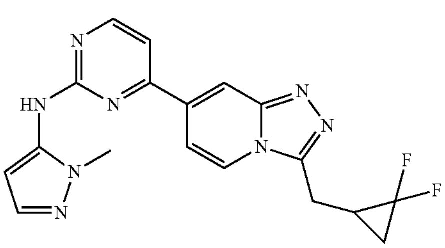 [SMILES: Cn1nccc1Nc1nccc(-c2ccn3c(CC4CC4(F)F)nnc3c2)n1] | 4-(3-((2,2-difluorocyclopropyl)methyl)-[1,2,4]triazolo[4,3-a]pyridin-7-yl)-N-(1-methyl-1H-pyrazol-5-yl)pyrimidin-2-amine | 383.1 (1.16 min) |
| 144 | 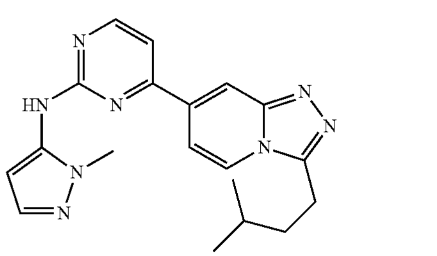 [SMILES: CC(C)CCc1nnc2cc(-c3ccnc(Nc4ccnn4C)n3)ccn12] | 4-(3-isopentyl-[1,2,4]triazolo[4,3-a]pyridin-7-yl)-N-(1-methyl-1H-pyrazol-5-yl)pyrimidin-2-amine | 363.2 (1.25 min) |

TABLE 2-continued

| Ex. # | Structure | Name | MS (ACPI+) M + 1 (retention time) |
|---|---|---|---|
| 145 | 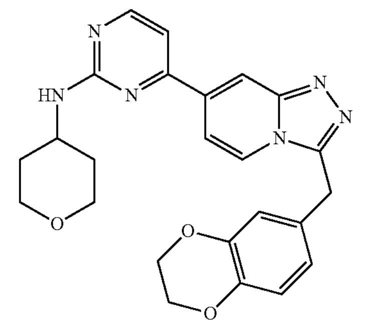 [SMILES: c1cc(-c2ccn3c(Cc4ccc5c(c4)OCCO5)nnc3c2)nc(NC2CCOCC2)n1] | 4-(3-((2,3-dihydrobenzo[b][1,4]dioxin-6-yl)methyl)-[1,2,4]triazolo[4,3-a]pyridin-7-yl)-N-(tetrahydro-2H-pyran-4-yl)pyrimidin-2-amine | 445.2 (1.25 min) |
| 146 | 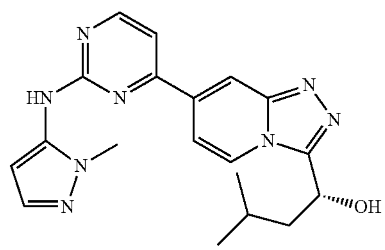 [SMILES: CC(C)C[C@@H](O)c1nnc2cc(-c3ccnc(Nc4ccnn4C)n3)ccn12] | (R)-3-methyl-1-(7-(2-((1-methyl-1H-pyrazol-5-yl)amino)pyrimidin-4-yl)-[1,2,4]triazolo[4,3-a]pyridin-3-yl)butan-1-ol | 379.2 (1.66 min) |
| 147 | 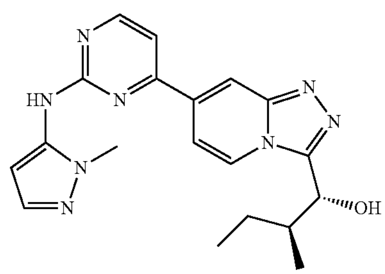 [SMILES: CC[C@H](C)[C@@H](O)c1nnc2cc(-c3ccnc(Nc4ccnn4C)n3)ccn12] | (1R,2S)-2-methyl-1-(7-(2-((1-methyl-1H-pyrazol-5-yl)amino)pyrimidin-4-yl)-[1,2,4]triazolo[4,3-a]pyridin-3-yl)butan-1-ol | 379.2 (1.22 min) |
| 148 | 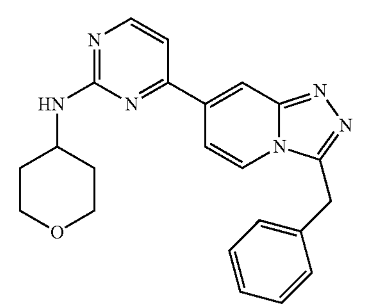 [SMILES: c1ccc(Cc2nnc3cc(-c4ccnc(NC5CCOCC5)n4)ccn23)cc1] | 4-(3-benzyl-[1,2,4]triazolo[4,3-a]pyridin-7-yl)-N-(tetrahydro-2H-pyran-4-yl)pyrimidin-2-amine | 387.1 (1.24 min) |
| 149 | 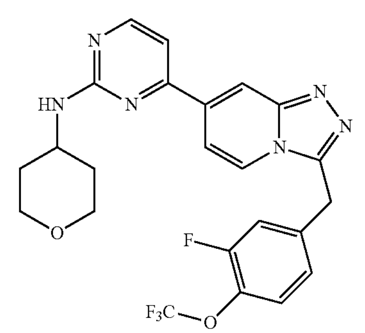 [SMILES: Fc1cc(Cc2nnc3cc(-c4ccnc(NC5CCOCC5)n4)ccn23)ccc1OC(F)(F)F] | 4-(3-(3-fluoro-4-(trifluoromethoxy)benzyl)-[1,2,4]triazolo[4,3-a]pyridin-7-yl)-N-(tetrahydro-2H-pyran-4-yl)pyrimidin-2-amine | 489.2 (1.67 min) |

TABLE 2-continued

| Ex. # | Structure | Name | MS (ACPI+) M + 1 (retention time) |
|---|---|---|---|
| 150 | 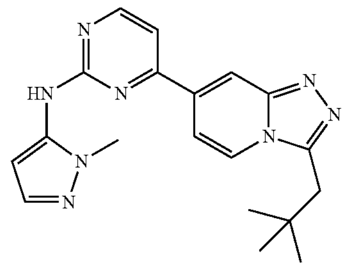 [SMILES: Cn1nccc1Nc1nccc(-c2ccn3c(CC(C)(C)C)nnc3c2)n1] | N-(1-methyl-1H-pyrazol-5-yl)-4-(3-neopentyl-[1,2,4]triazolo[4,3-a]pyridin-7-yl)pyrimidin-2-amine | 363.2 (1.22 min) |
| 151 | 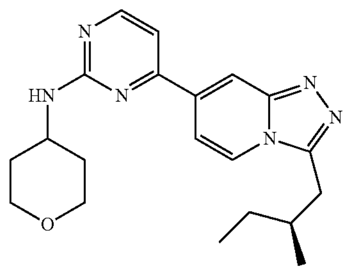 [SMILES: CC[C@H](C)Cc1nnc2cc(-c3ccnc(NC4CCOCC4)n3)ccn12] | (S)-4-(3-(2-methylbutyl)-[1,2,4]triazolo[4,3-a]pyridin-7-yl)-N-(tetrahydro-2H-pyran-4-yl)pyrimidin-2-amine | 367.2 (1.34 min) |
| 152 | 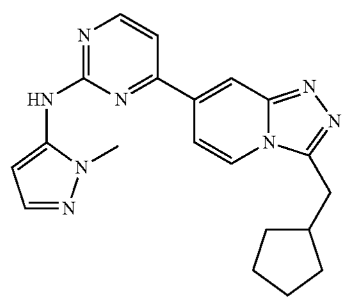 [SMILES: Cn1nccc1Nc1nccc(-c2ccn3c(CC4CCCC4)nnc3c2)n1] | 4-(3-(cyclopentylmethyl)-[1,2,4]triazolo[4,3-a]pyridin-7-yl)-N-(1-methyl-1H-pyrazol-5-yl)pyrimidin-2-amine | 375.2 (1.26 min) |
| 153 | 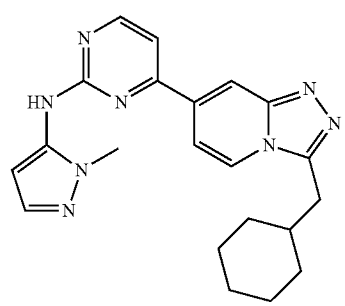 | 4-(3-(cyclohexylmethyl)-[1,2,4]triazolo[4,3-a]pyridin-7-yl)-N-(1-methyl-1H-pyrazol-5-yl)pyrimidin-2-amine | 389.2 (1.34 min) |
| 154 | 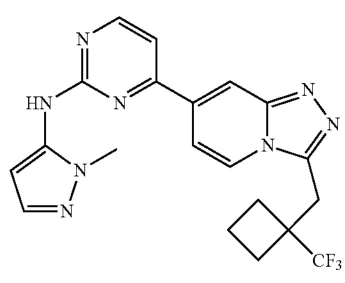 [SMILES: Cn1nccc1Nc1nccc(-c2ccn3c(CC4(C(F)(F)F)CCC4)nnc3c2)n1] | N-(1-methyl-1H-pyrazol-5-yl)-4-(3-((1-(trifluoromethyl)cyclobutyl)methyl-[1,2,4]triazolo[4,3-a]pyridin-7-yl)pyrimidin-2-amine | 429.2 (1.38 min) |

TABLE 2-continued

| Ex. # | Structure | Name | MS (ACPI+) M + 1 (retention time) |
|---|---|---|---|
| 155 | 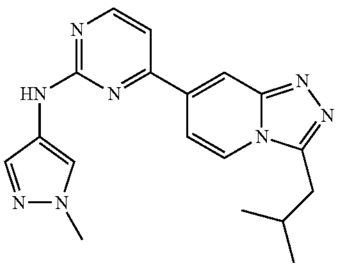 [SMILES: CC(C)Cc1nnc2cc(-c3ccnc(Nc4cnn(C)c4)n3)ccn12] | 4-(3-isobutyl-[1,2,4]triazolo[4,3-a]pyridin-7-yl)-N-(1-methyl-1H-pyrazol-4-yl)pyrimidin-2-amine | 349.2 (1.17 min) |
| 156 | 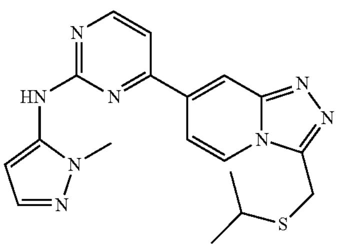 | 4-(3-((isopropylthio)methyl)-[1,2,4]triazolo[4,3-a]pyridin-7-yl)-N-(1-methyl-1H-pyrazol-5-yl)pyrimidin-2-amine | 381.1 (1.26 min) |
| 157 | 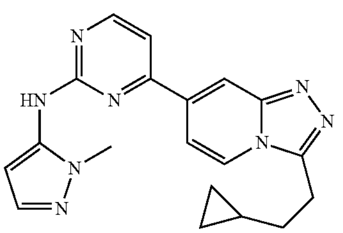 [SMILES: Cn1nccc1Nc1nccc(-c2ccn3c(CCC4CC4)nnc3c2)n1] | 4-(3-(2-cyclopropylethyl)-[1,2,4]triazolo[4,3-a]pyridin-7-yl)-N-(1-methyl-1H-pyrazol-5-yl)pyrimidin-2-amine | 361.1 (1.22 min) |
| 158 | 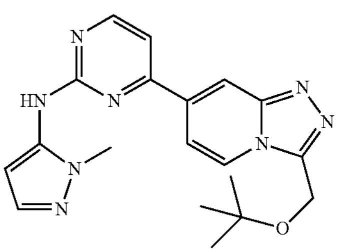 [SMILES: Cn1nccc1Nc1nccc(-c2ccn3c(COC(C)(C)C)nnc3c2)n1] | 4-(3-(tert-butoxymethyl)-[1,2,4]triazolo[4,3-a]pyridin-7-yl)-N-(1-methyl-1H-pyrazol-5-yl)pyrimidin-2-amine | 379.2 (1.20 min) |
| 159 | 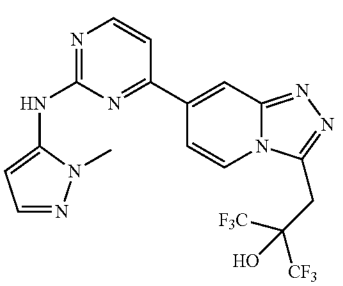 [SMILES: Cn1nccc1Nc1nccc(-c2ccn3c(CC(O)(C(F)(F)F)C(F)(F)F)nnc3c2)n1] | 1,1,1,3,3,3-hexafluoro-2-((7-(2-((1-methyl-1H-pyrazol-5-yl)amino)pyrimidin-4-yl)-[1,2,4]triazolo[4,3-a]pyridin-3-yl)methyl)propan-2-ol | 473.1 (1.23 min) |

TABLE 2-continued

| Ex. # | Structure | Name | MS (ACPI+) M + 1 (retention time) |
|---|---|---|---|
| 160 | 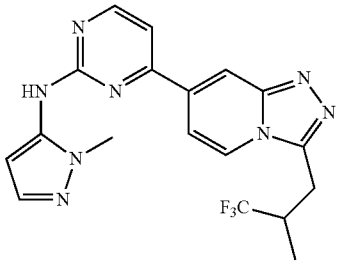 [SMILES: CC(Cc1nnc2cc(-c3ccnc(Nc4ccnn4C)n3)ccn12)C(F)(F)F] | N-(1-methyl-1H-pyrazol-5-yl)-4-(3-(3,3,3-trifluoro-2-methylpropyl)-[1,2,4]triazolo[4,3-a]pyridin-7-yl)pyrimidin-2-amine | 403.1 (1.25 min) |
| 161 | 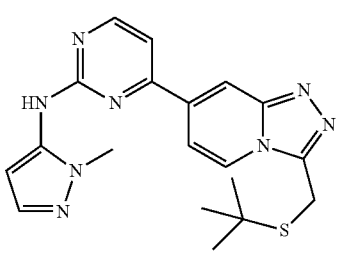 | 4-(3-((tert-butylthio)methyl)-[1,2,4]triazolo[4,3-a]pyridin-7-yl)-N-(1-methyl-1H-pyrazol-5-yl)pyrimidin-2-amine | 395.2 (1.34 min) |
| 162 | 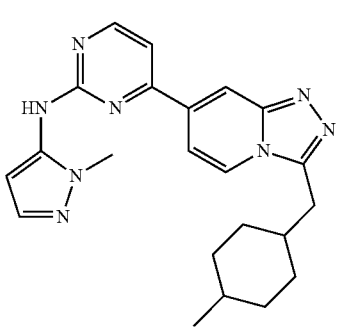 [SMILES: CC1CCC(Cc2nnc3cc(-c4ccnc(Nc5ccnn5C)n4)ccn23)CC1] | N-(1-methyl-1H-pyrazol-5-yl)-4-(3-((4-methylcyclohexyl)methyl)-[1,2,4]triazolo[4,3-a]pyridin-7-yl)pyrimidin-2-amine | 403.2 (1.49 min) |
| 163 | 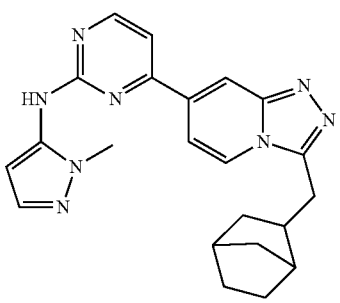 [SMILES: Cn1nccc1Nc1nccc(-c2ccn3c(CC4CC5CCC4C5)nnc3c2)n1] | 4-(3-(bicyclo[2.2.1]heptan-2-ylmethyl)-[1,2,4]triazolo[4,3-a]pyridin-7-yl)-N-(1-methyl-1H-pyrazol-5-yl)pyrimidin-2-amine | 401.2 (1.38 min) |
| 164 | 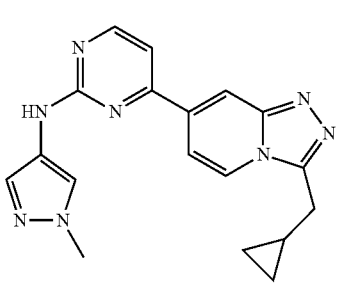 [SMILES: Cn1cc(Nc2nccc(-c3ccn4c(CC5CC5)nnc4c3)n2)cn1] | 4-(3-(cyclopropylmethyl)-[1,2,4]triazolo[4,3-a]pyridin-7-yl)-N-(1-methyl-1H-pyrazol-4-yl)pyrimidin-2-amine | 347.1 (1.09 min) |

TABLE 2-continued

| Ex. # | Structure | Name | MS (ACPI+) M + 1 (retention time) |
|---|---|---|---|
| 165 | 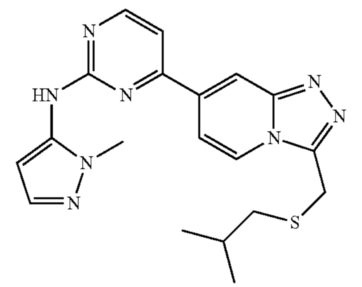 | 4-(3-((isobutylthio)methyl)-[1,2,4]triazolo[4,3-a]pyridin-7-yl)-N-(1-methyl-1H-pyrazol-5-yl)pyrimidin-2-amine | 395.1 (1.38 min) |
| 166 | 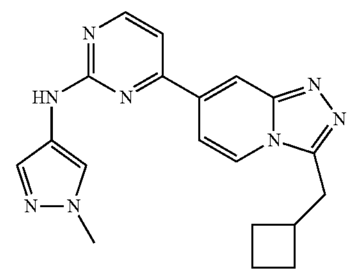 [SMILES: Cn1cc(Nc2nccc(-c3ccn4c(CC5CCC5)nnc4c3)n2)cn1] | 4-(3-(cyclobutylmethyl)-[1,2,4]triazolo[4,3-a]pyridin-7-yl)-N-(1-methyl-1H-pyrazol-4-yl)pyrimidin-2-amine | 361.2 (1.19 min) |
| 167 | 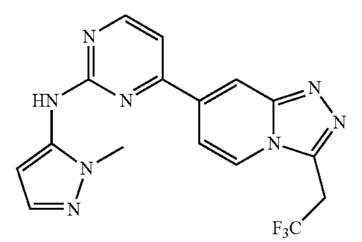 [SMILES: Cn1nccc1Nc1nccc(-c2ccn3c(CC(F)(F)F)nnc3c2)n1] | N-(1-methyl-1H-pyrazol-5-yl)-4-(3-(2,2,2-trifluoroethyl)-[1,2,4]triazolo[4,3-a]pyridin-7-yl)pyrimidin-2-amine | 375.1 (1.08 min) |
| 168 | 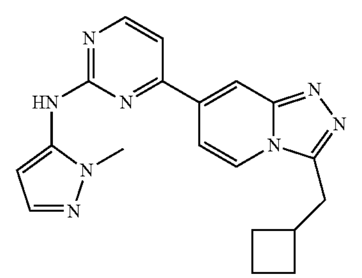 [SMILES: Cn1nccc1Nc1nccc(-c2ccn3c(CC4CCC4)nnc3c2)n1] | 4-(3-(cyclobutylmethyl)-[1,2,4]triazolo[4,3-a]pyridin-7-yl)-N-(1-methyl-1H-pyrazol-5-yl)pyrimidin-2-amine | 361.2 (0.99 min) |
| 169 | 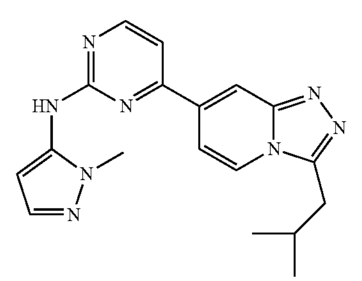 [SMILES: CC(C)Cc1nnc2cc(-c3ccnc(Nc4ccnn4C)n3)ccn12] | 4-(3-isobutyl-[1,2,4]triazolo[4,3-a]pyridin-7-yl)-N-(1-methyl-1H-pyrazol-5-yl)pyrimidin-2-amine | 349.2 (1.13 min) |

TABLE 2-continued

| Ex. # | Structure | Name | MS (ACPI+) M + 1 (retention time) |
|---|---|---|---|
| 170 | 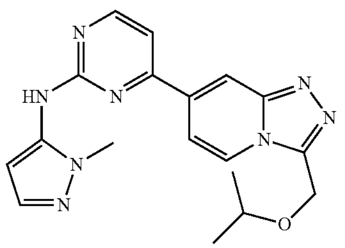 [SMILES: CC(C)OCc1nnc2cc(-c3ccnc(Nc4ccnn4C)n3)ccn12] | 4-(3-(isopropoxymethyl)-[1,2,4]triazolo[4,3-a]pyridin-7-yl)-N-(1-methyl-1H-pyrazol-5-yl)pyrimidin-2-amine | 365.2 (1.12 min) |
| 171 | 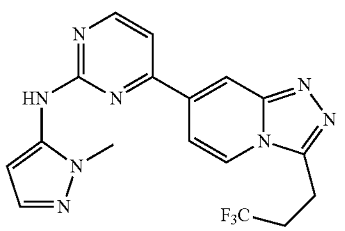 [SMILES: Cn1nccc1Nc1nccc(-c2ccn3c(CCC(F)(F)F)nnc3c2)n1] | N-(1-methyl-1H-pyrazol-5-yl)-4-(3-(3,3,3-trifluoropropyl)-[1,2,4]triazolo[4,3-a]pyridin-7-yl)pyrimidin-2-amine | 389.1 (1.17 min) |
| 172 | 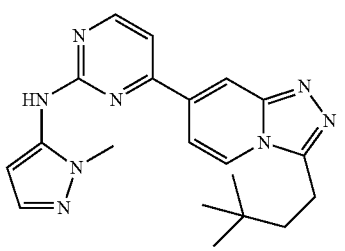 [SMILES: Cn1nccc1Nc1nccc(-c2ccn3c(CCC(C)(C)C)nnc3c2)n1] | 4-(3-(3,3-dimethylbutyl)-[1,2,4]triazolo[4,3-a]pyridin-7-yl)-N-(1-methyl-1H-pyrazol-5-yl)pyrimidin-2-amine | 377.2 (1.37 min) |
| 173 | 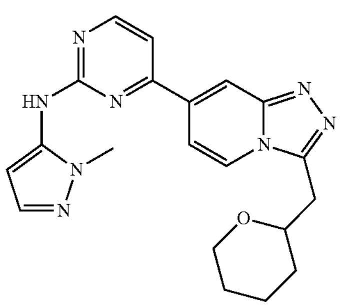 [SMILES: Cn1nccc1Nc1nccc(-c2ccn3c(CC4CCCCO4)nnc3c2)n1] | N-(1-methyl-1H-pyrazol-5-yl)-4-(3-((tetrahydro-2H-pyran-2-yl)methyl)-[1,2,4]triazolo[4,3-a]pyridin-7-yl)pyrimidin-2-amine | 391.2 (1.13 min) |
| 174 | 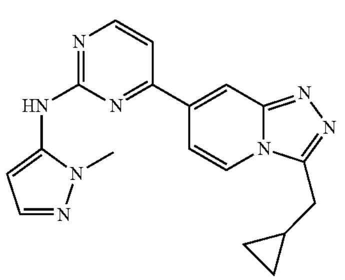 [SMILES: Cn1nccc1Nc1nccc(-c2ccn3c(CC4CC4)nnc3c2)n1] | 4-(3-(cyclopropylmethyl)-[1,2,4]triazolo[4,3-a]pyridin-7-yl)-N-(1-methyl-1H-pyrazol-5-yl)pyrimidin-2-amine | 347.2 (1.06 min) |

TABLE 2-continued

| Ex. # | Structure | Name | MS (ACPI+) M + 1 (retention time) |
|---|---|---|---|
| 175 | 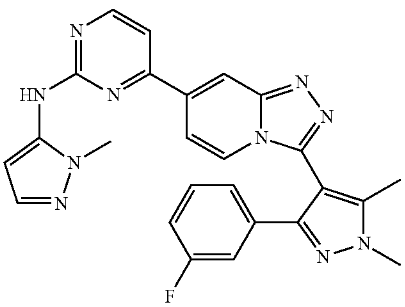 [SMILES: Cc1c(-c2nnc3cc(-c4ccnc(Nc5ccnn5C)n4)ccn23)c(-c2cccc(F)c2)nn1C] | 4-(3-(3-(3-fluorophenyl)-1,5-dimethyl-1H-pyrazol-4-yl)-[1,2,4]triazolo[4,3-a]pyridin-7-yl)-N-(1-methyl-1H-pyrazol-5-yl)pyrimidin-2-amine | 481.2 (1.31 min) |
| 176 | 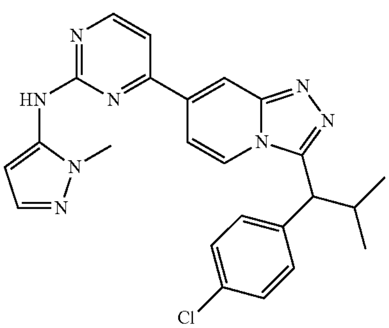 [SMILES: CC(C)C(c1ccc(Cl)cc1)c1nnc2cc(-c3ccnc(Nc4ccnn4C)n3)ccn12] | 4-(3-(1-(4-chlorophenyl)-2-methylpropyl)-[1,2,4]triazolo[4,3-a]pyridin-7-yl)-N-(1-methyl-1H-pyrazol-5-yl)pyrimidin-2-amine | 459.2 (1.54 min) |
| 177 | 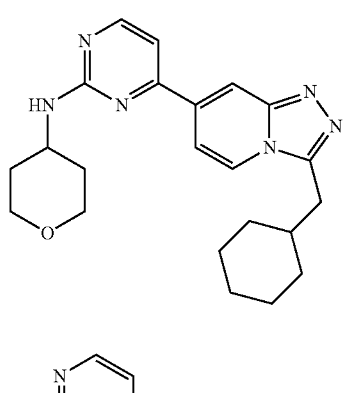 | 4-(3-(cyclohexylmethyl)-[1,2,4]triazolo[4,3-a]pyridin-7-yl)-N-(tetrahydro-2H-pyran-4-yl)pyrimidin-2-amine | 393.2 (1.38 min) |
| 178 | 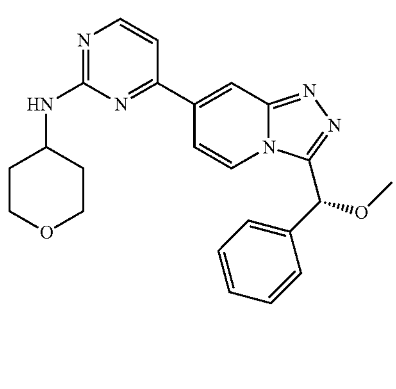 [SMILES: CO[C@H](c1ccccc1)c1nnc2cc(-c3ccnc(NC4CCOCC4)n3)ccn12] | (R)-4-(3-(methoxy(phenyl)methyl)-[1,2,4]triazolo[4,3-a]pyridin-7-yl)-N-(tetrahydro-2H-pyran-4-yl)pyrimidin-2-amine | 417.2 (1.31 min) |

TABLE 2-continued

| Ex. # | Structure | Name | MS (ACPI+) M + 1 (retention time) |
|---|---|---|---|
| 179 | 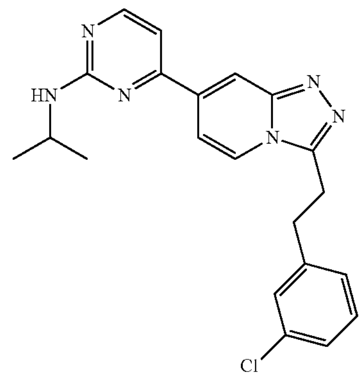 [SMILES: CC(C)Nc1nccc(-c2ccn3c(CCc4cccc(Cl)c4)nnc3c2)n1] | 4-(3-(3-chlorophenethyl)-[1,2,4]triazolo[4,3-a]pyridin-7-yl)-N-isopropylpyrimidin-2-amine | 393.1 (1.54 min) |
| 180 | 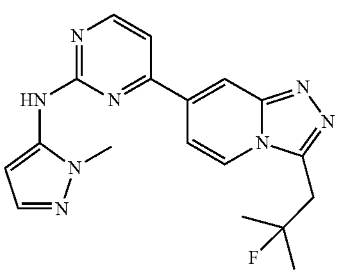 [SMILES: Cn1nccc1Nc1nccc(-c2ccn3c(CC(C)(C)F)nnc3c2)n1] | 4-(3-(2-fluoro-2-methylpropyl)-[1,2,4]triazolo[4,3-a]pyridin-7-yl)-N-(1-methyl-1H-pyrazol-5-yl)pyrimidin-2-amine | 367.2 (1.18 min) |
| 181 | 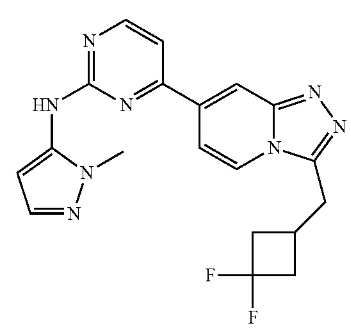 [SMILES: Cn1nccc1Nc1nccc(-c2ccn3c(CC4CC(F)(F)C4)nnc3c2)n1] | 4-(3-((3,3-difluorocyclobutyl)methyl)-[1,2,4]triazolo[4,3-a]pyridin-7-yl)-N-(1-methyl-1H-pyrazol-5-yl)pyrimidin-2-amine | 397.1 (1.22 min) |
| 182 | 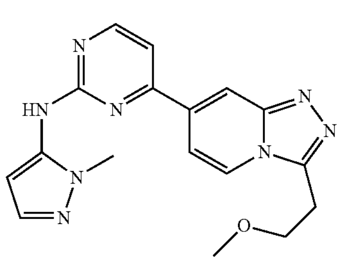 [SMILES: COCCc1nnc2cc(-c3ccnc(Nc4ccnn4C)n3)ccn12] | 4-(3-(2-methoxyethyl)-[1,2,4]triazolo[4,3-a]pyridin-7-yl)-N-(1-methyl-1H-pyrazol-5-yl)pyrimidin-2-amine | 351.2 (0.95 min) |

TABLE 2-continued

| Ex. # | Structure | Name | MS (ACPI+) M + 1 (retention time) |
|---|---|---|---|
| 183 | 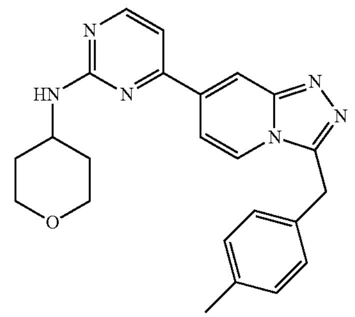 [SMILES: Cc1ccc(Cc2nnc3cc(-c4ccnc(NC5CCOCC5)n4)ccn23)cc1] | 4-(3-(4-methylbenzyl)-[1,2,4]triazolo[4,3-a]pyridin-7-yl)-N-(tetrahydro-2H-pyran-4-yl)pyrimidin-2-amine | 401.2 (1.56 min) |
| 184 | 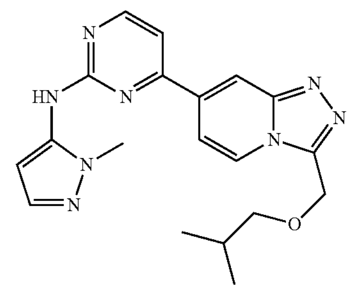 [SMILES: CC(C)COCc1nnc2cc(-c3ccnc(Nc4ccnn4C)n3)ccn12] | 4-(3-(isobutoxymethyl)-[1,2,4]triazolo[4,3-a]pyridin-7-yl)-N-(1-methyl-1H-pyrazol-5-yl)pyrimidin-2-amine | 379.2 (1.27 min) |
| 185 | 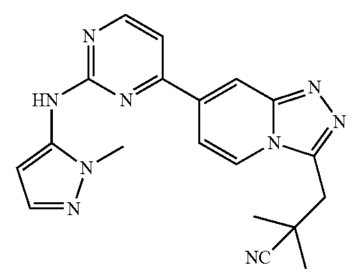 [SMILES: Cn1nccc1Nc1nccc(-c2ccn3c(CC(C)(C)C#N)nnc3c2)n1] | 2,2-dimethyl-3-(7-(2-((1-methyl-1H-pyrazol-5-yl)amino)pyrimidin-4-yl)-[1,2,4]triazolo[4,3-a]pyridin-3-yl)propanenitrile | 374.1 (1.04 min) |
| 186 | 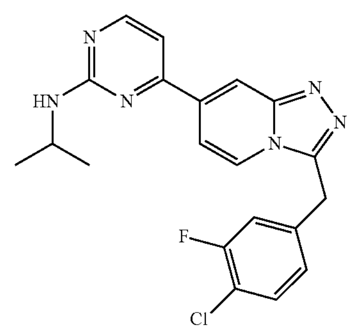 [SMILES: CC(C)Nc1nccc(-c2ccn3c(Cc4ccc(Cl)c(F)c4)nnc3c2)n1] | 4-(3-(4-chloro-3-fluorobenzyl)-[1,2,4]triazolo[4,3-a]pyridin-7-yl)-N-isopropylpyrimidin-2-amine | 397.1 (1.50 min) |
| 187 | 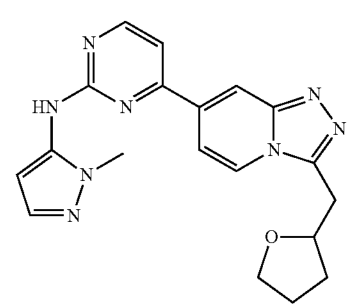 [SMILES: Cn1nccc1Nc1nccc(-c2ccn3c(CC4CCCO4)nnc3c2)n1] | N-(1-methyl-1H-pyrazol-5-yl)-4-(3-((tetrahydrofuran-2-yl)methyl)-[1,2,4]triazolo[4,3-a]pyridin-7-yl)pyrimidin-2-amine | 377.2 (1.02 min) |

TABLE 2-continued

| Ex. # | Structure | Name | MS (ACPI+) M + 1 (retention time) |
|---|---|---|---|
| 188 | 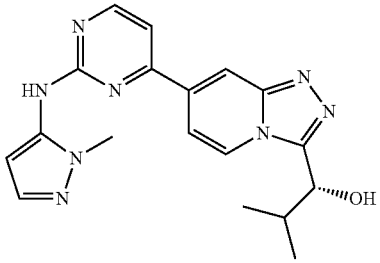 [SMILES: CC(C)[C@@H](O)c1nnc2cc(-c3ccnc(Nc4ccnn4C)n3)ccn12] | (R)-2-methyl-1-(7-(2-((1-methyl-1H-pyrazol-5-yl)amino)pyrimidin-4-yl)-[1,2,4]triazolo[4,3-a]pyridin-3-yl)propan-1-ol | 365.1 (0.87 min) |
| 189 | 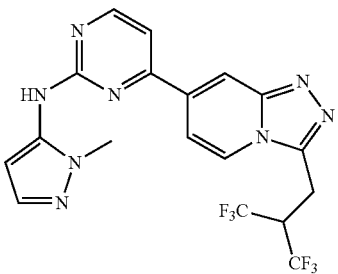 [SMILES: Cn1nccc1Nc1nccc(-c2ccn3c(CC(C(F)(F)F)C(F)(F)F)nnc3c2)n1] | N-(1-methyl-1H-pyrazol-5-yl)-4-(3-(3,3,3-trifluoro-2-(trifluoromethyl)propyl)-[1,2,4]triazolo[4,3-a]pyridin-7-yl)pyrimidin-2-amine | 457.1 (1.35 min) |
| 190 | 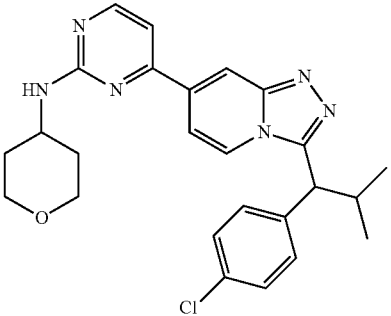 [SMILES: CC(C)C(c1ccc(Cl)cc1)c1nnc2cc(-c3ccnc(NC4CCOCC4)n3)ccn12] | 4-(3-(1-(4-chlorophenyl)-2-methylpropyl)-[1,2,4]triazolo[4,3-a]pyridin-7-yl)-N-(tetrahydro-2H-pyran-4-yl)pyrimidin-2-amine | 463.2 (1.70 min) |
| 191 | 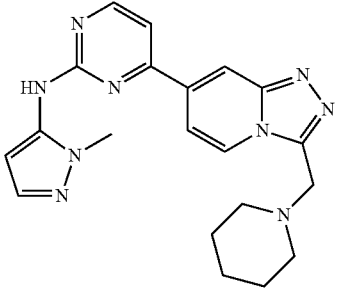 [SMILES: Cn1nccc1Nc1nccc(-c2ccn3c(CN4CCCCC4)nnc3c2)n1] | N-(1-methyl-1H-pyrazol-5-yl)-4-(3-(piperidin-1-ylmethyl)-[1,2,4]triazolo[4,3-a]pyridin-7-yl)pyrimidin-2-amine | 390.2 (0.89 min) |
| 192 | 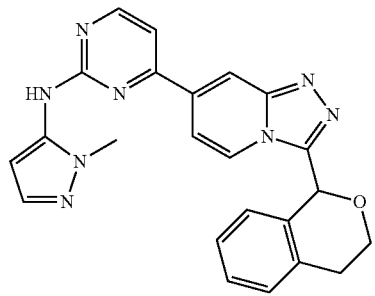 [SMILES: Cn1nccc1Nc1nccc(-c2ccn3c(C4OCCc5ccccc54)nnc3c2)n1] | 4-(3-(isochroman-1-yl)-[1,2,4]triazolo[4,3-a]pyridin-7-yl)-N-(1-methyl-1H-pyrazol-5-yl)pyrimidin-2-amine | 425.2 (1.27 min) |

TABLE 2-continued

| Ex. # | Structure | Name | MS (ACPI+) M + 1 (retention time) |
|---|---|---|---|
| 193 | 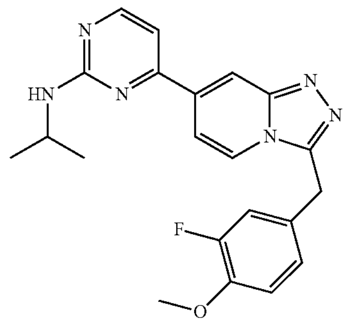 [SMILES: COc1ccc(Cc2nnc3cc(-c4ccnc(NC(C)C)n4)ccn23)cc1F] | 4-(3-(3-fluoro-4-methoxybenzyl)-[1,2,4]triazolo[4,3-a]pyridin-7-yl)-N-isopropylpyrimidin-2-amine | 393.2 (1.33 min) |
| 194 | 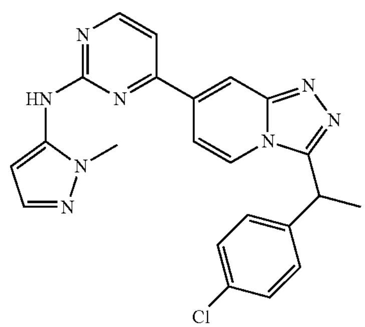 [SMILES: CC(c1ccc(Cl)cc1)c1nnc2cc(-c3ccnc(Nc4ccnn4C)n3)ccn12] | 4-(3-(1-(4-chlorophenyl)ethyl)-[1,2,4]triazolo[4,3-a]pyridin-7-yl)-N-(1-methyl-1H-pyrazol-5-yl)pyrimidin-2-amine | 417 (1.38 min) |
| 195 | 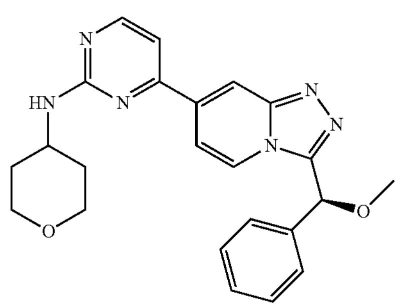 [SMILES: CO[C@@H](c1ccccc1)c1nnc2cc(-c3ccnc(NC4CCOCC4)n3)ccn12] | (S)-4-(3-(methoxy(phenyl)methyl)-[1,2,4]triazolo[4,3-a]pyridin-7-yl)-N-(tetrahydro-2H-pyran-4-yl)pyrimidin-2-amine | 417.2 (1.32 min) |
| 196 | 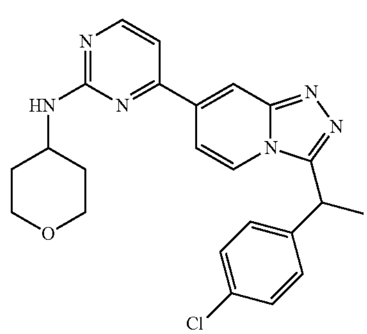 [SMILES: CC(c1ccc(Cl)cc1)c1nnc2cc(-c3ccnc(NC4CCOCC4)n3)ccn12] | 4-(3-(1-(4-chlorophenyl)ethyl)-[1,2,4]triazolo[4,3-a]pyridin-7-yl)-N-(tetrahydro-2H-pyran-4-yl)pyrimidin-2-amine | 435.1 (1.48 min) |

TABLE 2-continued

| Ex. # | Structure | Name | MS (ACPI+) M + 1 (retention time) |
|---|---|---|---|
| 197 | 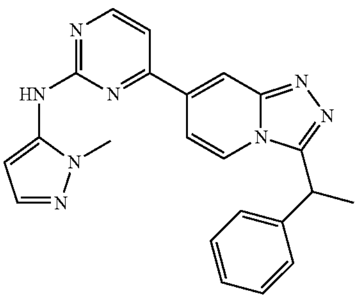 [SMILES: CC(c1ccccc1)c1nnc2cc(-c3ccnc(Nc4ccnn4C)n3)ccn12] | N-(1-methyl-1H-pyrazol-5-yl)-4-(3-(1-phenylethyl)-[1,2,4]triazolo[4,3-a]pyridin-7-yl)pyrimidin-2-amine | 397.2 (1.25 min) |
| 198 | 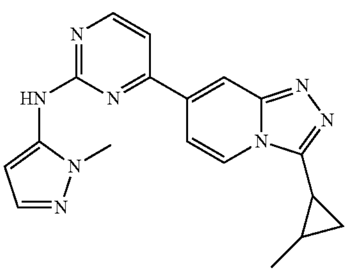 [SMILES: CC1CC1c1nnc2cc(-c3ccnc(Nc4ccnn4C)n3)ccn12] | N-(1-methyl-1H-pyrazol-5-yl)-4-(3-(2-methylcyclopropyl)-[1,2,4]triazolo[4,3-a]pyridin-7-yl)pyrimidin-2-amine | 347.2 (1.09 min) |
| 199 | 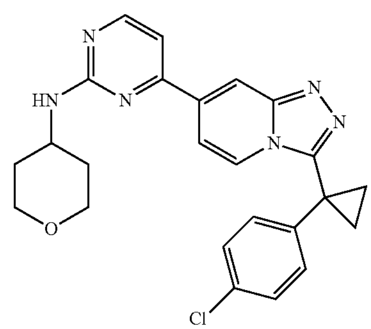 [SMILES: Clc1ccc(C2(c3nnc4cc(-c5ccnc(NC6CCOCC6)n5)ccn34)CC2)cc1] | 4-(3-(1-(4-chlorophenyl)cyclopropyl)-[1,2,4]triazolo[4,3-a]pyridin-7-yl)-N-(tetrahydro-2H-pyran-4-yl)pyrimidin-2-amine | 447.1 (1.51 min) |
| 200 | 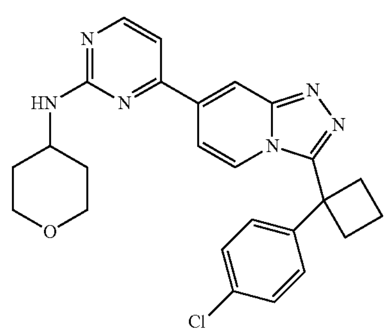 [SMILES: Clc1ccc(C2(c3nnc4cc(-c5ccnc(NC6CCOCC6)n5)ccn34)CCC2)cc1] | 4-(3-(1-(4-chlorophenyl)cyclobutyl)-[1,2,4]triazolo[4,3-a]pyridin-7-yl)-N-(tetrahydro-2H-pyran-4-yl)pyrimidin-2-amine | 461.2 (1.65 min) |

TABLE 2-continued

| Ex. # | Structure | Name | MS (ACPI+) M + 1 (retention time) |
|---|---|---|---|
| 201 | 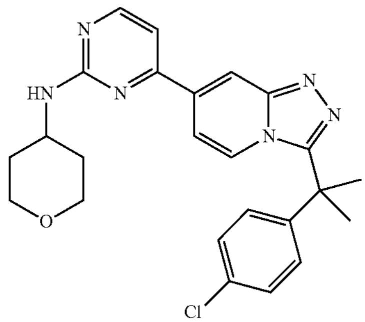 [SMILES: CC(C)(c1ccc(Cl)cc1)c1nnc2cc(-c3ccnc(NC4CCOCC4)n3)ccn12] | 4-(3-(2-(4-chlorophenyl)propan-2-yl)-[1,2,4]triazolo[4,3-a]pyridin-7-yl)-N-(tetrahydro-2H-pyran-4-yl)pyrimidin-2-amine | 449.2 (1.60 min) |
| 202 | 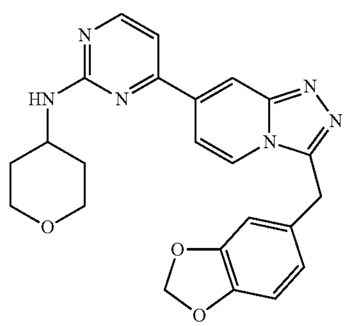 [SMILES: c1cc(-c2ccn3c(Cc4ccc5c(c4)OCO5)nnc3c2)nc(NC2CCOCC2)n1] | 4-(3-(benzo[d][1.3]dioxol-5-ylmethyl)-[1,2,4]triazolo[4,3-a]pyridin-7-yl)-N-(tetrahydro-2H-pyran-4-yl)pyrimidin-2-amine | 431.2 (1.40 min) |
| 203 | 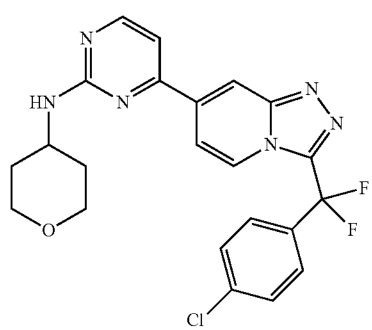 [SMILES: FC(F)(c1ccc(Cl)cc1)c1nnc2cc(-c3ccnc(NC4CCOCC4)n3)ccn12] | 4-(3-((4-chlorophenyl)difluoromethyl)-[1,2,4]triazolo[4,3-a]pyridin-7-yl)-N-(tetrahydro-2H-pyran-4-yl)pyrimidin-2-amine | 457.1 (1.78 min) |
| 204 | 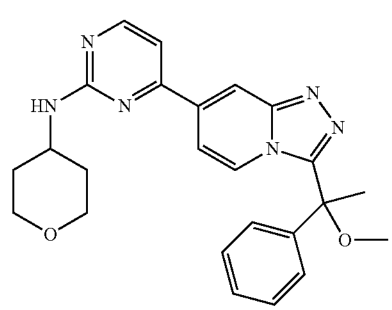 [SMILES: COC(C)(c1ccccc1)c1nnc2cc(-c3ccnc(NC4CCOCC4)n3)ccn12] | 4-(3-(1-methoxy-1-phenylethyl)-[1,2,4]triazolo[4,3-a]pyridin-7-yl)-N-(tetrahydro-2H-pyran-4-yl)pyrimidin-2-amine | 431.2 (1.63 min) |

TABLE 2-continued

| Ex. # | Structure | Name | MS (ACPI+) M + 1 (retention time) |
|---|---|---|---|
| 205 | 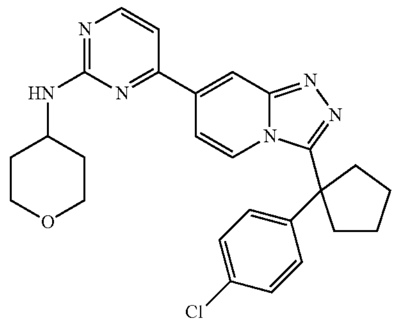 [SMILES: Clc1ccc(C2(c3nnc4cc(-c5ccnc(NC6CCOCC6)n5)ccn34)CCCC2)cc1] | 4-(3-(1-(4-chlorophenyl)cyclopentyl)-[1,2,4]triazolo[4,3-a]pyridin-7-yl)-N-(tetrahydro-2H-pyran-4-yl)pyrimidin-2-amine | 475.2 (1.80 min) |
| 206 | 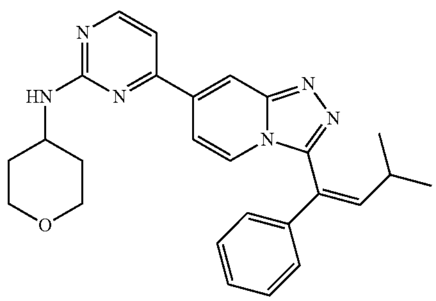 [SMILES: CC(C)/C=C(/c1ccccc1)c1nnc2cc(-c3ccnc(NC4CCOCC4)n3)ccn12] | (Z)-4-(3-(3-methyl-1-phenylbut-1-en-1-yl)-[1,2,4]triazolo[4,3-a]pyridin-7-yl)-N-(tetrahydro-2H-pyran-4-yl)pyrimidin-2-amine | 441.2 (1.80 min) |
| 207 | 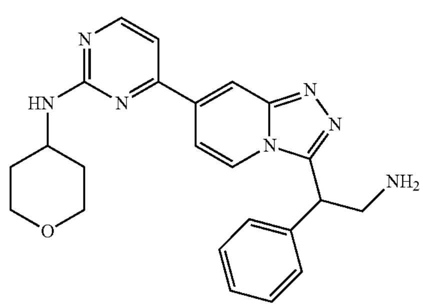 [SMILES: NCC(c1ccccc1)c1nnc2cc(-c3ccnc(NC4CCOCC4)n3)ccn12] | 4-(3-(2-amino-1-phenylethyl)-[1,2,4]triazolo[4,3-a]pyridin-7-yl)-N-(tetrahydro-2H-pyran-4-yl)pyrimidin-2-amine | 416.2 (0.92 min) |
| 208 | 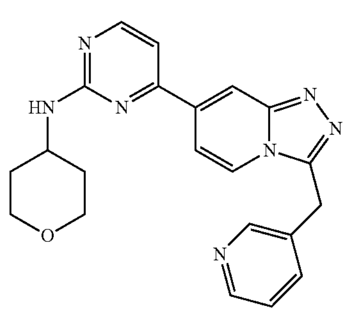 [SMILES: c1cncc(Cc2nnc3cc(-c4ccnc(NC5CCOCC5)n4)ccn23)c1] | 4-(3-(pyridin-3-ylmethyl)-[1,2,4]triazolo[4,3-a]pyridin-7-yl)-N-(tetrahydro-2H-pyran-4-yl)pyrimidin-2-amine | 388.1 (0.71 min) |

TABLE 2-continued

| Ex. # | Structure | Name | MS (ACPI+) M + 1 (retention time) |
|---|---|---|---|
| 209 | 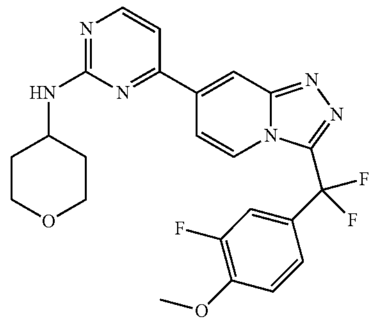 [SMILES: COc1ccc(C(F)(F)c2nnc3cc(-c4ccnc(NC5CCOCC5)n4)ccn23)cc1F] | 4-(3-(difluoro(3-fluoro-4-methoxyphenyl)methyl)-[1,2,4]triazolo[4,3-a]pyridin-7-yl)-N-(tetrahydro-2H-pyran-4-yl)pyrimidin-2-amine | 471.1 (1.49 min) |
| 210 | 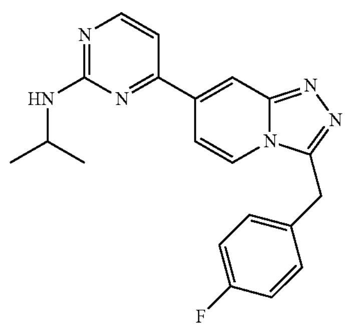 [SMILES: CC(C)Nc1nccc(-c2ccn3c(Cc4ccc(F)cc4)nnc3c2)n1] | 4-(3-(4-fluorobenzyl)-[1,2,4]triazolo[4,3-a]pyridin-7-yl)-N-isopropylpyrimidin-2-amine | 363.2 (1.35 min) |
| 211 | 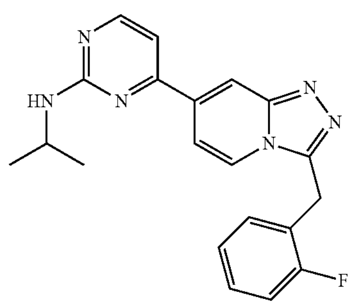 [SMILES: CC(C)Nc1nccc(-c2ccn3c(Cc4ccccc4F)nnc3c2)n1] | 4-(3-(2-fluorobenzyl)-[1,2,4]triazolo[4,3-a]pyridin-7-yl)-N-isopropylpyrimidin-2-amine | 349.1 (1.34 min) |
| 212 | 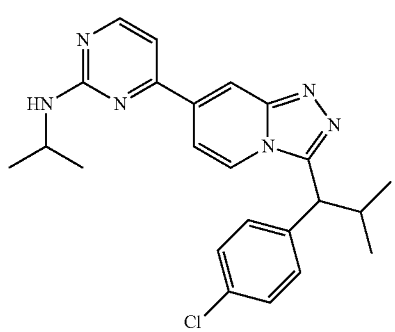 [SMILES: CC(C)Nc1nccc(-c2ccn3c(C(c4ccc(Cl)cc4)C(C)C)nnc3c2)n1] | 4-(3-(1-(4-chlorophenyl)-2-methylpropyl)-[1,2,4]triazolo[4,3-a]pyridin-7-yl)-N-isopropylpyrimidin-2-amine | 421.2 (1.73 min) |

TABLE 2-continued

| Ex. # | Structure | Name | MS (ACPI+) M + 1 (retention time) |
|---|---|---|---|
| 213 | 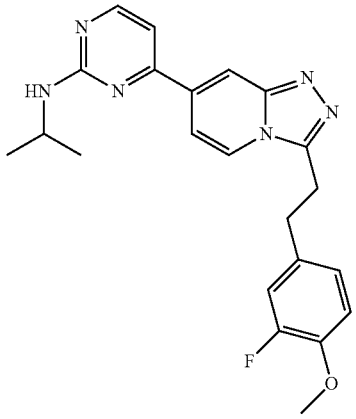 [SMILES: COc1ccc(CCc2nnc3cc(-c4ccnc(NC(C)C)n4)ccn23)cc1F] | 4-(3-(3-fluoro-4-methoxyphenethyl)-[1,2,4]triazolo[4,3-a]pyridin-7-yl)-N-isopropylpyrimidin-2-amine | 407.2 (1.38 min) |
| 214 | 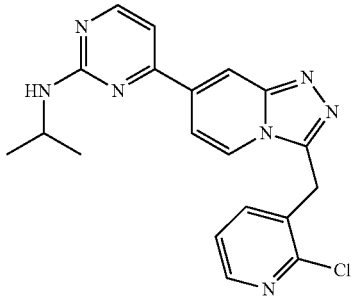 [SMILES: CC(C)Nc1nccc(-c2ccn3c(Cc4cccnc4Cl)nnc3c2)n1] | 4-(3-((2-chloropyridin-3-yl)methyl)-[1,2,4]triazolo[4,3-a]pyridin-7-yl)-N-isopropylpyrimidin-2-amine | 380.1 (1.16 min) |
| 215 | 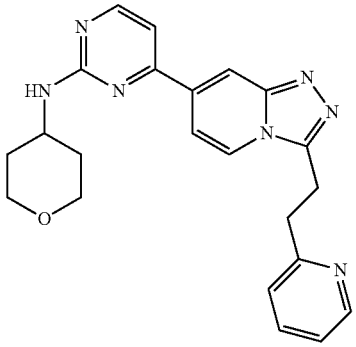 [SMILES: c1ccc(CCc2nnc3cc(-c4ccnc(NC5CCOCC5)n4)ccn23)nc1] | 4-(3-(2-(pyridin-2-yl)ethyl)-[1,2,4]triazolo[4,3-a]pyridin-7-yl)-N-(tetrahydro-2H-pyran-4-yl)pyrimidin-2-amine | 402.2 (0.80 min) |
| 216 | 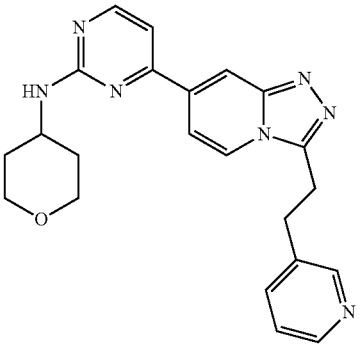 [SMILES: c1cncc(CCc2nnc3cc(-c4ccnc(NC5CCOCC5)n4)ccn23)c1] | 4-(3-(2-(pyridin-3-yl)ethyl)-[1,2,4]triazolo[4,3-a]pyridin-7-yl)-N-(tetrahydro-2H-pyran-4-yl)pyrimidin-2-amine | 402.2 (0.77 min) |

TABLE 2-continued

| Ex. # | Structure | Name | MS (ACPI+) M + 1 (retention time) |
|---|---|---|---|
| 217 | 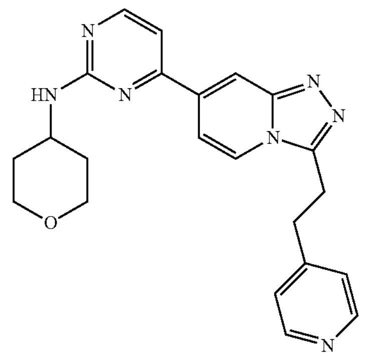 [SMILES: c1cc(CCc2nnc3cc(-c4ccnc(NC5CCOCC5)n4)ccn23)ccn1] | 4-(3-(2-(pyridin-4-yl)ethyl)-[1,2,4]triazolo[4,3-a]pyridin-7-yl)-N-(tetrahydro-2H-pyran-4-yl)pyrimidin-2-amine | 402.2 (0.76 min) |
| 218 | 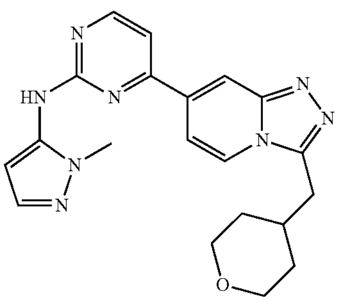 [SMILES: Cn1nccc1Nc1nccc(-c2ccn3c(CC4CCOCC4)nnc3c2)n1] | N-(1-methyl-1H-pyrazol-5-yl)-4-(3-((tetrahydro-2H-pyran-4-yl)methyl)-[1,2,4]triazolo[4,3-a]pyridin-7-yl)pyrimidin-2-amine | 391.2 (1.00 min) |
| 219 | 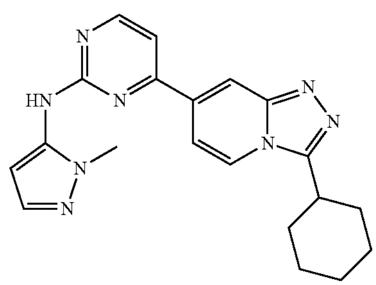 [SMILES: Cn1nccc1Nc1nccc(-c2ccn3c(C4CCCCC4)nnc3c2)n1] | 4-(3-cyclohexyl-[1,2,4]triazolo[4,3-a]pyridin-7-yl)-N-(1-methyl-1H-pyrazol-5-yl)pyrimidin-2-amine | 375.2 (1.25 min) |
| 220 | 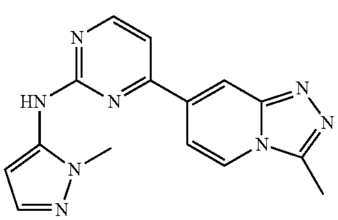 [SMILES: Cc1nnc2cc(-c3ccnc(Nc4ccnn4C)n3)ccn12] | N-(1-methyl-1H-pyrazol-5-yl)-4-(3-methyl-[1,2,4]triazolo[4,3-a]pyridin-7-yl)pyrimidin-2-amine | 307.0 (0.86 min) |
| 221 | 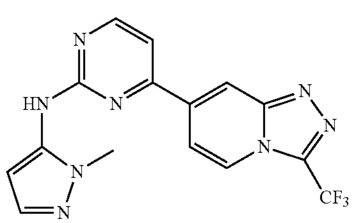 [SMILES: Cn1nccc1Nc1nccc(-c2ccn3c(C(F)(F)F)nnc3c2)n1] | N-(1-methyl-1H-pyrazol-5-yl)-4-(3-(trifluoromethyl)-[1,2,4]triazolo[4,3-a]pyridin-7-yl)pyrimidin-2-amine | 361.1 (1.16 min) |

TABLE 2-continued

| Ex. # | Structure | Name | MS (ACPI+) M + 1 (retention time) |
|---|---|---|---|
| 222 | 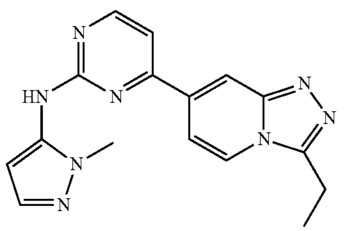 [SMILES: CCc1nnc2cc(-c3ccnc(Nc4ccnn4C)n3)ccn12] | 4-(3-ethyl-[1,2,4]triazolo[4,3-a]pyridin-7-yl)-N-(1-methyl-1H-pyrazol-5-yl)pyrimidin-2-amine | 321.1 (0.95 min) |
| 223 | 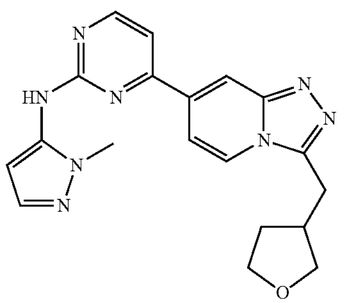 [SMILES: Cn1nccc1Nc1nccc(-c2ccn3c(CC4CCOC4)nnc3c2)n1] | N-(1-methyl-1H-pyrazol-5-yl)-4-(3-((tetrahydrofuran-3-yl)methyl)-[1,2,4]triazolo[4,3-a]pyridin-7-yl)pyrimidin-2-amine | 377.1 (0.96 min) |
| 224 | 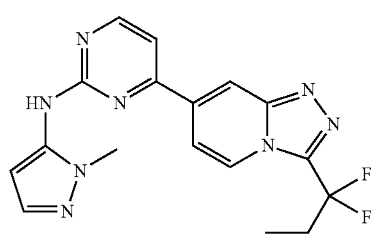 [SMILES: CCC(F)(F)c1nnc2cc(-c3ccnc(Nc4ccnn4C)n3)ccn12] | 4-(3-(1,1-difluoropropyl)-[1,2,4]triazolo[4,3-a]pyridin-7-yl)-N-(1-methyl-1H-pyrazol-5-yl)pyrimidin-2-amine | 371.1 (1.27 min) |
| 225 | 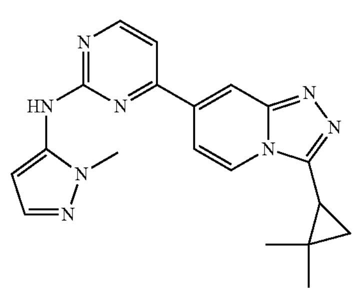 [SMILES: Cn1nccc1Nc1nccc(-c2ccn3c(C4CC4(C)C)nnc3c2)n1] | 4-(3-(2,2-dimethylcyclopropyl)-[1,2,4]triazolo[4,3-a]pyridin-7-yl)-N-(1-methyl-1H-pyrazol-5-yl)pyrimidin-2-amine | 361.2 (1.17 min) |
| 226 | 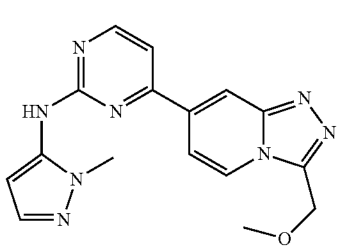 [SMILES: COCc1nnc2cc(-c3ccnc(Nc4ccnn4C)n3)ccn12] | 4-(3-(methoxymethyl)-[1,2,4]triazolo[4,3-a]pyridin-7-yl)-N-(1-methyl-1H-pyrazol-5-yl)pyrimidin-2-amine | 337.1 (0.96 min) |

TABLE 2-continued

| Ex. # | Structure | Name | MS (ACPI+) M + 1 (retention time) |
|---|---|---|---|
| 227 | 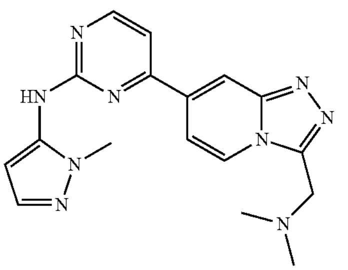 [SMILES: CN(C)Cc1nnc2cc(-c3ccnc(Nc4ccnn4C)n3)ccn12] | 4-(3-((dimethylamino)methyl)-[1,2,4]triazolo[4,3-a]pyridin-7-yl)-N-(1-methyl-1H-pyrazol-5-yl)pyrimidin-2-amine | 350.1 (0.37 min) |
| 228 | 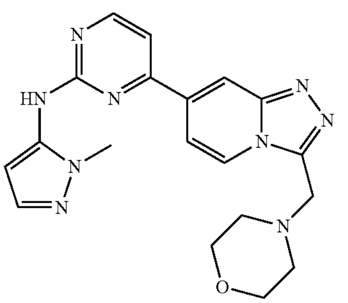 [SMILES: Cn1nccc1Nc1nccc(-c2ccn3c(CN4CCOCC4)nnc3c2)n1] | N-(1-methyl-1H-pyrazol-5-yl)-4-(3-(morpholinomethyl)-[1,2,4]triazolo[4,3-a]pyridin-7-yl)pyrimidin-2-amine | 392.2 (0.78 min) |
| 229 | 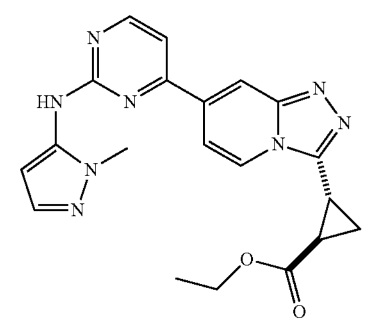 | (1R*,2R*)-ethyl 2-(7-(2-((1-methyl-1H-pyrazol-5-yl)amino)pyrimidin-4-yl)-[1,2,4]triazolo[4,3-a]pyridin-3-yl)cyclopropanecarboxylate | 405.2 (1.16 min) |
| 230 | 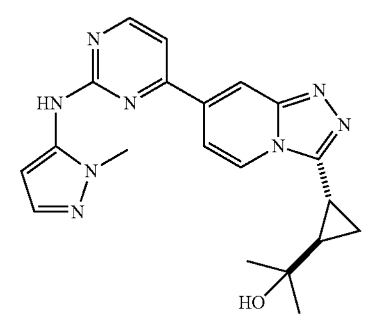 | 2-((1R*,2R*)-2-(7-(2-((1-methyl-1H-pyrazol-5-yl)amino)pyrimidin-4-yl)-[1,2,4]triazolo[4,3-a]pyridin-3-yl)cyclopropyl)propan-2-ol | 391.2 (1.01 min) |
| 231 | 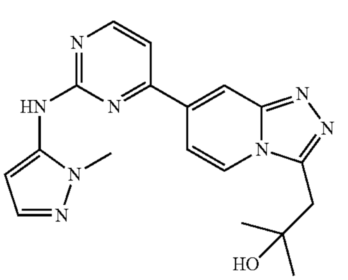 | 2-methyl-1-(7-(2-((1-methyl-1H-pyrazol-5-yl)amino)pyrimidin-4-yl)-[1,2,4]triazolo[4,3-a]pyridin-3-yl)propan-2-ol | 365.2 (0.99 min) |

TABLE 2-continued

| Ex. # | Structure | Name | MS (ACPI+) M + 1 (retention time) |
|---|---|---|---|
| 232 | 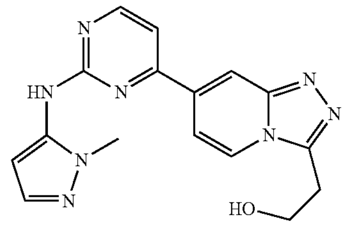 | 2-(7-(2-((1-methyl-1H-pyrazol-5-yl)amino)pyrimidin-4-yl)-[1,2,4]triazolo[4,3-a]pyridin-3-yl)ethanol | 337.1 (0.91 min) |
| 233 | 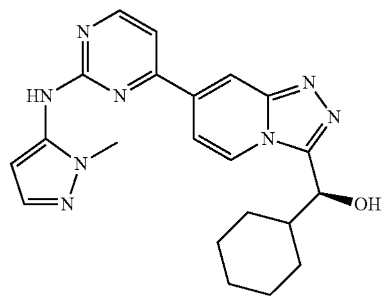 [SMILES: Cn1nccc1Nc1nccc(-c2ccn3c([C@@H](O)C4CCCCC4)nnc3c2)n1] | (S)-cyclohexyl(7-(2-((1-methyl-1H-pyrazol-5-yl)amino)pyrimidin-4-yl)-[1,2,4]triazolo[4,3-a]pyridin-3-yl)methanol | 405.2 (1.31 min) |
| 234 | 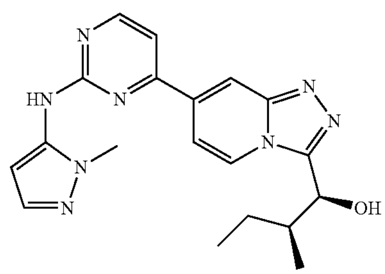 [SMILES: CC[C@H](C)[C@H](O)c1nnc2cc(-c3ccnc(Nc4ccnn4C)n3)ccn12] | (1S,2S)-2-methyl-1-(7-(2-((1-methyl-1H-pyrazol-5-yl)amino)pyrimidin-4-yl)-[1,2,4]triazolo[4,3-a]pyridin-3-yl)butan-1-ol | 379.2 (1.20 min) |
| 235 | 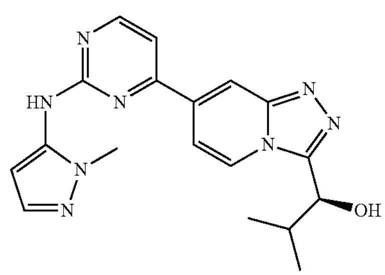 [SMILES: CC(C)[C@H](O)c1nnc2cc(-c3ccnc(Nc4ccnn4C)n3)ccn12] | (S)-2-methyl-1-(7-(2-((1-methyl-1H-pyrazol-5-yl)amino)pyrimidin-4-yl)-[1,2,4]triazolo[4,3-a]pyridin-3-yl)propan-1-ol | 365.1 (0.87 min) |
| 236 | 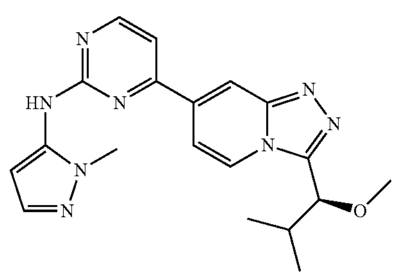 [SMILES: CO[C@H](c1nnc2cc(-c3ccnc(Nc4ccnn4C)n3)ccn12)C(C)C] | (S)-4-(3-(1-methoxy-2-methylpropyl)-[1,2,4]triazolo[4,3-a]pyridin-7-yl)-N-(1-methyl-1H-pyrazol-5-yl)pyrimidin-2-amine | 379.2 (1.26 min) |

TABLE 2-continued

| Ex. # | Structure | Name | MS (ACPI+) M + 1 (retention time) |
|---|---|---|---|
| 237 | 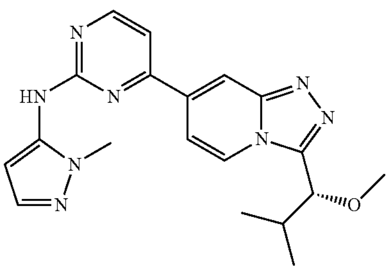 [SMILES: CO[C@@H](c1nnc2cc(-c3ccnc(Nc4ccnn4C)n3)ccn12)C(C)C] | (R)-4-(3-(1-methoxy-2-methylpropyl)-[1,2,4]triazolo[4,3-a]pyridin-7-yl)-N-(1-methyl-1H-pyrazol-5-yl)pyrimidin-2-amine | 379.2 (1.25 min) |
| 238 | 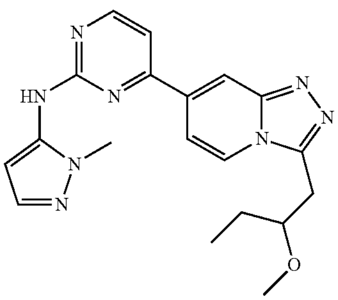 [SMILES: CCC(Cc1nnc2cc(-c3ccnc(Nc4ccnn4C)n3)ccn12)OC] | 4-(3-(2-methoxybutyl)-[1,2,4]triazolo[4,3-a]pyridin-7-yl)-N-(1-methyl-1H-pyrazol-5-yl)pyrimidin-2-amine | 379.2 (2.16 min) |
| 239 | 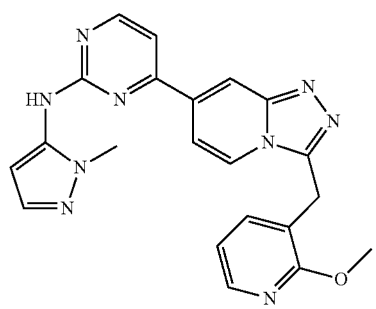 [SMILES: COc1ncccc1Cc1nnc2cc(-c3ccnc(Nc4ccnn4C)n3)ccn12] | 4-(3-((2-methoxypyridin-3-yl)methyl)-[1,2,4]triazolo[4,3-a]pyridin-7-yl)-N-(1-methyl-1H-pyrazol-5-yl)pyrimidin-2-amine | 414.2 (2.04 min) |
| 240 | 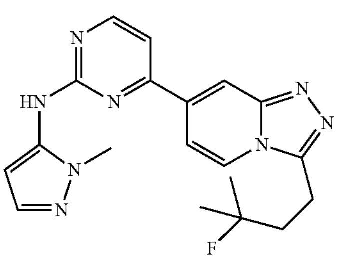 [SMILES: Cn1nccc1Nc1nccc(-c2ccn3c(CCC(C)(C)F)nnc3c2)n1] | 4-(3-(3-fluoro-3-methylbutyl)-[1,2,4]triazolo[4,3-a]pyridin-7-yl)-N-(1-methyl-1H-pyrazol-5-yl)pyrimidin-2-amine | 381.2 (2.19 min) |
| 241 | 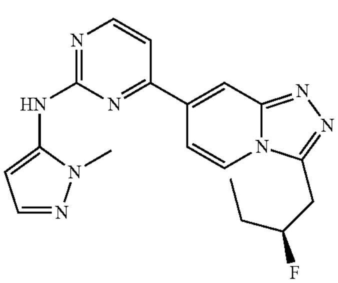 [SMILES: CC[C@H](F)Cc1nnc2cc(-c3ccnc(Nc4ccnn4C)n3)ccn12] | (S)-4-(3-(2-fluorobutyl)-[1,2,4]triazolo[4,3-a]pyridin-7-yl)-N-(1-methyl-1H-pyrazol-5-yl)pyrimidin-2-amine | 367.2 (2.16 min) |

TABLE 2-continued

| Ex. # | Structure | Name | MS (ACPI+) M + 1 (retention time) |
|---|---|---|---|
| 242 | 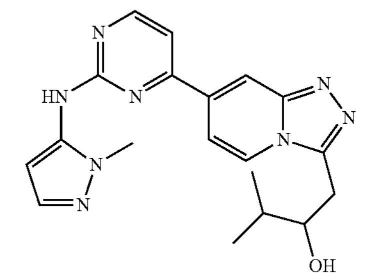 [SMILES: CC(C)C(O)Cc1nnc2cc(-c3ccnc(Nc4ccnn4C)n3)ccn12] | 3-methyl-1-(7-(2-((1-methyl-1H-pyrazol-5-yl)amino)pyrimidin-4-yl)-[1,2,4]triazolo[4,3-a]pyridin-3-yl)butan-2-ol | 379.1 (2.06 min) |
| 243 | 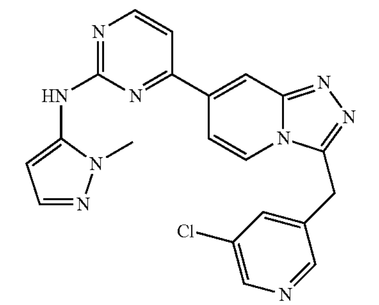 [SMILES: Cn1nccc1Nc1nccc(-c2ccn3c(Cc4cncc(Cl)c4)nnc3c2)n1] | 4-(3-((5-chloropyridin-3-yl)methyl)-[1,2,4]triazolo[4,3-a]pyridin-7-yl)-N-(1-methyl-1H-pyrazol-5-yl)pyrimidin-2-amine | 418.1 (2.05 min) |
| 244 | 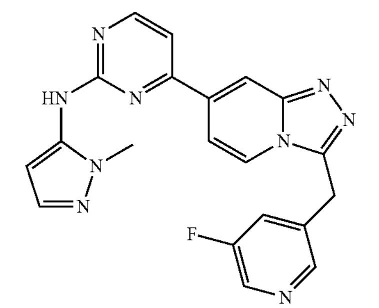 [SMILES: Cn1nccc1Nc1nccc(-c2ccn3c(Cc4cncc(F)c4)nnc3c2)n1] | 4-(3-((5-fluoropyridin-3-yl)methyl)-[1,2,4]triazolo[4,3-a]pyridin-7-yl)-N-(1-methyl-1H-pyrazol-5-yl)pyrimidin-2-amine | 402.2 (1.93 min) |
| 245 | 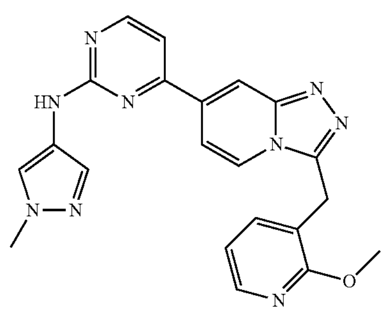 | 4-(3-((2-methoxypyridin-3-yl)methyl)-[1,2,4]triazolo[4,3-a]pyridin-7-yl)-N-(1-methyl-1H-pyrazol-4-yl)pyrimidin-2-amine | 414.2 (2.07 min) |
| 246 | 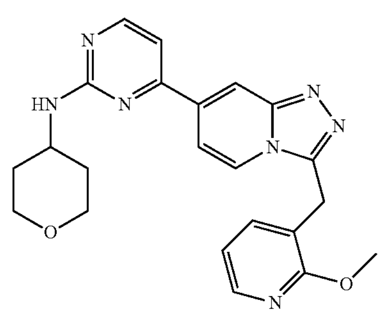 [SMILES: COc1ncccc1Cc1nnc2cc(-c3ccnc(NC4CCOCC4)n3)ccn12] | 4-(3-((2-methoxypyridin-3-yl)methyl)-[1,2,4]triazolo[4,3-a]pyridin-7-yl)-N-tetrahydro-2H-pyran-4-yl)pyrimidin-2-amine | 418.2 (2.08 min) |

TABLE 2-continued

| Ex. # | Structure | Name | MS (ACPI+) M + 1 (retention time) |
|---|---|---|---|
| 247 | 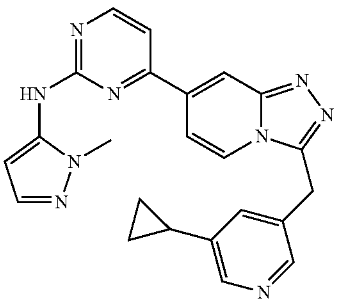 [SMILES: Cn1nccc1Nc1nccc(-c2ccn3c(Cc4cncc(C5CC5)c4)nnc3c2)n1] | 4-(3-((5-cyclopropylpyridin-3-yl)methyl)-[1,2,4]triazolo[4,3-a]pyridin-7-yl)-N-(1-methyl-1H-pyrazol-5-yl)pyrimidin-2-amine | 424.2 (1.83 min) |
| 248 | 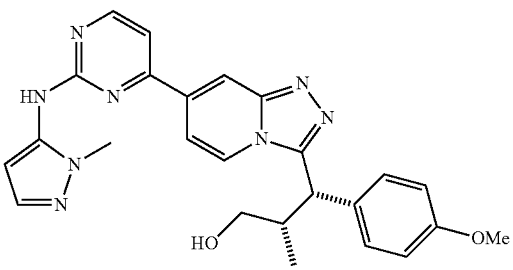 [SMILES: COc1ccc([C@@H](c2nnc3cc(-c4ccnc(Nc5ccnn5C)n4)ccn23)[C@H](C)CO)cc1] | (2S*,3S*)-3-(4-methoxyphenyl)-2-methyl-3-(7-(2-((1-methyl-1H-pyrazol-5-yl)amino)pyrimidin-4-yl)-[1,2,4]triazolo[4,3-a]pyridin-3-yl)propan-1-ol | 470.2 (1.92 min) |
| 249 | 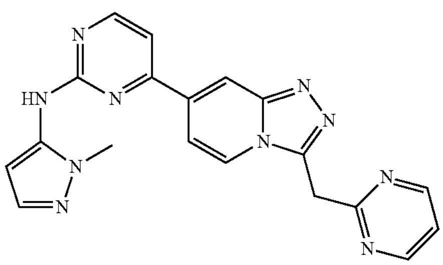 [SMILES: Cn1nccc1Nc1nccc(-c2ccn3c(Cc4ncccn4)nnc3c2)n1] | N-(1-methyl-1H-pyrazol-5-yl)-4-(3-(pyrimidin-2-ylmethyl)-[1,2,4]triazolo[4,3-a]pyridin-7-yl)pyrimidin-2-amine | 385.1 (1.75 min) |
| 250 | 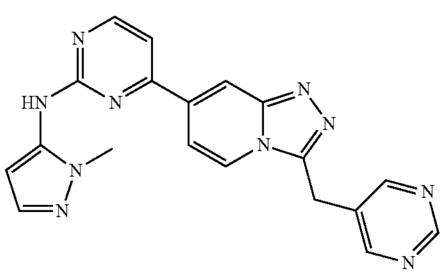 [SMILES: Cn1nccc1Nc1nccc(-c2ccn3c(Cc4cncnc4)nnc3c2)n1] | N-(1-methyl-1H-pyrazol-5-yl)-4-(3-(pyrimidin-5-ylmethyl)-[1,2,4]triazolo[4,3-a]pyridin-7-yl)pyrimidin-2-amine | 385.1 (1.69 min) |
| 251 | 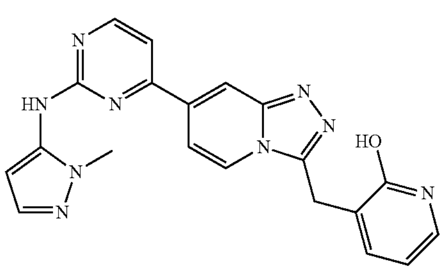 [SMILES: Cn1nccc1Nc1nccc(-c2ccn3c(Cc4cccnc4O)nnc3c2)n1] | 3-((7-(2-((1-methyl-1H-pyrazol-5-yl)amino)pyrimidin-4-yl)-[1,2,4]triazolo[4,3-a]pyridin-3-yl)methyl)pyridin-2-ol | 400.1 (1.70 min) |

TABLE 2-continued

| Ex. # | Structure | Name | MS (ACPI+) M + 1 (retention time) |
|---|---|---|---|
| 252 | 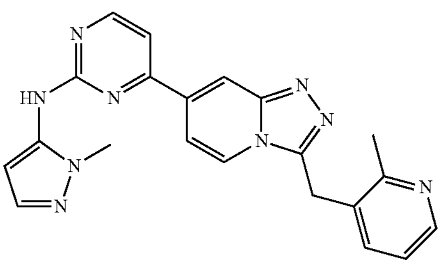 [SMILES: Cc1ncccc1Cc1nnc2cc(-c3ccnc(Nc4ccnn4C)n3)ccn12] | N-(1-methyl-1H-pyrazol-5-yl)-4-(3-((2-methylpyridin-3-yl)methyl)-[1,2,4]triazolo[4,3-a]pyridin-7-yl)pyrimidin-2-amine | 398.2 (0.89 min) |
| 253 | 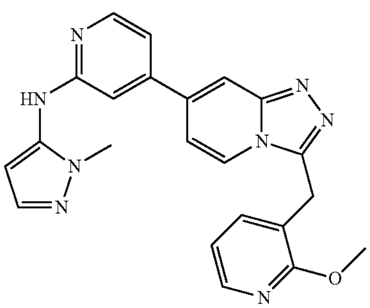 [SMILES: COc1ncccc1Cc1nnc2cc(-c3ccnc(Nc4ccnn4C)c3)ccn12] | 4-(3-((2-methoxypyridin-3-yl)methyl)-[1,2,4]triazolo[4,3-a]pyridin-7-yl)-N-(1-methyl-1H-pyrazol-5-yl)pyridin-2-amine | 413.2 (1.91 min) |
| 254 | 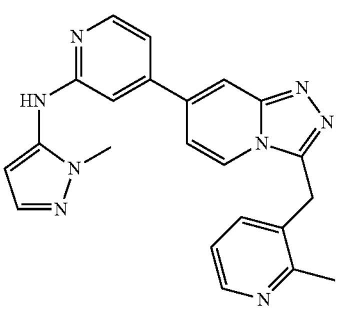 [SMILES: Cc1ncccc1Cc1nnc2cc(-c3ccnc(Nc4ccnn4C)c3)ccn12] | N-(1-methyl-1H-pyrazol-5-yl)-4-(3-((2-methylpyridin-3-yl)methyl)-[1,2,4]triazolo[4,3-a]pyridin-7-yl)pyridin-2-amine | 397.2 (0.34 min) |
| 255 | 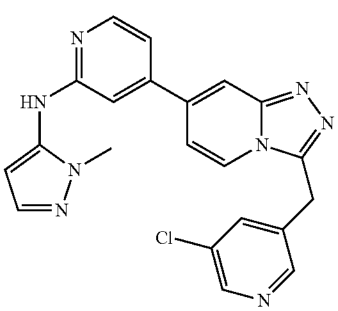 | 4-(3-((5-chloropyridin-3-yl)methyl)-[1,2,4]triazolo[4,3-a]pyridin-7-yl)-N-(1-methyl-1H-pyrazol-5-yl)pyridin-2-amine | 417.1 (1.91 min) |
| 256 | 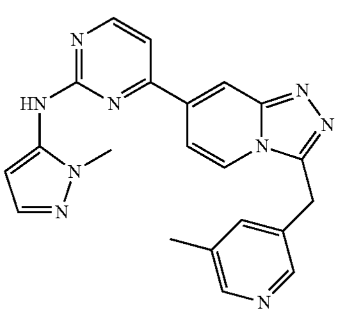 [SMILES: Cc1cncc(Cc2nnc3cc(-c4ccnc(Nc5ccnn5C)n4)ccn23)c1] | N-(1-methyl-1H-pyrazol-5-yl)-4-(3-((5-methylpyridin-3-yl)methyl)-[1,2,4]triazolo[4,3-a]pyridin-7-yl)pyrimidin-2-amine | 398.2 (1.63 min) |

TABLE 2-continued

| Ex. # | Structure | Name | MS (ACPI+) M + 1 (retention time) |
|---|---|---|---|
| 257 | 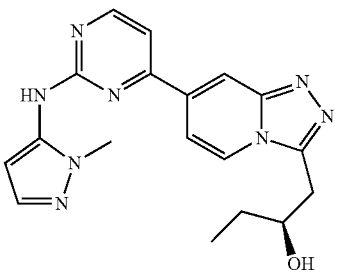 [SMILES: CC[C@H](O)Cc1nnc2cc(-c3ccnc(Nc4ccnn4C)n3)ccn12] | (S)-1-(7-(2-((1-methyl-1H-pyrazol-5-yl)amino)pyrimidin-4-yl)-[1,2,4]triazolo[4,3-a]pyridin-3-yl)butan-2-ol | 365.2 (1.90 min) |
| 258 | 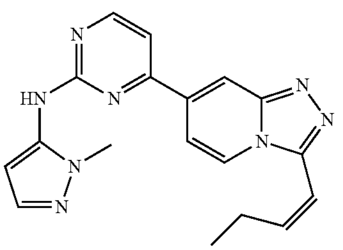 [SMILES: CC/C=C\c1nnc2cc(-c3ccnc(Nc4ccnn4C)n3)ccn12] | (E)-4-(3-(but-1-en-1-yl)-[1,2,4]triazolo[4,3-a]pyridin-7-yl)-N-(1-methyl-1H-pyrazol-5-yl)pyrimidin-2-amine | 347.1 (2.21 min) |
| 259 | 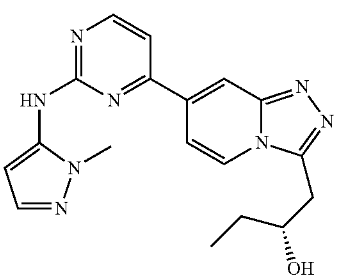 [SMILES: CC[C@@H](O)Cc1nnc2cc(-c3ccnc(Nc4ccnn4C)n3)ccn12] | (R)-1-(7-(2-((1-methyl-1H-pyrazol-5-yl)amino)pyrimidin-4-yl)-[1,2,4]triazolo[4,3-a]pyridin-3-yl)butan-2-ol | 365.1 (1.90 min) |
| 260 | 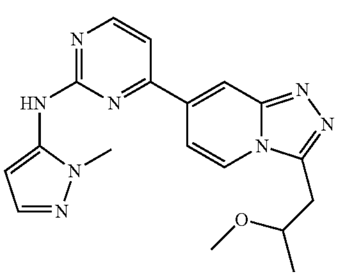 [SMILES: COC(C)Cc1nnc2cc(-c3ccnc(Nc4ccnn4C)n3)ccn12] | 4-(3-(2-methoxypropyl)-[1,2,4]triazolo[4,3-a]pyridin-7-yl)-N-(1-methyl-1H-pyrazol-5-yl)pyrimidin-2-amine | 365.2 (2.00 min) |
| 261 | 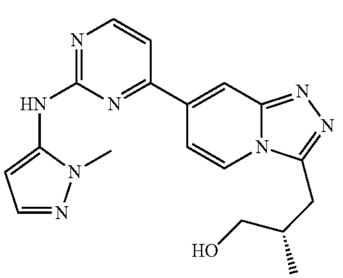 [SMILES: C[C@H](CO)Cc1nnc2cc(-c3ccnc(Nc4ccnn4C)n3)ccn12] | (S)-2-methyl-3-(7-(2-((1-methyl-1H-pyrazol-5-yl)amino)pyrimidin-4-yl)-[1,2,4]triazolo[4,3-a]pyridin-3-yl)propan-1-ol | 365.2 (1.87 min) |

TABLE 2-continued

| Ex. # | Structure | Name | MS (ACPI+) M + 1 (retention time) |
|---|---|---|---|
| 262 | 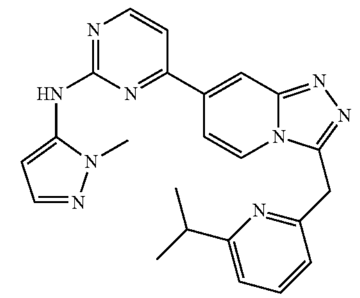 [SMILES: CC(C)c1cccc(Cc2nnc3cc(-c4ccnc(Nc5ccnn5C)n4)ccn23)n1] | 4-(3-((6-isopropylpyridin-2-yl)methyl)-[1,2,4]triazolo[4,3-a]pyridin-7-yl)-N-(1-methyl-1H-pyrazol-5-yl)pyrimidin-2-amine | 426.2 (2.06 min) |
| 263 | 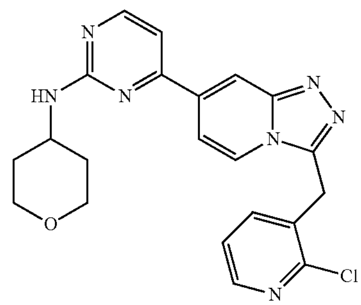 [SMILES: Clc1ncccc1Cc1nnc2cc(-c3ccnc(NC4CCOCC4)n3)ccn12] | 4-(3-((2-chloropyridin-3-yl)methyl)-[1,2,4]triazolo[4,3-a]pyridin-7-yl)-N-(tetrahydro-2H-pyran-4-yl)pyrimidin-2-amine | 422.1 (1.99 min) |
| 264 | 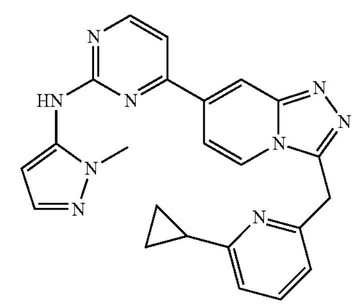 [SMILES: Cn1nccc1Nc1nccc(-c2ccn3c(Cc4cccc(C5CC5)n4)nnc3c2)n1] | 4-(3-((6-cyclopropylpyridin-2-yl)methyl)-[1,2,4]triazolo[4,3-a]pyridin-7-yl)-N-(1-methyl-1H-pyrazol-5-yl)pyrimidin-2-amine | 424.2 (2.04 min) |
| 265 | 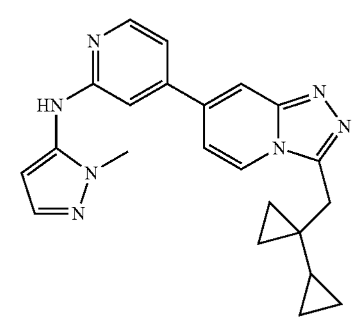 [SMILES: Cn1nccc1Nc1cc(-c2ccn3c(CC4(C5CC5)CC4)nnc3c2)ccn1] | 4-(3-([1,1'-bi(cyclopropan)]-1-ylmethyl)-[1,2,4]triazolo[4,3-a]pyridin-7-yl)-N-(1-methyl-1H-pyrazol-5-yl)pyridin-2-amine | 386.2 (2.25 min) |

TABLE 2-continued

| Ex. # | Structure | Name | MS (ACPI+) M + 1 (retention time) |
|---|---|---|---|
| 266 | 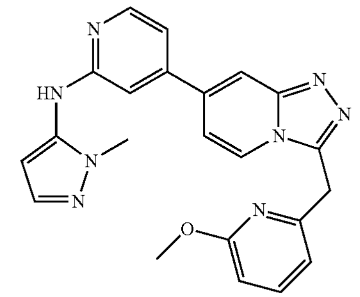 [SMILES: COc1cccc(Cc2nnc3cc(-c4ccnc(Nc5ccnn5C)c4)ccn23)n1] | 4-(3-((6-methoxypyridin-2-yl)methyl)-[1,2,4]triazolo[4,3-a]pyridin-7-yl)-N-(1-methyl-1H-pyrazol-5-yl)pyridin-2-amine | 413.2 (2.03 min) |
| 267 | 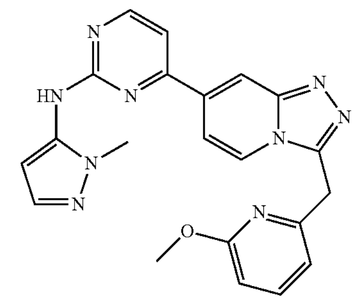 [SMILES: COc1cccc(Cc2nnc3cc(-c4ccnc(Nc5ccnn5C)n4)ccn23)n1] | 4-(3-((6-methoxypyridin-2-yl)methyl)-[1,2,4]triazolo[4,3-a]pyridin-7-yl)-N-(1-methyl-1H-pyrazol-5-yl)pyrimidin-2-amine | 414.1 (2.15 min) |
| 268 | 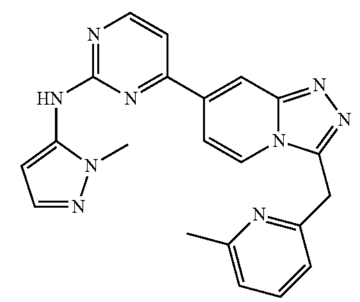 [SMILES: Cc1cccc(Cc2nnc3cc(-c4ccnc(Nc5ccnn5C)n4)ccn23)n1] | N-(1-methyl-1H-pyrazol-5-yl)-4-(3-((6-methylpyridin-2-yl)methyl)-[1,2,4]triazolo[4,3-a]pyridin-7-yl)pyrimidin-2-amine | 398.2 (1.66 min) |
| 269 | 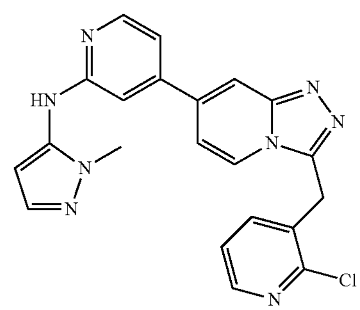 [SMILES: Cn1nccc1Nc1cc(-c2ccn3c(Cc4cccnc4Cl)nnc3c2)ccn1] | 4-(3-((2-chloropyridin-3-yl)methyl)-[1,2,4]triazolo[4,3-a]pyridin-7-yl)-N-(1-methyl-1H-pyrazol-5-yl)pyridin-2-amine | 417.1 (1.81 min) |
| 270 | 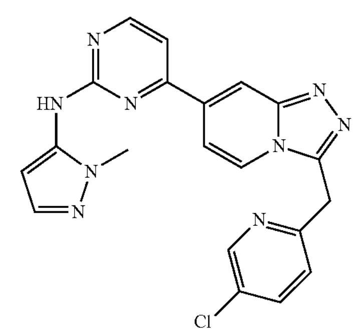 [SMILES: Cn1nccc1Nc1nccc(-c2ccn3c(Cc4ccc(Cl)cn4)nnc3c2)n1] | 4-(3-((5-chloropyridin-2-yl)methyl)-[1,2,4]triazolo[4,3-a]pyridin-7-yl)-N-(1-methyl-1H-pyrazol-5-yl)pyrim-2-amine | 418.1 (2.14 min) |

TABLE 2-continued

| Ex. # | Structure | Name | MS (ACPI+) M + 1 (retention time) |
|---|---|---|---|
| 271 | 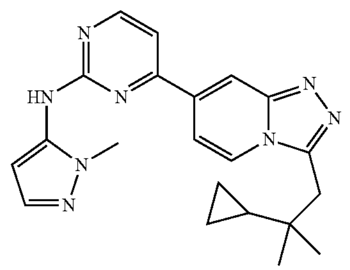 [SMILES: Cn1nccc1Nc1nccc(-c2ccn3c(CC(C)(C)C4CC4)nnc3c2)n1] | 4-(3-(2-cyclopropyl-2-methylpropyl)-[1,2,4]triazolo[4,3-a]pyridin-7-yl)-N-(1-methyl-1H-pyrazol-5-yl)pyrimidin-2-amine | 389.2 (2.38 min) |
| 272 | 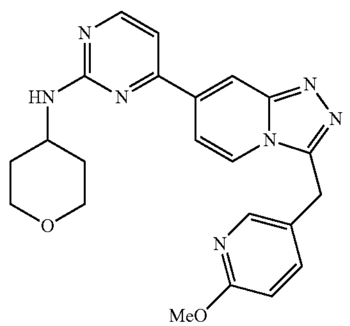 [SMILES: COc1ccc(Cc2nnc3cc(-c4ccnc(NC5CCOCC5)n4)ccn23)cn1] | 4-(3-((6-methoxypyridin-3-yl)methyl)-[1,2,4]triazolo[4,3-a]pyridin-7-yl)-N-(tetrahydro-2H-pyran-4-yl)pyrimidin-2-amine | 418.1 (2.01 min) |
| 273 | 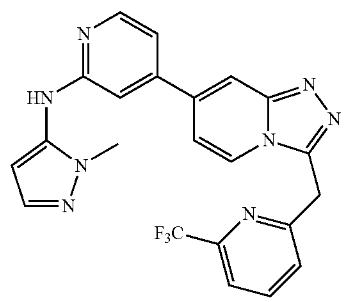 [SMILES: Cn1nccc1Nc1cc(-c2ccn3c(Cc4cccc(C(F)(F)F)n4)nnc3c2)ccn1] | N-(1-methyl-1H-pyrazol-5-yl)-4-(3-((6-(trifluoromethyl)pyridin-2-yl)methyl)-[1,2,4]triazolo[4,3-a]pyridin-7-yl)pyridin-2-amine | 451.1 (2.16 min) |
| 274 | 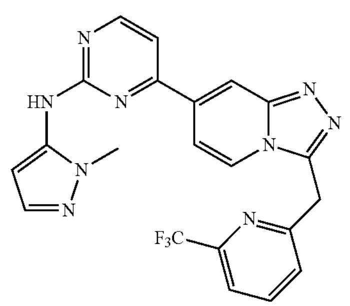 | N-(1-methyl-1H-pyrazol-5-yl)-4-(3-((6-(trifluoromethyl)pyridin-2-yl)methyl)-[1,2,4]triazolo[4,3-a]pyridin-7-yl)pyrimidin-2-amine | 452.1 (2.27 min) |
| 275 | 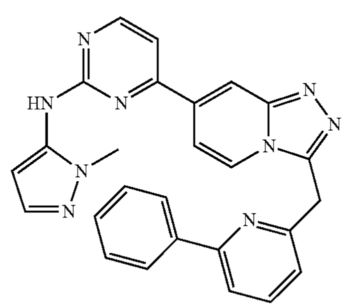 [SMILES: Cn1nccc1Nc1nccc(-c2ccn3c(Cc4cccc(-c5ccccc5)n4)nnc3c2)n1] | N-(1-methyl-1H-pyrazol-5-yl)-4-(3-((6-phenylpyridin-2-yl)methyl)-[1,2,4]triazolo[4,3-a]pyridin-7-yl)pyrimidin-2-amine | 460.1 (1.82 min) |

TABLE 2-continued

| Ex. # | Structure | Name | MS (ACPI+) M + 1 (retention time) |
|---|---|---|---|
| 276 | 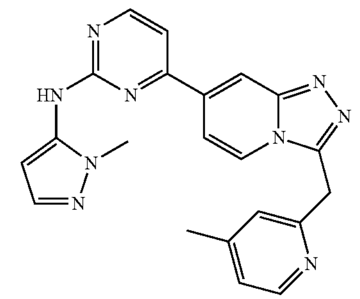 [SMILES: Cc1ccnc(Cc2nnc3cc(-c4ccnc(Nc5ccnn5C)n4)ccn23)c1] | N-(1-methyl-1H-pyrazol-5-yl)-4-(3-((4-methylpyridin-2-yl)methyl)-[1,2,4]triazolo[4,3-a]pyridin-7-yl)pyrimidin-2-amine | 398.2 (1.69 min) |
| 277 | 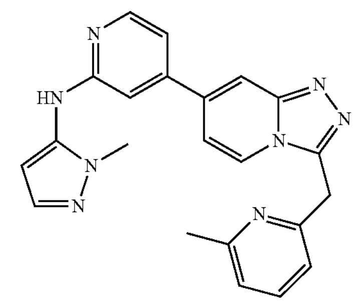 [SMILES: Cc1cccc(Cc2nnc3cc(-c4ccnc(Nc5ccnn5C)c4)ccn23)n1] | N-(1-methyl-1H-pyrazol-5-yl)-4-(3-((6-methylpyridin-2-yl)methyl)-[1,2,4]triazolo[4,3-a]pyridin-7-yl)pyridin-2-amine | 397.2 (1.45 min) |
| 278 | 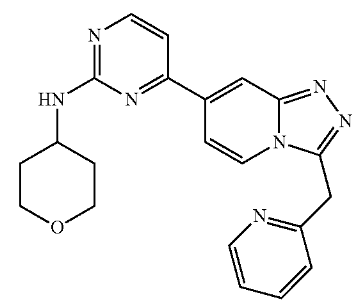 [SMILES: c1ccc(Cc2nnc3cc(-c4ccnc(NC5CCOCC5)n4)ccn23)nc1] | 4-(3-(pyridin-2-ylmethyl)-[1,2,4]triazolo[4,3-a]pyridin-7-yl)-N-(tetrahydro-2H-pyran-4-yl)pyrimidin-2-amine | 388.3 (1.72 min) |
| 279 | 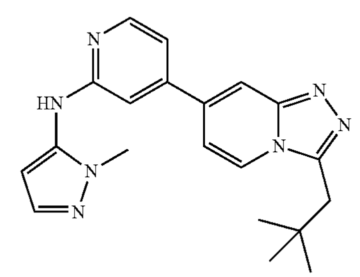 [SMILES: Cn1nccc1Nc1cc(-c2ccn3c(CC(C)(C)C)nnc3c2)ccn1] | N-(1-methyl-1H-pyrazol-5-yl)-4-(3-neopentyl-[1,2,4]triazolo[4,3-a]pyridin-7-yl)pyridin-2-amine | 362.2 (2.07 min) |
| 280 | 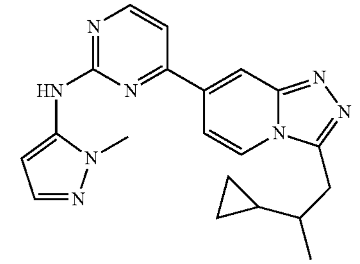 [SMILES: CC(Cc1nnc2cc(-c3ccnc(Nc4ccnn4C)n3)ccn12)C1CC1] | 4-(3-(2-cyclopropylpropyl)-[1,2,4]triazolo[4,3-a]pyridin-7-yl)-N-(1-methyl-1H-pyrazol-5-yl)pyrimidin-2-amine | 375.2 (2.35 min) |

TABLE 2-continued

| Ex. # | Structure | Name | MS (ACPI+) M + 1 (retention time) |
|---|---|---|---|
| 281 | 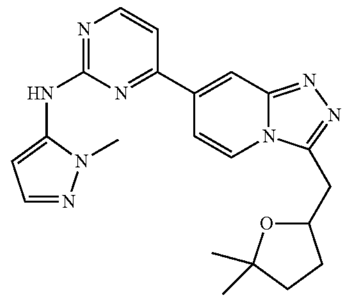 [SMILES: Cn1nccc1Nc1nccc(-c2ccn3c(CC4CCC(C)(C)O4)nnc3c2)n1] | 4-(3-((5,5-dimethyltetrahydrofuran-2-yl)methyl)-[1,2,4]triazolo[4,3-a]pyridin-7-yl)-N-methyl-1H-pyrazol-5-yl)pyrimidin-2-amine | 405.2 (2.20 min) |
| 282 | 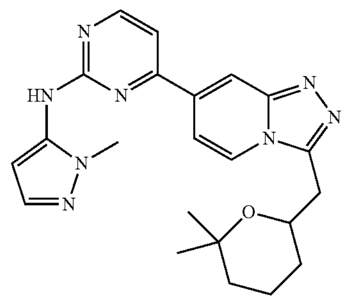 [SMILES: Cn1nccc1Nc1nccc(-c2ccn3c(CC4CCCC(C)(C)O4)nnc3c2)n1] | 4-(3-((6,6-dimethyltetrahydro-2H-pyran-2-yl)methyl)-[1,2,4]triazolo[4,3-a]pyridin-7-yl)-N-(1-methyl-1H-pyrazol-5-yl)pyrimidin-2-amine | 419.2 (2.42 min) |
| 283 | 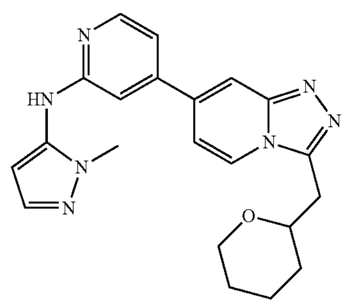 [SMILES: Cn1nccc1Nc1cc(-c2ccn3c(CC4CCCCO4)nnc3c2)ccn1] | N-(1-methyl-1H-pyrazol-5-yl)-4-(3-((tetrahydro-2H-pyran-2-yl)methyl)-[1,2,4]triazolo[4,3-a]pyridin-7-yl)pyridin-2-amine | 390.2 (1.96 min) |
| 284 | 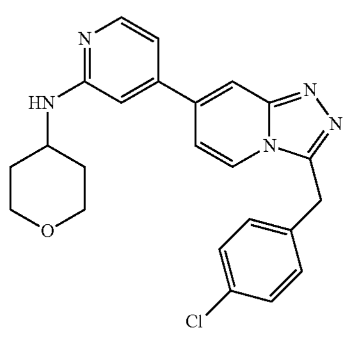 [SMILES: Clc1ccc(Cc2nnc3cc(-c4ccnc(NC5CCOCC5)c4)ccn23)cc1] | 4-(3-(4-chlorobenzyl)-[1,2,4]triazolo[4,3-a]pyridin-7-yl)-N-(tetrahydro-2H-pyran-4-yl)pyridin-2-amine | 420.1 (1.95 min) |

TABLE 2-continued

| Ex. # | Structure | Name | MS (ACPI+) M + 1 (retention time) |
|---|---|---|---|
| 285 | 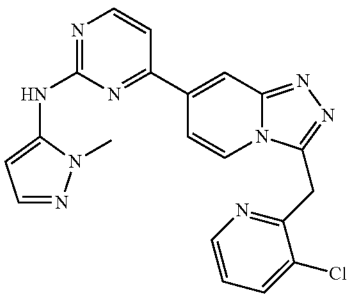 [SMILES: Cn1nccc1Nc1nccc(-c2ccn3c(Cc4ncccc4Cl)nnc3c2)n1] | 4-(3-((3-chloropyridin-2-yl)methyl)-[1,2,4]triazolo[4,3-a]pyridin-7-yl)-N-(1-methyl-1H-pyrazol-5-yl)pyrimidin-2-amine | 418.1 (2.06 min) |
| 286 | 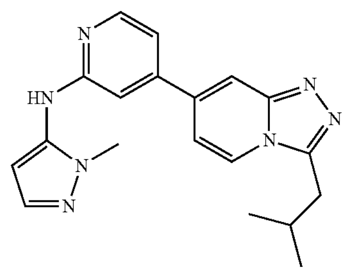 [SMILES: CC(C)Cc1nnc2cc(-c3ccnc(Nc4ccnn4C)c3)ccn12] | 4-(3-isobutyl-[1,2,4]triazolo[4,3-a]pyridin-7-yl)-N-(1-methyl-1H-pyrazol-5-yl)pyridin-2-amine | 348.2 (1.94 min) |
| 287 | 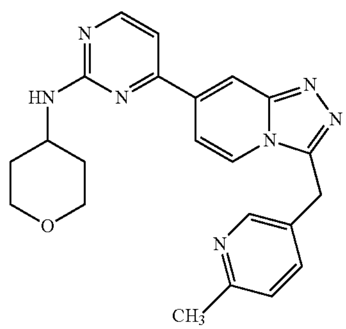 [SMILES: Cc1ccc(Cc2nnc3cc(-c4ccnc(NC5CCOCC5)n4)ccn23)cn1] | 4-(3-((6-chloropyridin-3-yl)methyl)-[1,2,4]triazolo[4,3-a]pyridin-7-yl)-N-(tetrahydro-2H-pyran-4-yl)pyrimidin-2-amine | 422.1 (2.05 min) |
| 288 | 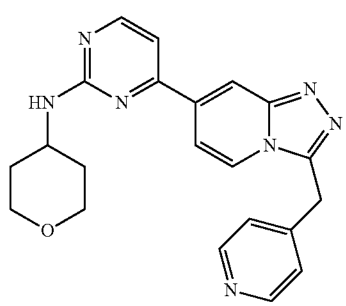 | 4-(3-(pyridin-4-ylmethyl)-[1,2,4]triazolo[4,3-a]pyridin-7-yl)-N-(tetrahydro-2H-pyran-4-yl)pyrimidin-2-amine | 388.2 (0.59 min) |
| 289 | 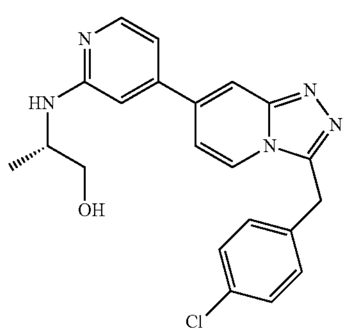 [SMILES: C[C@@H](CO)Nc1cc(-c2ccn3c(Cc4ccc(Cl)cc4)nnc3c2)ccn1] | (S)-2-((4-(3-(4-chlorobenzyl)-[1,2,4]triazolo[4,3-a]pyridin-7-yl)pyridin-2-yl)amino)propan-1-ol | 394.1 (1.90 min) |

TABLE 2-continued

| Ex. # | Structure | Name | MS (ACPI+) M + 1 (retention time) |
|---|---|---|---|
| 290 | 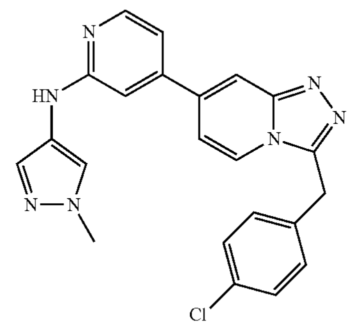 [SMILES: Cn1cc(Nc2cc(-c3ccn4c(Cc5ccc(Cl)cc5)nnc4c3)ccn2)cn1] | 4-(3-(4-chlorobenzyl)-[1,2,4]triazolo[4,3-a]pyridin-7-yl)-N-(1-methyl-1H-pyrazol-4-yl)pyridin-2-amine | 416.1 (2.00 min) |
| 291 | 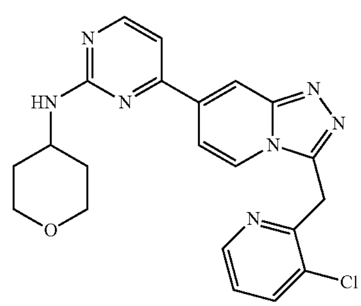 [SMILES: Clc1cccnc1Cc1nnc2cc(-c3ccnc(NC4CCOCC4)n3)ccn12] | 4-(3-((3-chloropyridin-2-yl)methyl)-[1,2,4]triazolo[4,3-a]pyridin-7-yl)-N-(tetrahydro-2H-pyran-4-yl)pyrimidin-2-amine | 422.1 (1.42 min) |
| 292 | 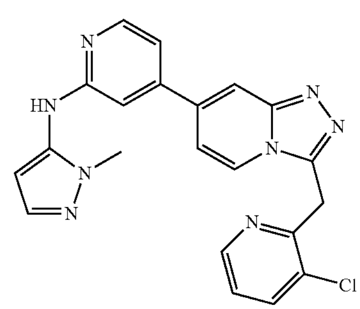 [SMILES: Cn1nccc1Nc1cc(-c2ccn3c(Cc4ncccc4Cl)nnc3c2)ccn1] | 4-(3-((3-chloropyridin-2-yl)methyl)-[1,2,4]triazolo[4,3-a]pyridin-7-yl)-N-(1-methyl-1H-pyrazol-5-yl)pyridin-2-amine | 417.1 (1.92 min) |
| 293 | 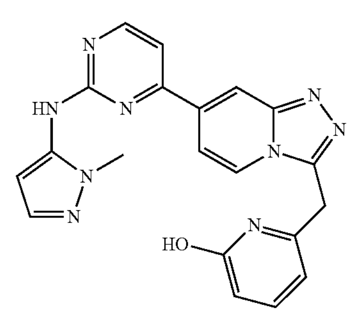 | 6-((7-(2-((1-methyl-1H-pyrazol-5-yl)amino)pyrimidin-4-yl)-[1,2,4]triazolo[4,3-a]pyridin-3-yl)methyl)pyridin-2-ol | 400.2 (1.71 min) |

TABLE 2-continued

| Ex. # | Structure | Name | MS (ACPI+) M + 1 (retention time) |
|---|---|---|---|
| 294 | 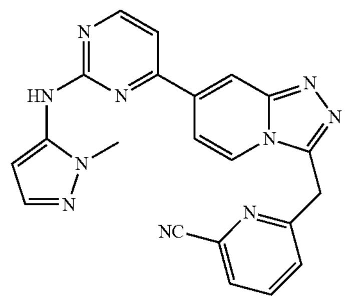 [SMILES: Cn1nccc1Nc1nccc(-c2ccn3c(Cc4cccc(C#N)n4)nnc3c2)n1] | 6-((7-(2-((1-methyl-1H-pyrazol-5-yl)amino)pyrimidin-4-yl)-[1,2,4]triazolo[4,3-a]pyridin-3-yl)methyl)picolinonitrile | 409.2 (1.99 min) |
| 295 | 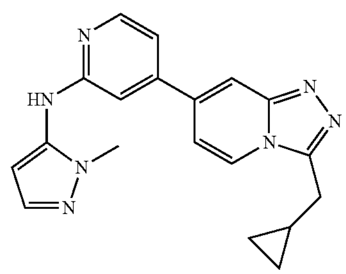 [SMILES: Cn1nccc1Nc1cc(-c2ccn3c(CC4CC4)nnc3c2)ccn1] | 4-(3-(cyclopropylmethyl)-[1,2,4]triazolo[4,3-a]pyridin-7-yl)-N-(1-methyl-1H-pyrazol-5-yl)pyridin-2-amine | 346.2 (1.83 min) |
| 296 | 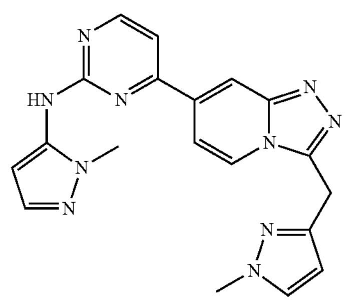 [SMILES: Cn1ccc(Cc2nnc3cc(-c4ccnc(Nc5ccnn5C)n4)ccn23)n1] | 4-(3-((1-methyl-1H-pyrazol-3-yl)methyl)-[1,2,4]triazolo[4,3-a]pyridin-7-yl)-N-(1-methyl-1H-pyrazol-5-yl)pyrimidin-2-amine | 387.2 (1.89 min) |
| 297 | 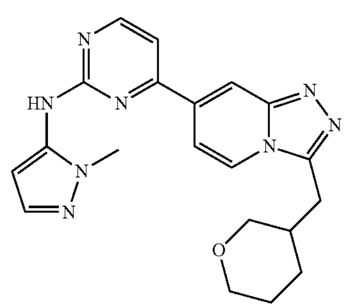 [SMILES: Cn1nccc1Nc1nccc(-c2ccn3c(CC4CCCOC4)nnc3c2)n1] | N-(1-methyl-1H-pyrazol-5-yl)-4-(3-((tetrahydro-2H-pyran-3-yl)methyl)-[1,2,4]triazolo[4,3-a]pyridin-7-yl)pyrimidin-2-amine | 391.2 (1.99 min) |
| 298 | 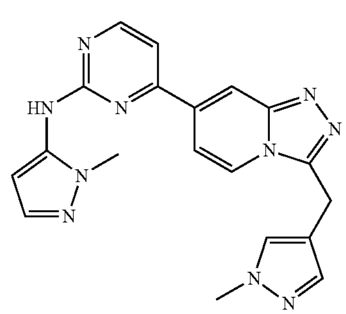 [SMILES: Cn1cc(Cc2nnc3cc(-c4ccnc(Nc5ccnn5C)n4)ccn23)cn1] | 4-(3-((1-methyl-1H-pyrazol-4-yl)methyl)-[1,2,4]triazolo[4,3-a]pyridin-7-yl)-N-(1-methyl-1H-pyrazol-5-yl)pyrimidin-2-amine | 387.2 (1.84 min) |

TABLE 2-continued

| Ex. # | Structure | Name | MS (ACPI+) M + 1 (retention time) |
|---|---|---|---|
| 299 | 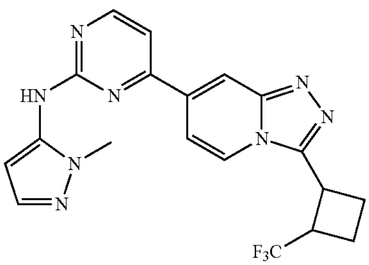 [SMILES: Cn1nccc1Nc1nccc(-c2ccn3c(C4CCC4C(F)(F)F)nnc3c2)n1] | N-(1-methyl-1H-pyrazol-5-yl)-4-(3-(2-(trifluoromethyl)cyclobutyl)-[1,2,4]triazolo[4,3-a]pyridin-7-yl)pyrimidin-2-amine | 415.2 (2.37 min) |
| 300 | 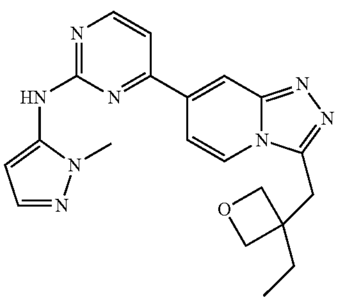 [SMILES: CCC1(Cc2nnc3cc(-c4ccnc(Nc5ccnn5C)n4)ccn23)COC1] | 4-(3-((3-ethyloxetan-3-yl)methyl)-[1,2,4]triazolo[4,3-a]pyridin-7-yl)-N-(1-methyl-1H-pyrazol-5-yl)pyrimidin-2-amine | 391.1 (2.06 min) |
| 301 | 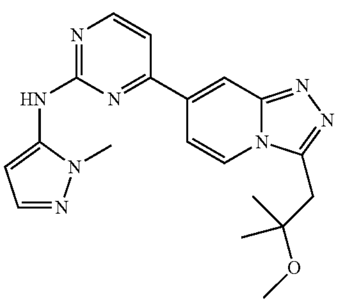 [SMILES: COC(C)(C)Cc1nnc2cc(-c3ccnc(Nc4ccnn4C)n3)ccn12] | 4-(3-(2-methoxy-2-methylpropyl)-[1,2,4]triazolo[4,3-a]pyridin-7-yl)-N-(1-methyl-1H-pyrazol-5-yl)pyrimidin-2-amine | 379.2 (1.14 min) |
| 302 | 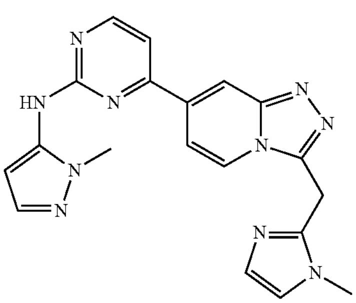 [SMILES: Cn1ccnc1Cc1nnc2cc(-c3ccnc(Nc4ccnn4C)n3)ccn12] | 4-(3-((1-methyl-1H-imidazol-2-yl)methyl)-[1,2,4]triazolo[4,3-a]pyridin-7-yl)-N-(1-methyl-1H-pyrazol-5-yl)pyrimidin-2-amine | 387.1 (0.52 min) |
| 303 | 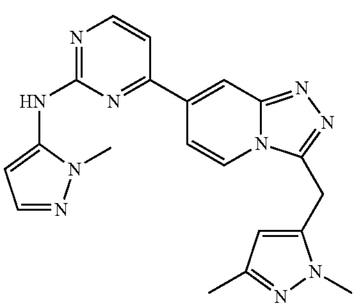 [SMILES: Cc1cc(Cc2nnc3cc(-c4ccnc(Nc5ccnn5C)n4)ccn23)n(C)n1] | 4-(3-((1,3-dimethyl-1H-pyrazol-5-yl)methyl)-[1,2,4]triazolo[4,3-a]pyridin-7-yl)-N-(1-methyl-1H-pyrazol-5-yl)pyrimidin-2-amine | 401.2 (1.04 min) |

TABLE 2-continued

| Ex. # | Structure | Name | MS (ACPI+) M + 1 (retention time) |
|---|---|---|---|
| 304 | 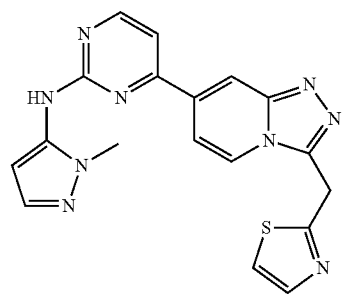 [SMILES: Cn1nccc1Nc1nccc(-c2ccn3c(Cc4nccs4)nnc3c2)n1] | N-(1-methyl-1H-pyrazol-5-yl)-4-(3-(thiazol-2-ylmethyl)-[1,2,4]triazolo[4,3-a]pyridin-7-yl)pyrimidin-2-amine | 390.1 |
| 305 | 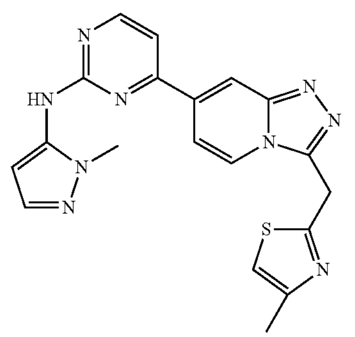 [SMILES: Cc1csc(Cc2nnc3cc(-c4ccnc(Nc5ccnn5C)n4)ccn23)n1] | N-(1-methyl-1H-pyrazol-5-yl)-4-(3-((4-methylthiazol-2-yl)methyl)-[1,2,4]triazolo[4,3-a]pyridin-7-yl)pyrimidin-2-amine | 404.1 |
| 306 | 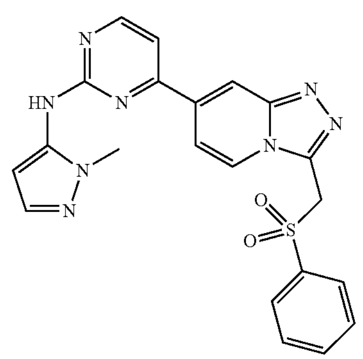 [SMILES: Cn1nccc1Nc1nccc(-c2ccn3c(CS(=O)(=O)c4ccccc4)nnc3c2)n1] | N-(1-methyl-1H-pyrazol-5-yl)-4-(3-((phenylsulfonyl)methyl)-[1,2,4]triazolo[4,3-a]pyridin-7-yl)pyrimidin-2-amine | 447.1 |
| 307 | 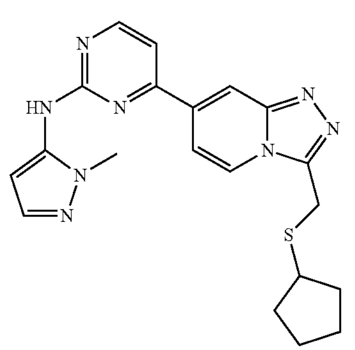 [SMILES: Cn1nccc1Nc1nccc(-c2ccn3c(CSC4CCCC4)nnc3c2)n1] | 4-(3-((cyclopentylthio)methyl)-[1,2,4]triazolo[4,3-a]pyridin-7-yl)-N-(1-methyl-1H-pyrazol-5-yl)pyrimidin-2-amine | 407.2 |

TABLE 2-continued

| Ex. # | Structure | Name | MS (ACPI+) M + 1 (retention time) |
|---|---|---|---|
| 308 | 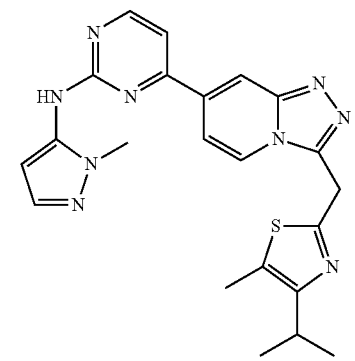 [SMILES: Cc1sc(Cc2nnc3cc(-c4ccnc(Nc5ccnn5C)n4)ccn23)nc1C(C)C] | 4-(3-((4-isopropyl-5-methylthiazol-2-yl)methyl)-[1,2,4]triazolo(4,3-a]pyridin-7-yl)-N-(1-methyl-1H-pyrazol-5-yl)pyrimidin-2-amine | 446.2 |
| 309 | 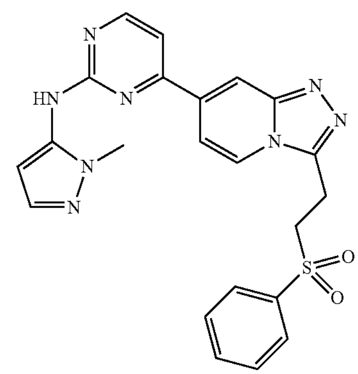 [SMILES: Cn1nccc1Nc1nccc(-c2ccn3c(CCS(=O)(=O)c4ccccc4)nnc3c2)n1] | N-(1-methyl-1H-pyrazol-5-yl)-4-(3-(2-(phenylsulfonyl)ethyl)-[1,2,4]triazolo[4,3-a]pyridin-7-yl)pyrimidin-2-amine | 461.1 |
| 310 | 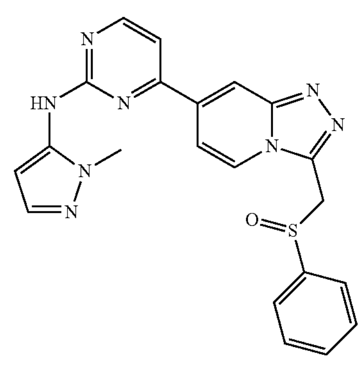 [SMILES: Cn1nccc1Nc1nccc(-c2ccn3c(CS(=O)c4ccccc4)nnc3c2)n1] | N-(1-methyl-1H-pyrazol-5-yl)-4-(3-((phenylsulfinyl)methyl)-[1,2,4]triazolo[4,3-a]pyridin-7-yl)pyrimidin-2-amine | 431.1 |
| 311 | 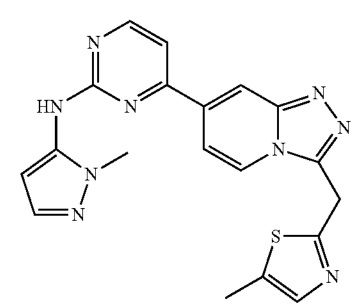 [SMILES: Cc1cnc(Cc2nnc3cc(-c4ccnc(Nc5ccnn5C)n4)ccn23)s1] | N-(1-methyl-1H-pyrazol-5-yl)-4-(3-((5-methylthiazol-2-yl)methyl)-[1,2,4]triazolo[4,3-a]pyridin-7-yl)pyrimidin-2-amine | 404.1 |

TABLE 2-continued

| Ex. # | Structure | Name | MS (ACPI+) M + 1 (retention time) |
|---|---|---|---|
| 312 | 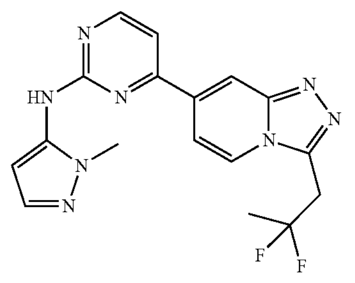 [SMILES: Cn1nccc1Nc1nccc(-c2ccn3c(CC(C)(F)F)nnc3c2)n1] | 4-(3-(2,2-difluoropropyl)-[1,2,4]triazolo[4,3-a]pyridin-7-yl)-N-(1-methyl-1H-pyrazol-5-yl)pyrimidin-2-amine | 371.1 (1.149 min) |
| 313 | 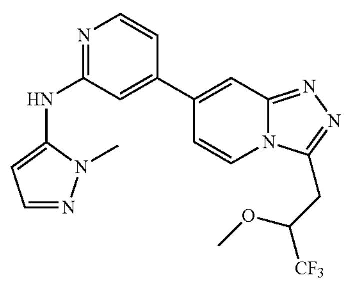 [SMILES: COC(Cc1nnc2cc(-c3ccnc(Nc4ccnn4C)c3)ccn12)C(F)(F)F] | N-(1-methyl-1H-pyrazol-5-yl)-4-(3-(3,3,3-trifluoro-2-methoxypropyl)-[1,2,4]triazolo[4,3-a]pyridin-7-yl)pyridin-2-amine | 418.1 (1.156 min) |
| 314 | 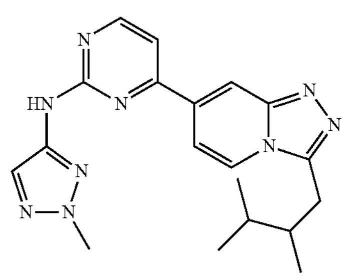 [SMILES: CC(C)C(C)Cc1nnc2cc(-c3ccnc(Nc4cnn(C)n4)n3)ccn12] | 4-(3-(2,3-dimethylbutyl)-[1,2,4]triazolo[4,3-a]pyridin-7-yl)-N-(2-methyl-2H-1,2,3-triazol-4-yl)pyrimidin-2-amine | 378.2 (1.491 min) |
| 315 | 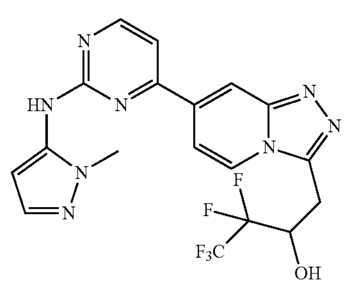 [SMILES: Cn1nccc1Nc1nccc(-c2ccn3c(CC(O)C(F)(F)C(F)(F)F)nnc3c2)n1] | 3,3,4,4,4-pentafluoro-1-(7-(2-((1-methyl-1H-pyrazol-5-yl)amino)pyrimidin-4-yl)-[1,2,4]triazolo[4,3-a]pyridin-3-yl)butan-2-ol | 455.1 (1.238 min) |
| 316 | 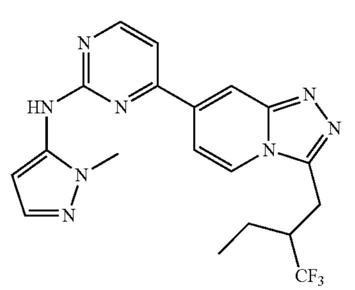 [SMILES: CCC(Cc1nnc2cc(-c3ccnc(Nc4ccnn4C)n3)ccn12)C(F)(F)F] | N-(1-methyl-1H-pyrazol-5-yl)-4-(3-(2-(trifluoromethyl)butyl)-[1,2,4]triazolo[4,3-a]pyridin-7-yl)pyrimidin-2-amine | 417.2 (1.368 min) |

TABLE 2-continued

| Ex. # | Structure | Name | MS (ACPI+) M + 1 (retention time) |
|---|---|---|---|
| 317 | 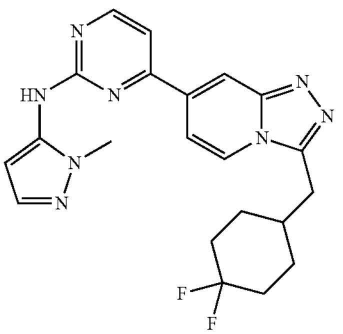 [SMILES: Cn1nccc1Nc1nccc(-c2ccn3c(CC4CCC(F)(F)CC4)nnc3c2)n1] | 4-(3-((4,4-difluorocyclohexyl)methyl)-[1,2,4]triazolo[4,3-a]pyridin-7-yl)-N-(1-methyl-1H-pyrazol-5-yl)pyrimidin-2-amine | 425.2 (1.322 min) |
| 318 | 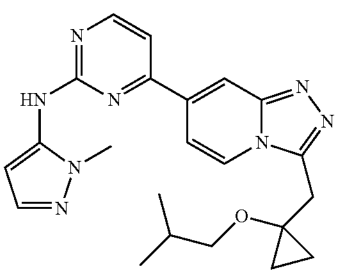 [SMILES: CC(C)COC1(Cc2nnc3cc(-c4ccnc(Nc5ccnn5C)n4)ccn23)CC1] | 4-(3-((1-isobutoxycyclopropyl)methyl)-[1,2,4]triazolo[4,3-a]pyridin-7-yl)-N-(1-methyl-1H-pyrazol-5-yl)pyrimidin-2-amine | 419.2 (1.412 min) |
| 319 | 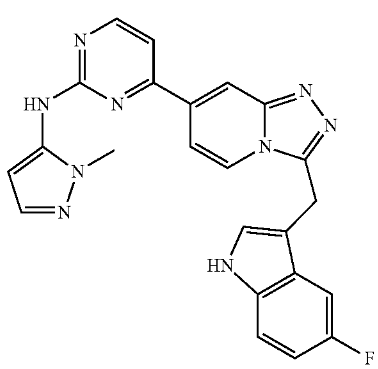 [SMILES: Cn1nccc1Nc1nccc(-c2ccn3c(Cc4c[nH]c5ccc(F)cc45)nnc3c2)n1] | 4-(3-((5-fluoro-1H-indol-3-yl)methyl)-[1,2,4]triazolo[4,3-a]pyridin-7-yl)-N-(1-methyl-1H-pyrazol-5-yl)pyrimidin-2-amine | 440.1 (1.269 min) |
| 320 | 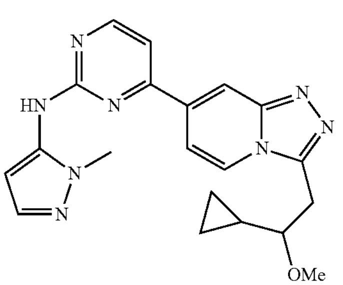 [SMILES: COC(Cc1nnc2cc(-c3ccnc(Nc4ccnn4C)n3)ccn12)C1CC1] | 4-(3-(2-cyclopropyl-2-methoxyethyl)-[1,2,4]triazolo[4,3-a]pyridin-7-yl)-N-(1-methyl-1H-pyrazol-5-yl)pyrimidin-2-amine | 391.1 (1.184 min) |

TABLE 2-continued

| Ex. # | Structure | Name | MS (ACPI+) M + 1 (retention time) |
|---|---|---|---|
| 321 | 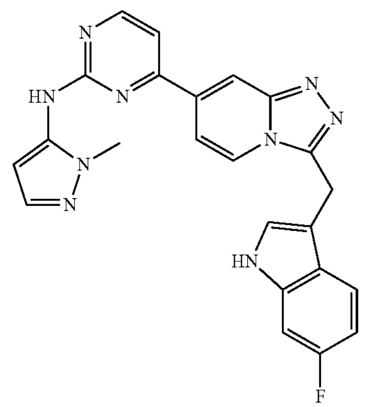 [SMILES: Cn1nccc1Nc1nccc(-c2ccn3c(Cc4c[nH]c5cc(F)ccc45)nnc3c2)n1] | 4-(3-((6-fluoro-1H-indol-3-yl(methyl)-[1,2,4]triazolo[4,3-a]pyridin-7-yl)-N-(1-methyl-1H-pyrazol-5-yl)pyrimidin-2-amine | 440.1 (1.274 min) |
| 322 | 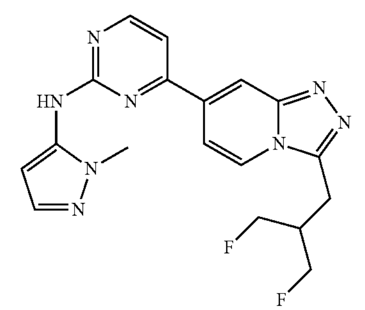 [SMILES: Cn1nccc1Nc1nccc(-c2ccn3c(CC(CF)CF)nnc3c2)n1] | 4-(3-(3-fluoro-2-(fluoromethyl)propyl)-[1,2,4]triazolo[4,3-a]pyridin-7-yl)-N-(1-methyl-1H-pyrazol-5-yl)pyrimidin-2-amine | 385.1 (1.127 min) |
| 323 | 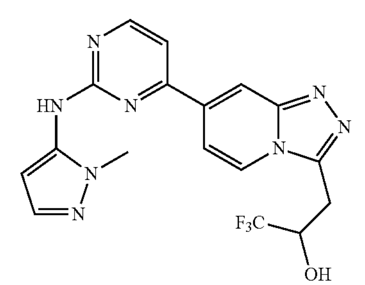 [SMILES: Cn1nccc1Nc1nccc(-c2ccn3c(CC(O)C(F)(F)F)nnc3c2)n1] | 1,1,1-trifluoro-3-(7-(2-((1-methyl-1H-pyrazol-5-yl)amino)pyrimidin-4-yl)-[1,2,4]triazolo[4,3-a]pyridin-3-yl)propan-2-ol | 405.1 (1.085 min) |
| 324 | 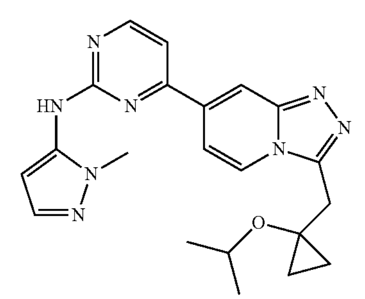 [SMILES: CC(C)OC1(Cc2nnc3cc(-c4ccnc(Nc5ccnn5C)n4)ccn23)CC1] | 4-(3-((1-isopropoxycyclopropyl)methyl)-[1,2,4]triazolo[4,3-a]pyridin-7-yl)-N-(1-methyl-1H-pyrazol-5-yl)pyrimidin-2-amine | 405.2 (1.246 min) |

| Ex. # | Structure | Name | MS (ACPI+) M + 1 (retention time) |
|---|---|---|---|
| 325 | 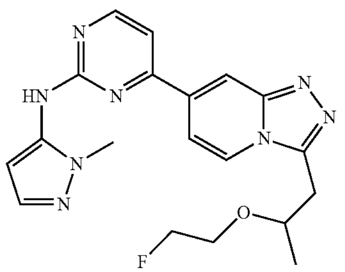 [SMILES: CC(Cc1nnc2cc(-c3ccnc(Nc4ccnn4C)n3)ccn12)OCCF] | 4-(3-(2-(2-fluoroethoxy)propyl)-[1,2,4]triazolo[4,3-a]pyridin-7-yl)-N-(1-methyl-1H-pyrazol-5-yl)pyrimidin-2-amine | 397.2 (1.117 min) |
| 326 | 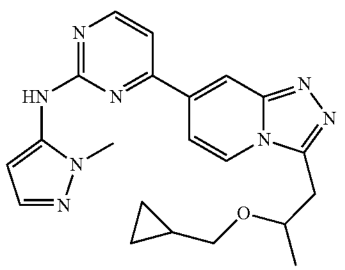 [SMILES: CC(Cc1nnc2cc(-c3ccnc(Nc4ccnn4C)n3)ccn12)OCC1CC1] | 4-(3-(2-(cyclopropylmethoxy)propyl)-[1,2,4]triazolo[4,3-a]pyridin-7-yl)-N-(1-methyl-1H-pyrazol-5-yl)pyrimidin-2-amine | 405.1 (1.255 min) |
| 327 | 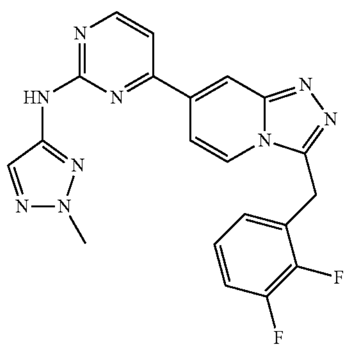 [SMILES: Cn1ncc(Nc2nccc(-c3ccn4c(Cc5cccc(F)c5F)nnc4c3)n2)n1] | 4-(3-(2,3-difluorobenzyl)-[1,2,4]triazolo[4,3-a]pyridin-7-yl)-N-(2-methyl-2H-1,2,3-triazol-4-yl)pyrimidin-2-amine | 420.1 (1.358 min) |
| 328 | 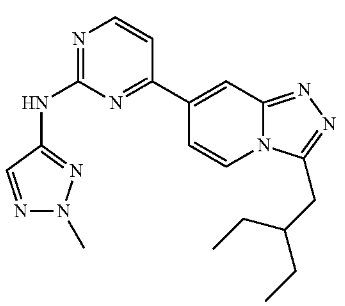 [SMILES: CCC(CC)Cc1nnc2cc(-c3ccnc(Nc4cnn(C)n4)n3)ccn12] | 4-(3-(2-ethylbutyl)-[1,2,4]triazolo[4,3-a]pyridin-7-yl)-N-(2-methyl-2H-1,2,3-triazol-4-yl)pyrimidin-2-amine | 378.2 (1.496 min) |
| 329 | 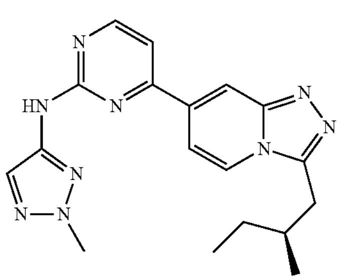 [SMILES: CC[C@H](C)Cc1nnc2cc(-c3ccnc(Nc4cnn(C)n4)n3)ccn12] | (S)-N-(2-methyl-2H-1,2,3-triazol-4-yl)-4-(3-(2-methylbutyl)-[1,2,4]triazolo[4,3-a]pyridin-7-yl)pyrimidin-2-amine | 364.2 (1.402 min) |

TABLE 2-continued

| Ex. # | Structure | Name | MS (ACPI+) M + 1 (retention time) |
|---|---|---|---|
| 330 | 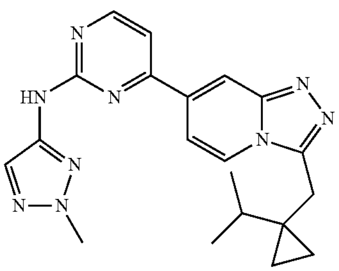 [SMILES: CC(C)C1(Cc2nnc3cc(-c4ccnc(Nc5cnn(C)n5)n4)ccn23)CC1] | 4-(3-((1-isopropylcyclopropyl)methyl)-[1,2,4]triazolo[4,3-a]pyridin-7-yl)-N-(2-methyl-2H-1,2,3-triazol-4-yl)pyrimidin-2-amine | 390.2 (1.520 min) |
| 331 | 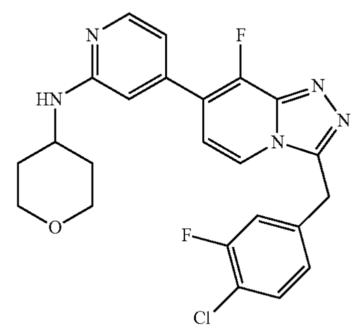 [SMILES: Fc1cc(Cc2nnc3c(F)c(-c4ccnc(NC5CCOCC5)c4)ccn23)ccc1Cl] | 4-(3-(4-chloro-3-(fluorobenzyl)-8-fluoro-[1,2,4]triazolo[4,3-a]pyridin-7-yl)-Nd-(tetrahydro-2H-pyran-4-yl)pyridin-2-amine | 456.1 (1.116 min) |
| 332 | 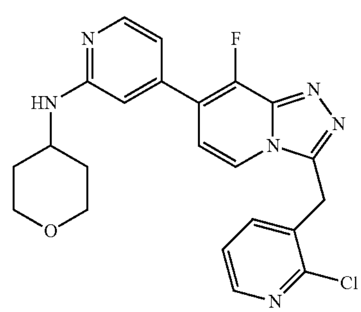 [SMILES: Fc1c(-c2ccnc(NC3CCOCC3)c2)ccn2c(Cc3cccnc3Cl)nnc12] | 4-(3-((2-chloropyridin-3-yl)methyl)-8-fluoro-[1,2,4]triazolo[4,3-a]pyridin-7-yl)-N-(tetrahydro-2H-pyran-4-yl)pyridin-2-amine | 439.1 (0.818 min) |
| 333 | 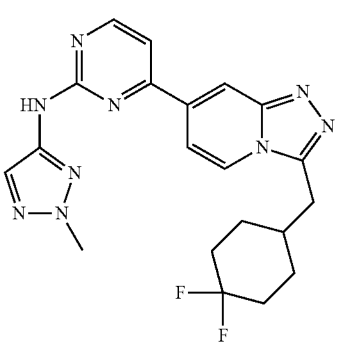 [SMILES: Cn1ncc(Nc2nccc(-c3ccn4c(CC5CCC(F)(F)CC5)nnc4c3)n2)n1] | 4-(3-((4,4-difluorocyclohexyl)methyl)-[1,2,4]triazolo[4,3-a]pyridin-7-yl)-N-(2-methyl-2H-1,2,3-triazol-4-yl)pyrimidin-2-amine | 426.2 (1.434 min) |

| Ex. # | Structure | Name | MS (ACPI+) M + 1 (retention time) |
|---|---|---|---|
| 334 | 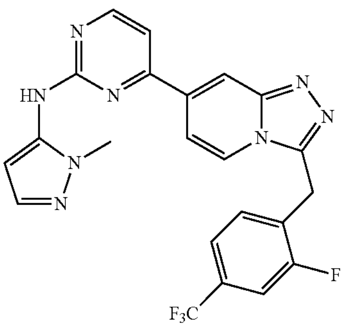 [SMILES: Cn1nccc1Nc1nccc(-c2ccn3c(Cc4ccc(C(F)(F)F)cc4F)nnc3c2)n1] | 4-(3-(2-fluoro-4-(trifluoromethyl)benzyl)-[1,2,4]triazolo[4,3-a]pyridin-7-yl)-N-(1-methyl-1H-pyrazol-5-yl)pyrimidin-2-amine | 469.1 (2.52 min) |
| 335 | 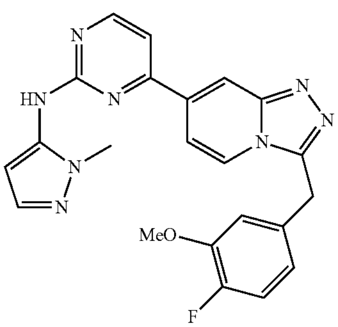 [SMILES: COc1cc(Cc2nnc3cc(-c4ccnc(Nc5ccnn5C)n4)ccn23)ccc1F] | 4-(3-(4-fluoro-3-methoxybenzyl)-[1,2,4]triazolo[4,3-a]pyridin-7-yl)-N-(1-methyl-1H-pyrazol-5-yl)pyrimidin-2-amine | 431.2 (2.31 min) |
| 336 | 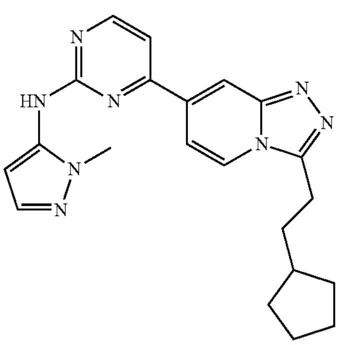 [SMILES: Cn1nccc1Nc1nccc(-c2ccn3c(CCC4CCCC4)nnc3c2)n1] | 4-(3-(2-cyclopentylethyl)-[1,2,4]triazolo[4,3-a]pyridin-7-yl)-N-(1-methyl-1H-pyrazol-5-yl)pyrimidin-2-amine | 389.2 (2.48 min) |
| 337 | 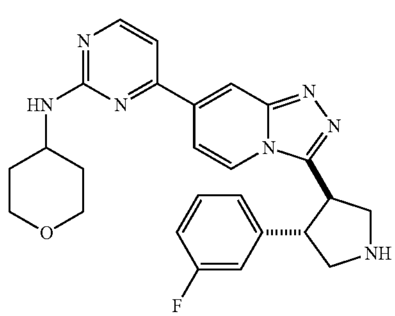 | 4-(3-((3R*,4S*)-4-(3-fluorophenyl)pyrrolidin-3-yl)-[1,2,4]triazolo[4,3-a]pyridin-7-yl)-N-(tetrahydro-2H-pyran-4-yl)pyrimidin-2-amine | 460.2 (1.84 min) |

TABLE 2-continued

| Ex. # | Structure | Name | MS (ACPI+) M + 1 (retention time) |
|---|---|---|---|
| 338 | 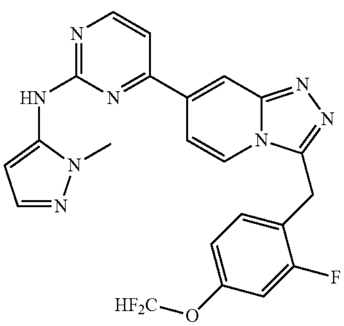 | 4-(3-(4-(difluoromethoxy)-2-fluorobenzyl)-[1,2,4]triazolo[4,3-a]pyridin-7-yl)-N-(1-methyl-1H-pyrazol-5-yl)pyrimidin-2-amine | 467.2 (2.43 min) |
| 339 | 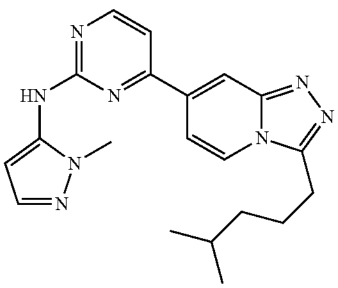 [SMILES: CC(C)CCCc1nnc2cc(-c3ccnc(Nc4ccnn4C)n3)ccn12] | N-(1-methyl-1H-pyrazol-5-yl)-4-(3-(4-methylpentyl)-[1,2,4]triazolo[4,3-a]pyridin-7-yl)pyrimidin-2-amine | 377.2 (1.77 min) |
| 340 | 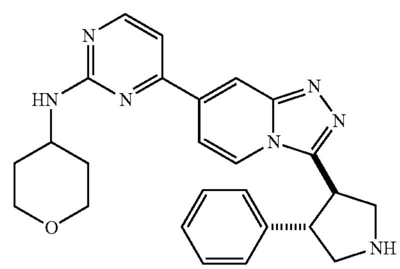 | 4-(3-((3R*,4S*)-4-phenylpyrrolidin-3-yl)-[1,2,4]triazolo[4,3-a]pyridin-7-yl)-N-(tetrahydro-2H-pyran-4-yl)pyrimidin-2-amine | 442.2 (1.82 min) |
| 341 | 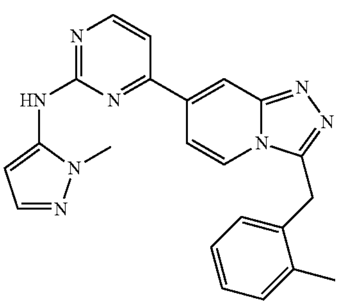 [SMILES: Cc1ccccc1Cc1nnc2cc(-c3ccnc(Nc4ccnn4C)n3)ccn12] | N-(1-methyl-1H-pyrazol-5-yl)-4-(3-(2-methylbenzyl)-[1,2,4]triazolo[4,3-a]pyridin-7-yl)pyrimidin-2-amine | 397.2 (2.29 min) |
| 342 | 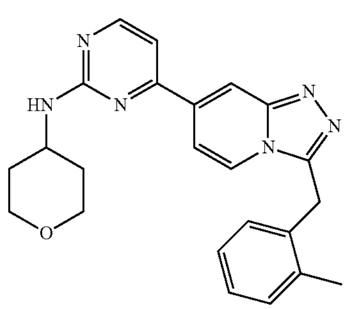 [SMILES: Cc1ccccc1Cc1nnc2cc(-c3ccnc(NC4CCOCC4)n3)ccn12] | 4-(3-(2-methylbenzyl)-[1,2,4]triazolo[4,3-a]pyridin-7-yl)-N-(tetrahydro-2H-pyran-4-yl)pyrimidin-2-amine | 401.2 (2.32 min) |

TABLE 2-continued

| Ex. # | Structure | Name | MS (ACPI+) M + 1 (retention time) |
|---|---|---|---|
| 343 | 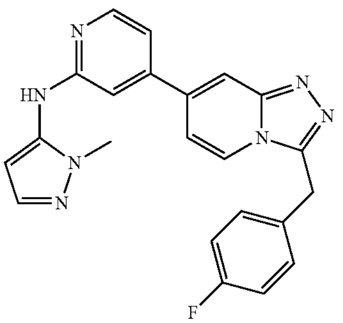 [SMILES: Cn1nccc1Nc1cc(-c2ccn3c(Cc4ccc(F)cc4)nnc3c2)ccn1] | 4-(3-(4-fluorobenzyl)-[1,2,4]triazolo[4,3-a]pyridin-7-yl)-N-(1-methyl-1H-pyrazol-5-yl)pyridin-2-amine | 400.1 (2.17 min) |
| 344 | 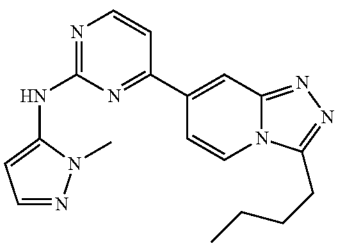 [SMILES: CCCCc1nnc2cc(-c3ccnc(Nc4ccnn4C)n3)ccn12] | 4-(3-butyl-[1,2,4]triazolo[4,3-a]pyridin-7-yl)-N-(1-methyl-1H-pyrazol-5-yl)pyrimidin-2-amine | 349.2 (2.19 min) |
| 345 | 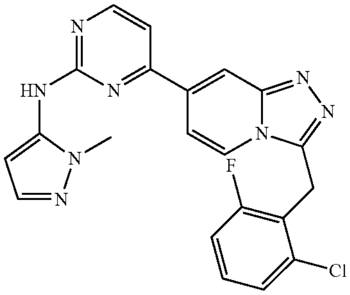 [SMILES: Cn1nccc1Nc1nccc(-c2ccn3c(Cc4c(F)cccc4Cl)nnc3c2)n1] | 4-(3-(2-chloro-6-fluorobenzyl)-[1,2,4]triazolo[4,3-a]pyridin-7-yl)-N-(1-methyl-1H-pyrazol-5-yl)pyrimidin-2-amine | 435.1 (2.28 min) |
| 346 | 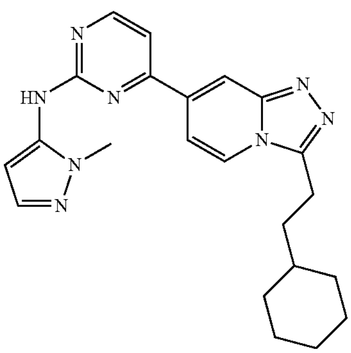 [SMILES: Cn1nccc1Nc1nccc(-c2ccn3c(CCC4CCCCC4)nnc3c2)n1] | 4-(3-(2-cyclohexylethyl)-[1,2,4]triazolo[4,3-a]pyridin-7-yl)-N-(1-methyl-1H-pyrazol-5-yl)pyrimidin-2-amine | 403.2 (2.62 min) |
| 347 | 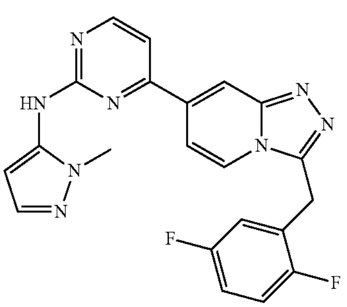 [SMILES: Cn1nccc1Nc1nccc(-c2ccn3c(Cc4cc(F)ccc4F)nnc3c2)n1] | 4-(3-(2,5-difluorobenzyl)-[1,2,4]triazolo[4,3-a]pyridin-7-yl)-N-(1-methyl-1H-pyrazol-5-yl)pyrimidin-2-amine | 419.1 (2.23 min) |

TABLE 2-continued

| Ex. # | Structure | Name | MS (ACPI+) M + 1 (retention time) |
|---|---|---|---|
| 348 | 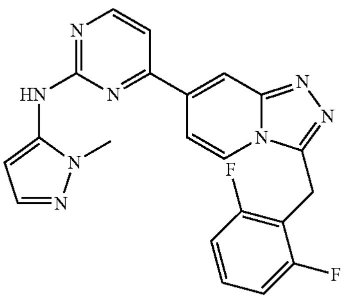 [SMILES: Cn1nccc1Nc1nccc(-c2ccn3c(Cc4c(F)cccc4F)nnc3c2)n1] | 4-(3-(2,6-difluorobenzyl)-[1,2,4]triazolo[4,3-a]pyridin-7-yl)-N-(1-methyl-1H-pyrazol-5-yl)pyrimidin-2-amine | 419.1 (2.21 min) |
| 349 | 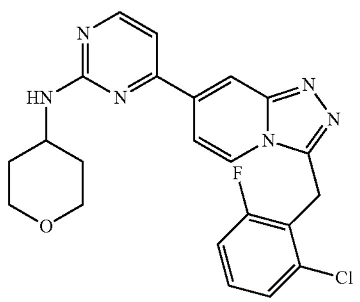 [SMILES: Fc1cccc(Cl)c1Cc1nnc2cc(-c3ccnc(NC4CCOCC4)n3)ccn12] | 4-(3-(2-chloro-6-fluorobenzyl)-[1,2,4]triazolo[4,3-a]pyridin-7-yl)-N-(tetrahydro-2H-pyran-4-yl)pyrimidin-2-amine | 439.1 (2.31 min) |
| 350 | 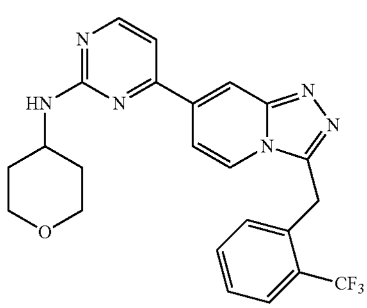 [SMILES: FC(F)(F)c1ccccc1Cc1nnc2cc(-c3ccnc(NC4CCOCC4)n3)ccn12] | N-(tetrahydro-2H-pyran-4-yl)-4-(3-(2-(trifluoromethyl)benzyl)-[1,2,4]triazolo[4,3-a]pyridin-7-yl)pyrimidin-2-amine | 455.2 (2.45 min) |
| 351 | 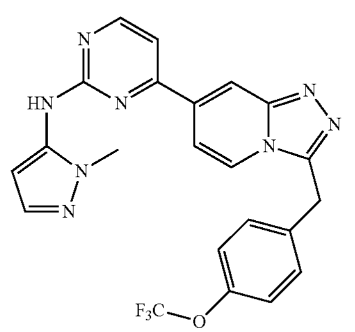 [SMILES: Cn1nccc1Nc1nccc(-c2ccn3c(Cc4ccc(OC(F)(F)F)cc4)nnc3c2)n1] | N-(1-methyl-1H-pyrazol-5-yl)-4-(3-(4-(trifluoromethoxy)benzyl)-[1,2,4]triazolo[4,3-a]pyridin-7-yl)pyrimidin-2-amine | 467.1 (2.57 min) |

TABLE 2-continued

| Ex. # | Structure | Name | MS (ACPI+) M + 1 (retention time) |
|---|---|---|---|
| 352 | 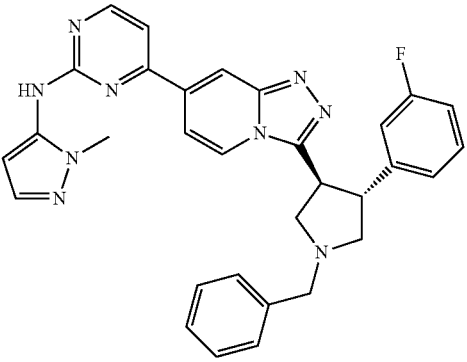 [SMILES: Cn1nccc1Nc1nccc(-c2ccn3c([C@@H]4CN(Cc5ccccc5)C[C@H]4c4cccc(F)c4)nnc3c2)n1] | 4-(3 -((3S,4R)-1-benzyl-4-(3-fluorophenyl)pyrrolidin-3-yl)-[1,2,4]triazolo[4,3-a]pyridin-7-yl)-N-(1-methyl-1H-pyrazol-5-yl)pyrimidin-2-amine | 546.2 (2.11 min) |
| 353 | 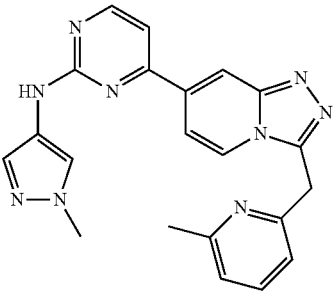 [SMILES: Cc1cccc(Cc2nnc3cc(-c4ccnc(Nc5cnn(C)c5)n4)ccn23)n1] | N-(1-methyl-1H-pyrazol-4-yl)-4-(3-((6-methylpyridin-2-yl)methyl)-[1,2,4]triazolo[4,3-a]pyridin-7-yl)pyrimidin-2-amine | 398.2 (1.72 min) |
| 354 | 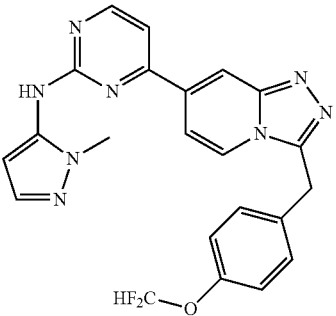 | 4-(3-(4-(difluoromethoxy)benzyl)-[1,2,4]triazolo[4,3-a]pyridin-7-yl)-N-(1-methyl-1H-pyrazol-5-yl)pyridin-2-amine | 448.2 (2.28 min) |
| 355 | 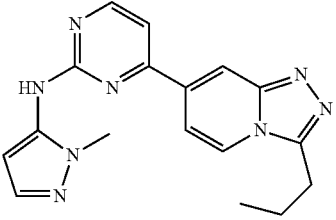 [SMILES: CCCc1nnc2cc(-c3ccnc(Nc4ccnn4C)n3)ccn12] | N-(1-methyl-1H-pyrazol-5-yl)-4-(3-propyl-[1,2,4]triazolo[4,3-a]pyridin-7-yl)pyrimidin-2-amine | 335.2 (2.03 min) |

TABLE 2-continued

| Ex. # | Structure | Name | MS (ACPI+) M + 1 (retention time) |
|---|---|---|---|
| 356 | 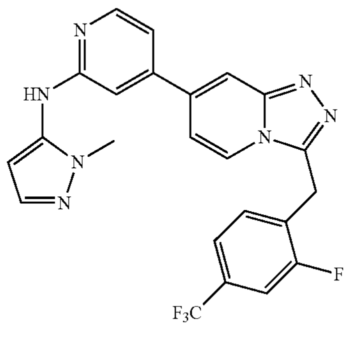 | 4-(3-(2-fluoro-4-(trifluoromethyl)benzyl)-[1,2,4]triazolo[4,3-a]pyridin-7-yl)-N-(1-methyl-1H-pyrazol-5-yl)pyridin-2-amine | 468.1 (2.43 min) |
| 357 | 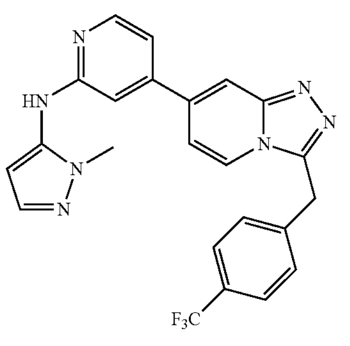 [SMILES: Cn1nccc1Nc1cc(-c2ccn3c(Cc4ccc(C(F)(F)F)cc4)nnc3c2)ccn1] | N-(1-methyl-1H-pyrazol-5-yl)-4-(3-(4-(trifluoromethyl)benzyl)-[1,2,4]triazolo[4,3-a]pyridin-7-yl)pyridin-2-amine | 450.1 (2.41 min) |
| 358 | 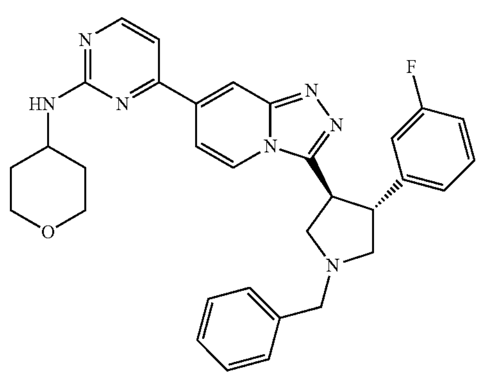 [SMILES: Fc1cccc([C@@H]2CN(Cc3ccccc3)C[C@H]2c2nnc3cc(-c4ccnc(NC5CCOCC5)n4)ccn23)c1] | 4-(3-((3S,4R)-1-benzyl-4-(3-fluorophenyl)pyrrolidin-3-yl)-[1,2,4]triazolo[4,3-a]pyridin-7-yl)-N-(tetrahydro-2H-pyran-4-yl)pyrimidin-2-amine | 550.2 (2.15 min) |
| 359 | 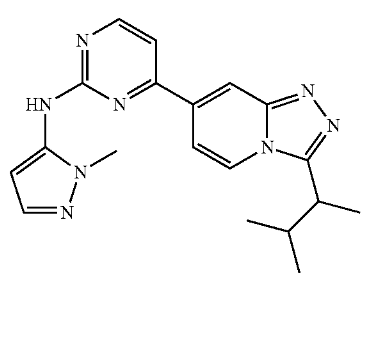 [SMILES: CC(C)C(C)c1nnc2cc(-c3ccnc(Nc4ccnn4C)n3)ccn12] | N-(1-methyl-1H-pyrazol-5-yl)-4-(3-(3-methylbutan-2-yl)-[1,2,4]triazolo[4,3-a]pyridin-7-yl)pyrimidin-2-amine | 363.2 (2.31 min) |

TABLE 2-continued

| Ex. # | Structure | Name | MS (ACPI+) M + 1 (retention time) |
|---|---|---|---|
| 360 | 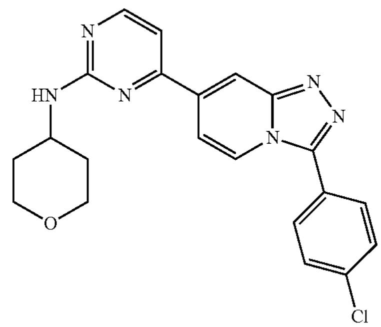 [SMILES: Clc1ccc(-c2nnc3cc(-c4ccnc(NC5CCOCC5)n4)ccn23)cc1] | 4-(3-(4-chlorophenyl)-[1,2,4]triazolo[4,3-a]pyridin-7-yl)-N-(tetrahydro-2H-pyran-4-yl)pyrimidin-2-amine | 407.1 (2.56 min) |
| 361 | 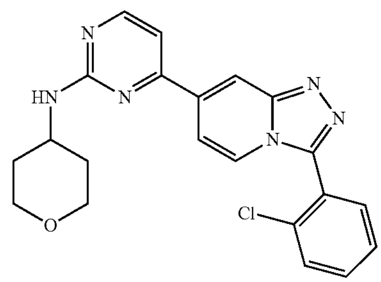 [SMILES: Clc1ccccc1-c1nnc2cc(-c3ccnc(NC4CCOCC4)n3)ccn12] | 4-(3-(2-chlorophenyl)-[1,2,4]triazolo[4,3-a]pyridin-7-yl)-N-(tetrahydro-2H-pyran-4-yl)pyrimidin-2-amine | 407.1 (2.43 min) |
| 362 | 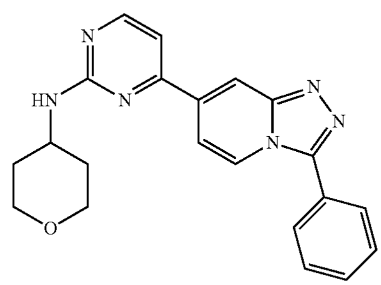 [SMILES: c1ccc(-c2nnc3cc(-c4ccnc(NC5CCOCC5)n4)ccn23)cc1] | 4-(3-phenyl-[1,2,4]triazolo[4,3-a]pyridin-7-yl)-N-(tetrahydro-2H-pyran-4-yl)pyrimidin-2-amine | 373.2 (2.19 min) |
| 363 | 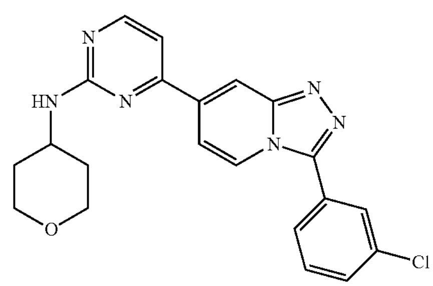 [SMILES: Clc1cccc(-c2nnc3cc(-c4ccnc(NC5CCOCC5)n4)ccn23)c1] | 4-(3-(3-chlorophenyl)-[1,2,4]triazolo[4,3-a]pyridin-7-yl)-N-(tetrahydro-2H-pyran-4-yl)pyrimidin-2-amine | 407.1 (2.40 min) |
| 364 | 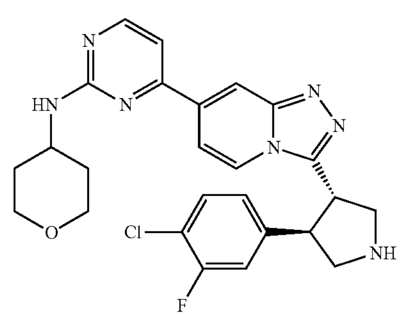 [SMILES: Fc1cc([C@@H]2CNC[C@H]2c2nnc3cc(-c4ccnc(NC5CCOCC5)n4)ccn23)ccc1Cl] | 4-(3-((3S,4R)-4-(4-chloro-3-fluorophenyl)pyrrolidin-3-yl)-[1,2,4]triazolo[4,3-a]pyridin-7-yl)-N-(tetrahydro-2H-pyran-4-yl)pyrimidin-2-amine | 494.1 (2.00 min) |

TABLE 2-continued

| Ex. # | Structure | Name | MS (ACPI+) M + 1 (retention time) |
|---|---|---|---|
| 365 | 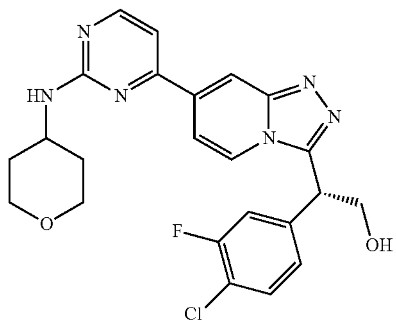 [SMILES: OC[C@H](c1ccc(Cl)c(F)c1)c1nnc2cc(-c3ccnc(NC4CCOCC4)n3)ccn12] | (R)-2-(4-chloro-3-fluorophenyl)-2-(7-(2-((tetrahydro-2H-pyran-4-yl)amino)pyrimidin-4-yl)-[1,2,4]triazolo[4,3-a]pyridin-3-yl)ethanol | 469.1 (2.32 min) |
| 366 | 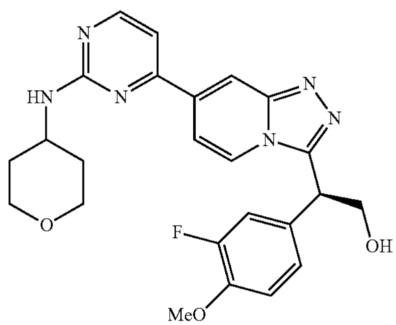 [SMILES: COc1ccc([C@H](CO)c2nnc3cc(-c4ccnc(NC5CCOCC5)n4)ccn23)cc1F] | (S)-2-(3-fluoro-4-methoxyphenyl)-2-(7-(2-((tetrahydro-2H-pyran-4-yl)amino)pyrimidin-4-yl)-[1,2,4]triazolo[4,3-a]pyridin-3-yl)ethanol | 465.2 (2.11 min) |
| 367 | 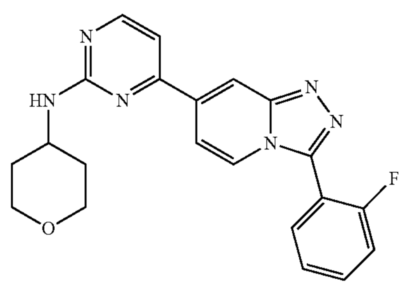 [SMILES: Fc1ccccc1-c1nnc2cc(-c3ccnc(NC4CCOCC4)n3)ccn12] | 4-(3-(2-fluorophenyl)-[1,2,4]triazolo[4,3-a]pyridin-7-yl)-N-(tetrahydro-2H-pyran-4-yl)pyrimidin-2-amine | 391.2 (2.21 min) |
| 368 | 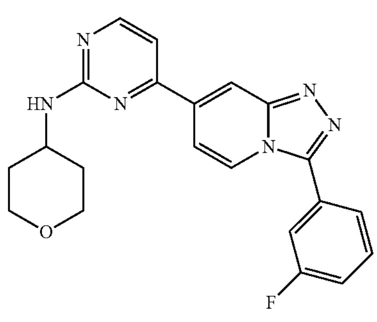 [SMILES: Fc1cccc(-c2nnc3cc(-c4ccnc(NC5CCOCC5)n4)ccn23)c1] | 4-(3-(3-fluorophenyl)-[1,2,4]triazolo[4,3-a]pyridin-7-yl)-N-(tetrahydro-2H-pyran-4-yl)pyrimidin-2-amine | 391.1 (2.25 min) |

TABLE 2-continued

| Ex. # | Structure | Name | MS (ACPI+) M + 1 (retention time) |
|---|---|---|---|
| 369 | 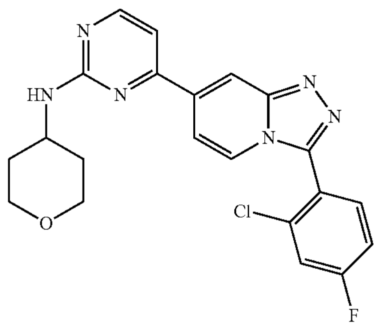 [SMILES: Fc1ccc(-c2nnc3cc(-c4ccnc(NC5CCOCC5)n4)ccn23)c(Cl)c1] | 4-(3-(2-chloro-4-fluorophenyl)-[1,2,4]triazolo[4,3-a]pyridin-7-yl)-N-(tetrahydro-2H-pyran-4-yl)pyrimidin-2-amine | 425.1 (2.35 min) |
| 370 | 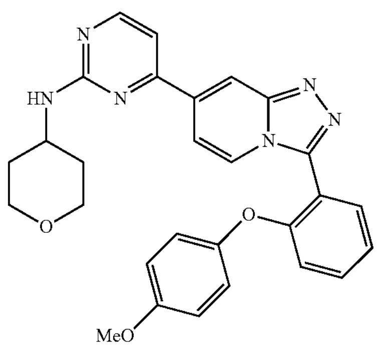 [SMILES: COc1ccc(Oc2ccccc2-c2nnc3cc(-c4ccnc(NC5CCOCC5)n4)ccn23)cc1] | 4-(3-(2-(4-methoxyphenoxy)phenyl)-[1,2,4]triazolo[4,3-a]pyridin-7-yl)-N-(tetrahydro-2H-pyran-4-yl)pyrimidin-2-amine | 495.2 (2.56 min) |
| 371 | 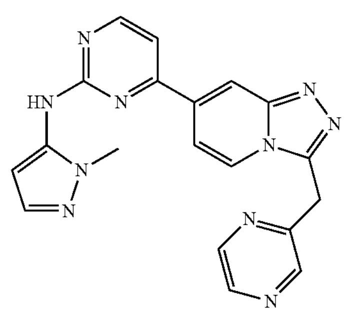 [SMILES: Cn1nccc1Nc1nccc(-c2ccn3c(Cc4cnccn4)nnc3c2)n1] | N-(1-methyl-1H-pyrazol-5-yl)-4-(3-(pyrazin-2-ylmethyl)-[1,2,4]triazolo[4,3-a]pyridin-7-yl)pyrimidin-2-amine | 385.1 (1.76 min) |
| 372 | 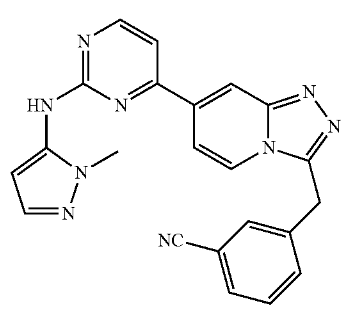 [SMILES: Cn1nccc1Nc1nccc(-c2ccn3c(Cc4cccc(C#N)c4)nnc3c2)n1] | 3-((7-(2-((1-methyl-1H-pyrazol-5-yl)amino)pyrimidin-4-yl)-[1,2,4]triazolo[4,3-a]pyridin-3-yl)methyl)benzonitrile | 408.2 (2.14 min) |

TABLE 2-continued

| Ex. # | Structure | Name | MS (ACPI+) M + 1 (retention time) |
|---|---|---|---|
| 373 | 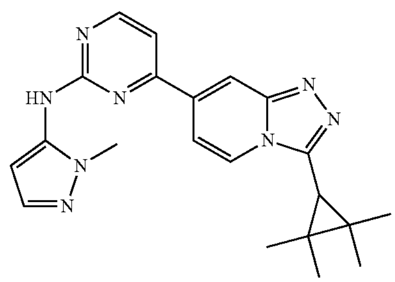 [SMILES: Cn1nccc1Nc1nccc(-c2ccn3c(C4C(C)(C)C4(C)C)nnc3c2)n1] | N-(1-methyl-1H-pyrazol-5-yl)-4-(3-(2,2,3,3-tetramethylcyclopropyl)-[1,2,4]triazolo[4,3-a]pyridin-7-yl)pyrimidin-2-amine | 389.2 (2.43 min) |
| 374 | 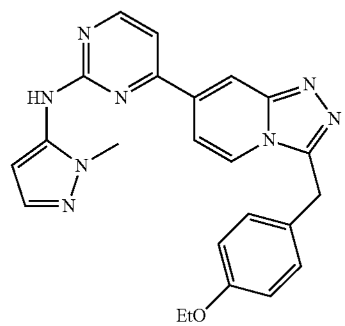 [SMILES: CCOc1ccc(Cc2nnc3cc(-c4ccnc(Nc5ccnn5C)n4)ccn23)cc1] | 4-(3-(4-ethoxybenzyl)-[1,2,4]triazolo[4,3-a]pyridin-7-yl)-N-(1-methyl-1H-pyrazol-5-yl)pyrimidin-2-amine | 427.2 (2.37 min) |
| 375 | 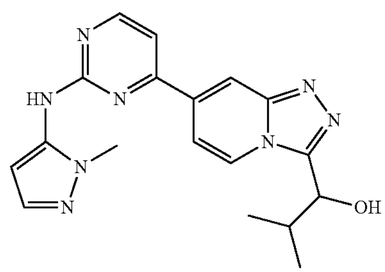 | 2-methyl-1-(7-(2-((1-methyl-1H-pyrazol-5-yl)amino)pyrimidin-4-yl)-[1,2,4]triazolo[4,3-a]pyridin-3-yl)propan-1-ol | 365.1 (0.87 min) |
| 376 | 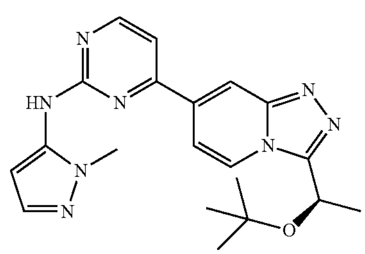 [SMILES: C[C@@H](OC(C)(C)C)c1nnc2cc(-c3ccnc(Nc4ccnn4C)n3)ccn12] | (R)-4-(3-(1-(tert-butoxy)ethyl)-[1,2,4]triazolo[4,3-a]pyridin-7-yl)-N-(1-methyl-1H-pyrazol-5-yl)pyrimidin-2-amine | 393.2 (1.07 min) |
| 377 | 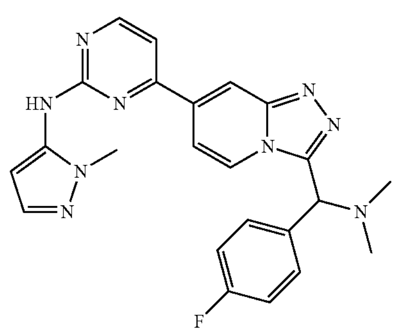 [SMILES: CN(C)C(c1ccc(F)cc1)c1nnc2cc(-c3ccnc(Nc4ccnn4C)n3)ccn12] | 4-(3-((dimethylamino)(4-fluorophenyl)methyl)-[1,2,4]triazolo[4,3-a]pyridin-7-yl)-N-(1-methyl-1H-pyrazol-5-yl)pyrimidin-2-amine | 444.2 (1.12 min) |

TABLE 2-continued

| Ex. # | Structure | Name | MS (ACPI+) M + 1 (retention time) |
|---|---|---|---|
| 378 | 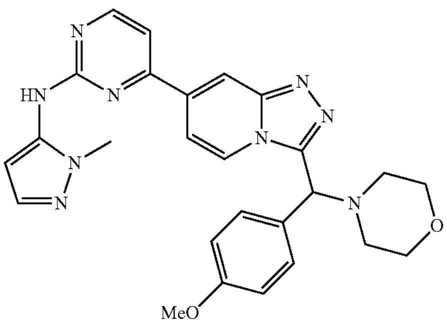 [SMILES: COc1ccc(C(c2nnc3cc(-c4ccnc(Nc5ccnn5C)n4)ccn23)N2CCOCC2)cc1] | 4-(3-((4-methoxyphenyl)(morpholino)methyl)-[1,2,4]triazolo[4,3-a]pyridin-7-yl)-N-(1-methyl-1H-pyrazol-5-yl)pyrimidin-2-amine | 496.2 (M − H) (1.05 min) |
| 379 | 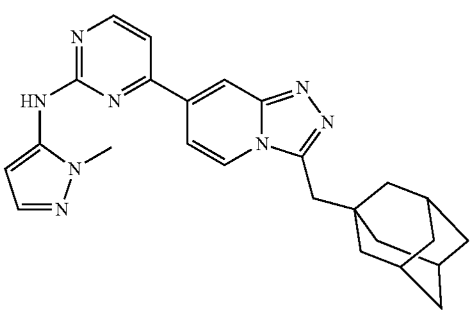 [SMILES: Cn1nccc1Nc1nccc(-c2ccn3c(CC45CC6CC(CC(C6)C4)C5)nnc3c2)n1] | 4-(3-((1s,3s)-adamantan-1-ylmethyl)-[1,2,4]triazolo[4,3-a]pyridin-7-yl)-N-(1-methyl-1H-pyrazol-5-yl)pyrimidin-2-amine | 441.2 (1.32 min) |
| 380 | 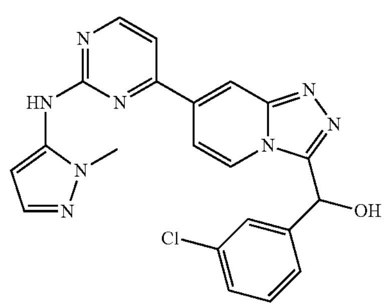 [SMILES: Cn1nccc1Nc1nccc(-c2ccn3c(C(O)c4cccc(Cl)c4)nnc3c2)n1] | (3-chlorophenyl)(7-(2-((1-methyl-1H-pyrazol-5-yl)amino)pyrimidin-4-yl)-[1,2,4]triazolo[4,3-a]pyridin-3-yl)methanol | 431.1 (M − H) (1.06 min) |
| 381 | 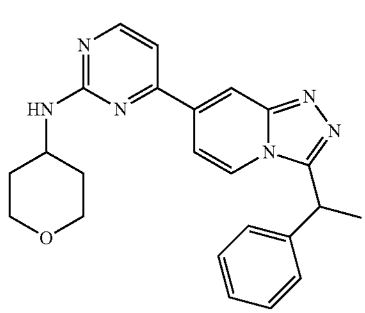 [SMILES: CC(c1ccccc1)c1nnc2cc(-c3ccnc(NC4CCOCC4)n3)ccn12] | 4-(3-(1-phenylethyl)-[1,2,4]triazolo[4,3-a]pyridin-7-yl)-N-(tetrahydro-2H-pyran-4-yl)pyrimidin-2-amine | 401.2 |

TABLE 2-continued

| Ex. # | Structure | Name | MS (ACPI+) M + 1 (retention time) |
|---|---|---|---|
| 382 | 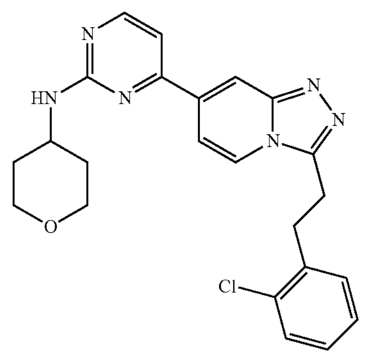 [SMILES: Clc1ccccc1CCc1nnc2cc(-c3ccnc(NC4CCOCC4)n3)ccn12] | 4-(3-(2-chlorophenethyl)-[1,2,4]triazolo[4,3-a]pyridin-7-yl)-N-(tetrahydro-2H-pyran-4-yl)pyrimidin-2-amine | 435.1 |
| 383 | 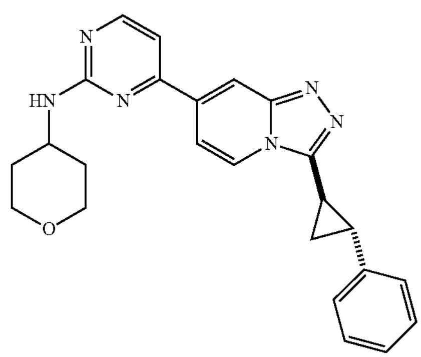 | 4-(3-((1R*,2R*)-2-phenylcyclopropyl)-[1,2,4]triazolo[4,3-a]pyridin-7-yl)-N-(tetrahydro-2H-pyran-4-yl)pyrimidin-2-amine | 413.2 |
| 384 | 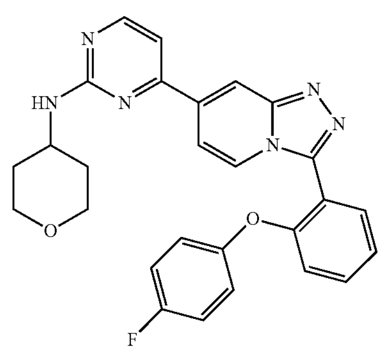 [SMILES: Fc1ccc(Oc2ccccc2-c2nnc3cc(-c4ccnc(NC5CCOCC5)n4)ccn23)cc1] | 4-(3-(2-(4-fluorophenoxy)phenyl)-[1,2,4]triazolo[4,3-a]pyridin-7-yl)-N-(tetrahydro-2H-pyran-4-yl)pyrimidin-2-amine | 483.1 |
| 385 | 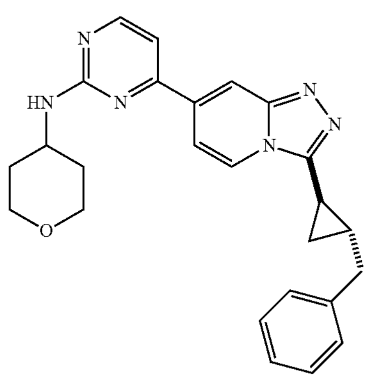 | 4-(3-((1R*,2S*)-2-benzylcyclopropyl)-[1,2,4]triazolo[4,3-a]pyridin-7-yl)-N-(tetrahydro-2H-pyran-4-yl)pyrimidin-2-amine | 427.2 |

TABLE 2-continued

| Ex. # | Structure | Name | MS (ACPI+) M + 1 (retention time) |
|---|---|---|---|
| 386 | 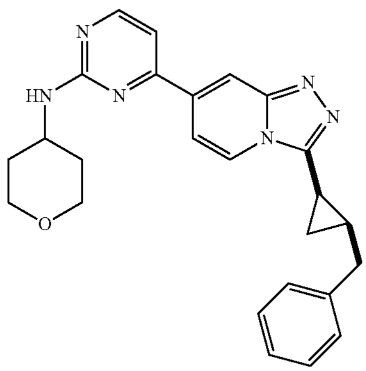 | 4-(3-((1R*,2R*)-2-benzylcyclopropyl)-[1,2,4]triazolo[4,3-a]pyridin-7-yl)-N-(tetrahydro-2H-pyran-4-yl)pyrimidin-2-amine | 427.2 |
| 387 | 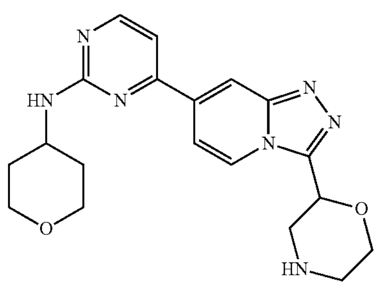 | 4-(3-(morpholin-2-yl)-[1,2,4]triazolo[4,3-a]pyridin-7-yl)-N-(tetrahydro-2H-pyran-4-yl)pyrimidin-2-amine | 382.2 |
| 388 | 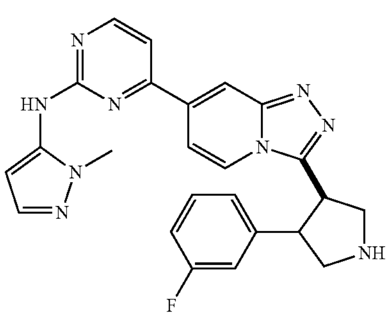 | 4-(3-((3R*,4S*)-4-(3-fluorophenyl)pyrrolidin-3-yl)-[1,2,4]triazolo[4,3-a]pyridin-7-yl)-N-(1-methyl-1H-pyrazol-5-yl)pyrimidin-2-amine | 456.2 |
| 389 | 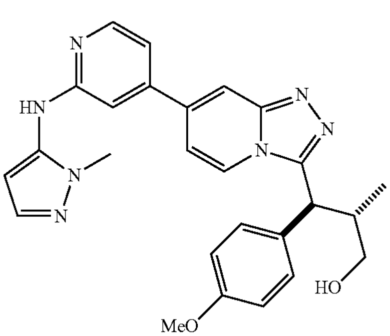 [SMILES: COc1ccc([C@@H](c2nnc3cc(-c4ccnc(Nc5ccnn5C)c4)ccn23)[C@H](C)CO)cc1] | (2S*,3S*)-3-(4-methoxyphenyl)-2-methyl-3-(7-(2-((1-methyl-1H-pyrazol-5-yl)amino)pyridin-4-yl)-[1,2,4]triazolo[4,3-a]pyridin-3-yl)propan-1-ol | 470.2 |

TABLE 2-continued

| Ex. # | Structure | Name | MS (ACPI+) M + 1 (retention time) |
|---|---|---|---|
| 390 | 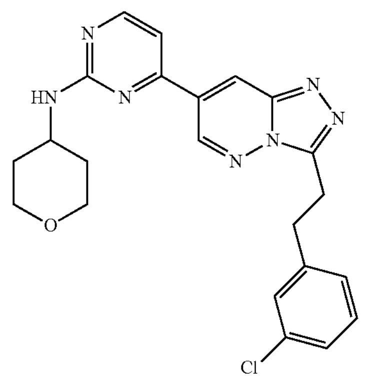 [SMILES: Clc1cccc(CCc2nnc3cc(-c4ccnc(NC5CCOCC5)n4)cnn23)c1] | 4-(3-(3-chlorophenethyl)-[1,2,4]triazolo[4,3-b]pyridazin-7-yl)-N-(tetrahydro-2H-pyran-4-yl)pyrimidin-2-amine | 436.1 |
| 391 | 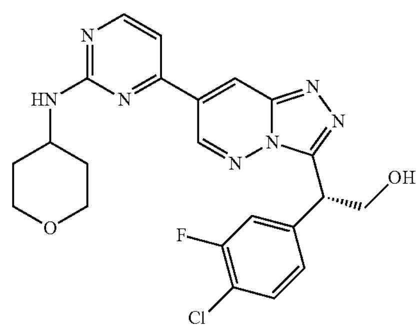 [SMILES: OC[C@H](c1ccc(Cl)c(F)c1)c1nnc2cc(-c3ccnc(NC4CCOCC4)n3)cnn12] | (R)-2-(4-chloro-3-fluorophenyl)-2-(7-(2-((tetrahydro-2H-pyran-4-yl)amino)pyrimidin-4-yl)-[1,2,4]triazolo[4,3-b]pyridazin-3-yl)ethanol | 470.1 |
| 392 | 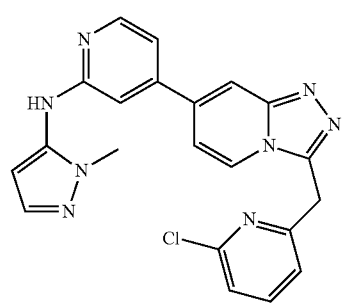 | 4-(3-((6-chloropyridin-2-yl)methyl)-[1,2,4]triazolo[4,3-a]pyridin-7-yl)-N-(1-methyl-1H-pyrazol-5-yl)pyridin-2-amine | 417.1 |
| 393 | 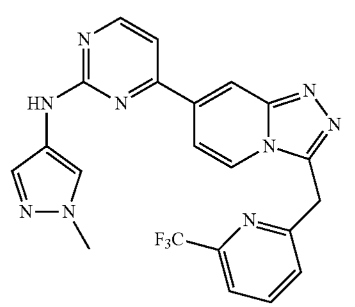 [SMILES: Cn1cc(Nc2nccc(-c3ccn4c(Cc5cccc(C(F)(F)F)n5)nnc4c3)n2)cn1] | N-(1-methyl-1H-pyrazol-4-yl)-4-(3-((6-(trifluoromethyl)pyridin-2-yl)methyl)-[1,2,4]triazolo[4,3-a]pyridin-7-yl)pyrimidin-2-amine | 452.1 |

TABLE 2-continued

| Ex. # | Structure | Name | MS (ACPI+) M + 1 (retention time) |
|---|---|---|---|
| 394 | 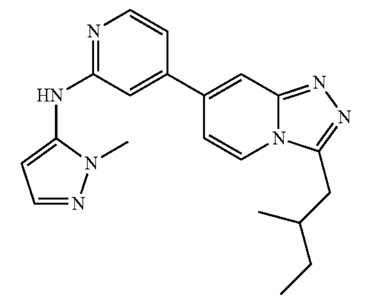 [SMILES: CC[C@H](C)Cc1nnc2cc(-c3ccnc(Nc4ccnn4C)c3)ccn12] | N-(1-methyl-1H-pyrazol-5-yl)-4-(3-(2-methylbutyl)-[1,2,4]triazolo[4,3-a]pyridin-7-yl)pyridin-2-amine | 362.2 |
| 395 | 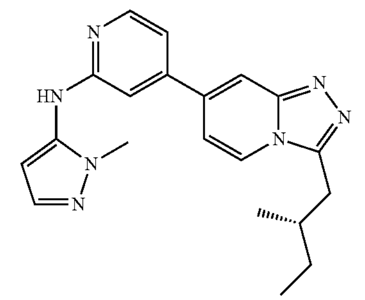 | (S)-N-(1-methyl-1H-pyrazol-5-yl)-4-(3-(2-methylbutyl)-[1,2,4]triazolo[4,3-a]pyridin-7-yl)pyridin-2-amine | 362.2 |
| 396 | 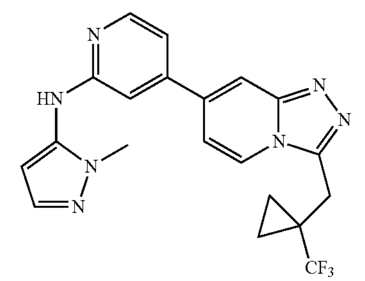 [SMILES: Cn1nccc1Nc1cc(-c2ccn3c(CC4(C(F)(F)F)CC4)nnc3c2)ccn1] | N-(1-methyl-1H-pyrazol-5-yl)-4-(3-((1-(trifluoromethyl)cyclopropyl)methyl)-[1,2,4]triazolo[4,3-a]pyridin-7-yl)pyridin-2-amine | 414.2 |
| 397 | 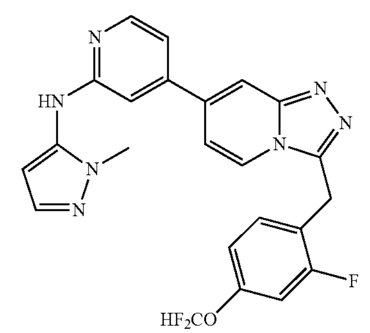 | 4-(3-(4-(difluoromethoxy)-2-fluorobenzyl)-[1,2,4]triazolo[4,3-a]pyridin-7-yl)-N-(1-methyl-1H-pyrazol-5-yl)pyridin-2-amine | 466.2 |
| 398 | 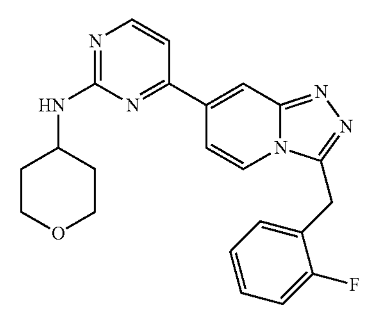 [SMILES: Fc1ccccc1Cc1nnc2cc(-c3ccnc(NC4CCOCC4)n3)ccn12] | 4-(3-(2-fluorobenzyl)-[1,2,4]triazolo[4,3-a]pyridin-7-yl)-N-(tetrahydro-2H-pyran-4-yl)pyrimidin-2-amine | 405.2 |

TABLE 2-continued

| Ex. # | Structure | Name | MS (ACPI+) M + 1 (retention time) |
|---|---|---|---|
| 399 | 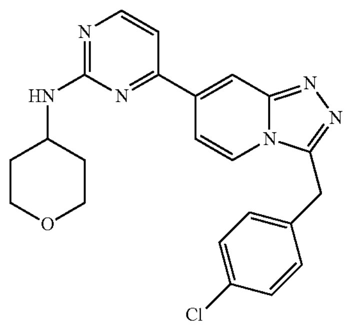 [SMILES: Clc1ccc(Cc2nnc3cc(-c4ccnc(NC5CCOCC5)n4)ccn23)cc1] | 4-(3-(4-chlorobenzyl)-[1,2,4]triazolo[4,3-a]pyridin-7-yl)-N-(tetrahydro-2H-pyran-4-yl)pyrimidin-2-amine | 421.1 |
| 400 | 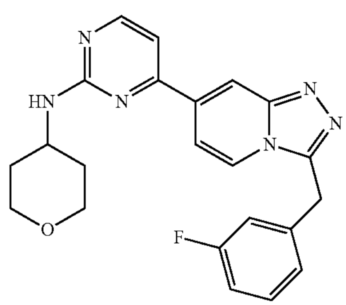 [SMILES: Fc1cccc(Cc2nnc3cc(-c4ccnc(NC5CCOCC5)n4)ccn23)c1] | 4-(3-(3-fluorobenzyl)-[1,2,4]triazolo[4,3-a]pyridin-7-yl)-N-(tetrahydro-2H-pyran-4-yl)pyrimidin-2-amine | 405.2 |
| 401 | 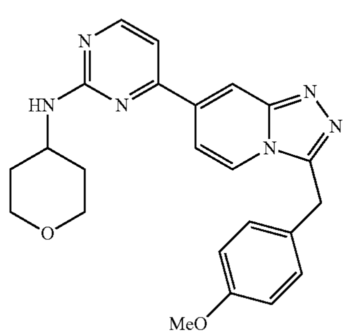 [SMILES: COc1ccc(Cc2nnc3cc(-c4ccnc(NC5CCOCC5)n4)ccn23)cc1] | 4-(3-(4-methoxybenzyl)-[1,2,4]triazolo[4,3-a]pyridin-7-yl)-N-(tetrahydro-2H-pyran-4-yl)pyrimidin-2-amine | 417.2 |
| 402 | 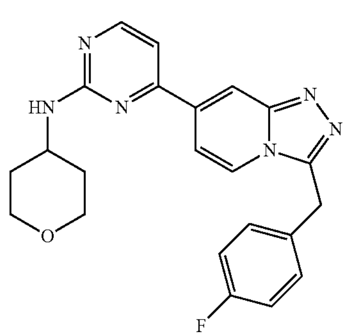 [SMILES: Fc1ccc(Cc2nnc3cc(-c4ccnc(NC5CCOCC5)n4)ccn23)cc1] | 4-(3-(4-fluorobenzyl)-[1,2,4]triazolo[4,3-a]pyridin-7-yl)-N-(tetrahydro-2H-pyran-4-yl)pyrimidin-2-amine | 405.2 |

TABLE 2-continued

| Ex. # | Structure | Name | MS (ACPI+) M + 1 (retention time) |
|---|---|---|---|
| 403 | 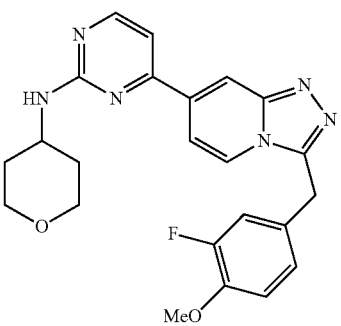 [SMILES: COc1ccc(Cc2nnc3cc(-c4ccnc(NC5CCOCC5)n4)ccn23)cc1F] | 4-(3-(3-fluoro-4-methoxybenzyl)-[1,2,4]triazolo[4,3-a]pyridin-7-yl)-N-(tetrahydro-2H-pyran-4-yl)pyrimidin-2-amine | 435.2 |
| 404 | 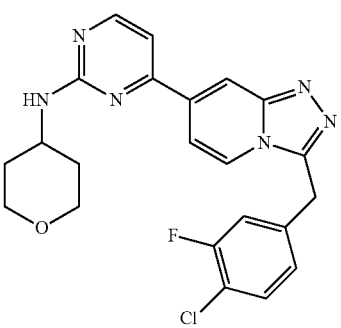 [SMILES: Fc1cc(Cc2nnc3cc(-c4ccnc(NC5CCOCC5)n4)ccn23)ccc1Cl] | 4-(3-(4-chloro-3-fluorobenzyl)-[1,2,4]triazolo[4,3-a]pyridin-7-yl)-N-(tetrahydro-2H-pyran-4-yl)pyrimidin-2-amine | 439.2 |
| 405 | 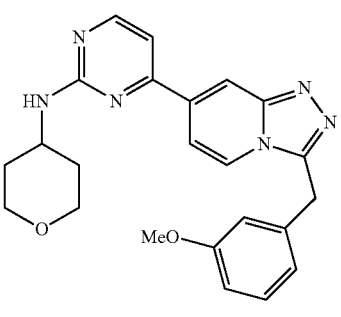 [SMILES: COc1cccc(Cc2nnc3cc(-c4ccnc(NC5CCOCC5)n4)ccn23)c1] | 4-(3-(3-methoxybenzyl)-[1,2,4]triazolo[4,3-a]pyridin-7-yl)-N-(tetrahydro-2H-pyran-4-yl)pyrimidin-2-amine | 417.2 |
| 406 | 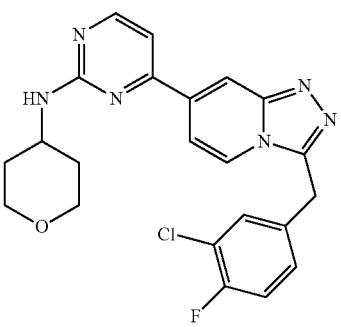 [SMILES: Fc1ccc(Cc2nnc3cc(-c4ccnc(NC5CCOCC5)n4)ccn23)cc1Cl] | 4-(3-(3-chloro-4-fluorobenzyl)-[1,2,4]triazolo[4,3-a]pyridin-7-yl)-N-(tetrahydro-2H-pyran-4-yl)pyrimidin-2-amine | 439.2 |

TABLE 2-continued

| Ex. # | Structure | Name | MS (ACPI+) M + 1 (retention time) |
|---|---|---|---|
| 407 | 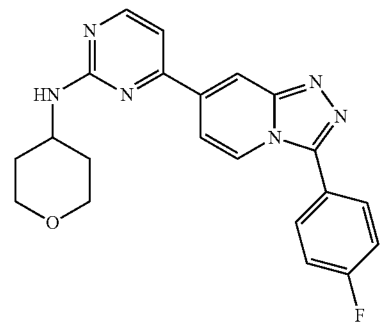 [SMILES: Fc1ccc(-c2nnc3cc(-c4ccnc(NC5CCOCC5)n4)ccn23)cc1] | 4-(3-(4-fluorophenyl)-[1,2,4]triazolo[4,3-a]pyridin-7-yl)-N-(tetrahydro-2H-pyran-4-yl)pyrimidin-2-amine | 391.2 |
| 408 | 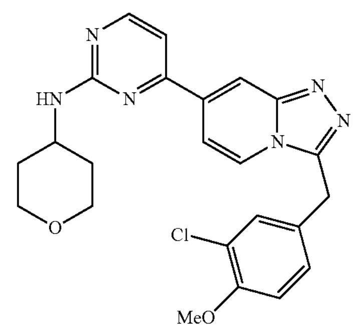 [SMILES: COc1ccc(Cc2nnc3cc(-c4ccnc(NC5CCOCC5)n4)ccn23)cc1Cl] | 4-(3-(3-chloro-4-methoxybenzyl)-[1,2,4]triazolo[4,3-a]pyridin-7-yl)-N-(tetrahydro-2H-pyran-4-yl)pyrimidin-2-amine | 451.2 |
| 409 | 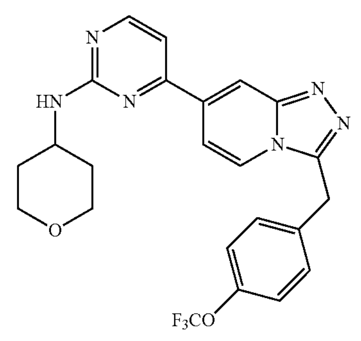 [SMILES: FC(F)(F)Oc1ccc(Cc2nnc3cc(-c4ccnc(NC5CCOCC5)n4)ccn23)cc1] | N-(tetrahydro-2H-pyran-4-yl)-4-(3-(4-(trifluoromethoxy)benzyl)-[1,2,4]triazolo[4,3-a]pyridin-7-yl)pyrimidin-2-amine | 477.2 |
| 410 | 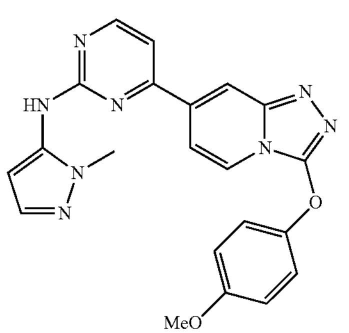 [SMILES: COc1ccc(Oc2nnc3cc(-c4ccnc(Nc5ccnn5C)n4)ccn23)cc1] | 4-(3-(4-methoxyphenoxy)-[1,2,4]triazolo[4,3-a]pyridin-7-yl)-N-(1-methyl-1H-pyrazol-5-yl)pyrimidin-2-amine | 415.2 |

TABLE 2-continued

| Ex. # | Structure | Name | MS (ACPI+) M + 1 (retention time) |
|---|---|---|---|
| 411 | 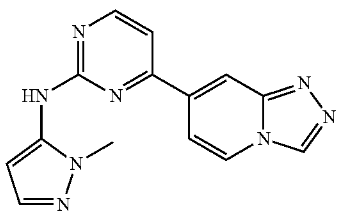 [SMILES: Cn1nccc1Nc1nccc(-c2ccn3cnnc3c2)n1] | 4-([1,2,4]triazolo[4,3-a]pyridin-7-yl)-N-(1-methyl-1H-pyrazol-5-yl)pyrimidin-2-amine | 293.1 |
| 412 | 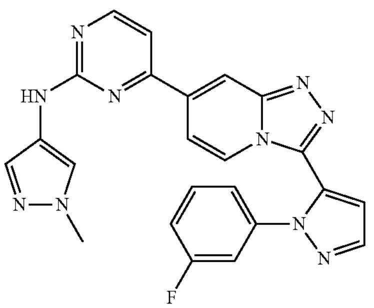 [SMILES: Cn1cc(Nc2nccc(-c3ccn4c(-c5ccnn5-c5cccc(F)c5)nnc4c3)n2)cn1] | 4-(3-(1-(3-fluorophenyl)-1H-pyrazol-5-yl)-[1,2,4]triazolo[4,3-a]pyridin-7-yl)-N-(1-methyl-1H-pyrazol-4-yl)pyrimidin-2-amine | 452.9 |
| 413 | 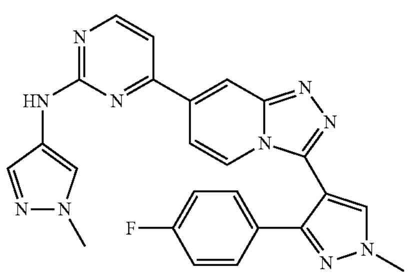 [SMILES: Cn1cc(Nc2nccc(-c3ccn4c(-c5cn(C)nc5-c5ccc(F)cc5)nnc4c3)n2)cn1] | 4-(3-(3-(4-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 467.0 |
| 414 | 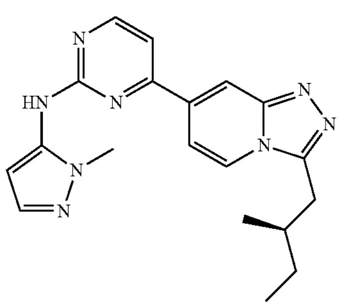 [SMILES: CC[C@@H](C)Cc1nnc2cc(-c3ccnc(Nc4ccnn4C)n3)ccn12] | (R)-N-(1-methyl-1H-pyrazol-5-yl)-4-(3-(2-methylbutyl)-[1,2,4]triazolo[4,3-a]pyridin-7-yl)pyrimidin-2-amine | 363.2 |
| 415 | 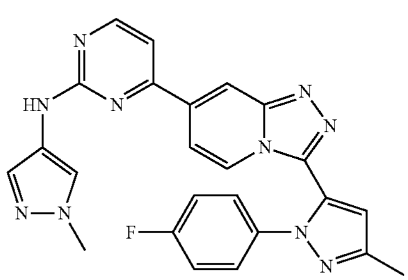 [SMILES: Cc1cc(-c2nnc3cc(-c4ccnc(Nc5cnn(C)c5)n4)ccn23)n(-c2ccc(F)cc2)n1] | 4-(3-(1-(4-fluorophenyl)-3-methyl-1H-pyrazol-5-yl)-[1,2,4]triazolo[4,3-a]pyridin-7-yl)-N-(1-methyl-1H-pyrazol-4-yl)pyrimidin-2-amine | 467.2 |

TABLE 2-continued

| Ex. # | Structure | Name | MS (ACPI+) M + 1 (retention time) |
|---|---|---|---|
| 416 | 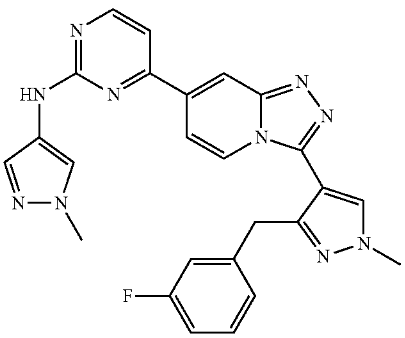 [SMILES: Cn1cc(Nc2nccc(-c3ccn4c(-c5cn(C)nc5Cc5cccc(F)c5)nnc4c3)n2)cn1] | 4-(3-(3-(3-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 481.1 |
| 417 | 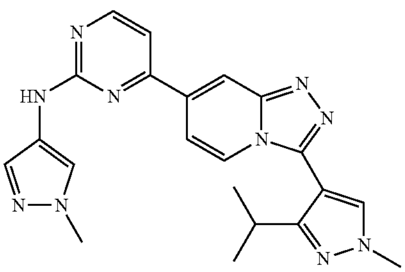 [SMILES: CC(C)c1nn(C)cc1-c1nnc2cc(-c3ccnc(Nc4cnn(C)c4)n3)ccn12] | 4-(3-(3-isopropyl-1-methyl-1H-pyrazol-4-yl)-[1,2,4]triazolo[4,3-a]pyridin-7-yl)-N-(1-methyl-1H-pyrazol-4-yl)pyrimidin-2-amine | 415.0 |
| 418 | 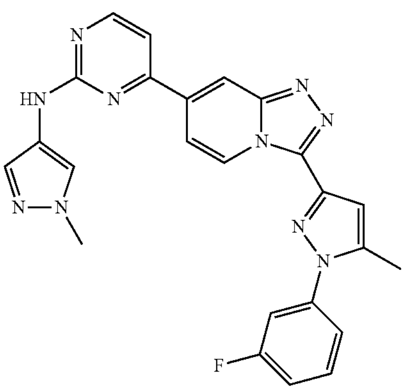 [SMILES: Cc1cc(-c2nnc3cc(-c4ccnc(Nc5cnn(C)c5)n4)ccn23)nn1-c1cccc(F)c1] | 4-(3-(1-(3-fluorophenyl)-5-methyl-1H-pyrazol-3-yl)-[1,2,4]triazolo[4,3-a]pyridin-7-yl)-N-(1-methyl-1H-pyrazol-4-yl)pyrimidin-2-amine | 467.0 |
| 419 | 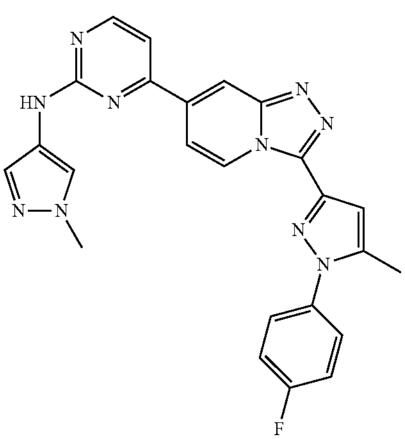 [SMILES: Cc1cc(-c2nnc3cc(-c4ccnc(Nc5cnn(C)c5)n4)ccn23)nn1-c1ccc(F)cc1] | 4-(3-(1-(4-fluorophenyl)-5-methyl-1H-pyrazol-3-yl)-[1,2,4]triazolo[4,3-a]pyridin-7-yl)-N-(1-methyl-1H-pyrazol-4-yl)pyrimidin-2-amine | 467.0 |

TABLE 2-continued

| Ex. # | Structure | Name | MS (ACPI+) M + 1 (retention time) |
|---|---|---|---|
| 420 | 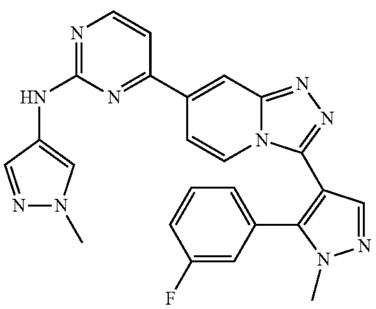 [SMILES: Cn1cc(Nc2nccc(-c3ccn4c(-c5cnn(C)c5-c5cccc(F)c5)nnc4c3)n2)cn1] | 4-(3-(5-(3-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 467.0 |
| 421 | 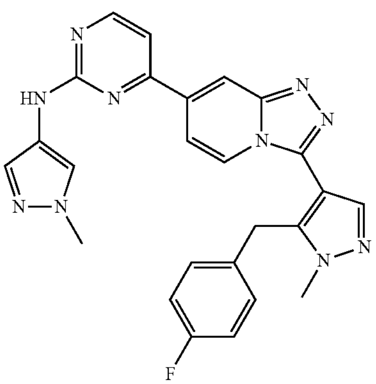 [SMILES: Cn1cc(Nc2nccc(-c3ccn4c(-c5cnn(C)c5Cc5ccc(F)cc5)nnc4c3)n2)cn1] | 4-(3-(5-(4-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 481.0 |
| 422 | 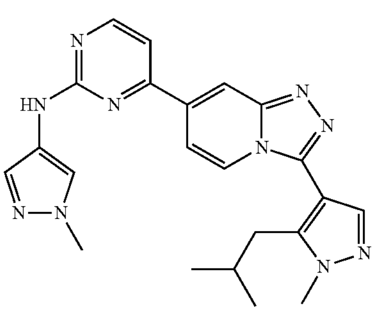 [SMILES: CC(C)Cc1c(-c2nnc3cc(-c4ccnc(Nc5cnn(C)c5)n4)ccn23)cnn1C] | 4-(3-(5-isobutyl-1-methyl-1H-pyrazol-4-yl)-[1,2,4]triazolo[4,3-a]pyridin-7-yl)-N-(1-methyl-1H-pyrazol-4-yl)pyrimidin-2-amine | 429.0 |
| 423 | 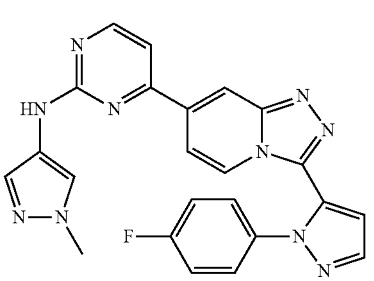 [SMILES: Cn1cc(Nc2nccc(-c3ccn4c(-c5ccnn5-c5ccc(F)cc5)nnc4c3)n2)cn1] | 4-(3-(1-(4-fluorophenyl)-1H-pyrazol-5-yl)-[1,2,4]triazolo[4,3-a]pyridin-7-yl)-N-(1-methyl-1H-pyrazol-4-yl)pyrimidin-2-amine | 452.9 |

TABLE 2-continued

| Ex. # | Structure | Name | MS (ACPI+) M + 1 (retention time) |
|---|---|---|---|
| 424 | 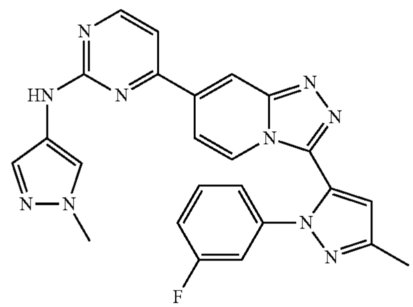 [SMILES: Cc1cc(-c2nnc3cc(-c4ccnc(Nc5cnn(C)c5)n4)ccn23)n(-c2cccc(F)c2)n1] | 4-(3-(1-(3-fluorophenyl)-3-methyl-1H-pyrazol-5-yl)-[1,2,4]triazolo[4,3-a]pyridin-1-yl)-N-(1-methyl-1H-pyrazol-4-yl)pyrimidin-2-amine | 467.0 |
| 425 | 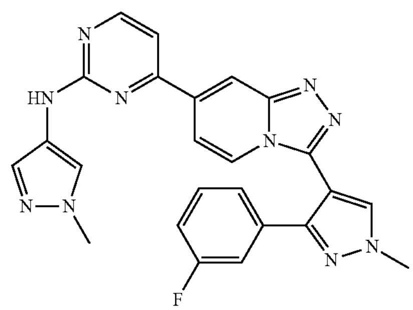 [SMILES: Cn1cc(Nc2nccc(-c3ccn4c(-c5cn(C)nc5-c5cccc(F)c5)nnc4c3)n2)cn1] | 4-(3-(3-(3-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 467.0 |
| 426 | 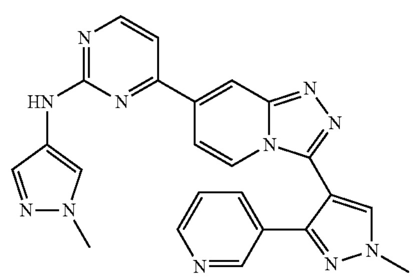 [SMILES: Cn1cc(Nc2nccc(-c3ccn4c(-c5cn(C)nc5-c5cccnc5)nnc4c3)n2)cn1] | N-(1-methyt-1H-pyrazol-4-yl)-4-(3-(1-methyl-3-(pyridin-3-yl)-1H-pyrazol-4-yl)-[1,2,4]triazolo[4,3-a]pyridin-7-yl)pyrimidin-2-amine | 450.0 |
| 427 | 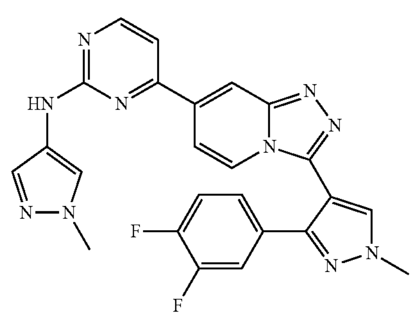 [SMILES: Cn1cc(Nc2nccc(-c3ccn4c(-c5cn(C)nc5-c5ccc(F)c(F)c5)nnc4c3)n2)cn1] | 4-(3-(3-(3,4-difluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 485.1 |
| 428 | 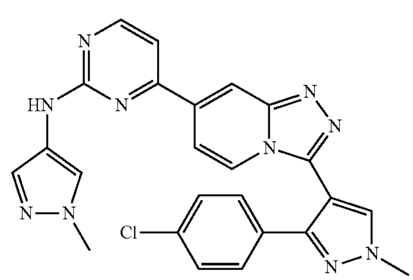 | 4-(3-(3-(4-chlorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 482.9 |

TABLE 2-continued

| Ex. # | Structure | Name | MS (ACPI+) M + 1 (retention time) |
|---|---|---|---|
| 429 | 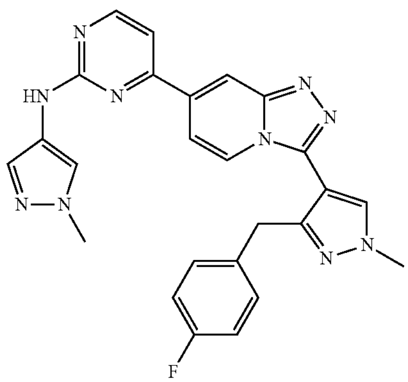 [SMILES: Cn1cc(Nc2nccc(-c3ccn4c(-c5cn(C)nc5Cc5ccc(F)cc5)nnc4c3)n2)cn1] | 4-(3-(3-(4-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 481.0 |
| 430 | 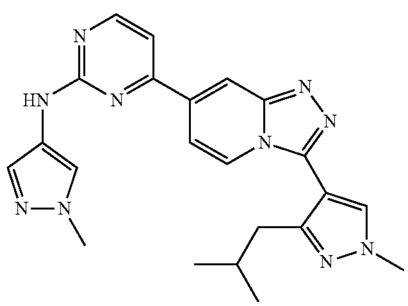 [SMILES: CC(C)Cc1nn(C)cc1-c1nnc2cc(-c3ccnc(Nc4cnn(C)c4)n3)ccn12] | 4-(3-(3-isobutyl-1-methyl-1H-pyrazol-4-yl)-[1,2,4]triazolo[4,3-a]pyridin-7-yl)-N-(1-methyl-1H-pyrazol-4-yl)pyrimidin-2-amine | 429.0 |
| 431 | 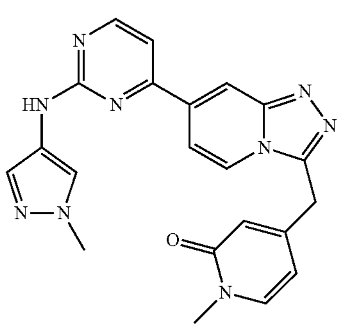 [SMILES: Cn1cc(Nc2nccc(-c3ccn4c(Cc5ccn(C)c(=O)c5)nnc4c3)n2)cn1] | 1-methyl-4-((7-(2-((1-methyl-1H-pyrazol-4-yl)amino)pyrimidin-4-yl)-[1,2,4]triazolo[4,3-a]pyridin-3-yl)methyl)pyridin-2(1H)-one | 413.9 |
| 432 | 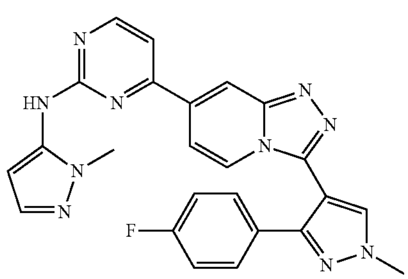 [SMILES: Cn1cc(-c2nnc3cc(-c4ccnc(Nc5ccnn5C)n4)ccn23)c(-c2ccc(F)cc2)n1] | 4-(3-(3-(4-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 467.0 |

TABLE 2-continued

| Ex. # | Structure | Name | MS (ACPI+) M + 1 (retention time) |
|---|---|---|---|
| 433 | 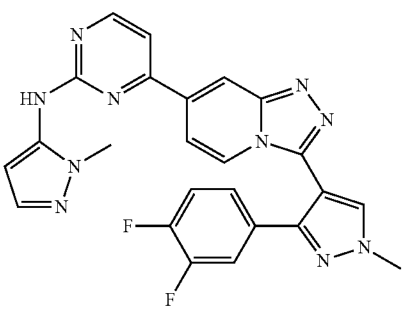 [SMILES: Cn1cc(-c2nnc3cc(-c4ccnc(Nc5ccnn5C)n4)ccn23)c(-c2ccc(F)c(F)c2)n1] | 4-(3-(3-(3,4-difluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 485.0 |
| 434 | 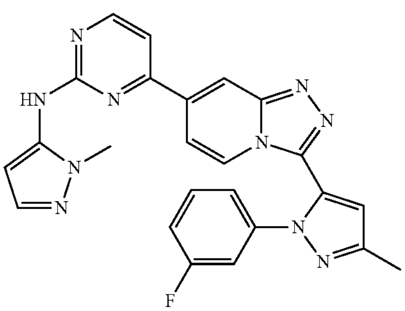 [SMILES: Cc1cc(-c2nnc3cc(-c4ccnc(Nc5ccnn5C)n4)ccn23)n(-c2cccc(F)c2)n1] | 4-(3-(1-(3-fluorophenyl)-3-methyl-1H-pyrazol-5-yl)-[1,2,4]triazolo[4,3-a]pyridin-7-yl)-N-(1-methyl-1H-pyrazol-5-yl)pyrimidin-2-amine | 467.0 |
| 435 | 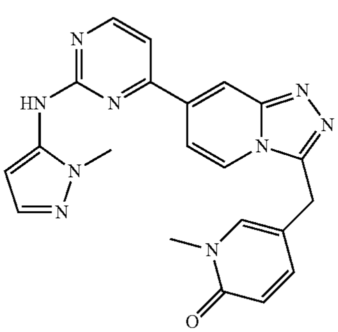 [SMILES: Cn1nccc1Nc1nccc(-c2ccn3c(Cc4ccc(=O)n(C)c4)nnc3c2)n1] | 1-methyl-5-((7-(2-((1-methyl-1H-pyrazol-5-yl)amino)pyrimidin-4-yl)-[1,2,4]triazolo[4,3-a]pyridin-3-yl)methyl)pyridin-2(1H)-one | 413.9 |
| 436 | 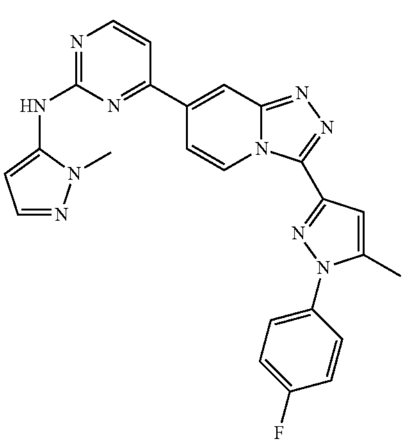 [SMILES: Cc1cc(-c2nnc3cc(-c4ccnc(Nc5ccnn5C)n4)ccn23)nn1-c1ccc(F)cc1] | 4-(3-(1-(4-fluorophenyl)-5-methyl-1H-pyrazol-3-yl)-[1,2,4]triazolo[4,3-a]pyridin-7-yl)-N-(1-methyl-1H-pyrazol-5-yl)pyrimidin-2-amine | 437.0 |

TABLE 2-continued

| Ex. # | Structure | Name | MS (ACPI+) M + 1 (retention time) |
|---|---|---|---|
| 437 | 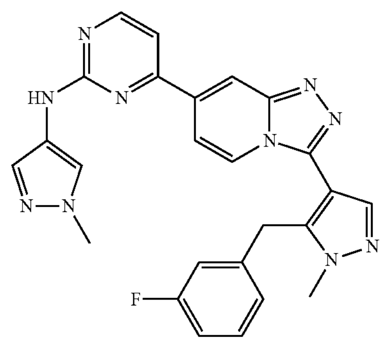 [SMILES: Cn1cc(Nc2nccc(-c3ccn4c(-c5cnn(C)c5Cc5cccc(F)c5)nnc4c3)n2)cn1] | 4-(3-(5-(3-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 481.2 |
| 438 | 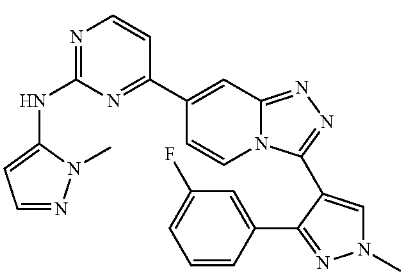 [SMILES: Cn1cc(-c2nnc3cc(-c4ccnc(Nc5ccnn5C)n4)ccn23)c(-c2cccc(F)c2)n1] | 4-(3-(3-(3-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 466.9 |
| 439 | 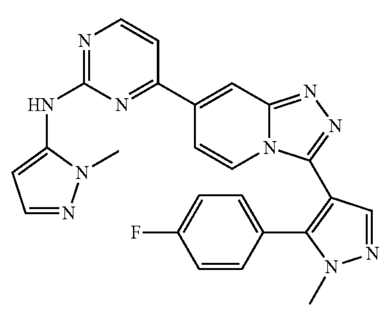 [SMILES: Cn1nccc1Nc1nccc(-c2ccn3c(-c4cnn(C)c4-c4ccc(F)cc4)nnc3c2)n1] | 4-(3-(5-(4-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 467.0 |
| 440 | 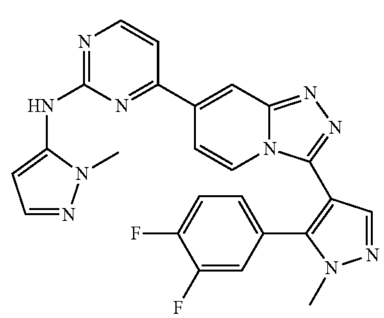 [SMILES: Cn1nccc1Nc1nccc(-c2ccn3c(-c4cnn(C)c4-c4ccc(F)c(F)c4)nnc3c2)n1] | 4-(3-(5-(3,4-difluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 484.9 |

TABLE 2-continued

| Ex. # | Structure | Name | MS (ACPI+) M + 1 (retention time) |
|---|---|---|---|
| 441 | 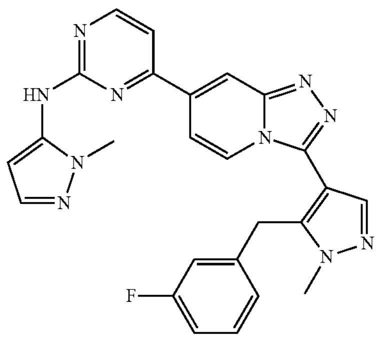 [SMILES: Cn1nccc1Nc1nccc(-c2ccn3c(-c4cnn(C)c4Cc4cccc(F)c4)nnc3c2)n1] | 4-(3-(5-(3-fluorobenzyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 480.9 |
| 442 | 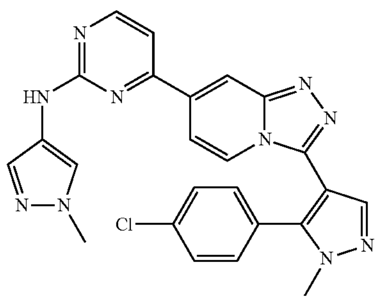 [SMILES: Cn1cc(Nc2nccc(-c3ccn4c(-c5cnn(C)c5-c5ccc(Cl)cc5)nnc4c3)n2)cn1] | 4-(3-(5-(4-chlorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine | 483.0 |
| 443 | 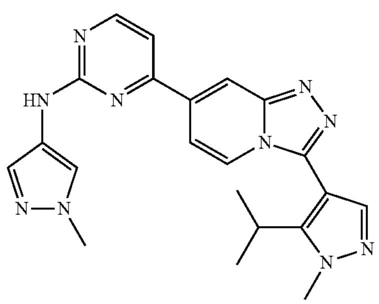 [SMILES: CC(C)c1c(-c2nnc3cc(-c4ccnc(Nc5cnn(C)c5)n4)ccn23)cnn1C] | 4-(3-(5-isopropyl-1-methyl-1H-pyrazol-4-yl)-[1,2,4]triazolo[4,3-a]pyridin-7-yl)-N-(1-methyl-1H-pyrazol-4-yl)pyrimidin-2-amine | 415.0 |
| 444 | 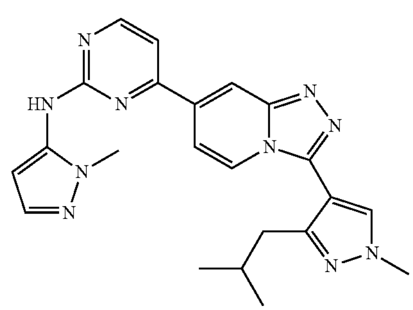 [SMILES: CC(C)Cc1nn(C)cc1-c1nnc2cc(-c3ccnc(Nc4ccnn4C)n3)ccn12] | 4-(3-(3-isobutyl-1-methyl-1H-pyrazol-4-yl)-[1,2,4]triazolo[4,3-a]pyridin-7-yl)-N-(1-methyl-1H-pyrazol-5-yl)pyrimidin-2-amine | 429.0 |

TABLE 2-continued

| Ex. # | Structure | Name | MS (ACPI+) M + 1 (retention time) |
|---|---|---|---|
| 445 | 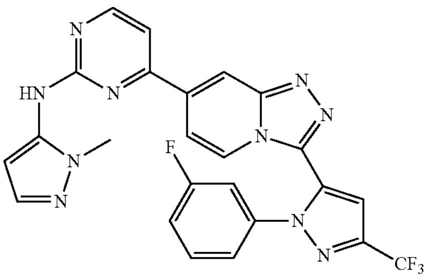 [SMILES: Cn1nccc1Nc1nccc(-c2ccn3c(-c4cc(C(F)(F)F)nn4-c4cccc(F)c4)nnc3c2)n1] | 4-(3-(1-(3-fluorophenyl)-3-(trifluoromethyl)-1H-pyrazol-5-yl)-[1,2,4]triazolo[4,3-a]pyridin-7-yl)-N-(1-methyl-1H-pyrazol-5-yl)pyrimidin-2-amine | 521.2 |
| 446 | 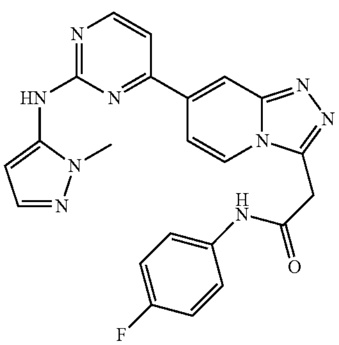 [SMILES: Cn1nccc1Nc1nccc(-c2ccn3c(CC(=O)Nc4ccc(F)cc4)nnc3c2)n1] | N-(4-fluorophenyl)-2-(7-(2-((1-methyl-1H-pyrazol-5-yl)amino)pyrimidin-4-yl)-[1,2,4]triazolo[4,3-a]pyridin-3-yl)acetamide | 443.9 |
| 447 | 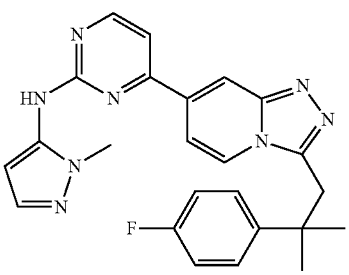 [SMILES: Cn1nccc1Nc1nccc(-c2ccn3c(CC(C)(C)c4ccc(F)cc4)nnc3c2)n1] | 4-(3-(2-(4-fluorophenyl)-2-methylpropyl)-[1,2,4]triazolo[4,3-a]pyridin-7-yl)-N-(1-methyl-1H-pyrazol-5-yl)pyrimidin-2-amine | 443.0 |
| 448 | 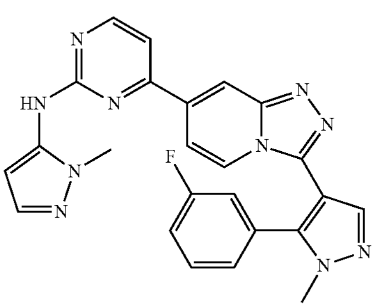 [SMILES: Cn1nccc1Nc1nccc(-c2ccn3c(-c4cnn(C)c4-c4cccc(F)c4)nnc3c2)n1] | 4-(3-(5-(3-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 467.0 |
| 449 | 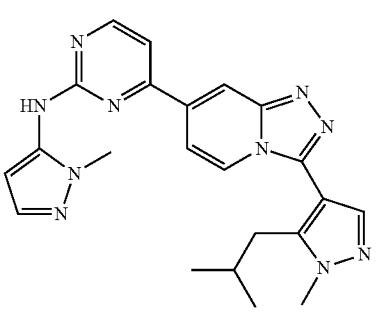 [SMILES: CC(C)Cc1c(-c2nnc3cc(-c4ccnc(Nc5ccnn5C)n4)ccn23)cnn1C] | 4-(3-(5-isobutyl-1-methyl-1H-pyrazol-4-yl)-[1,2,4]triazolo[4,3-a]pyridin-7-yl)-N-(1-methyl-1H-pyrazol-5-yl)pyrimidin-2-amine | 428.9 |

TABLE 2-continued

| Ex. # | Structure | Name | MS (ACPI+) M + 1 (retention time) |
|---|---|---|---|
| 450 | 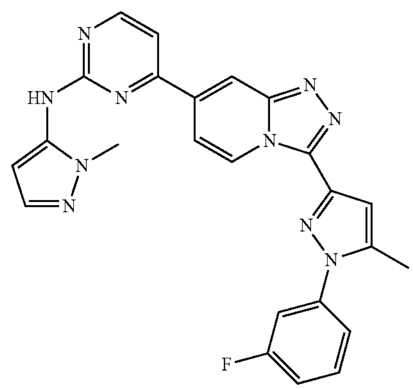 [SMILES: Cc1cc(-c2nnc3cc(-c4ccnc(Nc5ccnn5C)n4)ccn23)nn1-c1cccc(F)c1] | 4-(3-(1-(3-fluorophenyl)-5-methyl-1H-pyrazol-3-yl)-[1,2,4]triazolo[4,3-a]pyridin-7-yl)-N-(1-methyl-1H-pyrazol-5-yl)pyrimidin-2-amine | 467.0 |
| 451 | 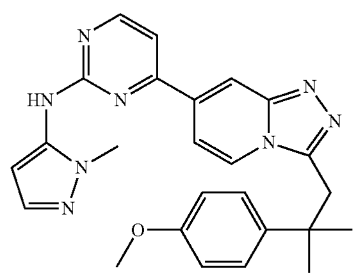 | 4-(3-(2-(4-methoxyphenyl)-2-methylpropyl)-[1,2,4]triazolo[4,3-a]pyridin-7-yl)-N-(1-methyl-1H-pyrazol-5-yl)pyrimidin-2-amine | 455.0 |
| 452 | 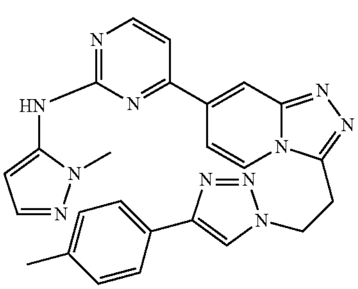 [SMILES: Cc1ccc(-c2cn(CCc3nnc4cc(-c5ccnc(Nc6ccnn6C)n5)ccn34)nn2)cc1] | N-(1-methyl-1H-pyrazol-5-yl)-4-(3-(2-(4-(p-tolyl)-1H-1,2,3-triazol-1-yl)ethyl)-[1,2,4]triazolo[4,3-a]pyridin-7-yl)pyrimidin-2-amine | 478.0 |
| 453 | 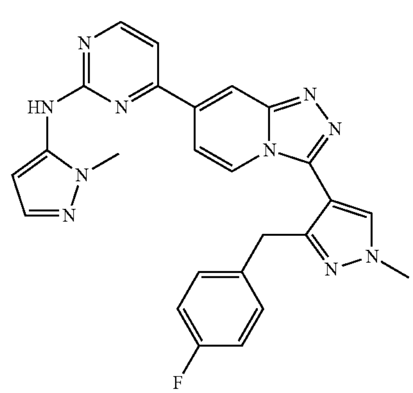 [SMILES: Cn1cc(-c2nnc3cc(-c4ccnc(Nc5ccnn5C)n4)ccn23)c(Cc2ccc(F)cc2)n1] | 4-(3-(3-(4-fluorobenzyl)-1-methyl-1H-pyrazol-4-yl)-[1,2,4]triazolo[4,3-a]pyridin-7-yl)-N-(1-methyl-1H-pyrazol-5-yl)pyrimidin-2-amine | 481.0 |

TABLE 2-continued

| Ex. # | Structure | Name | MS (ACPI+) M + 1 (retention time) |
|---|---|---|---|
| 454 | 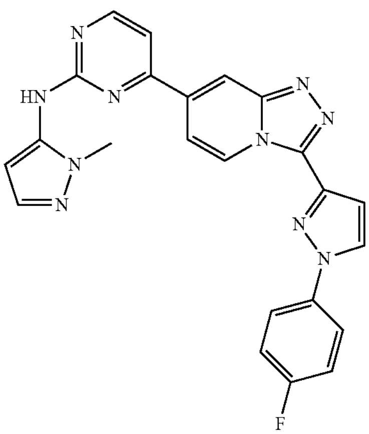 [SMILES: Cn1nccc1Nc1nccc(-c2ccn3c(-c4ccn(-c5ccc(F)cc5)n4)nnc3c2)n1] | 4-(3-(1-(4-fluorophenyl)-1H-pyrazol-3-yl)-[1,2,4]triazolo[4,3-a]pyridin-7-yl)-N-(1-methyl-1H-pyrazol-5-yl)pyrimidin-2-amine | 453.1 |
| 455 | 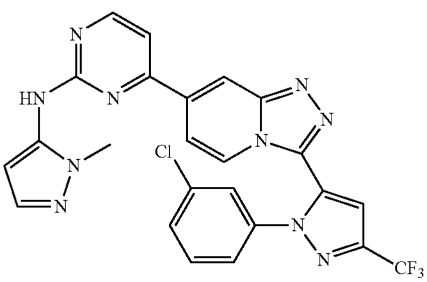 [SMILES: Cn1nccc1Nc1nccc(-c2ccn3c(-c4cc(C(F)(F)F)nn4-c4cccc(Cl)c4)nnc3c2)n1] | 4-(3-(1-(3-chlorophenyl)-3-(trifluoromethyl)-1H-pyrazol-5-yl)-[1,2,4]triazolo[4,3-a]pyridin-7-yl)-N-(1-methyl-1H-pyrazol-5-yl)pyrimidin-2-amine | 536.9 |
| 456 | 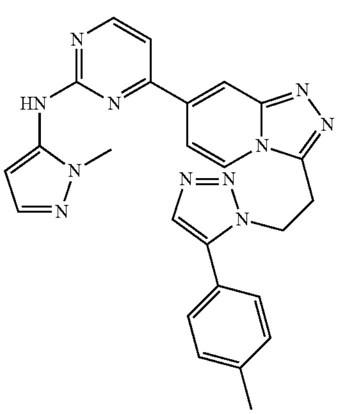 [SMILES: Cc1ccc(-c2cnnn2CCc2nnc3cc(-c4ccnc(Nc5ccnn5C)n4)ccn23)cc1] | N-(1-methyl-1H-pyrazol-5-yl)-4-(3-(2-(5-(p-tolyl)-1H-1,2,3-triazol-1-yl)ethyl)-[1,2,4]triazolo[4,3-a]pyridin-7-yl)pyrimidin-2-amine | 478.0 |
| 457 | 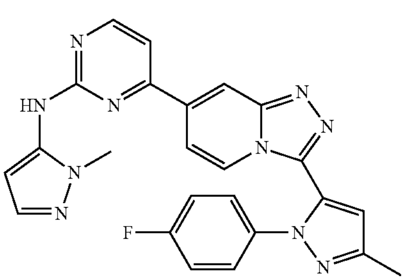 [SMILES: Cc1cc(-c2nnc3cc(-c4ccnc(Nc5ccnn5C)n4)ccn23)n(-c2ccc(F)cc2)n1] | 4-(3-(1-(4-fluorophenyl)-3-methyl-1H-pyrazol-5-yl)-[1,2,4]triazolo[4,3-a]pyridin-7-yl)-N-(1-methyl-1H-pyrazol-5-yl)pyrimidin-2-amine | 467.0 |

TABLE 2-continued

| Ex. # | Structure | Name | MS (ACPI+) M + 1 (retention time) |
|---|---|---|---|
| 458 | 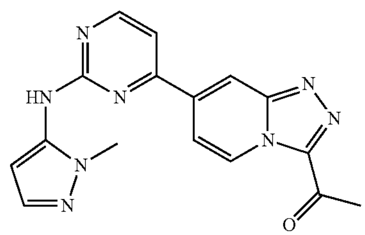 [SMILES: CC(=O)c1nnc2cc(-c3ccnc(Nc4ccnn4C)n3)ccn12] | 1-(7-(2-((1-methyl-1H-pyrazol-5-yl)amino)pyrimidin-4-yl)-[1,2,4]triazolo[4,3-a]pyridin-3-yl)ethanone | 334.9 |
| 459 | 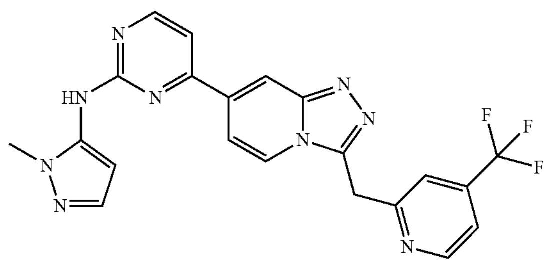 [SMILES: Cn1nccc1Nc1nccc(-c2ccn3c(Cc4cc(C(F)(F)F)ccn4)nnc3c2)n1] | N-(1-methyl-1H-pyrazol-5-yl)-4-(3-((4-(trifluoromethyl)pyridin-2-yl)methyl)-[1,2,4]triazolo[4,3-a]pyridin-7-yl)pyrimidin-2-amine | 451.9 |
| 460 | 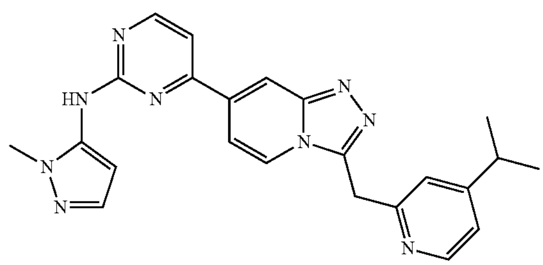 [SMILES: CC(C)c1ccnc(Cc2nnc3cc(-c4ccnc(Nc5ccnn5C)n4)ccn23)c1] | 4-(3-((4-isopropylpyridin-2-yl)methyl)-[1,2,4]triazolo[4,3-a]pyridin-7-yl)-N-(1-methyl-1H-pyrazol-5-yl)pyrimidin-2-amine | 426.0 |
| 461 | 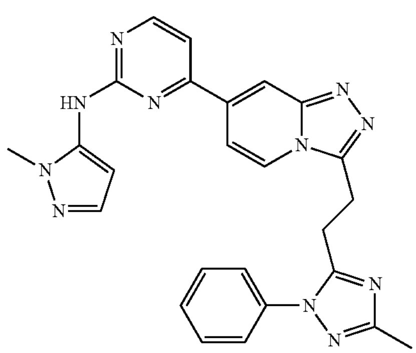 | 4-(3-(2-(3-methyl-1-phenyl-1H-1,2,4-triazol-5-yl)ethyl)-[1,2,4]triazolo[4,3-a]pyridin-7-yl)-N-(1-methyl-1H-pyrazol-5-yl)pyrimidin-2-amine | 478.0 |
| 462 | 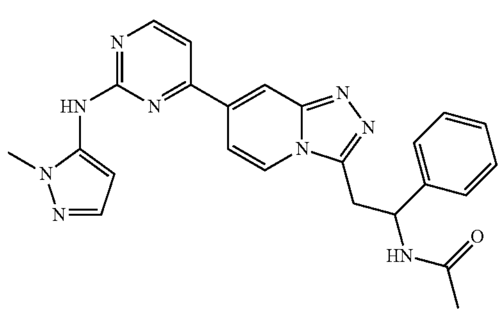 [SMILES: CC(=O)NC(Cc1nnc2cc(-c3ccnc(Nc4ccnn4C)n3)ccn12)c1ccccc1] | N-(2-(7-(2-((1-methyl-1H-pyrazol-5-yl)amino)pyrimidin-4-yl)-[1,2,4]triazolo[4,3-a]pyridin-3-yl)-1-phenylethyl)acetamide | 454.0 |

TABLE 2-continued

| Ex. # | Structure | Name | MS (ACPI+) M + 1 (retention time) |
|---|---|---|---|
| 463 | 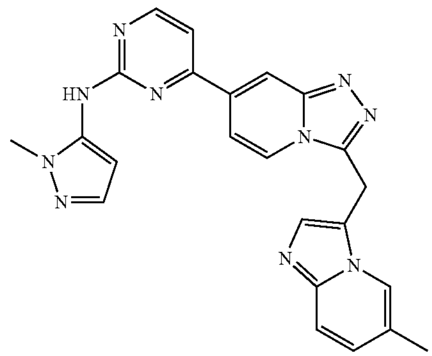 | N-(1-methyl-1H-pyrazol-5-yl)-4-(3-((6-methylimidazo[1,2-a]pyridin-3-yl)methyl)-[1,2,4]triazolo[4,3-a]pyridin-7-yl)pyrimidin-2-amine | 437.0 |
| 464 | 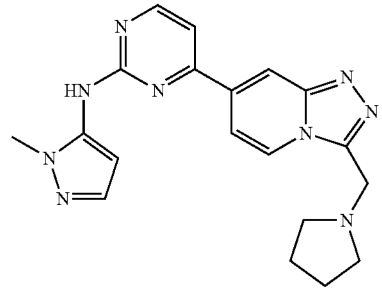 [SMILES: Cn1nccc1Nc1nccc(-c2ccn3c(CN4CCCC4)nnc3c2)n1] | N-(1-methyl-1H-pyrazol-5-yl)-4-(3-(pyrrolidin-1-ylmethyl)-[1,2,4]triazolo[4,3-a]pyridin-7-yl)pyrimidin-2-amine | 376.0 |
| 465 | 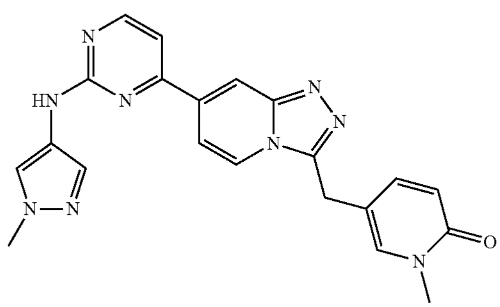 [SMILES: Cn1cc(Nc2nccc(-c3ccn4c(Cc5ccc(=O)n(C)c5)nnc4c3)n2)cn1] | 1-methyl-5-((7-(2-((1-methyl-1H-pyrazol-4-yl)amino)pyrimidin-4-yl)-[1,2,4]triazolo[4,3-a]pyridin-3-yl)methyl)pyridin-2(1H)-one | 413.9 |
| 466 | 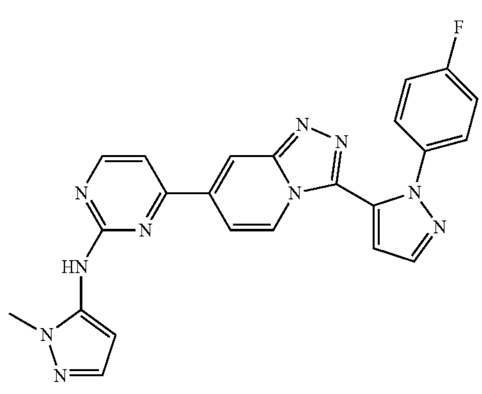 [SMILES: Cn1nccc1Nc1nccc(-c2ccn3c(-c4ccnn4-c4ccc(F)cc4)nnc3c2)n1] | 4-(3-(1-(4-fluorophenyl)-1H-pyrazol-5-yl)-[1,2,4]triazolo[4,3-a]pyridin-7-yl)-N-(1-methyl-1H-pyrazol-5-yl)pyrimidin-2-amine | 452.9 |

TABLE 2-continued

| Ex. # | Structure | Name | MS (ACPI+) M + 1 (retention time) |
|---|---|---|---|
| 467 | 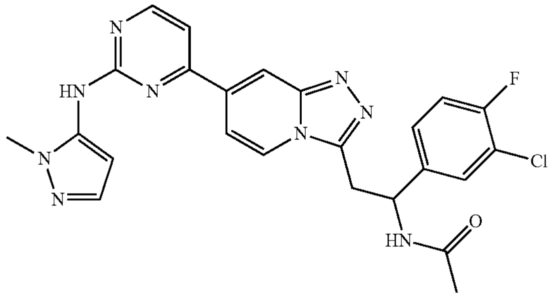 [SMILES: CC(=O)NC(Cc1nnc2cc(-c3ccnc(Nc4ccnn4C)n3)ccn12)c1ccc(F)c(Cl)c1] | N-(1-(3-chloro-4-fluorophenyl)-2-(7-(2-((1-methyl-1H-pyrazol-5-yl)amino)pyrimidin-4-yl)-[1,2,4]triazolo[4,3-a]pyridin-3-yl)ethyl)acetamide | 506.0 |
| 468 | 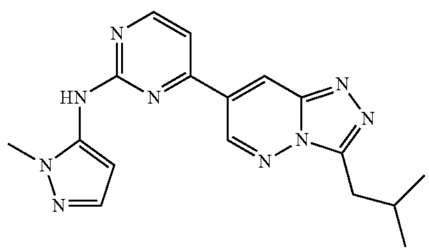 [SMILES: CC(C)Cc1nnc2cc(-c3ccnc(Nc4ccnn4C)n3)cnn12] | 4-(3-isobutyl-[1,2,4]triazolo[4,3-b]pyridazin-7-yl)-N-(1-methyl-1H-pyrazol-5-yl)pyrimidin-2-amine | 349.9 |
| 469 | 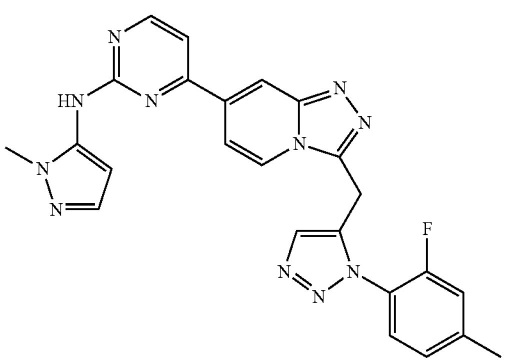 | 4-(3-((1-(2-fluoro-4-methylphenyl)-1H-1,2,3-triazol-5-yl)methyl)-[1,2,4]triazolo[4,3-a]pyridin-7-yl)-N-(1-methyl-1H-pyrazol-5-yl)pyrimidin-2-amine | 482.0 |
| 470 | 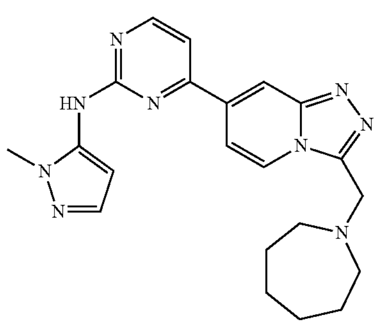 [SMILES: Cn1nccc1Nc1nccc(-c2ccn3c(CN4CCCCCC4)nnc3c2)n1] | 4-(3-(azepan-1-ylmethyl)-[1,2,4]triazolo[4,3-a]pyridin-7-yl)-N-(1-methyl-1H-pyrazol-5-yl)pyrimidin-2-amine | 403.9 |

TABLE 2-continued

| Ex. # | Structure | Name | MS (ACPI+) M + 1 (retention time) |
|---|---|---|---|
| 471 | 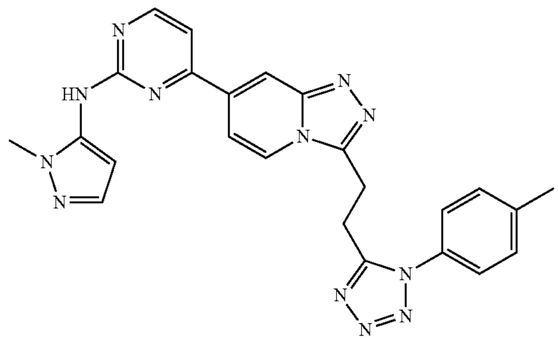 | N-(1-methyl-1H-pyrazol-5-yl)-4-(3-(2-(1-(p-tolyl)-1H-tetrazol-5-yl)ethyl)-[1,2,4]triazolo[4,3-a]pyridin-7-yl)pyrimidin-2-amine | 479.0 |
| 472 | 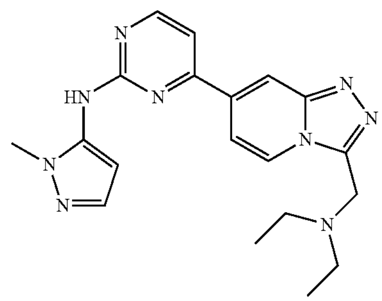 [SMILES: CCN(CC)Cc1nnc2cc(-c3ccnc(Nc4ccnn4C)n3)ccn12] | 4-(3-((diethylamino)methyl)-[1,2,4]triazolo[4.3-a]pyridin-7-yl)-N-(1-methyl-1H-pyrazol-5-yl)pyrimidin-2-amine | 377.9 |
| 473 | 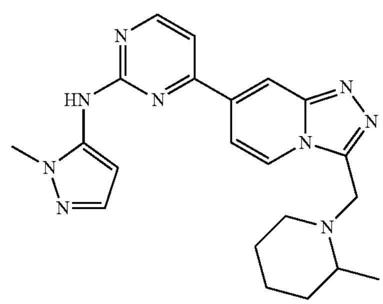 | N-(1-methyl-1H-pyrazol-5-yl)-4-(3-((2-methylpiperidin-1-yl)methyl)-[1,2,4 ]triazolo[4,3-a]pyridin-7-yl)pyrimidin-2-amine | 404.0 |
| 474 | 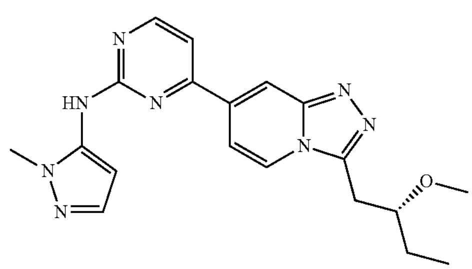 | (R)-4-(3-(2-methoxybutyl)-[1,2,4]triazolo[4,3-a]pyridin-7-yl)-N-(1-methyl-1H-pyrazol-5-yl)pyrimidin-2-amine | 379.2 |
| 475 | 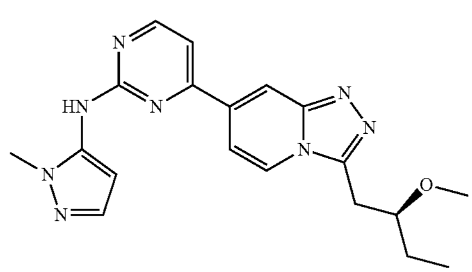 | (S)-4-(3-(2-methoxybutyl)-?[1,2,4]triazolo[4,3-a]pyridin-7-yl)-N-(1-methyl-1H-pyrazol-5-yl)pyrimidin-2-amine | 379.2 |

| Ex. # | Structure | Name | MS (ACPI+) M + 1 (retention time) |
|---|---|---|---|
| 476 | 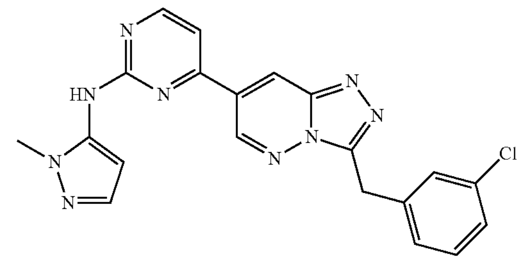 [SMILES: Cn1nccc1Nc1nccc(-c2cnn3c(Cc4cccc(Cl)c4)nnc3c2)n1] | 4-(3-(3-chlorobenzyl)-[1,2,4]triazolo[4,3-b]pyridazin-7-yl)-N-(1-methyl-1H-pyrazol-5-yl)pyrimidin-2-amine | 418.1 |
| 477 | 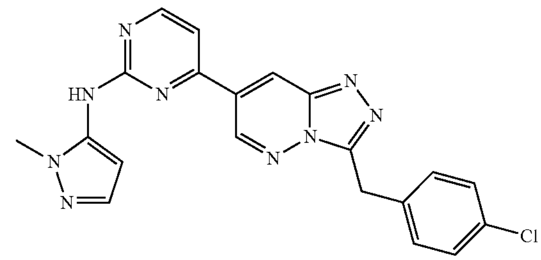 [SMILES: Cn1nccc1Nc1nccc(-c2cnn3c(Cc4ccc(Cl)cc4)nnc3c2)n1] | 4-(3-(4-chlorobenzyl)-[1,2,4]triazolo[4,3-b]pyridazin-7-yl)-N-(1-methyl-1H-pyrazol-5-yl)pyrimidin-2-amine | 417.8 |
| 478 | 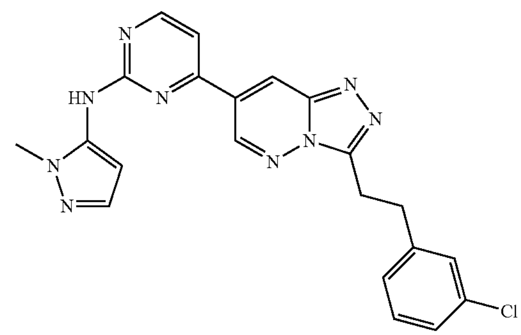 [SMILES: Cn1nccc1Nc1nccc(-c2cnn3c(CCc4cccc(Cl)c4)nnc3c2)n1] | 4-(3-(3-chlorophenethyl)-[1,2,4]triazolo[4,3-b]pyridazin-7-yl)-N-(1-methyl-1H-pyrazol-5-yl)pyrimidin-2-amine | 431.9 |
| 479 | 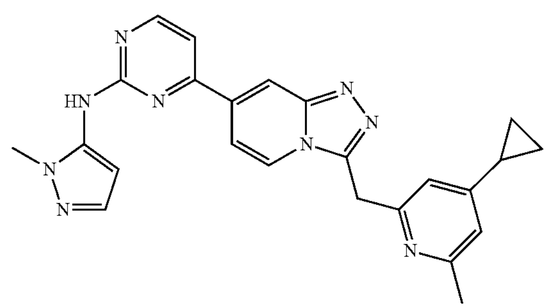 [SMILES: Cc1cc(C2CC2)cc(Cc2nnc3cc(-c4ccnc(Nc5ccnn5C)n4)ccn23)n1] | 4-(3-((4-cyclopropyl-6-methylpyridin-2-yl)methyl)-[1,2,4]triazolo[4,3-a]pyridin-7-yl)-N-(1-methyl-1H-pyrazol-5-yl)pyrimidin-2-amine | 437.9 |
| 480 | 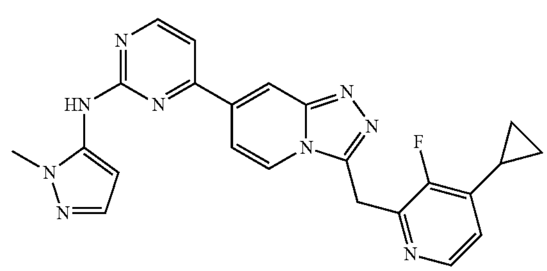 [SMILES: Cn1nccc1Nc1nccc(-c2ccn3c(Cc4nccc(C5CC5)c4F)nnc3c2)n1] | 4-(3-((4-cyclopropyl-3-fluoropyridin-2-yl)methyl)-[1,2,4]triazolo[4,3-a]pyridin-7-yl)-N-(1-methyl-1H-pyrazol-5-yl)pyrimidin-2-amine | 441.9 |

TABLE 2-continued

| Ex. # | Structure | Name | MS (ACPI+) M + 1 (retention time) |
|---|---|---|---|
| 481 | 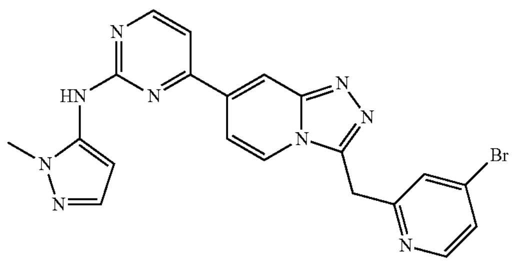 [SMILES: Cn1nccc1Nc1nccc(-c2ccn3c(Cc4cc(Br)ccn4)nnc3c2)n1] | 4-(3-((4-bromopyridin-2-yl)methyl)-[1,2,4]triazolo[4,3-a]pyridin-7-yl)-N-(1-methyl-1H-pyrazol-5-yl)pyrimidin-2-amine | 462.1 |
| 482 | 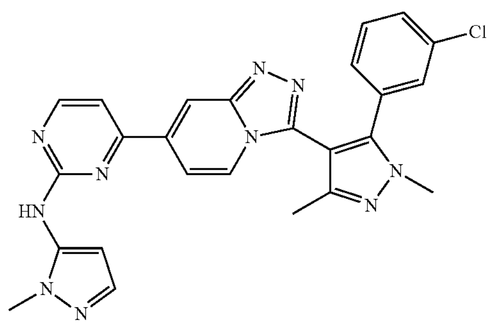 [SMILES: Cc1nn(C)c(-c2cccc(Cl)c2)c1-c1nnc2cc(-c3ccnc(Nc4ccnn4C)n3)ccn12] | 4-(3-(5-(3-chlorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine | 497.0 |
| 483 | 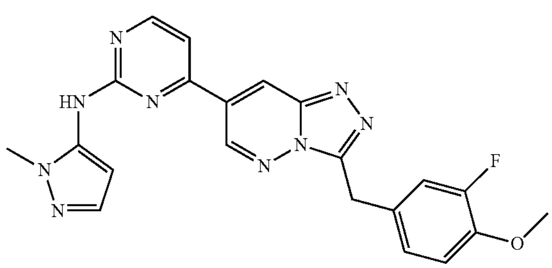 | 4-(3-(3-fluoro-4-methoxybenzyl)-[1,2,4]triazolo[4,3-b]pyridazin-7-yl)-N-(1-methyl-1H-pyrazol-5-yl)pyrimidin-2-amine | 431.9 |
| 484 | 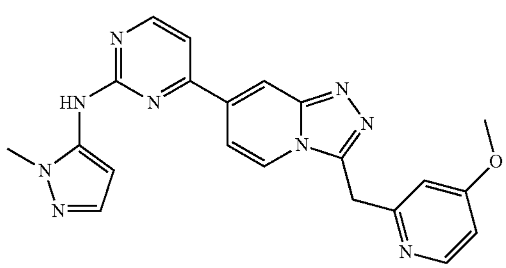 [SMILES: COc1ccnc(Cc2nnc3cc(-c4ccnc(Nc5ccnn5C)n4)ccn23)c1] | 4-(3-((4-methoxypyridin-2-yl)methyl)-[1,2,4]triazolo[4,3-a]pyridin-7-yl)-N-(1-methyl-1H-pyrazol-5-yl)pyrimidin-2-amine | 413.9 |
| 485 | 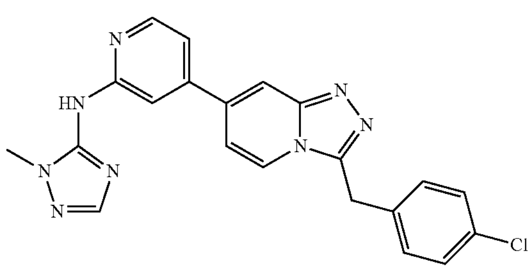 [SMILES: Cn1ncnc1Nc1cc(-c2ccn3c(Cc4ccc(Cl)cc4)nnc3c2)ccn1] | 4-(3-(4-chlorobenzyl)-[1,2,4]triazolo[4,3-a]pyridin-7-yl)-N-(1-methyl-1H-1,2,4-triazol-5-yl)pyridine-amine | 417.2 |

TABLE 2-continued

| Ex. # | Structure | Name | MS (ACPI+) M + 1 (retention time) |
|---|---|---|---|
| 486 | 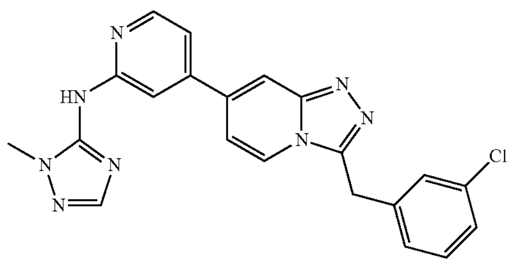 [SMILES: Cn1ncnc1Nc1cc(-c2ccn3c(Cc4cccc(Cl)c4)nnc3c2)ccn1] | 4-(3-(3-chlorobenzyl)-[1,2,4]triazolo[4,3-a]pyridin-7-yl)-N-(1-methyl-1H-1,2,4-triazol-5-yl)pyridin-2-amine | 417.2 |
| 487 | 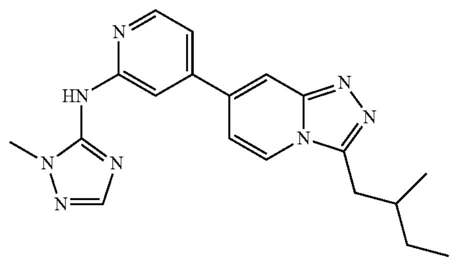 [SMILES: CCC(C)Cc1nnc2cc(-c3ccnc(Nc4ncnn4C)c3)ccn12] | N-(1-methyl-1H-1,2,4-triazol-5-yl)-4-(3-(2-methylbutyl)-[1,2,4]triazolo[4,3-a]pyridin-7-yl)pyridin-2-amine | 363.2 |
| 488 | 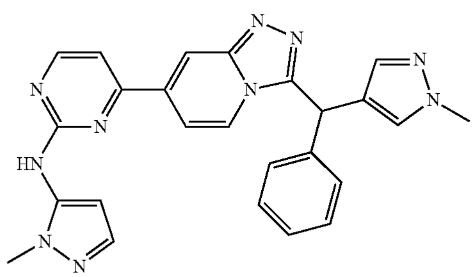 | 4-(3-((1-methyl-1H-pyrazol-4-yl)(pheny)methyl)-[1,2,4]triazolo[4,3-a]pyridin-7-yl)-N-(1-methyl-1H-pyrazol-5-yl)pyrimidin-2-amine | 463.1 |
| 489 | 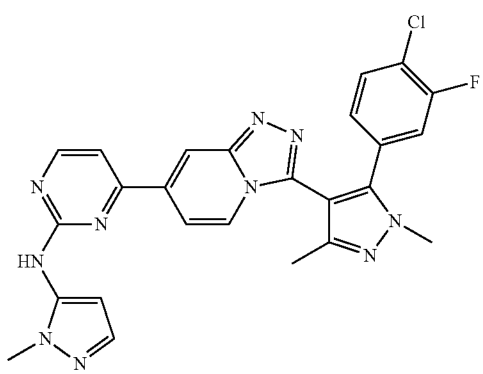 | 4-(3-(5-(4-chloro-3-fluorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine | 514.9 |
| 490 | 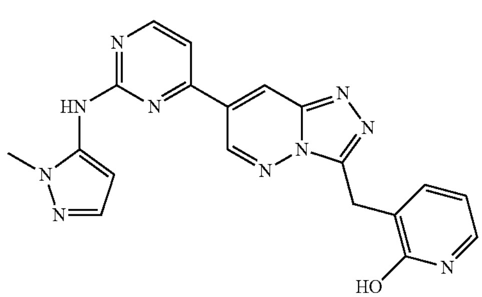 [SMILES: Cn1nccc1Nc1nccc(-c2cnn3c(Cc4cccnc4O)nnc3c2)n1] | 3-((7-(2-((1-methyl-1H-pyrazol-5-yl)amino)pyrimidin-4-yl)-[1,2,4]triazolo[4,3-b]pyridazin-3-yl)methyl)pyridin-2-ol | 400.9 |

TABLE 2-continued

| Ex. # | Structure | Name | MS (ACPI+) M + 1 (retention time) |
|---|---|---|---|
| 491 | 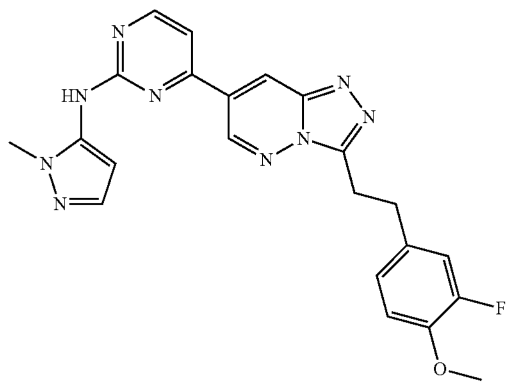 [SMILES: COc1ccc(CCc2nnc3cc(-c4ccnc(Nc5ccnn5C)n4)cnn23)cc1F] | 4-(3-(3-fluoro-4-methoxyphenethyl)-[1,2,4]triazolo[4,3-b]pyridazin-7-yl)-N-(1-methyl-1H-pyrazol-5-yl)pyrimidin-2-amine | 446.0 |
| 492 | 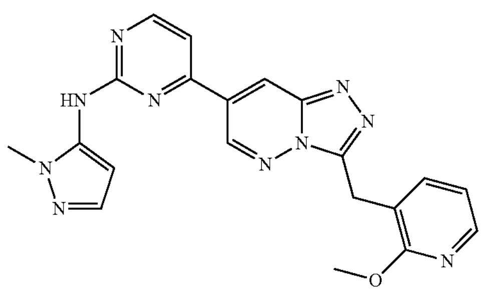 [SMILES: COc1ncccc1Cc1nnc2cc(-c3ccnc(Nc4ccnn4C)n3)cnn12] | 4-(3-((2-methoxypyridin-3-yl)methyl)-[1,2,4]triazolo[4,3-b]pyridazin-7-yl)-N-(1-methyl-1H-pyrazol-5-yl)pyrimidin-2-amine | 414.9 |
| 493 | 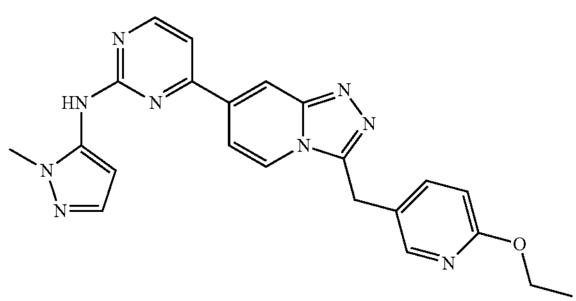 [SMILES: CCOc1ccc(Cc2nnc3cc(-c4ccnc(Nc5ccnn5C)n4)ccn23)cn1] | 4-(3-((6-ethoxypyridin-3-yl)methyl)-[1,2,4]triazolo[4,3-a]pyridin-7-yl)-N-(1-methyl-1H-pyrazol-5-yl)pyrimidin-2-amine | 427.9 |
| 494 | 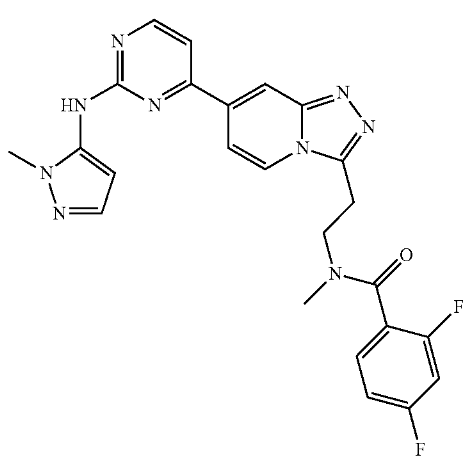 [SMILES: CN(CCc1nnc2cc(-c3ccnc(Nc4ccnn4C)n3)ccn12)C(=O)c1ccc(F)cc1F] | 2,4-difluoro-N-methyl-N-(2-(7-(2-((1-methyl-1H-pyrazol-5-yl)amino)pyrimidin-4-yl)-[1,2,4]triazolo[4,3-a]pyridin-3-yl)ethyl)benzamide | 490.0 |

TABLE 2-continued

| Ex. # | Structure | Name | MS (ACPI+) M + 1 (retention time) |
|---|---|---|---|
| 495 | 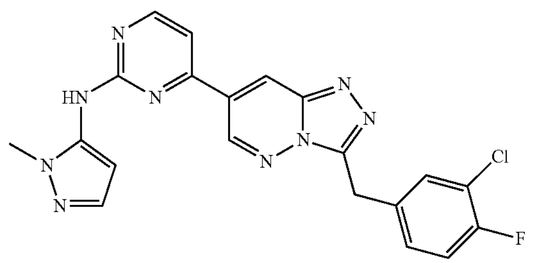 [SMILES: Cn1nccc1Nc1nccc(-c2cnn3c(Cc4ccc(F)c(Cl)c4)nnc3c2)n1] | 4-(3-(3-chloro-4-fluorobenzyl)-[1,2,4]triazolo[4,3-b]pyridazin-7-yl)-N-(1-methyl-1H-pyrazol-5-yl)pyrimidin-2-amine | 435.9 |
| 496 | 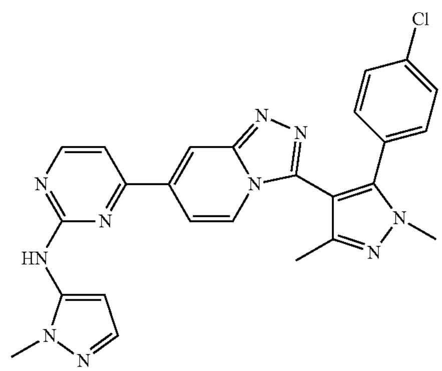 [SMILES: Cc1nn(C)c(-c2ccc(Cl)cc2)c1-c1nnc2cc(-c3ccnc(Nc4ccnn4C)n3)ccn12] | 4-(3-(5-(4-chlorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine | 496.9 |
| 497 | 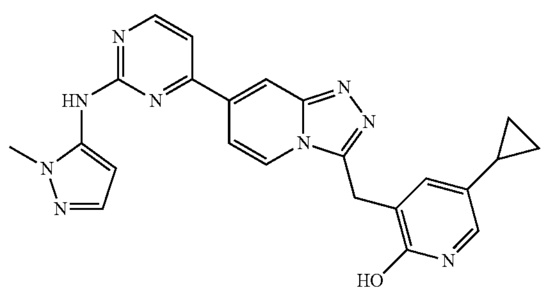 [SMILES: Cn1nccc1Nc1nccc(-c2ccn3c(Cc4cc(C5CC5)cnc4O)nnc3c2)n1] | 5-cyclopropyl-3-((7-(2-((1-methyl-1H-pyrazol-5-yl)amino)pyrimidin-4-yl)-[1,2,4]triazolo[4,3-a]pyridin-3-yl)methyl)pyridin-2-ol | 439.9 |
| 498 | 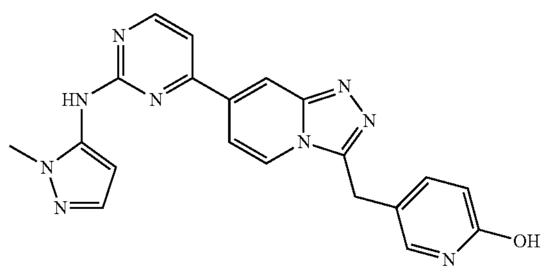 [SMILES: Cn1nccc1Nc1nccc(-c2ccn3c(Cc4ccc(O)nc4)nnc3c2)n1] | 5-((7-(2-((1-methyl-1H-pyrazol-5-yl)amino)pyrimidin-4-yl)-[1,2,4]triazolo[4,3-a]pyridin-3-yl)methyl)pyridin-2-ol | 399.9 |
| 499 | 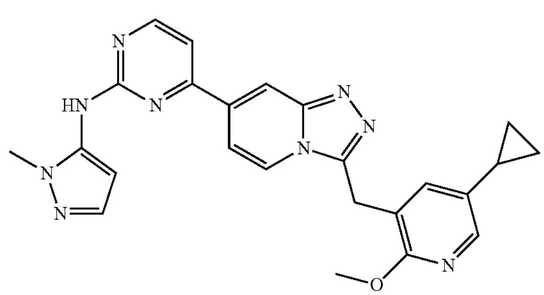 [SMILES: COc1ncc(C2CC2)cc1Cc1nnc2cc(-c3ccnc(Nc4ccnn4C)n3)ccn12] | 4-(3-((5-cyclopropyl-2-methoxypyridin-3-yl)methyl)-[1,2,4]triazolo[4,3-a]pyridin-7-yl)-N-(1-methyl-1H-pyrazol-5-yl)pyrimidin-2-amine | 454.0 |

TABLE 2-continued

| Ex. # | Structure | Name | MS (ACPI+) M + 1 (retention time) |
|---|---|---|---|
| 500 | 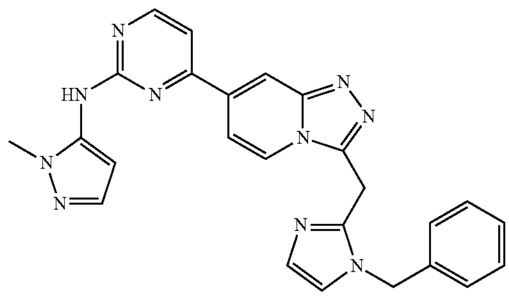 [SMILES: Cn1nccc1Nc1nccc(-c2ccn3c(Cc4nccn4Cc4ccccc4)nnc3c2)n1] | 4-(3-((1-benzyl-1H-imidazol-2-yl)methyl)-[1,2,4]triazolo[4,3-a]pyridin-7-yl)-N-(1-methyl-1H-pyrazol-5-yl)pyrimidin-2-amine | 463.0 |
| 501 | 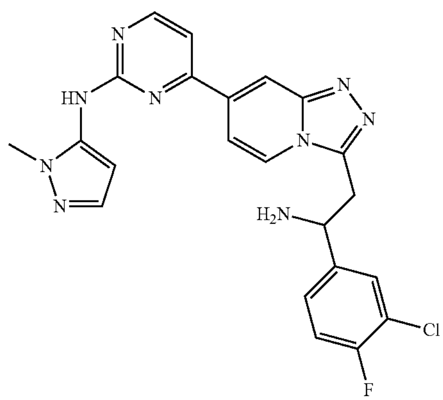 [SMILES: Cn1nccc1Nc1nccc(-c2ccn3c(CC(N)c4ccc(F)c(Cl)c4)nnc3c2)n1] | 4-(3-(2-amino-2-(3-chloro-4-fluorophenyl)ethyl)-[1,2,4]triazolo[4,3-a]pyridin-7-yl)-N-(1-methyl-1H-pyrazol-5-yl)pyrimidin-2-amine | 463.9 |
| 502 | 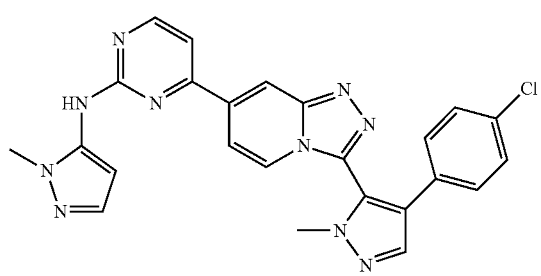 [SMILES: Cn1nccc1Nc1nccc(-c2ccn3c(-c4c(-c5ccc(Cl)cc5)cnn4C)nnc3c2)n1] | 4-(3-(4-(4-chlorophenyl)-1-methyl-1H-pyrazol-5-yl)-[1,2,4]triazolo[4,3-a]pyridin-7-yl)-N-(1-methyl-1H-pyrazol-5-yl)pyrimidin-2-amine | 483.1 |
| 503 | 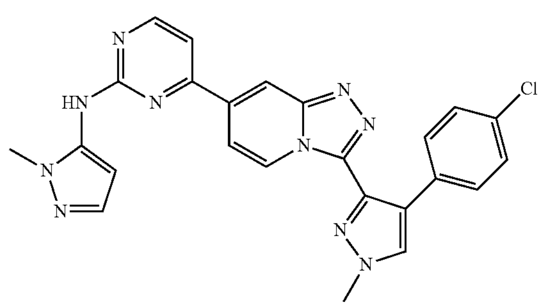 [SMILES: Cn1cc(-c2ccc(Cl)cc2)c(-c2nnc3cc(-c4ccnc(Nc5ccnn5C)n4)ccn23)n1] | 4-(3-(4-(4-chlorophenyl)-1-methyl-1H-pyrazol-3-yl)-[1,2,4]triazolo[4,3-a]pyridin-7-yl)-N-(1-methyl-1H-pyrazol-5-yl)pyrimidin-2-amine | 483.0 |

TABLE 2-continued

| Ex. # | Structure | Name | MS (ACPI+) M + 1 (retention time) |
|---|---|---|---|
| 504 | 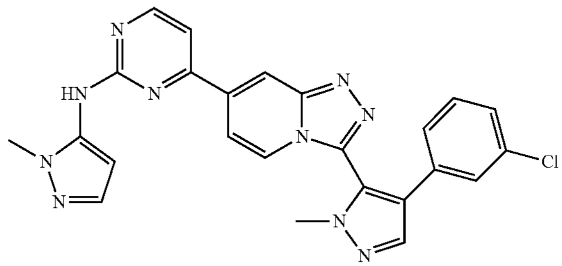 [SMILES: Cn1nccc1Nc1nccc(-c2ccn3c(-c4c(-c5cccc(Cl)c5)cnn4C)nnc3c2)n1] | 4-(3-(4-(3-chlorophenyl)-1-methyl-1H-pyrazol-5-yl)-[1,2,4]triazolo[4,3-a]pyridin-7-yl)-N-(1-methyl-1H-pyrazol-5-yl)pyrimidin-2-amine | 483.0 |
| 505 | 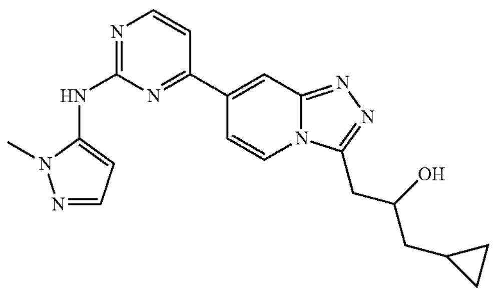 [SMILES: Cn1nccc1Nc1nccc(-c2ccn3c(CC(O)CC4CC4)nnc3c2)n1] | 1-cyclopropyl-3-(7-(2-((1-methyl-1H-pyrazol-5-yl)amino)pyrimidin-4-yl)-[1,2,4]triazolo[4,3-a]pyridin-3-yl)propan-2-ol | 391.0 |
| 506 | 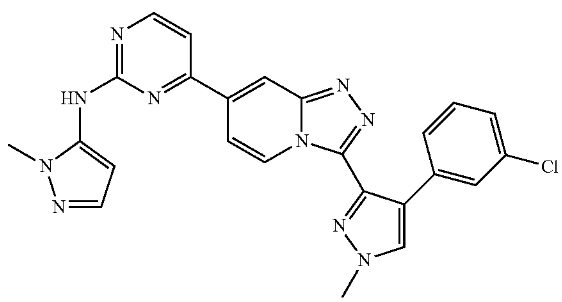 [SMILES: Cn1cc(-c2cccc(Cl)c2)c(-c2nnc3cc(-c4ccnc(Nc5ccnn5C)n4)ccn23)n1] | 4-(3-(4-(3-chlorophenyl)-1-methyl-1H-pyrazol-3-yl)-[1,2,4]triazolo[4,3-a]pyridin-7-yl)-N-(1-methyl-1H-pyrazol-5-yl)pyrimidin-2-amine | 483.2 |
| 507 | 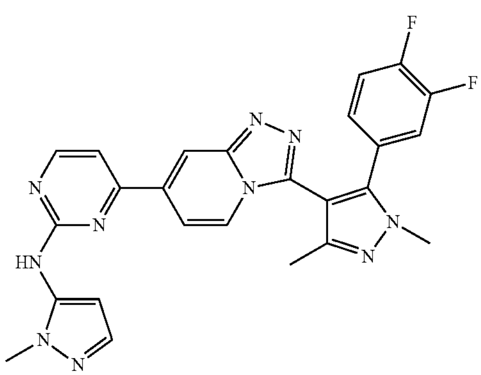 [SMILES: Cc1nn(C)c(-c2ccc(F)c(F)c2)c1-c1nnc2cc(-c3ccnc(Nc4ccnn4C)n3)ccn12] | 4-(3-(5-(3,4-difluorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine | 498.9 |
| 508 | 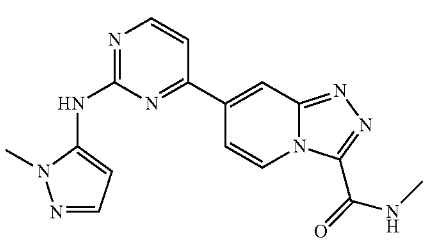 | N-methyl-7-(2-((1-methyl-1H-pyrazol-5-yl)amino)pyrimidin-4-yl)-[1,2,4]triazolo[4,3-a]pyridine-3-carboxamide | 350.2 |

TABLE 2-continued

| Ex. # | Structure | Name | MS (ACPI+) M + 1 (retention time) |
|---|---|---|---|
| 509 | 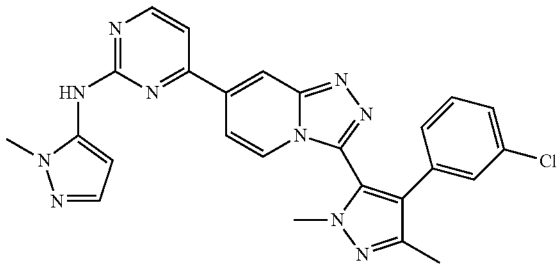 [SMILES: Cc1nn(C)c(-c2nnc3cc(-c4ccnc(Nc5ccnn5C)n4)ccn23)c1-c1cccc(Cl)c1] | 4-(3-(4-(3-chlorophenyl)-1,3-dimethyl-1H-pyrazol-5-yl)-[1,2,4]triazolo[4,3-a]pyridin-7-yl)-N-(1-methyl-1H-pyrazol-5-yl)pyrimidin-2-amine | 496.9 |
| 510 | 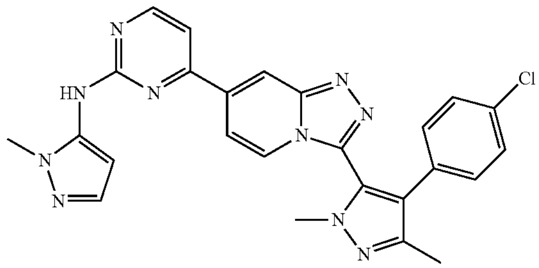 [SMILES: Cc1nn(C)c(-c2nnc3cc(-c4ccnc(Nc5ccnn5C)n4)ccn23)c1-c1ccc(Cl)cc1] | 4-(3-(4-(4-chlorophenyl)-1,3-dimethyl-1H-pyrazol-5-yl)-[1,2,4]triazolo[4,3-a]pyridin-7-yl)-N-(1-methyl-1H-pyrazol-5-yl)pyrimidin-2-amine | 496.9 |
| 511 | 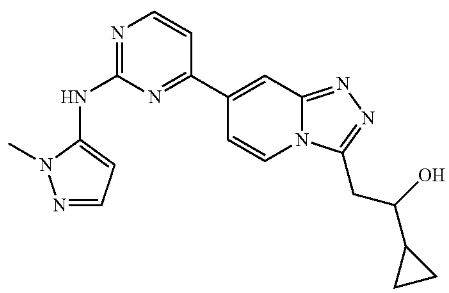 [SMILES: Cn1nccc1Nc1nccc(-c2ccn3c(CC(O)C4CC4)nnc3c2)n1] | 1-cyclopropyl-2-(7-(2-((1-methyl-1H-pyrazol-5-yl)amino)pyrimidin-4-yl)-[1,2,4]triazolo[4,3-a]pyridin-3-yl)ethanol | 376.9 |
| 512 | 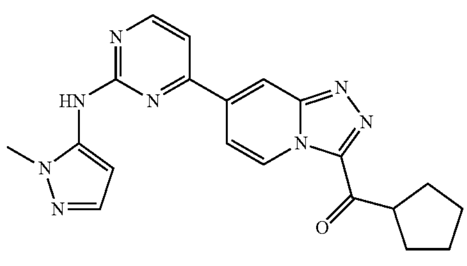 [SMILES: Cn1nccc1Nc1nccc(-c2ccn3c(C(=O)C4CCCC4)nnc3c2)n1] | (7-(2-((1-methyl-1H-pyrazol-5-yl)amino)pyrimidin-4-yl)-[1,2,4]triazolo[4,3-a]pyridin-3-yl)(pyrrolidin-1-yl)methanone | 390.2 |
| 513 | 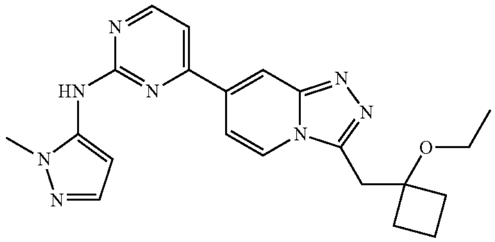 [SMILES: CCOC1(Cc2nnc3cc(-c4ccnc(Nc5ccnn5C)n4)ccn23)CCC1] | 4-(3-((1-ethoxycyclobutyl)methyl)-[1,2,4]triazolo[4,3-a]pyridin-7-yl)-N-(1-methyl-1H-pyrazol-5-yl)pyrimidin-2-amine | 404.9 |

TABLE 2-continued

| Ex. # | Structure | Name | MS (ACPI+) M + 1 (retention time) |
|---|---|---|---|
| 514 | 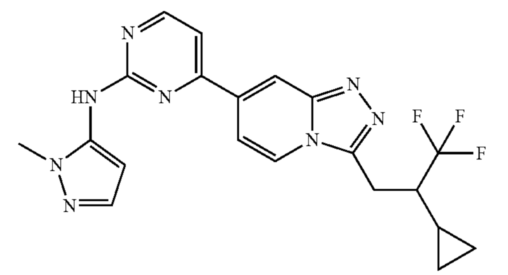 [SMILES: Cn1nccc1Nc1nccc(-c2ccn3c(CC(C4CC4)C(F)(F)F)nnc3c2)n1] | 4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine | 428.9 |
| 515 | 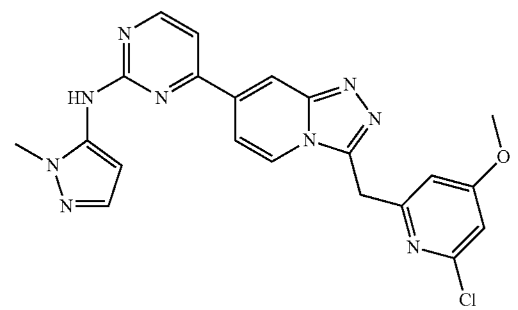 [SMILES: COc1cc(Cl)nc(Cc2nnc3cc(-c4ccnc(Nc5ccnn5C)n4)ccn23)c1] | 4-(3-((6-chloro-4-methoxypyridin-2-yl)methyl)-[1,2,4]triazolo[4,3-a]pyridin-7-yl)-N-(1-methyl-1H-pyrazol-5-yl)pyrimidin-2-amine | 447.9 |
| 516 | 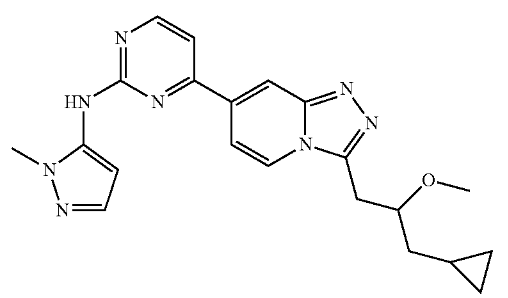 [SMILES: COC(Cc1nnc2cc(-c3ccnc(Nc4ccnn4C)n3)ccn12)CC1CC1] | 4-(3-(3-cyclopropyl-2-methoxypropyl)-[1,2,4]triazolo[4,3-a]pyridin-7-yl)-N-(1-methyl-1H-pyrazol-5-yl)pyrimidin-2-amine | 405.0 |
| 517 | 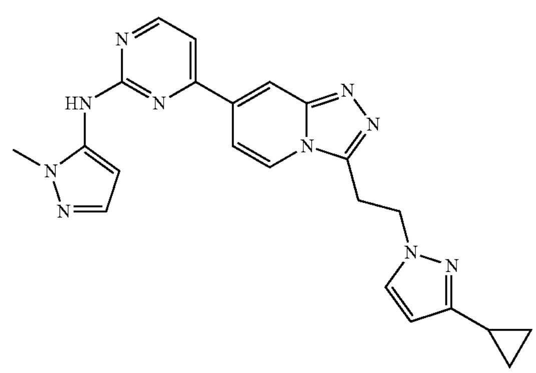 [SMILES: Cn1nccc1Nc1nccc(-c2ccn3c(CCn4ccc(C5CC5)n4)nnc3c2)n1] | 4-(3-(2-(3-cyclopropyl-1H-pyrazol-1-yl)ethyl)-[1,2,4]triazolo[4,3-a]pyridin-7-yl)-N-(1-methyl-1H-pyrazol-5-yl)pyrimidin-2-amine | 427.2 |
| 518 | 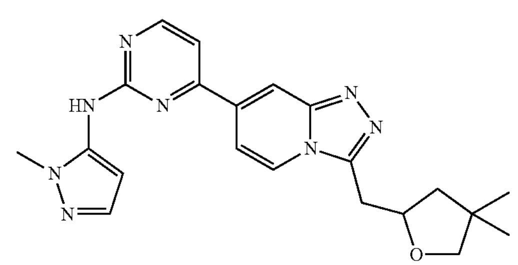 | 4-(3-((4,4-dimethyltetrahydrofuran-2-yl)methyl)-[1,2,4]triazolo[4,3-a]pyridin-7-yl)-N-(1-methyl-1H-pyrazol-5-yl)pyrimidin-2-amine (Enantiomer 1) | 405.4 |

TABLE 2-continued

| Ex. # | Structure | Name | MS (ACPI+) M + 1 (retention time) |
|---|---|---|---|
| 519 | 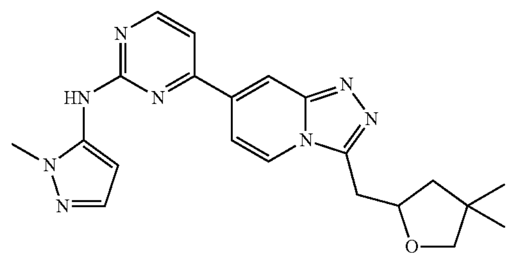 | 4-(3-((4,4-dimethyltetrahydrofuran-2-yl)methyl)-[1,2,4]triazolo[4,3-a]pyridin-7-yl)-N-(1-methyl-1H-pyrazol-5-yl)pyrimidin-2-amine (Enantiomer 2) | 405.4 |
| 520 | 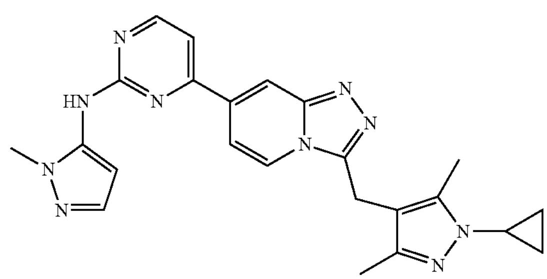 [SMILES: Cc1nn(C2CC2)c(C)c1Cc1nnc2cc(-c3ccnc(Nc4ccnn4C)n3)ccn12] | 4-(3-((1-cyclopropyl-3,5-dimethyl-1H-pyrazol-4-yl)methyl)-[1,2,4]triazolo[4,3-a]pyridin-7-yl)-N-(1-methyl-1H-pyrazol-5-yl)pyrimidin-2-amine | 441.4 |
| 521 | 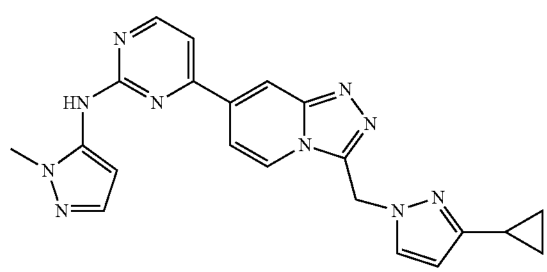 [SMILES: Cn1nccc1Nc1nccc(-c2ccn3c(Cn4ccc(C5CC5)n4)nnc3c2)n1] | 4-(3-((3-cyclopropyl-1H-pyrazol-1-yl)methyl)-[1,2,4]triazolo[4,3-a]pyridin-7-yl)-N-(1-methyl-1H-pyrazol-5-yl)pyrimidin-2-amine | 413.2 |
| 522 | 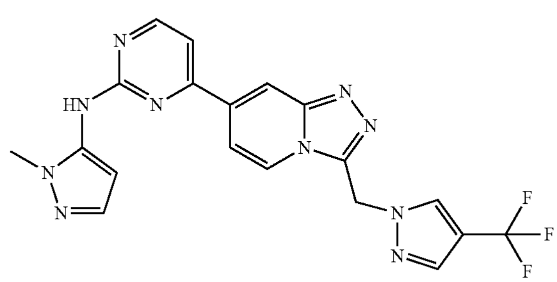 [SMILES: Cn1nccc1Nc1nccc(-c2ccn3c(Cn4cc(C(F)(F)F)cn4)nnc3c2)n1] | N-(1-methyl-1H-pyrazol-5-yl)-4-(3-((4-(trifluoromethyl)-1H-pyrazol-1-yl)methyl)-[1,2,4]triazolo[4,3-a]pyridin-7-yl)pyrimidin-2-amine | 441.2 |
| 523 | 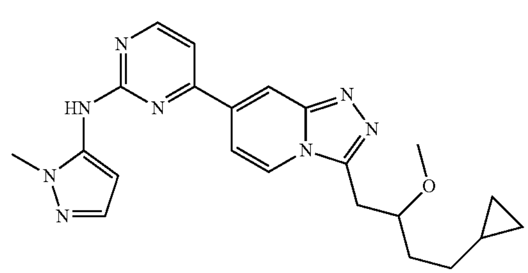 [SMILES: COC(CCC1CC1)Cc1nnc2cc(-c3ccnc(Nc4ccnn4C)n3)ccn12] | 4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine | 419.0 |

TABLE 2-continued

| Ex. # | Structure | Name | MS (ACPI+) M + 1 (retention time) |
|---|---|---|---|
| 524 | 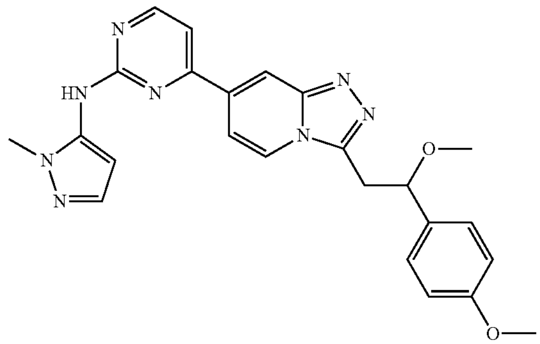 | 4-(3-(2-methoxy-2-(4-methoxyphenyl)ethyl)-[1,2,4]triazolo[4,3-a]pyridin-7-yl)-N-(1-methyl-1H-pyrazol-5-yl)pyrimidin-2-amine | 457.0 |
| 525 | 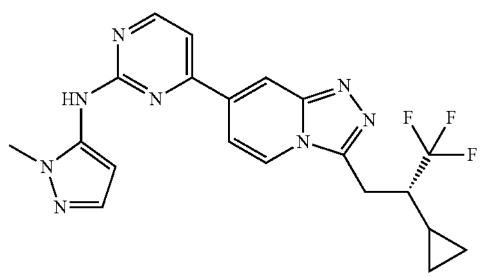 [SMILES: Cn1nccc1Nc1nccc(-c2ccn3c(C[C@@H](C4CC4)C(F)(F)F)nnc3c2)n1] | (S)-4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine | 428.9 |
| 526 | 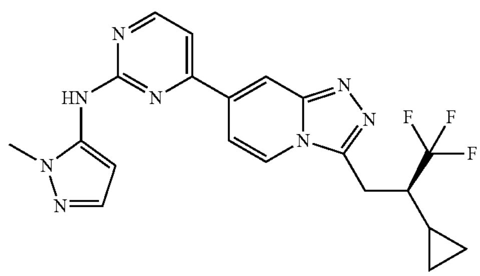 [SMILES: Cn1nccc1Nc1nccc(-c2ccn3c(C[C@H](C4CC4)C(F)(F)F)nnc3c2)n1] | (R)-4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine | 428.9 |
| 527 | 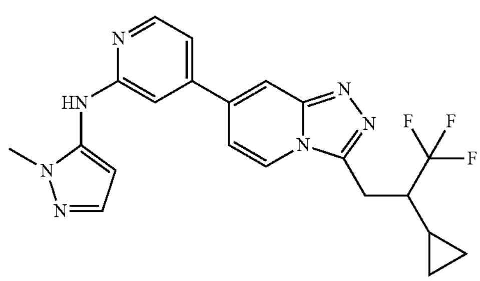 [SMILES: Cn1nccc1Nc1cc(-c2ccn3c(CC(C4CC4)C(F)(F)F)nnc3c2)ccn1] | 4-(3-(2-cyclopropyl-3,3,3-trifluoropropyl)-[1,2,4]triazolo[4,3-a]pyridin-7-yl)-N-(1-methyl-1H-pyrazol-5-yl)pyridin-2-amine | 428.9 |
| 528 | 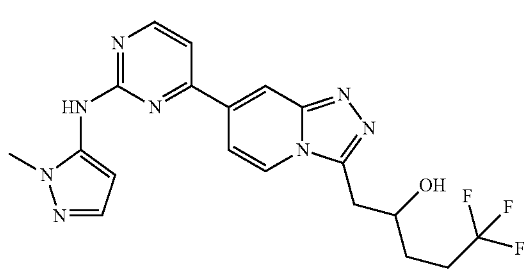 [SMILES: Cn1nccc1Nc1nccc(-c2ccn3c(CC(O)CCC(F)(F)F)nnc3c2)n1] | 5,5,5-trifluoro-1-(7-(2-((1-methyl-1H-pyrazol-5-yl)amino)pyrimidin-4-yl)-[1,2,4]triazolo[4,3-a]pyridin-3-yl)penlan-2-ol | 433.2 |

TABLE 2-continued

| Ex. # | Structure | Name | MS (ACPI+) M + 1 (retention time) |
|---|---|---|---|
| 529 | 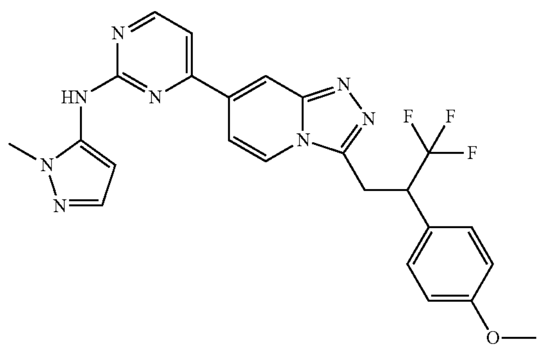 | N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine | 495.0 |
| 530 | 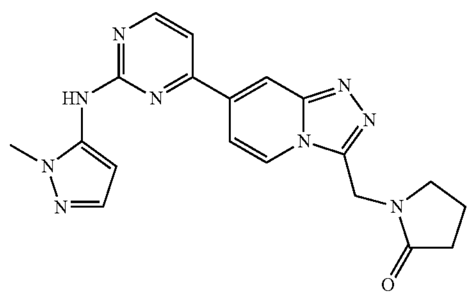 [SMILES: Cn1nccc1Nc1nccc(-c2ccn3c(CN4CCCC4=O)nnc3c2)n1] | 1-((7-(2-((1-methyl-1H-pyrazol-5-yl)amino)pyrimidin-4-yl)-[1,2,4]triazolo[4,3-a]pyridin-3-yl)methyl)pyrrolidin-2-one | 390.2 |
| 531 | 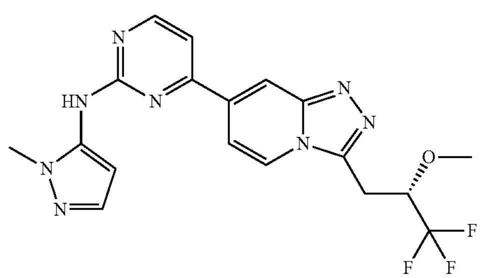 [SMILES: CO[C@@H](Cc1nnc2cc(-c3ccnc(Nc4ccnn4C)n3)ccn12)C(F)(F)F] | (S)-N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine | 419.1 |
| 532 | 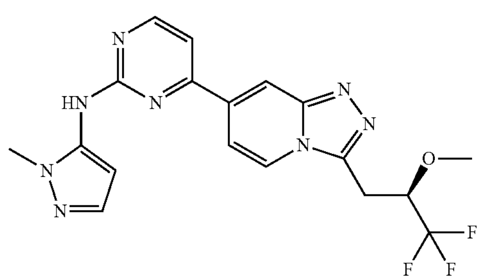 [SMILES: CO[C@H](Cc1nnc2cc(-c3ccnc(Nc4ccnn4C)n3)ccn12)C(F)(F)F] | (R)-N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine | 419.1 |
| 533 | 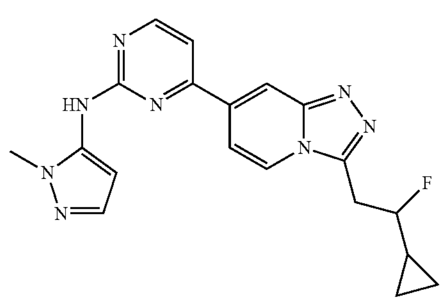 [SMILES: Cn1nccc1Nc1nccc(-c2ccn3c(CC(F)C4CC4)nnc3c2)n1] | 4-(3-(2-cyclopropyl-2-fluoroethyl)-[1,2,4]triazolo[4,3-a]pyridin-7-yl)-N-(1-methyl-1H-pyrazol-5-yl)pyrimidin-2-amine | 379.0 |

TABLE 2-continued

| Ex. # | Structure | Name | MS (ACPI+) M + 1 (retention time) |
|---|---|---|---|
| 534 | 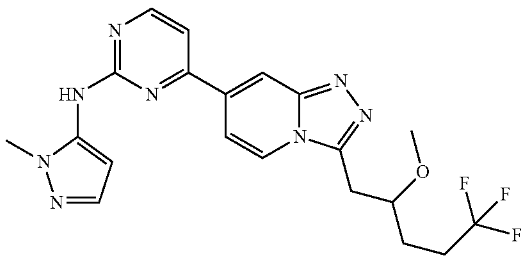 | N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine | 447.1 |
| 535 | 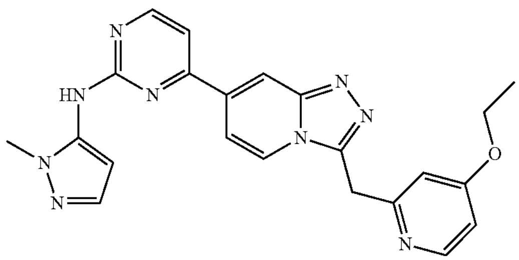 [SMILES: CCOc1ccnc(Cc2nnc3cc(-c4ccnc(Nc5ccnn5C)n4)ccn23)c1] | 4-(3-((4-ethoxypyridin-2-yl)methyl)-[1,2,4]triazolo[4,3-a]pyridin-7-yl)-N-(1-methyl-1H-pyrazol-5-yl)pyrimidin-2-amine | 428.0 |
| 536 | 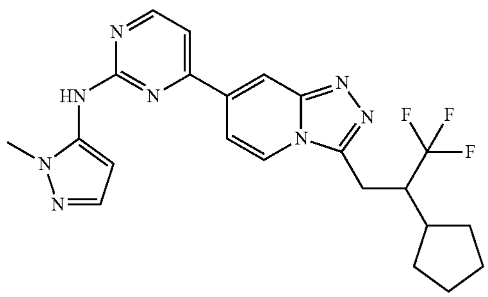 [SMILES: Cn1nccc1Nc1nccc(-c2ccn3c(CC(C4CCCC4)C(F)(F)F)nnc3c2)n1] | 4-(3-(2-cyclopentyl-3,3,3-trifluoropropyl)-[1,2,4]triazolo[4,3-a]pyridin-7-yl)-N-(1-methyl-1H-pyrazol-5-yl)pyrimidin-2-amine | 457.1 |
| 537 | 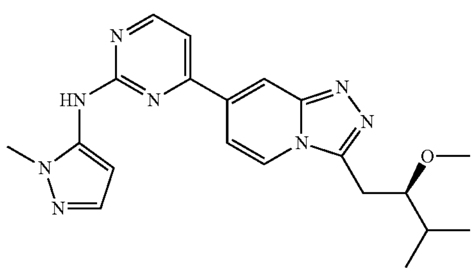 [SMILES: CO[C@H](Cc1nnc2cc(-c3ccnc(Nc4ccnn4C)n3)ccn12)C(C)C] | (R)-4-(3-(2-methoxy-3-methylbutyl)-[1,2,4]triazolo[4,3-a]pyridin-7-yl)-N-(1-methyl-1H-pyrazol-5-yl)pyrimidin-2-amine | 393.2 |
| 538 | 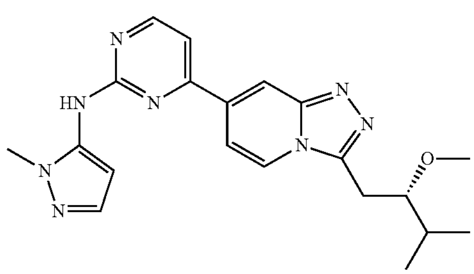 [SMILES: CO[C@@H](Cc1nnc2cc(-c3ccnc(Nc4ccnn4C)n3)ccn12)C(C)C] | (S)-4-(3-(2-methoxy-3-methylbutyl)-[1,2,4]triazolo[4,3-a]pyridin-7-yl)-N-(1-methyl-1H-pyrazol-5-yl)pyrimidin-2-amine | 393.2 |

TABLE 2-continued

| Ex. # | Structure | Name | MS (ACPI+) M + 1 (retention time) |
|---|---|---|---|
| 539 | 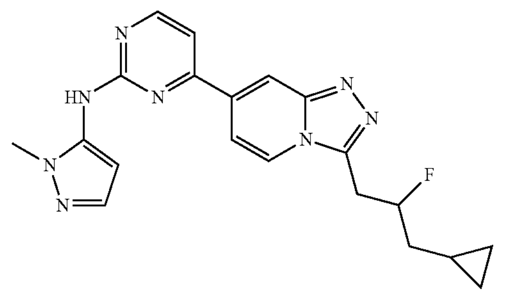 [SMILES: Cn1nccc1Nc1nccc(-c2ccn3c(CC(F)CC4CC4)nnc3c2)n1] | 4-(3-(3-cyclopropyl-2-fluoropropyl)-[1,2,4]triazolo[4,3-a]pyridin-7-yl)-N-(1-methyl-1H-pyrazol-5-yl)pyrimidin-2-amine | 393.0 |
| 540 | 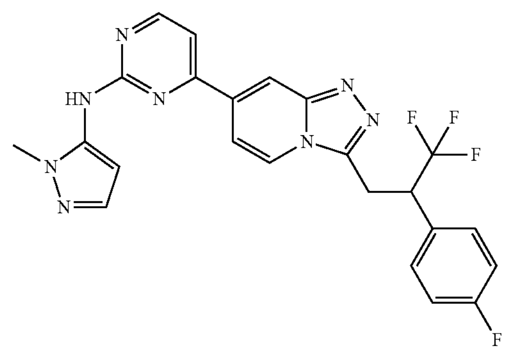 [SMILES: Cn1nccc1Nc1nccc(-c2ccn3c(CC(c4ccc(F)cc4)C(F)(F)F)nnc3c2)n1] | N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine | 482.9 |
| 541 | 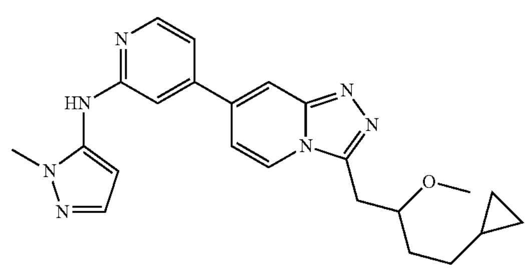 | 4-(3-(4-cyclopropyl-2-methoxybutyl)-[1,2,4]triazolo[4,3-a]pyridin-7-yl)-N-(1-methyl-1H-pyrazol-5-yl)pyridin-2-amine | 418.0 |
| 542 | 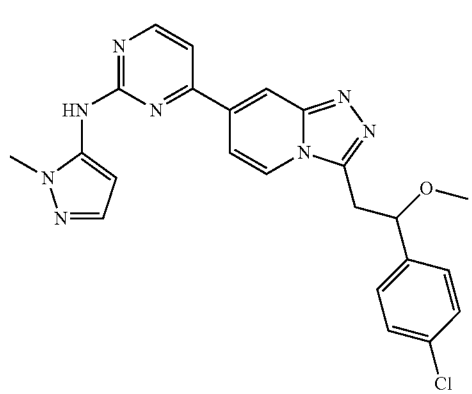 | 4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine | 460.9 |

TABLE 2-continued

| Ex. # | Structure | Name | MS (ACPI+) M + 1 (retention time) |
|---|---|---|---|
| 543 | 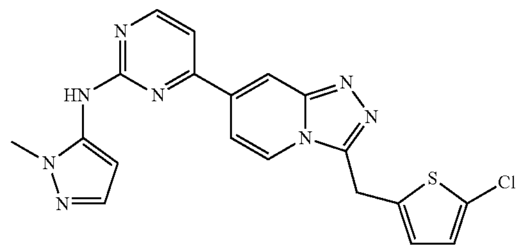 [SMILES: Cn1nccc1Nc1nccc(-c2ccn3c(Cc4ccc(Cl)s4)nnc3c2)n1] | 4-(3-((5-chlorothiophen-2-yl)methyl)-[1,2,4]triazolo[4,3-a]pyridin-7-yl)-N-(1-methyl-1H-pyrazol-5-yl)pyrimidin-2-amine | 422.8 |
| 544 | 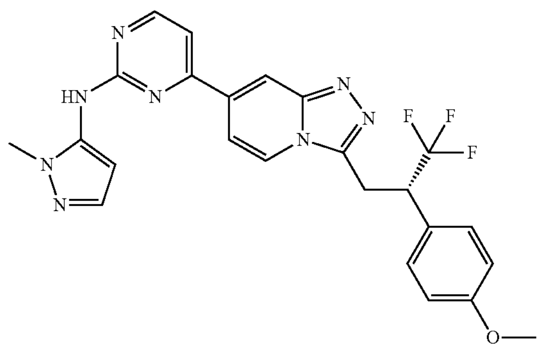 | (S)-N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine | 495.2 |
| 545 | 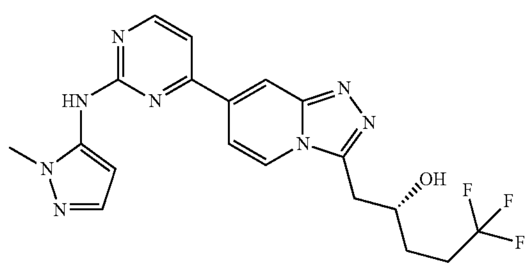 | (R)-5,5,5-trifluoro-1-(7-(2-((1-methyl-1H-pyrazol-5-yl)amino)pyrimidin-4-yl)-[1,2,4]triazolo[4,3-a]pyridin-3-yl)pentan-2-ol | 433.1 |
| 546 | 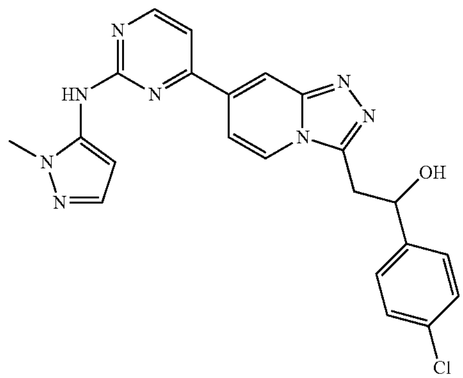 [SMILES: Cn1nccc1Nc1nccc(-c2ccn3c(CC(O)c4ccc(Cl)cc4)nnc3c2)n1] | 1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol | 447.1 |

TABLE 2-continued

| Ex. # | Structure | Name | MS (ACPI+) M + 1 (retention time) |
|---|---|---|---|
| 547 | 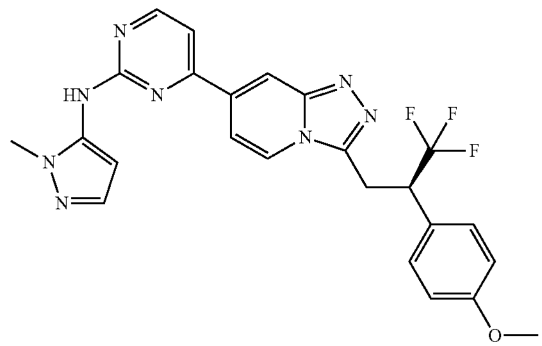 | (R)-N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine | 495.2 |
| 548 | 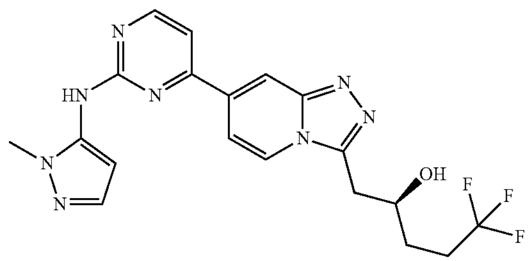 [SMILES: Cn1nccc1Nc1nccc(-c2ccn3c(C[C@@H](O)CCC(F)(F)F)nnc3c2)n1] | (S)-5,5,5-trifluoro-1-(7-(2-((1-methyl-1H-pyrazol-5-yl)amino)pyrimidin-4-yl)-[1,2,4]triazolo[4,3-a]pyridin-3-yl)pentan-2-ol | 433.2 |
| 549 | 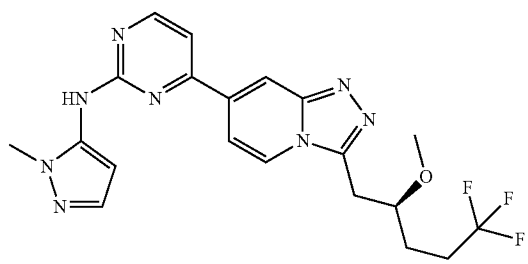 [SMILES: CO[C@@H](CCC(F)(F)F)Cc1nnc2cc(-c3ccnc(Nc4ccnn4C)n3)ccn12] | (S)-N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine | 447.1 |
| 550 | 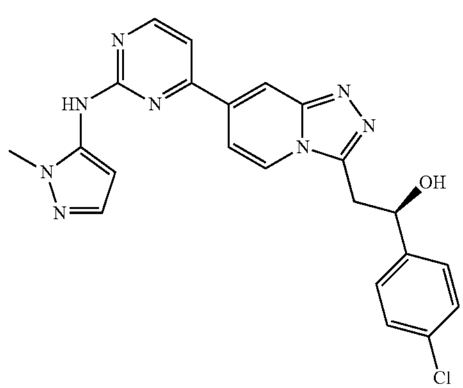 [SMILES: Cn1nccc1Nc1nccc(-c2ccn3c(C[C@@H](O)c4ccc(Cl)cc4)nnc3c2)n1] | (R)-1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol | 447.1 |

TABLE 2-continued

| Ex. # | Structure | Name | MS (ACPI+) M + 1 (retention time) |
|---|---|---|---|
| 551 | 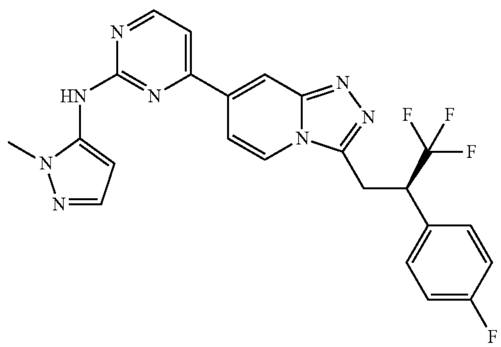 [SMILES: Cn1nccc1Nc1nccc(-c2ccn3c(C[C@H](c4ccc(F)cc4)C(F)(F)F)nnc3c2)n1] | (R)-N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine | 483.1 |
| 552 | 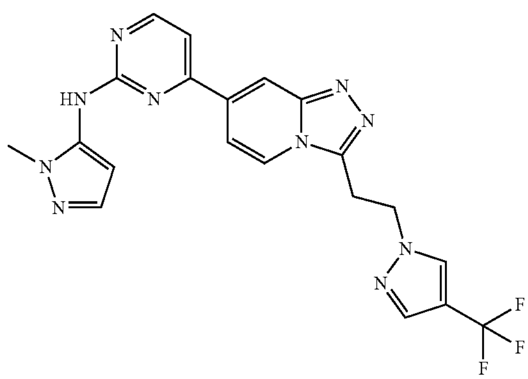 [SMILES: Cn1nccc1Nc1nccc(-c2ccn3c(CCn4cc(C(F)(F)F)cn4)nnc3c2)n1] | N-(1-methyl-1H-pyrazol-5-yl)-4-(3-(2-(4-(trifluoromethyl)-1H-pyrazol-1-yl)ethyl)-[1,2,4]triazolo[4,3-a]pyridin-7-yl)pyrimidin-2-amine | 455.2 |
| 553 | 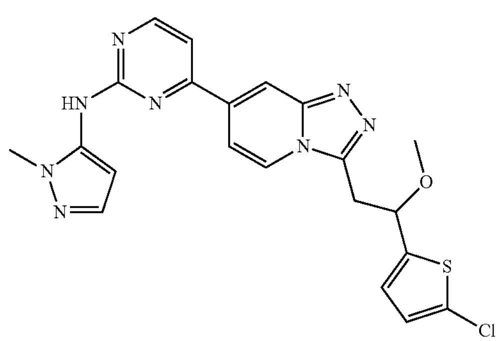 [SMILES: COC(Cc1nnc2cc(-c3ccnc(Nc4ccnn4C)n3)ccn12)c1ccc(Cl)s1] | 4-(3-(2-(5-chlorothiophen-2-yl)-2-methoxyethyl)-[1,2,4]triazolo[4,3-a]pyridin-7-yl)-N-(1-methyl-1H-pyrazol-5-yl)pyrimidin-2-amine | 466.9 |
| 554 | 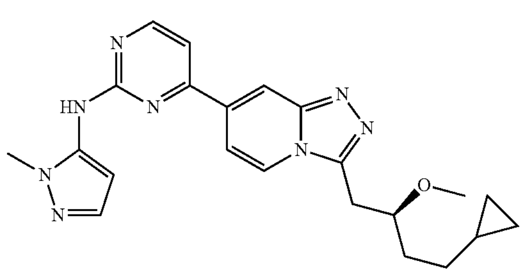 [SMILES: CO[C@@H](CCC1CC1)Cc1nnc2cc(-c3ccnc(Nc4ccnn4C)n3)ccn12] | (S)-4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine | 419.2 |

TABLE 2-continued

| Ex. # | Structure | Name | MS (ACPI+) M + 1 (retention time) |
|---|---|---|---|
| 555 | 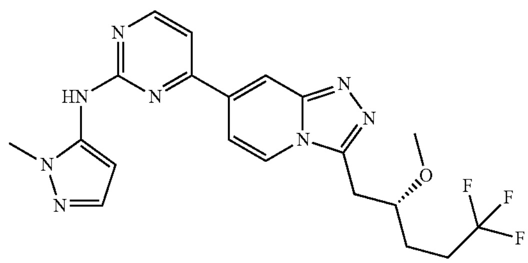 | (R)-N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine | 446.4 |
| 556 | 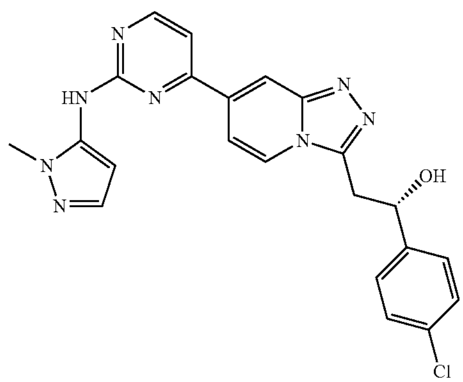 | (S)-1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol | 447.1 |
| 557 | 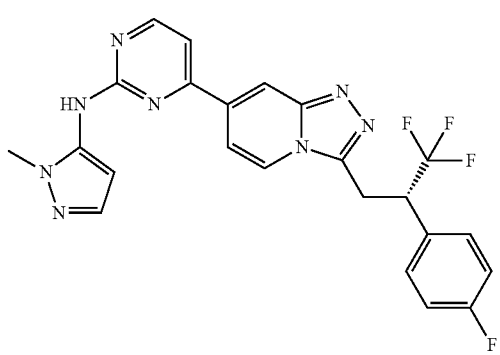 | (S)-N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine | 483.1 |
| 558 | 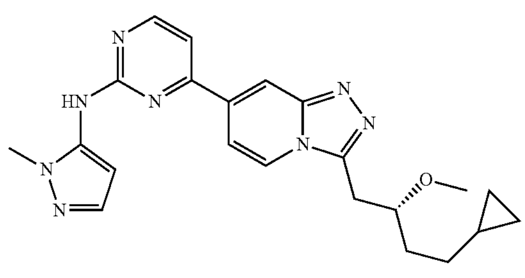 [SMILES: CO[C@H](CCC1CC1)Cc1nnc2cc(-c3ccnc(Nc4ccnn4C)n3)ccn12] | (R)-4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine | 419.2 |

US 9,670,208 B2

TABLE 2-continued

| Ex. # | Structure | Name | MS (ACPI+) M + 1 (retention time) |
|---|---|---|---|
| 559 | 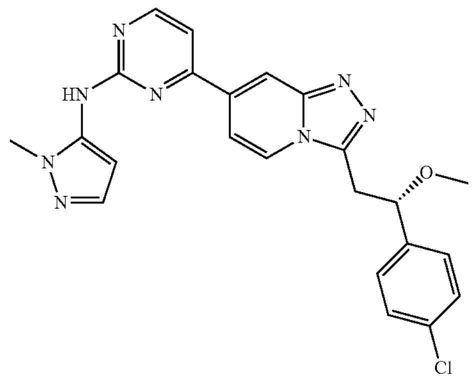 | (S)-4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine | 461.2 |
| 560 | 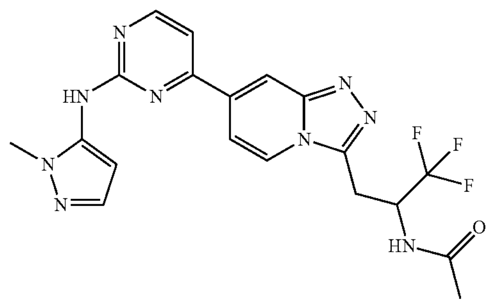 [SMILES: CC(=O)NC(Cc1nnc2cc(-c3ccnc(Nc4ccnn4C)n3)ccn12)C(F)(F)F] | N-(1,1,1-trifluoro-3-(7-(2-((1-methyl-1H-pyrazol-5-yl)amino)pyrimidin-4-yl)-[1,2,4]triazolo[4,3-a]pyridin-3-yl)propan-2-yl)acetamide | 445.9 |
| 561 | 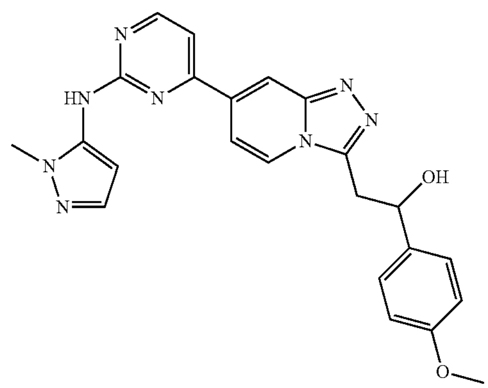 | 1-(4-methoxyphenyl)-2-(7-(2-((1-methyl-1H-pyrazol-5-yl)amino)pyrimidin-4-yl)-[1,2,4]triazolo[4,3-a]pyridin-3-yl)ethanol | 442.9 |
| 562 | 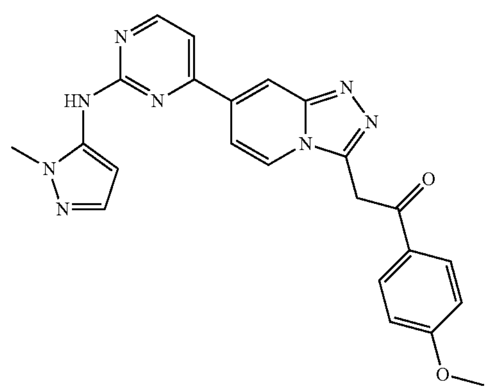 | 1-(4-methoxyphenyl)-2-(7-(2-((1-methyl-1H-pyrazol-5-yl)amino)pyrimidin-4-yl)-[1,2,4]triazolo[4,3-a]pyridin-3-yl)ethanone | 440.9 |

TABLE 2-continued

| Ex. # | Structure | Name | MS (ACPI+) M + 1 (retention time) |
|---|---|---|---|
| 563 | 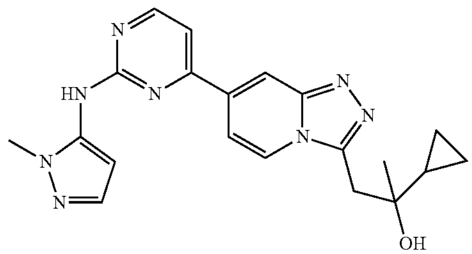 [SMILES: Cn1nccc1Nc1nccc(-c2ccn3c(CC(C)(O)C4CC4)nnc3c2)n1] | 2-cyclopropyl-1-(7-(2-((1-methyl-1H-pyrazol-5-yl)amino)pyrimidin-4-yl)-[1,2,4]triazolo[4,3-a]pyridin-3-yl)propan-2-ol | 390.8 |
| 564 | 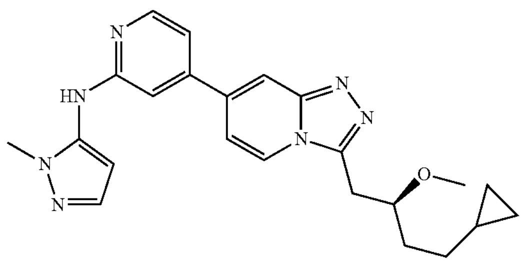 [SMILES: CO[C@@H](CCC1CC1)Cc1nnc2cc(-c3ccnc(Nc4ccnn4C)c3)ccn12] | (S)-4-(3-(4-cyclopropyl-2-methoxybutyl)-[1,2,4]triazolo[4,3-a]pyridin-7-yl)-N-(1-methyl-1H-pyrazol-5-yl)pyridin-2-amine | |
| 565 | 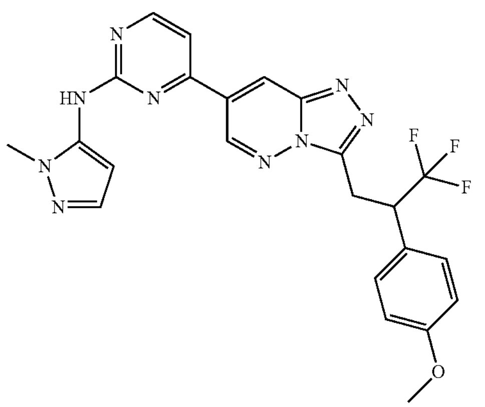 [SMILES: COc1ccc(C(Cc2nnc3cc(-c4ccnc(Nc5ccnn5C)n4)cnn23)C(F)(F)F)cc1] | N-(1-methyl-1H-pyrazol-5-yl)-4-(3-(3,3,3-trifluoro-2-(4-methoxyphenyl)propyl)-[1,2,4]triazolo[4,3-b]pyridazin-7-yl)pyrimidin-2-amine | 459.9 |
| 566 | 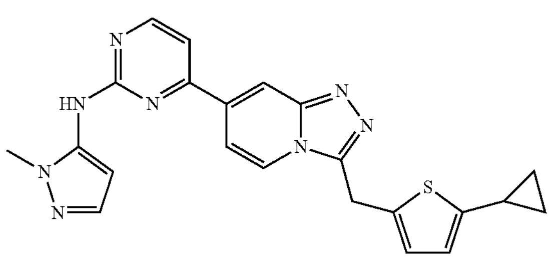 [SMILES: Cn1nccc1Nc1nccc(-c2ccn3c(Cc4ccc(C5CC5)s4)nnc3c2)n1] | 4-(3-((5-cyclopropylthiophen-2-yl)methyl)-[1,2,4]triazolo[4,3-a]pyridin-7-yl)-N-(1-methyl-1H-pyrazol-5-yl)pyrimidin-2-amine | 428.9 |
| 567 | 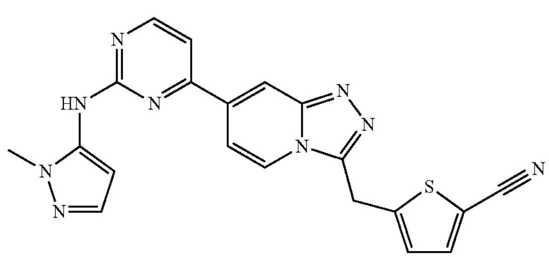 [SMILES: Cn1nccc1Nc1nccc(-c2ccn3c(Cc4ccc(C#N)s4)nnc3c2)n1] | 5-((7-(2-((1-methyl-1H-pyrazol-5-yl)amino)pyrimidin-4-yl)-[1,2,4]triazolo[4,3-a]pyridin-3-yl)methyl)thiophene-2-carbonitrile | 414.0 |

TABLE 2-continued

| Ex. # | Structure | Name | MS (ACPI+) M + 1 (retention time) |
|---|---|---|---|
| 568 | 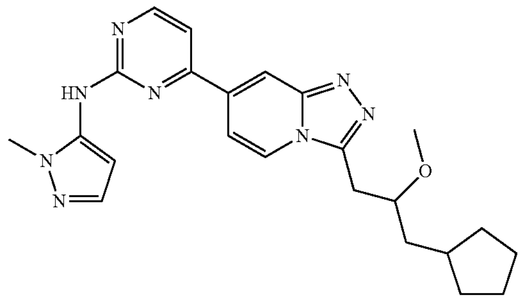 [SMILES: COC(Cc1nnc2cc(-c3ccnc(Nc4ccnn4C)n3)ccn12)CC1CCCC1] | 4-(3-(3-cyclopentyl-2-methoxypropyl)-[1,2,4]triazolo[4,3-a]pyridin-7-yl)-N-(1-methyl-1H-pyrazol-5-yl)pyrimidin-2-amine | 432.9 |
| 569 | 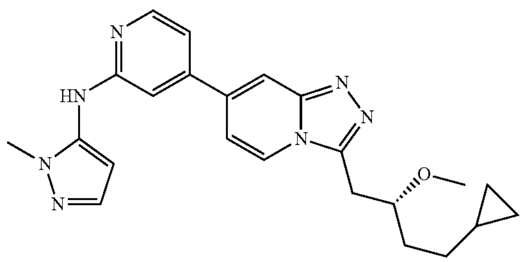 [SMILES: CO[C@H](CCC1CC1)Cc1nnc2cc(-c3ccnc(Nc4ccnn4C)c3)ccn12] | (R)-4-(3-(4-cyclopropyl-2-methoxybutyl)-[1,2,4]triazolo[4,3-a]pyridin-7-yl)-N-(1-methyl-1H-pyrazol-5-yl)pyridin-2-amine | 418.2 |
| 570 | 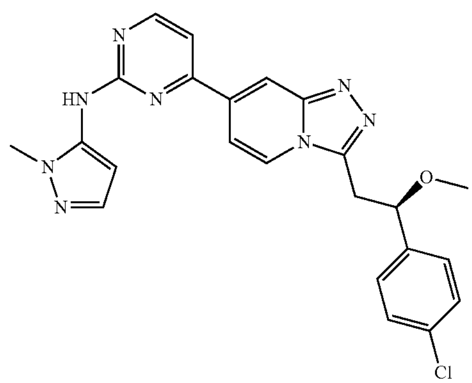 | (R)-4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine | 461.1 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

What is claimed is:

1. A compound of Formula I:

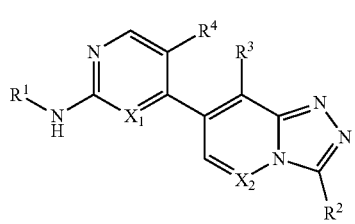

or a stereoisomer, tautomer or pharmaceutically acceptable salt thereof, wherein:

$X_1$ is N;

$X_2$ is selected from CH and N;

$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$; (d) a 3 to 7 membered saturated or partially unsaturated heterocyclyl optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$; and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;

$R^2$ is selected from (a) hydrogen; (b) $C_1$-$C_{12}$ alkyl optionally substituted by one to eight $R^f$ groups; (c) $C_2$-$C_{12}$ alkenyl optionally substituted by one to eight $R^f$ groups; (d) $OR^g$; (e) $C_3$-$C_7$ cycloalkyl optionally substituted with one to six groups selected from halogen; OH; $C_1$-$C_3$ alkyl optionally substituted with halogen, OH or phenyl optionally substituted with halogen; C(=O)O ($C_1$-$C_3$ alkyl), wherein the alkyl may be optionally substituted with halogen or OH; and phenyl optionally substituted with halogen; (f) phenyl optionally substituted with one to four groups selected from halogen, $C_1$-$C_3$ alkyl optionally substituted with halogen, OH or methoxy, and phenoxy optionally substituted with halogen, OH or methoxy; (g) 4 to 7 membered saturated or partially unsaturated heterocyclyl containing one to three heteroatoms selected from N, O and S, wherein the heterocyclyl may be optionally substituted with one to four $R^h$ groups; (h) a 5 to 6 membered heteroaryl containing one to four heteroatoms selected from N, O and S, wherein the heteroaryl may be optionally substituted with one to four $R^i$ groups; and (i) a 9 to 10 membered bicyclic heterocyclyl containing one to three heteroatoms selected from N, O and S, wherein the heterocyclyl may be optionally substituted with one to four $R^h$ groups;

$R^3$ is selected from hydrogen and halogen;

$R^4$ is selected from hydrogen and halogen;

each $R^a$, $R^b$, $R^c$, $R^d$ and $R^e$ are independently selected from hydrogen and $C_1$-$C_6$ alkyl;

each $R^f$ is independently selected from (a) halogen; (b) CN; (c) oxo; (d) $OR^j$; (e) $SR^k$; (f) $S(O)R^k$; (g) $S(O)_2R^k$; (h) $NR^mR^n$; (i) $C_3$-$C_6$ cycloalkyl optionally substituted with one to three $R^p$ groups; (j) phenyl optionally substituted by one to four $R^q$ groups; (k) a 4 to 7 membered saturated or partially unsaturated heterocyclyl containing one to three heteroatoms selected from N, O and S, wherein the heterocyclyl may be optionally substituted with one to three groups selected from halogen, oxo and $C_1$-$C_3$ alkyl optionally substituted with halogen; (l) a 5 to 6 membered heteroaryl containing one to four heteroatoms selected from N, O and S, wherein the heteroaryl may be optionally substituted by one to three $R^s$ groups; (m) $C_7$-$C_{10}$ bicyclic cycloalkyl optionally substituted with one to three groups selected from halogen and $C_1$-$C_3$ alkyl optionally substituted with halogen; (n) a 9 to 10 membered bicyclic heterocyclyl containing one to three heteroatoms selected from N, O and S, wherein the bicyclic heterocyclyl may be optionally substituted with one to three groups selected from halogen and $C_1$-$C_3$ alkyl optionally substituted with halogen; (o) a 9 to 10 membered bicyclic heteroaryl containing one to four heteroatoms selected from N, O and S, wherein the bicyclic heteroaryl is substituted with one to three groups selected from halogen, CN and $C_1$-$C_3$ alkyl optionally substituted with halogen; and (p) adamantanyl;

$R^g$ is independently selected from hydrogen, $C_1$-$C_4$ alkyl, $C_3$-$C_6$ cycloalkyl and phenyl, wherein the alkyl, cycloalkyl and phenyl may be optionally substituted with halogen;

each $R^h$ is selected from halogen; OH; $C_1$-$C_3$ alkyl optionally substituted with one to three groups selected from halogen, OH, CN, methoxy, oxo, cyclopropyl and phenyl optionally substituted by one to three groups selected from halogen, CN, methyl and methoxy; $C_1$-$C_3$ alkoxy optionally substituted by halogen or OH; oxo; phenyl optionally substituted with one to three groups selected from halogen, OH, CN, methyl and methoxy; phenoxy wherein the phenoxy optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy;

each $R^i$ is selected from halogen; OH; $C_1$-$C_4$ alkyl optionally substituted with one to three groups selected from halogen, OH, CN, methoxy, oxo, cyclopropyl and phenyl optionally substituted by one to three groups selected from halogen, CN, methyl and methoxy; $C_1$-$C_3$ alkoxy optionally substituted by halogen or OH; phenyl optionally substituted with one to three groups selected from halogen, OH, CN, methyl and methoxy; benzyl optionally substituted with one to three groups selected from halogen, OH, CN, methyl and methoxy; and a 5 to 6 membered heteroaryl containing one to four heteroatoms selected from N, O and S, wherein the heteroaryl may be optionally substituted by one to four groups selected from halogen, OH, CN, methyl and methoxy;

each $R^j$ is independently selected from hydrogen, $C_1$-$C_4$ alkyl, cyclopropyl and phenyl, wherein the alkyl and phenyl may be optionally substituted with halogen;

each $R^k$ is independently selected from $C_1$-$C_4$ alkyl, $C_5$ cycloalkyl, phenyl and benzyl, wherein the phenyl may be optionally substituted with halogen;

each $R^m$ and $R^n$ are independently selected from hydrogen, $C_1$-$C_2$ alkyl and phenyl, wherein the alkyl may be substituted with oxo or phenyl substituted with halogen, and wherein the phenyl may be substituted with halogen;

each $R^p$ is independently selected from halogen, $OR^t$, cyclopropyl and $C_1$-$C_3$ alkyl optionally substituted with halogen;

each $R^q$ is independently selected from halogen, CN, $OR^u$, $SR^u$, $C_3$-$C_6$ cycloalkyl optionally substituted with halogen, and $C_1$-$C_3$ alkyl optionally substituted with halogen;

each $R^s$ is independently selected from halogen, CN, $OR^w$, $C_1$-$C_3$ alkyl, $C_3$-$C_6$ cycloalkyl, phenyl and benzyl, wherein the alkyl, cycloalkyl, phenyl and benzyl may be optionally substituted with one to three groups selected from halogen and methyl;

each $R^t$ is independently selected from hydrogen and $C_1$-$C_4$ alkyl optionally substituted with halogen;

each $R^u$ is independently selected from hydrogen and $C_1$-$C_4$ alkyl optionally substituted with halogen; and each $R^w$ is independently selected from hydrogen and $C_1$-$C_3$ alkyl optionally substituted with halogen.

2. The compound of claim 1, wherein the compound has the structure of Formula VIII:

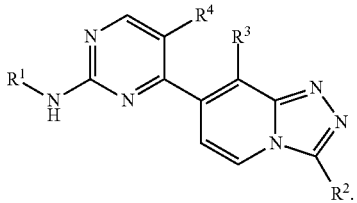

3. The compound of claim 1, wherein the compound has the structure of Formula IX:

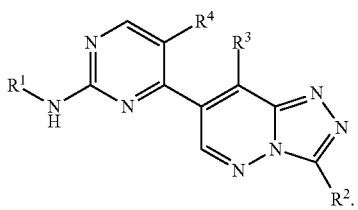

4. The compound of claim 1, wherein $R^3$ is hydrogen and $R^4$ is selected from hydrogen and halogen, or $R^3$ is selected from hydrogen and halogen and $R^4$ is hydrogen.

5. The compound of claim 1, wherein $R^3$ is hydrogen and $R^4$ is selected from hydrogen and fluorine, or $R^3$ is selected from hydrogen and fluorine and $R^4$ is hydrogen.

6. The compound of claim 1, wherein $R^1$ is selected from methyl, ethyl, isopropyl, tent-butyl, isobutyl, 2-hydroxyethyl, 1-hydroxymethylpropyl, 1-hydroxypropan-2-yl, 2-methoxy-1-methyl-ethyl, 2-hydroxypropyl, 2-hydroxy-1-hydroxymethyl-ethyl, acetyl, 2,2,2-trifluoro-1-methyl-ethyl, 2,2,2-trifluoro-1-hydroxymethyl -ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol -4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 1-methyl-1H-1,2,4-triazol-5-yl, 5-chloropyrazin-2-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopentyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl.

7. The compound of claim 1, wherein $R^1$ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl.

8. The compound of claim 1, wherein $R^1$ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

9. The compound of claim 1, wherein $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methyl-1,2,3-triazol-4-yl, 1-methyl-1,2,4-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

10. The compound of claim 1, wherein $R^1$ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydro-2H-pyran-4-yl, 3-fluorotetrahydropyran-4-yl, 2-(hydroxymethyl)tetrahydropyran-4-yl, (4-tetrahydro-2H-pyran-2-yl)methyl acetate, tetrahydrofuran-3-yl, 3-methyloxetan-3-yl, oxetany-3-ylmethyl, 2-methoxyethyl, 1-methyl-1H-pyrazol-5-yl, 1-methyl-1H-pyrazol-4-yl, 2-methylpyrazol- 3-yl, 2,5-dimethylpyrazol-3-yl, 1,3-dimethylpyrazol-4-yl, 2-methyl-2H-1,2,3-triazol-4-yl and 1-methyl-1H-1,2,4-triazol-5-yl.

11. The compound of claim 1, wherein:
$R^1$ is selected from (a) $C_1$-$C_6$ alkyl optionally substituted with OH; (b) 5 to 6 membered heterocyclyl; and (c) 5 to 6 membered heteroaryl substituted with $C_1$-$C_3$ alkyl;
$R^2$ is selected from (a) hydrogen; (b) $C_1$-$C_6$ alkyl optionally substituted by one to seven $R^f$ groups; (c) $C_4$-$C_5$ alkenyl substituted with phenyl; (d) $OR^g$; (e) $C_3$-$C_6$ cycloalkyl optionally substituted with one to four groups selected from $C_1$-$C_3$ alkyl optionally substituted with halogen, OH or phenyl; C(=O)O($C_1$-$C_3$ alkyl); and phenyl substituted with halogen; (f) phenyl optionally substituted with halogen or phenoxy substituted with halogen or methoxy; (g) a 5 to 6 membered saturated or partially unsaturated heterocyclyl containing one or two heteroatoms selected from N and O, wherein the heterocyclyl may be optionally substituted with one to three $R^h$ groups; (h) a 5 membered heteroaryl containing two heteroatoms selected from N and O, wherein the heteroaryl is substituted with one to three $R^i$ groups; and (i) a 10 membered bicyclic heterocyclyl containing one O heteroatom;
each $R^f$ is independently selected from (a) halogen; (b) CN; (c) oxo; (d) $OR^j$; (e) $SR^k$; (f) $S(O)R^k$; (g) $S(O)_2R^k$; (h) $NR^mR^n$; (i) $C_3$-$C_6$ cycloalkyl optionally substituted with one or two $R^p$ groups; (j) phenyl optionally substituted by one to three $R^q$ groups; (k) a 4 to 7 membered saturated or partially unsaturated heterocyclyl containing one or two heteroatoms selected from N and O, wherein the heterocyclyl may be optionally substituted with one or two groups selected from oxo and $C_1$-$C_3$ alkyl; (l) a 5 to 6 membered heteroaryl containing one to four heteroatoms selected from N and S, wherein the heteroaryl may be optionally substituted by one or two $R^s$ groups; (m) $C_7$ bicyclic cycloalkyl; (n) a 9 to 10 membered bicyclic heterocyclyl containing two O heteroatoms; (o) a 9 membered bicyclic heteroaryl containing one or two N heteroatoms, and wherein the heteroaryl is substituted with one or two groups selected from halogen, CN and methyl; and (p) adamantanyl;
$R^g$ is phenyl substituted with methoxy;
each $R^h$ is selected from $C_1$-$C_3$ alkyl optionally substituted with one to three groups selected from halogen, oxo, cyclopropyl and phenyl optionally substituted by two groups selected from halogen, CN and methoxy; oxo; phenyl optionally substituted with halogen; phenoxy optionally substituted with halogen; and a 6 membered heteroaryl containing one N heteroatom, wherein the heteroaryl is substituted by two groups selected from halogen and methoxy;
each $R^i$ is selected from $C_1$-$C_4$ alkyl, phenyl, benzyl, and a 6 membered heteroaryl containing one N heteroatom, wherein the alkyl, phenyl and benzyl may be optionally substituted with halogen;
each $R^j$ is independently selected from hydrogen, $C_1$-$C_4$ alkyl, cyclopropyl and phenyl, wherein the alkyl and phenyl may be optionally substituted with halogen;
each $R^k$ is independently selected from $C_1$-$C_4$ alkyl, $C_5$ cycloalkyl, phenyl and benzyl, wherein the phenyl may be optionally substituted with halogen;
each $R^m$ and $R^n$ are independently selected from hydrogen, $C_1$-$C_2$ alkyl and phenyl, wherein the alkyl may be substituted with oxo or phenyl substituted with halogen, and wherein the phenyl may be substituted with halogen;
each $R^p$ is independently selected from halogen, $OR^t$, cyclopropyl and $C_1$-$C_3$ alkyl optionally substituted with halogen;
each $R^q$ is independently selected from halogen, methyl, CN, $CF_3$, methoxy, ethoxy, difluoromethoxy, trifluoromethoxy, methylthio and $C_3$-$C_4$ cycloalkyl;
each $R^s$ is independently selected from halogen, OH, CN, methoxy, ethoxy, cyclopropyl, benzyl, $C_1$-$C_3$ alkyl optionally substituted with halogen, and phenyl optionally substituted with one or two groups selected from halogen and methyl; and
each $R^t$ is independently $C_1$-$C_4$ alkyl optionally substituted with halogen.

12. The compound of claim 1, wherein $R^1$ is selected from isopropyl, 1-hydroxypropan-2-yl, 1-methyl-1H-pyrazol-5-yl, 1-methyl-1H-pyrazol-4-yl, tetrahydro-2H-pyran-4-yl, 2-methyl-2H-1,2,3-triazol-4-yl and 1-methyl-1H-1,2,4-triazol-5-yl.

13. The compound of claim 1, wherein $R^2$ is selected from hydrogen, methyl, ethyl, 2-methylbutyl, 2,3-dimethylbutyl, 2,2-dimethylbutyl, 2-ethylbutyl, 3-methylpentyl, 2-methylpentyl, isopentyl, neopentyl, isobutyl, 3,3-dimethylbutyl, butyl, propyl, trifluoromethyl, 4-methylpentyl, 3-methylbutan-2-yl, 2-fluorobutyl, 4,4,4-trifluoro-2-methylbutyl, 3,3,3-trifluoro-2-methylpropyl, 2,2,2-trifluoroethyl, 3,3,3-trifluoropropyl, 2-fluoro-2-methylpropyl, 3,3,3-trifluoro-2-(trifluoromethyl)propyl, 1,1-difluoropropyl, 3-fluoro-3-methylbutyl, 2,2-difluoropropyl, 2-(trifluoromethyl)butyl, 3-fluoro-2-(fluoromethyl)propyl, 2-cyano-2-methylpropyl, 1-oxoethyl, 1-hydroxy-3-methylbutyl, 2-methoxy-3-methylbutyl, 2-ethoxybutyl, phenoxymethyl, (4-fluorophenoxy)methyl, 3-methoxy-2-methylpropyl, 3,3,3-trifluoro-2-methoxypropyl, 2-ethoxy-3,3,3-trifluoropropyl, 2-ethoxyethyl, 1-(tert-butoxy)ethyl, 1-hydroxybutyl, tert-butoxymethyl, 3,3,3-trifluoro-2-hydroxy-2-(trifluoromethyl)propyl, isopropoxymethyl, 2-methoxyethyl, isobutoxymethyl, 1-hydroxy-2-methylpropyl, methoxymethyl, 2-hydroxy-2-methylpropyl, 2-hydroxyethyl, 1-hydroxy-2-methylbutyl, 1-methoxy-2-methylpropyl, 2-methoxybutyl, 2-hydroxy-3-methylbutyl, 2-hydroxybutyl, 2-methoxypropyl, 3-hydroxy-2-methylpropyl, 2-methoxy-2-methylpropyl, 3,3,4,4,4-pentafluoro-2-(hydroxy)butyl, 3,3,3-trifluoro-2-(hydroxy)propyl, 2-(2-fluoroethoxy)propyl, 2-(cyclopropylmethoxy)propyl, 5,5,5-trifluoro-2-hydroxypentyl, 5,5,5-trifluoro-2-methoxypentyl, (benzylthio)methyl, 2-(methylthio)butyl, 2-(methylthio)ethyl, 2-(methylthio)propyl, (phenylthio)methyl, 2-(phenylthio)ethyl, ((4-fluorophenyl)thio)methyl, ((2-fluorophenyl)thio)methyl, (isopropylthio)methyl, (tert-butylthio)methyl, (isobutylthio)methyl, (cyclopentylthio)methyl, (phenylsulfinyl)methyl, (phenylsulfonyl)methyl, 2-(phenylsulfonyl)ethyl, (dimethylamino)methyl, 2-((4-fluorophenyl)amino)-2-oxoethyl, (diethylamino)methyl, 2-(2,4-difluoro-N-methylbenzamido)ethyl, (methylamino)oxomethyl, 2-acetamido-3,3,3-trifluoropropyl, cyclohexyl(hydroxyl)methyl, (1-methoxycyclobutyl)methyl, (1-methoxycyclopropyl)methyl, (1-(2-fluoroethoxy)cyclopropyl)methyl, [1,1'-bi(cyclopropan)]-1-ylmethyl, (1-ethylcyclobutyl)methyl, (1-(trifluoromethyl)cyclopropyl)methyl, (1-isopropylcyclopropyl)methyl, (1-ethylcyclopropyl)methyl, (1-methylcyclopropyl)methyl, (2,2-difluorocyclopropyl)methyl, cyclopentylmethyl, cyclohexylmethyl, (1-(trifluoromethyl)cyclobutyl)methyl, cyclopropylethyl, (4-methylcyclohexyl)methyl, cyclopropylmethyl, cyclobutylmethyl, (3,3-difluorocyclobutyl)methyl, 2-cyclopropyl-2-methylpropyl, 2-cyclopropylpropyl, (4,4-difluorocyclohexyl)methyl, (1-isobutoxycyclopropyl)methyl, (1-isopropoxycyclopropyl)methyl, 2-cyclopropyl-2-methoxyethyl, 2-cyclopentylethyl, 2-cyclohexylethyl, 3-cyclopropyl-2-hydroxypropyl, 2-cyclopropyl-2-hydroxyethyl, (1-ethoxycyclobutyl) methyl, 2-cyclopropyl-3,3,3-trifluoropropyl, 3-cyclopropyl-2-methoxypropyl, 4-cyclopropyl-2-methoxybutyl, 2-cyclopropyl-2-fluoroethyl, 2-cyclopentyl-3,3,3-trifluoropropyl, 3-cyclopropyl-2-fluoropropyl, 2-cyclopropyl-2-hydroxypropyl, 3-cyclopentyl-2-methoxypropyl, benzyl, 2-fluorobenzyl, 2-chlorobenzyl, 2-methoxybenzyl, 2-(trifluoromethyl) benzyl, 2-methylbenzyl, 3-bromobenzyl, 3-chlorobenzyl, 3-fluorobenzyl, 3-cyclopropylbenzyl, 3-cyclobutylbenzyl, 3-(trifluoromethyl)benzyl, 3-methoxybenzyl, 3-(difluoromethoxy)benzyl, 3-(trifluoromethoxy)benzyl, 3-cyanobenzyl, 4-chlorobenzyl, 4-fluorobenzyl, 4-(trifluoromethyl)benzyl, 4-methoxybenzyl, 4-(difluoromethoxy)benzyl, 4-(methylthio)benzyl, 4-methylbenzyl, 4-(trifluoromethoxy) benzyl, 4-ethoxybenzyl, 2,3-difluorobenzyl, 2,3-dichlorobenzyl, 2-fluoro-4-methoxybenzyl, 2-chloro-4-fluorobenzyl, 2,4-dichlorobenzyl, 2,4-difluorobenzyl, 2-fluoro-4-(trifluoromethyl)benzyl, 2,5-difluorobenzyl, 2-chloro-6-fluorobenzyl, 2,6-difluorobenzyl, 3-fluoro-4-methoxybenzyl, 3-fluoro-4-(trifluoromethoxy)benzyl, 3,4-difluorobenzyl, 3-chloro-4-fluorobenzyl, 3-chloro-4-methoxybenzyl, 3-chloro-5-fluorobenzyl, 3-fluoro-5-(trifluoromethyl)benzyl, 3,5-difluorobenzyl, 3,5-difluorobenzyl, 4-chloro-2-fluorobenzyl, 4-(difluoromethoxy)-2-fluorobenzyl, 4-chloro-3-fluorobenzyl, 4-fluoro-3-methoxybenzyl, 2,3-difluoro-4-methoxybenzyl, 2,3,4-trifluorobenzyl, 2,4,5-trifluorobenzyl, 3,5-difluoro-4-methoxybenzyl, 4-ethoxy-2,3-difluorobenzyl, (3-chlorophenyl)(hydroxy)methyl, (4-chlorophenyl)(methoxy)methyl, 3-hydroxy-1-(4-methoxyphenyl)-2-methylpropyl, 3-hydroxy-1-(4-methoxyphenyl)propyl, phenethyl, 3-chlorophenethyl, 4-chlorophenethyl, 1-(4-chlorophenyl)ethyl, 2-(4-fluorophenyl)-1-hydroxy-2-methylpropyl, 1-hydroxy-2-phenylethyl, 2-(4-fluorophenyl)-1-hydroxyethyl, 1-methoxy-2-phenylethyl, 1-(3-fluoro-4-methoxyphenyl)-3-hydroxypropan-2-yl, 1-(4-chlorophenyl)-2-methylpropyl, 1-phenylethyl, 2-(4-chlorophenyl)propan-2-yl, methoxy(phenyl)methyl, (4-chlorophenyl)difluoromethyl, 1-methoxy-1-phenylethyl, difluoro(3-fluoro-4-methoxyphenyl)methyl, 3-fluoro-4-methoxyphenethyl, 2-amino-1-phenethyl, 1-(4-chloro-3-fluorophenyl)-2-(hydroxy)ethyl, 1-(3-fluoro-4-methoxyphenyl)-2-(hydroxy)ethyl, (dimethylamino)(4-fluorophenyl)methyl, 2-chlorophenethyl, 2-(4-fluorophenyl)-2-methylpropyl, 2-(4-methoxyphenyl)-2-methylpropyl, 2-acetamido-2-phenylethyl, 2-acetamido-2-(3-chloro-4-fluorophenyl)ethyl, 2-methoxy-2-(4-methoxyphenyl)ethyl, 3,3,3-trifluoro-2-(4-methoxyphenyl)propyl, 3,3,3-trifluoro-2-(4-fluorophenyl)propyl, 2-(4-chlorophenyl)-2-methoxyethyl, 2-(4-chlorophenyl)-2-hydroxyethyl, 3,3,3-trifluoro-2-(4-methoxyphenyl)propyl, 2-hydroxy-2-(4-methoxyphenyl)ethyl, 2-(4-methoxyphenyl)-2-oxoethyl, phenyl(piperidin-1-yl)methyl, (tetrahydropyran-2-yl)methyl, (tetrahydrofuran-2-yl)methyl, piperdin-1-ylmethyl, (tetrahydropyran-4-yl)methyl, (tetrahydrofuran-3yl)methyl, morpholinomethyl, (5,5-dimethyltetrahydrofuran-2-yl)methyl, (6,6-dimethyltetrahydropyran-2-yl)methyl, (tetrahydropyran-3-yl)methyl, (3-ethyloxetan-3-yl)methyl, (4-methoxyphenyl)(morpholino)methyl, (1-methyl-6-oxo-1,6-dihydropyridin-3-yl)methyl, pyrrolidin-1-ylmethyl, (1-methyl-6-oxo-1,6-dihydropyridin-3-yl)methyl, azepan-1-ylmethyl, (2-methylpiperidin-1-yl)methyl, pyrrolidine-1-carbonyl, (4,4-dimethyltetrahydrofuran-2-yl)methyl, (2-oxopyrrolidin-1-yl)methyl, (1-methyl-2-oxo-1,2-dihydropyridin-4-yl) methyl, thiophen-2-ylmethyl, pyridin-3-ylmethyl, pyrimidin-2-ylmethyl, pyrimidin-5-ylmethyl, pyridin-4-ylmethyl, thiazol-2-ylmethyl, pyrazin-2-ylmethyl, pyridin-2-ylmethyl, (1-methylpyrazol-3-yl)methyl, (1-methylpyrazol-4-yl)methyl, (1-methylimidazol-2-yl)methyl, (1-benzylimidazol-2-yl)methyl, (1-(2-fluoro-4-methylphenyl)-1,2,3-triazol-5-yl)methyl, (1-methylpyrazol-4-yl)(phenyl)methyl, (1-cyclopropyl-3,5-dimethylpyrazol-4-yl)methyl, (1,3-dimethylpyrazol-5-yl)methyl, (2-methoxypyridin-3-yl)methyl, (2-chloropyridin-3-yl)methyl, (2-hydroxypyridin-3-yl)methyl, (2-methylpyridin-3-yl)methyl, (3-chloropyridin-2-yl)methyl, (3-cyclopropylpyrazol-1-yl)methyl, (4-cyclopropylpyridin-2-yl)methyl, (4-methylpyridin-2-yl)methyl, (4-methylthiazol-2-yl)methyl, (4-isopropyl-5-methylthiazol-2-yl)methyl, (4-(trifluoromethyl)pyridin-2-yl)methyl, (4-isopropylpyridin-2-yl)methyl, (4-cyclopropyl-6-methylpyridin-2-yl)methyl, (4-cyclopropyl-3-fluoropyridin-2-yl) methyl, (4-bromopyridin-2-yl)methyl, (4-methoxypyridin-2-yl)methyl, (4-(trifluoromethyl)pyrazol-1-yl)methyl, (4-ethoxypyridin-2-yl)methyl, (5-bromopyridin-3-yl) methyl, (5-chloropyridin-3-yl)methyl, (5-fluoropyridin-3-yl)methyl, (5-cyclopropylpyridin-3-yl)methyl, (5-methylpyridin-3-yl)methyl, (5-chloropyridin-2-yl)methyl, (5-methylthiazol-2-yl)methyl, (5-cyclopropyl-2-hydroxypyridin-3-yl)methyl, (5-cyclopropyl-2-methoxypyridin-3-yl)methyl, (5-chlorothiophen-2-yl)methyl, (5-cyclopropylthiophen-2-yl)methyl, (5-cyanothiophen-2-yl)methyl, (6-chloropyridin-2-yl)methyl, (6-methoxypyridin-2-yl) methyl, (6-isopropylpyridin-2-yl)methyl, (6-cyclopropylpyridin-2-yl)methyl, (6-methylpyridin-2-yl)methyl, (6-methoxypyridin-3-yl)methyl, (6-(trifluoromethyl)pyridin-2-yl)methyl, (6-phenylpyridin-2-yl)methyl, (6-chloropyridin-3-yl)methyl, (6-hydroxypyridin-2-yl)methyl, (6-cyanopyridin-2-yl)methyl, (6-ethoxypyridin-3-yl)methyl, (6-hydroxypyridin-3-yl)methyl, (6-chloro-4-methoxypyridin-2-yl)methyl, 2-(pyridin-2-yl)ethyl, 2-(pyridin-3-yl)ethyl, 2-(pyridin-4-yl)ethyl, 2-(4-(p-tolyl)-1,2,3-triazol-1-yl)ethyl, 2-(5-(p-tolyl)-1,2,3-triazol-1-yl)ethyl, 2-(3-methyl-1-phenyl-1,2,4-triazol-5-yl)ethyl, 2-(1-(p-tolyl)tetrazol-5-yl)ethyl, 2-amino-2-(3-chloro-4-fluorophenyl)ethyl, 2-(3-cyclopropylpyrazol-1-yl)ethyl, 2-(4-(trifluoromethyl)pyrazol-1-yl)ethyl, 2-(5-chlorothiophen-2-yl)-2-methoxyethyl, bicyclo[2.2.1]heptan-2-ylmethyl, (2,3-dihydrobenzo[b][1,4]dioxin-6-yl)methyl, benzo[d][1,3]dioxo1-5-ylmethyl, (5-fluoroindol-3-yl)methyl, (6-fluoroindol-3-yl)methyl, (6-methylimidazo[1,2-a]pyridin-3-yl)methyl, adamantan-1-ylmethyl, 3-methyl-1-phenylbut-1-en-1-yl, but-1-en-1-yl, 4-methoxyphenoxy, 2-(2-fluoropropan-2-yl)cyclopropyl, cyclohexyl, 2,2-dimethylcyclopropyl, 2-(ethoxycarbonyl)cyclopropyl, 2-(2-hydroxypropan-2-yl)cyclopropyl, 2-(trifluoromethyl)cyclobutyl, 2-methylcyclopropyl, 1-(4-chlorophenyl)cyclopropyl, 1-(4-chlorophenyl)cyclobutyl, 1-(4-chlorophenyl)cyclopentyl, 2,2,3,3-tetramethylcyclopropyl, 2-phenylcyclopropyl, 2-benzylcyclopropyl, phenyl, 2-chlorophenyl, 2-fluorophenyl, 2-(4-methoxyphenoxy)phenyl, 3-chlorophenyl, 3-fluorophenyl, 4-chlorophenyl, 2-chloro-4-fluorophenyl, 2-(4-fluorophenoxy)phenyl, 4-(2-fluoro-6-methoxybenzyl)morpholin-2-yl, 1-(2-fluoro-6-methoxybenzyl)piperidin-3-yl, 5-(2,6-difluorophenoxy)-1-methylpiperidin-3-yl, (5-chloro-2-fluorobenzyl)piperidin-3-yl, piperdin-3-yl, ((5-fluoro-2-methoxypyridin-3-yl)methyl)piperidin-3-yl, 1-(5-cyano-2-fluorobenzyl)piperidin-3-yl, 1-methyl-5-oxo-3-phenylpyrrolidin-2-yl, 4-(cyclopropylmethyl)morpholin-2-yl, 4-(2-fluoro-6-methoxybenzoyl)morpholin-2-yl, 4-(2,6-difluorobenzoyl)morpholin-2-yl, 4-(3,3,3-trifluoropropyl)morpholin-2-yl, 4-(3-fluorophenyl)pyrrolidin-3-yl, 4-phenylpyrrolidin-3-yl, 1-benzyl-4-(3-fluorophenyl)pyrrolidin-3-yl, 4-(4-chloro-3-fluorophenyl)pyrrolidin-3-yl, morpholin-2-yl, 1-phenyl-1H-pyrazol-5-yl, 1-methyl-3-(pyridin-3-yl)-1H-pyrazol-4-yl, 3-phenyl-1H-pyrazol-4-yl, 3-isopropyl-1-methyl-1H-pyrazol-4-yl, 3-methyl-5-phenylisoxazol-4-yl, 3-isobutyl-1-methyl-1H-pyrazol-4-yl, 5-isobutyl-1-methyl-1H-pyrazol-4-yl, 5-isopropyl-1-methyl-1H-pyrazol-4-yl, 1-(3-fluorophenyl)-1H-pyrazol-5-yl, 1-(3-fluorophenyl)-5-methyl-1H-pyrazol-3-yl, 1-(3-fluorophenyl)-3-methyl-1H-pyrazol-5-yl, 1-(3-fluorophenyl)-3-(trifluoromethyl)-1H-pyrazol-5-yl, 1-(3-chlorophenyl)-3-(trifluoromethyl)-1H-pyrazol-5-yl, 1-(4-fluorophenyl)-3-methyl-1H-pyrazol-5-yl, 1-(4-fluorophenyl)-5-methyl-1H-pyrazol-3-yl, 1-(4-fluorophenyl)-1H-pyrazol-5-yl, 1-(4-fluorophenyl)-1H-pyrazol-3-yl, 3-(3-chlorophenyl)-1,5-dimethyl-1H-pyrazol-4-yl, 3-(3-fluorophenyl)-1,5-dimethyl-1H-pyrazol-4-yl, 3-(3-fluorobenzyl)-1-methyl-1H-pyrazol-4-yl, 3-(3-fluorophenyl)-1-methyl-1H-pyrazol-4-yl, 3-(4-fluorophenyl)-1-methyl-1H-pyrazol-4-yl, 3-(4-chlorophenyl)-1-methyl-1H-pyrazol-4-yl, 3-(4-fluorobenzyl)-1-methyl-1H-pyrazol-4-yl, 3-(3,4-difluorophenyl)-1-methyl-1H-pyrazol-4-yl, 4-(3-chlorophenyl)-1-methyl-1H-pyrazol-5-yl, 4-(3-chlorophenyl)-1-methyl-1H-pyrazol-3-yl, 4-(3-chlorophenyl)-1,3-dimethyl-1H-pyrazol-5-yl, 4-(4-chlorophenyl)-1-methyl-1H-pyrazol-5-yl, 4-(4-chlorophenyl)-1-methyl-1H-pyrazol-3-yl, 4-(4-chlorophenyl)-1,3-dimethyl-1H-pyrazol-5-yl, 5-(3-fluorophenyl)-1-methyl-1H-pyrazol-4-yl, 5-(3-fluorobenzyl)-1-methyl-1H-pyrazol-4-yl, 5-(3-chlorophenyl)-1,3-dimethyl-1H-pyrazol-4-yl, 5-(4-fluorobenzyl)-1-methyl-1H-pyrazol-4-yl, 5-(4-fluorophenyl)-1-methyl-1H-pyrazol-4-yl, 5-(4-chlorophenyl)-1-methyl-1H-pyrazol-4-yl, 5-(4-chloro-3-fluorophenyl)-1,3-dimethyl-1H-pyrazol-4-yl, 5-(4-chlorophenyl)-1,3-dimethyl-1H-pyrazol-4-yl, 5-(3,4-difluorophenyl)-1-methyl-1H-pyrazol-4-yl, 5-(3,4-difluorophenyl)-1,3-dimethyl-1H-pyrazol-4-yl, 1,5-dimethyl-3-phenyl-1H-pyrazol-4-yl and isochroman-1-yl.

14. The compound of claim 1, wherein $R^2$ is $C_1$-$C_6$ alkyl optionally substituted by one to seven $R^f$ groups.

15. The compound of claim 1, wherein the compound has the structure of Formula X:

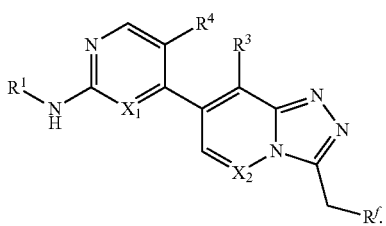

16. The compound of claim 1, wherein $R^2$ is $C_1$-$C_6$ alkyl.
17. The compound of claim 1, wherein the compound is:
4-(3-(4-(2-fluoro-6-methoxybenzyl)morpholin-2-yl)-[1,2,4]triazolo[4,3-a]pyridin-7-yl)-N-(1-methyl-1H-pyrazol-5-yl)pyrimidin-2-amine;
4-(3-(4-(2-fluoro-6-methoxybenzyl)morpholin-2-yl)-[1,2,4]triazolo[4,3-a]pyridin-7-yl)-N-(tetrahydro-2H-pyran-4-yl)pyrimidin-2-amine;
4-(3-(1-(2-fluoro-6-methoxybenzyl)piperidin-3-yl)-[1,2,4]triazolo[4,3-a]pyridin-7-yl)-N-(tetrahydro-2H-pyran-4-yl)pyrimidin-2-amine;
4-(3-(3-bromobenzyl)-[1,2,4]triazolo[4,3-a]pyridin-7-yl)-N-(1-methyl-1H-pyrazol-5-yl)pyrimidin-2-amine;
4-(3-(3-cyclopropylbenzyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(4-(methylthio)benzyl)-[1,2,4]triazolo[4,3-a]pyridin-7-yl)pyrimidin-2-amine;
(R)-cyclohexyl (7-(2-((1-methyl-1H-pyrazol-5-yl)amino)pyrimidin-4-yl)-[1,2,4]triazolo[4,3-a]pyridin-3-yl)methanol ;
N-(1-methyl-1H-pyrazol-5-yl)-4-(3-(thiophen-2-yl methyl)-[1,2,4]triazolo[4,3-a]pyridin-7-yl)pyrimidin-2-amine;
4-(3-benzyl-[1,2,4]triazolo[4,3-a]pyridin-7-yl)-N-(1-methyl-1H-pyrazol-5-yl)pyrimidin-2-amine;
4-(3-(3-(3-chlorophenyl)-1,5-dimethyl-1H-pyrazol-4-yl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(2-methylbutyl)-[1,2,4]triazolo[4,3-a]pyridin-7-yl)pyrimidin-2-amine;
N-(1-methyl-1H-pyrazol-4-yl)-4-(3-(2-methylbutyl)-[1,2,4]triazolo[4,3-a]pyridin-7-yl)pyrimidin-2-amine;
(S)-3-methyl-1-(7-(2-((1-methyl-1H-pyrazol-5-yl)amino)pyrimidin-4-yl)-[1,2,4]triazolo[4,3-a]pyridin-3-yl)butan-1-ol;
4-(3-((benzylthio)methyl)-[1,2,4]triazolo[4,3-a]pyridin-7-yl)-N-(1-methyl-1H-pyrazol-5-yl)pyrimidin-2-amine;
4-(3-(3-cyclobutylbenzyl)-[1,2,4]triazolo[4,3-a]pyridin-7-yl)-N-(1-methyl-1H-pyrazol-5-yl)pyrimidin-2-amine;
4-(3-((1S*,2S*)-2-(2-fluoropropan-2-yl)cyclopropyl)-[1,2,4]triazolo[4,3-a]pyridin-7-yl)-N-(1-methyl-1H-pyrazol-5-yl)pyrimidin-2-amine;
(R)-4-(3-(2-fluorobutyl)-[1,2,4]triazolo[4,3-a]pyridin-7-yl)-N-(1-methyl-1H-pyrazol-5-yl)pyrimidin-2-amine;
4-(3-((6-chloropyridin-2-yl)methyl)-[1,2,4]triazolo[4,3-a]pyridin-7-yl)-N-(1-methyl-1H-pyrazol-5-yl)pyrimidin-2-amine;
4-(3((5-bromopyridin-3-yl)methyl)-[1,2,4]triazolo[4,3-a]pyridin-7-yl)-N-(1-methyl-1H-pyrazol-5-yl)pyrimidin-2-amine;
4-(3-(2-methoxy-3-methylbutyl)-[1,2,4]triazolo[4,3-a]pyridin-7-yl)-N-(1-methyl-1H-pyrazol-5-yl)pyrimidin-2-amine;
4-(3-((1-methoxycyclobutyl)methyl)-[1,2,4]triazolo[4,3-a]pyridin-7-yl)-N-(1-methyl-1H-pyrazol-5-yl)pyrimidin-2-amine;
4-(3-(2-ethoxybutyl)-[1,2,4]triazolo[4,3-a]pyridin-7-yl)-N-(1-methyl-1H-pyrazol-5-yl)pyrimidin-2-amine;
4-(3-((1-methoxycyclopropyl)methyl)-[1,2,4]triazolo[4,3-a]pyridin-7-yl)-N-(1-methyl-1H-pyrazol-5-yl)pyrimidin-2-amine;
(2S*,3S*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol;
(2S*,3R*)-3-(4-methoxyphenyl)-2-methyl-3-(7-(2-((tetrahydro-2H-pyran-4-yl)amino)pyrimidin-4-yl)-[1,2,4]triazolo[4,3-a]pyridin-3-yl)propan-1-ol;
4-(3-((1-(2-fluoroethoxy)cyclopropyl)methyl)-[1,2,4]triazolo[4,3-a]pyridin-7-yl)-N-(1-methyl-1H-pyrazol-5-yl)pyrimidin-2-amine;

3-(4-methoxyphenyl)-3-(7-(2-((tetrahydro-2H-pyran-4-yl)amino)pyrimidin-4-yl)-[1,2,4]triazolo[4,3-a]pyridin-3-yl)propan-1-ol;

4-(3-([1,1'-bi(cyclopropan)]-1-ylmethyl)-[1,2,4]triazolo[4,3-a]pyridin-7-yl)-N-(1-methyl-1H-pyrazol-5-yl)pyrimidin-2-amine;

4-(3-(2,3-dimethylbutyl)-[1,2,4]triazolo[4,3-a]pyridin-7-yl)-N-(1-methyl-1H-pyrazol-5-yl)pyrimidin-2-amine;

4-(3-((1-ethylcyclobutyl)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-((1-(trifluoromethyl)cyclopropyl)methyl)-[1,2,4]triazolo[4,3-a]pyridin-7-yl)pyrimidin-2-amine;

4-(3-((1-isopropylcyclopropyl)methyl)-[1,2,4]triazolo[4,3-a]pyridin-7-yl)-N-(1-methyl-1H-pyrazol-5-yl)pyrimidin-2-amine;

4-(3-(2,2-dimethylbutyl)-[1,2,4]triazolo[4,3-a]pyridin-7-yl)-N-(1-methyl-1H-pyrazol-5-yl)pyrimidin-2-amine;

4-(3-((1-ethylcyclopropyl)methyl)-[1,2,4]triazolo[4,3-a]pyridin-7-yl)-N-(1-methyl-1H-pyrazol-5-yl)pyrimidin-2-amine;

4-(3((4-cyclopropylpyridin-2-yl)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-((1-methylcyclopropyl)methyl)-[1,2,4]triazolo[4,3-a]pyridin-7-yl)pyrimidin-2-amine;

4-(3((6-chloropyridin-2-yl)methyl)-[1,2,4]triazolo[4,3-a]pyridin-7-yl)-N-(tetrahydro-2H-pyran-4-yl)pyrimidin-2-amine;

4-(3-(3-fluoro-4-methoxybenzyl)-[1,2,4]triazolo[4,3-a]pyridin-7-yl)-N-(1-methyl-1H-pyrazol-5-yl)pyrimidin-2-amine;

4-(3-(3-chloro-5-fluorobenzyl)-[1,2,4]triazolo[4,3-a]pyridin-7-yl)-N-(1-methyl-1H-pyrazol-5-yl)pyrimidin-2-amine;

4-(3-(2,3-difluoro-4-methoxybenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(3-(trifluoromethyl)benzyl)-[1,2,4]triazolo[4,3-a]pyridin-7-yl)pyrimidin-2-amine;

4-(3-(3-fluoro-5-(trifluoromethyl)benzyl)-[1,2,4]triazolo[4,3-a]pyridin-7-yl)-N-(1-methyl-1H-pyrazol-5-yl)pyrimidin-2-amine;

4-(3-(3,5-difluoro-4-methoxybenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(2,3,4-trifluorobenzyl)-[1,2,4]triazolo[4,3-a]pyridin-7-yl)pyrimidin-2-amine;

4-(3-(3-chlorobenzyl)-[1,2,4]triazolo[4,3-a]pyridin-7-yl)-N-(1-methyl-1H-pyrazol-5-yl)pyrimidin-2-amine;

4-(3-(2-fluoro-4-methoxybenzyl)-[1,2,4]triazolo[4,3-a]pyridin-7-yl)-N-(1-methyl-1H-pyrazol-5-yl)pyrimidin-2-amine;

4-(3-(4-methoxybenzyl)-[1,2,4]triazolo[4,3-a]pyridin-7-yl)-N-(1-methyl-1H-pyrazol-5-yl)pyrimidin-2-amine;

4-(3-(3-(difluoromethoxy)benzyl)-[1,2,4]triazolo[4,3-a]pyridin-7-yl)-N-(1-methyl-1H-pyrazol-5-yl)pyrimidin-2-amine;

4-(3-(2,3-difluorobenzyl)-[1,2,4]triazolo[4,3-a]pyridin-7-yl)-N-(1-methyl-1H-pyrazol-5-yl)pyrimidin-2-amine;

4-(3-(2-chloro-4-fluorobenzyl)-[1,2,4]triazolo[4,3-a]pyridin-7-yl)-N-(1-methyl-1H-pyrazol-5-yl)pyrimidin-2-amine;

4-(3-(2-fluorobenzyl)-[1,2,4]triazolo[4,3-a]pyridin-7-yl)-N-(1-methyl-1H-pyrazol-5-yl)pyrimidin-2-amine;

4-(3-(3,4-difluorobenzyl)-[1,2,4]triazolo[4,3-a]pyridin-7-yl)-N-(1-methyl-1H-pyrazol-5-yl)pyrimidin-2-amine;

4-(3-(4-ethoxy-2,3-difluorobenzyl)-[1,2,4]triazolo[4,3-a]pyridin-7-yl)-N-(1-methyl-1H-pyrazol-5-yl)pyrimidin-2-amine;

4-(3-(3,5-difluorobenzyl)-[1,2,4]triazolo[4,3-a]pyridin-7-yl)-N-(1-methyl-1H-pyrazol-5-yl)pyrimidin-2-amine;

4-(3-(2,3-dichlorobenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(3-(trifluoromethoxy)benzyl)-[1,2,4]triazolo[4,3-a]pyridin-7-yl)pyrimidin-2-amine;

4-(3-(4-chloro-2-fluorobenzyl)-[1,2,4]triazolo[4,3-a]pyridin-7-yl)-N-(1-methyl-1H-pyrazol-5-yl)pyrimidin-2-amine;

4-(3-(2-chlorobenzyl)-[1,2,4]triazolo[4,3-a]pyridin-7-yl)-N-(1-methyl-1H-pyrazol-5-yl)pyrimidin-2-amine;

4-(3-(4-chloro-3-fluorobenzyl)-[1,2,4]triazolo[4,3-a]pyridin-7-yl)-N-(1-methyl-1H-pyrazol-5-yl)pyrimidin-2-amine;

4-(3-(2-ethylbutyl)-[1,2,4]triazolo[4,3-a]pyridin-7-yl)-N-(1-methyl-1H-pyrazol-5-yl)pyrimidin-2-amine;

4-(3-(2,4-dichlorobenzyl)-[1,2,4]triazolo[4,3-a]pyridin-7-yl)-N-(1-methyl-1H-pyrazol-5-yl)pyrimidin-2-amine;

4-(3-(3-methoxybenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(3-methylpentyl)-[1,2,4]triazolo[4,3-a]pyridin-7-yl)pyrimidin-2-amine;

N-(1-methyl-1H-pyrazol-5-yl)-4-(3-(2,4,5-trifluorobenzyl)-[1,2,4]triazolo[4,3-a]pyridin-7-yl)pyrimidin-2-amine;

4-(3-(2,4-difluorobenzyl)-[1,2,4]triazolo[4,3-a]pyridin-7-yl)-N-(1-methyl-1H-pyrazol-5-yl)pyrimidin-2-amine;

4-(3-(4-(difluoromethoxy)benzyl)-[1,2,4]triazolo[4,3-a]pyridin-7-yl)-N-(1-methyl-1H-pyrazol-5-yl)pyrimidin-2-amine;

4-(3-(3-fluorobenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(2-(methylthio)butyl)-[1,2,4]triazolo[4,3-a]pyridin-7-yl)pyrimidin-2-amine;

4-(3-(4-chlorobenzyl)-[1,2,4]triazolo[4,3-a]pyridin-7-yl)-N-(1-methyl-1H-pyrazol-5-yl)pyrimidin-2-amine;

4-(3-(4-fluorobenzyl)-[1,2,4]triazolo[4,3-a]pyridin-7-yl)-N-(1-methyl-1H-pyrazol-5-yl)pyrimidin-2-amine;

4-(3-(2-methoxybenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(2-(methylthio)ethyl)-[1,2,4]triazolo[4,3-a]pyridin-7-yl)pyrimidin-2-amine;

N-(1-methyl-1H-pyrazol-5-yl)-4-(3-(2-methylpentyl)-[1,2,4]triazolo[4,3-a]pyridin-7-yl)pyrimidin-2-amine;

N-(1-methyl-1H-pyrazol-5-yl)-4-(3-(2-(trifluoromethyl)benzyl)-[1,2,4]triazolo[4,3-a]pyridin-7-yl)pyrimidin-2-amine;

N-(1-methyl-1H-pyrazol-5-yl)-4-(3-(2-(methylthio)propyl)-[1,2,4]triazolo[4,3-a]pyridin-7-yl)pyrimidin-2-amine;

N-(1-methyl-1H-pyrazol-5-yl)-4-(3-(4-(trifluoromethyl)benzyl)-[1,2,4]triazolo[4,3-a]pyridin-7-yl)pyrimidin-2-amine;

4-(3-(3-chlorobenzyl)-[1,2,4]triazolo[4,3-a]pyridin-7-yl)-N-(1-methyl-1H-pyrazol-4-yl)pyrimidin-2-amine;

4-(3-(3-fluoro-4-methoxybenzyl)-[1,2,4]triazolo[4,3-a]pyridin-7-yl)-N-(1-methyl-1H-pyrazol-4-yl)pyrimidin-2-amine;
4-(3-(2-ethylbutyl)-[1,2,4]triazolo[4,3-a]pyridin-7-yl)-N-(1-methyl-1H-pyrazol-4-yl)pyrimidin-2-amine;
4-(3-(4-methoxybenzyl)-[1,2,4]triazolo[4,3-a]pyridin-7-yl)-N-(1-methyl-1H-pyrazol-4-yl)pyrimidin-2-amine;
4-(3-(2-chlorobenzyl)-[1,2,4]triazolo[4,3-a]pyridin-7-yl)-N-(1-methyl-1H-pyrazol-4-yl)pyrimidin-2-amine;
4-(3-(4-fluorobenzyl)-[1,2,4]triazolo[4,3-a]pyridin-7-yl)-N-(1-methyl-1H-pyrazol-4-yl)pyrimidin-2-amine;
4-(3-(4-chlorobenzyl)-[1,2,4]triazolo[4,3-a]pyridin-7-yl)-N-(1-methyl-1H-pyrazol-4-yl)pyrimidin-2-amine;
4-(3-(4-chloro-3-fluorobenzyl)-[1,2,4]triazolo[4,3-a]pyridin-7-yl)-N-(1-methyl-1H-pyrazol-4-yl)pyrimidin-2-amine;
4-(3-(3-fluorobenzyl)-[1,2,4]triazolo[4,3-a]pyridin-7-yl)-N-(1-methyl-1H-pyrazol-4-yl)pyrimidin-2-amine;
4-(3-((6-methoxypyridin-2-yl)methyl)-[1,2,4]triazolo[4,3-a]pyridin-7-yl)-N-(1-methyl-1H-pyrazol-4-yl)pyrimidin-2-amine;
4-(3-(2-chlorobenzyl)-[1,2,4]triazolo[4,3-a]pyridin-7-yl)-N-(tetrahydro-2H-pyran-4-yl)pyrimidin-2-amine;
4-(3-(4-chlorophenethyl)-[1,2,4]triazolo[4,3-a]pyridin-7-yl)-N-(tetrahydro-2H-pyran-4-yl)pyrimidin-2-amine;
4-(3-(3-chlorophenethyl)-[1,2,4]triazolo[4,3-a]pyridin-7-yl)-N-(tetrahydro-2H-pyran-4-yl)pyrimidin-2-amine;
4-(3-phenethyl-[1,2,4]triazolo[4,3-a]pyridin-7-yl)-N-(tetrahydro-2H-pyran-4-yl)pyrimidin-2-amine;
4-(3-(2-methoxybenzyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-((phenylthio)methyl)-[1,2,4]triazolo[4,3-a]pyridin-7-yl)pyrimidin-2-amine;
N-(1-methyl-1H-pyrazol-5-yl)-4-(3-(2-(phenylthio)ethyl)-[1,2,4]triazolo[4,3-a]pyridin-7-yl)pyrimidin-2-amine;
4-(3-(((4-fluorophenyl)thio)methyl)-[1,2,4]triazolo[4,3-a]pyridin-7-yl)-N-(1-methyl-1H-pyrazol-5-yl)pyrimidin-2-amine;
4-(3-(((2-fluorophenyl)thio)methyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(phenoxymethyl)-[1,2,4]triazolo[4,3-a]pyridin-7-yl)pyrimidin-2-amine;
4-(3-((4-fluorophenoxy)methyl)-[1,2,4]triazolo[4,3-a]pyridin-7-yl)-N-(1-methyl-1H-pyrazol-5-yl)pyrimidin-2-amine;
4-(3-(3-methoxy-2-methylpropyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine;
N-(1-methyl-1H-pyrazol-5-yl)-4-(3-(4,4,4-trifluoro-2-methylbutyl)-[1,2,4]triazolo[4,3-a]pyridin-7-yl)pyrimidin-2-amine;
4-(3-(2-ethoxy-3,3,3-trifluoropropyl)-[1,2,4]triazolo[4,3-a]pyridin-7-yl)-N-(1-methyl-1H-pyrazol-5-yl)pyrimidin-2-amine;
4-(3-(2-ethoxyethyl)-[1,2,4]triazolo[4,3-a]pyridin-7-yl)-N-(1-methyl-1H-pyrazol-5-yl)pyrimidin-2-amine;
4-(3-(5-(2,6-difluorophenoxy)-1-methylpiperidin-3-yl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(phenyl(piperidin-1-yl)methyl)-[1,2,4]triazolo[4,3-a]pyridin-7-yl)pyrimidin-2-amine;
(S)-N-(1-methyl-1H-pyrazol-5-yl)-4-(3-(2-methylbutyl)-[1,2,4]triazolo[4,3-a]pyridin-7-yl)pyrimidin-2-amine;
(R)-(3-chlorophenyl)(7-(2-((1-methyl-1H-pyrazol-5-yl)amino)pyrimidin-4-yl)-[1,2,4]triazolo[4,3-a]pyridin-3-yl)methanol;
(S)-4-(3-(1-(tert-butoxy)ethyl)-[1,2,4]triazolo[4,3-a]pyridin-7-yl)-N-(1-methyl-1H-pyrazol-5-yl)pyrimidin-2-amine;
2-(4-fluorophenyl)-2-methyl-1-(7-(2-((1-methyl-1H-pyrazol-5-yl)amino)pyrimidin-4-yl)-[1,2,4]triazolo[4,3-a]pyridin-3-yl)propan-1-ol;
(R)-1-(7-(2-((1-methyl-1H-pyrazol-5-yl)amino)pyrimidin-4-yl)-[1,2,4]triazolo[4,3-a]pyridin-3-yl)-2-phenylethanol;
2-(4-fluorophenyl)-1-(7-(2-((1-methyl-1H-pyrazol-5-yl)amino)pyrimidin-4-yl)-[1,2,4]triazolo[4,3-a]pyridin-3-yl)ethanol;
(R)-4-(3-(1-methoxy-2-phenylethyl)-[1,2,4]triazolo[4,3-a]pyridin-7-yl)-N-(1-methyl-1H-pyrazol-5-yl)pyrimidin-2-amine;
5-fluoro-4-(3-(4-methoxybenzyl)-[1,2,4]triazolo[4,3-a]pyridin-7-yl)-N-(tetrahydro-2H-pyran-4-yl)pyrimidin-2-amine;
(R)-2-(3-fluoro-4-methoxyphenyl)-2-(7-(2-((tetrahydro-2H-pyran-4-yl)amino)pyrimidin-4-yl)-[1,2,4]triazolo[4,3-b]pyridazin-3-yl)ethanol;
4-(3-(4-methoxybenzyl)-[1,2,4]triazolo[4,3-b]pyridazin-7-yl)-N-(tetrahydro-2H-pyran-4-yl)pyrimidin-2-amine;
4-(3-((4-chlorophenyl)(methoxy)methyl)-[1,2,4]triazolo[4,3-b]pyridazin-7-yl)-N-(tetrahydro-2H-pyran-4-yl)pyrimidin-2-amine;
4-(3-(1-(5-chloro-2-fluorobenzyl)piperidin-3-yl)-[1,2,4]triazolo[4,3-a]pyridin-7-yl)-N-(tetrahydro-2H-pyran-4-yl)pyrimidin-2-amine;
4-(3-(1,5-dimethyl-3-phenyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1,5-dimethyl-3-phenyl-1H-pyrazol-4-yl)-[1,2,4]triazolo[4,3-a]pyridin-7-yl)-N-(1-methyl-1H-pyrazol-4-yl)pyrimidin-2-amine;
4-(3-(1,5-dimethyl-3-phenyl-1H-pyrazol-4-yl)-[1,2,4]triazolo[4,3-a]pyridin-7-yl)-N-(tetrahydro-2H-pyran-4-yl)pyrimidin-2-amine;
4-(3-(piperidin-3-yl)-[1,2,4]triazolo[4,3-a]pyridin-7-yl)-N-(tetrahydro-2H-pyran-4-yl)pyrimidin-2-amine;
4-(3-(1-((5-fluoro-2-methoxypyridin-3-yl)methyl)piperidin-3-yl)-[1,2,4]triazolo[4,3-a]pyridin-7-yl)-N-(tetrahydro-2H-pyran-4-yl)pyrimidin-2-amine;
4-(3-(3-phenyl-1H-pyrazol-4-yl)-[1,2,4]triazolo[4,3-a]pyridin-7-yl)-N-(tetrahydro-2H-pyran-4-yl)pyrimidin-2-amine;
4-fluoro-3-((3-(7-(2-((tetrahydro-2H-pyran-4-yl)amino)pyrimidin-4-yl)-[1,2,4]triazolo[4,3-a]pyridin-3-yl)piperidin-1-yl)methyl)benzonitrile
4-(3-(1-phenyl-1H-pyrazol-5-yl)-[1,2,4]triazolo[4,3-a]pyridin-7-yl)-N-(tetrahydro-2H-pyran-4-yl)pyrimidin-2-amine;
1-methyl-4-phenyl-5-(7-(2-((tetrahydro-2H-pyran-4-yl)amino)pyrimidin-4-yl)-[1,2,4]triazolo[4,3-a]pyridin-3-yl)pyrrolidin-2-one;
4-(3-(4-(cyclopropylmethyl)morpholin-2-yl)-[1,2,4]triazolo[4,3-a]pyridin-7-yl)-N-(1-methyl-1H-pyrazol-5-yl)pyrimidin-2-amine;

4-(3-(3-methyl-5-phenylisoxazol-4-yl)-[1,2,4]triazolo[4,3-a]pyridin-7-yl)-N-(tetrahydro-2H-pyran-4-yl)pyrimidin-2-amine;
(2-fluoro-6-methoxyphenyl)(2-(7-(2-((1-methyl-1H-pyrazol-5-yl)amino)pyrimidin-4-yl)-[1,2,4]triazolo[4,3-a]pyridin-3-yl)morpholino)methanone;
(2,6-difluorophenyl)(2-(7-(2-((tetrahydro-2H-pyran-4-yl)amino)pyrimidin-4-yl)-[1,2,4]triazolo[4,3-a]pyridin-3-yl)morpholino)methanone;
N-(tetrahydro-2H-pyran-4-yl)-4-(3-(4-(3,3,3-trifluoropropyl)morpholin-2-yl)-[1,2,4]triazolo[4,3-a]pyridin-7-yl)pyrimidin-2-amine;
4-(3-([1,1'-bi(cyclopropan)]-1-ylmethyl)-[1,2,4]triazolo[4,3-a]pyridin-7-yl)-N-(tetrahydro-2H-pyran-4-yl)pyrimidin-2-amine;
4-(3-((2,2-difluorocyclopropyl)methyl)-[1,2,4]triazolo[4,3-a]pyridin-7-yl)-N-(1-methyl-1H-pyrazol-5-yl)pyrimidin-2-amine;
4-(3-isopentyl-[1,2,4]triazolo[4,3-a]pyridin-7-yl)-N-(1-methyl-1H-pyrazol-5-yl)pyrimidin-2-amine;
4-(3-((2,3-dihydrobenzo[b][1,4]dioxin-6-yl)methyl)-[1,2,4]triazolo[4,3-a]pyridin-7-yl)-N-(tetrahydro-2H-pyran-4-yl)pyrimidin-2-amine;
(R)-3-methyl-1-(7-(2-((1-methyl-1H-pyrazol-5-yl)amino)pyrimidin-4-yl)-[1,2,4]triazolo[4,3-a]pyridin-3-yl)butan-1-ol ;
(1R,2S)-2-methyl-1-(7-(2-((1-methyl-1H-pyrazol-5-yl)amino)pyrimidin-4-yl)-[1,2,4]triazolo[4,3-a]pyridin-3-yl)butan-1-ol ;
4-(3-benzyl-[1,2,4]triazolo[4,3-a]pyridin-7-yl)-N-(tetrahydro-2H-pyran-4-yl)pyrimidin-2-amine;
4-(3-(3-fluoro-4-(trifluoromethoxy)benzyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-neopentyl-[1,2,4]triazolo[4,3-a]pyridin-7-yl)pyrimidin-2-amine;
(S)-4-(3-(2-methylbutyl)-[1,2,4]triazolo[4,3-a]pyridin-7-yl)-N-(tetrahydro-2H-pyran-4-yl)pyrimidin-2-amine;
4-(3-(cyclopentylmethyl)-[1,2,4]triazolo[4,3-a]pyridin-7-yl)-N-(1-methyl-1H-pyrazol-5-yl)pyrimidin-2-amine;
4-(3-(cyclohexylmethyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-((1-(trifluoromethyl)cyclobutyl)methyl)-[1,2,4]triazolo[4,3-a]pyridin-7-yl)pyrimidin-2-amine;
4-(3-isobutyl-[1,2,4]triazolo[4,3-a]pyridin-7-yl)-N-(1-methyl-1H-pyrazol-4-yl)pyrimidin-2-amine;
4-(3-((isopropylthio)methyl)-[1,2,4]triazolo[4,3-a]pyridin-7-yl)-N-(1-methyl-1H-pyrazol-5-yl)pyrimidin-2-amine;
4-(3-(2-cyclopropylethyl)-[1,2,4]triazolo[4,3-a]pyridin-7-yl)-N-(1-methyl-1H-pyrazol-5-yl)pyrimidin-2-amine;
4-(3-(tert-butoxymethyl)-[1,2,4]triazolo[4,3-a]pyridin-7-yl)-N-(1-methyl-1H-pyrazol-5-yl)pyrimidin-2-amine;
1,1,1,3,3,3-hexafluoro-2-((7-(2-((1-methyl-1H-pyrazol-5-yl)amino)pyrimidin-4-yl)-[1,2,4]triazolo[4,3-a]pyridin-3-yl)methyl)propan-2-ol;
N-(1-methyl-1H-pyrazol-5-yl)-4-(3-(3,3,3-trifluoro-2-methylpropyl)-[1,2,4]triazolo[4,3-a]pyridin-7-yl)pyrimidin-2-amine;
4-(3-((tert-butylthio)methyl)-[1,2,4]triazolo[4,3-a]pyridin-7-yl)-N-(1-methyl-1H-pyrazol-5-yl)pyrimidin-2-amine
N-(1-methyl-1H-pyrazol-5-yl)-4-(3-((4-methylcyclohexyl)methyl)-[1,2,4]triazolo[4,3-a]pyridin-7-yl)pyrimidin-2-amine;
4-(3-(bicyclo[2.2.1]heptan-2-ylmethyl)-[1,2,4]triazolo[4,3-a]pyridin-7-yl)-N-(1-methyl-1H-pyrazol-5-yl)pyrimidin-2-amine;
4-(3-(cyclopropylmethyl)-[1,2,4]triazolo[4,3-a]pyridin-7-yl)-N-(1-methyl-1H-pyrazol-4-yl)pyrimidin-2-amine;
4-(3-((isobutylthio)methyl)-[1,2,4]triazolo[4,3-a]pyridin-7-yl)-N-(1-methyl-1H-pyrazol-5-yl)pyrimidin-2-amine;
4-(3-(cyclobutylmethyl)-[1,2,4]triazolo[4,3-a]pyridin-7-yl)-N-(1-methyl-1H-pyrazol-4-yl)pyrimidin-2-amine;
N-(1-methyl-1H-pyrazol-5-yl)-4-(3-(2,2,2-trifluoroethyl)-[1,2,4]triazolo[4,3-a]pyridin-7-yl)pyrimidin-2-amine;
4-(3-(cyclobutylmethyl)-[1,2,4]triazolo[4,3-a]pyridin-7-yl)-N-(1-methyl-1H-pyrazol-5-yl)pyrimidin-2-amine;
4-(3-isobutyl-[1,2,4]triazolo[4,3-a]pyridin-7-yl)-N-(1-methyl-1H-pyrazol-5-yl)pyrimidin-2-amine;
4-(3-(isopropoxymethyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(3,3,3-trifluoropropyl)-[1,2,4]triazolo[4,3-a]pyridin-7-yl)pyrimidin-2-amine;
4-(3-(3,3-dimethylbutyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-((tetrahydro-2H-pyran-2-yl)methyl)-[1,2,4]triazolo[4,3-a]pyridin-7-yl)pyrimidin-2-amine;
4-(3-(cyclopropylmethyl)-[1,2,4]triazolo[4,3-a]pyridin-7-yl)-N-(1-methyl-1H-pyrazol-5-yl)pyrimidin-2-amine;
4-(3-(3-(3-fluorophenyl)-1,5-dimethyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1-(4-chlorophenyl)-2-methylpropyl)-[1,2,4]triazolo[4,3-a]pyridin-7-yl)-N-(1-methyl-1H-pyrazol-5-yl)pyrimidin-2-amine;
4-(3-(cyclohexylmethyl)-[1,2,4]triazolo[4,3-a]pyridin-7-yl)-N-(tetrahydro-2H-pyran-4-yl)pyrimidin-2-amine;
(R)-4-(3-(methoxy(phenyl)methyl)-[1,2,4]triazolo[4,3-a]pyridin-7-yl)-N-(tetrahydro-2H-pyran-4-yl)pyrimidin-2-amine;
4-(3-(3-chlorophenethyl)-[1,2,4]triazolo[4,3-a]pyridin-7-yl)-N-isopropylpyrimidin-2-amine;
4-(2-fluoro-2-methylpropyl)-[1,2,4]triazolo[4,3-a]pyridin-7-yl)-N-(1-methyl-1H-pyrazol-5-yl)pyrimidin-2-amine;
4-(3-((3,3-difluorocyclobutyl)methyl)-[1,2,4]triazolo[4,3-a]pyridin-7-yl)-N-(1-methyl-1H-pyrazol-5-yl)pyrimidin-2-amine;
4-(3-(2-methoxyethyl)-[1,2,4]triazolo[4,3-a]pyridin-7-yl)-N-(1-methyl-1H-pyrazol-5-yl)pyrimidin-2-amine;
4-(3-(4-methylbenzyl)-[1,2,4]triazolo[4,3-a]pyridin-7-yl)-N-(tetrahydro-2H-pyran-4-yl)pyrimidin-2-amine;
4-(3-(isobutoxymethyl)-[1,2,4]triazolo[4,3-a]pyridin-7-yl)-N-(1-methyl-1H-pyrazol-5-yl)pyrimidin-2-amine;
2,2-dimethyl-3-(7-(2-((1-methyl-1H-pyrazol-5-yl)amino)pyrimidin-4-yl)-[1,2,4]triazolo[4,3-a]pyridin-3-yl)propanenitrile;
4-(3-(4-chloro-3-fluorobenzyl)-[1,2,4]triazolo[4,3-a]pyridin-7-yl)-N-isopropylpyrimidin-2-amine
N-(1-methyl-1H-pyrazol-5-yl)-4-(3-((tetrahydrofuran-2-yl)methyl)-[1,2,4]triazolo[4,3-a]pyridin-7-yl)pyrimidin-2-amine;
(R)-2-methyl-1-(7-(2-((1-methyl-1H-pyrazol-5-yl)amino)pyrimidin-4-yl)-[1,2,4]triazolo[4,3-a]pyridin-3-yl)propan-1-ol;

N-(1-methyl-1H-pyrazol-5-yl)-4-(3-(3,3,3-trifluoro-2-(trifluoromethyl)propyl)-[1,2,4]triazolo[4,3-a]pyridin-7-yl)pyrimidin-2-amine;
4-(3-(1-(4-chlorophenyl)-2-methylpropyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-(piperidin-1-ylmethyl)-[1,2,4]triazolo[4,3-a]pyridin-7-yl)pyrimidin-2-amine;
4-(3-(isochroman-1-yl)-[1,2,4]triazolo[4,3-a]pyridin-7-yl)-N-(1-methyl-1H-pyrazol-5-yl)pyrimidin-2-amine;
4-(3-(3-fluoro-4-methoxybenzyl)-[1,2,4]triazolo[4,3-a]pyridin-7-yl)-N-isopropylpyrimidin-2-amine;
4-(3-(1-(4-chlorophenyl)ethyl)-[1,2,4]triazolo[4,3-a]pyridin-7-yl)-N-(1-methyl-1H-pyrazol-5-yl)pyrimidin-2-amine;
(S)-4-(3-(methoxy(phenyl)methyl)-[1,2,4]triazolo[4,3-a]pyridin-7-yl)-N-(tetrahydro-2H-pyran-4-yl)pyrimidin-2-amine;
4-(3-(1-(4-chlorophenyl)ethyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-(1-phenylethyl)-[1,2,4]triazolo[4,3-a]pyridin-7-yl)pyrimidin-2-amine;
N-(1-methyl-1H-pyrazol-5-yl)-4-(3-(2-methylcyclopropyl)-[1,2,4]triazolo[4,3-a]pyridin-7-yl)pyrimidin-2-amine;
4-(3-(1-(4-chlorophenyl)cyclopropyl)-[1,2,4]triazolo[4,3-a]pyridin-7-yl)-N-(tetrahydro-2H-pyran-4-yl)pyrimidin-2-amine;
4-(3-(1-(4-chlorophenyl)cyclobutyl)-[1,2,4]triazolo[4,3-a]pyridin-7-yl)-N-(tetrahydro-2H-pyran-4-yl)pyrimidin-2-amine;
4-(3-(2-(4-chlorophenyl)propan-2-yl)-[1,2,4]triazolo[4,3-a]pyridin-7-yl)-N-(tetrahydro-2H-pyran-4-yl)pyrimidin-2-amine;
4-(3-(benzo[d][1,3]dioxol-5-ylmethyl)-[1,2,4]triazolo[4,3-a]pyridin-7-yl)-N-(tetrahydro-2H-pyran-4-yl)pyrimidin-2-amine;
4-(3-((4-chlorophenyl)difluoromethyl)-[1,2,4]triazolo[4,3-a]pyridin-7-yl)-N-(tetrahydro-2H-pyran-4-yl)pyrimidin-2-amine;
4-(3-(1-methoxy-1-phenylethyl)-[1,2,4]triazolo[4,3-a]pyridin-7-yl)-N-(tetrahydro-2H-pyran-4-yl)pyrimidin-2-amine;
4-(3-(1-(4-chlorophenyl)cyclopentyl)-[1,2,4]triazolo[4,3-a]pyridin-7-yl)-N-(tetrahydro-2H-pyran-4-yl)pyrimidin-2-amine;
(Z)-4-(3-(3-methyl-1-phenylbut-1-en-1-yl)-[1,2,4]triazolo[4,3-a]pyridin-7-yl)-N-(tetrahydro-2H-pyran-4-yl)pyrimidin-2-amine;
4-(3-(2-amino-1-phenylethyl)-[1,2,4]triazolo[4,3-a]pyridin-7-yl)-N-(tetrahydro-2H-pyran-4-yl)pyrimidin-2-amine;
4-(3-(pyridin-3-ylmethyl)-[1,2,4]triazolo[4,3-a]pyridin-7-yl)-N-(tetrahydro-2H-pyran-4-yl)pyrimidin-2-amine;
4-(3-(difluoro(3-fluoro-4-methoxyphenyl)methyl)-[1,2,4]triazolo[4,3-a]pyridin-7-yl)-N-(tetrahydro-2H-pyran-4-yl)pyrimidin-2-amine;
4-(3-(4-fluorobenzyl)-[1,2,4]triazolo[4,3-a]pyridin-7-yl)-N-isopropylpyrimidin-2-amine;
4-(3-(2-fluorobenzyl)-[1,2,4]triazolo[4,3-a]pyridin-7-yl)-N-isopropylpyrimidin-2-amine;
4-(3-(1-(4-chlorophenyl)-2-methylpropyl)-[1,2,4]triazolo[4,3-a]pyridin-7-yl)-N-isopropylpyrimidin-2-amine;
4-(3-(3-fluoro-4-methoxyphenethyl)-[1,2,4]triazolo[4,3-a]pyridin-7-yl)-N-isopropylpyrimidin-2-amine;
4-(3-((2-chloropyridin-3-yl)methyl)-[1,2,4]triazolo[4,3-a]pyridin-7-yl)-N-isopropylpyrimidin-2-amine;
4-(3-(2-(pyridin-2-yl)ethyl)-[1,2,4]triazolo[4,3-a]pyridin-7-yl)-N-(tetrahydro-2H-pyran-4-yl)pyrimidin-2-amine;
4-(3-(2-(pyridin-3-yl)ethyl)-[1,2,4]triazolo[4,3-a]pyridin-7-yl)-N-(tetrahydro-2H-pyran-4-yl)pyrimidin-2-amine;
4-(3-(2-(pyridin-4-yl)ethyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-((tetrahydro-2H-pyran-4-yl)methyl)-[1,2,4]triazolo[4,3-a]pyridin-7-yl)pyrimidin-2-amine;
4-(3-cyclohexyl-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-methyl-[1,2,4]triazolo[4,3-a]pyridin-7-yl)pyrimidin-2-amine;
N-(1-methyl-1H-pyrazol-5-yl)-4-(3-(trifluoromethyl)-[1,2,4]triazolo[4,3-a]pyridin-7-yl)pyrimidin-2-amine;
4-(3-ethyl-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-((tetrahydrofuran-3-yl)methyl)-[1,2,4]triazolo[4,3-a]pyridin-7-yl)pyrimidin-2-amine;
4-(3-(1,1-difluoropropyl)-[1,2,4]triazolo[4,3-a]pyridin-7-yl)-N-(1-methyl-1H-pyrazol-5-yl)pyrimidin-2-amine;
4-(3-(2,2-dimethylcyclopropyl)-[1,2,4]triazolo[4,3-a]pyridin-7-yl)-N-(1-methyl-1H-pyrazol-5-yl)pyrimidin-2-amine;
4-(3-(methoxymethyl)-[1,2,4]triazolo[4,3-a]pyridin-7-yl)-N-(1-methyl-1H-pyrazol-5-yl)pyrimidin-2-amine;
4-(3-((dimethylamino)methyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(morpholinomethyl)-[1,2,4]triazolo[4,3-a]pyridin-7-yl)pyrimidin-2-amine;
(1R*,2R*)-ethyl 2-(7-(2-((1-methyl-1H-pyrazol-5-yl)amino)pyrimidin-4-yl)-[1,2,4]triazolo[4,3-a]pyridin-3-yl)cyclopropanecarboxylate
2-((1R*,2R*)-2-(7-(2-((1-methyl-1H-pyrazol-5-yl)amino)pyrimidin-4-yl)-[1,2,4]triazolo[4,3-a]pyridin-3-yl)cyclopropyl)propan-2-ol;
2-methyl-1-(7-(2-((1-methyl-1H-pyrazol-5-yl)amino)pyrimidin-4-yl)-[1,2,4]triazolo[4,3-a]pyridin-3-yl)propan-2-ol;
2-(7-(2-((1-methyl-1H-pyrazol-5-yl)amino)pyrimidin-4-yl)-[1,2,4]triazolo[4,3-a]pyridin-3-yl)ethanol;
(S)-cyclohexyl(7-(2-((1-methyl-1H-pyrazol-5-yl)amino)pyrimidin-4-yl)-[1,2,4]triazolo[4,3-a]pyridin-3-yl)methanol;
(1S,2S)-2-methyl-1-(7-(2-((1-methyl-1H-pyrazol-5-yl)amino)pyrimidin-4-yl)-[1,2,4]triazolo[4,3-a]pyridin-3-yl)butan-1-ol;
(S)-2-methyl-1-(7-(2-((1-methyl-1H-pyrazol-5-yl)amino)pyrimidin-4-yl)-[1,2,4]triazolo[4,3-a]pyridin-3-yl)propan-1-ol;
(S)-4-(3-(1-methoxy-2-methylpropyl)-[1,2,4]triazolo[4,3-a]pyridin-7-yl)-N-(1-methyl-1H-pyrazol-5-yl)pyrimidin-2-amine;
(R)-4-(3-(1-methoxy-2-methylpropyl)-[1,2,4]triazolo[4,3-a]pyridin-7-yl)-N-(1-methyl-1H-pyrazol-5-yl)pyrimidin-2-amine;
4-(3-(2-methoxybutyl)-[1,2,4]triazolo[4,3-a]pyridin-7-yl)-N-(1-methyl-1H-pyrazol-5-yl)pyrimidin-2-amine;

4-(3-((2-methoxypyridin-3-yl)methyl)-[1,2,4]triazolo[4,3-a]pyridin-7-yl)-N-(1-methyl-1H-pyrazol-5-yl)pyrimidin-2-amine;
4-(3-(3-fluoro-3-methylbutyl)-[1,2,4]triazolo[4,3-a]pyridin-7-yl)-N-(1-methyl-1H-pyrazol-5-yl)pyrimidin-2-amine;
(S)-4-(3-(2-fluorobutyl)-[1,2,4]triazolo[4,3-a]pyridin-7-yl)-N-(1-methyl-1H-pyrazol-5-yl)pyrimidin-2-amine;
3-methyl-1-(7-(2-((1-methyl-1H-pyrazol-5-yl)amino)pyrimidin-4-yl)-[1,2,4]triazolo[4,3-a]pyridin-3-yl)butan-2-ol;
4-(3-((5-chloropyridin-3-yl)methyl)-[1,2,4]triazolo[4,3-a]pyridin-7-yl)-N-(1-methyl-1H-pyrazol-5-yl)pyrimidin-2-amine;
4-(3-((5-fluoropyridin-3-yl)methyl)-[1,2,4]triazolo[4,3-a]pyridin-7-yl)-N-(1-methyl-1H-pyrazol-5-yl)pyrimidin-2-amine;
4-(3-((2-methoxypyridin-3-yl)methyl)-[1,2,4]triazolo[4,3-a]pyridin-7-yl)-N-(1-methyl-1H-pyrazol-4-yl)pyrimidin-2-amine;
4-(3-((2-methoxypyridin-3-yl)methyl)-[1,2,4]triazolo[4,3-a]pyridin-7-yl)-N-(tetrahydro-2H-pyran-4-yl)pyrimidin-2-amine;
4-(3-((5-cyclopropylpyridin-3-yl)methyl)-[1,2,4]triazolo[4,3-a]pyridin-7-yl)-N-(1-methyl-1H-pyrazol-5-yl)pyrimidin-2-amine;
(2S*,3S*)-3-(4-methoxyphenyl)-2-methyl-3-(7-(2-((1-methyl-1H-pyrazol-5-yl)amino)pyrimidin-4-yl)-[1,2,4]triazolo[4,3-a]pyridin-3-yl)propan-1-ol;
N-(1-methyl-1H-pyrazol-5-yl)-4-(3-(pyrimidin-2-ylmethyl)-[1,2,4]triazolo[4,3-a]pyridin-7-yl)pyrimidin-2-amine;
N-(1-methyl-1H-pyrazol-5-yl)-4-(3-(pyrimidin-5-ylmethyl)-[1,2,4]triazolo[4,3-a]pyridin-7-yl)pyrimidin-2-amine;
3-((7-(2-((1-methyl-1H-pyrazol-5-yl)amino)pyrimidin-4-yl)-[1,2,4]triazolo[4,3-a]pyridin-3-yl)methyl)pyridin-2-ol
N-(1-methyl-1H-pyrazol-5-yl)-4-(3-((2-methylpyridin-3-yl)methyl)-[1,2,4]triazolo[4,3-a]pyridin-7-yl)pyrimidin-2-amine;
N-(1-methyl-1H-pyrazol-5-yl)-4-(3-((5-methylpyridin-3-yl)methyl)-[1,2,4]triazolo[4,3-a]pyridin-7-yl)pyrimidin-2-amine;
(S)-1-(7-(2-((1-methyl-1H-pyrazol-5-yl)amino)pyrimidin-4-yl)-[1,2,4]triazolo[4,3-a]pyridin-3-yl)butan-2-ol;
(E)-4-(3-(but-1-en-1-yl)-[1,2,4]triazolo[4,3-a]pyridin-7-yl)-N-(1-methyl-1H-pyrazol-5-yl)pyrimidin-2-amine;
(R)-1-(7-(2-((1-methyl-1H-pyrazol-5-yl)amino)pyrimidin-4-yl)-[1,2,4]triazolo[4,3-a]pyridin-3-yl)butan-2-ol;
4-(3-(2-methoxypropyl)-[1,2,4]triazolo[4,3-a]pyridin-7-yl)-N-(1-methyl-1H-pyrazol-5-yl)pyrimidin-2-amine;
(S)-2-methyl-3-(7-(2-((1-methyl-1H-pyrazol-5-yl)amino)pyrimidin-4-yl)-[1,2,4]triazolo[4,3-a]pyridin-3-yl)propan-1-ol;
4-(3-((6-isopropylpyridin-2-yl)methyl)-[1,2,4]triazolo[4,3-a]pyridin-7-yl)-N-(1-methyl-1H-pyrazol-5-yl)pyrimidin-2-amine;
4-(3-((2-chloropyridin-3-yl)methyl)-[1,2,4]triazolo[4,3-a]pyridin-7-yl)-N-(tetrahydro-2H-pyran-4-yl)pyrimidin-2-amine;
4-(3((6-cyclopropylpyridin-2-yl)methyl)-[1,2,4]triazolo[4,3-a]pyridin-7-yl)-N-(1-methyl-1H-pyrazol-5-yl)pyrimidin-2-amine;
4-(3-((6-methoxypyridin-2-yl)methyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-((6-methylpyridin-2-yl)methyl)-[1,2,4]triazolo[4,3-a]pyridin-7-yl)pyrimidin-2-amine;
4-(3-((5-chloropyridin-2-yl)methyl)-[1,2,4]triazolo[4,3-a]pyridin-7-yl)-N-(1-methyl-1H-pyrazol-5-yl)pyrimidin-2-amine;
4-(3-(2-cyclopropyl-2-methylpropyl)-[1,2,4]triazolo[4,3-a]pyridin-7-yl)-N-(1-methyl-1H-pyrazol-5-yl)pyrimidin-2-amine;
4-(3-((6-methoxypyridin-3-yl)methyl)-[1,2,4]triazolo[4,3-a]pyridin-7-yl)-N-(tetrahydro-2H-pyran-4-yl)pyrimidin-2-amine;
N-(1-methyl-1H-pyrazol-5-yl)-4-(3-((6-(trifluoromethyl)pyridin-2-yl)methyl)-[1,2,4]triazolo[4,3-a]pyridin-7-yl)pyrimidin-2-amine;
N-(1-methyl-1H-pyrazol-5-yl)-4-(3-((6-phenylpyridin-2-yl)methyl)-[1,2,4]triazolo[4,3-a]pyridin-7-yl)pyrimidin-2-amine;
N-(1-methyl-1H-pyrazol-5-yl)-4-(3-((4-methylpyridin-2-yl)methyl)-[1,2,4]triazolo[4,3-a]pyridin-7-yl)pyrimidin-2-amine;
4-(3-(pyridin-2-ylmethyl)-[1,2,4]triazolo[4,3-a]pyridin-7-yl)-N-(tetrahydro-2H-pyran-4-yl)pyrimidin-2-amine;
4-(3-(2-cyclopropylpropyl)-[1,2,4]triazolo[4,3-a]pyridin-7-yl)-N-(1-methyl-1H-pyrazol-5-yl)pyrimidin-2-amine;
4-(3-((5,5-dimethyltetrahydrofuran-2-yl)methyl)-[1,2,4]triazolo[4,3-a]pyridin-7-yl)-N-(1-methyl-1H-pyrazol-5-yl)pyrimidin-2-amine;
4-(3((6,6-dimethyltetrahydro-2H-pyran-2-yl)methyl)-[1,2,4]triazolo[4,3-a]pyridin-7-yl)-N-(1-methyl-1H-pyrazol-5-yl)pyrimidin-2-amine;
4-(3-((3-chloropyridin-2-yl)methyl)-[1,2,4]triazolo[4,3-a]pyridin-7-yl)-N-(1-methyl-1H-pyrazol-5-yl)pyrimidin-2-amine;
4-(3-((6-chloropyridin-3-yl)methyl)-[1,2,4]triazolo[4,3-a]pyridin-7-yl)-N-(tetrahydro-2H-pyran-4-yl)pyrimidin-2-amine;
4-(3-(pyridin-4-ylmethyl)-[1,2,4]triazolo[4,3-a]pyridin-7-yl)-N-(tetrahydro-2H-pyran-4-yl)pyrimidin-2-amine;
4-(3-((3-chloropyridin-2-yl)methyl)-[1,2,4]triazolo[4,3-a]pyridin-7-yl)-N-(tetrahydro-2H-pyran-4-yl)pyrimidin-2-amine;
6-((7-(2-((1-methyl-1H-pyrazol-5-yl)amino)pyrimidin-4-yl)-[1,2,4]triazolo[4,3-a]pyridin-3-yl)methyl)pyridin-2-ol;
6-((7-(2-((1-methyl-1H-pyrazol-5-yl)amino)pyrimidin-4-yl)-[1,2,4]triazolo[4,3-a]pyridin-3-yl)methyl)picolinonitrile;
4-(3-((1-methyl-1H-pyrazol-3-yl)methyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-((tetrahydro-2H-pyran-3-yl)methyl)-[1,2,4]triazolo[4,3-a]pyridin-7-yl)pyrimidin-2-amine;
4-(3-((1-methyl-1H-pyrazol-4-yl)methyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(2-(trifluoromethyl)cyclobutyl)-[1,2,4]triazolo[4,3-a]pyridin-7-yl)pyrimidin-2-amine;
4-(3-((3-ethyloxetan-3-yl)methyl)-[1,2,4]triazolo[4,3-a]pyridin-7-yl)-N-(1-methyl-1H-pyrazol-5-yl)pyrimidin-2-amine;

4-(3-(2-methoxy-2-methylpropyl)-[1,2,4]triazolo[4,3-a]pyridin-7-yl)-N-(1-methyl-1H-pyrazol-5-yl)pyrimidin-2-amine;

4-(3-((1-methyl-1H-imidazol-2-yl)methyl)-[1,2,4]triazolo[4,3-a]pyridin-7-yl)-N-(1-methyl-1H-pyrazol-5-yl)pyrimidin-2-amine;

4-(3-((1,3-dimethyl-1H-pyrazol-5-yl)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(thiazol-2-ylmethyl)-[1,2,4]triazolo[4,3-a]pyridin-7-yl)pyrimidin-2-amine;

N-(1-methyl-1H-pyrazol-5-yl)-4-(3-((4-methylthiazol-2-yl)methyl)-[1,2,4]triazolo[4,3-a]pyridin-7-yl)pyrimidin-2-amine;

N-(1-methyl-1H-pyrazol-5-yl)-4-(3-((phenylsulfonyl)methyl)-[1,2,4]triazolo[4,3-a]pyridin-7-yl)pyrimidin-2-amine;

4-(3-((cyclopentylthio)methyl)-[1,2,4]triazolo[4,3-a]pyridin-7-yl)-N-(1-methyl-1H-pyrazol-5-yl)pyrimidin-2-amine;

4-(3-((4-isopropyl-5-methylthiazol-2-yl)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(2-(phenylsulfonyl)ethyl)-[1,2,4]triazolo[4,3-a]pyridin-7-yl)pyrimidin-2-amine;

N-(1-methyl-1H-pyrazol-5-yl)-4-(3-((phenylsulfinyl)methyl)-[1,2,4]triazolo[4,3-a]pyridin-7-yl)pyrimidin-2-amine;

N-(1-methyl-1H-pyrazol-5-yl)-4-(3-((5-methylthiazol-2-yl)methyl)-[1,2,4]triazolo[4,3-a]pyridin-7-yl)pyrimidin-2-amine;

4-(3-(2,2-difluoropropyl)-[1,2,4]triazolo[4,3-a]pyridin-7-yl)-N-(1-methyl-1H-pyrazol-5-yl)pyrimidin-2-amine 4-(3-(2,3-dimethylbutyl)-[1,2,4]triazolo[4,3-a]pyridin-7-yl)-N-(2-methyl-2H-1,2,3-triazol-4-yl)pyrimidin-2-amine;

3,3,4,4,4-pentafluoro-1-(7-(2-((1-methyl-1H-pyrazol-5-yl)amino)pyrimidin-4-yl)-[1,2,4]triazolo[4,3-a]pyridin-3-yl)butan-2-ol;

N-(1-methyl-1H-pyrazol-5-yl)-4-(3-(2-(trifluoromethyl)butyl)-[1,2,4]triazolo[4,3-a]pyridin-7-yl)pyrimidin-2-amine;

4-(3-((4,4-difluorocyclohexyl)methyl)-[1,2,4]triazolo[4,3-a]pyridin-7-yl)-N-(1-methyl-1H-pyrazol-5-yl)pyrimidin-2-amine;

4-(3-((1-isobutoxycyclopropyl)methyl)-[1,2,4]triazolo[4,3-a]pyridin-7-yl)-N-(1-methyl-1H-pyrazol-5-yl)pyrimidin-2-amine;

4-(3-((5-fluoro-1H-indol-3-yl)methyl)-[1,2,4]triazolo[4,3-a]pyridin-7-yl)-N-(1-methyl-1H-pyrazol-5-yl)pyrimidin-2-amine;

4-(3-(2-cyclopropyl-2-methoxyethyl)-[1,2,4]triazolo[4,3-a]pyridin-7-yl)-N-(1-methyl-1H-pyrazol-5-yl)pyrimidin-2-amine;

4-(3-((6-fluoro-1H-indol-3-yl)methyl)-[1,2,4]triazolo[4,3-a]pyridin-7-yl)-N-(1-methyl-1H-pyrazol-5-yl)pyrimidin-2-amine;

4-(3-(3-fluoro-2-(fluoromethyl)propyl)-[1,2,4]triazolo[4,3-a]pyridin-7-yl)-N-(1-methyl-1H-pyrazol-5-yl)pyrimidin-2-amine;

1,1,1-trifluoro-3-(7-(2-((1-methyl-1H-pyrazol-5-yl)amino)pyrimidin-4-yl)-[1,2,4]triazolo[4,3-a]pyridin-3-yl)propan-2-ol;

4-(3-((1-isopropoxycyclopropyl)methyl)-[1,2,4]triazolo[4,3-a]pyridin-7-yl)-N-(1-methyl-1H-pyrazol-5-yl)pyrimidin-2-amine;

4-(3-(2-(2-fluoroethoxy)propyl)-[1,2,4]triazolo[4,3-a]pyridin-7-yl)-N-(1-methyl-1H-pyrazol-5-yl)pyrimidin-2-amine;

4-(3-(2-(cyclopropylmethoxy)propyl)-[1,2,4]triazolo[4,3-a]pyridin-7-yl)-N-(1-methyl-1H-pyrazol-5-yl)pyrimidin-2-amine;

4-(3-(2,3-difluorobenzyl)-[1,2,4]triazolo[4,3-a]pyridin-7-yl)-N-(2-methyl-2H-1,2,3-triazol-4-yl)pyrimidin-2-amine;

4-(3-(2-ethylbutyl)-[1,2,4]triazolo[4,3-a]pyridin-7-yl)-N-(2-methyl-2H-1,2,3-triazol-4-yl)pyrimidin-2-amine;

(S)-N-(2-methyl-2H-1,2,3-triazol-4-yl)-4-(3-(2-methylbutyl)-[1,2,4]triazolo[4,3-a]pyridin-7-yl)pyrimidin-2-amine;

4-(3-((1-isopropylcyclopropyl)methyl)-[1,2,4]triazolo[4,3-a]pyridin-7-yl)-N-(2-methyl-2H-1,2,3-triazol-4-yl)pyrimidin-2-amine;

4-(3((4,4-difluorocyclohexyl)methyl)-[1,2,4]triazolo[4,3-a]pyridin-7-yl)-N-(2-methyl-2H-1,2,3-triazol-4-yl)pyrimidin-2-amine;

4-(3-(2-fluoro-4-(trifluoromethyl)benzyl)-[1,2,4]triazolo[4,3-a]pyridin-7-yl)-N-(1-methyl-1H-pyrazol-5-yl)pyrimidin-2-amine;

4-(3-(4-fluoro-3-methoxybenzyl)-[1,2,4]triazolo[4,3-a]pyridin-7-yl)-N-(1-methyl-1H-pyrazol-5-yl)pyrimidin-2-amine;

4-(3-(2-cyclopentylethyl)-[1,2,4]triazolo[4,3-a]pyridin-7-yl)-N-(1-methyl-1H-pyrazol-5-yl)pyrimidin-2-amine;

4-(3-((3R*,4S*)-4-(3-fluorophenyl)pyrrolidin-3-yl)-[1,2,4]triazolo[4,3-a]pyridin-7-yl)-N-(tetrahydro-2H-pyran-4-yl)pyrimidin-2-amine;

4-(3-(4-(difluoromethoxy)-2-fluorobenzyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(4-methylpentyl)-[1,2,4]triazolo[4,3-a]pyridin-7-yl)pyrimidin-2-amine;

4-(3-((3R*,4S*)-4-phenylpyrrolidin-3-yl)-[1,2,4]triazolo[4,3-a]pyridin-7-yl)-N-(tetrahydro-2H-pyran-4-yl)pyrimidin-2-amine;

N-(1-methyl-1H-pyrazol-5-yl)-4-(3-(2-methylbenzyl)-[1,2,4]triazolo[4,3-a]pyridin-7-yl)pyrimidin-2-amine;

4-(3-(2-methylbenzyl)-[1,2,4]triazolo[4,3-a]pyridin-7-yl)-N-(tetrahydro-2H-pyran-4-yl)pyrimidin-2-amine;

4-(3-butyl-[1,2,4]triazolo[4,3-a]pyridin-7-yl)-N-(1-methyl-1H-pyrazol-5-yl)pyrimidin-2-amine;

4-(3-(2-chloro-6-fluorobenzyl)-[1,2,4]triazolo[4,3-a]pyridin-7-yl)-N-(1-methyl-1H-pyrazol-5-yl)pyrimidin-2-amine;

4-(3-(2-cyclohexylethyl)-[1,2,4]triazolo[4,3-a]pyridin-7-yl)-N-(1-methyl-1H-pyrazol-5-yl)pyrimidin-2-amine;

4-(3-(2,5-difluorobenzyl)-[1,2,4]triazolo[4,3-a]pyridin-7-yl)-N-(1-methyl-1H-pyrazol-5-yl)pyrimidin-2-amine;

4-(3-(2,6-difluorobenzyl)-[1,2,4]triazolo[4,3-a]pyridin-7-yl)-N-(1-methyl-1H-pyrazol-5-yl)pyrimidin-2-amine;

4-(3-(2-chloro-6-fluorobenzyl)-[1,2,4]triazolo[4,3-a]pyridin-7-yl)-N-(tetrahydro-2H-pyran-4-yl)pyrimidin-2-amine;

N-(tetrahydro-2H-pyran-4-yl)-4-(3-(2-(trifluoromethyl)benzyl)-[1,2,4]triazolo[4,3-a]pyridin-7-yl)pyrimidin-2-amine;

N-(1-methyl-1H-pyrazol-5-yl)-4-(3-(4-(trifluoromethoxy)benzyl)-[1,2,4]triazolo[4,3-a]pyridin-7-yl)pyrimidin-2-amine;

4-(3-((3S,4R)-1-benzyl-4-(3-fluorophenyl)pyrrolidin-3-yl)-[1,2,4]triazolo[4,3-a]pyridin-7-yl)-N-(1-methyl-1H-pyrazol-5-yl)pyrimidin-2-amine;

N-(1-methyl-1H-pyrazol-4-yl)-4-(3-((6-methylpyridin-2-yl)methyl)-[1,2,4]triazolo[4,3-a]pyridin-7-yl)pyrimidin-2-amine;

N-(1-methyl-1H-pyrazol-5-yl)-4-(3-propyl-[1,2,4]triazolo[4,3-a]pyridin-7-yl)pyrimidin-2-amine;

4-(3-((3S,4R)-1-benzyl-4-(3-fluorophenyl)pyrrolidin-3-yl)-[1,2,4]triazolo[4,3-a]pyridin-7-yl)-N-(tetrahydro-2H-pyran-4-yl)pyrimidin-2-amine;

N-(1-methyl-1H-pyrazol-5-yl)-4-(3-(3-methylbutan-2-yl)-[1,2,4]triazolo[4,3-a]pyridin-7-yl)pyrimidin-2-amine;

4-(3-(4-chlorophenyl)-[1,2,4]triazolo[4,3-a]pyridin-7-yl)-N-(tetrahydro-2H-pyran-4-yl)pyrimidin-2-amine;

4-(3-(2-chlorophenyl)-[1,2,4]triazolo[4,3-a]pyridin-7-yl)-N-(tetrahydro-2H-pyran-4-yl)pyrimidin-2-amine;

4-(3-phenyl-[1,2,4]triazolo[4,3-a]pyridin-7-yl)-N-(tetrahydro-2H-pyran-4-yl)pyrimidin-2-amine;

4-(3-(3-chlorophenyl)-[1,2,4]triazolo[4,3-a]pyridin-7-yl)-N-(tetrahydro-2H-pyran-4-yl)pyrimidin-2-amine;

4-(3-((3S,4R)-4-(4-chloro-3-fluorophenyl)pyrrolidin-3-yl)-[1,2,4]triazolo[4,3-a]pyridin-7-yl)-N-(tetrahydro-2H-pyran-4-yl)pyrimidin-2-amine;

(R)-2-(4-chloro-3-fluorophenyl)-2-(7-(2-((tetrahydro-2H-pyran-4-yl)amino)pyrimidin-4-yl)-[1,2,4]triazolo[4,3-a]pyridin-3-yl)ethanol;

(S)-2-(3-fluoro-4-methoxyphenyl)-2-(7-(2-((tetrahydro-2H-pyran-4-yl)amino)pyrimidin-4-yl)-[1,2,4]triazolo[4,3-a]pyridin-3-yl)ethanol;

4-(3-(2-fluorophenyl)-[1,2,4]triazolo[4,3-a]pyridin-7-yl)-N-(tetrahydro-2H-pyran-4-yl)pyrimidin-2-amine;

4-(3-(3-fluorophenyl)-[1,2,4]triazolo[4,3-a]pyridin-7-yl)-N-(tetrahydro-2H-pyran-4-yl)pyrimidin-2-amine;

4-(3-(2-chloro-4-fluorophenyl)-[1,2,4]triazolo[4,3-a]pyridin-7-yl)-N-(tetrahydro-2H-pyran-4-yl)pyrimidin-2-amine;

4-(3-(2-(4-methoxyphenoxy)phenyl)-[1,2,4]triazolo[4,3-a]pyridin-7-yl)-N-(tetrahydro-2H-pyran-4-yl)pyrimidin-2-amine;

N-(1-methyl-1H-pyrazol-5-yl)-4-(3-(pyrazin-2-ylmethyl)-[1,2,4]triazolo[4,3-a]pyridin-7-yl)pyrimidin-2-amine;

3-((7-(2-((1-methyl-1H-pyrazol-5-yl)amino)pyrimidin-4-yl)-[1,2,4]triazolo[4,3-a]pyridin-3-yl)methyl)benzonitrile;

N-(1-methyl-1H-pyrazol-5-yl)-4-(3-(2,2,3,3-tetramethylcyclopropyl)-[1,2,4]triazolo[4,3-a]pyridin-7-yl)pyrimidin-2-amine;

4-(3-(4-ethoxybenzyl)-[1,2,4]triazolo[4,3-a]pyridin-7-yl)-N-(1-methyl-1H-pyrazol-5-yl)pyrimidin-2-amine;

2-methyl-1-(7-(2-((1-methyl-1H-pyrazol-5-yl)amino)pyrimidin-4-yl)-[1,2,4]triazolo[4,3-a]pyridin-3-yl)propan-1-ol;

(R)-4-(3-(1-(tert-butoxy)ethyl)-[1,2,4]triazolo[4,3-a]pyridin-7-yl)-N-(1-methyl-1H-pyrazol-5-yl)pyrimidin-2-amine;

4-(3-((dimethylamino)(4-fluorophenyl)methyl)-[1,2,4]triazolo[4,3-a]pyridin-7-yl)-N-(1-methyl-1H-pyrazol-5-yl)pyrimidin-2-amine;

4-(3-((4-methoxyphenyl)(morpholino)methyl)-[1,2,4]triazolo[4,3-a]pyridin-7-yl)-N-(1-methyl-1H-pyrazol-5-yl)pyrimidin-2-amine;

4-(3-((1s,3s)-adamantan-1-ylmethyl)-[1,2,4]triazolo[4,3-a]pyridin-7-yl)-N-(1-methyl-1H-pyrazol-5-yl)pyrimidin-2-amine;

(3-chlorophenyl)(7-(2-((1-methyl-1H-pyrazol-5-yl)amino)pyrimidin-4-yl)-[1,2,4]triazolo[4,3-a]pyridin-3-yl)methanol;

4-(3-(1-phenylethyl)-[1,2,4]triazolo[4,3-a]pyridin-7-yl)-N-(tetrahydro-2H-pyran-4-yl)pyrimidin-2-amine;

4-(3-(2-chlorophenethyl)-[1,2,4]triazolo[4,3-a]pyridin-7-yl)-N-(tetrahydro-2H-pyran-4-yl)pyrimidin-2-amine;

4-(3-((1R*,2R*)-2-phenylcyclopropyl)-[1,2,4]triazolo[4,3-a]pyridin-7-yl)-N-(tetrahydro-2H-pyran-4-yl)pyrimidin-2-amine;

4-(3-(2-(4-fluorophenoxy)phenyl)-[1,2,4]triazolo[4,3-a]pyridin-7-yl)-N-(tetrahydro-2H-pyran-4-yl)pyrimidin-2-amine;

4-(3-((1R*,2S*)-2-benzylcyclopropyl)-[1,2,4]triazolo[4,3-a]pyridin-7-yl)-N-(tetrahydro-2H-pyran-4-yl)pyrimidin-2-amine;

4-(3-((1R*,2R*)-2-benzylcyclopropyl)-[1,2,4]triazolo[4,3-a]pyridin-7-yl)-N-(tetrahydro-2H-pyran-4-yl)pyrimidin-2-amine;

4-(3-(morpholin-2-yl)-[1,2,4]triazolo[4,3-a]pyridin-7-yl)-N-(tetrahydro-2H-pyran-4-yl)pyrimidin-2-amine;

4-(3-((3R*,4S*)-4-(3-fluorophenyl)pyrrolidin-3-yl)-[1,2,4]triazolo[4,3-a]pyridin-7-yl)-N-(1-methyl-1H-pyrazol-5-yl)pyrimidin-2-amine;

4-(3-(3-chlorophenethyl)-[1,2,4]triazolo[4,3-b]pyridazin-7-yl)-N-(tetrahydro-2H-pyran-4-yl)pyrimidin-2-amine;

(R)-2-(4-chloro-3-fluorophenyl)-2-(7-(2-((tetrahydro-2H-pyran-4-yl)amino)pyrimidin-4-yl)-[1,2,4]triazolo[4,3-b]pyridazin-3-yl)ethanol;

N-(1-methyl-1H-pyrazol-4-yl)-4-(3-((6-(trifluoromethyl)pyridin-2-yl)methyl)-[1,2,4]triazolo[4,3-a]pyridin-7-yl)pyrimidin-2-amine;

4-(3-(2-fluorobenzyl)-[1,2,4]triazolo[4,3-a]pyridin-7-yl)-N-(tetrahydro-2H-pyran-4-yl)pyrimidin-2-amine;

4-(3-(4-chlorobenzyl)-[1,2,4]triazolo[4,3-a]pyridin-7-yl)-N-(tetrahydro-2H-pyran-4-yl)pyrimidin-2-amine;

4-(3-(3-fluorobenzyl)-[1,2,4]triazolo[4,3-a]pyridin-7-yl)-N-(tetrahydro-2H-pyran-4-yl)pyrimidin-2-amine;

4-(3-(4-methoxybenzyl)-[1,2,4]triazolo[4,3-a]pyridin-7-yl)-N-(tetrahydro-2H-pyran-4-yl)pyrimidin-2-amine;

4-(3-(4-fluorobenzyl)-[1,2,4]triazolo[4,3-a]pyridin-7-yl)-N-(tetrahydro-2H-pyran-4-yl)pyrimidin-2-amine;

4-(3-(3-fluoro-4-methoxybenzyl)-[1,2,4]triazolo[4,3-a]pyridin-7-yl)-N-(tetrahydro-2H-pyran-4-yl)pyrimidin-2-amine;

4-(3-(4-chloro-3-fluorobenzyl)-[1,2,4]triazolo[4,3-a]pyridin-7-yl)-N-(tetrahydro-2H-pyran-4-yl)pyrimidin-2-amine;

4-(3-(3-methoxybenzyl)-[1,2,4]triazolo[4,3-a]pyridin-7-yl)-N-(tetrahydro-2H-pyran-4-yl)pyrimidin-2-amine;

4-(3-(3-chloro-4-fluorobenzyl)-[1,2,4]triazolo[4,3-a]pyridin-7-yl)-N-(tetrahydro-2H-pyran-4-yl)pyrimidin-2-amine;

4-(3-(4-fluorophenyl)-[1,2,4]triazolo[4,3-a]pyridin-7-yl)-N-(tetrahydro-2H-pyran-4-yl)pyrimidin-2-amine;

4-(3-(3-chloro-4-methoxybenzyl)-[1,2,4]triazolo[4,3-a]pyridin-7-yl)-N-(tetrahydro-2H-pyran-4-yl)pyrimidin-2-amine N-(tetrahydro-2H-pyran-4-yl)-4-(3-(4-(trifluoromethoxy)benzyl)-[1,2,4]triazolo[4,3-a]pyridin-7-yl)pyrimidin-2-amine;

4-(3-(4-methoxyphenoxy)-[1,2,4]triazolo[4,3-a]pyridin-7-yl)-N-(1-methyl-1H-pyrazol-5-yl)pyrimidin-2-amine;

4-([1,2,4]triazolo[4,3-a]pyridin-7-yl)-N-(1-methyl-1H-pyrazol-5-yl)pyrimidin-2-amine;

4-(3-(1-(3-fluorophenyl)-1H-pyrazol-5-yl)-[1,2,4]triazolo[4,3-a]pyridin-7-yl)-N-(1-methyl-1H-pyrazol-4-yl)pyrimidin-2-amine;

4-(3-(4-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
(R)-N-(1-methyl-1H-pyrazol-5-yl)-4-(3-(2-methylbutyl)-[1,2,4]triazolo[4,3-a]pyridin-7-yl)pyrimidin-2-amine;
4-(3-(1-(4-fluorophenyl)-3-methyl-1H-pyrazol-5-yl)-[1,2,4]triazolo[4,3-a]pyridin-7-yl)-N-(1-methyl-1H-pyrazol-4-yl)pyrimidin-2-amine;
4-(3-(3-(3-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-isopropyl-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(1-(3-fluorophenyl)-5-methyl-1H-pyrazol-3-yl)-[1,2,4]triazolo[4,3-a]pyridin-7-yl)-N-(1-methyl-1H-pyrazol-4-yl)pyrimidin-2-amine;
4-(3-(1-(4-fluorophenyl)-5-methyl-1H-pyrazol-3-yl)-[1,2,4]triazolo[4,3-a]pyridin-7-yl)-N-(1-methyl-1H-pyrazol-4-yl)pyrimidin-2-amine;
4-(3-(5-(3-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(5-(4-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(5-isobutyl-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(1-(4-fluorophenyl)-1H-pyrazol-5-yl)-[1,2,4]triazolo[4,3-a]pyridin-7-yl)-N-(1-methyl-1H-pyrazol-4-yl)pyrimidin-2-amine;
4-(3-(1-(3-fluorophenyl)-3-methyl-1H-pyrazol-5-yl)-[1,2,4]triazolo[4,3-a]pyridin-7-yl)-N-(1-methyl-1H-pyrazol-4-yl)pyrimidin-2-amine;
4-(3-(3-fluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
N-(1-methyl-1H-pyrazol-4-yl)-4-(3-(1-methyl-3-(pyridin-3-yl)-1H-pyrazol-4-yl)-[1,2,4]triazolo[4,3-a]pyridin-7-yl)pyrimidin-2-amine;
4-(3-(3,4-difluorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-(4-chlorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-(4-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-isobutyl-1-methyl-1H-pyrazol-4-yl)-[1,2,4]triazolo[4,3-a]pyridin-7-yl)-N-(1-methyl-1H-pyrazol-4-yl)pyrimidin-2-amine;
1-methyl-4-((7-(2-((1-methyl-1H-pyrazol-4-yl)amino)pyrimidin-4-yl)-[1,2,4]triazolo[4,3-a]pyridin-3-yl)methyl)pyridin-2(1H)-one;
4-(3-(3-(4-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(3-(3,4-difluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1-(3-fluorophenyl)-3-methyl-1H-pyrazol-5-yl)-[1,2,4]triazolo[4,3-a]pyridin-7-yl)-N-(1-methyl-1H-pyrazol-5-yl)pyrimidin-2-amine;
1-methyl-5-((7-(2-((1-methyl-1H-pyrazol-5-yl)amino)pyrimidin-4-yl)-[1,2,4]triazolo[4,3-a]pyridin-3-yl)methyl)pyridin-2(1H)-one;
4-(3-(1-(4-fluorophenyl)-5-methyl-1H-pyrazol-3-yl)-[1,2,4]triazolo[4,3-a]pyridin-7-yl)-N-(1-methyl-1H-pyrazol-5-yl)pyrimidin-2-amine;
4-(3-(5-(3-fluorobenzyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-(3-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(5-(4-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(5-(3,4-difluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(5-(3-fluorobenzyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(5-(4-chlorophenyl)-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(5-isopropyl-1-methyl-1H-pyrazol-4-yl)-[1,2,4]triazolo[4,3-a]pyridin-7-yl)-N-(1-methyl-1H-pyrazol-4-yl)pyrimidin-2-amine;
4-(3-(3-isobutyl-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1-(3-fluorophenyl)-3-(trifluoromethyl)-1H-pyrazol-5-yl)-[1,2,4]triazolo[4,3-a]pyridin-7-yl)-N-(1-methyl-1H-pyrazol-5-yl)pyrimidin-2-amine;
N-(4-fluorophenyl)-2-(7-(2-((1-methyl-1H-pyrazol-5-yl)amino)pyrimidin-4-yl)-[1,2,4]triazolo[4,3-a]pyridin-3-yl)acetamide;
4-(3-(2-(4-fluorophenyl)-2-methylpropyl)-[1,2,4]triazolo[4,3-a]pyridin-7-yl)-N-(1-methyl-1H-pyrazol-5-yl)pyrimidin-2-amine;
4-(3-(5-(3-fluorophenyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(5-isobutyl-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1-(3-fluorophenyl)-5-methyl-1H-pyrazol-3-yl)-[1,2,4]triazolo[4,3-a]pyridin-7-yl)-N-(1-methyl-1H-pyrazol-5-yl)pyrimidin-2-amine;
4-(3-(2-(4-methoxyphenyl)-2-methylpropyl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(2-(4-(p-tolyl)-1H-1,2,3-triazol-1-yl)ethyl)-[1,2,4]triazolo[4,3-a]pyridin-7-yl)pyrimidin-2-amine;
4-(3-(3-(4-fluorobenzyl)-1-methyl-1H-pyrazol-4-yl)-[1,2,4]triazolo[4,3-a]pyridin-7-yl)-N-(1-methyl-1H-pyrazol-5-yl)pyrimidin-2-amine;
4-(3-(1-(4-fluorophenyl)-1H-pyrazol-3-yl)-[1,2,4]triazolo[4,3-a]pyridin-7-yl)-N-(1-methyl-1H-pyrazol-5-yl)pyrimidin-2-amine;
4-(3-(1-(3-chlorophenyl)-3-(trifluoromethyl)-1H-pyrazol-5-yl)-[1,2,4]triazolo[4,3-a]pyridin-7-yl)-N-(1-methyl-1H-pyrazol-5-yl)pyrimidin-2-amine;
N-(1-methyl-1H-pyrazol-5-yl)-4-(3-(2-(5-(p-tolyl)-1H-1,2,3-triazol-1-yl)ethyl)-[1,2,4]triazolo[4,3-a]pyridin-7-yl)pyrimidin-2-amine;

4-(3-(1-(4-fluorophenyl)-3-methyl-1H-pyrazol-5-yl)-[1,2,4]triazolo[4,3-a]pyridin-7-yl)-N-(1-methyl-1H-pyrazol-5-yl)pyrimidin-2-amine;

1-(7-(2-((1-methyl-1H-pyrazol-5-yl)amino)pyrimidin-4-yl)-[1,2,4]triazolo[4,3-a]pyridin-3-yl)ethanone;

N-(1-methyl-1H-pyrazol-5-yl)-4-(3-((4-(trifluoromethyl)pyridin-2-yl)methyl)-[1,2,4]triazolo[4,3-a]pyridin-7-yl)pyrimidin-2-amine;

4-(3-((4-isopropylpyridin-2-yl)methyl)-[1,2,4]triazolo[4,3-a]pyridin-7-yl)-N-(1-methyl-1H-pyrazol-5-yl)pyrimidin-2-amine;

4-(3-(2-(3-methyl-1-phenyl-1H-1,2,4-triazol-5-yl)ethyl)-[1,2,4]triazolo[4,3-a]pyridin-7-yl)-N-(1-methyl-1H-pyrazol-5-yl)pyrimidin-2-amine;

N-(2-(7-(2-((1-methyl-1H-pyrazol-5-yl)amino)pyrimidin-4-yl)-[1,2,4]triazolo[4,3-a]pyridin-3-yl)-1-phenylethyl)acetamide;

N-(1-methyl-1H-pyrazol-5-yl)-4-(3-((6-methylimidazo[1,2-a]pyridin-3-yl)methyl)-[1,2,4]triazolo[4,3-a]pyridin-7-yl)pyrimidin-2-amine;

N-(1-methyl-1H-pyrazol-5-yl)-4-(3-(pyrrolidin-1-ylmethyl)-[1,2,4]triazolo[4,3-a]pyridin-7-yl)pyrimidin-2-amine;

1-methyl-5-((7-(2-((1-methyl-1H-pyrazol-4-yl)amino)pyrimidin-4-yl)-[1,2,4]triazolo[4,3-a]pyridin-3-yl)methyl)pyridin-2(1H)-one;

4-(3-(1-(4-fluorophenyl)-1H-pyrazol-5-yl)-[1,2,4]triazolo[4,3-a]pyridin-7-yl)-N-(1-methyl-1H-pyrazol-5-yl)pyrimidin-2-amine;

N-(1-(3-chloro-4-fluorophenyl)-2-(7-(2-((1-methyl-1H-pyrazol-5-yl)amino)pyrimidin-4-yl)-[1,2,4]triazolo[4,3-a]pyridin-3-yl)ethyl)acetamide 4-(3-isobutyl-[1,2,4]triazolo[4,3-b]pyridazin-7-yl)-N-(1-methyl-1H-pyrazol-5-yl)pyrimidin-2-amine 4-(3-((1-(2-fluoro-4-methylphenyl)-1H-1,2,3-triazol-5-yl)methyl)-[1,2,4]triazolo[4,3-a]pyridin-7-yl)-N-(1-methyl-1H-pyrazol-5-yl)pyrimidin-2-amine;

4-(3-(azepan-1-ylmethyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(2-(1-(p-tolyl)-1H-tetrazol-5-yl)ethyl)-[1,2,4]triazolo[4,3-a]pyridin-7-yl)pyrimidin-2-amine;

4-(3-((diethylamino)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-((2-methylpiperidin-1-yl)methyl)-[1,2,4]triazolo[4,3-a]pyridin-7-yl)pyrimidin-2-amine;

(R)-4-(3-(2-methoxybutyl)-[1,2,4]triazolo[4,3-a]pyridin-7-yl)-N-(1-methyl-1H-pyrazol-5-yl)pyrimidin-2-amine;

(S)-4-(3-(2-methoxybutyl)-[1,2,4]triazolo[4,3-a]pyridin-7-yl)-N-(1-methyl-1H-pyrazol-5-yl)pyrimidin-2-amine;

4-(3-(3-chlorobenzyl)-[1,2,4]triazolo[4,3-b]pyridazin-7-yl)-N-(1-methyl-1H-pyrazol-5-yl)pyrimidin-2-amine;

4-(3-(4-chlorobenzyl)-[1,2,4]triazolo[4,3-b]pyridazin-7-yl)-N-(1-methyl-1H-pyrazol-5-yl)pyrimidin-2-amine;

4-(3-(3-chlorophenethyl)-[1,2,4]triazolo[4,3-b]pyridazin-7-yl)-N-(1-methyl-1H-pyrazol-5-yl)pyrimidin-2-amine;

4-(3-((4-cyclopropyl-6-methylpyridin-2-yl)methyl)-[1,2,4]triazolo[4,3-a]pyridin-7-yl)-N-(1-methyl-1H-pyrazol-5-yl)pyrimidin-2-amine;

4-(3-((4-cyclopropyl-3-fluoropyridin-2-yl)methyl)-[1,2,4]triazolo[4,3-a]pyridin-7-yl)-N-(1-methyl-1H-pyrazol-5-yl)pyrimidin-2-amine;

4-(3-((4-bromopyridin-2-yl)methyl)-[1,2,4]triazolo[4,3-a]pyridin-7-yl)-N-(1-methyl-1H-pyrazol-5-yl)pyrimidin-2-amine;

4-(3-(5-(3-chlorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine;

4-(3-(3-fluoro-4-methoxybenzyl)-[1,2,4]triazolo[4,3-b]pyridazin-7-yl)-N-(1-methyl-1H-pyrazol-5-yl)pyrimidin-2-amine;

4-(3-((4-methoxypyridin-2-yl)methyl)-[1,2,4]triazolo[4,3-a]pyridin-7-yl)-N-(1-methyl-1H-pyrazol-5-yl)pyrimidin-2-amine;

4-(3-((1-methyl-1H-pyrazol-4-yl)(phenyl)methyl)-[1,2,4]triazolo[4,3-a]pyridin-7-yl)-N-(1-methyl-1H-pyrazol-5-yl)pyrimidin-2-amine;

4-(3-(5-(4-chloro-3-fluorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine;

3-((7-(2-((1-methyl-1H-pyrazol-5-yl)amino)pyrimidin-4-yl)-[1,2,4]triazolo[4,3-b]pyridazin-3-yl)methyl)pyridin-2-ol;

4-(3-(3-fluoro-4-methoxyphenethyl)-[1,2,4]triazolo[4,3-b]pyridazin-7-yl)-N-(1-methyl-1H-pyrazol-5-yl)pyrimidin-2-amine;

4-(3-((2-methoxypyridin-3-yl)methyl)-[1,2,4]triazolo[4,3-b]pyridazin-7-yl)-N-(1-methyl-1H-pyrazol-5-yl)pyrimidin-2-amine;

4-(3-((6-ethoxypyridin-3-yl)methyl)-[1,2,4]triazolo[4,3-a]pyridin-7-yl)-N-(1-methyl-1H-pyrazol-5-yl)pyrimidin-2-amine;

2,4-difluoro-N-methyl-N-(2-(7-(2-((1-methyl-1H-pyrazol-5-yl)amino)pyrimidin-4-yl)-[1,2,4]triazolo[4,3-a]pyridin-3-yl)ethyl)benzamide;

4-(3-(3-chloro-4-fluorobenzyl)-[1,2,4]triazolo[4,3-b]pyridazin-7-yl)-N-(1-methyl-1H-pyrazol--yl)pyrimidin-2-amine;

4-(3-(5-(4-chlorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine;

5-cyclopropyl-3-((7-(2-(1-methyl-1H-pyrazol-5-yl)amino)pyrimidin-4-yl)-[1,2,4]triazolo[4,3-a]pyridin-3-yl)methyl)pyridin-2-ol;

5-((7-(2-((1-methyl-1H-pyrazol-5-yl)amino)pyrimidin-4-yl)-[1,2,4]triazolo[4,3-a]pyridin-3-yl)methyl)pyridin-2-ol;

4-(3-((5-cyclopropyl-2-methoxypyridin-3-yl)methyl)-[1,2,4]triazolo[4,3-a]pyridin-7-yl)-N-(1-methyl-1H-pyrazol-5-yl)pyrimidin-2-amine;

4-(3-((1-benzyl-1H-imidazol-2-yl)methyl)-[1,2,4]triazolo[4,3-a]pyridin-7-yl)-N-(1-methyl-1H-pyrazol-5-yl)pyrimidin-2-amine;

4-(3-(2-amino-2-(3-chloro-4-fluorophenyl)ethyl)-[1,2,4]triazolo[4,3-a]pyridin-7-yl)-N-(1-methyl-1H-pyrazol-5-yl)pyrimidin-2-amine;

4-(3-(4-(4-chlorophenyl)-1-methyl-1H-pyrazol-5-yl)-[1,2,4]triazolo[4,3-a]pyridin-7-yl)-N-(1-methyl-1H-pyrazol-5-yl)pyrimidin-2-amine;

4-(3-(4-(4-chlorophenyl)-1-methyl-1H-pyrazol-3-yl)-[1,2,4]triazolo[4,3-a]pyridin-7-yl)-N-(1-methyl-1H-pyrazol-5-yl)pyrimidin-2-amine;

4-(3-(4-(3-chlorophenyl)-1-methyl-1H-pyrazol-5-yl)-[1,2,4]triazolo[4,3-a]pyridin-7-yl)-N-(1-methyl-1H-pyrazol-5-yl)pyrimidin-2-amine;

1-cyclopropyl-3-(7-(2-((1-methyl-1H-pyrazol-5-yl)amino)pyrimidin-4-yl)-[1,2,4]triazolo[4,3-a]pyridin-3-yl)propan-2-ol;

4-(3-(4-(3-chlorophenyl)-1-methyl-1H-pyrazol-3-yl)-[1, 2,4]triazolo[4,3-a]pyridin-7-yl)-N-(1-methyl-1H-pyrazol-5-yl)pyrimidin-2-amine;

4-(3-(5-(3,4-difluorophenyl)-1,3-dimethyl-1H-pyrazol-4-yl)-[1,2,4]triazolo[4,3-a]pyridin-7-yl)-N-(1-methyl-1H-pyrazol-5-yl)pyrimidin-2-amine;

N-methyl-7-(2-((1-methyl-1H-pyrazol-5-yl)amino)pyrimidin-4-yl)-[1,2,4]triazolo[4,3-a]pyridine-3-carboxamide;

4-(3-(4-(3-chlorophenyl)-1,3-dimethyl-1H-pyrazol-5-yl)-[1,2,4]triazolo[4,3-a]pyridin-7-yl)-N-(1-methyl-1H-pyrazol-5-yl)pyrimidin-2-amine;

4-(3-(4-(4-chlorophenyl)-1,3-dimethyl-1H-pyrazol-5-yl)-[1,2,4]triazolo[4,3-a]pyridin-7-yl)-N-(1-methyl-1H-pyrazol-5-yl)pyrimidin-2-amine;

1-cyclopropyl-2-(7-(2-((1-methyl-1H-pyrazol-5-yl)amino)pyrimidin-4-yl)-[1,2,4]triazolo[4,3-a]pyridin-3-yl)ethanol;

(7-(2-((1-methyl-1H-pyrazol-5-yl)amino)pyrimidin-4-yl)-[1,2,4]triazolo[4,3-a]pyridin-3-yl)(pyrrolidin-1-yl)methanone;

4-(3-((1-ethoxycyclobutyl)methyl)-[1,2,4]triazolo[4,3-a]pyridin-7-yl)-N-(1-methyl-1H-pyrazol-5-yl)pyrimidin-2-amine;

4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine;

4-(3-((6-chloro-4-methoxypyridin-2-yl)methyl)-[1,2,4]triazolo[4,3-a]pyridin-7-yl)-N-(1-methyl-1H-pyrazol-5-yl)pyrimidin-2-amine;

4-(3-(3-cyclopropyl-2-methoxypropyl)-[1,2,4]triazolo[4,3-a]pyridin-7-yl)-N-(1-methyl-1H-pyrazol-5-yl)pyrimidin-2-amine;

4-(3-(2-(3-cyclopropyl-1H-pyrazol-1-yl)ethyl)-[1,2,4]triazolo[4,3-a]pyridin-7-yl)-N-(1-methyl-1H-pyrazol-5-yl)pyrimidin-2-amine;

4-(3-((4,4-dimethyltetrahydrofuran-2-yl)methyl)-[1,2,4]triazolo[4,3-a]pyridin-7-yl)-N-(1-methyl-1H-pyrazol-5-yl)pyrimidin-2-amine;

4-(3-((1-cyclopropyl-3,5-dimethyl-1H-pyrazol-4-yl)methyl)-[1,2,4]triazolo[4,3-a]pyridin-7-yl)-N-(1-methyl-1H-pyrazol-5-yl)pyrimidin-2-amine;

4-(3-((3-cyclopropyl-1H-pyrazol-1-yl)methyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-((4-(trifluoromethyl)-1H-pyrazol-1-yl)methyl)-[1,2,4]triazolo[4,3-a]pyridin-7-yl)pyrimidin-2-amine;

4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine;

4-(3-(2-methoxy-2-(4-methoxyphenyl)ethyl)-[1,2,4]triazolo[4,3-a]pyridin-7-yl)-N-(1-methyl-1H-pyrazol-5-yl)pyrimidin-2-amine;

(S)-4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine;

(R)-4-(3-(2-cyclopropyl-3,3,3-trifluoropropyl)-[1,2,4]triazolo[4,3-a]pyridin-7-yl)-N-(1-methyl-1H-pyrazol-5-yl)pyrimidin-2-amine;

5,5,5-trifluoro-1-(7-(2-((1-methyl-1H-pyrazol-5-yl)amino)pyrimidin-4-yl)-[1,2,4]triazolo[4,3-a]pyridin-3-yl)pentan-2-ol;

N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine;

1-((7-(2-((1-methyl-1H-pyrazol-5-yl)amino)pyrimidin-4-yl)-[1,2,4]triazolo[4,3-a]pyridin-3-yl)methyl)pyrrolidin-2-one;

(S)-N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine;

(R)-N-(1-methyl-1H-pyrazol-5-yl)-4-(3-(3,3,3-trifluoro-2-methoxypropyl)-[1,2,4]triazolo[4,3-a]pyridin-7-yl)pyrimidin-2-amine;

4-(3-(2-cyclopropyl-2-fluoroethyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine;

4-(3-((4-ethoxypyridin-2-yl)methyl)-[1,2,4]triazolo[4,3-a]pyridin-7-yl)-N-(1-methyl-1H-pyrazol-5-yl)pyrimidin-2-amine;

4-(3-(2-cyclopentyl-3,3,3-trifluoropropyl)-[1,2,4]triazolo[4,3-a]pyridin-7-yl)-N-(1-methyl-1H-pyrazol-5-yl)pyrimidin-2-amine;

(R)-4-(3-(2-methoxy-3-methylbutyl)-[1,2,4]triazolo[4,3-a]pyridin-7-yl)-N-(1-methyl-1H-pyrazol-5-yl)pyrimidin-2-amine;

(S)-4-(3-(2-methoxy-3-methylbutyl)-[1,2,4]triazolo[4,3-a]pyridin-7-yl)-N-(1-methyl-1H-pyrazol-5-yl)pyrimidin-2-amine;

4-(3-(3-cyclopropyl-2-fluoropropyl)-[1,2,4]triazolo[4,3-a]pyridin-7-yl)-N-(1-methyl-1H-pyrazol-5-yl)pyrimidin-2-amine;

N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine;

4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine;

4-(3-((5-chlorothiophen-2-yl)methyl)-[1,2,4]triazolo[4,3-a]pyridin-7-yl)-N-(1-methyl-1H-pyrazol-5-yl)pyrimidin-2-amine;

(S)-N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine;

(R)-5,5,5-trifluoro-1-(7-(2-((1-methyl-1H-pyrazol-5-yl)amino)pyrimidin-4-yl)-[1,2,4]triazolo[4,3-a]pyridin-3-yl)pentan-2-ol;

1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol;

(R)-N-(1-methyl-1H-pyrazol-5-yl)-4-(3-(3,3,3-trifluoro-2-(4-methoxyphenyl)propyl)-[1,2,4]triazolo[4,3-a]pyridin-7-yl)pyrimidin-2-amine;

(S)-5,5,5-trifluoro-1-(7-(2-((1-methyl-1H-pyrazol-5-yl)amino)pyrimidin-4-yl)-[1,2,4]triazolo[4,3-a]pyridin-3-yl)pentan-2-ol;

(S)-N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine;

(R)-1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol;

(R)-N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine;

N-(1-methyl-1H-pyrazol-5-yl)-4-(3-(2-(4-(trifluoromethyl)-1H-pyrazol-1-yl)ethyl)-[1,2,4]triazolo[4,3-a]pyridin-7-yl)pyrimidin-2-amine;

4-(3-(2-(5-chlorothiophen-2-yl)-2-methoxyethyl)-[1,2,4]triazolo[4,3-a]pyridin-7-yl)-N-(1-methyl-1H-pyrazol-5-yl)pyrimidin-2-amine;

(S)-4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine;

(R)-N-(1-methyl-1H-pyrazol-5-yl)-4-(3-(5,5,5-trifluoro-2-methoxypentyl)-[1,2,4]triazolo[4,3-a]pyridin-7-yl)pyrimidin-2-amine;

(S)-1-(4-chlorophenyl)-2-(7-(2-((1-methyl-1H-pyrazol-5-yl)amino)pyrimidin-4-yl)-[1,2,4]triazolo[4,3-a]pyridin-3-yl)ethanol;

(S)-N-(1-methyl-1H-pyrazol-5-yl)-4-(3-(3,3,3-trifluoro-2-(4-fluorophenyl)propyl)-[1,2,4]triazolo[4,3-a]pyridin-7-yl)pyrimidin-2-amine;

(R)-4-(3-(4-cyclopropyl-2-methoxybutyl)-[1,2,4]triazolo[4,3-a]pyridin-7-yl)-N-(1-methyl-1H-pyrazol-5-yl)pyrimidin-2-amine;

(S)-4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine;

N-(1,1,1-trifluoro-3-(7-(2-((1-methyl-1H-pyrazol-5-yl)amino)pyrimidin-4-yl)-[1,2,4]triazolo[4,3-a]pyridin-3-yl)propan-2-yl)acetamide;

1-(4-methoxyphenyl)-2-(7-(2-((1-methyl-1H-pyrazol-5-yl)amino)pyrimidin-4-yl)-[1,2,4]triazolo[4,3-a]pyridin-3-yl)ethanol;

1-(4-methoxyphenyl)-2-(7-(2-((1-methyl-1H-pyrazol-5-yl)amino)pyrimidin-4-yl)-[1,2,4]triazolo[4,3-a]pyridin-3-yl)ethanone;

2-cyclopropyl-1-(7-(2-((1-methyl-1H-pyrazol-5-yl)amino)pyrimidin-4-yl)-[1,2,4]triazolo[4,3-a]pyridin-3-yl)propan-2-ol;

N-(1-methyl-1H-pyrazol-5-yl)-4-(3-(3,3,3-trifluoro-2-(4-methoxyphenyl)propyl)-[1,2,4]triazolo[4,3-b]pyridazin-7-yl)pyrimidin-2-amine;

4-(3-((5-cyclopropylthiophen-2-yl)methyl)-[1,2,4]triazolo[4,3-a]pyridin-7-yl)-N-(1-methyl-1H-pyrazol-5-yl)pyrimidin-2-amine;

5-((7-(2-((1-methyl-1H-pyrazol-5-yl)amino)pyrimidin-4-yl)-[1,2,4]triazolo[4,3-a]pyridin-3-yl)methyl)thiophene-2-carbonitrile;

4-(3-(3-cyclopentyl-2-methoxypropyl)-[1,2,4]triazolo[4,3-a]pyridin-7-yl)-N-(1-methyl-1H-pyrazol-5-yl)pyrimidin-2-amine;

or (R)-4-(3-(2-(4-chlorophenyl)-2-methoxyethyl)-[1,2,4]triazolo[4,3-a]pyridin-7-yl)-N-(1-methyl-1H-pyrazol-5-yl)pyrimidin-2-amine;

or a pharmaceutically acceptable salt thereof.

18. A pharmaceutical composition comprising a compound of claim 1 or a stereoisomer, tautomer or pharmaceutically acceptable salt thereof.

19. A pharmaceutical composition comprising a compound of claim 1 or a stereoisomer, tautomer or pharmaceutically acceptable salt thereof and at least one pharmaceutically acceptable excipient.

* * * * *

UNITED STATES PATENT AND TRADEMARK OFFICE
CERTIFICATE OF CORRECTION

PATENT NO. : 9,670,208 B2
APPLICATION NO. : 15/197445
DATED : June 6, 2017
INVENTOR(S) : James F. Blake et al.

Page 1 of 1

It is certified that error appears in the above-identified patent and that said Letters Patent is hereby corrected as shown below:

In the Claims

Column 341, Line 40, Claim 6, please delete "-hydroxymethyl -ethyl" and insert
-- -hydroxymethyl-ethyl --;

Column 366, Line 41, Claim 17, please delete "-3-((7(2-(1-methyl-" and insert
-- -3-((7-(2-((1-methyl- -- therefor.

Signed and Sealed this
Fifteenth Day of May, 2018

Andrei Iancu
*Director of the United States Patent and Trademark Office*